US010329546B2

(12) United States Patent
Graycar et al.

(10) Patent No.: US 10,329,546 B2

(45) **Date of Patent: *Jun. 25, 2019**

(54) COMPOSITIONS AND METHODS COMPRISING A LIPOLYTIC ENZYME VARIANT

(71) Applicant: DANISCO US INC, Palo Alto, CA (US)

(72) Inventors: Thomas P. Graycar, Pacifica, CA (US); Ayrookaran J. Poulose, Belmont, CA (US); David A. Estell, San Mateo, CA (US)

(73) Assignee: DANISCO US INC, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/791,710

(22) Filed: Oct. 24, 2017

(65) Prior Publication Data

US 2018/0037876 A1 Feb. 8, 2018

Related U.S. Application Data

(63) Continuation of application No. 14/906,225, filed as application No. PCT/US2014/047174 on Jul. 18, 2014, now abandoned.

(60) Provisional application No. 61/856,524, filed on Jul. 19, 2013.

(51) Int. Cl.
*C12N 9/20* (2006.01)
*C11D 3/386* (2006.01)

(52) U.S. Cl.
CPC ............ *C12N 9/20* (2013.01); *C11D 3/38627* (2013.01); *C11D 3/38681* (2013.01); *C12Y 301/01003* (2013.01)

(58) Field of Classification Search
CPC ........................................................ C12N 9/20
See application file for complete search history.

(56) References Cited

U.S. PATENT DOCUMENTS

| | | | | |
|---|---|---|---|---|
| 5,965,422 | A | 10/1999 | Loffler et al. | |
| 6,103,505 | A | 8/2000 | Clausen et al. | |
| 6,558,715 | B1 | 5/2003 | Rey et al. | |
| 6,624,129 | B1 * | 9/2003 | Borch | C11D 1/83 435/196 |
| 7,157,263 | B2 * | 1/2007 | Munk | C11D 3/38627 435/18 |
| 7,465,570 | B2 * | 12/2008 | Borch | A21D 8/042 426/20 |
| 8,273,348 | B2 * | 9/2012 | Svendsen | C12N 9/20 424/94.2 |

FOREIGN PATENT DOCUMENTS

| | | | |
|---|---|---|---|
| CA | 2005087 | | 12/1989 |
| EP | 0219269 | A2 | 4/1987 |
| EP | 0374700 | A2 | 12/1989 |
| EP | 585988 | A1 | 7/1993 |
| EP | 0808903 | A2 | 3/1997 |
| EP | 785994 | A1 | 7/1997 |
| WO | 1994004035 | A1 | 3/1994 |
| WO | 1994025577 | A1 | 11/1994 |
| WO | 1996013580 | A1 | 5/1996 |
| WO | 2007087242 | A2 | 8/2007 |
| WO | 2007087318 | A2 | 8/2007 |
| WO | 2007087508 | A2 | 8/2007 |

OTHER PUBLICATIONS

Sonia Longhi et al., Structure-activity of cutinase, a small lipolytic enzyme, Biochimica et Biophysica Acta, 1999, pp. 185-196, vol. 1441.
International Search Report—PCT/US2014/047174—dated Mar. 6, 2015.

* cited by examiner

*Primary Examiner* — Karen Cochrane Carlson

(57) ABSTRACT

The present invention provides lipolytic enzyme variants. Specifically, the present invention provides lipolytic enzyme variants having two, three, or more modifications as compared to a parent lipolytic enzyme and having at least one improved property. In addition, the present invention provides compositions comprising a lipolytic enzyme variant of the invention. The present invention also provides methods of cleaning using compositions comprising a lipolytic enzyme variant of the invention.

16 Claims, No Drawings

Specification includes a Sequence Listing.

SEQUENCE LISTING

```
<160> NUMBER OF SEQ ID NOS: 3

<210> SEQ ID NO 1
<211> LENGTH: 269
<212> TYPE: PRT
<213> ORGANISM: Thermomyces lanuginosa
<220> FEATURE:
<221> NAME/KEY: misc_feature
<223> OTHER INFORMATION: sequence of the lipolytic enzyme from
      Thermomyces lanuginosa (TLL)

<400> SEQUENCE: 1

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45
```

```
Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265


<210> SEQ ID NO 2
<211> LENGTH: 269
<212> TYPE: PRT
<213> ORGANISM: Thermomyces lanuginosa
<220> FEATURE:
<221> NAME/KEY: misc_feature
<223> OTHER INFORMATION: sequence of the reference lipolytic enzyme,
      which is a variant from Thermomyces lanuginosa (TLL)

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
```

-continued

```
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Arg Arg Arg Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265


<210> SEQ ID NO 3
<211> LENGTH: 834
<212> TYPE: DNA
<213> ORGANISM: Artificial Sequence
<220> FEATURE:
<223> OTHER INFORMATION: Nucleotide sequence of the synthetic TLL gene

<400> SEQUENCE: 3

gctagcgcag ctggcaaaga agttagccaa gatctgttca accaattcaa ccttttcgct     60

caatactctg cagctgctta ctgcggaaag aacaacgatg cacctgctgg tactaacatc    120

acttgcacag gtaacgcatg tcctgaagta gaaaaagctg atgctacatt tctttactct    180

tttgaagata gcggcgtcgg cgatgttacc ggtttcttag ctctggataa cacaaacaaa    240

cttatcgtcc ttagcttcag aggctctcgc tcaatcgaaa actggatcgg taaccttaat    300

tttgacttga aagaaatcaa cgatatctgc tctggttgcc gtggccatga cggattcaca    360

tcatcttgga gaagcgtcgc agacacgctt cgccaaaaag tagaagatgc cgtacgcgaa    420

cacccagatt acagagtagt tttcacaggt cactctcttg gcggagcttt agcaacagta    480

gcaggcgctg atctccgcgg taacggatac gacattgatg tcttctctta cggcgctccg    540

cgcgtcggta acagagcgtt tgctgaattt ttaactgtac aaacaggcgg aactctttat    600

cgcatcactc acacaaacga tattgtcccg cgcttacctc cgagagaatt tggttactca    660

cacagctctc ctgaatactg gatcaaaagc ggtacattgg tacctgttac tcgaaacgat    720

atcgtcaaaa ttgaaggaat tgacgccacc ggcggcaaca accaaccgaa catccctgac    780

atcccggcac acctttggta cttcggctta atcggaacat gcctttaaaa gctt          834
```

COMPOSITIONS AND METHODS COMPRISING A LIPOLYTIC ENZYME VARIANT

CROSS REFERENCE TO RELATED APPLICATIONS

This application is a Continuation of U.S. application Ser. No. 14/906,225, filed Jan. 19, 2016, which is a 371 of International Application No. PCT/US14/47174, filed Jul. 18, 2014, and claims the benefit of priority from U.S. provisional application U.S. Ser. No. 61/856,524, filed Jul. 19, 2013, all of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 20171023_NB40409USCNT_SeqLst.txt created on Oct. 23, 2017 and having a size of 7 kilobytes and is filed concurrently with the specification. The sequence listing contained in this ASCII formatted document is part of the specification and is herein incorporated by reference in its entirety.

BACKGROUND OF THE INVENTION

Lipolytic enzymes, including lipases and cutinases, have been employed in detergent cleaning compositions for the removal of oily stains. One mechanism by which lipolytic enzymes function is by hydrolyzing triglycerides to generate fatty acids. However, these enzymes are often inhibited by surfactants and other components present in cleaning composition, interfering with their ability to remove oily stains. Accordingly, the need exists for lipolytic enzymes that have improved function and can be effective in the harsh environment of cleaning compositions.

SUMMARY OF THE INVENTION

The present invention provides improved lipolytic enzymes, especially enzymes useful for detergent compositions. Specifically, the present invention provides lipolytic enzyme variants having two or more modifications, such as a substitution, as compared to a parent lipolytic enzyme that have improved lipolytic activity, such as improved hydrolysis of p-nitrophenyl butyrate, p-nitrophenyl caprylate, or p-nitrophenyl palmitate, increased pNPP/pNPB or pNPO/pNPB specific activity ratio, increased pNPB/pNPP specific activity ratio, increased thermostability, increased detergent stability, increased LAS stability, increased fabric adhesion, decreased fabric adhesion, or increased cleaning performance. This improved activity can improve effectiveness of the variant enzyme in a wash cycle. The present invention provides variant lipolytic enzymes, including, but not limited to, variant lipase lipolytic enzymes, that are particularly well suited to and useful in a variety of cleaning applications. The invention also provides methods of cleaning using lipolytic enzyme variants of the present invention.

In some embodiments, the invention is a lipolytic enzyme variant or an active fragment thereof comprising at least two, three, four, five, six, seven, eight, nine or ten or more amino acid modifications to a parent lipolytic enzyme, wherein a first amino acid modification is at a position of the lipolytic enzyme variant selected from the group consisting of 4, 11, 18, 23, 24, 27, 29, 33, 45, 48, 49, 51, 56, 58, 73, 75, 77, 90, 91, 94, 111, 130, 137, 154, 156, 163, 187, 189, 227, 233, 252, 256, and 264, wherein the amino acid positions of the variant are numbered by correspondence with the amino acid sequence of *Thermomyces lanuginosa lipase* set forth in SEQ ID NO: 1.

In some embodiments, the invention is a lipolytic enzyme variant or active fragment thereof, wherein the variant or active fragment thereof comprises amino acid modifications of Table 2-2, wherein the amino acid positions of the variant are numbered by correspondence with the amino acid sequence of *Thermomyces lanuginosa lipase* set forth in SEQ ID NO: 1.

In some of the above embodiments, the variant or active fragment has lipolytic activity. In some of the above embodiments, the variant or active fragment has a performance index (pI) relative to the parent lipolytic enzyme for hydrolysis of p-nitrophenyl butyrate, p-nitrophenyl caprylate, or p-nitrophenyl palmitate is greater than 1.0, with some instances wherein the performance index is measured using the p-nitrophenyl butyrate, p-nitrophenyl caprylate, or p-nitrophenyl palmitate assay of Example 1.

In some of the above embodiments, the variant or active fragment has increased pNPP/pNPB or pNPO/pNPB specific activity ratio, increased pNPB/pNPP specific activity ratio, increased thermostability, increased detergent stability, increased LAS stability, increased fabric adhesion, decreased fabric adhesion, or increased cleaning performance.

In some embodiments, the invention is a composition comprising at least one lipolytic enzyme variant as listed above. The composition can be a cleaning composition or cleaning additive. In some embodiments, the invention further includes an additional enzyme from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, laccase, and amylase.

In one embodiment, the invention is a method hydrolyzing a fatty acid ester or triglyceride comprising contacting the fatty acid ester or triglyceride with a lipolytic enzyme variant listed above. In one embodiment, the invention is a method of cleaning, comprising contacting a surface or an item with a cleaning composition comprising at least one lipolytic enzyme variant listed above.

DESCRIPTION OF THE INVENTION

The present invention provides improved lipolytic enzymes, especially enzymes useful for detergent compositions. Specifically, the present invention provides lipolytic enzyme variants having two or more modifications, such as a substitution, as compared to a parent lipolytic enzyme that have improved lipolytic activity, such as improved hydrolysis of fatty acid esters or triglycerides, or for example, p-nitrophenyl butyrate, p-nitrophenyl caprylate, or p-nitrophenyl palmitate. The present invention provides variant lipolytic enzymes, including, but not limited to, variant lipase lipolytic enzymes, that are particularly well suited to and useful in a variety of cleaning applications. The invention includes compositions comprising at least one of the variant lipolytic enzymes (e.g., variant lipases) set forth herein. Some such compositions comprise detergent compositions. The invention provides *Thermomyces* species variant lipolytic enzymes and compositions comprising one or more such variant lipases. The lipolytic enzyme variants of the present invention can be combined with other enzymes useful in detergent compositions. The invention also provides methods of cleaning using lipolytic enzyme variants of the present invention.

The invention includes enzyme variants of lipolytic enzymes having two or more modifications from a parent lipolytic enzyme. A parent lipolytic enzyme can be the wild-type enzyme or any starting reference lipolytic enzyme from which the variant lipolytic enzyme was derived.

Additionally, the invention provides modifications, such as a substitution, at two, three, or more amino acid positions in a lipolytic enzyme which can be useful in a detergent composition where favorable modifications result in an improved performing index (pI) for lipolytic activity compared to a parent lipolytic enzyme, such as SEQ ID NO:1, or to a reference lipase enzyme, such as SEQ ID NO: 2. These amino acid positions can be considered useful positions for combinatorial modifications to a parent lipolytic enzyme.

Unless defined otherwise herein, all technical and scientific terms used herein have the same meaning as commonly understood by one of ordinary skill in the art to which this invention pertains. Although many methods and materials similar or equivalent to those described herein find use in the practice of the present invention, some methods and materials are described herein. Accordingly, the terms defined immediately below are more fully described by reference to the specification as a whole. All patents, patent applications, articles and publications mentioned herein, both supra and infra, are hereby expressly incorporated herein by reference.

Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context in which they are used by those of skill in the art.

It is intended that every maximum numerical limitation given throughout this specification include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used through out this disclosure. It is also understood that a polypeptide can be coded for by more than one nucleotide sequence due to the degeneracy of the genetic code. Mutations can be named by the one letter code for the parent amino acid, followed by a number and then the one letter code for the variant amino acid. For example, mutating glycine (G) at position 87 to serine (S) can be represented as "G087S" or "G87S". Multiple mutations can be indicated by inserting a "–," "+," or "," between the mutations. For example, mutations at positions 87 and 90 can be represented as either "G087S-A090Y" or "G87S–A90Y" or "G87S+A90Y" or "G087S+A090Y".

The terms "derived from" and "obtained from" refer not only to a lipolytic enzyme produced or producible by a strain of the organism in question, but also a lipolytic enzyme encoded by a DNA sequence isolated from such strain and produced in a host organism containing such DNA sequence. Additionally, the term refers to a lipolytic enzyme which is encoded by a DNA sequence of synthetic and/or cDNA origin and which has the identifying characteristics of the lipolytic enzyme in question. To exemplify, "lipolytic enzymes derived from *Thermomyces lanuginosa*" refers to those enzymes having lipolytic activity which are naturally produced by *Thermomyces lanuginosa*, as well as to lipolytic enzymes like those produced by *Thermomyces lanuginosa* sources but which through the use of genetic engineering techniques are produced by non-*Thermomyces lanuginosa* organisms transformed with a nucleic acid encoding the lipolytic enzymes.

As used herein, "% identity or percent identity" refers to sequence similarity. Percent identity may be determined using standard techniques known in the art (See e.g., Smith and Waterman, Adv. Appl. Math. 2:482 [1981]; Needleman and Wunsch, J. Mol. Biol. 48:443 [1970]; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters include a default gap weight of 3.00, a default gap length weight of 0.10, and weighted end gaps. Other useful algorithm is the BLAST algorithms described by Altschul et al., (See, Altschul et al., J. Mol. Biol. 215:403-410 [1990]; and Karlin and Altschul, Proc. Natl. Acad. Sci. USA 90:5873-5787 [1993]). The BLAST program uses several search parameters, most of which are set to the default values.

The NCBI BLAST algorithm finds the most relevant sequences in terms of biological similarity but is not recommended for query sequences of less than 20 residues (Altschul, S F et al. (1997) Nucleic Acids Res. 25:3389-3402 and Schaffer, A A et al. (2001) Nucleic Acids Res. 29:2994-3005). Example default BLAST parameters for a nucleic acid sequence searches are:

| | |
|---|---|
| Neighboring words threshold: | 11 |
| E-value cutoff: | 10 |
| Scoring Matrix: | NUC.3.1 (match = 1, mismatch = −3) |
| Gap Opening: | 5 |
| Gap Extension: | 2 |

and the following parameters for amino acid sequence searches:

| | |
|---|---|
| Word size: | 3 |
| E-value cutoff: | 10 |

-continued

| | |
|---|---|
| Scoring Matrix: | BLOSUM62 |
| Gap Opening: | 11 |
| Gap extension: | 1 |

A percent (%) amino acid sequence identity value is determined by the number of matching identical residues divided by the total number of residues of the "reference" sequence including any gaps created by the program for optimal/maximum alignment. If a sequence is 90% identical to SEQ ID NO: A, SEQ ID NO: A is the "reference" sequence. BLAST algorithms refer the "reference" sequence as "query" sequence.

The CLUSTAL W algorithm is another example of a sequence alignment algorithm. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF. |

In CLUSTAL algorithms, deletions occurring at either terminus are included. For example, a variant with five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A polypeptide of interest may be said to be "substantially identical" to a reference polypeptide if the polypeptide of interest comprises an amino acid sequence having at least about 60%, least about 65%, least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having least about 60%, least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is partially or completely separated from other components, including but not limited to for example, other proteins, nucleic acids, cells, etc. Similarly, a polypeptide, protein or peptide is "isolated" when it is partially or completely separated from other components, including but not limited to for example, other proteins, nucleic acids, cells, etc. On a molar basis, an isolated species is more abundant than are other species in a composition. For example, an isolated species may comprise at least about 50%, about 70%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a protein or nucleic acid sample, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure variant lipolytic enzyme or polynucleotide encoding a variant lipolytic enzyme of the invention, respectively) will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

The position of an amino acid residue in a given amino acid sequence is typically numbered herein using the numbering of the position of the corresponding amino acid residue of the *Thermomyces lanuginosa lipase* TLL amino acid sequence shown in SEQ ID NO: 1. The *T. lanuginosa lipase* TLL amino acid sequence of SEQ ID NO: 1, thus serves as a reference parent sequence. A given amino acid sequence, such as a variant lipolytic enzyme amino acid sequence described herein, can be aligned with the TLL sequence (SEQ ID NO: 1) using an alignment algorithm as described herein, and an amino acid residue in the given amino acid sequence that aligns (preferably optimally aligns) with an amino acid residue in the TLL sequence can be conveniently numbered by reference to the corresponding amino acid residue in the lipase TLL sequence.

Lipolytic Enzymes of the Invention

As used herein, a lipolytic enzyme includes an enzyme, polypeptide, or protein exhibiting a lipid degrading capability such as a capability of degrading a triglyceride or a phospholipid. The lipolytic enzyme can be, for example, a lipase, a phospholipase, an esterase, a polyesterase, or a cutinase. Lipolytic enzymes can be lipolytic enzymes having an alpha/beta hydrolase fold. These enzymes typically have a catalytic triad of serine, aspartic acid and histidine residues. The alpha/beta hydrolases include lipases and cutinases. Cutinases show little, if any, interfacial activation, where lipases often undergo a conformational change in the presence of a lipid-water interface (Longhi and Cambillau (1999) Biochimica et Biophysica Acta 1441:185-96). An active fragment of a lipolytic enzyme is a portion of a lipolytic enzyme that retains a lipid degrading capability. An active fragment retains the catalytic triad. As used herein, lipolytic activity can be determined according to any procedure known in the art (see, e.g., Gupta et al., *Biotechnol. Appl. Biochem.,* 37:63-71, 2003; U.S. Pat. No. 5,990,069; and International Patent Publication No. WO 96/18729A1).

In some embodiments, lipolytic enzymes of the present invention are □/□ hydrolases. In some embodiments, lipolytic enzymes of the present invention are lipases. In some embodiments, lipolytic enzymes of the present invention are cutinases. In some embodiments, lipolytic enzymes of the present invention are polyesterases.

Productive Positions of Lipolytic Enzymes

The invention provides modifications, such as a substitution, at two, three, four, five, six, seven, eight, nine or ten or more amino acid positions in a lipolytic enzyme which can be useful in a detergent composition where favorable modifications result in an improved performing index (pI) for lipolytic activity, such as improved hydrolysis of fatty acid esters or triglycerides, or for example, p-nitrophenyl butyrate, p-nitrophenyl caprylate, or p-nitrophenyl palmitate, increased pNPP/pNPB or pNPO/pNPB specific activity ratio, increased pNPB/pNPP specific activity ratio, increased thermostability, increased detergent stability, increased LAS stability, increased fabric adhesion, decreased fabric adhesion, or increased cleaning performance, compared to the parent lipolytic enzyme. These amino acid positions can be considered useful positions for combinatorial modifications to a parent lipolytic enzyme.

Lipolytic enzyme amino acid positions found to be useful positions can have different modifications that are suitable for use in a detergent composition. Modifications can include an insertion, deletion or substitution at the particular position. In one embodiment, a modification is a substitution.

In some embodiments, the invention is a lipolytic enzyme variant or an active fragment thereof comprising at least two, three, four, five, six, seven, eight, nine or ten or more amino acid modifications to a parent lipolytic enzyme, wherein a first amino acid modification is at a position of the lipolytic enzyme variant selected from the group consisting of 4, 11, 18, 23, 24, 27, 29, 33, 45, 48, 49, 51, 56, 58, 73, 75, 77, 90, 91, 94, 111, 130, 137, 154, 156, 163, 187, 189, 227, 233, 252, 256, and 264, wherein the amino acid positions of the variant are numbered by correspondence with the amino acid sequence of *Thermomyces lanuginosa lipase* set forth in SEQ ID NO: 1. In some embodiments, the invention is a lipolytic enzyme variant or an active fragment thereof, wherein the at least two, three, four, five, six, seven, eight, nine or ten or more amino acid modifications to a parent lipolytic enzyme are at a position of the lipolytic enzyme variant selected from the group consisting of 4, 11, 18, 23, 24, 27, 29, 33, 45, 48, 49, 51, 56, 58, 73, 75, 77, 90, 91, 94, 111, 130, 137, 154, 156, 163, 187, 189, 227, 233, 252, 256, and 264, wherein the amino acid positions of the variant are numbered by correspondence with the amino acid sequence of *Thermomyces lanuginosa lipase* set forth in SEQ ID NO: 1.

In some embodiments, a lipolytic enzyme variant or active fragment thereof of the invention can have two or more modifications, where the modifications are A018K/D027S, A018K/E045F, A018K/L075D, A018K/L075Q, A018K/T189D, D027E/G163P, D027N/E056K, D027N/N233Q, D027S/N033D, D027S/P256T, D111A/L264R, D130A/L264R, D130A/T189Q, D130A/V187N, D130A/V187T, E045F/N073R, E045F/T189D, F051T/L075R, G023K/D130A, G023K/L264R, G023Q/L075Q, K024A/L075Q, K024A/V154I, L075Q/D130A, L075Q/G156W, L075R/L264R, L227M/L264R, N011K/D027S, N033D/E045F, N073R/L075D, N094R/G156W, P029E/N033D, S058M/L264R, V187T/L264R, A018K/A049V/L075Q, A018K/A049V/V187T, A018K/D027S/E045F, A018K/D027S/N073R, A018K/D027S/T189D, A018K/E045F/N073R, A018K/E045F/T189D, A018K/E045F/V187T, A018K/G023K/G156W, A018K/G023K/L075Q, A018K/G023Q/L075Q, A018K/K024A/V154I, A018K/L075D/T189D, A018K/L075Q/G156W, A018K/L075Q/V187T, A018K/N033D/L075D, A018K/N033D/T189D, A018K/N073R/L075D, A018K/P029E/T189D, A018K/V154I/G156W, A049V/L075Q/T189D, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D111A/D130A/L264R, D130A/T189Q/L264R, D130A/V154I/G156W, D130A/V187N/L264R, D130A/V187T/L264R, E045F/L075D/T189D, E045F/N073R/L075D, E056K/D130A/L264R, E056K/D130A/T189Q, F051T/I252Q/L264R, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/D111A/L264R, G023Q/D130A/G156W, G023Q/E045F/V077I, G023Q/E056K/L075R, G023Q/K024A/G156W, G023Q/L075Q/V077I, G023Q/L075Q/V187T, G163P/L227M/L264R, I090F/N233Q/P256T, K024A/D130A/V154I, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/N094R/V154I, L075Q/V077I/T189D, L075Q/V154I/V187T, L075Q/V187N/L264R, L075Q/V187T/L264R, L075Q/V187T/T189D, L075R/

D130A/L264R, L075R/D130A/V187T, L075R/V187N/L264R, L075R/V187T/L264R, N011K/D027S/S058M, N011K/N233Q/P256T, N033D/E045F/L075D, N033D/E045F/N073R, N033D/N073R/T189D, N073R/L075D/T189D, N094R/D130A/V187T, P029E/E045F/L075D, P029E/L075D/T189D, P029E/N033D/E045F, P029E/N033D/L075D, P029E/N073R/L075D, Q004D/D027S/P256T, Q004D/N233Q/P256T, Q004D/S058M/N233Q, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/N073R, A018K/D027S/E045F/T189D, A018K/D027S/L075D/T189D, A018K/D027S/N033D/L075D, A018K/D027S/P029E/T189D, A018K/D111A/G156W/T189Q, A018K/D130A/G156W/V187T, A018K/E045F/A049V/G156W, A018K/E045F/A049V/V187T, A018K/E045F/L075D/T189D, A018K/E045F/L075Q/T189D, A018K/E045F/L075Q/V187T, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/K024A/D130A/G156W, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/L075D, A018K/P029E/N033D/T189D, A018K/P029E/N073R/L075D, A018K/V154I/G156W/V187T, A049V/L075Q/V077I/T189D, A049V/L075Q/V187T/T189D, D027E/D048Q/G163P/L264R, D027E/D130A/N233Q/L264R, D027E/D137Q/G163P/L227M, D027E/D137Q/L227M/L264R, D027E/G163P/L227M/L264R, D027E/L227M/N233Q/L264R, D027E/S058M/G163P/L264R, D027N/E056K/N233Q/P256T, D027N/E056K/S058M/P256T, D027N/S058M/N233Q/P256T, D027Q/E056K/N233Q/P256T, D027Q/S058M/I090F/P256T, D027S/D130A/I252Q/L264R, D027S/E045F/L075D/T189D, D027S/E045F/N073R/L075D, D027S/E045F/N073R/T189D, D027S/E056K/D111A/V154I, D027S/E056K/I090F/P256T, D027S/N033D/E045F/N073R, D027S/N033D/E045F/T189D, D027S/N033D/L075D/T189D, D027S/N033D/N073R/L075D, D027S/N033D/N073R/T189D, D027S/P029E/E045F/L075D, D027S/P029E/E045F/L075D, D045F/N073R, D027S/P029E/E045F/T189D, D027S/P029E/L075D/T189D, D027S/P029E/N033D/E045F, D027S/P029E/N033D/L075D, D027S/P029E/N033D/N073R, D027S/P029E/N033D/T189D, D048Q/D130A/G163P/L264R, D048Q/D137Q/G163P/L227M, D048Q/G163P/N233Q/L264R, D111A/D130A/V154I/G156W, D111A/D130A/V154I/L264R, D111A/D130A/V187T/L264R, D130A/G163P/L227M/L264R, D130A/G163P/N233Q/L264R, E045F/A049V/G156W/V187T, E045F/L075Q/G156W/V187T, E056K/D130A/V187N/L264R, E056K/D130A/V187T/L264R, E056K/L075Q/V187N/L264R, F051T/D130A/I252Q/L264R, F051T/L075G/I252Q/L264R, F051T/L075Q/I252Q/L264R, G023K/D027Q/F051T/L075Q, G023K/D027S/L075Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/E056K/D130A/L264R, G023K/E056K/D130A/V187N, G023K/E056K/L075R/L264R, G023K/E056K/V187T/L264R, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187N/L264R, G023K/L075R/V187T/L264R, G023Q/A049V/L075Q/T189D, G023Q/A049V/L075Q/V077I, G023Q/A049V/V077I/G156W, G023Q/D027S/D111A/G156W, G023Q/E045F/A049V/T189D, G023Q/E045F/A049V/V187T, G023Q/E045F/L075Q/G156W, G023Q/E045F/L075Q/V187T, G023Q/F051T/I252Q/L264R, G023Q/G091Q/I252Q/L264R, G023Q/K024A/D130A/G156W, G023Q/K024A/L075R/G156W, G023Q/K024A/L075R/V154I, G023Q/K024A/V077I/G156W, G023Q/L075Q/D130A/L264R, G023Q/L075Q/G156W/V187N, G023Q/L075Q/G156W/V187T, G023Q/L075Q/V187T/L264R, G023Q/V154I/G156W/V187N, G091Q/V187T/I252Q/L264R, K024A/D130A/V154I/V187T, K024A/L075Q/D130A/G156W, K024A/L075Q/D130A/V154I, K024A/L075Q/V187T/T189Q, K024A/L075R/G156W/V187N, L075G/D130A/V187T/I252Q, L075G/G091Q/V187N/L264R, L075G/V187H/I252Q/L264R, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075Q/V187N/T189Q/L264R, L075R/D111A/V154I/G156W, L075R/D130A/V154I/L264R, L075R/D130A/V187T/L264R, N011K/D027N/E056K/S058M, N011K/D027N/S058M/P256T, N011K/D027Q/S058M/P256T, N011K/D027S/E056K/P256T, N011K/D027S/N233Q/P256T, N011K/D027S/S058M/N233Q, N011K/E056K/N233Q/P256T, N011K/E056K/S058M/P256T, N011K/G023K/L075Q/D111A, N011K/S058M/N233Q/P256T, N033D/E045F/N073R/T189A, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027Q/N233Q, Q004D/N011K/D027S/P256T, Q004D/N011K/E056K/S058M, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/A049V/L075Q/V187T/T189D, A018K/D027S/E045F/L075D/T189D, A018K/D027S/E045F/N073R/D137V, A018K/D027S/N033D/E045F/T189D, A018K/D027S/N033D/L075D/T189D, A018K/D027S/N033D/N073R/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/D130A/G156W/V187T/L264R, A018K/E045F/A049V/L075Q/G156W, A018K/E045F/A049V/L075Q/T189D, A018K/E045F/A049V/L075Q/V187T, A018K/E045F/N073R/L075D/T189D, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/

K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/D130A/V187N, A018K/K024A/N094R/G156W/V187T, A018K/L075Q/D111A/D130A/V187T, A018K/L075Q/G156W/V187T/T189D, A018K/L075Q/N094R/D130A/V187N, A018K/L075Q/N094R/G156W/V187N, A018K/L075Q/V077I/N094R/G156W, A018K/L075Q/V187T/T189Q/L264R, A018K/N033D/E045F/L075D/T189D, A018K/P029E/E045F/N073R/L075D, A018K/P029E/N033D/N073R/L075D, A018K/V077I/G156W/V187T/T189D, D027E/D048Q/D137Q/L227M/L264R, D027E/D048Q/G163P/N233Q/L264R, D027E/D048Q/L227M/N233Q/L264R, D027E/D048Q/S058M/G163P/N233Q, D027E/D130A/D137Q/G163P/L264R, D027E/D130A/G163P/L227M/L264R, D027E/D130A/G163P/N233Q/L264R, D027E/D137Q/G163P/L227M/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027N/E056K/S058M/N233Q/P256T, D027N/S058M/I090F/N233Q/P256T, D027Q/E056K/I090F/N233Q/P256T, D027Q/E056K/S058M/N233Q/P256T, D027Q/F051T/L075Q/D130A/L264R, D027S/E056K/D111A/V187N/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075Q/D111A/D130A/V187N, D027S/L075R/V154I/T189Q/L264R, D027S/N033D/E045F/N073R/L075D, D027S/N033D/N073R/L075D/T189D, D027S/P029E/E045F/N073R/L075D, D027S/P029E/E045F/N073R/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/G163P/L227M/N233Q/L264R, D130A/V154I/G156W/V187N/T189Q, E045F/A049V/L075Q/V187T/T189D, E056K/D130A/V187H/I252Q/L264R, E056K/L075G/V187N/I252Q/L264R, E056K/L075Q/G156W/T189Q/L264R, E056K/L075R/D130A/V187N/L264R, E056K/L075R/D130A/V187T/L264R, E056K/N094R/G156W/V187N/L264R, E056K/S058M/I090F/N233Q/P256T, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/L075R/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/L075G/I252Q/L264R, G023Q/D027S/V154I/V187N/L264R, G023Q/E045F/A049V/G156W/T189D, G023Q/E045F/A049V/L075Q/V077I, G023Q/E045F/A049V/V077I/T189D, G023Q/E045F/L075Q/G156W/T189D, G023Q/E045F/L075Q/V077I/V187T, G023Q/E056K/V187N/I252Q/L264R, G023Q/F051T/L075Q/G091Q/I252Q, G023Q/K024A/L075Q/D130A/G156W, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075G/D130A/V187T/I252Q/L264R, L075Q/D111A/D130A/V187T/T189Q, L075Q/D111A/V187N/T189Q/L264R, L075Q/D130A/V187T/T189Q/L264R, L075Q/N094R/D130A/G156W/V187T, L075Q/V077I/D130A/G156W/V187N, L075Q/V154I/V187N/T189Q/L264R, L075R/D111A/D130A/V187N/T189Q, L075R/D130A/V154I/T189Q/L264R, L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/I090F/P256T, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/E045F/L075D/T189D, P029E/N033D/K074S/L075D/T189D, P029E/N033D/N073R/L075D/T189D, Q004D/D027N/E056K/S058M/P256T, Q004D/D027N/I090F/N233Q/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, Q004D/N011K/I090F/N233Q/P256T, S058M/D130A/D137Q/G163P/L264R, S058M/D130A/G163P/L227M/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/A049V/L075Q/G156W/V187T/T189D, A018K/D027S/N033D/E045F/L075D/T189D, A018K/D027S/N033D/E045F/N073R/L075D, A018K/D027S/N033D/N073R/L075D/T189D, A018K/D027S/P029E/N033D/E045F/L075D, A018K/D027S/P029E/N033D/L075D/

T189D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D111A/L264R, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/G156W, A018K/G023Q/A049V/L075Q/V077I/V187T, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/D111A/V187N/T189Q/L264R, A018K/K024A/L075Q/N094R/V154I/G56W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/G156W/V187N, A018K/L075Q/D111A/V154I/T189Q/L264R, A018K/L075Q/D130A/V154I/T189Q/L264R, A018K/L075Q/D130A/V187N/T189Q/L264R, A018K/L075R/D130A/V154I/G156W/V187N, A018K/N033D/E045F/N073R/L075D/T189D, A018K/N094R/D111A/D130A/V154I/V187N, A018K/P029E/N033D/E045F/L075D/T189D, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/D130A/G163P/L264R, D027E/D048Q/S058M/D130A/L227M/N233Q, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/E056K/S058M/I090F/N233Q/P256T, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/G091Q/D130A/V187N/I252Q/L264R, D027S/L075Q/D111A/G156W/V187N/T189Q, D027S/L075Q/G091Q/V187H/I252Q/L264R, D027S/P029E/N033D/E045F/N073R/L075D, D027S/P029E/N033D/E045F/N073R/T189D, D027S/P029E/N033D/N073R/L075D/T189D, D048Q/D130A/G163P/L227M/N233Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/G163P/N233Q/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, D111A/D130A/V154I/G156W/V187N/L264R, E045F/A049V/L075Q/V077I/V187T/T189D, F051T/E056K/D130A/V187N/I252Q/L264R, F051T/E056K/L075Q/V187H/I252Q/L264R, F051T/L075G/G091Q/D130A/I252Q/L264R, F051T/L075G/G091Q/V187H/I252Q/L264R, F051T/L075G/G091Q/V187T/I252Q/L264R, F051T/L075R/D130A/V187N/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/D130A/V187N/I252Q/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075G/D130A/V187T/I252Q/L264R, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/F051T/L075Q/V187T/L264R, G023Q/D027S/L075G/D130A/V187H/L264R, G023Q/D027S/L075Q/D111A/G156W/L264R, G023Q/D027S/L075Q/D130A/V187T/I252Q, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/E056K/D111A/D130A/V187N/T189Q, G023Q/E056K/L075Q/D130A/V154I/L264R, G023Q/F051T/D130A/V187T/I252Q/L264R, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/G091Q/V187N/I252Q/L264R, G023Q/L075Q/N094R/D111A/G156W/L264R, G023Q/L075Q/V077I/N094R/D130A/V187Q, G023Q/L075R/V154I/G156W/V187N/L264R, K024A/D111A/D130A/V187T/T189Q/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/

L075Q/V154I/V187T/T189Q/L264R, K024A/L075R/D111A/V154I/G156W/V187N, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075Q/N094R/D111A/G156W/T189Q/L264R, L075R/D130A/V154I/G156W/V187N/L264R, N011K/D027N/E056K/I090F/N233Q/P256T, N011K/D027N/E056K/S058M/N233Q/P256T, N011K/D027N/S058M/I090F/N233Q/P256T, N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/I090F/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/D130A/V154I/G156W/V187T/L264R, A018K/K024A/L075Q/D111A/G156W/V187N/L264R, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/K024A/N094R/D130A/G156W/V187T/L264R, A018K/L075Q/D111A/D130A/V154I/G156W/L264R, A018K/L075Q/D111A/V154I/V187T/T189Q/L264R, A018K/L075Q/D130A/G156W/V187N/T189Q/L264R, A018K/L075Q/N094R/D111A/V154I/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027E/S058M/D130A/G163P/L227M/N233Q/L264R, D027E/S058M/D137Q/G163P/L227M/N233Q/L264R, D027Q/F051T/L075G/D130A/V187H/I252Q/L264R, D027Q/F051T/L075Q/D130A/V187T/I252Q/L264R, D027Q/F051T/L075Q/G091Q/D130A/V187T/I252Q, D027Q/F051T/S058M/L075Q/G091Q/I252Q/L264R, D027Q/L075G/G091Q/D130A/V187H/I252Q/L264R, D027S/E056K/L075R/D111A/G156W/V187N/L264R, D027S/F051T/L075G/G091Q/V187T/I252Q/L264R, D027S/F051T/S058M/L075Q/V187N/I252Q/L264R, D027S/F051T/S058M/L075R/D130A/I252Q/L264R, D027S/L075R/V154I/G156W/V187N/T189Q/L264R, D027S/P029E/N033D/E045F/N073R/L075D/T189D, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, E056K/L075Q/D111A/D130A/G156W/V187N/T189Q, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027Q/F051T/L075G/D130A/V187H/L264R, G023K/D027S/F051T/S058M/G091Q/V187N/I252Q, G023K/D027S/F051T/S058M/L075Q/D130A/V187N, G023K/D027S/L075Q/N094R/V154I/G156W/T189Q, G023K/F051T/E056K/L075R/D130A/V187T/I252Q, G023K/F051T/L075Q/G091Q/D130A/V187H/I252Q, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/N094R/V154I/G156W/V187N, G023K/K024A/L075Q/V077I/D130A/G156W/V187Q, G023K/K024A/N094R/V154I/G156W/V187N/T189Q, G023K/L075Q/D111A/D130A/V154I/G156W/L264R, G023K/L075Q/D111A/V154I/G156W/T189Q/L264R, G023K/L075Q/D130A/G156W/V187N/T189Q/L264R, G023K/L075Q/N094R/D130A/V154I/V187N/L264R, G023K/L075Q/N094R/V154I/G156W/V187T/L264R, G023K/L075R/N094R/V154I/G156W/V187N/L264R, G023Q/D027S/F051T/E056K/D130A/I252Q/L264R, G023Q/D027S/L075Q/G091Q/N187T/I252Q/L264R, G023Q/D027S/L075Q/V154I/G156W/V187N/L264R, G023Q/D027S/S058M/L075Q/D130A/I252Q/L264R, G023Q/E045F/A049V/V077I/G156W/V187T/T189D, G023Q/E045F/L075Q/V077I/G156W/V187T/T189D, G023Q/E056K/L075Q/D111A/G156W/V187N/L264R, G023Q/E056K/L075Q/D130A/V154I/G156W/T189Q, G023Q/E056K/L075R/D111A/D130A/V187N/T189Q, G023Q/F051T/E056K/L075R/G091Q/V187H/I252Q, G023Q/F051T/G091Q/D130A/V187H/I252Q/L264R, G023Q/F051T/L075Q/G091Q/V187H/I252Q/L264R, G023Q/F051T/L075R/G091Q/V187N/I252Q/L264R, G023Q/F051T/S058M/G091Q/D130A/I252Q/L264R, G023Q/K024A/L075Q/V077I/D130A/G156W/V187N, G023Q/K024A/L075Q/V077I/D130A/V154I/G156W, G023Q/L075G/G091Q/D130A/V187T/I252Q/L264R, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, G023Q/S058M/L075G/G091Q/D130A/I252Q/L264R, K024A/L075Q/D111A/D130A/V154I/G156W/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/

L264R, N011K/A018K/K024A/V077I/V154I/G156W/T189Q, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, N011K/G023Q/L075Q/V154I/V187N/T189Q/L264R, Q004D/D027N/E056K/S058M/I090F/N233Q/P256T, Q004D/N011K/D027N/S058M/I090F/N233Q/P256T, Q004D/N011K/D027Q/E056K/S058M/N233Q/P256T, Q004D/N011K/D027Q/S058M/I090F/N233Q/P256T, Q004D/N011K/D027S/E056K/S058M/N233Q/P256T, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/K024A/L075R/D111A/V154I/V187T/L264R, A018K/G023K/L075Q/V077I/D130A/V154I/G156W/V187N, A018K/G023K/L075R/V077I/N094R/D130A/G156W/V187Q, A018K/G023Q/E045F/L075Q/V077I/G156W/V187T/T189D, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, A018K/K024A/L075R/D130A/V154I/G156W/V187T/L264R, A018K/L075Q/N094R/D111A/V154I/G156W/T189Q/L264R, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/E056K/L075G/D130A/V187T/I252Q/L264R, G023K/D027S/F051T/E056K/L075Q/G091Q/V187H/I252Q, G023K/D027S/F051T/E056K/L075R/D130A/V187T/L264R, G023K/D027S/F051T/S058M/L075Q/V187H/I252Q/L264R, G023K/E056K/L075Q/D130A/V154I/V187N/T189Q/L264R, G023K/F051T/E056K/L075R/G091Q/D130A/V187T/L264R, G023K/K024A/L075Q/N094R/V154I/G156W/V187T/L264R, G023K/K024A/L075R/N094R/V154I/G156W/V187T/T189Q, G023K/L075Q/D111A/V154I/G156W/V187N/T189Q/L264R, G023K/L075Q/N094R/D130A/V154I/G156W/V187N/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/L075R/N094R/V154I/G156W/V187N/T189Q, G023Q/D027S/S058M/G091Q/D130A/V187H/I252Q/L264R, G023Q/E056K/L075Q/D111A/V154I/V187N/T189Q/L264R, G023Q/E056K/L075Q/N094R/D111A/G156W/T189Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/N094R/D130A/V154I/G156W/T189Q/L264R, G023Q/L075Q/V077I/N094R/D130A/V154I/G156W/V187Q, G023Q/S058M/L075R/G091Q/D130A/V187H/I252Q/L264R, K024A/D111A/D130A/V154I/G156W/V187T/T189Q/L264R, N011K/G023K/D027S/L075Q/D111A/D130A/V154I/T189Q, N011K/G023K/D027S/L075R/V154I/G156W/V187N/T189Q, N011K/G023K/E056K/L075Q/D130A/V154I/T189Q/L264R, N011K/G023K/L075Q/D111A/G156W/V187N/T189Q/L264R, N011K/G023Q/D027S/L075Q/N094R/V154I/G156W/T189Q, N011K/G023Q/D027S/N094R/V154I/G156W/T189Q/L264R, N011K/G023Q/L075Q/D111A/D130A/V154I/V187N/L264R, N011K/G023Q/L075Q/N094R/V154I/G156W/T189Q/L264R, A018K/G023K/K024A/L075Q/N094R/D111A/D130A/V154I/T189Q, A018K/G023K/K024A/L075Q/N094R/D130A/V154I/G156W/V187N, A018K/G023K/K024A/L075Q/N094R/D130A/V187T/T189Q/L264K, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, A018K/K024A/L075Q/N094R/V154I/G156W/V187N/T189Q/L264R, D027Q/F051T/S058M/L075G/G091Q/D130A/V187T/I252Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/F051T/E056K/L075G/G091Q/V187N/I252Q/L264R, G023Q/D027S/L075Q/N094R/D111A/D130A/V154I/G156W/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, G023Q/F051T/S058M/L075Q/G091Q/D130A/V187H/I252Q/L264R, N011K/G023K/D027S/E056K/L075R/D111A/G156W/V187N/L264R, N011K/G023K/L075R/D111A/D130A/V154I/V187N/T189Q/L264R, N011K/G023Q/L075Q/D111A/V154I/G156W/V187N/T189Q/L264R, N011K/G023K/L075R/V077I/D130A/V154I/G156W/V187T/T189Q, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/E045F/A049V/S058M/N073S/L075Q/V187T/T189D, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/S058M/L075Q/V077I/R108K/H135F/G156W/

V187H, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023K/K024A/L075R/V077I/D130A/V154I/V187T/T189Q, N011K/G023K/L075R/N094R/D111A/V154I/G156W/V187N/T189Q/L264R, N011K/G023Q/D027S/E056K/L075R/D130A/V154I/G156W/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D, A018K/G023Q/D027S/P029E/E045F/A049V/S058M/N073S/L075Q/R108K/H135F/V187T/T189D, or A018K/G023Q/D027S/P029E/N033D/E045F/A049V/S058M/N073S/K074S/L075Q/V077I/N101D/R108K/H135F/D137V/G156W/V187T/T189D, wherein the amino acid positions of the variant are numbered by correspondence with the amino acid sequence of *Thermomyces lanuginosa lipase* set forth in SEQ ID NO: 1. In some embodiments, the variant or active fragment has lipolytic activity, for example, a performance index (pI) relative to the parent lipolytic enzyme for hydrolysis of p-nitrophenyl butyrate, p-nitrophenyl caprylate, or p-nitrophenyl palmitate is greater than 1.0 at a pH of 6 or 8.

In any of the above embodiments, the invention provides variant lipolytic enzymes of the invention that exhibit one of more of the following properties: improved lipolytic activity, such as improved hydrolysis of p-nitrophenyl butyrate, p-nitrophenyl caprylate, or p-nitrophenyl palmitate, increased pNPP/pNPB or pNPO/pNPB specific activity ratio, increased pNPB/pNPP specific activity ratio, increased thermostability, increased detergent stability, increased LAS stability, increased fabric adhesion, decreased fabric adhesion, increased cleaning performance, improved hand wash performance, improved hand or manual dishwashing performance, improved automatic dishwashing performance, improved laundry performance, and/or improved stability relative to a parent lipolytic enzyme (e.g., wild-type lipolytic enzyme, such as a wild-type lipase) or reference enzyme (such as SEQ ID NO: 2).

These amino acid positions can be considered useful positions for combinatorial modifications to a parent lipolytic enzyme. Thus, the invention includes lipolytic enzymes having one or more modifications at any of the above positions.

Polypeptides of the Invention

The present invention provides novel polypeptides, which may be collectively referred to as "polypeptides of the invention." Polypeptides of the invention include isolated, recombinant, substantially pure, or non-naturally occurring variant lipolytic enzyme polypeptides, including for example, variant lipolytic enzyme polypeptides, having enzymatic activity (e.g., lipolytic activity). In some embodiments, polypeptides of the invention are useful in cleaning applications and can be incorporated into cleaning compositions that are useful in methods of cleaning an item or a surface (e.g., of surface of an item) in need of cleaning.

In some embodiments, the lipolytic enzyme variant can be a variant of a parent lipolytic enzyme from the Genus *Thermomyces*. Various lipolytic enzymes have been found in the genus *Thermomyces* that have a high identity to each other and to the lipolytic enzyme from *Thermomyces lanuginosa* (TLL) as shown in SEQ ID NO: 1. In other embodiments, the lipolytic enzyme variant can be a variant of a parent lipolytic enzyme such as *Verrucosispora, Saccharomonospora, Streptomyces, Micromonospora, Streptosporangium, Amycolatopsis, Cellulomonas, Actinosynnema, Kribbella, Thermomonospora, Deinococcus, Kineococcus, Nocardiopsis, Frankia, Jonesia, Pseudomonas, Acidovorax* or Nocardioidaceae.

The sequence of the lipolytic enzyme from *Thermomyces lanuginosa* (TLL) is shown below:

```
                                              (SEQ ID NO: 1)
EVSQDLFNQFNLFAQYSAAAYCGKNNDAPAGTNITCTGNACPEVEKADAT

FLYSFEDSGVGDVTGFLALDNTNKLIVLSFRGSRSIENWIGNLNFDLKEI

NDICSGCRGHDGFTSSWRSVADTLRQKVEDAVREHPDYRVVFTGHSLGGA

LATVAGADLRGNGYDIDVFSYGAPRVGNRAFAEFLTVQTGGTLYRITHTN

DIVPRLPPREFGYSHSSPEYWIKSGTLVPVTRNDIVKIEGIDATGGNNQP

NIPDIPAHLWYFGLIGTCL.
```

In some embodiments, the lipolytic enzyme variant can be a variant having 50, 60, 70, 75, 80, 85, 90, 95, 96, 97, 98, 99 or 100% identity to a lipolytic enzyme from the genus *Thermomyces*. In some embodiments, the lipolytic enzyme variant can be a variant having 50, 60, 70, 75, 80, 85, 90, 95, 96, 97, 98, 99 or 100% identity to a lipolytic enzyme from the species *Thermomyces lanuginosa*, the lipolytic enzyme having the sequence shown in SEQ ID NO: 1.

In a particular embodiment, the invention is an enzyme derived from the genus *Thermomyces*. In a particular embodiment, the invention is an enzyme derived from a lipolytic enzyme from the species *Thermomyces lanuginosa*, the lipolytic enzyme having the sequence shown in SEQ ID NO: 1.

Described are compositions and methods relating to lipase cloned from *Thermomyces lanuginosa* (TLL). The compositions and methods are based, in part, on the observation that cloned and expressed TLL has carboxylic ester hydrolase activity (acts on carboxylic acid esters) in the presence of a detergent compositions. TLL also demonstrates excellent stability in detergent compositions, even in the presence of protease enzyme. These features of TLL makes it well suited for use in a variety of cleaning applications, where the enzyme can hydrolyze lipids in the presence of surfactants and other components found in detergent compositions.

While TLL shows activity against a variety of natural and synthetic substrates, the enzyme has shown a preference for C4-C16 substrates. This specificity makes TLL well suited for hydrolysis of short-chain triglycerides and for performing transesterification reactions involving short-chain fatty acids.

In any of the above embodiments, the variant lipolytic enzyme of the invention can have improved lipolytic activity on C4-C16 substrates relative to the parent lipolytic enzyme. In some embodiments, variants of the invention have an increased pNPP/pNPB or pNPO/pNPB specific activity ratio. In some embodiments, variants of the invention have an increased pNPB/pNPP specific activity ratio. In any of the above embodiments, the variant lipolytic enzyme of the invention can have a performance index (pI) relative to a parent lipolytic enzyme (e.g. SEQ ID NO:1) for hydrolysis of p-nitrophenyl butyrate, p-nitrophenyl caprylate, or p-nitrophenyl palmitate is greater than 1.0. This can be measured at pH 6 or 8. In any of the above embodiments, the variant lipolytic enzyme of the invention can have a performance index (pI) relative to a parent lipolytic enzyme (e.g. SEQ ID NO:1) for detergent stability that is greater than 1.0. In any of the above embodiments, the variant lipolytic enzyme of the invention can have a performance index (pI) relative to a parent lipolytic enzyme (e.g. SEQ ID NO:1) for LAS stability that is greater than 1.0. In any of the above embodiments, the variant lipolytic enzyme of the invention can have a performance index (pI) relative to a parent lipolytic enzyme (e.g. SEQ ID NO:1) for fabric adhesion that is greater than 1.0. In any of the above embodiments, the variant lipolytic enzyme of the invention can have a performance index (pI) relative to a parent lipolytic enzyme (e.g. SEQ ID NO:1) for fabric adhesion that is less than 1.0. In any of the above embodiments, the variant lipolytic enzyme of the invention can have a performance index (pI) relative to a parent lipolytic enzyme (e.g. SEQ ID NO: 1) for cleaning performance that is greater than 1.0. This can be measured using a CS-61 microswatch assay using Tide® half dose+adjuvant or Tide® full dose. In any of the above embodiments, the variant lipolytic enzyme of the invention can have a performance index (pI) relative to a reference lipolytic enzyme (e.g. SEQ ID NO: 2) that is greater than 1.0 for hydrolysis of p-nitrophenyl butyrate, p-nitrophenyl caprylate, or p-nitrophenyl palmitate, detergent stability, LAS stability, fabric adhesion, or cleaning performance. In any of the above embodiments, the variant lipolytic enzyme of the invention can have a performance index (pI) relative to a reference lipolytic enzyme (e.g. SEQ ID NO: 2) that is less than 1.0 for fabric adhesion.

The sequence of the reference lipolytic enzyme, which is a variant from *Thermomyces lanuginosa* (TLL) is shown below:

```
                                        (SEQ ID NO: 2)
EVSQDLFNQFNLFAQYSAAAYCGKNNDAPAGTNITCTGNACPEVEKADAT

FLYSFEDSGVGDVTGFLALDNTNKLIVLSFRGSRSIENWIGNLNFDLKEI

NDICSGCRGHDGFTSSWRSVADTLRQKVEDAVREHPDYRVVFTGHSLGGA

LATVAGADLRGNGYDIDVFSYGAPRVGNRAFAEFLTVQTGGTLYRITHTN

DIVPRLPPREFGYSHSSPEYWIKSGTLVPVRRRDIVKIEGIDATGGNNQP

NIPDIPAHLWYFGLIGTCL.
```

In several of the above embodiments, the present compositions and methods provide a variant TLL polypeptide. The parent TLL polypeptide *Thermomyces lanuginosa lipase* was described in WO1994025577. The mature TLL polypeptide has the amino acid sequence of SEQ ID NO: 1. Similar, substantially identical TLL polypeptides may occur in nature, e.g., in other strains or isolates of *T. lanuginosa*. These and other recombinant TLL polypeptides are encompassed by the present compositions and methods.

In any of the above embodiments, the invention includes an isolated, recombinant, substantially pure, or non-naturally occurring variant lipolytic enzyme having lipolytic activity, which polypeptide comprises a polypeptide sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to a parent lipolytic enzyme as provided herein.

In some embodiments, the variant polypeptide is a variant having a specified degree of amino acid sequence homology to the exemplified TLL polypeptide, e.g., at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO: 1. Homology can be determined by amino acid sequence alignment, e.g., using a program such as BLAST, ALIGN, or CLUSTAL, as described herein.

Also provided is an isolated, recombinant, substantially pure, or non-naturally occurring sequence which encodes a variant lipolytic enzyme having lipolytic activity, said variant lipolytic enzyme (e.g., variant lipase) comprising an amino acid sequence which differs from the amino acid sequence of SEQ ID NO: 1 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, or no more than 2 amino acid residue(s), wherein amino acid positions of the variant lipase are numbered according to the numbering of corresponding amino acid positions in the amino acid sequence of *Thermomyces lanuginosa lipase* TLL shown in SEQ ID NO: 1 as determined by alignment of the variant lipolytic enzyme amino acid sequence with the *Thermomyces lanuginosa lipase* TLL amino acid sequence.

In some embodiments, the present invention relates to isolated polypeptides having lipase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with the mature polypeptide coding sequence of SEQ ID NO: 1, or a full-length complementary strand thereof (J. Sambrook, E. F. Fritsch, and T. Maniatis, 1989, Molecular Cloning, A Laboratory Manual, 2d edition, Cold Spring Harbor, New York).

As noted above, the variant lipolytic enzyme polypeptides of the invention have enzymatic activities (e.g., lipolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant lipolytic enzyme polypeptides of the invention are described infra. The enzymatic activity (e.g., lipolytic enzyme activity) of a variant lipolytic enzyme polypeptide of the invention can be determined readily using procedures well known to those of ordinary skill in the art. The performance of variant lipolytic enzymes of the invention in removing stains (e.g., a lipid stain), cleaning hard surfaces, or cleaning laundry, dishware or tableware item(s) can be readily determined using procedures well known in the art.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded variant lipolytic enzyme compared to the variant lipolytic enzyme encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

In some embodiments, the present invention provides a genus of polypeptides comprising variant lipolytic enzyme polypeptides having the desired enzymatic activity (e.g., lipolytic enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., lipolytic enzyme activity or lipase activity, as reflected in the cleaning activity or performance of the variant lipolytic enzyme). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, in some embodiments, the invention provides an isolated or recombinant variant lipolytic enzyme polypeptide (e.g., variant lipase) having lipolytic activity, said variant lipolytic enzyme polypeptide comprising an amino acid sequence having at least about 90%, about 95%, about 96%, about 97%, about 98%, about 99%, or about 99.5% sequence identity to the amino acid sequence of SEQ ID NO: 1. A conservative substitution of one amino acid for another in a variant lipolytic enzyme of the invention is not expected to alter significantly the enzymatic activity or cleaning performance activity of the variant lipolytic enzyme. Enzymatic activity or cleaning performance activity of the resultant lipolytic enzyme can be readily determined using the standard assays and the assays described herein.

Conservatively substituted variations of a polypeptide sequence of the invention (e.g., variant lipolytic enzymes of the invention) include substitutions of a small percentage, sometimes less than about 25%, about 20%, about 15%, about 14%, about 13%, about 12%, about 11%, about 10%, about 9%, about 8%, about 7%, or about 6% of the amino acids of the polypeptide sequence, or less than about 5%, about 4%, about 3%, about 2%, or about 1%, of the amino acids of the polypeptide sequence, with a conservatively selected amino acid of the same conservative substitution group.

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include variant lipolytic enzyme polypeptides, including variant lipase polypeptides having enzymatic activity (e.g., lipolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. The synthesis of the nucleic acids of the invention can be also facilitated (or alternatively accomplished) by any suitable method known in the art, including but not limited to chemical synthesis using the classical phosphoramidite method (See e.g., Beaucage et al. Tetrahedron Letters 22:1859-69 (1981)); or the method described by Matthes et al. (See, Matthes et al., EMBO J. 3:801-805 (1984), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 (1984); and Itakura et al., Science 198:1056 (1984)).

Methods for Making Modified Variant Lipolytic Enzymes of the Invention

A variety of methods are known in the art that are suitable for generating modified polynucleotides of the invention that encode variant lipolytic enzymes of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., variant lipolytic enzymes) include DNA shuffling methodologies, methods based on non-homologous recombination of genes, such as ITCHY (See, Ostermeier et al., 7:2139-44 (1999)), SCRACHY (See, Lutz et al. 98:11248-53 (2001)), SHIPREC (See, Sieber et al., 19:456-60 (2001)), and NRR (See, Bittker et al., 20:1024-9 (2001); Bittker et al., 101:7011-6 (2004)), and methods that rely on the use of oligonucleotides to insert random and targeted mutations, deletions and/or insertions (See, Ness et al., 20:1251-5 (2002); Coco et al., 20:1246-50 (2002); Zha et al., 4:34-9 (2003); Glaser et al., 149:3903-13 (1992)).

Vectors, Cells, and Methods for Producing Variant Lipolytic Enzymes of the Invention The present invention provides isolated or recombinant vectors comprising at least one polynucleotide of the invention described herein (e.g., a polynucleotide encoding a variant lipolytic enzyme of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to *bacillus* cells, such as *B. subtilis* cells. Some such cells comprise fungal cells, including, but are not limited to *Trichoderma* cells, such as *T. reesei* cells. The invention also provides recombinant cells (e.g., recombinant host cells) comprising at least one variant lipolytic enzyme of the invention.

In some embodiments, the invention provides a vector comprising a nucleic acid or polynucleotide of the invention. In some embodiments, the vector is an expression vector or expression cassette in which a polynucleotide sequence of the invention which encodes a variant lipolytic enzyme of the invention is operably linked to one or additional nucleic acid segments required for efficient gene expression (e.g., a promoter operably linked to the polynucleotide of the invention which encodes a variant lipolytic enzyme of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pXX, pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92; See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624).

For expression and production of a protein of interest (e.g., variant lipolytic enzyme) in a cell, at least one expression vector comprising at least one copy of a polynucleotide encoding the modified lipolytic enzyme, and preferably comprising multiple copies, is transformed into the cell under conditions suitable for expression of the lipolytic enzyme. In some embodiments of the present invention, a polynucleotide sequence encoding the variant lipolytic enzyme (as well as other sequences included in the vector) is integrated into the genome of the host cell, while in other embodiments, a plasmid vector comprising a polynucleotide sequence encoding the variant lipolytic enzyme remains as autonomous extra-chromosomal element within the cell. The invention provides both extrachromosomal nucleic acid elements as well as incoming nucleotide sequences that are integrated into the host cell genome. The vectors described herein are useful for production of the variant lipolytic enzymes of the invention. In some embodiments, a polynucleotide construct encoding the variant lipolytic enzyme is present on an integrating vector that enables the integration and optionally the amplification of the polynucleotide encoding the variant lipolytic enzyme into the bacterial chromosome. Examples of sites for integration are well known to those skilled in the art. In some embodiments, transcription of a polynucleotide encoding a variant lipolytic enzyme of the invention is effectuated by a promoter that is the wild-type promoter for the selected precursor lipolytic enzyme. In some other embodiments, the promoter is heterologous to the precursor lipolytic enzyme, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *T. lanuginosa* (BAN) amylase gene, the *B. subtilis* alkaline lipolytic enzyme gene, the *B. clausii* alkaline lipolytic enzyme gene the *B. pumilis* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

Variant lipolytic enzymes of the present invention can be produced in host cells of any suitable Gram-positive microorganism, including bacteria and fungi. For example, in some embodiments, the variant lipolytic enzyme is produced in host cells of fungal and/or bacterial origin. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the variant lipolytic enzymes are produced by *Bacillus* sp. host cells. Examples of *Bacillus* sp. host cells that find use in the production of the variant lipolytic enzymes of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells are used for production of variant lipolytic enzymes. U.S. Pat. Nos. 5,264,366 and 4,760,025 (RE 34,606) describe various *Bacillus* host strains that can be used for producing variant lipolytic enzymes of the invention, although other suitable strains can be used.

Several industrial bacterial strains that can be used to produce variant lipolytic enzymes of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol. 172:824-834 [1990]; and Olmos et al., Mol. Gen. Genet. 253:562-567 [1997]). One suitable host strain is a *Bacillus subtilis* carrying a degU32(Hy) mutation. In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a variant lipolytic enzyme of the invention is a *Bacillus* host strain that already includes a mutation in one or more of the above-mentioned genes. In addition, *Bacillus* sp. host cells that comprise mutation(s) and/or deletions of endogenous lipolytic enzyme genes find use. In some embodiments, the *Bacillus* host cell comprises a deletion of the aprE and the nprE genes. In other embodiments, the *Bacillus* sp. host cell comprises a deletion of 5 lipolytic enzyme genes, while in other embodiments, the *Bacillus* sp. host cell comprises a deletion of 9 lipolytic enzyme genes (See e.g., U.S. Pat. Appln. Pub. No. 2005/0202535, incorporated herein by reference).

Host cells are transformed with at least one nucleic acid encoding at least one variant lipolytic enzyme of the invention using any suitable method known in the art. Whether the nucleic acid is incorporated into a vector or is used without the presence of plasmid DNA, it is typically introduced into a microorganism, in some embodiments, preferably an *E. coli* cell or a competent *Bacillus* cell. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid or polynucleotide sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and congression, transduction, and protoplast fusion are well known and suited for use in the present invention. Methods of transformation are used to introduce a DNA construct or vector comprising a nucleic acid encoding a variant lipolytic enzyme of the present invention into a host cell. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J.

Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a variant lipolytic enzyme of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one variant lipolytic enzyme or at least one nucleic acid of the invention. Also provided are compositions comprising at least one nucleic acid, vector, or DNA construct of the invention.

In some embodiments, host cells transformed with at least one polynucleotide sequence encoding at least one variant lipolytic enzyme of the invention are cultured in a suitable nutrient medium under conditions permitting the expression of the present lipolytic enzyme, after which the resulting lipolytic enzyme is recovered from the culture. The medium used to culture the cells comprises any conventional medium suitable for growing the host cells, such as minimal or complex media containing appropriate supplements. Suitable media are available from commercial suppliers or may be prepared according to published recipes (See e.g., the catalogues of the American Type Culture Collection). In some embodiments, the lipolytic enzyme produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a variant lipolytic enzyme finds use in the present invention.

In some embodiments, a variant lipolytic enzyme produced by a recombinant host cell is secreted into the culture medium. A nucleic acid sequence that encodes a purification facilitating domain may be used to facilitate purification of soluble proteins. A vector or DNA construct comprising a polynucleotide sequence encoding a variant lipolytic enzyme may further comprise a nucleic acid sequence encoding a purification facilitating domain to facilitate purification of the variant lipolytic enzyme (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system (e.g., protein A domains available from Immunex Corp., Seattle, Wash.). The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a variant lipolytic enzyme of the invention, are well known. Various assays for detecting and measuring activity of lipolytic enzymes (e.g., variant lipolytic enzymes of the invention), are also known to those of ordinary skill in the art. As used herein, lipolytic activity may be determined according to any procedure known in the art. For example, assays such as gel-diffusion assays of lipolysis of triacylglycerol, titrimetry using a pH-stat method to measure release of fatty acids, release of p-nitrophenol from p-Nitrophenyl esters using spectrophotometry, and ELISA assays can be used to determine lipase activity and/or specificity (See, e.g. Gupta et al., Biotechnol. Appl. Biochem, 37: 63-71, 2003). Other assays can be found, for example in U.S. Pat. No. 5,990,069; and International Publication No. WO96/18729A1.

A variety of methods can be used to determine the level of production of a mature lipolytic enzyme (e.g., mature variant lipolytic enzymes of the present invention) in a host cell. Such methods include, but are not limited to, for example, methods that utilize either polyclonal or monoclonal antibodies specific for the lipolytic enzyme. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature variant lipolytic enzyme of the invention. A mature variant lipolytic enzyme does not include a signal peptide or a propeptide sequence. Some methods comprise making or producing a variant lipolytic enzyme of the invention in a recombinant bacterial host cell, such as for example, a *Bacillus* sp. cell (e.g., a *B. subtilis* cell). In some embodiments, the invention provides a method of producing a variant lipolytic enzyme of the invention, the method comprising cultivating a recombinant host cell comprising a recombinant expression vector comprising a nucleic acid encoding a variant lipolytic enzyme of the invention under conditions conducive to the production of the variant lipolytic enzyme. Some such methods further comprise recovering the variant lipolytic enzyme from the culture.

In some embodiments the invention provides methods of producing a variant lipolytic enzyme of the invention, the methods comprising: (a) introducing a recombinant expression vector comprising a nucleic acid encoding a variant lipolytic enzyme of the invention into a population of cells (e.g., bacterial cells, such as *B. subtilis* cells); and (b) culturing the cells in a culture medium under conditions conducive to produce the variant lipolytic enzyme encoded by the expression vector. Some such methods further comprise: (c) isolating the variant lipolytic enzyme from the cells or from the culture medium.

Fabric and Home Care Products

In some embodiments, the lipolytic enzyme variants of the present invention can be used in compositions comprising an adjunct material and a lipolytic enzyme variant, wherein the composition is a fabric and home care product. Examples of suitable compositions are described in Example 1.

In some embodiments, the fabric and home care product compositions comprising at least one lipolytic enzyme variant comprise one or more of the following ingredients (based on total composition weight): from about 0.0005 wt % to about 0.5 wt %, from about 0.001 wt % to about 0.1 wt %, or even from about 0.002 wt % to about 0.05 wt % of said lipolytic enzyme variant; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % bacterial cleaning cellulases; and/or from about 0.05 wt % to about 20 wt % Guerbet nonionic surfactants.

As used herein, "wash performance" of a lipolytic enzyme (e.g., a variant lipolytic enzyme of the invention) refers to the contribution of the lipolytic enzyme to washing that provides additional cleaning performance to the detergent as compared to the detergent without the addition of the variant lipolytic enzyme to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

In some embodiments, the fabric and home care product composition is a granular or powder laundry detergent.

In some embodiments, the fabric and home care product composition is a liquid laundry detergent or a dish washing detergent.

It is intended that the fabric and home care product is provided in any suitable form, including a fluid or solid. The fabric and home care product can be in the form of a unit dose pouch, especially when in the form of a liquid, and typically the fabric and home care product is at least partially, or even completely, enclosed by a water-soluble pouch. In addition, in some embodiments of the fabric and home care products comprising at least one lipolytic enzyme variant, the fabric and home care product may have any combination of parameters and/or characteristics detailed above.

Cleaning Compositions

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning composition or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one variant lipolytic enzyme of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant lipolytic enzymes of the present invention in the cleaning compositions, then suitable methods of keeping the cleaning adjunct materials and the lipolytic enzyme(s) separated (i.e., not in contact with each other) until combination of the two components is appropriate are used. Such separation methods include any suitable method known in the art (e.g., gelcaps, encapsulation, tablets, physical separation, etc.).

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant lipolytic enzymes of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more lipolytic enzymes. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the lipolytic enzyme variants provided herein, alone or in combination with other lipolytic enzymes and/or additional enzymes. The required level of enzyme is achieved by the addition of one or more lipolytic enzyme variants of the present invention. Typically the present cleaning compositions comprise at least about 0.0001 weight percent, from about 0.0001 to about 10, from about 0.001 to about 1, or even from about 0.01 to about 0.1 weight percent of at least one of the variant lipolytic enzymes of the present invention.

The cleaning compositions herein are typically formulated such that, during use in aqueous cleaning operations, the wash water will have a pH of from about 5.0 to about 11.5, or about 6.0 to 8.0 or even from about 7.5 to about 10.5. Liquid product formulations are typically formulated to have a neat pH from about 3.0 to about 9.0 or even from about 3 to about 8. Granular laundry products are typically formulated to have a pH from about 6 to about 11, or even from about 8 to about 10. Techniques for controlling pH at recommended usage levels include the use of buffers, alkalis, acids, etc., and are well known to those skilled in the art.

Suitable "low pH cleaning compositions" typically have a neat pH of from about 3 to about 8, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 8. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant lipolytic enzyme(s) is/are employed in a granular composition or liquid, it is desirable for the variant lipolytic enzyme to be in the form of an encapsulated particle to protect the variant lipolytic enzyme from other components of the granular composition during storage. In addition, encapsulation is also a means of controlling the availability of the variant lipolytic enzyme during the cleaning process. In some embodiments, encapsulation enhances the performance of the variant lipolytic enzyme(s) and/or additional enzymes. In this regard, the variant lipolytic enzymes of the present invention are encapsulated with any suitable encapsulating material known in the art. In some embodiments, the encapsulating material typically encapsulates at least part of the catalyst for the variant lipolytic enzyme(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant lipolytic enzymes of the present invention find particular use in the cleaning industry, including, but not limited to laundry and dish detergents. These applications place enzymes under various environmental stresses. The variant lipolytic enzymes of the present invention provide advantages over many currently used enzymes, due to their stability under various conditions.

Indeed, there are a variety of wash conditions including varying detergent formulations, wash water volumes, wash water temperatures, and lengths of wash time, to which lipolytic enzymes involved in washing are exposed. In addition, detergent formulations used in different geographical areas have different concentrations of their relevant components present in the wash water. For example, European detergents typically have about 2000-9000 ppm of detergent components in the wash water, while Japanese detergents typically have approximately 500-1500 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm #divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant lipolytic enzymes that show surprising wash performance in at least one set of wash conditions (e.g., water temperature, water hardness, and/or detergent concentration). In some embodiments, the variant lipolytic enzymes of the present invention are comparable in wash performance to other lipase lipolytic enzymes. In some embodiments, the variant lipolytic enzymes of the present invention exhibit enhanced wash performance as compared to lipase lipolytic enzymes currently commercially available. Thus, in some embodiments of the present invention, the variant lipolytic enzymes provided herein exhibit enhanced oxidative stability, enhanced thermostability, enhanced cleaning capabilities under various conditions, and/or enhanced chelator stability. In addition, the variant lipolytic enzymes of the present invention find use in cleaning compositions that do not include detergents, again either alone or in combination with builders and stabilizers.

In some embodiments of the present invention, the cleaning compositions comprise at least one variant lipolytic enzyme of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one variant lipolytic enzyme at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise a lipolytic enzyme variant as described above as the major enzymatic component, such as in a mono-component composition. In some embodiments, the cleaning compositions of the present invention comprise one or more additional detergent enzymes, which provide cleaning performance and/or fabric care and/or dishwashing benefits. Examples of suitable enzymes include, but are not limited to, proteases, perhydrolases, hemicellulases, cellulases, peroxidases, lipolytic enzymes, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combinations or mixtures thereof. In some embodiments, a combination of enzymes is used (i. e., a "cocktail") comprising conventional applicable enzymes like lipolytic enzyme, lipase, cutinase and/or cellulase in conjunction with amylase is used.

For example, a lipolytic enzyme variant of the invention can be combined with a protease. Suitable proteolytic enzymes include those of animal, vegetable or microbial origin. In some embodiments, microbial proteolytic enzymes are used. In some embodiments, the proteolytic enzyme is preferably an alkaline microbial proteolytic enzyme or a trypsin-like proteolytic enzyme. Examples of alkaline lipolytic enzymes include lipases, especially those derived from *Bacillus* (e.g., *lentus, amyloliquefaciens*, Carlsberg, 309, 147 and 168). Additional examples include those mutant proteolytic enzymes described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease enzyme described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (Genencor); ALCALASE®, SAVINASE®, PRIMASE®, DURAZYM™ POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* lipase; Kao Corp., Tokyo, Japan). Various proteolytic enzymes are described in WO95/23221, WO 92/21760, U.S. Pat. Publ. No. 2008/0090747, and U.S. Pat. Nos. 5,801,039, 5,340,735, 5,500,364, 5,855,625, US RE 34,606, 5,955,340, 5,700,676, 6,312,936, and 6,482,628, and various other patents. In some further embodiments, metalloprotease enzymes find use in the present invention, including but not limited to the neutral metalloprotease enzyme described in WO 07/044993.

In some embodiments of the present invention, the cleaning compositions of the present invention further comprise proteases at a level from about 0.00001% to about 10% of protease by weight of the composition and the balance of cleaning adjunct materials by weight of composition. In some other embodiments of the present invention, the cleaning compositions of the present invention also comprise proteases at a level of about 0.0001% to about 10%, about 0.001% to about 5%, about 0.001% to about 2%, about 0.005% to about 0.5% protease by weight of the composition.

In some embodiments, a lipolytic enzyme variant of the invention can be combined with an amylase. In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874, 276). In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some embodiments, mixtures of the above mentioned enzymes are encompassed herein, in particular one or more additional lipolytic enzyme, amylase, protease, mannanase, and/or at least one cellulase. Indeed, it is contemplated that various mixtures of these enzymes will find use in the present invention. It is also contemplated that the varying levels of the variant lipolytic enzyme(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant lipolytic enzymes of the present invention in the cleaning compositions, then suitable methods of keeping the cleaning adjunct materials and the lipolytic enzyme(s) separated (i.e., not in contact with each other) until combination of the two components is appropriate are used. Such separation methods include any suitable method known in the art (e.g., gelcaps, encapsulation, tablets, physical separation, etc.).

In some embodiments, an effective amount of one or more variant lipolytic enzyme(s) provided herein is included in compositions useful for cleaning a variety of surfaces in need of lipid stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant lipolytic enzymes of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant lipolytic enzymes of the present invention. Thus, in some embodiments, the compositions comprising at least one variant lipolytic enzyme of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant lipolytic enzyme of the present invention are fabric cleaning compositions such as those described in U.S. Pat. Nos. 6,610,642 and 6,376,450. In addition, the variant lipolytic enzymes of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant lipolytic enzyme provided herein. Thus, in some embodiments, the compositions comprising at least one variant lipolytic enzyme of the present invention is a hard surface cleaning composition such as those described in U.S. Pat. Nos. 6,610,642, 6,376,450, and 6,376,450.

In yet further embodiments, the present invention provides dishwashing compositions comprising at least one variant lipolytic enzyme provided herein. Thus, in some embodiments, the compositions comprising at least one variant lipolytic enzyme of the present invention is a hard surface cleaning composition such as those in U.S. Pat. Nos. 6,610,642 and 6,376,450. In some still further embodiments, the present invention provides dishwashing compositions comprising at least one variant lipolytic enzyme provided herein. In some further embodiments, the compositions comprising at least one variant lipolytic enzyme of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the variant lipolytic enzymes provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant lipolytic enzymes of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, the cleaning compositions of the present invention contain at least one chelating agent. Suitable chelating agents include, but are not limited to, copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949).

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible lipolytic enzyme inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, item, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Compositions for Cleaning

An aspect of the present compositions and methods is a cleaning composition that includes a lipolytic enzyme as a component. An lipolytic enzyme polypeptide can be used as a component in detergent compositions for hand washing, laundry washing, dishwashing, and other hard-surface cleaning.

In certain embodiments, a lipolytic enzyme is incorporated into detergents at or near a concentration conventionally used for lipolytic enzyme in detergents. For example, a lipolytic enzyme polypeptide may be added in amount corresponding to 0.00001-1 mg (calculated as pure enzyme protein) of lipolytic enzyme per liter of wash/dishwash liquor. Exemplary formulations are provided herein, as exemplified by the following:

A lipolytic enzyme polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically lipolytic enzymes, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present α-lipolytic enzyme are described, below. Many of these compositions can be provided in unit dose format for ease of use. Unit dose formulations and packaging are described in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1.

Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixures thereof) and polymeric carboxylate (such as maleate/acrylate random copolymer or polyacrylate homopolymer).

The composition may further include saturated or unsaturated fatty acid, e.g., saturated or unsaturated $C_{12}$-$C_{24}$ fatty acid (0 wt % to 10 wt %); deposition aids (examples for which include polysaccharides, e.g., cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further include enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally includes silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition can include enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

Automatic Dishwashing (ADW) Detergent Composition

Exemplary ADW detergent composition includes non-ionic surfactants, including ethoxylated non-ionic surfactants, alcohol alkoxylated surfactants, epoxy-capped poly (oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

Additional Detergent Compositions

Additional exemplary detergent formulations to which the present lipolytic enzyme can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6HsNa_3O_7$/$C_6HsO_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7$/$C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6HsNa_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$s alcohol, 7 EO, or $C_{12}$-1s alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," *Nature* 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present lipolytic enzyme polypeptide may be incorporated at a concentration conventionally employed in detergents. It is at present contemplated that, in the detergent composition, the enzyme may be added in an amount corresponding to 0.00001-1.0 mg (calculated as pure enzyme protein) of lipolytic enzyme polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases: Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, KANNASE™, and BLAZE™ (Novo Nordisk A/S and Novozymes A/S); MAXATASE®, MAXACAL™, MAXAPEM™, PROPERASE®, PURAFECT®, PURAFECT OXP™, FN2™, and FN3™ (Danisco US Inc.). Other exemplary proteases include NprE from *Bacillus* amyloliquifaciens and ASP from Cellulomonas sp. strain 69B4.

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta,* 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S and Novozymes A/S).

Polyesterases: Suitable polyesterases can be included in the composition, such as those described in, for example, WO 01/34899, WO 01/14629, and U.S. Pat. No. 6,933,140.

Amylases: The compositions can be combined with other amylases, such as non-production enhanced amylase. These can include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, and PURASTAR® (from Danisco US Inc.).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (Danisco US Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Representative detergent formulations that beneficially include a lipolytic enzyme polypeptide of the present invention include the detergent formulations found in WO2013063460, pages 78-152, and in particular the tables of pages 94 to 152 are hereby incorporated by reference. The lipolytic enzymes are normally incorporated into the detergent composition at a level of from 0.00001% to 10% of enzyme protein by weight of the composition. In some embodiments, the detergent composition comprises more than 0.0001%, 0.001%, 0.01%, or 0.1% of the lipolytic enzyme by weight of the composition. In some embodiments, the detergent composition comprises less than 1%, 0.1%, 0.01%, or 0.001% of the lipolytic enzyme by weight of the composition.

Methods of Assessing Lipolytic Enzyme Activity in Detergent Compositions

Numerous lipolytic cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

Processes of Making and Using Cleaning Compositions

The cleaning compositions of the present invention are formulated into any suitable form and prepared by any suitable process chosen by the formulator, (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various formats for unit doses are provided in EP 2 100 947, and are known in the art.

Methods of Use

In some embodiments, the cleaning compositions of the present invention find use in cleaning surfaces (e.g., dishware), laundry, hard surfaces, contact lenses, etc. In some embodiments, at least a portion of the surface is contacted with at least one embodiment of the cleaning compositions of the present invention, in neat form or diluted in a wash liquor, and then the surface is optionally washed and/or rinsed. For purposes of the present invention, "washing" includes, but is not limited to, scrubbing, and mechanical washing. In some embodiments, the cleaning compositions of the present invention are used at concentrations of from about 500 ppm to about 15,000 ppm in solution. In some embodiments in which the wash solvent is water, the water temperature typically ranges from about 5° C. to about 90° C.

The present invention provides methods for cleaning or washing an item or surface (e.g., hard surface) in need of cleaning, including, but not limited to methods for cleaning or washing a dishware item, a tableware item, a fabric item, a laundry item, personal care item, etc., or the like, and methods for cleaning or washing a hard or soft surface (e.g., a hard surface of an item).

In some embodiments, the present invention provides a method for cleaning an item, object, or surface in need of cleaning, the method comprising contacting the item or surface (or a portion of the item or surface desired to be cleaned) with at least one variant lipase lipolytic enzyme of the present invention or a composition of the present invention for a sufficient time and/or under conditions suitable and/or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. As used herein, a "dishware item" is an item generally used in serving or eating food. A dishware item can be, but is not limited to for example, a dish, plate, cup, bowl, etc., and the like. As used herein, "tableware" is a broader term that includes, but is not limited to for example, dishes, cutlery, knives, forks, spoons, chopsticks, glassware, pitchers, sauce boats, drinking vessels, serving items, etc. It is intended that "tableware item" includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition (e.g., a power laundry detergent composition or a liquid laundry detergent composition), and the item to be cleaned is a fabric item. In some other embodiments, the cleaning composition is a laundry pre-treatment composition.

In some embodiments, the present invention provides methods for cleaning or washing a fabric item optionally in need of cleaning or washing, respectively. In some embodiments, the methods comprise providing a composition comprising the variant lipolytic enzyme, including but not limited to fabric or laundry cleaning composition, and a fabric item or laundry item in need of cleaning, and contacting the fabric item or laundry item (or a portion of the item desired to be cleaned) with the composition under conditions sufficient or effective to clean or wash the fabric or laundry item to a desired degree.

In some embodiments, the present invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one lipase variant of the invention or a composition of the invention comprising at least one such lipase variant for a sufficient time and/or under conditions sufficient or effective to clean or wash the item or surface to a desired degree. Such compositions include, but are not limited to for example, a cleaning composition or detergent composition of the invention (e.g., a hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some embodiments, the method is repeated one or more times, particularly if additional cleaning or washing is desired. For example, in some instance, the method optionally further comprises allowing the item or surface to remain in contact with the at least one variant lipolytic enzyme or composition for a period of time sufficient or effective to clean or wash the item or surface to the desired degree. In some embodiments, the methods further comprise rinsing the item or surface with water and/or another liquid. In some embodiments, the methods further comprise contacting the item or surface with at least one variant lipolytic enzyme of the invention or a composition of the invention again and allowing the item or surface to remain in contact with the at least one variant lipolytic enzyme or composition for a period of time sufficient to clean or wash the item or surface to the desired degree. In some embodiments, the cleaning composition is a dishwashing detergent composition and the item to be cleaned is a dishware or tableware item. In some embodiments of the present methods, the cleaning composition is an automatic dishwashing detergent composition or a hand dishwashing detergent composition and the item to be cleaned is a dishware or tableware item. In some embodiments of the methods, the cleaning composition is a laundry detergent composition and the item to be cleaned is a fabric item.

The present invention also provides methods of cleaning a tableware or dishware item in an automatic dishwashing machine, the method comprising providing an automatic dishwashing machine, placing an amount of an automatic dishwashing composition comprising at least one lipase variant of the present invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). In some embodiments, the methods include any automatic dishwashing composition described herein, which comprises, but is not limited to at least one lipase variant provided herein. The amount of automatic dishwashing composition to be used can be readily determined according to the manufacturer's instructions or suggestions and any form of automatic dishwashing composition comprising at least one variant lipolytic enzyme of the invention (e.g., liquid, powder, solid, gel, tablet, etc.), including any described herein, may be employed.

The present invention also provides methods for cleaning a surface, item or object optionally in need of cleaning, the method comprises contacting the item or surface (or a portion of the item or surface desired to be cleaned) with at least one variant lipase of the present invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to for example, scrubbing and mechanical agitation. In some embodiments, the cleaning compositions are employed at concentrations of from about 500 ppm to about 15,000 ppm in solution (e.g., aqueous solution). When the wash solvent is water, the water temperature typically ranges from about 5° C. to about 90° C. and when the surface, item or object comprises a fabric, the water to fabric mass ratio is typically from about 1:1 to about 30:1.

The present invention also provides methods of cleaning a laundry or fabric item in an washing machine, the method comprising providing an washing machine, placing an amount of a laundry detergent composition comprising at least one variant lipase of the invention sufficient to clean the laundry or fabric item in the machine (e.g., by placing the composition in an appropriate or provided detergent compartment or dispenser in the machine), placing the laundry or fabric item in the machine, and operating the machine so as to clean the laundry or fabric item (e.g., as per the manufacturer's instructions). The methods of the present invention include any laundry washing detergent composition described herein, comprising but not limited to at least one of any variant lipase provided herein. The amount of laundry detergent composition to be used can be readily determined according to manufacturer's instructions or suggestions and any form of laundry detergent composition comprising at least one variant lipolytic enzyme of the invention (e.g., solid, powder, liquid, tablet, gel, etc.), including any described herein, may be employed.

The present invention also provides methods of improved hydrolysis of carboxylic ester bonds, such as in long chain triglycerides. The hydrolysis reaction can be useful in a variety of industries, including detergent cleaning, food, flavor industry, biocatalytic resolution of pharmaceuticals, production of chemicals, development of biosensors, bioremediation and cosmetics and perfumes.

In some embodiments, the variants of the present invention can be used for transesterification in organic solvents, such as for the production of cocoa butter equivalents (for example, through transesterification of palm oil) and human milk fat substitutes, and in the preparation of glyceride products, such as in the production of butter or margarine. In some embodiments, the variants of the present invention can be used for hydrolysis of tallow. In some embodiments, the variants of the present invention can be used for modifying food flavor, for example, by synthesis of esters of short chain fatty acids and alcohols. In some embodiments, the variants of the present invention can be used for production of leaner meat by aiding in fat removal, or aiding in sausage fermentation, or modifying the flavor of other foods such as cheese, rice, soybean milk or apple wine (see US20110262591). In some embodiments, the variants of the present invention can be used for baking (see WO1994004035, EP585988, EP785994)

In some embodiments, the variants of the present invention can be used for production of soap through hydrolysis of lipids. In some embodiments, the variants of the present invention can be used for personal care uses, such as cosmetics, where the variants can aid in the production of emollients, such as isopropyl myristate, isopropyl palmitate or 2-ethylhexylpalmitate. In some embodiments, the variants of the present invention can be used for aiding in digestion, treatment of gastrointestinal disturbances, dyspepsias, and cutaneous manifestations of digestive allergies.

In some embodiments, the variants of the present invention can be used for resolving racemic mixtures of pharmaceutical compounds. In some embodiments, the variants of the present invention can be used for production of biodiesel.

In some embodiments, the variants of the present invention can be used for production of biodegradable polymers, such as 1-butyl oleate or trimethylolpropane ester.

In some embodiments, the variants of the present invention can be used in the textile industry for removal of size lubricants, improvement of dying properties. In some embodiments, the variants of the present invention can be used for degreasing, such as for degreasing of animal hides, sheepskin or wool. In some embodiments, the variants of the present invention can be used for increasing the pulping rate of pulp. It is also useful in control of pitch during pulp and paper manufacturing (see EP374700).

In some embodiments, the variants of the present invention can be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269, EP 808,903, and U.S. Pat. No. 6,103,505.

The present invention also provides methods of use in baking according to U.S. Pat. No. 6,558,715.

EXPERIMENTAL

The present invention is described in further detail in the following examples which are not in any way intended to limit the scope of the invention as claimed.

Example 1

Methods

The following assays are standard assays used in the examples described below. Occasionally specific protocols call for deviations from these standard assays. In those cases, deviations from these standard assay protocols below are identified in the examples.

A. Performance Index

The performance index (PI) of an enzyme compares the performance of the variant (measured value) and the standard enzyme (theoretical value or measured value) at the same protein concentration. In addition, the theoretical values can be calculated, using the parameters of the Langmuir equation of the standard enzyme.

A performance index (PI) that is greater than 1 (PI>1) indicates improved performance by a variant as compared to the parent (e.g. SEQ ID NO:1) or a reference sequence (e.g. SEQ ID NO: 2, Lipex®, Novozymes), while a PI of 1 (PI=1) identifies a variant that performs the same as the standard, and a PI that is less than 1 (PI<1) identifies a variant that performs worse than the standard.

B. Hydrolysis of p-Nitrophenyl Esters Assay

The TLL variants are assayed for lipase activity on three different para-nitrophenyl (pNP) ester substrates of varying alkyl chain lengths to determine the chain length preference of TLL variants. Table 1-1 provides details of the pNP ester substrates.

TABLE 1-1

| pNP Ester Substrates | | | |
|---|---|---|---|
| Substrate | Abbr | Chain-length | Source |
| p-nitrophenyl butyrate | pNPB | C4 | Sigma (CAS 2635-84-9) |
| p-nitrophenyl caprylate (octanoate) | pNPO | C8 | Fluka (CAS 1956-10-1) |
| p-nitrophenyl palmitate | pNPP | C16 | Sigma (CAS 1492-30-4) |

A reaction emulsion with pNP ester substrates is prepared using 0.8 mM pNP ester pre-suspended in ethanol (5%) in 0.05 M HEPES adjusted to pH 8.2. or in 0.05 M MES, adjusted to pH 6.0. The pNP-ester/buffer suspensions are mixed and transferred to a 96-well microtiter plate (MTP) containing the enzyme sample, in a total volume of 200 µL. Dilution of the enzyme samples and their transfer volumes are adjusted to keep the reaction within a linear range. The generation of liberated pNP is monitored over a period of 3 minutes at $OD_{405}$ nm and corrected using blank values (no enzyme). The pNP product generated per second is calculated using a pNP standard curve and then normalized to the added enzyme sample in the well (mol pNP/s per added mg enzyme). When using the p-nitrophenyl caprylate at pH 6.0 pNP-ester/buffer suspensions are mixed and transferred to a 96-well microtiter plate (MTP) containing the enzyme sample, in a total volume of 150 μL. The plates are sealed and shaken for 10 minutes at 900 rpm at 25° C. in an iEMS shaker (Thermo scientific). After incubation 50 μl of 0.2M HEPES pH8.2 including 0.5% Triton X-100 is added. The generation of liberated pNP is read at $OD_{405}$ nm and corrected using blank values (no enzyme). The performance index for hydrolysis is determined by comparing the hydrolysis of the variant enzyme on a particular pNP ester substrate with that of a reference TLL enzyme (SEQ ID NO: 1 or 2).

Chain length preference for lipases is determined by calculating the ratio of specific activities for pairs of substrates with different alkyl chain lengths. A ratio greater than one indicates a preference for longer chain length when dividing the specific activity of a lipase for hydrolysis of p-nitrophenyl palmitate by its specific activity for hydrolysis of p-nitrophenyl butyrate. For the same calculation, a ratio of less than one would indicate a preference for shorter alkyl chain length. Comparing the specific activity ratio for hydrolysis of a variant enzyme for a particular pNP ester substrate pair with that of a standard enzyme provides a measure of the level of change in alkyl chain length preference for the TLL variants.

C. Detergent Stability Assay

Accelerated detergent stability of the TLL variants is monitored by stressing the variants in a 10% (v/v) solution of the heavy duty liquid (HDL) detergent known commercially as Tide coldwater liquid (P&G, US; heat treated) at elevated temperature.

The raw ferment of the lipases are diluted 20× with 10% (v/v) solution of Tide coldwater liquid detergent in a 96-well PCR plate. Following mixing, 2 μL is transferred to 96 well plate wells containing 198 μL pNP octanoate substrate and activity is measured as described in B to generate the unstressed value. The PCR plate is sealed and incubated in a PCR machine for 30 min at 42° C. After end incubation the plate is cooled for 3 min at 4° C. prior to measuring activity again. Activity of the variant enzymes is determined by transferring 4 ul of the incubated mixtures to a 96 well plate containing 196.1 of pNP octanoate/buffer suspension, and activity is measured as described in section B to generate the stressed value.

The performance index for detergent stability is determined by comparing the activity ratio of stressed vs. unstressed for the variant enzyme with that of a reference TLL enzyme (SEQ ID NO:1 or 2).

D. Thermostability Assay

Accelerated thermostability of the TLL variants is monitored by stressing the variants in 50 mM HEPES, pH 8.2, with 1 ppm subtilisin BPN'-Y217L protease at elevated temperature.

95 μL of 50 mM HEPES, pH 8.2 with protease is transferred to 96-well PCR plate wells containing 5 μL of the enzyme sample. Following mixing, activity of the variant enzymes is determined by transferring 2 μl of the buffer/lipase mixtures to a 96 well plate containing 198 μl of pNP octanoate/buffer suspension, and activity is measured as described in section B.

The PCR plate is sealed and incubated in a PCR machine for 30 min at 69° C. After incubation the plate is cooled at 4° C. for 3 min prior to measuring activity. Activity of the variant enzymes is determined by transferring 4 ul of the incubated mixtures to a 96 well plate containing 196.1 of pNP octanoate/buffer suspension, activity is measured as described in section B.

A thermostability activity ratio is calculated based on enzyme activity after heating, divided by enzyme activity before heating, and is expressed as percentage remaining activity. The performance index for accelerated thermostability is determined by comparing the activity ratio of the variant enzyme, with that of the similarly treated reference TLL enzyme (SEQ ID NO:1 or 2).

E. LAS-Stability Assay

Accelerated LAS (linear alkylbenzene sulphonate, specifically sodium dodecyl benzene sulphonate, Sigma Cat. No. 289957) stability of the TLL variants is monitored by stressing the variants in 0.1% LAS diluted in HEPES buffer, pH 8.

80 μL of 0.1% LAS (w/v) at pH 8.2 is transferred to 96-well PCR plate wells containing 20 μL of the enzyme sample. Following mixing, activity of the variant enzymes is determined by transferring 2 ul of the buffer/lipase mixtures to a 96 well plate containing 198 ul of pNP octanoate/buffer suspension, and activity is measured as described in section B.

The PCR plate is sealed and incubated in a PCR machine for 30 min at 25° C. After incubation the plate is cooled at 4° C. for 3 min prior to measuring activity. Activity of the variant enzymes is determined by transferring 4 μl of the incubated mixtures to a 96 well plate containing 196 μl of pNP octanoate/buffer suspension, activity is measured as described in section B.

A LAS-stability activity ratio is calculated based on enzyme activity after incubation in LAS, divided by enzyme activity in the absence of LAS, and is expressed as percentage remaining activity. The performance index for LAS-stability is determined by comparing the activity ratio of the variant enzyme, with that of the similarly treated reference TLL enzyme (SEQ ID NO:1 or 2).

F. CS-61 Microswatch Assay

Cleaning performance of the lipase variants is tested in a microswatch assay. CS-61 swatches, which are pre-stained cotton swatches stained with beef fat and a red dye (Center for Testmaterial, CFT, The Netherlands) are used in a 96-well plate format. Swatches are cut into 5 mm diameter pieces and placed in each well of the MTP.

The performance of the lipase variants are tested in two detergent backgrounds, full dosage Tide coldwater liquid (heat treated for three hours at 95° C., final dosage: 0.92 g/1), and half dose Tide coldwater liquid (heat treated for three hours at 95° C.), plus adjuvant (n-dodecyl-3-D-Maltopyranoside) (final dosage detergent: 0.46 g/L, adjuvant: 0.272 μM).

Samples of lipase variants to be tested are obtained from Millipore filtered culture broth of cultures grown in MTP plates. The buffers used are 20 mM HEPES (final concentration) pH 8.2 and the water hardness is adjusted to 6 gpg 2:1 Ca:Mg. A volume of 246 μl of the HDL detergent solution (described above) is added to each swatch-containing well of the 96-well plate. To initiate the reaction, enzyme samples are added at a volume of 4 μL into each well. The plates are sealed and shaken for 30 minutes at 900 rpm at 30° C. in an iEMS shaker (Thermo scientific). After incubation, the fabrics are rinsed 3 times with de-ionized water using a Hydrospeed plate washer (Tecan, Austria) and dried at 50° C. over night. Stain removal is quantified using RGB measurements of the rinsed and dried fabrics, taken with a scanner (MiCrotek Scan Maker 900). Images are imported into Photoshop CSII where RGB values are extracted from the swatch containing areas using IPTK 5.0 from Reindeer Graphics. Percent Soil removal (SRI) values of the washed fabric are calculated in relation to the unwashed fabrics using the formula:

$$\%\ \text{Soil Removal}(SRI)=(\Delta E/\Delta E_{initial})*100$$

$$\text{Where } \Delta E=\sqrt{(R_{after}-R_{before})^2+(G_{after}-G_{before})^2+(B_{after}-B_{before})^2}$$

$$\text{Where } \Delta E_{initial}=\sqrt{(R_{white}-R_{before})^2+(G_{white}-G_{before})^2+(B_{white}-B_{before})^2}$$

The performance index for cleaning performance is calculated by comparing the SRI of the variant enzyme with the SRI of a reference TLL enzyme (SEQ ID NO: 1 or 2) at the same enzyme dose as the variant. A Langmuir fit is used to calculate what the SRI for the standard enzyme would be at the same enzyme dose as the variant.

G. Fabric Adhesion Assay

Adherence of the TLL variants to cotton fabric in a detergent solution (0.46 g/l heat inactivated Tide coldwater liquid detergent buffered with 20 mM HEPES pH 8.2 and water hardness at a concentration of 6 gpg 2:1 Ca:Mg) is tested using a microswatch assay. Bleached cotton swatches, EMPA 221, were cut into 5 mm diameter pieces and placed into each well of a 96 well plate (3641, Corning). A volume of 95 μL of the detergent solution is added to each swatch containing well of the plate. To initiate the assay, 5 μl of raw ferment is mixed into each well with 3 plates run as replicate determinations. The plates are sealed and shaken for 10 min at 900 rpm and 30° C. in an iEMS shaker (Thermo Scientific). After incubation, the microswatch plates are rinsed 3 times with tap water using a Hydrospeed platewasher (Tecan, Austria). The level of fabric bound enzyme is measured by adding 200 μL of pNP octanoate/buffer suspension to each well of the rinsed plates. Following incubation for 5 min at 30° C. in an iEMS shaker (Thermo Scientific), 150 μL are then transferred to a new 96 well plate and OD 405 nm is measured and blank subtracted. The performance index for fabric adhesion is determined by comparing the activity level of each TLL variant with that of the similarly treated reference TLL enzyme (SEQ ID NO:1 or 2).

H. Detergents

Commercially available detergent is used:

Tide coldwater liquid (P&G). Purchased commercially August 2010 and heat treated (three hours at 95° C.) to inactivate enzymes in the product formulation.

I. Protein Determination Assay

A 96-well round-bottom MTP (5042-1385, Agilent, 0.5 mL polypropylene) containing 60 μL of filtered culture broth per well was used for the High Performance Liquid Chromatography (HPLC) protein determination method. 10 μL of each sample was injected onto an Agilent 1290 (Hewlett Packard) (U)HPLC equipped with an Acquity UPLC BEH300 C41.7 μm, 2.1×50 mm column (Waters) column. Protein was bound to the column using MiliQ with 0.1% trifluoroacetic acid and eluted over a gradient up to 70% acetonitrile with 0.1% trifluoroacetic acid. Absorbance was measured at 220 nm and eluted peaks integrated using ChemStation software (Agilent Technologies). The protein concentration of TLL variants was determined based on a standard curve of purified TLL-protein.

Example 2

Generation of TLL Variants

A. Generation of TLL Combinatorial Libraries

For production in *bacillus* cells, the pHYT-TLLwt plasmid DNA (described in U.S. Patent Application No. 61/713,436) served as template to produce combinatorial libraries at pre-selected sites in the mature region (SEQ ID NO: 3 of U.S. Patent Application No. 61/713,436). GeneArt AG (Regensburg, Germany) was commissioned to create combinatorial libraries using their standard protocols. The libraries consisted of transformed *B. subtilis* cells containing the expression plasmid encoding TLL variant sequences. The corresponding codons for each site of interest were held as wild type or substituted with codons for at least one non-wild type amino acid.

SEQ ID NO:3 sets forth the nucleotide sequence of the synthetic TLL gene

```
gctagcgcagctggcaaagaagttagccaagatctgttcaaccaattcaa
cctttcgctcaatactctgcagctgcttactgcggaaagaacaacgatg
cacctgctggtactaacatcacttgcacaggtaacgcatgtcctgaagta
gaaaaagctgatgctacatttctttactcttttgaagatagcggcgtcgg
cgatgttaccggtttcttagctctggataacacaaacaaacttatcgtcc
ttagcttcagaggctctcgctcaatcgaaaactggatcggtaaccttaat
tttgacttgaaagaaatcaacgatatctgctctggttgccgtggccatga
cggattcacatcatcttggagaagcgtcgcagacacgcttcgccaaaaag
tagaagatgccgtacgcgaacacccagattacagagtagttttcacaggt
cactctcttggcggagctttagcaacagtagcaggcgctgatctccgcgg
taacggatacgacattgatgtcttctcttacggcgctccgcgcgtcggta
acagagcgtttgctgaatttttaactgtacaaacaggcggaactctttat
cgcatcactcacacaaacgatattgtcccgcgcttacctccgagagaatt
tggttactcacacagctctcctgaatactggatcaaaagcggtacattgg
tacctgttactcgaaacgatatcgtcaaaattgaaggaattgacgccacc
```

-continued

```
ggcggcaacaaccaaccgaacatccctgacatcccggcacacctttggta

cttcggcttaatcggaacatgcctttaaaagctt
```

For production in fungal cells, DNA sequences containing variants of the coding region for lipase from the filamentous fungus *Thermomyces lanuginosus* were ordered synthetically (Invitrogen, USA) carrying the attB1 and attB2 sites to allow for the Gateway® BP recombination cloning into the pDonor221 vector (Invitrogen, USA). The pDonor-TLL plasmids were sequence verified by the vendor. All variants were recombined via the Gateway® LR technology with the destination vector pTTTpyr2 resulting in final expression plasmids pTTTpyrG2-TLL variants. Plasmids were generated in the *Escherichia coli* TOP 10 strain, purified, and used for fungal transformation as described further.

The expression vector contains the *Trichoderma reesei* cbhI promoter and terminator regions allowing strong and inducible expression of a gene of interest, the *Aspergillus nidulans* amdS and pyr2 selective markers conferring growth of transformants on minimal medium with acetamide in the absence of uridine. The plasmids are maintained autonomously in the fungal cell due to *T. reesei* derived telomere regions. Usage of replicative plasmids results in increased frequencies of transformation and circumvents problems of locus-dependent expression observed with integrative fungal transformation.

Using a PEG-Protoplast method a *T. reesei* strain deleted for major cellulases (ΔcbhI Δcbh2 Δegl1 Δegl2 Δegl3 Δbgl1 pyr2-) was transformed with plasmid DNA. For protoplasts preparation, spores were grown for 16-24 hours at 28° C. in *Trichoderma* Minimal Medium MM (20 g/L glucose, 15 g/L $KH_2PO_4$, pH 4.5, 5 g/L $(NH_4)_2SO_4$, 0.6 g/L $MgSO_4.7H_2O$, 0.6 g/L $CaCl_2.2H_2O$, 1 ml of 1000× *T. reesei* trace elements solution (5 g/L $FeSO_4*7H_2O$, 1.4 g/L $ZnSO_4*7H_2O$, 1.6 g/L $MnSO_4.H_2O$, 3.7 g/L $CoCl_2.6H_2O$)) containing 5 mM uridine at shaking speed of 150 rpm. Germinating spores were harvested by centrifugation and treated with 50 mg/ml of Glucanex G200 (Novozymes AG, Switzerland) solution to lysate the fungal cell walls. Further preparation of protoplasts was performed by a standard method, as described by Penttila et al. [Gene 61(1987) 155-164].

Transformation mixtures containing approximately 1 µg of DNA and $5\times10^6$ protoplasts in a total volume of 50 µl were mixed with 200 µl of 25% PEG solution, diluted with equal volume of 1.2 M sorbitol/10 mM Tris, pH7.5/10 mM $CaCl_2$ solution and mixed with 1 ml of 3% agarose Minimal Medium (MM) ((20 g/L glucose, 15 g/L $KH_2PO_4$, 1 g/L $CaCl_2*2H_2O$, 1 g/L $MgSO_4.7H_2O$, pH 4.5, 2.5 ml/L of 400× *T. reesei* trace elements (175 g/L citric acid, 200 g/L $FeSO_4*7H_2O$, 16 g/L $ZnSO_4.7H_2O$, 3.2 g/L $CuSO_4.5H_2O$, 1.4 g/L $MnSO_4.H_2O$, 0.8 g/L boric acid)) containing 1 M sorbitol and 10 mM $NH_4Cl$. After growth of transformants, spores from each well were pooled and repatched on fresh plates with MM containing 10 mM acetamide for additional selective pressure. Once sporulated, spores were harvested and used for inoculation of liquid cultures either in a 24-well MTP format (for screening) or shake flasks (for validation studies) in the following production medium: 37 g/L glucose, 1 g/L sophorose, 9 g/L casmino acids, 10 g/L $(NH_4)_2SO_4$, 5 g/L $KH_2PO_4$, 1 g/L $CaCl_2.2H_2O$, 1 g/L $MgSO_4.7H_2O$, 33 g/L 1,4-Piperazinebis(propanesulfonic acid), pH 5.5, 2.5 ml/L of 400× *T. reesei* trace elements). 1 ml of production medium was added to produce variants in 24 well MTPs. For shake flasks, volumes were scaled up.

Plates were grown for 6 days at 28° C. and 80% humidity with shaking at 200 rpm. Culture supernatants were harvested by filtration. For larger scale fermentation and purification, spores from selected transformants were inoculated in the 500 ml of the same production medium and grown in 2 L shake flasks for 6 days at 28° C. with agitation followed by filtration and concentration. Expression of the variants was monitored by SDS-PAGE analysis.

The combinatorial libraries with combination of positions at which substitutions were created are shown in Table 2-1 below.

TABLE 2-1

TLL libraries and combination of positions at which substitutions were created

| Library Name | Combination of positions at which substitutions were created in the libraries | | | | | | | | | | | | |
|---|---|---|---|---|---|---|---|---|---|---|---|---|---|
| AJ1 | G023 | D027 | F051 | E056 | S058 | L075 | G091 | D130 | V187 | I252 | L264 | | |
| AJ2 | G023 | E056 | L075 | D130 | V187 | L264 | | | | | | | |
| AJ3 | D027 | D048 | 058 | D130 | D137 | G163 | L227 | N233 | L264 | | | | |
| TG1 | A018 | G023 | K024 | L075 | V077 | N094 | D130 | V154 | G156 | V187 | | | |
| TG2 | Q004 | N011 | D027 | E056 | S058 | I090 | N233 | P256 | | | | | |
| TG3 | A018 | G023 | K024 | L075 | N094 | D111 | D130 | V154 | G156 | V187 | T189 | L264 | |
| TG5 | N011 | G023 | D027 | E056 | L075 | N094 | D111 | D130 | V154 | G156 | V187 | T189 | L264 |
| DAE1 | A018 | D027 | P029 | N033 | E045 | N073 | L075 | T189 | | | | | |
| DAE2 | A018 | G023 | E045 | A049 | L075 | V077 | G156 | V187 | T189 | | | | |

B. Generation of TLL Synthetic Gene Variants

The pHYT-TLLwt plasmid DNA (described in U.S. Patent Application No. 61/713,436) served as template to produce variants, each with a fixed set of mutations at pre-selected sites in the mature region (SEQ ID NO: 3 of U.S. Patent Application No. 61/713,436). GeneArt AG (Regensburg, Germany) was commissioned to create these variants using their gene synthesis technology. The variants consisted of transformed *B. subtilis* cells containing the expression plasmid encoding TLL variant sequences. GeneArt provided the variants in a 96 well plate, one variant per well, with the cultures frozen in glycerol. The variants generated in this manner are listed in Table 2-2 below.

TABLE 2-2

| List of TLL Synthetic Gene Variants: |
| --- |
| A018K/D027S, A018K/E045F, A018K/L075D, |
| A018K/L075Q, A018K/T189D, D027E/G163P, D027N/E056K, D027N/N233Q, D027S/N033D, |
| D027S/P256T, D111A/L264R, D130A/L264R, D130A/T189Q, D130A/V187N, D130A/V187T, |
| E045F/N073R, E045F/T189D, F051T/L075R, G023K/D130A, G023K/L264R, G023Q/L075Q, |
| K024A/L075Q, K024A/V154I, L075Q/D130A, L075Q/G156W, L075R/L264R, L227M/L264R, |
| N011K/D027S, N033D/E045F, N073R/L075D, N094R/G156W, P029E/N033D, S058M/L264R, |
| V187T/L264R, A018K/A049V/L075Q, A018K/A049V/V187T, A018K/D027S/E045F, |
| A018K/D027S/N073R, A018K/D027S/T189D, A018K/E045F/N073R, A018K/E045F/T189D, |
| A018K/E045F/V187T, A018K/G023K/G156W, A018K/G023K/L075Q, A018K/G023Q/L075Q, |
| A018K/K024A/V154I, A018K/L075D/T189D, A018K/L075Q/G156W, A018K/L075Q/V187T, |
| A018K/N033D/L075D, A018K/N033D/T189D, A018K/N073R/L075D, A018K/P029E/T189D, |
| A018K/V154I/G156W, A049V/L075Q/T189D, A049V/V187T/T189D, D027E/S058M/G163P, |
| D027N/N233Q/P256T, D027N/S058M/P256T, D027Q/N233Q/P256T, D027Q/S058M/P256T, |
| D027S/L075Q/G091Q, D027S/N033D/T189D, D027S/N073R/L075D, D027S/N233Q/P256T, |
| D027S/S058M/P256T, D111A/D130A/L264R, D130A/T189Q/L264R, D130A/V154I/G156W, |
| D130A/V187N/L264R, D130A/V187T/L264R, E045F/L075D/T189D, E045F/N073R/L075D, |
| E056K/D130A/L264R, E056K/D130A/T189Q, F051T/I252Q/L264R, G023K/D130A/L264R, |
| G023K/D130A/V187T, G023K/E056K/V187T, G023K/L075R/L264R, G023K/V187N/L264R, |
| G023K/V187T/L264R, G023Q/A049V/T189D, G023Q/D111A/L264R, G023Q/D130A/G156W, |
| G023Q/E045F/V077I, G023Q/E056K/L075R, G023Q/K024A/G156W, G023Q/L075Q/V077I, |
| G023Q/L075Q/V187T, G163P/L227M/L264R, I090F/N233Q/P256T, K024A/D130A/V154I, |
| K024A/L075Q/G156W, K024A/L075Q/V077I, L075G/D130A/V187H, L075Q/D111A/D130A, |
| L075Q/D130A/V187T, L075Q/G156W/T189D, L075Q/G156W/V187N, L075Q/G156W/V187T, |
| L075Q/N094R/V154I, L075Q/V077I/T189D, L075Q/V154I/V187T, L075Q/V187N/L264R, |
| L075Q/V187T/L264R, L075Q/V187T/T189D, L075R/D130A/L264R, L075R/D130A/V187T, |
| L075R/V187N/L264R, L075R/V187T/L264R, N011K/D027S/S058M, N011K/N233Q/P256T, |
| N033D/E045F/L075D, N033D/E045F/N073R, N033D/N073R/T189D, N073R/L075D/T189D, |
| N094R/D130A/V187T, P029E/E045F/L075D, P029E/L075D/T189D, P029E/N033D/E045F, |
| P029E/N033D/L075D, P029E/N073R/L075D, Q004D/D027S/P256T, Q004D/N233Q/P256T, |
| Q004D/S058M/N233Q, S058M/L227M/L264R, V077I/D130A/V154I, V077I/V187A/T189D, |
| V187N/T189Q/L264R, A018K/A049V/L075Q/T189D, A018K/A049V/L075Q/V187T, |
| A018K/D027S/E045F/N073R, A018K/D027S/E045F/T189D, A018K/D027S/L075D/T189D, |
| A018K/D027S/N033D/L075D, A018K/D027S/P029E/T189D, A018K/D111A/G156W/T189Q, |
| A018K/D130A/G156W/V187T, A018K/E045F/A049V/G156W, A018K/E045F/A049V/V187T, |
| A018K/E045F/L075D/T189D, A018K/E045F/L075Q/T189D, A018K/E045F/L075Q/V187T, |
| A018K/G023K/D111A/T189Q, A018K/G023Q/A049V/T189D, A018K/G023Q/A049V/V187T, |
| A018K/G023Q/E045F/T189D, A018K/G023Q/E045F/V187T, A018K/G023Q/G156W/V187T, |
| A018K/G023Q/L075Q/T189D, A018K/G023Q/L075Q/V077I, A018K/G023Q/L075Q/V187T, |
| A018K/G023Q/L075R/D130A, A018K/G023Q/V077I/G156W, A018K/G023Q/V077I/V187T, |
| A018K/G023Q/V187T/T189D, A018K/K024A/D130A/G156W, A018K/L075Q/G156W/T189D, |
| A018K/L075Q/G156W/V187T, A018K/L075Q/N094R/D111A, A018K/L075Q/N094R/D130A, |
| A018K/L075Q/N094R/V187Q, A018K/L075Q/V077I/N094R, A018K/L075Q/V187T/T189D, |
| A018K/N033D/L075D/T189D, A018K/N073R/L075D/T189D, A018K/P029E/N033D/L075D, |
| A018K/P029E/N033D/T189D, A018K/P029E/N073R/L075D, A018K/V154I/G156W/V187T, |
| A049V/L075Q/V077I/T189D, A049V/L075Q/V187T/T189D, D027E/D048Q/G163P/L264R, |
| D027E/D130A/N233Q/L264R, D027E/D137Q/G163P/L227M, D027E/D137Q/L227M/L264R, |
| D027E/G163P/L227M/L264R, D027E/L227M/N233Q/L264R, D027E/S058M/G163P/L264R, |
| D027N/E056K/N233Q/P256T, D027N/E056K/S058M/P256T, D027N/S058M/N233Q/P256T, |
| D027Q/E056K/N233Q/P256T, D027Q/S058M/I090F/P256T, D027S/D130A/I252Q/L264R, |
| D027S/E045F/L075D/T189D, D027S/E045F/N073R/L075D, D027S/E045F/N073R/T189D, |
| D027S/E056K/D111A/V154I, D027S/E056K/I090F/P256T, D027S/N033D/E045F/N073R, |
| D027S/N033D/E045F/T189D, D027S/N033D/L075D/T189D, D027S/N033D/N073R/L075D, |
| D027S/N033D/N073R/T189D, D027S/P029E/E045F/L075D, D027S/P029E/E045F/N073R, |
| D027S/P029E/E045F/T189D, D027S/P029E/L075D/T189D, D027S/P029E/N033D/E045F, |
| D027S/P029E/N033D/L075D, D027S/P029E/N033D/N073R, D027S/P029E/N033D/T189D, |
| D048Q/D130A/G163P/L264R, D048Q/D137Q/G163P/L227M, D048Q/G163P/N233Q/L264R, |
| D111A/D130A/V154I/G156W, D111A/D130A/V154I/L264R, D111A/D130A/V187T/L264R, |
| D130A/G163P/L227M/L264R, D130A/G163P/N233Q/L264R, E045F/A049V/G156W/V187T, |
| E045F/L075Q/G156W/V187T, E056K/D130A/V187N/L264R, E056K/D130A/V187T/L264R, |
| E056K/L075Q/V187N/L264R, F051T/D130A/I252Q/L264R, F051T/L075G/I252Q/L264R, |
| F051T/L075Q/I252Q/L264R, G023K/D027Q/F051T/L075Q, G023K/D027S/L075Q/L264R, |
| G023K/D111A/D130A/L264R, G023K/D130A/G156W/T189Q, G023K/D130A/V187N/L264R, |
| G023K/D130A/V187T/L264R, G023K/D130A/V187T/T189Q, G023K/E056K/D130A/L264R, |
| G023K/E056K/D130A/V187N, G023K/E056K/L075R/L264R, G023K/E056K/V187T/L264R, |
| G023K/K024A/V154I/V187N, G023K/L075Q/D130A/V187N, G023K/L075Q/G156W/L264R, |
| G023K/L075Q/G156W/V187N, G023K/L075R/D130A/L264R, G023K/L075R/V187N/L264R, |
| G023K/L075R/V187T/L264R, G023Q/A049V/L075Q/T189D, G023Q/A049V/L075Q/V077I, |
| G023Q/A049V/V077I/G156W, G023Q/D027S/D111A/G156W, G023Q/E045F/A049V/T189D, |
| G023Q/E045F/A049V/V187T, G023Q/E045F/L075Q/G156W, G023Q/E045F/L075Q/V187T, |
| G023Q/F051T/I252Q/L264R, G023Q/G091Q/I252Q/L264R, G023Q/K024A/D130A/G156W, |
| G023Q/K024A/L075R/G156W, G023Q/K024A/L075R/V154I, G023Q/K024A/V077I/G156W, |
| G023Q/L075Q/D130A/L264R, G023Q/L075Q/G156W/V187N, G023Q/L075Q/G156W/V187T, |
| G023Q/L075Q/V187T/L264R, G023Q/V154I/G156W/V187N, G091Q/V187T/I252Q/L264R, |
| K024A/D130A/V154I/V187T, K024A/L075Q/D130A/G156W, K024A/L075Q/D130A/V154I, |
| K024A/L075Q/V187T/T189Q, K024A/L075R/G156W/V187N, L075G/D130A/V187T/I252Q, |
| L075G/G091Q/V187N/L264R, L075G/V187H/I252Q/L264R, L075Q/D130A/G156W/V187N, |
| L075Q/D130A/V154I/G156W, L075Q/G156W/V187T/L264R, L075Q/V077I/D130A/V187Q, |
| L075Q/V077I/G156W/V187N, L075Q/V077I/N094R/G156W, L075Q/V077I/V154I/V187Q, |

TABLE 2-2-continued

| List of TLL Synthetic Gene Variants: |
| --- |
| L075Q/V077I/V187T/T189D, L075Q/V187N/T189Q/L264R, L075R/D111A/V154I/G156W, L075R/D130A/V154I/L264R, L075R/D130A/V187T/L264R, N011K/D027N/E056K/S058M, N011K/D027N/S058M/P256T, N011K/D027Q/S058M/P256T, N011K/D027S/E056K/P256T, N011K/D027S/N233Q/P256T, N011K/D027S/S058M/N233Q, N011K/E056K/N233Q/P256T, N011K/E056K/S058M/P256T, N011K/G023K/L075Q/D111A, N011K/S058M/N233Q/P256T, N033D/E045F/N073R/T189A, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027Q/N233Q, Q004D/N011K/D027S/P256T, Q004D/N011K/E056K/S058M, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/A049V/L075Q/V187T/T189D, A018K/D027S/E045F/L075D/T189D, A018K/D027S/E045F/N073R/D137V, A018K/D027S/N033D/E045F/T189D, A018K/D027S/N033D/L075D/T189D, A018K/D027S/N033D/N073R/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/D130A/G156W/V187T/L264R, A018K/E045F/A049V/L075Q/G156W, A018K/E045F/A049V/L075Q/T189D, A018K/E045F/A049V/L075Q/V187T, A018K/E045F/N073R/L075D/T189D, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/D130A/V187N, A018K/K024A/N094R/G156W/V187T, A018K/L075Q/D111A/D130A/V187T, A018K/L075Q/G156W/V187T/T189D, A018K/L075Q/N094R/D130A/V187N, A018K/L075Q/N094R/G156W/V187N, A018K/L075Q/V077I/N094R/G156W, A018K/L075Q/V187T/T189Q/L264R, A018K/N033D/E045F/L075D/T189D, A018K/P029E/E045F/N073R/L075D, A018K/P029E/N033D/N073R/L075D, A018K/V077I/G156W/V187T/T189D, D027E/D048Q/D137Q/L227M/L264R, D027E/D048Q/G163P/N233Q/L264R, D027E/D048Q/L227M/N233Q/L264R, D027E/D048Q/S058M/G163P/N233Q, D027E/D130A/D137Q/G163P/L264R, D027E/D130A/G163P/L227M/L264R, D027E/D130A/G163P/N233Q/L264R, D027E/D137Q/G163P/L227M/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027N/E056K/S058M/N233Q/P256T, D027N/S058M/I090F/N233Q/P256T, D027Q/E056K/I090F/N233Q/P256T, D027Q/E056K/S058M/N233Q/P256T, D027Q/F051T/L075Q/D130A/L264R, D027S/E056K/D111A/V187N/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075Q/D111A/D130A/V187N, D027S/L075R/V154I/T189Q/L264R, D027S/N033D/E045F/N073R/L075D, D027S/N033D/N073R/L075D/T189D, D027S/P029E/E045F/N073R/L075D, D027S/P029E/E045F/N073R/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/G163P/L227M/N233Q/L264R, D130A/V154I/G156W/V187N/T189Q, E045F/A049V/L075Q/V187T/T189D, E056K/D130A/V187H/I252Q/L264R, E056K/L075G/V187N/I252Q/L264R, E056K/L075Q/G156W/T189Q/L264R, E056K/L075R/D130A/V187N/L264R, E056K/L075R/D130A/V187T/L264R, E056K/N094R/G156W/V187N/L264R, E056K/S058M/I090F/N233Q/P256T, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/L075R/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, |

TABLE 2-2-continued

| List of TLL Synthetic Gene Variants: |
| --- |
| G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/L075G/I252Q/L264R, G023Q/D027S/V154I/V187N/L264R, G023Q/E045F/A049V/G156W/T189D, G023Q/E045F/A049V/L075Q/V077I, G023Q/E045F/A049V/V077I/T189D, G023Q/E045F/L075Q/G156W/T189D, G023Q/E045F/L075Q/V077I/V187T, G023Q/E056K/V187N/I252Q/L264R, G023Q/F051T/L075Q/G091Q/I252Q, G023Q/K024A/L075Q/D130A/G156W, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075G/D130A/V187T/I252Q/L264R, L075Q/D111A/D130A/V187T/T189Q, L075Q/D111A/V187N/T189Q/L264R, L075Q/D130A/V187T/T189Q/L264R, L075Q/N094R/D130A/G156W/V187T, L075Q/V077I/D130A/G156W/V187N, L075Q/V154I/V187N/T189Q/L264R, L075R/D111A/D130A/V187N/T189Q, L075R/D130A/V154I/T189Q/L264R, L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/I090F/P256T, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/E045F/L075D/T189D, P029E/N033D/K074S/L075D/T189D, P029E/N033D/N073R/L075D/T189D, Q004D/D027N/E056K/S058M/P256T, Q004D/D027N/I090F/N233Q/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, Q004D/N011K/I090F/N233Q/P256T, S058M/D130A/D137Q/G163P/L264R, S058M/D130A/G163P/L227M/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/A049V/L075Q/G156W/V187T/T189D, A018K/D027S/N033D/E045F/L075D/T189D, A018K/D027S/N033D/E045F/N073R/L075D, A018K/D027S/N033D/N073R/L075D/T189D, A018K/D027S/P029E/N033D/E045F/L075D, A018K/D027S/P029E/N033D/L075D/T189D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D111A/L264R, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/G156W, A018K/G023Q/A049V/L075Q/V077I/V187T, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/G156W/V187N, A018K/L075Q/D111A/V154I/T189Q/L264R, A018K/L075Q/D130A/V154I/T189Q/L264R, A018K/L075Q/D130A/V187N/T189Q/L264R, A018K/L075R/D130A/V154I/G156W/V187N, A018K/N033D/E045F/N073R/L075D/T189D, A018K/N094R/D111A/D130A/V154I/V187N, A018K/P029E/N033D/E045F/L075D/T189D, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/D130A/G163P/L264R, D027E/D048Q/S058M/D130A/L227M/N233Q, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/E056K/S058M/I090F/N233Q/P256T, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, |

TABLE 2-2-continued

| List of TLL Synthetic Gene Variants: |
|---|
| D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/G091Q/D130A/V187N/I252Q/L264R, D027S/L075Q/D111A/G156W/V187N/T189Q, D027S/L075Q/G091Q/V187H/I252Q/L264R, D027S/P029E/N033D/E045F/N073R/L075D, D027S/P029E/N033D/E045F/N073R/T189D, D027S/P029E/N033D/N073R/L075D/T189D, D048Q/D130A/G163P/L227M/N233Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/G163P/N233Q/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, D111A/D130A/V154I/G156W/V187N/L264R, E045F/A049V/L075Q/V077I/V187T/T189D, F051T/E056K/D130A/V187N/I252Q/L264R, F051T/E056K/L075Q/V187H/I252Q/L264R, F051T/L075G/G091Q/D130A/I252Q/L264R, F051T/L075G/G091Q/V187H/I252Q/L264R, F051T/L075G/G091Q/V187T/I252Q/L264R, F051T/L075R/D130A/V187N/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/D130A/V187N/I252Q/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075G/D130A/V187T/I252Q/L264R, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/F051T/L075Q/V187T/L264R, G023Q/D027S/L075G/D130A/V187H/L264R, G023Q/D027S/L075Q/D111A/G156W/L264R, G023Q/D027S/L075Q/D130A/V187T/I252Q, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/E056K/D111A/D130A/V187N/T189Q, G023Q/E056K/L075Q/D130A/V154I/L264R, G023Q/F051T/D130A/V187T/I252Q/L264R, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/G091Q/V187N/I252Q/L264R, G023Q/L075Q/N094R/D111A/G156W/L264R, G023Q/L075Q/V077I/N094R/D130A/V187Q, G023Q/L075R/V154I/G156W/V187N/L264R, K024A/D111A/D130A/V187T/T189Q/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/L075R/D111A/V154I/G156W/V187N, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075Q/N094R/D111A/G156W/T189Q/L264R, L075R/D130A/V154I/G156W/V187N/L264R, N011K/D027N/E056K/I090F/N233Q/P256T, N011K/D027N/E056K/S058M/N233Q/P256T, N011K/D027N/S058M/I090F/N233Q/P256T, N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/I090F/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, |

TABLE 2-2-continued

| List of TLL Synthetic Gene Variants: |
|---|
| A018K/G023Q/L075R/V077I/N094R/G156W/V187N, |
| A018K/K024A/D130A/V154I/G156W/V187T/L264R, |
| A018K/K024A/L075Q/D111A/G156W/V187N/L264R, |
| A018K/K024A/L075Q/D130A/G156W/V187T/T189Q, |
| A018K/K024A/L075Q/D130A/V154I/G156W/V187T, |
| A018K/K024A/L075Q/V077I/N094R/D130A/G156W, |
| A018K/K024A/N094R/D130A/G156W/V187T/L264R, |
| A018K/L075Q/D111A/D130A/V154I/G156W/L264R, |
| A018K/L075Q/D111A/V154I/V187T/T189Q/L264R, |
| A018K/L075Q/D130A/G156W/V187N/T189Q/L264R, |
| A018K/L075Q/N094R/D111A/V154I/V187T/L264R, |
| D027E/D048Q/D130A/D137Q/G163P/N233Q/L264R, |
| D027E/D048Q/D137Q/G163P/L227M/N233Q/L264R, |
| D027E/D048Q/S058M/D130A/D137Q/G163P/L264R, |
| D027E/D048Q/S058M/D130A/G163P/L227M/L264R, |
| D027E/D048Q/S058M/D130A/G163P/N233Q/L264R, |
| D027E/D048Q/S058M/D137Q/G163P/L227M/L264R, |
| D027E/D130A/D137Q/G163P/L227M/N233Q/L264R, |
| D027E/S058M/D130A/D137Q/G163P/L227M/L264R, |
| D027E/S058M/D130A/D137Q/G163P/N233Q/L264R, |
| D027E/S058M/D130A/G163P/L227M/N233Q/L264R, |
| D027E/S058M/D137Q/G163P/L227M/N233Q/L264R, |
| D027Q/F051T/L075G/D130A/V187H/I252Q/L264R, |
| D027Q/F051T/L075Q/D130A/V187T/I252Q/L264R, |
| D027Q/F051T/L075Q/G091Q/D130A/V187T/I252Q, |
| D027Q/F051T/S058M/L075Q/G091Q/I252Q/L264R, |
| D027Q/L075G/G091Q/D130A/V187H/I252Q/L264R, |
| D027S/E056K/L075R/D111A/G156W/V187N/L264R, |
| D027S/F051T/L075G/G091Q/V187T/I252Q/L264R, |
| D027S/F051T/S058M/L075Q/V187N/I252Q/L264R, |
| D027S/F051T/S058M/L075R/D130A/I252Q/L264R, |
| D027S/L075R/V154I/G156W/V187N/T189Q/L264R, |
| D027S/P029E/N033D/E045F/N073R/L075D/T189D, |
| D048Q/D130A/D137Q/G163P/L227M/N233Q/L264R, |
| D048Q/S058M/D130A/D137Q/G163P/L227M/L264R, |
| D048Q/S058M/D130A/D137Q/L227M/N233Q/L264R, |
| D048Q/S058M/D130A/G163P/L227M/N233Q/L264R, |
| D048Q/S058M/D137Q/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075Q/G091Q/D130A/V187H/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/G091Q/V187N/I252Q, |
| G023K/D027S/F051T/S058M/L075Q/D130A/V187N, |
| G023K/D027S/L075Q/N094R/V154I/G156W/T189Q, |
| G023K/F051T/E056K/L075R/D130A/V187T/I252Q, |
| G023K/F051T/L075Q/G091Q/D130A/V187H/I252Q, |
| G023K/K024A/L075Q/D111A/D130A/T189Q/L264R, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/K024A/N094R/V154I/G156W/V187N/T189Q, |
| G023K/L075Q/D111A/D130A/V154I/G156W/L264R, |
| G023K/L075Q/D111A/V154I/G156W/T189Q/L264R, |
| G023K/L075Q/D130A/G156W/V187N/T189Q/L264R, |
| G023K/L075Q/N094R/D130A/V154I/V187N/L264R, |
| G023K/L075Q/N094R/V154I/G156W/V187T/L264R, |
| G023K/L075R/N094R/V154I/G156W/V187N/L264R, |
| G023Q/D027S/F051T/E056K/D130A/I252Q/L264R, |
| G023Q/D027S/L075Q/G091Q/V187T/I252Q/L264R, |
| G023Q/D027S/L075Q/V154I/G156W/V187N/L264R, |
| G023Q/D027S/S058M/L075Q/D130A/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D111A/G156W/V187N/L264R, |
| G023Q/E056K/L075Q/D130A/V154I/G156W/T189Q, |
| G023Q/E056K/L075R/D111A/D130A/V187N/T189Q, |
| G023Q/F051T/E056K/L075R/G091Q/V187H/I252Q, |
| G023Q/F051T/G091Q/D130A/V187H/I252Q/L264R, |
| G023Q/F051T/L075Q/G091Q/V187H/I252Q/L264R, |
| G023Q/F051T/L075R/G091Q/V187N/I252Q/L264R, |
| G023Q/F051T/S058M/G091Q/D130A/I252Q/L264R, |
| G023Q/K024A/L075Q/V077I/D130A/G156W/V187N, |
| G023Q/K024A/L075Q/V077I/D130A/V154I/G156W, |
| G023Q/L075G/G091Q/D130A/V187T/I252Q/L264R, |
| G023Q/L075Q/D111A/D130A/V154I/G156W/L264R, |

TABLE 2-2-continued

| List of TLL Synthetic Gene Variants: |
|---|
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| G023Q/S058M/L075G/G091Q/D130A/I252Q/L264R, |
| K024A/L075Q/D111A/D130A/V154I/G156W/L264R, |
| K024A/L075Q/D111A/D130A/V187N/T189Q/L264R, |
| K024A/L075R/D130A/V154I/G156W/T189Q/L264R, |
| L075Q/D111A/D130A/G156W/V187N/T189Q/L264R, |
| N011K/A018K/K024A/V077I/V154I/G156W/T189Q, |
| N011K/D027N/E056K/S058M/I090F/N233Q/P256T, |
| N011K/D027S/D111A/D130A/V154I/V187N/T189Q, |
| N011K/E056K/L075Q/D111A/D130A/V154I/L264R, |
| N011K/E056K/L075Q/D130A/V154I/V187N/T189Q, |
| N011K/G023K/L075Q/D111A/D130A/V154I/V187N, |
| N011K/G023Q/L075Q/V154I/V187N/T189Q/L264R, |
| Q004D/D027N/E056K/S058M/I090F/N233Q/P256T, |
| Q004D/N011K/D027N/S058M/I090F/N233Q/P256T, |
| Q004D/N011K/D027Q/E056K/S058M/N233Q/P256T, |
| Q004D/N011K/D027Q/S058M/I090F/N233Q/P256T, |
| Q004D/N011K/D027S/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| A018K/K024A/L075Q/V077I/N094R/D130A/V154I/G156W, |
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| D027E/D048Q/S058M/D137Q/G163P/L227M/N233Q/L264R, |
| D027E/S058M/D130A/D137Q/G163P/L227M/N233Q/L264R, |
| D048Q/S058M/D130A/D137Q/G163P/L227M/N233Q/L264R, |
| F051T/E056K/L075G/G091Q/D130A/V187H/I252Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/D027S/F051T/S058M/L075Q/V187H/I252Q/L264R, |
| G023K/E056K/L075Q/D130A/V154I/V187N/T189Q/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |
| G023K/L075Q/N094R/D130A/V154I/G156W/V187N/L264R, |
| G023Q/D027Q/F051T/L075Q/G091Q/D130A/I252Q/L264R, |
| G023Q/D027Q/F051T/S058M/L075R/D130A/V187T/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/D027S/L075R/N094R/V154I/G156W/V187N/T189Q, |
| G023Q/D027S/S058M/G091Q/D130A/V187H/I252Q/L264R, |
| G023Q/E056K/L075Q/D111A/V154I/V187N/T189Q/L264R, |
| G023Q/E056K/L075Q/N094R/D111A/G156W/T189Q/L264R, |
| G023Q/F051T/L075Q/G091Q/D130A/V187H/I252Q/L264R, |
| G023Q/F051T/L075Q/G091Q/D130A/V187T/I252Q/L264R, |
| G023Q/F051T/L075R/G091Q/D130A/V187T/I252Q/L264R, |
| G023Q/K024A/L075Q/V077I/D130A/V154I/G156W/V187N, |
| G023Q/K024A/L075Q/V077I/N094R/D130A/V154I/V187N, |
| G023Q/L075Q/D111A/D130A/V154I/G156W/V187N/L264R, |
| G023Q/L075Q/N094R/D111A/D130A/G156W/T189Q/L264R, |
| G023Q/L075Q/N094R/D130A/V154I/G156W/T189Q/L264R, |
| G023Q/L075Q/V077I/N094R/D130A/V154I/G156W/V187Q, |
| G023Q/S058M/L075R/G091Q/D130A/V187H/I252Q/L264R, |
| K024A/D111A/D130A/V154I/G156W/V187T/T189Q/L264R, |
| N011K/G023K/D027S/L075Q/D111A/D130A/V154I/T189Q, |
| N011K/G023K/D027S/L075R/V154I/G156W/V187N/T189Q, |
| N011K/G023K/E056K/L075Q/D130A/V154I/T189Q/L264R, |
| N011K/G023K/L075Q/D111A/G156W/V187N/T189Q/L264R, |

TABLE 2-2-continued

| List of TLL Synthetic Gene Variants: |
|---|
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/D111A/D130A/V154I/V187N/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075Q/N094R/D130A/V154I/G156W/V187N, |
| A018K/G023K/K024A/L075Q/N094R/D130A/V187T/T189Q/L264K, |
| A018K/G023K/K024A/L075R/V077I/D130A/V154I/G156W/V187N, |
| A018K/G023K/K024A/V077I/D130A/V154I/G156W/V187T/T189Q, |
| A018K/G023K/L075Q/N094R/D111A/V154I/G156W/T189Q/L264R, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |
| A018K/G023Q/K024A/L075R/N094R/D130A/V154I/G156W/V187N, |
| A018K/K024A/L075Q/N094R/V154I/G156W/V187N/T189Q/L264R, |
| D027Q/F051T/S058M/L075G/G091Q/D130A/V187T/I252Q/L264R, |
| D027S/E056K/L075Q/N094R/D111A/D130A/V154I/G156W/L264R, |
| D027S/E056K/L075Q/N094R/D111A/D130A/V187N/T189Q/L264R, |
| G023K/D027S/F051T/E056K/S058M/L075Q/G091Q/V187N/L264R, |
| G023K/D027S/F051T/E056K/S058M/L075R/G091Q/V187H/I252Q, |
| G023K/D027S/L075Q/D111A/D130A/V154I/G156W/T189Q/L264R, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023K/L075Q/D111A/D130A/V154I/G156W/V187T/T189Q/L264R, |
| G023Q/D027S/F051T/E056K/L075G/G091Q/V187N/I252Q/L264R, |
| G023Q/D027S/L075Q/N094R/D111A/D130A/V154I/G156W/L264R, |
| G023Q/D027S/L075Q/N094R/D130A/V154I/G156W/V187N/L264R, |
| G023Q/E056K/L075Q/D111A/D130A/V154I/G156W/T189Q/L264R, |
| G023Q/F051T/S058M/L075G/G091Q/D130A/V187T/I252Q/L264R, |
| G023Q/F051T/S058M/L075Q/G091Q/D130A/V187H/I252Q/L264R, |
| N011K/G023K/D027S/E056K/L075R/D111A/G156W/V187N/L264R, |
| N011K/G023K/L075R/D111A/D130A/V154I/V187N/T189Q/L264R, |
| N011K/G023Q/L075Q/D111A/V154I/G156W/V187N/T189Q/L264R, |
| N011K/G023K/L075R/V077I/D130A/V154I/G156W/V187T/T189Q, |
| A018K/G023Q/D027S/E045F/A049V/N073S/L075Q/R108K/V187T/T189D, |
| A018K/G023Q/D027S/E045F/A049V/S058M/L075Q/R108K/V187T/T189D, |
| A018K/G023Q/D027S/E045F/A049V/S058M/N073S/L075Q/V187T/T189D, |
| A018K/G023Q/D027S/P029E/S058M/L075Q/V077I/H135F/G156W/V187T, |
| A018K/G023Q/D027S/P029E/S058M/L075Q/V077I/R108K/H135F/V187H, |
| A018K/G023Q/D027S/S058M/L075Q/V077I/R108K/H135F/G156W/V187H, |
| A018K/G023Q/K024A/L075Q/V077I/N094R/D130A/V154I/G156W/V187Q, |
| G023K/D027S/F051T/E056K/S058M/L075G/G091Q/D130A/I252Q/L264R, |
| G023Q/D027S/F051T/E056K/L075R/G091Q/D130A/V187H/I252Q/L264R, |
| G023Q/D027S/F051T/E056K/S058M/L075R/G091Q/D130A/V187H/I252Q, |
| G023Q/L075R/N094R/D111A/D130A/V154I/G156W/V187N/T189Q/L264R, |
| N011K/A018K/G023K/K024A/L075R/V077I/D130A/V154I/V187T/T189Q, |
| N011K/G023K/L075R/N094R/D111A/V154I/G156W/V187N/T189Q/L264R, |
| N011K/G023Q/D027S/E056K/L075R/D130A/V154I/G156W/T189Q/L264R, |
| N011K/G023Q/E056K/L075R/D111A/D130A/V154I/G156W/V187N/L264R, |
| N011K/G023Q/L075Q/N094R/D111A/D130A/V154I/G156W/V187N/L264R, |
| A018K/G023K/L075R/N094R/D111A/D130A/V154I/G156W/V187N/T189Q/L264R, |
| A018K/G023Q/D027S/E045F/A049V/S058M/N073S/L075Q/R108K/V187T/T189D, |
| A018K/G023Q/D027S/P029E/S058M/L075Q/V077I/R108K/H135F/G156W/V187T, |
| N011K/G023Q/D027S/L075Q/N094R/D111A/V154I/G156W/V187N/T189Q/L264R, |
| A018K/G023Q/D027S/P029E/E045F/A049V/S058M/N073S/L075Q/R108K/V187T/T189D, |
| A018K/G023Q/D027S/P029E/E045F/A049V/S058M/N073S/L075Q/R108K/H135F/V187T/T189D, |
| A018K/G023Q/D027S/P029E/N033D/E045F/A049V/S058M/N073S/K074S/L075Q/V077I/N101D/R108K/ H135F/D137V/G156W/V187T/T189D |

Example 3

Ester Hydrolysis Activity of TLL Combinatorial Variants

TLL variants created as described in Example 2 were assayed for lipase activity on p-nitrophenyl butyrate, p-nitrophenyl caprylate (octanoate), and p-nitrophenyl palmitate substrates as described in Example 1. The performance index was calculated for the variants compared to TLL (SEQ ID NO:1), or the reference sequence, SEQ ID NO: 2.

TABLE 3-1

| TLL variants with Performance Index >1 compared to TLL SEQ ID NO: 1 for p-nitrophenyl butyrate hydrolysis at pH 8 are shown below. |
| --- |
| A018K/L075D, D027N/E056K, D027S/N033D, D130A/L264R, D130A/V187N, E045F/N073R, K024A/L075Q, K024A/V154I, L075Q/D130A, L075R/L264R, P029E/N033D, V187T/L264R, A018K/E045F/N073R, A018K/G023K/G156W, A018K/G023K/L075Q, A018K/L075D/T189D, A018K/V154I/G156W, A049V/L075Q/T189D, A049V/V187T/T189D, D027E/S058M/G163P, D027N/N233Q/P256T, D027S/L075Q/G091Q, D027S/N033D/T189D, D130A/V187T/L264R, E045F/L075D/T189D, E056K/D130A/T189Q, G023K/E056K/V187T, G023Q/A049V/T189D, G023Q/D111A/L264R, G023Q/L075Q/V187T, G163P/L227M/L264R, L075G/D130A/V187H, L075Q/D111A/D130A, L075Q/G156W/V187N, L075Q/V187N/L264R, L075R/D130A/L264R, L075R/D130A/V187T, L075R/V187T/L264R, N073R/L075D/T189D, P029E/N033D/E045F, V077I/D130A/V154I, V187N/T189Q/L264R, A018K/D027S/E045F/N073R, A018K/D027S/N033D/L075D, A018K/E045F/L075D/T189D, A018K/E045F/L075Q/T189D, A018K/G023K/D111A/T189Q, A018K/G023Q/E045F/T189D, A018K/G023Q/E045F/V187T, A018K/G023Q/L075R/D130A, A018K/G023Q/V077I/V187T, A018K/L075Q/G156W/V187T, A018K/L075Q/N094R/D130A, A018K/L075Q/V077I/N094R, A018K/P029E/N073R/L075D, D027E/D048Q/G163P/L264R, D027E/D137Q/G163P/L227M, D027E/S058M/G163P/L264R, D027N/E056K/N233Q/P256T, D027Q/E056K/N233Q/P256T, D027S/E045F/N073R/L075D, D027S/E045F/N073R/T189D, D027S/N033D/E045F/N073R, D027S/N033D/E045F/T189D, D027S/N033D/L075D/T189D, D027S/N033D/N073R/T189D, D027S/P029E/E045F/N073R, D027S/P029E/L075D/T189D, D027S/P029E/N033D/L075D, D048Q/D130A/G163P/L264R, D048Q/G163P/N233Q/L264R, E045F/A049V/G156W/V187T, E045F/L075Q/G156W/V187T, G023K/D027Q/F051T/L075Q, G023K/L075Q/G156W/V187N, G023K/L075R/D130A/L264R, G023Q/A049V/L075Q/V077I, G023Q/A049V/V077I/G156W, G023Q/D027S/D111A/G156W, G023Q/K024A/L075R/G156W, G023Q/K024A/L075R/V154I, G023Q/L075Q/D130A/L264R, G023Q/V154I/G156W/V187N, K024A/L075Q/D130A/V154I, K024A/L075R/G156W/V187N, L075G/G091Q/V187N/L264R, L075Q/D130A/G156W/V187N, L075Q/V077I/G156W/V187N, N011K/D027S/E056K/P256T, N011K/E056K/N233Q/P256T, N011K/S058M/N233Q/P256T, N033D/E045F/N073R/T189A, P029E/N033D/L075D/T189D, P029E/N073R/L075D/T189D, Q004D/D027N/S058M/P256T, Q004D/D027S/I090F/P256T, Q004D/N011K/D027Q/N233Q, S058M/D137Q/G163P/N233Q, S058M/L075Q/G091Q/I252Q, A018K/A049V/L075Q/V187T/T189D, A018K/D027S/E045F/L075D/T189D, A018K/D027S/E045F/N073R/D137V, A018K/D027S/N033D/L075D/T189D, A018K/D027S/P029E/N033D/L075D, A018K/G023K/K024A/L075R/N094R, A018K/G023Q/E045F/A049V/V187T, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/T189D, A018K/K024A/L075R/D130A/V154I, A018K/K024A/N094R/D130A/V187N, A018K/L075Q/D111A/D130A/V187T, A018K/L075Q/N094R/D130A/V187N, A018K/L075Q/N094R/G156W/V187N, A018K/P029E/N033D/N073R/L075D, A018K/V077I/G156W/V187T/T189D, D027E/S058M/D130A/G163P/L264R, D027E/S058M/D137Q/G163P/N233Q, D027E/S058M/G163P/L227M/L264R, D027N/S058M/I090F/N233Q/P256T, D027S/E056K/D111A/V187N/L264R, D027S/E056K/S058M/N233Q/P256T, D027S/L075Q/D111A/D130A/V187N, D027S/L075R/V154I/T189Q/L264R, D027S/P029E/N033D/E045F/N073R, D048Q/D130A/G163P/L227M/L264R, D048Q/D137Q/G163P/L227M/L264R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/D137Q/G163P/N233Q/L264R, E045F/A049V/L075Q/V187T/T189D, F051T/S058M/L075Q/G091Q/I252Q, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/L075R/D130A/V187N/L264R, G023K/N094R/G156W/V187N/T189Q, G023Q/A049V/L075Q/G156W/V187T, G023Q/E045F/A049V/L075Q/V077I, G023Q/F051T/L075Q/G091Q/I252Q, G023Q/K024A/L075Q/G156W/V187Q, G023Q/K024A/L075R/D130A/V154I, G023Q/L075Q/V077I/D130A/G156W, K024A/L075R/D111A/V154I/V187T, K024A/L075R/G156W/V187N/T189Q, K024A/L075R/V154I/G156W/V187Q, L075Q/D130A/V187T/T189Q/L264R, L075Q/N094R/D130A/G156W/V187T, L075R/D111A/D130A/V187N/T189Q, L075R/D130A/V154I/T189Q/L264R, L075R/D130A/V187T/T189Q/L264R, N011K/D027N/E056K/N233Q/P256T, N011K/D027Q/E056K/S058M/N233Q, N011K/D027Q/I090F/N233Q/P256T, N011K/D027S/E056K/N233Q/P256T, N011K/G023K/D111A/G156W/L264R, P029E/N033D/E045F/L075D/T189D, Q004D/D027S/E056K/N233Q/P256T, Q004D/D027S/S058M/N233Q/P256T, Q004D/N011K/D027Q/E056K/N233Q, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023K/K024A/N094R/D130A/V154I, A018K/G023K/L075Q/D130A/G156W/V187N, A018K/G023K/L075Q/V077I/G156W/V187Q, A018K/G023K/L075R/N094R/D130A/V187N, A018K/G023Q/A049V/L075Q/V077I/G156W, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/G156W/V187T/T189D, A018K/G023Q/E045F/L075Q/G156C/V187T, A018K/G023Q/K024A/L075R/N094R/G156W, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/T189Q/L264R, A018K/L075Q/D130A/V187N/T189Q/L264R, A018K/N033D/E045F/N073R/L075D/T189D, |

TABLE 3-1-continued

| TLL variants with Performance Index >1 compared to TLL SEQ ID NO: 1 for p-nitrophenyl butyrate hydrolysis at pH 8 are shown below. |
|---|
| A018K/N094R/D111A/D130A/V154I/V187N, A018K/P029E/N033D/E045F/L075D/T189D, D027E/D048Q/D137Q/G163P/L227M/L264R, D027E/D048Q/S058M/D130A/G163P/L264R, D027E/D048Q/S058M/G163P/L227M/L264R, D027E/D048Q/S058M/G163P/N233Q/L264R, D027E/D137Q/G163P/L227M/N233Q/L264R, D027E/S058M/D137Q/G163P/N233Q/L264R, D027Q/E056K/S058M/D130A/I252Q/L264R, D027Q/E056K/S058M/I090F/N233Q/P256T, D027Q/F051T/L075Q/D130A/V187H/L264R, D027Q/S058M/L075R/D130A/V187T/I252Q, D027S/E056K/S058M/V187T/I252Q/L264R, D027S/P029E/N033D/E045F/N073R/T189D, D048Q/S058M/D137Q/G163P/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075Q/V154I/G156W/V187Q, G023K/K024A/L075R/D130A/V154I/V187N, G023K/N094R/D111A/G156W/V187T/L264R, G023Q/E056K/D111A/D130A/V187N/T189Q, G023Q/E056K/L075Q/D130A/V154I/L264R, G023Q/F051T/D130A/V187T/I252Q/L264R, G023Q/K024A/L075Q/D130A/V154I/G156W, G023Q/L075Q/N094R/D111A/G156W/L264R, G023Q/L075R/V154I/G156W/V187N/L264R, K024A/L075Q/D111A/V154I/V187N/T189Q, K024A/L075Q/N094R/D130A/V154I/L264R, K024A/L075Q/V077I/N094R/D130A/V187N, K024A/L075Q/V154I/V187T/T189Q/L264R, L075Q/D111A/D130A/V154I/G156W/T189Q, L075Q/D130A/V154I/G156W/V187N/L264R, L075Q/N094R/D111A/G156W/T189Q/L264R, L075R/D130A/V154I/G156W/V187N/L264R, N011K/D027N/E056K/S058M/N233Q/P256T, N011K/D027S/E056K/S058M/I090F/P256T, Q004D/D027N/E056K/S058M/N233Q/P256T, Q004D/N011K/D027Q/E056K/S058M/N233Q, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/K024A/L075Q/V077I/N094R/V154I, A018K/G023Q/K024A/L075R/N094R/G156W/V187N, A018K/G023Q/L075R/V077I/N094R/G156W/V187N, A018K/K024A/L075Q/D130A/V154I/G156W/V187T, A018K/K024A/L075Q/V077I/N094R/D130A/G156W, A018K/L075Q/D111A/D130A/V154I/G156W/L264R, A018K/L075Q/N094R/D111A/V154I/V187T/L264R, D027E/D048Q/S058M/D130A/G163P/L227M/L264R, D027E/D048Q/S058M/D130A/G163P/N233Q/L264R, D027E/S058M/D130A/D137Q/G163P/N233Q/L264R, D027Q/F051T/L075G/D130A/V187H/I252Q/L264R, D027S/E056K/L075R/D111A/G156W/V187N/L264R, D027S/F051T/L075G/G091Q/V187T/I252Q/L264R, D048Q/S058M/D130A/D137Q/G163P/L227M/L264R, D048Q/S058M/D130A/G163P/L227M/N233Q/L264R, D048Q/S058M/D137Q/G163P/L227M/N233Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/D027S/L075Q/N094R/V154I/G156W/T189Q, G023K/K024A/L075Q/D111A/D130A/T189Q/L264R, G023K/K024A/N094R/V154I/G156W/V187N/T189Q, G023Q/E056K/L075Q/D111A/G156W/V187N/L264R, G023Q/E056K/L075R/D111A/D130A/V187N/T189Q, G023Q/F051T/G091Q/D130A/V187H/I252Q/L264R, G023Q/L075Q/D111A/D130A/V154I/G156W/L264R, G023Q/L075Q/D130A/V154I/V187N/T189Q/L264R, G023Q/L075Q/V077I/N094R/D130A/G156W/V187N, K024A/L075Q/D111A/D130A/V154I/G156W/L264R, K024A/L075R/D130A/V154I/G156W/T189Q/L264R, N011K/A018K/K024A/V077I/V154I/G156W/T189Q, N011K/D027S/D111A/D130A/V154I/V187N/T189Q, N011K/E056K/L075Q/D111A/D130A/V154I/L264R, Q004D/N011K/D027N/S058M/I090F/N233Q/P256T, Q004D/N011K/D027Q/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/L075R/V077I/N094R/D130A/G156W/V187Q, A018K/G023Q/K024A/L075R/N094R/D130A/V154I/G156W, A018K/G023Q/K024A/L075R/V077I/N094R/D130A/G156W, G023K/D027S/F051T/E056K/L075Q/G091Q/V187H/I252Q, |

TABLE 3-1-continued

| TLL variants with Performance Index >1 compared to TLL SEQ ID NO: 1 for p-nitrophenyl butyrate hydrolysis at pH 8 are shown below. |
|---|
| G023K/E056K/L075Q/D130A/V154I/V187N/T189Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/K024A/L075Q/V077I/N094R/D130A/V154I/V187N, G023Q/L075Q/N094R/D111A/D130A/G156W/T189Q/L264R, G023Q/L075Q/N094R/D130A/V154I/G156W/T189Q/L264R, K024A/D111A/D130A/V154I/G156W/V187T/T189Q/L264R, N011K/G023K/D027S/L075Q/D111A/D130A/V154I/T189Q, A018K/G023K/K024A/L075Q/N094R/D111A/D130A/V154I/T189Q, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, A018K/G023Q/D027S/P029E/L075Q/V077I/R108K/H135F/V187H, A018K/G023Q/E045F/A049V/N073S/L075Q/R108K/V187T/T189D, G023K/D027S/F051T/E056K/S058M/L075R/G091Q/V187H/I252Q, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/E056K/L075Q/D111A/D130A/V154I/G156W/T189Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/K024A/L075Q/V077I/N094R/D130A/V154I/G156W/V187Q, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, A018K/G023Q/D027S/P029E/N033D/E045F/A049V/S058M/N073S/K074S/L075Q/V077I/N101D/R108K/ H135F/D137V/G156W/V187T/T189D |

TABLE 3-2

| TLL variants with Performance Index for expression ≥0.5 and Performance Index >1 for p-nitrophenyl butyrate hydrolysis at pH 8 compared to TLL SEQ ID NO: 1 are shown below. |
|---|
| A018K/L075D, D027S/N033D, D130A/L264R, D130A/V187N, E045F/N073R, K024A/V154I, L075R/L264R, P029E/N033D, V187T/L264R, A018K/E045F/N073R, A018K/L075D/T189D, A018K/V154I/G156W, D027E/S058M/G163P, D027S/L075Q/G091Q, D027S/N033D/T189D, D130A/V187T/L264R, G023K/E056K/V187T, G023Q/A049V/T189D, G163P/L227M/L264R, L075G/D130A/V187H, L075Q/V187N/L264R, L075R/D130A/L264R, L075R/D130A/V187T, L075R/V187T/L264R, P029E/N033D/E045F, V187N/T189Q/L264R, A018K/E045F/L075D/T189D, A018K/G023K/D111A/T189Q, A018K/L075Q/V077I/N094R, A018K/P029E/N073R/L075D, D027E/D048Q/G163P/L264R, D027E/D137Q/G163P/L227M, D027E/S058M/G163P/L264R, D027Q/E056K/N233Q/P256T, D027S/E045F/N073R/T189D, D027S/N033D/E045F/N073R, D027S/N033D/E045F/T189D, D027S/N033D/L075D/T189D, D027S/N033D/N073R/T189D, D027S/P029E/E045F/N073R, D027S/P029E/L075D/T189D, D027S/P029E/N033D/L075D, D048Q/D130A/G163P/L264R, D048Q/G163P/N233Q/L264R, E045F/A049V/G156W/V187T, E045F/L075Q/G156W/V187T, G023K/D027Q/F051T/L075Q, G023K/L075R/D130A/L264R, G023Q/A049V/V077I/G156W, G023Q/K024A/L075R/G156W, G023Q/L075Q/D130A/L264R, L075G/G091Q/V187N/L264R, N033D/E045F/N073R/T189A, P029E/N073R/L075D/T189D, Q004D/D027N/S058M/P256T, S058M/D137Q/G163P/N233Q, S058M/L075Q/G091Q/I252Q, A018K/D027S/E045F/L075D/T189D, A018K/D027S/P029E/N033D/L075D, A018K/G023Q/K024A/L075Q/G156W, A018K/G023Q/V077I/D130A/G156W, A018K/K024A/L075R/D130A/V154I, A018K/K024A/N094R/D130A/V187N, A018K/P029E/N033D/N073R/L075D, D027E/S058M/D130A/G163P/L264R, D027E/S058M/D137Q/G163P/N233Q, D027E/S058M/G163P/L227M/L264R, D027S/E056K/D111A/V187N/L264R, D027S/L075R/V154I/T189Q/L264R, D048Q/D130A/G163P/L227M/L264R, D048Q/D137Q/G163P/L227M/L264R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/D137Q/G163P/N233Q/L264R, E045F/A049V/L075Q/V187T/T189D, F051T/S058M/L075Q/G091Q/I252Q, G023K/E056K/L075R/D130A/V187T, G023K/E056K/L075R/V187T/L264R, G023K/L075Q/V077I/D130A/G156W, G023K/L075R/D130A/V187N/L264R, G023K/N094R/G156W/V187N/T189Q, G023Q/F051T/L075Q/G091Q/I252Q, G023Q/K024A/L075Q/G156W/V187Q, G023Q/L075Q/V077I/D130A/G156W, K024A/L075R/V154I/G156W/V187Q, N011K/G023K/D111A/G156W/L264R, S058M/D130A/D137Q/G163P/L264R, |

TABLE 3-2-continued

| TLL variants with Performance Index for expression ≥0.5 and Performance Index >1 for p-nitrophenyl butyrate hydrolysis at pH 8 compared to TLL SEQ ID NO: 1 are shown below. |
|---|
| S058M/D130A/G163P/L227M/L264R, S058M/G163P/L227M/N233Q/L264R, A018K/D027S/N033D/N073R/L075D/T189D, A018K/G023K/L075Q/V077I/G156W/V187Q, A018K/G023Q/K024A/L075R/N094R/G156W, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D048Q/D137Q/G163P/L227M/L264R, D027E/D048Q/S058M/D130A/G163P/L264R, D027E/D048Q/S058M/G163P/L227M/L264R, D027E/D048Q/S058M/G163P/N233Q/L264R, D027E/D137Q/G163P/L227M/N233Q/L264R, D027E/S058M/D137Q/G163P/N233Q/L264R, D027Q/E056K/S058M/D130A/I252Q/L264R, D027Q/S058M/L075R/D130A/V187T/I252Q, D027S/E056K/S058M/V187T/I252Q/L264R, D048Q/S058M/D137Q/G163P/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/E056K/D111A/D130A/V187N/T189Q, G023Q/E056K/L075Q/D130A/V154I/L264R, G023Q/F051T/D130A/V187T/I252Q/L264R, K024A/L075Q/D111A/V154I/V187N/T189Q, K024A/L075Q/N094R/D130A/V154I/L264R, K024A/L075Q/V077I/N094R/D130A/V187N, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, A018K/K024A/L075Q/V077I/N094R/D130A/G156W, D027E/D048Q/S058M/D130A/G163P/L227M/L264R, D027E/D048Q/S058M/D130A/G163P/N233Q/L264R, D048Q/S058M/D130A/D137Q/G163P/L227M/L264R, D048Q/S058M/D130A/G163P/L227M/N233Q/L264R, D048Q/S058M/D137Q/G163P/L227M/N233Q/L264R, G023K/D027S/F051T/S058M/L075Q/D130A/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, G023Q/L075Q/V077I/N094R/D130A/G156W/V187N, N011K/A018K/K024A/V077I/V154I/G156W/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, G023K/D027S/F051T/E056K/L075Q/G091Q/V187H/I252Q, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, A018K/G023K/K024A/V077I/D130A/V154I/G156W/V187T/T189Q, A018K/G023Q/D027S/P029E/L075Q/V077I/R108K/H135F/V187H, G023K/K024A/L075Q/N094R/V154I/G156W/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 3-3

| TLL variants with Performance Index for expression ≥0.5 and Performance Index ≥50% of the maximum PI value for p-nitrophenyl butyrate hydrolysis at pH 8 compared to TLL SEQ ID NO: 1 are shown below. |
|---|
| D130A/L264R, A018K/E045F/N073R, A018K/L075D/T189D, D027S/N033D/T189D, L075G/D130A/V187H, L075Q/V187N/L264R, L075R/D130A/L264R, L075R/D130A/V187T, A018K/E045F/L075D/T189D, A018K/L075Q/V077I/N094R, A018K/P029E/N073R/L075D, D027S/N033D/L075D/T189D, D027S/P029E/L075D/T189D, D027S/P029E/N033D/L075D, D048Q/D130A/G163P/L264R, G023K/D027Q/F051T/L075Q, G023K/L075R/D130A/L264R, G023Q/K024A/L075R/G156W, L075G/G091Q/V187N/L264R, P029E/N073R/L075D/T189D, A018K/D027S/E045F/L075D/T189D, A018K/D027S/P029E/N033D/L075D, |

TABLE 3-3-continued

| TLL variants with Performance Index for expression ≥0.5 and Performance Index ≥50% of the maximum PI value for p-nitrophenyl butyrate hydrolysis at pH 8 compared to TLL SEQ ID NO: 1 are shown below. |
|---|
| A018K/G023Q/K024A/L075Q/G156W, A018K/K024A/L075R/D130A/V154I, A018K/K024A/N094R/D130A/V187N, A018K/P029E/N033D/N073R/L075D, D027S/L075R/V154I/T189Q/L264R, D130A/D137Q/G163P/N233Q/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, G023Q/L075Q/V077I/D130A/G156W, K024A/L075R/V154I/G156W/V187Q, N011K/G023K/D111A/G156W/L264R, A018K/D027S/N033D/N073R/L075D/T189D, A018K/G023K/L075Q/V077I/G156W/V187Q, A018K/G023Q/N094R/D130A/G156W/V187Q, A018K/K024A/L075Q/N094R/V154I/G156W, A018K/K024A/L075Q/V077I/D130A/V187N, D027E/D048Q/D137Q/G163P/L227M/L264R, D027E/D048Q/S058M/D130A/G163P/L264R, D027E/D048Q/S058M/G163P/N233Q/L264R, D027E/D137Q/G163P/L227M/N233Q/L264R, D027Q/S058M/L075R/D130A/V187T/I252Q, D027S/E056K/S0581M/V187T/I252Q/L264R, F051T/L075G/G091Q/D130A/I252Q/L264R, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/K024A/L075Q/V154I/G156W/V187Q, G023K/K024A/L075R/D130A/V154I/V187N, G023K/N094R/D111A/G156W/V187T/L264R, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/V077I/N094R/D130A/G156W, G023Q/E056K/L075R/D111A/D130A/V187N/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, G023K/D027S/F051T/E056K/L075Q/G091Q/V187H/I252Q, G023Q/D027S/E056K/L075R/D111A/V154I/G156W/L264R, G023K/K024A/L075Q/N094R/V154I/G156W/V187N/T189Q/L264R, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023K/L075R/N094R/D111A/D130A/V154I/G156W/V187N/T189Q/L264R |

TABLE 3-4

| TLL variants with Performance Index >1 compared to Reference sequence SEQ ID NO: 2 for p-nitrophenyl butyrate hydrolysis at pH 8 are shown below. |
|---|
| A018K/L075D, D027N/E056K, D027S/N033D, D130A/L264R, D130A/V187N, E045F/N073R, K024A/L075Q, K024A/V154I, L075Q/D130A, L075R/L264R, P029E/N033D, V187T/L264R, A018K/E045F/N073R, A018K/G023K/G156W, A018K/G023K/L075Q, A018K/L075D/T189D, A018K/V154I/G156W, A049V/L075Q/T189D, A049V/V187T/T189D, D027E/S058M/G163P, D027N/N233Q/P256T, D027S/L075Q/G091Q, D027S/N033D/T189D, D130A/V187T/L264R, E045F/L075D/T189D, E056K/D130A/T189Q, G023K/D130A/V187T, G023K/E056K/V187T, G023Q/A049V/T189D, G023Q/D111A/L264R, G023Q/L075Q/V187T, G163P/L227M/L264R, K024A/D130A/V154I, L075G/D130A/V187H, L075Q/D111A/D130A, L075Q/G156W/V187N, L075Q/V187N/L264R, L075R/D130A/L264R, L075R/D130A/V187T, L075R/V187T/L264R, N073R/L075D/T189D, N094R/D130A/V187T, P029E/N033D/E045F, Q004D/D027S/P256T, V077I/D130A/V154I, V187N/T189Q/L264R, A018K/D027S/E045F/N073R, A018K/D027S/N033D/L075D, A018K/E045F/L075D/T189D, A018K/E045F/L075Q/T189D, A018K/G023K/D111A/T189Q, A018K/G023Q/E045F/T189D, A018K/G023Q/E045F/V187T, A018K/G023Q/L075R/D130A, A018K/G023Q/V077I/V187T, A018K/L075Q/G156W/V187T, A018K/L075Q/N094R/D130A, A018K/L075Q/V077I/N094R, A018K/P029E/N073R/L075D, D027E/D048Q/G163P/L264R, D027E/D137Q/G163P/L227M, D027E/S058M/G163P/L264R, D027N/E056K/N233Q/P256T, D027Q/E056K/N233Q/P256T, D027S/E045F/N073R/L075D, D027S/E045F/N073R/T189D, D027S/N033D/E045F/N073R, D027S/N033D/E045F/T189D, D027S/N033D/L075D/T189D, D027S/N033D/N073R/T189D, D027S/P029E/E045F/N073R, D027S/P029E/L075D/T189D, D027S/P029E/N033D/L075D, D048Q/D130A/G163P/L264R, D048Q/G163P/N233Q/L264R, E045F/A049V/G156W/V187T, E045F/L075Q/G156W/V187T, G023K/D027Q/F051T/L075Q, G023K/K024A/V154I/V187N, G023K/L075Q/G156W/V187N, G023K/L075R/D130A/L264R, G023Q/A049V/L075Q/V077I, G023Q/A049V/V077I/G156W, G023Q/D027S/D111A/G156W, G023Q/E045F/L075Q/V187T, G023Q/K024A/L075R/G156W, G023Q/K024A/L075R/V154I, G023Q/L075Q/D130A/L264R, G023Q/V154I/G156W/V187N, K024A/L075Q/D130A/V154I, K024A/L075R/G156W/V187N, L075G/G091Q/V187N/L264R, L075Q/D130A/G156W/V187N, L075Q/V077I/G156W/V187N, N011K/D027S/E056K/P256T, N011K/E056K/N233Q/P256T, N011K/S058M/N233Q/P256T, N033D/E045F/N073R/T189A, P029E/N033D/L075D/T189D, P029E/N073R/L075D/T189D, Q004D/D027N/E056K/P256T, Q004D/D027N/S058M/P256T, Q004D/D027S/I090F/P256T, Q004D/N011K/D027Q/N233Q, S058M/D137Q/G163P/N233Q, S058M/L075Q/G091Q/I252Q, A018K/A049V/L075Q/V187T/T189D, A018K/D027S/E045F/L075D/T189D, A018K/D027S/E045F/N073R/D137V, A018K/D027S/N033D/L075D/T189D, A018K/D027S/P029E/N033D/L075D, |

TABLE 3-4-continued

| TLL variants with Performance Index >1 compared to Reference sequence SEQ ID NO: 2 for p-nitrophenyl butyrate hydrolysis at pH 8 are shown below. |
|---|
| A018K/G023K/K024A/L075R/N094R, A018K/G023Q/E045F/A049V/V187T, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/T189D, A018K/K024A/L075R/D130A/V154I, A018K/K024A/N094R/D130A/V187N, A018K/L075Q/D111A/D130A/V187T, A018K/L075Q/N094R/D130A/V187N, A018K/L075Q/N094R/G156W/V187N, A018K/P029E/N033D/N073R/L075D, A018K/V077I/G156W/V187T/T189D, D027E/S058M/D130A/G163P/L264R, D027E/S058M/D137Q/G163P/N233Q, D027E/S058M/G163P/L227M/L264R, D027N/S058M/I090F/N233Q/P256T, D027S/E056K/D111A/V187N/L264R, D027S/E056K/S058M/N233Q/P256T, D027S/L075Q/D111A/D130A/V187N, D027S/L075R/V154I/T189Q/L264R, D027S/P029E/N033D/E045F/N073R, D048Q/D130A/G163P/L227M/L264R, D048Q/D137Q/G163P/L227M/L264R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/D137Q/G163P/N233Q/L264R, E045F/A049V/L075Q/V187T/T189D, F051T/L075G/G091Q/D130A/L264R, F051T/L075Q/G091Q/D130A/L264R, F051T/S058M/L075Q/G091Q/I252Q, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/L075R/D130A/V187N/L264R, G023K/N094R/G156W/V187N/T189Q, G023Q/A049V/L075Q/G156W/V187T, G023Q/E045F/A049V/L075Q/V077I, G023Q/F051T/L075Q/G091Q/I252Q, G023Q/K024A/L075Q/G156W/V187Q, G023Q/K024A/L075R/D130A/V154I, G023Q/L075Q/V077I/D130A/G156W, K024A/L075R/D111A/V154I/V187T, K024A/L075R/G156W/V187N/T189Q, K024A/L075R/V154I/G156W/V187Q, L075Q/D130A/V187T/T189Q/L264R, L075Q/N094R/D130A/G156W/V187T, L075R/D111A/D130A/V187N/T189Q, L075R/D130A/V154I/T189Q/L264R, L075R/D130A/V187T/T189Q/L264R, N011K/D027N/E056K/N233Q/P256T, N011K/D027Q/E056K/S058M/N233Q, N011K/D027Q/I090F/N233Q/P256T, N011K/D027S/E056K/N233Q/P256T, N011K/G023K/D111A/G156W/L264R, P029E/N033D/E045F/L075D/T189D, Q004D/D027S/E056K/N233Q/P256T, Q004D/D027S/S058M/N233Q/P256T, Q004D/N011K/D027Q/E056K/N233Q, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023K/K024A/N094R/D130A/V154I, A018K/G023K/L075Q/D130A/G156W/V187N, A018K/G023K/L075Q/V077I/G156W/V187Q, A018K/G023K/L075R/N094R/D130A/V187N, A018K/G023Q/A049V/L075Q/V077I/G156W, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/G156W/V187T/T189D, A018K/G023Q/E045F/L075Q/G156C/V187T, A018K/G023Q/K024A/L075R/N094R/G156W, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/T189Q/L264R, A018K/L075Q/D130A/V187N/T189Q/L264R, A018K/N033D/E045F/N073R/L075D/T189D, A018K/N094R/D111A/D130A/V154I/V187N, A018K/P029E/N033D/E045F/L075D/T189D, D027E/D048Q/D137Q/G163P/L227M/L264R, D027E/D048Q/S058M/D130A/G163P/L264R, D027E/D048Q/S058M/G163P/L227M/L264R, D027E/D048Q/S058M/G163P/N233Q/L264R, D027E/D137Q/G163P/L227M/N233Q/L264R, D027E/S058M/D137Q/G163P/N233Q/L264R, D027Q/E056K/S058M/D130A/I252Q/L264R, D027Q/E056K/S058M/I090F/N233Q/P256T, D027Q/F051T/L075G/G091Q/V187N/I252Q, D027Q/F051T/L075Q/D130A/V187H/L264R, D027Q/S058M/L075R/D130A/V187T/I252Q, D027S/E056K/S058M/V187T/I252Q/L264R, D027S/P029E/N033D/E045F/N073R/T189D, D048Q/S058M/D137Q/G163P/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075Q/V154I/G156W/V187Q, G023K/K024A/L075R/D130A/V154I/V187N, G023K/N094R/D111A/G156W/V187T/L264R, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/L075Q/N094R/D111A/G156W/L264R, G023Q/L075R/V154I/G156W/V187N/L264R, K024A/L075Q/D111A/V154I/V187N/T189Q, K024A/L075Q/N094R/D130A/V154I/L264R, K024A/L075Q/V077I/N094R/D130A/V187N, K024A/L075Q/V154I/V187T/T189Q/L264R, L075Q/D111A/D130A/V154I/G156W/T189Q, L075Q/D130A/V154I/G156W/V187N/L264R, L075Q/N094R/D111A/G156W/T189Q/L264R, L075R/D130A/V154I/G156W/V187N/L264R, N011K/D027N/E056K/S058M/N233Q/P256T, N011K/D027S/E056K/S058M/I090F/P256T, N011K/G023Q/L075Q/D130A/V187N/T189Q, Q004D/D027N/E056K/S058M/N233Q/P256T, Q004D/N011K/D027Q/E056K/S058M/N233Q, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/E045F/L075Q/V077I/G156W/V187T/T189D, A018K/G023K/K024A/L075Q/D130A/G156W/V187N, A018K/G023K/K024A/L075Q/N094R/G156W/V187Q, |

TABLE 3-4-continued

| TLL variants with Performance Index >1 compared to Reference sequence SEQ ID NO: 2 for p-nitrophenyl butyrate hydrolysis at pH 8 are shown below. |
|---|
| A018K/G023K/K024A/L075Q/N094R/V154I/V187Q, |
| A018K/G023K/K024A/L075R/N094R/D130A/V154I, |
| A018K/G023K/K024A/L075R/V154I/G156W/V187Q, |
| A018K/G023K/K024A/N094RV154I/V187T/L264R, |
| A018K/G023K/L075Q/V077I/N094R/V154I/G156W, |
| A018K/G023Q/E045F/A049V/L075Q/G156W/V187T, |
| A018K/G023Q/E045F/L075Q/G156W/V187T/T189D, |
| A018K/G023Q/K024A/L075Q/V077I/N094R/V154I, |
| A018K/G023Q/K024A/L075R/N094R/G156W/V187N, |
| A018K/G023Q/L075R/V077I/N094R/G156W/V187N, |
| A018K/K024A/L075Q/D130A/V154I/G156W/V187T, |
| A018K/K024A/L075Q/V077I/N094R/D130A/G156W, |
| A018K/L075Q/D111A/D130A/V154I/G156W/L264R, |
| A018K/L075Q/N094R/D111A/V154I/V187T/L264R, |
| D027E/D048Q/D130A/D137Q/G163P/N233Q/L264R, |
| D027E/D048Q/S058M/D130A/D137Q/G163P/L264R, |
| D027E/D048Q/S058M/D130A/G163P/L227M/L264R, |
| D027E/D048Q/S058M/D130A/G163P/N233Q/L264R, |
| D027E/D048Q/S058M/D137Q/G163P/L227M/L264R, |
| D027E/S058M/D130A/D137Q/G163P/N233Q/L264R, |
| D027Q/F051T/L075G/D130A/V187H/I252Q/L264R, |
| D027S/E056K/L075R/D111A/G156W/V187N/L264R, |
| D027S/F051T/L075G/G091Q/V187T/I252Q/L264R, |
| D048Q/S058M/D130A/D137Q/G163P/L227M/L264R, |
| D048Q/S058M/D130A/G163P/L227M/N233Q/L264R, |
| D048Q/S058M/D137Q/G163P/L227M/N233Q/L264R, |
| E056K/L075Q/D111A/D130A/G156W/V187N/T189Q, |
| G023K/D027Q/F051T/L075G/D130A/V187H/L264R, |
| G023K/D027S/F051T/S058M/L075Q/D130A/V187N, |
| G023K/D027S/L075Q/N094R/V154I/G156W/T189Q, |
| G023K/K024A/L075Q/D111A/D130A/T189Q/L264R, |
| G023K/K024A/N094R/V154I/G156W/V187N/T189Q, |
| G023Q/E056K/L075Q/D111A/G156W/V187N/L264R, |
| G023Q/E056K/L075R/D111A/D130A/V187N/T189Q, |
| G023Q/F051T/G091Q/D130A/V187H/I252Q/L264R, |
| G023Q/L075Q/D111A/D130A/V154I/G156W/L264R, |
| G023Q/L075Q/D130A/V154I/V187N/T189Q/L264R, |
| G023Q/L075Q/V077I/N094R/D130A/G156W/V187N, |
| K024A/L075Q/D111A/D130A/V154I/G156W/L264R, |
| K024A/L075R/D130A/V154I/G156W/T189Q/L264R, |
| N011K/A018K/K024A/V077I/V154I/G156W/T189Q, |
| N011K/D027S/D111A/D130A/V154I/V187N/T189Q, |
| N011K/E056K/L075Q/D111A/D130/V154I/L264R, |
| Q004D/N011K/D027N/S058M/I090F/N233Q/P256T, |
| Q004D/N011K/D027Q/E056K/S058M/N233Q/P256T, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/L075R/V077I/N094R/D130A/G156W/V187Q, |
| A018K/G023Q/K024A/L075R/N094R/D130A/V154I/G156W, |
| A018K/G023Q/K024A/L075R/V077I/N094R/D130A/G156W, |
| D048Q/S058M/D130A/D137Q/G163P/L227M/N233Q/L264R, |
| G023K/D027S/F051T/E056K/L075Q/G091Q/V187H/I252Q, |
| G023K/E056K/L075Q/D130A/V154I/V187N/T189Q/L264R, |
| G023Q/D027Q/F051T/S058M/L075R/D130A/V187T/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/F051T/S058M/G091Q/D130A/V187N/I252Q, |
| G023Q/D027S/L075R/N094R/V154I/G156W/V187N/T189Q, |
| G023Q/K024A/L075Q/V077I/N094R/D130A/V154I/V187N, |
| G023Q/L075Q/N094R/D111A/D130A/G156W/T189Q/L264R, |
| G023Q/L075Q/N094R/D130A/V154I/G156W/T189Q/L264R, |
| K024A/D111A/D130A/V154I/G156W/V187T/T189Q/L264R, |
| N011K/G023K/D027S/L075Q/D111A/D130A/V154I/T189Q, |
| A018K/G023K/K024A/L075Q/N094R/D111A/D130A/V154I/T189Q, |
| A018K/G023K/K024A/L075R/V077I/D130A/V154I/G156W/V187N, |
| A018K/G023K/K024A/V077I/D130A/V154I/G156W/V187T/T189Q, |
| A018K/G023K/L075Q/N094R/D111A/V154I/G156W/T189Q/L264R, |
| A018K/G023Q/D027S/P029E/L075Q/V077I/R108K/H135F/V187H, |
| A018K/G023Q/E045F/A049V/N073S/L075Q/R108K/V187T/T189D, |
| G023K/D027S/F051T/E056K/S058M/L075R/G091Q/V187H/I252Q, |
| G023K/K024A/L075Q/N094R/V154I/G156W/V187N/T189Q/L264R, |
| G023K/K024A/N094R/D130A/V154I/G156W/V187T/T189Q/L264R, |
| G023K/L075Q/D111A/D130A/V154I/G156W/V187T/T189Q/L264R, |
| G023Q/D027S/L075Q/N094R/D111A/D130A/V154I/G156W/L264R, |
| G023Q/E056K/L075Q/D111A/D130A/V154I/G156W/T189Q/L264R, |
| N011K/G023K/L075R/D111A/D130A/V154I/V187N/T189Q/L264R, |

TABLE 3-4-continued

| TLL variants with Performance Index >1 compared to Reference sequence SEQ ID NO: 2 for p-nitrophenyl butyrate hydrolysis at pH 8 are shown below. |
|---|
| N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/K024A/L075Q/V077I/N094R/D130A/V154I/G156W/V187Q, N011K/A018K/G023K/K024A/L075R/V077I/D130A/V154I/V187T/T189Q, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 3-5

| TLL variants with Performance Index for expression ≥0.5 compared to TLL SEQ ID NO: 1 and Performance Index >1 for p-nitrophenyl butyrate hydrolysis at pH 8 compared to SEQ ID NO: 2 are shown below. |
|---|
| A018K/L075D, D027S/N033D, D130A/L264R, D130A/V187N, E045F/N073R, K024A/V154I, L075R/L264R, P029E/N033D, V187T/L264R, A018K/E045F/N073R, A018K/L075D/T189D, A018K/V154I/G156W, D027E/S058M/G163P, D027S/L075Q/G091Q, D027S/N033D/T189D, D130A/V187T/L264R, G023K/D130A/V187T, G023K/E056K/V187T, G023Q/A049V/T189D, G163P/L227M/L264R, K024A/D130A/V154I, L075G/D130A/V187H, L075Q/V187N/L264R, L075R/D130A/L264R, L075R/D130A/V187T, L075R/V187T/L264R, N094R/D130A/V187T, P029E/N033D/E045F, Q004D/D027S/P256T, V187N/T189Q/L264R, A018K/E045F/L075D/T189D, A018K/G023K/D111A/T189Q, A018K/L075Q/V077I/N094R, A018K/P029E/N073R/L075D, D027E/D048Q/G163P/L264R, D027E/D137Q/G163P/L227M, D027E/S058M/G163P/L264R, D027Q/E056K/N233Q/P256T, D027S/E045F/N073R/T189D, D027S/N033D/E045F/N073R, D027S/N033D/E045F/T189D, D027S/N033D/L075D/T189D, D027S/N033D/N073R/T189D, D027S/P029E/E045F/N073R, D027S/P029E/L075D/T189D, D027S/P029E/N033D/L075D, D048Q/D130A/G163P/L264R, D048Q/G163P/N233Q/L264R, E045F/A049V/G156W/V187T, E045F/L075Q/G156W/V187T, G023K/D027Q/F051T/L075Q, G023K/K024A/V154I/V187N, G023K/L075R/D130A/L264R, G023Q/A049V/V077I/G156W, G023Q/K024A/L075R/G156W, G023Q/L075Q/D130A/L264R, L075G/G091Q/V187N/L264R, N033D/E045F/N073R/T189A, P029E/N073R/L075D/T189D, Q004D/D027N/E056K/P256T, Q004D/D027N/S058M/P256T, S058M/D137Q/G163P/N233Q, S058M/L075Q/G091Q/I252Q, A018K/D027S/E045F/L075D/T189D, A018K/D027S/P029E/N033D/L075D, A018K/G023Q/K024A/L075Q/G156W, A018K/G023Q/V077I/D130A/G156W, A018K/K024A/L075R/D130A/V154I, A018K/K024A/N094R/D130A/V187N, A018K/P029E/N033D/N073R/L075D, D027E/S058M/D130A/G163P/L264R, D027E/S058M/D137Q/G163P/N233Q, D027E/S058M/G163P/L227M/L264R, D027S/E056K/D111A/V187N/L264R, D027S/L075R/V154I/T189Q/L264R, D048Q/D130A/G163P/L227M/L264R, D048Q/D137Q/G163P/L227M/L264R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/D137Q/G163P/N233Q/L264R, E045F/A049V/L075Q/V187T/T189D, F051T/L075G/G091Q/D130A/L264R, F051T/L075Q/G091Q/D130A/L264R, F051T/S058M/L075Q/G091Q/I252Q, G023K/E056K/L075R/D130A/V187T, G023K/E056K/L075R/V187T/L264R, G023K/L075Q/V077I/D130A/G156W, G023K/L075R/D130A/V187N/L264R, G023K/N094R/G156W/V187N/T189Q, G023Q/F051T/L075Q/G091Q/I252Q, G023Q/K024A/L075Q/G156W/V187Q, G023Q/L075Q/V077I/D130A/G156W, K024A/L075R/V154I/G156W/V187Q, N011K/G023K/D111A/G156W/L264R, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023K/L075Q/V077I/G156W/V187Q, A018K/G023Q/K024A/L075R/N094R/G156W, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D048Q/D137Q/G163P/L227M/L264R, D027E/D048Q/S058M/D130A/G163P/L264R, D027E/D048Q/S058M/G163P/L227M/L264R, D027E/D048Q/S058M/G163P/N233Q/L264R, D027E/D137Q/G163P/L227M/N233Q/L264R, D027E/S058M/D137Q/G163P/N233Q/L264R, D027Q/E056K/S058M/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D048Q/S058M/D137Q/G163P/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075Q/D130A/V187H/I252Q, G023Q/K024A/D130A/V154I/G156W/V187Q, K024A/L075Q/D111A/V154I/V187N/T189Q, K024A/L075Q/N094R/D130A/V154I/L264R, K024A/L075Q/V077I/N094R/D130A/V187N, |

TABLE 3-5-continued

| TLL variants with Performance Index for expression ≥0.5 compared to TLL SEQ ID NO: 1 and Performance Index >1 for p-nitrophenyl butyrate hydrolysis at pH 8 compared to SEQ ID NO: 2 are shown below. |
| --- |
| S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, A018K/K024A/L075Q/V077I/N094R/D130A/G156W, D027E/D048Q/D130A/D137Q/G163P/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D048Q/S058M/D130A/D137Q/G163P/L227M/L264R, D048Q/S058M/D130A/G163P/L227M/N233Q/L264R, D048Q/S058M/D137Q/G163P/L227M/N233Q/L264R, G023K/D027S/F051T/S058M/L075Q/D130A/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, G023Q/L075Q/V077I/N094R/D130A/G156W/V187N, N011K/A018K/K024A/V077I/V154I/G156W/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D048Q/S058M/D130A/D137Q/G163P/L227M/N233Q/L264R, G023K/D027S/F051T/E056K/L075Q/G091Q/V187H/I252Q, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, A018K/G023K/K024A/V077I/D130A/V154I/G156W/V187T/T189Q, A018K/G023Q/D027S/P029E/L075Q/V077I/R108K/H135F/V187H, G023K/K024A/L075Q/N094R/V154I/G156W/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 3-6

| TLL variants with Performance Index for expression ≥0.5 compared to TLL SEQ ID NO: 1 and Performance Index ≥50% of the maximum PI value for p-nitrophenyl butyrate hydrolysis at pH 8 compared to SEQ ID NO: 2 are shown below. |
| --- |
| D130A/L264R, A018K/E045F/N073R, A018K/L075D/T189D, D027S/N033D/T189D, L075G/D130A/V187H, L075Q/V187N/L264R, L075R/D130A/L264R, L075R/D130A/V187T, A018K/E045F/L075D/T189D, A018K/L075Q/V077I/N094R, A018K/P029E/N073R/L075D, D027S/N033D/L075D/T189D, D027S/P029E/L075D/T189D, D027S/P029E/N033D/L075D, D048Q/D130A/G163P/L264R, G023K/D027Q/F051T/L075Q, G023K/L075R/D130A/L264R, G023Q/K024A/L075R/G156W, L075G/G091Q/V187N/L264R, P029E/N073R/L075D/T189D, A018K/D027S/E045F/L075D/T189D, A018K/D027S/P029E/N033D/L075D, A018K/G023Q/K024A/L075Q/G156W, A018K/K024A/L075R/D130A/V154I, A018K/K024A/N094R/D130A/V187N, A018K/P029E/N033D/N073R/L075D, D027S/L075R/V154I/T189Q/L264R, D130A/D137Q/G163P/N233Q/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, G023Q/L075Q/V077I/D130A/G156W, K024A/L075R/V154I/G156W/V187Q, N011K/G023K/D111A/G156W/L264R, A018K/D027S/N033D/N073R/L075D/T189D, A018K/G023K/L075Q/V077I/G156W/V187Q, A018K/G023Q/N094R/D130A/G156W/V187Q, A018K/K024A/L075Q/N094R/V154I/G156W, A018K/K024A/L075Q/V077I/D130A/V187N, D027E/D048Q/D137Q/G163P/L227M/L264R, D027E/D048Q/S058M/D130A/G163P/L264R, D027E/D048Q/S058M/G163P/N233Q/L264R, D027E/D137Q/G163P/L227M/N233Q/L264R, D027Q/S058M/L075R/D130A/V187T/I252Q, D027S/E056K/S058M/V187T/I252Q/L264R, F051T/L075G/G091Q/D130A/I252Q/L264R, |

TABLE 3-6-continued

| TLL variants with Performance Index for expression ≥0.5 compared to TLL SEQ ID NO: 1 and Performance Index ≥50% of the maximum PI value for p-nitrophenyl butyrate hydrolysis at pH 8 compared to SEQ ID NO: 2 are shown below. |
|---|
| G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/K024A/L075Q/V154I/G156W/V187Q, G023K/K024A/L075R/D130A/V154I/V187N, G023K/N094R/D111A/G156W/V187T/L264R, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/V077I/N094R/D130A/G156W, G023Q/E056K/L075R/D111A/D130A/V187N/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, G023K/D027S/F051T/E056K/L075Q/G091Q/V187H/I252Q, G023Q/D027S/E056K/L075R/D111A/V154I/G156W/L264R, G023K/K024A/L075Q/N094R/V154I/G156W/V187N/T189Q/L264R, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023K/L075R/N094R/D111A/D130A/V154I/G156W/V187N/T189Q/L264R |

TABLE 3-7

| TLL variants with Performance Index >1 compared to TLL SEQ ID NO: 1 for p-nitrophenyl caprylate (octanoate) hydrolysis at pH 8 are shown below. |
|---|
| A018K/L075Q, D027S/N033D, D130A/L264R, K024A/L075Q, L227M/L264R, P029E/N033D, A018K/G023K/L075Q, A018K/G023Q/L075Q, A018K/L075D/T189D, A018K/L075Q/G156W, A018K/L075Q/V187T, A018K/N073R/L075D, A018K/P029E/T189D, A049V/V187T/T189D, D027S/N033D/T189D, E045F/N073R/L075D, G023K/V187N/L264R, G023Q/L075Q/V187T, L075G/D130A/V187H, L075Q/D111A/D130A, L075Q/D130A/V187T, L075Q/G156W/T189D, L075Q/G156W/V187N, L075Q/V187N/L264R, L075R/D130A/L264R, L075R/D130A/V187T, N073R/L075D/T189D, P029E/N033D/E045F, V077I/V187A/T189D, A018K/A049V/L075Q/T189D, A018K/D027S/N033D/L075D, A018K/D027S/P029E/T189D, A018K/E045F/L075D/T189D, A018K/E045F/L075Q/V187T, A018K/G023K/D111A/T189Q, A018K/G023Q/E045F/V187T, A018K/G023Q/G156W/V187T, A018K/G023Q/L075Q/V077I, A018K/G023Q/L075Q/V187T, A018K/G023Q/L075R/D130A, A018K/G023Q/V077I/V187T, A018K/G023Q/V187T/T189D, A018K/L075Q/G156W/V187T, A018K/L075Q/N094R/D111A, A018K/L075Q/V077I/N094R, A018K/P029E/N033D/T189D, D027E/D137Q/G163P/L227M, D027E/L227M/N233Q/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075Q/G156W/V187N, G023K/L075R/D130A/L264R, G023Q/E045F/A049V/T189D, G023Q/E045F/L075Q/G156W, G023Q/K024A/L075R/V154I, K024A/L075Q/D130A/G156W, K024A/L075Q/V187T/T189Q, K024A/L075R/G156W/V187N, L075Q/D130A/G156W/V187N, L075Q/V077I/D130A/V187Q, L075Q/V077I/V187T/T189D, L075R/D130A/V154I/L264R, N011K/D027S/E056K/P256T, N011K/S058M/N233Q/P256T, P029E/E045F/L075D/T189D, P029E/N033D/L075D/T189D, P029E/N073R/L075D/T189D, Q004D/N011K/D027N/P256T, A018K/D027S/N033D/L075D/T189D, A018K/D027S/P029E/E045F/T189D, A018K/D027S/P029E/N033D/L075D, A018K/D027S/P029E/N073R/L075D, A018K/G023K/K024A/L075R/N094R, A018K/G023Q/A049V/L075Q/V187T, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/K024A/L075Q/D130A/L264R, A018K/K024A/L075Q/V154I/G156W, A018K/K024A/N094R/D130A/V187N, A018K/L075Q/D111A/D130A/V187T, A018K/L075Q/N094R/D130A/V187N, A018K/L075Q/N094R/G156W/V187N, A018K/L075Q/V077I/N094R/G156W, A018K/P029E/N033D/N073R/L075D, D027E/D048Q/S058M/G163P/N233Q, D027E/D130A/G163P/N233Q/L264R, D027S/E056K/S058M/N233Q/P256T, D027S/L075R/V154I/T189Q/L264R, D027S/P029E/N033D/E045F/N073R, D130A/D137Q/G163P/N233Q/L264R, E056K/L075Q/G156W/T189Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/N094R/G156W/V187N/T189Q, G023Q/A049V/L075Q/G156W/V187T, G023Q/A049V/L075Q/V187T/T189D, G023Q/D027S/V154I/V187N/L264R, G023Q/E045F/L075Q/V077I/V187T, G023Q/K024A/L075Q/G156W/V187Q, G023Q/K024A/L075Q/V077I/V187Q, G023Q/K024A/V077I/D130A/V154I, G023Q/L075Q/V077I/D130A/G156W, G023Q/L075Q/V077I/G156W/V187N, K024A/L075R/V154I/G156W/V187Q, L075R/D130A/V154I/T189Q/L264R, L075R/D130A/V187T/T189Q/L264R, N011K/D027N/E056K/N233Q/P256T, N011K/G023K/D111A/G156W/L264R, |

TABLE 3-7-continued

| TLL variants with Performance Index >1 compared to TLL SEQ ID NO: 1 for p-nitrophenyl caprylate (octanoate) hydrolysis at pH 8 are shown below. |
|---|
| N011K/G023K/E056K/L075Q/T189Q, A018K/D027S/N033D/N073R/L075D/T189D, A018K/D027S/P029E/N033D/E045F/L075D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/L075Q/D130A/G156W/V187N, A018K/G023K/L075Q/V077I/G156W/V187Q, A018K/G023K/L075R/N094R/D130A/V187N, A018K/G023K/L075R/V077I/D130A/V154I, A018K/G023Q/K024A/L075R/N094R/G156W, A018K/G023Q/L075Q/G156W/V187T/T189D, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/N094R/D111A/D130A/V154I/V187N, D027E/D048Q/D130A/D137Q/G163P/L264R, D027E/D048Q/D137Q/G163P/L227M/L264R, D027E/D048Q/S058M/G163P/N233Q/L264R, D027E/D130A/D137Q/G163P/L227M/L264R, D027E/D130A/G163P/L227M/N233Q/L264R, D027Q/F051T/L075Q/D130A/V187H/L264R, D027Q/S058M/L075R/D130A/V187T/I252Q, D027S/P029E/N033D/E045F/N073R/T189D, D048Q/S058M/D130A/G163P/N233Q/L264R, E045F/A049V/L075Q/V077I/V187T/T189D, G023K/D027S/L075R/D130A/V187T/I252Q, G023K/E056K/L075R/D130A/T189Q/L264R, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/N094R/D111A/G156W/V187T/L264R, G023Q/E045F/A049V/L075Q/V077I/V187T, G023Q/E045F/L075Q/V077I/G156W/V187T, G023Q/K024A/L075Q/D130A/V154I/G156W, G023Q/L075R/V154I/G156W/V187N/L264R, K024A/L075Q/D111A/V154I/V187N/T189Q, K024A/L075Q/D130A/G156W/T189Q/L264R, K024A/L075Q/V077I/N094R/D130A/V187N, K024A/L075Q/V154I/V187N/T189Q/L264R, K024A/L075Q/V154I/V187T/T189Q/L264R, L075R/D130A/V154I/G156W/V187N/L264R, N011K/D027N/E056K/S058M/N233Q/P256T, N011K/D027S/E056K/S058M/N233Q/P256T, N011K/E056K/L075Q/D130A/V187N/T189Q, Q004D/D027N/E056K/S058M/N233Q/P256T, A018K/D027S/P029E/N033D/N073R/L075D/T189D, |
| A018K/G023K/K024A/L075Q/D130A/G156W/V187N, |
| A018K/G023K/K024A/L075Q/N094R/G156W/V187Q, |
| A018K/G023K/K024A/L075Q/N094R/V154I/V187Q, |
| A018K/G023K/K024A/L075Q/V077I/N094R/G156W, |
| A018K/G023K/K024A/L075R/N094R/D130A/V1541, |
| A018K/G023K/K024A/L075R/V154I/G156W/V187Q, |
| A018K/G023K/K024A/N094R/V154I/V187T/L264R, |
| A018K/G023K/L075Q/V077I/N094R/V154I/G156W, |
| A018K/G023Q/E045F/A049V/L075Q/G156W/V187T, |
| A018K/G023Q/K024A/L075Q/V077I/N094R/V154I, |
| A018K/G023Q/K024A/L075R/D130A/V154I/V187N, |
| A018K/G023Q/K024A/L075R/V077I/D130A/G156W, |
| A018K/G023Q/L075R/V077I/N094R/G156W/V187N, |
| A018K/K024A/L075Q/D111A/G156W/V187N/L264R, |
| A018K/K024A/L075Q/D130A/G156W/V187T/T189Q, |
| A018K/K024A/L075Q/V077I/N094R/D130A/G156W, |
| A018K/L075Q/D111A/V154I/V187T/T189Q/L264R, |
| A018K/L075Q/N094R/D111A/V154I/V187T/L264R, |
| D027E/D130A/D137Q/G163P/L227M/N233Q/L264R, |
| D027Q/F051T/L075G/D130A/V187H/I252Q/L264R, |
| D027S/F051T/L075G/G091Q/V187T/I252Q/L264R, |
| D048Q/D130A/D137Q/G163P/L227M/N233Q/L264R, |
| E056K/L075Q/D111A/D130A/G156W/V187N/T189Q, |
| G023K/D027Q/F051T/L075G/D130A/V187H/L264R, |
| G023K/D027S/F051T/S058M/L075Q/D130A/V187N, |
| G023K/K024A/L075Q/D111A/D130A/T189Q/L264R, |
| G023K/K024A/L075Q/D111A/V154I/G156W/V187N, |
| G023K/L075R/N094R/V154I/G156W/V187N/L264R, |
| G023Q/D027S/L075Q/G091Q/V187T/I252Q/L264R, |
| G023Q/E056K/L075Q/D111A/G156W/V187N/L264R, |
| G023Q/E056K/L075Q/D130A/V154I/G156W/T189Q, |
| G023Q/E056K/L075R/D111A/D130A/V187N/T189Q, |
| G023Q/L075Q/D111A/D130A/V154I/G156W/L264R, |
| G023Q/L075Q/D130A/V154I/G156W/T189Q/L264R, |
| G023Q/L075Q/D130A/V154I/V187N/T189Q/L264R, |
| K024A/L075Q/D111A/D130A/V154I/G156W/L264R, |
| K024A/L075Q/D111A/D130A/V187N/T189Q/L264R, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023Q/K024A/L075Q/V077I/D130A/G156W/V187Q, |
| A018K/G023Q/K024A/L075R/N094R/D130A/V154I/G156W, |
| A018K/K024A/L075Q/V077I/N094R/D130A/V154I/G156W, |
| A018K/K024A/L075R/D130A/V154I/G156W/V187T/L264R, |
| D027E/D048Q/D130A/D137Q/G163P/L227M/N233Q/L264R, |
| G023K/D027S/E056K/L075G/D130A/V187T/I252Q/L264R, |
| G023K/D027S/F051T/E056K/L075Q/G091Q/V187H/I252Q, |

TABLE 3-7-continued

| TLL variants with Performance Index >1 compared to TLL SEQ ID NO: 1 for p-nitrophenyl caprylate (octanoate) hydrolysis at pH 8 are shown below. |
|---|
| G023K/K024A/L075R/N094R/V154I/G156W/V187T/T189Q, G023K/L075Q/D111A/V154I/G156W/V187N/T189Q/L264R, G023Q/D027S/E056K/S058M/L075R/G091Q/V187N/I252Q, G023Q/D027S/L075R/N094R/V154I/G156W/V187N/T189Q, G023Q/E056K/L075Q/N094R/D111A/G156W/T189Q/L264R, G023Q/K024A/L075Q/V077I/D130A/V154I/G156W/V187N, G023Q/K024A/L075Q/V077I/N094R/D130A/V154I/V187N, G023Q/L075Q/N094R/D111A/D130A/G156W/T189Q/L264R, K024A/D111A/D130A/V154I/G156W/V187T/T189Q/L264R, N011K/G023Q/D027S/L075Q/N094R/V154I/G156W/T189Q, A018K/G023K/K024A/L075Q/N094R/D111A/D130A/V154I/T189Q, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, G023K/D027S/F051T/E056K/S058M/L075R/G091Q/V187H/I252Q, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D130A/V154I/G156W/V187N/L264R, N011K/G023K/L075R/D111A/D130A/V154I/V187N/T189Q/L264R, A018K/G023Q/D027S/E045F/A049V/S058M/L075Q/R108K/V187T/T189D, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, A018K/G023K/L075R/N094R/D111A/D130A/V154I/G156W/V187N/T189Q/L264R, A018K/G023Q/D027S/P029E/E045F/A049V/S058M/N073S/L075Q/R108K/V187T/T189D |

TABLE 3-8

| TLL variants with Performance Index for expression ≥0.5 and Performance Index >1 for p-nitrophenyl caprylate (octanoate) hydrolysis at pH 8 compared to TLL SEQ ID NO: 1 are shown below. |
|---|
| D027S/N033D, D130A/L264R, L227M/L264R, P029E/N033D, A018K/L075D/T189D, A018K/P029E/T189D, D027S/N033D/T189D, G023K/V187N/L264R, L075G/D130A/V187H, L075Q/V187N/L264R, L075R/D130A/L264R, L075R/D130A/V187T, P029E/N033D/E045F, A018K/D027S/P029E/T189D, A018K/E045F/L075D/T189D, A018K/G023K/D111A/T189Q, A018K/L075Q/V077I/N094R, D027E/D137Q/G163P/L227M, D027E/L227M/N233Q/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075R/D130A/L264R, P029E/N073R/L075D/T189D, A018K/D027S/P029E/N033D/L075D, A018K/G023Q/K024A/L075Q/G156W, A018K/K024A/N094R/D130A/V187N, A018K/P029E/N033D/N073R/L075D, D027E/D130A/G163P/N233Q/L264R, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, G023Q/L075Q/V077I/D130A/G156W, K024A/L075R/V154I/G156W/V187Q, N011K/G023K/D111A/G156W/L264R, A018K/D027S/N033D/N073R/L075D/T189D, A018K/D027S/P029E/N033D/E045F/L075D, A018K/G023K/L075Q/V077I/G156W/V187Q, A018K/G023Q/K024A/L075R/N094R/G156W, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137Q/G163P/L264R, D027E/D048Q/D137Q/G163P/L227M/L264R, D027E/D048Q/S058M/G163P/N233Q/L264R, D027E/D130A/D137Q/G163P/L227M/L264R, D027E/D130A/G163P/L227M/N233Q/L264R, D027Q/S058M/L075R/D130A/V187T/I252Q, G023K/D027S/L075R/D130A/V187T/I252Q, G023K/E056K/L075R/D130A/T189Q/L264R, G023K/K024A/L075Q/V154I/G156W/V187Q, G023K/K024A/L075R/D130A/V154I/V187N, G023K/N094R/D111A/G156W/V187T/L264R, K024A/L075Q/D111A/V154I/V187N/T189Q, K024A/L075Q/V077I/N094R/D130A/V187N, A018K/D027S/P029E/N033D/N073R/L075D/T189D, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/V077I/N094R/D130A/G156W, D027E/D130A/D137Q/G163P/L227M/N233Q/L264R, D048Q/D130A/D137Q/G163P/L227M/N233Q/L264R, G023K/D027S/F051T/S058M/L075Q/D130A/V187N, G023Q/E056K/L075R/D111A/D130A/V187N/T189Q, A018K/G023K/K024A/L075Q/N094R/D130A/G156W/V187Q, A018K/G023K/K024A/L075Q/V077I/N094R/D130A/G156W, |

TABLE 3-8-continued

| TLL variants with Performance Index for expression ≥0.5 and Performance Index >1 for p-nitrophenyl caprylate (octanoate) hydrolysis at pH 8 compared to TLL SEQ ID NO: 1 are shown below. |
|---|
| D027E/D048Q/D130A/D137Q/G163P/L227M/N233Q/L264R, G023K/D027S/F051T/E056K/L075Q/G091Q/V187H/I252Q, G023Q/D027S/L075R/N094R/V154I/G156W/V187N/T189Q, A018K/G023K/K024A/V077I/D130A/V154I/G156W/V187T/T189Q, G023K/K024A/L075Q/N094R/V154I/G156W/V187N/T189Q/L264R, A018K/G023Q/D027S/P029E/S058M/L075Q/V077I/R108K/H135F/V187H, A018K/G023K/L075R/N094R/D111A/D130A/V154I/G156W/V187N/T189Q/L264R |

TABLE 3-9

| TLL variants with Performance Index for expression ≥0.5 and Performance Index ≥50% of the maximum PI value for p-nitrophenyl caprylate (octanoate) hydrolysis at pH 8 compared to TLL SEQ ID NO: 1 are shown below. |
|---|
| L227M/L264R, A018K/L075D/T189D, A018K/P029E/T189D, D027S/N033D/T189D, G023K/V187N/L264R, L075R/D130A/V187T, A018K/D027S/P029E/T189D, A018K/L075Q/V077I/N094R, D027E/L227M/N233Q/L264R, D027S/N033D/L075D/T189D, D027S/P029E/E045F/T189D, D027S/P029E/N033D/E045F, D027S/P029E/N033D/L075D, D048Q/D130A/G163P/L264R, D130A/G163P/L227M/L264R, G023K/L075R/D130A/L264R, P029E/N073R/L075D/T189D, A018K/D027S/P029E/N033D/L075D, A018K/K024A/N094R/D130A/V187N, A018K/P029E/N033D/N073R/L075D, D027E/D130A/G163P/N233Q/L264R, D027S/L075R/V154I/T189Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, K024A/L075R/V154I/G156W/V187Q, A018K/D027S/P029E/N033D/E045F/L075D, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D130A/D137Q/G163P/L227M/L264R, D027E/D130A/G163P/L227M/N233Q/L264R, G023K/E056K/L075R/D130A/T189Q/L264R, G023K/K024A/L075Q/V154I/G156W/V187Q, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023Q/L075R/V077I/N094R/G156W/V187N, A018K/K024A/L075Q/V077I/N094R/D130A/G156W, A018K/G023K/K024A/L075Q/V077I/N094R/D130A/G156W, D027E/D048Q/D130A/D137Q/G163P/L227M/N233Q/L264R, G023K/K024A/L075Q/N094R/V154I/G156W/V187N/T189Q/L264R, A018K/G023K/L075R/N094R/D111A/D130A/V154I/G156W/V187N/T189Q/L264R |

TABLE 3-10

| TLL variants with Performance Index >1 compared to Reference sequence SEQ ID NO: 2 for p-nitrophenyl caprylate (octanoate) hydrolysis at pH 8 are shown below. |
|---|
| A018K/L075Q, D130A/L264R, K024A/L075Q, L227M/L264R, A018K/G023K/L075Q, A018K/G023Q/L075Q, A018K/L075D/T189D, A018K/L075Q/G156W, A018K/L075Q/V187T, A018K/N073R/L075D, A018K/P029E/T189D, A049V/V187T/T189D, D027S/N033D/T189D, E045F/N073R/L075D, G023K/V187N/L264R, G023Q/L075Q/V187T, L075G/D130A/V187H, L075Q/D111A/D130A, L075Q/D130A/V187T, L075Q/G156W/T189D, L075Q/G156W/V187N, L075R/D130A/L264R, L075R/D130A/V187T, N073R/L075D/T189D, V077I/V187A/T189D, A018K/A049V/L075Q/T189D, A018K/D027S/N033D/L075D, A018K/D027S/P029E/T189D, A018K/E045F/L075Q/V187T, A018K/G023K/D111A/T189Q, A018K/G023Q/L075Q/V077I, A018K/G023Q/L075Q/V187T, A018K/G023Q/L075R/D130A, A018K/G023Q/V187T/T189D, A018K/L075Q/N094R/D111A, A018K/L075Q/V077I/N094R, A018K/P029E/N033D/T189D, D027E/L227M/N233Q/L264R, D027S/N033D/L075D/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075R/D130A/L264R, G023Q/E045F/L075Q/G156W, G023Q/K024A/L075R/V154I, K024A/L075Q/D130A/G156W, K024A/L075Q/V187T/T189Q, K024A/L075R/G156W/V187N, L075Q/D130A/G156W/V187N, L075Q/V077I/D130A/V187Q, L075Q/V077I/V187T/T189D, L075R/D130A/V154I/L264R, P029E/E045F/L075D/T189D, P029E/N033D/L075D/T189D, P029E/N073R/L075D/T189D, Q004D/N011K/D027N/P256T, A018K/D027S/N033D/L075D/T189D, A018K/D027S/P029E/E045F/T189D, A018K/D027S/P029E/N033D/L075D, A018K/D027S/P029E/N073R/L075D, A018K/G023K/K024A/L075R/N094R, A018K/G023Q/E045F/L075Q/V187T, A018K/G023Q/K024A/L075Q/G156W, A018K/G023Q/L075Q/G156W/V187T, A018K/K024A/L075Q/V154I/G156W, A018K/K024A/N094R/D130A/V187N, A018K/L075Q/D111A/D130A/V187T, A018K/L075Q/N094R/D130A/V187N, A018K/L075Q/N094R/G156W/V187N, A018K/L075Q/V077I/N094R/G156W, A018K/P029E/N033D/N073R/L075D, |

TABLE 3-10-continued

| TLL variants with Performance Index >1 compared to Reference sequence SEQ ID NO: 2 for p-nitrophenyl caprylate (octanoate) hydrolysis at pH 8 are shown below. |
| --- |
| D027E/D048Q/S058M/G163P/N233Q, D027E/D130A/G163P/N233Q/L264R, D027S/L075R/V154I/T189Q/L264R, D027S/P029E/N033D/E045F/N073R, D130A/D137Q/G163P/N233Q/L264R, E056K/L075Q/G156W/T189Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/N094R/G156W/V187N/T189Q, G023Q/A049V/L075Q/G156W/V187T, G023Q/A049V/L075Q/V187T/T189D, G023Q/E045F/L075Q/V077I/V187T, G023Q/K024A/L075Q/G156W/V187Q, G023Q/K024A/L075Q/V077I/V187Q, G023Q/K024A/V077I/D130A/V154I, G023Q/L075Q/V077I/G156W/V187N, K024A/L075R/V154I/G156W/V187Q, L075R/D130A/V187T/T189Q/L264R, N011K/D027N/E056K/N233Q/P256T, N011K/G023K/E056K/L075Q/T189Q, A018K/D027S/N033D/N073R/L075D/T189D, A018K/D027S/P029E/N033D/E045F/L075D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/L075Q/D130A/G156W/V187N, A018K/G023K/L075R/N094R/D130A/V187N, A018K/G023K/L075R/V077I/D130A/V154I, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/L075Q/D130A/V154I/T189Q/L264R, D027E/D048Q/D130A/D137Q/G163P/L264R, D027E/D048Q/D137Q/G163P/L227M/L264R, D027E/D048Q/S058M/G163P/N233Q/L264R, D027E/D130A/D137Q/G163P/L227M/L264R, D027E/D130A/G163P/L227M/N233Q/L264R, D027Q/F051T/L075Q/D130A/V187H/L264R, D027Q/S058M/L075R/D130A/V187T/I252Q, D048Q/S058M/D130A/G163P/N233Q/L264R, E045F/A049V/L075Q/V077I/V187T/T189D, G023K/D027S/L075R/D130A/V187T/I252Q, G023K/E056K/L075R/D130A/T189Q/L264R, G023K/K024A/L075Q/N094R/D130A/G156W, G023K/K024A/L075Q/V154I/G156W/V187Q, G023K/L075Q/D111A/D130A/V154I/V187N, G023K/L075Q/N094R/V154I/V187T/L264R, G023Q/K024A/L075Q/D130A/V154I/G156W, K024A/L075Q/D111A/V154I/V187N/T189Q, K024A/L075Q/D130A/G156W/T189Q/L264R, K024A/L075Q/V154I/V187N/T189Q/L264R, K024A/L075Q/V154I/V187T/T189Q/L264R, L075R/D130A/V154I/G156W/V187N/L264R, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/K024A/L075Q/V077I/N094R/V154I, A018K/G023Q/K024A/L075R/D130A/V154I/V187N, A018K/G023Q/K024A/L075R/V077I/D130A/G156W, A018K/G023Q/L075R/V077I/N094R/G156W/V187N, A018K/K024A/L075Q/D111A/G156W/V187N/L264R, A018K/K024A/L075Q/D130A/G156W/V187T/T189Q, A018K/K024A/L075Q/V077I/N094R/D130A/G156W, A018K/L075Q/D111A/V154I/V187T/T189Q/L264R, D027E/D130A/D137Q/G163P/L227M/N233Q/L264R, E056K/L075Q/D111A/D130A/G156W/V187N/T189Q, G023K/D027Q/F051T/L075G/D130A/V187H/L264R, G023K/K024A/L075Q/D111A/V154I/G156W/V187N, G023K/L075R/N094R/V154I/G156W/V187N/L264R, G023Q/D027S/L075Q/G091Q/V187T/I252Q/L264R, G023Q/E056K/L075Q/D111A/G156W/V187N/L264R, G023Q/E056K/L075Q/D130A/V154I/G156W/T189Q, G023Q/E056K/L075R/D111A/D130A/V187N/T189Q, G023Q/L075Q/D130A/V154I/G156W/T189Q/L264R, G023Q/L075Q/D130A/V154I/V187N/T189Q/L264R, K024A/L075Q/D111A/D130A/V154I/G156W/L264R, K024A/L075Q/D111A/D130A/V187N/T189Q/L264R, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/N094R/D130A/G156W, A018K/G023K/K024A/L075R/D111A/V154I/V187T/L264R, A018K/G023K/L075Q/V077I/D130A/V154I/G156W/V187N, A018K/G023Q/K024A/L075Q/V077I/D130A/G156W/V187Q, A018K/G023Q/K024A/L075R/N094R/D130A/V154I/G156W, A018K/K024A/L075Q/V077I/N094R/D130A/V154I/G156W, A018K/K024A/L075R/D130A/V154I/G156W/V187T/L264R, D027E/D048Q/D130A/D137Q/G163P/L227M/N233Q/L264R, G023K/D027S/E056K/L075G/D130A/V187T/I252Q/L264R, G023K/D027S/F051T/E056K/L075Q/G091Q/V187H/I252Q, G023K/K024A/L075R/N094R/V154I/G156W/V187T/T189Q, G023K/L075Q/D111A/V154I/G156W/V187N/T189Q/L264R, G023Q/D027S/E056K/S058M/L075R/G091Q/V187N/I252Q, G023Q/E056K/L075Q/N094R/D111A/G156W/T189Q/L264R, G023Q/K024A/L075Q/V077I/N094R/D130A/V154I/V187N, |

TABLE 3-10-continued

| TLL variants with Performance Index >1 compared to Reference sequence SEQ ID NO: 2 for p-nitrophenyl caprylate (octanoate) hydrolysis at pH 8 are shown below. |
|---|
| G023Q/L075Q/N094R/D111A/D130A/G156W/T189Q/L264R, K024A/D111A/D130A/V154I/G156W/V187T/T189Q/L264R, N011K/G023Q/D027S/L075Q/N094R/V154I/G156W/T189Q, A018K/G023K/K024A/L075Q/N094R/D111A/D130A/V154I/T189Q, A018K/G023K/K024A/L075R/V077I/D130A/V154I/G156W/V187N, A018K/G023K/L075Q/N094R/D111A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023Q/D027S/L075Q/N094R/D130A/V154I/G156W/V187N/L264R, N011K/G023K/L075R/D111A/D130A/V154I/V187N/T189Q/L264R, A018K/G023Q/D027S/E045F/A049V/S058M/L075Q/R108K/V187T/T189D, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, A018K/G023K/L075R/N094R/D111A/D130A/V154I/G156W/V187N/T189Q/L264R, A018K/G023Q/D027S/P029E/E045F/A049V/S058M/N073S/L075Q/R108K/V187T/T189D |

TABLE 3-11

| TLL variants with Performance Index for expression ≥0.5 compared to TLL SEQ ID NO: 1 and Performance Index >1 for p-nitrophenyl caprylate (octanoate) hydrolysis at pH 8 compared to SEQ ID NO: 2 are shown below. |
|---|
| D130A/L264R, L227M/L264R, A018K/L075D/T189D, A018K/P029E/T189D, D027S/N033D/T189D, G023K/V187N/L264R, L075G/D130A/V187H, L075R/D130A/L264R, L075R/D130A/V187T, A018K/D027S/P029E/T189D, A018K/G023K/D111A/T189Q, A018K/L075Q/V077I/N094R, D027E/L227M/N233Q/L264R, D027S/N033D/L075D/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075R/D130A/L264R, P029E/N073R/L075D/T189D, A018K/D027S/P029E/N033D/L075D, A018K/G023Q/K024A/L075Q/G156W, A018K/K024A/N094R/D130A/V187N, A018K/P029E/N033D/N073R/L075D, D027E/D130A/G163P/N233Q/L264R, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, K024A/L075R/V154I/G156W/V187Q, A018K/D027S/N033D/N073R/L075D/T189D, A018K/D027S/P029E/N033D/E045F/L075D, A018K/G023Q/N094R/D130A/G156W/V187Q, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D048Q/S058M/G163P/N233Q/L264R, D027E/D130A/D137Q/G163P/L227M/L264R, D027E/D130A/G163P/L227M/N233Q/L264R, D027Q/S058M/L075R/D130A/V187T/I252Q, G023K/D027S/L075R/D130A/V187T/I252Q, G023K/E056K/L075R/D130A/T189Q/L264R, G023K/K024A/L075Q/V154I/G156W/V187Q, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/V077I/N094R/D130A/G156W, D027E/D130A/D137Q/G163P/L227M/N233Q/L264R, G023Q/E056K/L075R/D111A/D130A/V187N/T189Q, A018K/G023K/K024A/L075Q/N094R/D130A/G156W/V187Q, A018K/G023K/K024A/L075Q/V077I/N094R/D130A/G156W, D027E/D048Q/D130A/D137Q/G163P/L227M/N233Q/L264R, G023K/D027S/F051T/E056K/L075Q/G091Q/V187H/I252Q, G023K/K024A/L075Q/N094R/V154I/G156W/V187N/T189Q/L264R, A018K/G023Q/D027S/P029E/S058M/L075Q/V077I/R108K/H135F/V187H, A018K/G023K/L075R/N094R/D111A/D130A/V154I/G156W/V187N/T189Q/L264R |

TABLE 3-12

| TLL variants with Performance Index for expression ≥0.5 compared to TLL SEQ ID NO: 1 and Performance Index ≥50% of the maximum PI value for p-nitrophenyl caprylate (octanoate) hydrolysis at pH 8 compared to SEQ ID NO: 2 are shown below. |
|---|
| L227M/L264R, A018K/L075D/T189D, A018K/P029E/T189D, D027S/N033D/T189D, G023K/V187N/L264R, L075R/D130A/V187T, A018K/D027S/P029E/T189D, A018K/L075Q/V077I/N094R, D027E/L227M/N233Q/L264R, D027S/N033D/L075D/T189D, D027S/P029E/E045F/T189D, D027S/P029E/N033D/E045F, D027S/P029E/N033D/L075D, D048Q/D130A/G163P/L264R, D130A/G163P/L227M/L264R, G023K/L075R/D130A/L264R, P029E/N073R/L075D/T189D, A018K/D027S/P029E/N033D/L075D, |

TABLE 3-12-continued

| TLL variants with Performance Index for expression ≥0.5 compared to TLL SEQ ID NO: 1 and Performance Index ≥50% of the maximum PI value for p-nitrophenyl caprylate (octanoate) hydrolysis at pH 8 compared to SEQ ID NO: 2 are shown below. |
|---|
| A018K/K024A/N094R/D130A/V187N, A018K/P029E/N033D/N073R/L075D, D027E/D130A/G163P/N233Q/L264R, D027S/L075R/V154I/T189Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, K024A/L075R/V154I/G156W/V187Q, A018K/D027S/P029E/N033D/E045F/L075D, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D130A/D137Q/G163P/L227M/L264R, D027E/D130A/G163P/L227M/N233Q/L264R, G023K/E056K/L075R/D130A/T189Q/L264R, G023K/K024A/L075Q/V154I/G156W/V187Q, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023Q/L075R/V077I/N094R/G156W/V187N, A018K/K024A/L075Q/V077I/N094R/D130A/G156W, A018K/G023K/K024A/L075Q/V077I/N094R/D130A/G156W, D027E/D048Q/D130A/D137Q/G163P/L227M/N233Q/L264R, G023K/K024A/L075Q/N094R/V154I/G156W/V187N/T189Q/L264R, A018K/G023K/L075R/N094R/D111A/D130A/V154I/G156W/V187N/T189Q/L264R |

TABLE 3-13

| TLL variants with Performance Index >1 compared to TLL SEQ ID NO: 1 for p-nitrophenyl palmitate hydrolysis at pH 8 are shown below. |
|---|
| A018K/E045F, D027S/N033D, D130A/L264R, D130A/V187T, G023K/L264R, K024A/L075Q, L075R/L264R, S058M/L264R, V187T/L264R, A018K/A049V/L075Q, A018K/D027S/E045F, A018K/E045F/T189D, A018K/L075D/T189D, A018K/L075Q/V187T, A018K/N033D/T189D, A018K/N073R/L075D, A018K/P029E/T189D, A049V/V187T/T189D, D027N/N233Q/P256T, D027Q/N233Q/P256T, D027S/N033D/T189D, D111A/D130A/L264R, D130A/V187N/L264R, F051T/I252Q/L264R, G023K/D130A/L264R, G023K/E056K/V187T, G023K/L075R/L264R, G023K/V187N/L264R, G023K/V187T/L264R, G023Q/L075Q/V187T, G163P/L227M/L264R, K024A/L075Q/V077I, L075G/D130A/V187H, L075Q/D111A/D130A, L075Q/G156W/V187N, L075Q/V187N/L264R, L075Q/V187T/L264R, L075R/D130A/L264R, L075R/D130A/V187T, P029E/N073R/L075D, Q004D/D027S/P256T, V187N/T189Q/L264R, A018K/D027S/N033D/L075D, A018K/E045F/L075D/T189D, A018K/G023K/D111A/T189Q, A018K/G023Q/L075R/D130A, A018K/G023Q/V077I/V187T, A018K/L075Q/N094R/V187Q, A018K/L075Q/V077I/N094R, A018K/N073R/L075D/T189D, A018K/P029E/N073R/L075D, D027E/D048Q/G163P/L264R, D027E/D130A/N233Q/L264R, D027E/D137Q/G163P/L227M, D027E/G163P/L227M/L264R, D027Q/S058M/I090F/P256T, D027S/D130A/I252Q/L264R, D027S/E045F/N073R/L075D, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/L075D, D048Q/D130A/G163P/L264R, D048Q/G163P/N233Q/L264R, E056K/D130A/V187N/L264R, F051T/D130A/I252Q/L264R, F051T/L075G/I252Q/L264R, F051T/L075Q/I252Q/L264R, G023K/D027Q/F051T/L075Q, G023K/D130A/V187N/L264R, G023K/D130A/V187T/L264R, G023K/E056K/L075R/L264R, G023K/L075Q/D130A/V187N, G023K/L075Q/G156W/V187N, G023K/L075R/D130A/L264R, G023K/L075R/V187T/L264R, G023Q/E045F/A049V/T189D, G023Q/F051T/I252Q/L264R, G023Q/G091Q/I252Q/L264R, G023Q/K024A/L075R/V154I, G023Q/L075Q/D130A/L264R, G023Q/L075Q/V187T/L264R, G091Q/V187T/I252Q/L264R, K024A/D130A/V154I/V187T, K024A/L075Q/D130A/G156W, K024A/L075R/G156W/V187N, L075G/D130A/V187T/I252Q, L075G/V187H/I252Q/L264R, L075Q/D130A/G156W/V187N, L075Q/V077I/D130A/V187Q, N011K/S058M/N233Q/P256T, P029E/E045F/N073R/T189D, P029E/N033D/L075D/T189D, P029E/N073R/L075D/T189D, Q004D/D027N/E056K/P256T, Q004D/N011K/D027S/P256T, S058M/G163P/L227M/L264R, S058M/G163P/N233Q/L264R, S058M/L075Q/I252Q/L264R, A018K/D027S/N033D/L075D/T189D, A018K/D027S/P029E/N033D/L075D, A018K/D130A/G156W/V187N/L264R, A018K/G023K/K024A/L075R/N094R, A018K/G023Q/E045F/A049V/V187T, A018K/G023Q/E045F/L075Q/V187T, A018K/G023Q/E045F/V077I/T189D, A018K/G023Q/K024A/L075Q/G156W, A018K/G023Q/L075Q/G156W/V187T, A018K/K024A/L075Q/D130A/L264R, A018K/K024A/L075Q/V154I/G156W, A018K/K024A/L075R/N094R/D130A, A018K/L075Q/D111A/D130A/V187T, A018K/L075Q/N094R/D130A/V187N, A018K/L075Q/N094R/G156W/V187N, A018K/L075Q/V077I/N094R/G156W, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027E/S058M/G163P/L227M/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075R/V154I/T189Q/L264R, D027S/N033D/E045F/N073R/L075D, D027S/N033D/N073R/L075D/T189D, D027S/P029E/N073R/L075D/T189D, D048Q/D130A/G163P/L227M/L264R, D048Q/D137Q/G163P/L227M/L264R, D048Q/D137Q/G163P/N233Q/L264R, D048Q/S058M/D137Q/G163P/N233E, D048Q/S058M/D137Q/N233Q/L264R, D048Q/S058M/G163P/N233Q/L264R, D130A/D137Q/G163P/L227M/L264R, |

TABLE 3-13-continued

| TLL variants with Performance Index >1 compared to TLL SEQ ID NO: 1 for p-nitrophenyl palmitate hydrolysis at pH 8 are shown below. |
|---|
| D130A/D137Q/G163P/N233Q/L264R, E056K/L075G/V187N/I252Q/L264R, E056K/L075Q/G156W/T189Q/L264R, F051T/D130A/V187T/I252Q/L264R, F051T/L075G/D130A/I252Q/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187T/L264R, G023K/L075Q/D111A/D130A/V187T, G023K/L075Q/V077I/D130A/G156W, G023K/L075R/D130A/V187N/L264R, G023K/N094R/G156W/V187N/T189Q, G023Q/A049V/L075Q/G156W/V187T, G023Q/E056K/V187N/I252Q/L264R, G023Q/F051T/L075Q/G091Q/I252Q, G023Q/K024A/L075Q/G156W/V187N, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/G156W/V187N, K024A/L075R/V154I/G156W/V187Q, L075G/D130A/V187T/I252Q/L264R, L075Q/V154I/V187N/T189Q/L264R, L075R/D130A/V187T/T189Q/L264R, N011K/G023K/D111A/G156W/L264R, N011K/G023K/E056K/L075Q/T189Q, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023K/L075Q/D130A/G156W/V187N, A018K/G023Q/L075Q/G156W/V187T/T189D, A018K/G023Q/N094R/D130A/G156W/V187Q, A018K/K024A/D111A/V187N/T189Q/L264R, A018K/K024A/L075Q/N094R/V154I/G156W, A018K/K024A/L075R/D130A/V187N/T189Q, A018K/K024A/V077I/N094R/D130A/G156W, A018K/L075Q/D130A/V187N/T189Q/L264R, D027E/D048Q/D130A/D137H/G163P/L264R, D027E/D048Q/D130A/G163P/L227M/L264R, D027E/D048Q/D137Q/G163P/L227M/L264R, D027E/D048Q/S058M/G163P/N233Q/L264R, D027E/D130A/D137Q/G163P/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/L075Q/D130A/I252Q/L264R, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/D130A/V187T/I252Q/L264R, G023Q/F051T/G091Q/V187N/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/K024A/V077I/D130A/G156W/V187N, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D111A/V154I/V187N/T189Q, K024A/L075Q/V154I/V187T/T189Q/L264R, L075Q/D130A/V154I/G156W/V187N/L264R, L075Q/G091Q/D130A/V187H/I252Q/L264R, L075R/D130A/V154I/G156W/V187N/L264R, N011K/D027Q/E056K/S058M/N233Q/P256T, N011K/D027S/E056K/S058M/N233Q/P256T, N011K/E056K/L075Q/D130A/V187N/T189Q, Q004D/D027N/E056K/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023Q/K024A/L075Q/V077I/N094R/V154I, A018K/G023Q/L075R/V077I/N094R/G156W/V187N, A018K/K024A/D130A/V154I/G156W/V187T/L264R, A018K/K024A/L075Q/D130A/V154I/G156W/V187T, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075G/D130A/V187H/I252Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, |

TABLE 3-13-continued

| TLL variants with Performance Index >1 compared to TLL SEQ ID NO: 1 for p-nitrophenyl palmitate hydrolysis at pH 8 are shown below. |
|---|
| D027S/F051T/L075G/G091Q/V187T/I252Q/L264R, |
| D027S/F051T/S058M/L075Q/V187N/I252Q/L264R, |
| D027S/F051T/S058M/L075R/D130A/I252Q/L264R, |
| D048Q/S058M/D130A/D137Q/G163P/L227M/L264R, |
| D048Q/S058M/D130A/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075Q/G091Q/D130A/V187H/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/L075Q/D130A/V187N, |
| G023K/K024A/L075Q/D111A/D130A/T189Q/L264R, |
| G023K/L075R/N094R/V154I/G156W/V187N/L264R, |
| G023Q/D027S/F051T/E056K/D130A/I252Q/L264R, |
| G023Q/D027S/L075Q/G091Q/V187T/I252Q/L264R, |
| G023Q/D027S/S058M/L075Q/D130A/I252Q/L264R, |
| G023Q/E056K/L075Q/D111A/G156W/V187N/L264R, |
| G023Q/E056K/L075Q/D130A/V154I/G156W/T189Q, |
| G023Q/F051T/L075Q/G091Q/V187H/I252Q/L264R, |
| G023Q/F051T/S058M/G091Q/D130A/I252Q/L264R, |
| G023Q/K024A/L075Q/V077I/D130A/G156W/V187N, |
| G023Q/L075G/G091Q/D130A/V187T/I252Q/L264R, |
| G023Q/L075Q/D111A/D130A/V154I/G156W/L264R, |
| G023Q/L075Q/D130A/V154I/G156W/T189Q/L264R, |
| G023Q/L075Q/D130A/V154I/V187N/T189Q/L264R, |
| G023Q/S058M/L075G/G091Q/D130A/I252Q/L264R, |
| K024A/L075Q/D111A/D130A/V154I/G156W/L264R, |
| Q004D/N011K/D027N/S058M/I090F/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023Q/K024A/L075Q/V077I/D130A/G156W/V187Q, |
| A018K/G023Q/K024A/L075R/N094R/D130A/V154I/G156W, |
| D027E/D048Q/S058M/D137Q/G163P/L227M/N233Q/L264R, |
| D027E/S058M/D130A/D137Q/G163P/L227M/N233Q/L264R, |
| D048Q/S058M/D130A/D137Q/G163P/L227M/N233Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/S058M/L075Q/V187H/I252Q/L264R, |
| G023K/L075Q/D111A/V154I/G156W/V187N/T189Q/L264R, |
| G023Q/D027Q/F051T/L075Q/G091Q/D130A/I252Q/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/S058M/G091Q/D130A/V187H/I252Q/L264R, |
| G023Q/E056K/L075Q/N094R/D111A/G156W/T189Q/L264R, |
| G023Q/F051T/L075Q/G091Q/D130A/V187H/I252Q/L264R, |
| G023Q/F051T/L075Q/G091Q/D130A/V187T/I252Q/L264R, |
| G023Q/F051T/L075R/G091Q/D130A/V187T/I252Q/L264R, |
| G023Q/K024A/L075Q/V077I/N094R/D130A/V154I/V187N, |
| G023Q/L075Q/N094R/D111A/D130A/G156W/T189Q/L264R, |
| G023Q/S058M/L075R/G091Q/D130A/V187H/I252Q/L264R, |
| K024A/D111A/D130A/V154I/G156W/V187T/T189Q/L264R, |
| N011K/G023Q/D027S/L075Q/N094R/V154I/G156W/T189Q, |
| N011K/G023Q/L075Q/D111A/D130A/V154I/V187N/L264R, |
| A018K/G023K/K024A/L075R/V077I/D130A/V154I/G156W/V187N, |
| A018K/G023K/K024A/V077I/D130A/V154I/G156W/V187T/T189Q, |
| A018K/G023Q/K024A/L075R/N094R/D130A/V154I/G156W/V187N, |
| D027Q/F051T/S058M/L075G/G091Q/D130A/V187T/I252Q/L264R, |
| G023K/D027S/F051T/E056K/S058M/L075R/G091Q/V187H/I252Q, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023Q/D027S/L075Q/N094R/D130A/V154I/G156W/V187N/L264R, |
| G023Q/F051T/S058M/L075Q/G091Q/D130A/V187H/I252Q/L264R, |
| N011K/G023K/L075R/D111A/D130A/V154I/V187N/T189Q/L264R, |
| N011K/G023K/L075R/V077I/D130A/V154I/G156W/V187T/T189Q, |
| A018K/G023Q/D027S/P029E/S058M/L075Q/V077I/R108K/H135F/V187H, |
| A018K/G023Q/K024A/L075Q/V077I/N094R/D130A/V154I/G156W/V187Q, |
| G023K/D027S/F051T/E056K/S058M/L075G/G091Q/D130A/I252Q/L264R, |
| N011K/G023Q/E056K/L075R/D111A/D130A/V154I/G156W/V187N/L264R, |
| A018K/G023K/L075R/N094R/D111A/D130A/V154I/G156W/V187N/T189Q/L264R, |
| A018K/G023Q/D027S/P029E/S058M/L075Q/V077I/R108K/H135F/G156W/V187T |

TABLE 3-14

| TLL variants with Performance Index for expression ≥0.5 and Performance Index >1 for p-nitrophenyl palmitate hydrolysis at pH 8 compared to TLL SEQ ID NO: 1 are shown below. |
|---|
| A018K/E045F, D027S/N033D, D130A/L264R, D130A/V187T, G023K/L264R, L075R/L264R, S058M/L264R, V187T/L264R, A018K/L075D/T189D, A018K/N033D/T189D, A018K/P029E/T189D, D027S/N033D/T189D, D111A/D130A/L264R, D130A/V187N/L264R, F051T/I252Q/L264R, G023K/D130A/L264R, G023K/E056K/V187T, G023K/L075R/L264R, G023K/V187N/L264R, G023K/V187T/L264R, G163P/L227M/L264R, L075G/D130A/V187H, L075Q/V187N/L264R, L075Q/V187T/L264R, L075R/D130A/L264R, L075R/D130A/V187T, Q004D/D027S/P256T, V187N/T189Q/L264R, A018K/E045F/L075D/T189D, A018K/G023K/D111A/T189Q, A018K/L075Q/V077I/N094R, A018K/P029E/N073R/L075D, D027E/D048Q/G163P/L264R, D027E/D130A/N233Q/L264R, D027E/D137Q/G163P/L227M, D027E/G163P/L227M/L264R, D027S/D130A/I252Q/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/L075D, D048Q/D130A/G163P/L264R, D048Q/G163P/N233Q/L264R, E056K/D130A/V187N/L264R, F051T/D130A/I252Q/L264R, F051T/L075G/I252Q/L264R, F051T/L075Q/I252Q/L264R, G023K/D027Q/F051T/L075Q, G023K/D130A/V187N/L264R, G023K/D130A/V187T/L264R, G023K/E056K/L075R/L264R, G023K/L075R/D130A/L264R, G023K/L075R/V187T/L264R, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, P029E/N073R/L075D/T189D, Q004D/D027N/E056K/P256T, Q004D/N011K/D027S/P256T, S058M/G163P/L227M/L264R, S058M/G163P/N233Q/L264R, S058M/L075Q/I252Q/L264R, A018K/D027S/P029E/N033D/L075D, A018K/D130A/G156W/V187N/L264R, A018K/G023Q/K024A/L075Q/G156W, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027E/S058M/G163P/L227M/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/D130A/G163P/L227M/L264R, D048Q/D137Q/G163P/L227M/L264R, D048Q/D137Q/G163P/N233Q/L264R, D048Q/S058M/D137Q/G163P/N233E, D048Q/S058M/D137Q/N233Q/L264R, D048Q/S058M/G163P/N233Q/L264R, D130A/D137Q/G163P/L227M/L264R, D130A/D137Q/G163P/N233Q/L264R, E056K/L075G/V187N/I252Q/L264R, F051T/D130A/V187T/I252Q/L264R, F051T/L075G/D130A/I252Q/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/L075R/D130A/V187N/L264R, G023K/N094R/G156W/V187N/T189Q, G023Q/E056K/V187N/I252Q/L264R, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, K024A/L075R/V154I/G156W/V187Q, L075G/D130A/V187T/I252Q/L264R, N011K/G023K/D111A/G156W/L264R, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023Q/N094R/D130A/G156W/V187Q, A018K/K024A/D111A/V187N/T189Q/L264R, A018K/K024A/L075Q/N094R/V154I/G156W, D027E/D048Q/D130A/D137H/G163P/L264R, D027E/D048Q/D130A/G163P/L227M/L264R, D027E/D048Q/D137Q/G163P/L227M/L264R, D027E/D048Q/S058M/G163P/N233Q/L264R, D027E/D130A/D137Q/G163P/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/L075Q/D130A/I252Q/L264R, G023K/K024A/L075Q/V154I/G156W/V187Q, G023K/K024A/L075R/D130A/V154I/V187N, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/D130A/V187T/I252Q/L264R, G023Q/F051T/G091Q/V187N/I252Q/L264R, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023Q/L075R/V077I/N094R/G156W/V187N, A018K/K024A/D130A/V154I/G156W/V187T/L264R, |

TABLE 3-14-continued

| TLL variants with Performance Index for expression ≥0.5 and Performance Index >1 for p-nitrophenyl palmitate hydrolysis at pH 8 compared to TLL SEQ ID NO: 1 are shown below. |
|---|
| A018K/K024A/L075Q/D130A/V154I/G156W/V187T, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/L075Q/D130A/V187N, G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, A018K/G023K/K024A/L075Q/N094R/D130A/G156W/V187Q, A018K/G023K/K024A/L075Q/V077I/D130A/V154I/G156W, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023K/D027S/F051T/E056K/L075Q/G091Q/V187H/I252Q, G023K/D027S/F051T/S058M/L075Q/V187H/I252Q/L264R, G023Q/D027Q/F051T/L075Q/G091Q/D130A/I252Q/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023K/L075R/V077I/D130A/V154I/G156W/V187T/T189Q, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T |

TABLE 3-15

| TLL variants with Performance Index for expression ≥0.5 and Performance Index ≥50% of the maximum PI value for for p-nitrophenyl palmitate hydrolysis at pH 8 compared to TLL SEQ ID NO: 1 are shown below. |
|---|
| D130A/L264R, D130A/V187T, A018K/L075D/T189D, A018K/P029E/T189D, D027S/N033D/T189D, G023K/V187N/L264R, L075G/D130A/V187H, L075Q/V187N/L264R, L075R/D130A/L264R, L075R/D130A/V187T, Q004D/D027S/P256T, A018K/L075Q/V077I/N094R, D027S/D130A/I252Q/L264R, D027S/P029E/E045F/T189D, D027S/P029E/L075D/T189D, D027S/P029E/N033D/L075D, D048Q/D130A/G163P/L264R, F051T/L075Q/I252Q/L264R, G023K/L075R/D130A/L264R, G023K/L075R/V187T/L264R, G023Q/F051T/I252Q/L264R, G023Q/G091Q/I252Q/L264R, G091Q/V187T/I252Q/L264R, L075G/V187H/I252Q/L264R, P029E/N073R/L075D/T189D, Q004D/N011K/D027S/P256T, S058M/G163P/L227M/L264R, S058M/L075Q/I252Q/L264R, A018K/D027S/P029E/N033D/L075D, A018K/G023Q/K024A/L075Q/G156W, A018K/P029E/N033D/N073R/L075D, D027E/D048Q/G163P/N233Q/L264R, D027E/D130A/G163P/L227M/L264R, D027E/G163P/L227M/N233Q/L264R, D027S/F051T/V187N/I252Q/L264R, D027S/L075R/V154I/T189Q/L264R, D048Q/D137Q/G163P/N233Q/L264R, D130A/D137Q/G163P/N233Q/L264R, F051T/D130A/V187T/I252Q/L264R, F051T/L075G/D130A/I252Q/L264R, F051T/L075Q/V187N/I252Q/L264R, |

TABLE 3-15-continued

| TLL variants with Performance Index for expression ≥0.5 and Performance Index ≥50% of the maximum PI value for for p-nitrophenyl palmitate hydrolysis at pH 8 compared to TLL SEQ ID NO: 1 are shown below. |
|---|
| G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/L075R/D130A/V187N/L264R, G023Q/K024A/L075Q/G156W/V187Q, G023Q/L075Q/G091Q/I252Q/L264R, K024A/L075R/V154I/G156W/V187Q, S058M/G163P/L227M/N233Q/L264R, A018K/D027S/N033D/N073R/L075D/T189D, A018K/K024A/L075Q/N094R/V154I/G156W, D027E/D048Q/D130A/G163P/L227M/L264R, D027E/D048Q/D137Q/G163P/L227M/L264R, D027E/D048Q/S058M/G163P/N233Q/L264R, D027E/D137Q/G163P/L227M/N233Q/L264R, D027E/S058M/D130A/L227M/N233Q/L264R, D027Q/L075Q/D130A/V187T/I252Q/L264R, D027Q/S058M/L075R/D130A/V187T/I252Q, F051T/E056K/D130A/V187N/I252Q/L264R, F051T/L075G/G091Q/D130A/I252Q/L264R, F051T/L075G/G091Q/V187T/I252Q/L264R, G023K/D027S/L075R/D130A/V187T/I252Q, G023K/E056K/L075R/D130A/T189Q/L264R, G023K/F051T/D130A/V187N/I252Q/L264R, G023K/K024A/L075Q/V154I/G156W/V187Q, G023K/K024A/L075R/D130A/V154I/V187N, G023Q/L075Q/G091Q/V187N/I252Q/L264R, A018K/D027S/P029E/N033D/N073R/L075D/T189D, A018K/G023K/K024A/L075Q/N094R/G156W/V187Q, A018K/K024A/L075Q/D130A/V154I/G156W/V187T, D027E/S058M/D130A/G163P/L227M/N233Q/L264R, D027Q/F051T/L075Q/D130A/V187T/I252Q/L264R, D027Q/F051T/S058M/L075Q/G091Q/I252Q/L264R, D027S/F051T/S058M/L075Q/V187N/I252Q/L264R, F051T/L075R/G091Q/D130A/V187T/I252Q/L264R, G023Q/D027S/F051T/E056K/D130A/I252Q/L264R, G023Q/F051T/S058M/G091Q/D130A/I252Q/L264R, A018K/G023K/K024A/L075Q/N094R/D130A/G156W/V187Q, G023Q/D027Q/F051T/L075Q/G091Q/D130A/I252Q/L264R, G023Q/D027S/E056K/S058M/L075G/G091Q/V187T/L264R, G023Q/F051T/L075Q/G091Q/D130A/V187T/I252Q/L264R, G023Q/F051T/L075R/G091Q/D130A/V187T/I252Q/L264R, G023K/K024A/L075Q/N094R/V154I/G156W/V187N/T189Q/L264R, N011K/G023Q/E056K/L075R/D111A/D130A/V154I/G156W/V187N/L264R |

TALBE 3-16

| TLL variants with Performance Index >1 compared to Reference sequence SEQ ID NO: 2 for p-nitrophenyl palmitate hydrolysis at pH 8 are shown below. |
|---|
| A018K/E045F, D027S/N033D, D111A/L264R, D130A/L264R, D130A/V187T, G023K/L264R, K024A/L075Q, L075R/L264R, S058M/L264R, V187T/L264R, A018K/A049V/L075Q, A018K/D027S/E045F, A018K/E045F/T189D, A018K/L075D/T189D, A018K/L075Q/V187T, A018K/N033D/T189D, A018K/N073R/L075D, A018K/P029E/T189D, A049V/V187T/T189D, D027N/N233Q/P256T, D027Q/N233Q/P256T, D027S/L075Q/G091Q, D027S/N033D/T189D, D111A/D130A/L264R, D130A/V187N/L264R, E045F/L075D/T189D, F051T/I252Q/L264R, G023K/D130A/L264R, G023K/E056K/V187T, G023K/L075R/L264R, G023K/V187N/L264R, G023K/V187T/L264R, G023Q/E056K/L075R, G023Q/L075Q/V187T, G163P/L227M/L264R, K024A/L075Q/V077I, L075G/D130A/V187H, L075Q/D111A/D130A, L075Q/G156W/V187N, L075Q/V187N/L264R, L075Q/V187T/L264R, L075R/D130A/L264R, L075R/D130A/V187T, L075R/V187T/L264R, N073R/L075D/T189D, P029E/N073R/L075D, Q004D/D027S/P256T, V187N/T189Q/L264R, A018K/D027S/N033D/L075D, A018K/E045F/L075D/T189D, A018K/G023K/D111A/T189Q, A018K/G023Q/L075R/D130A, A018K/G023Q/V077I/V187T, A018K/G023Q/V187T/T189D, A018K/L075Q/N094R/V187Q, A018K/L075Q/V077I/N094R, A018K/N073R/L075D/T189D, A018K/P029E/N073R/L075D, D027E/D048Q/G163P/L264R, D027E/D130A/N233Q/L264R, D027E/D137Q/G163P/L227M, D027E/G163P/L227M/L264R, D027E/S058M/G163P/L264R, D027Q/S058M/I090F/P256T, D027S/D130A/I252Q/L264R, D027S/E045F/N073R/L075D, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/L075D, D048Q/D130A/G163P/L264R, D048Q/G163P/N233Q/L264R, D111A/D130A/V154I/L264R, E056K/D130A/V187N/L264R, F051T/D130A/I252Q/L264R, F051T/L075G/I252Q/L264R, F051T/L075Q/I252Q/L264R, G023K/D027Q/F051T/L075Q, G023K/D130A/V187N/L264R, G023K/D130A/V187T/L264R, G023K/E056K/L075R/L264R, G023K/L075Q/D130A/V187N, G023K/L075Q/G156W/V187N, G023K/L075R/D130A/L264R, G023K/L075R/V187T/L264R, G023Q/E045F/A049V/T189D, G023Q/F051T/I252Q/L264R, G023Q/G091Q/I252Q/L264R, G023Q/K024A/L075R/V154I, G023Q/L075Q/D130A/L264R, G023Q/L075Q/V187T/L264R, G091Q/V187T/I252Q/L264R, K024A/D130A/V154I/V187T, K024A/L075Q/D130A/G156W, K024A/L075R/G156W/V187N, L075G/D130A/V187T/I252Q, L075G/V187H/I252Q/L264R, L075Q/D130A/G156W/V187N, L075Q/V077I/D130A/V187Q, N011K/S058M/N233Q/P256T, P029E/E045F/N073R/T189D, P029E/N033D/L075D/T189D, P029E/N073R/L075D/T189D, Q004D/D027N/E056K/P256T, Q004D/N011K/D027S/P256T, S058M/G163P/L227M/L264R, S058M/G163P/N233Q/L264R, S058M/L075Q/G091Q/I252Q, S058M/L075Q/I252Q/L264R, A018K/D027S/N033D/L075D/T189D, A018K/D027S/P029E/N033D/L075D, A018K/D130A/G156W/V187N/L264R, A018K/G023K/K024A/L075R/N094R, A018K/G023Q/A049V/L075Q/V077I, A018K/G023Q/E045F/A049V/V187T, A018K/G023Q/E045F/L075Q/V187T, |

TALBE 3-16-continued

| TLL variants with Performance Index >1 compared to Reference sequence SEQ ID NO: 2 for p-nitrophenyl palmitate hydrolysis at pH 8 are shown below. |
|---|
| A018K/G023Q/E045F/V077I/T189D, A018K/G023Q/K024A/L075Q/G156W, A018K/G023Q/L075Q/G156W/V187T, A018K/G023Q/L075Q/V187T/T189D, A018K/K024A/L075Q/D130A/L264R, A018K/K024A/L075Q/V154I/G156W, A018K/K024A/L075R/N094R/D130A, A018K/L075Q/D111A/D130A/V187T, A018K/L075Q/N094R/D130A/V187N, A018K/L075Q/N094R/G156W/V187N, A018K/L075Q/V077I/N094R/G156W, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075R/V154I/T189Q/L264R, D027S/N033D/E045F/N073R/L075D, D027S/N033D/N073R/L075D/T189D, D027S/P029E/N073R/L075D/T189D, D048Q/D130A/G163P/L227M/L264R, D048Q/D137Q/G163P/L227M/L264R, D048Q/D137Q/G163P/N233Q/L264R, D048Q/S058M/D137Q/G163P/N233E, D048Q/S058M/D137Q/N233Q/L264R, D048Q/S058M/G163P/N233Q/L264R, D130A/D137Q/G163P/L227M/L264R, D130A/D137Q/G163P/N233Q/L264R, E056K/L075G/V187N/I252Q/L264R, E056K/L075Q/G156W/T189Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187T/L264R, G023K/L075Q/D111A/D130A/V187T, G023K/L075Q/V077I/D130A/G156W, G023K/L075R/D130A/V187N/L264R, G023K/N094R/G156W/V187N/T189Q, G023Q/A049V/L075Q/G156W/V187T, G023Q/E056K/V187N/I252Q/L264R, G023Q/F051T/L075Q/G091Q/I252Q, G023Q/K024A/L075Q/G156W/V187N, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/G156W/V187N, K024A/L075R/V154I/G156W/V187Q, L075G/D130A/V187T/I252Q/L264R, L075Q/V154I/V187N/T189Q/L264R, L075R/D130A/V154I/T189Q/L264R, L075R/D130A/V187T/T189Q/L264R, N011K/G023K/D111A/G156W/L264R, N011K/G023K/E056K/L075Q/T189Q, S058M/D130A/D137Q/G163P/L264R, S058M/D130A/G163P/L227M/L264R, S058M/G163P/L227M/N233Q/L264R, A018K/D027S/N033D/N073R/L075D/T189D, A018K/G023K/K024A/N094R/D130A/V154I, A018K/G023K/L075Q/D130A/G156W/V187N, A018K/G023Q/L075Q/G156W/V187T/T189D, A018K/G023Q/N094R/D130A/G156W/V187Q, A018K/K024A/D111A/V187N/T189Q/L264R, A018K/K024A/L075Q/N094R/V154I/G156W, A018K/K024A/L075R/D130A/V187N/T189Q, A018K/K024A/V077I/N094R/D130A/G156W, A018K/L075Q/D130A/V187N/T189Q/L264R, A018K/N094R/D111A/D130A/V154I/V187N, D027E/D048Q/D130A/D137H/G163P/L264R, D027E/D048Q/D130A/G163P/L227M/L264R, D027E/D048Q/D137Q/G163P/L227M/L264R, D027E/D048Q/S058M/G163P/L227M/L264R, D027E/D048Q/S058M/G163P/N233Q/L264R, D027E/D130A/D137Q/G163P/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/D130A/V187N/I252Q/L264R, G023K/F051T/L075Q/D130A/I252Q/L264R, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/D130A/V187T/I252Q/L264R, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/V077I/D130A/G156W/V187N, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D111A/V154I/V187N/T189Q, K024A/L075Q/V154I/V187T/T189Q/L264R, K024A/L075R/D111A/V154I/G156W/V187N, L075Q/D130A/V154I/G156W/V187N/L264R, L075Q/G091Q/D130A/V187H/I252Q/L264R, L075R/D130A/V154I/G156W/V187N/L264R, N011K/D027Q/E056K/S058M/N233Q/P256T, N011K/D027S/E056K/S058M/N233Q/P256T, N011K/E056K/L075Q/D130A/V187N/T189Q, Q004D/D027N/E056K/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, |

TALBE 3-16-continued

| TLL variants with Performance Index >1 compared to Reference sequence SEQ ID NO: 2 for p-nitrophenyl palmitate hydrolysis at pH 8 are shown below. |
|---|
| A018K/G023K/K024A/L075Q/D130A/G156W/V187N, |
| A018K/G023K/K024A/L075Q/N094R/G156W/V187Q, |
| A018K/G023K/K024A/L075R/N094R/D130A/V154I, |
| A018K/G023K/K024A/L075R/V154I/G156W/V187Q, |
| A018K/G023K/K024A/N094R/V154I/V187T/L264R, |
| A018K/G023Q/K024A/L075Q/V077I/N094R/V154I, |
| A018K/G023Q/L075R/V077I/N094R/G156W/V187N, |
| A018K/K024A/D130A/V154I/G156W/V187T/L264R, |
| A018K/K024A/L075Q/D130A/V154I/G156W/V187T, |
| A018K/L075Q/D130A/G156W/V187N/T189Q/L264R, |
| D027E/D048Q/D130A/D137Q/G163P/N233Q/L264R, |
| D027E/D048Q/D137Q/G163P/L227M/N233Q/L264R, |
| D027E/D048Q/S058M/D130A/D137Q/G163P/L264R, |
| D027E/D048Q/S058M/D130A/G163P/L227M/L264R, |
| D027E/D048Q/S058M/D130A/G163P/N233Q/L264R, |
| D027E/D048Q/S058M/D137Q/G163P/L227M/L264R, |
| D027E/S058M/D130A/D137Q/G163P/L227M/L264R, |
| D027E/S058M/D130A/G163P/L227M/N233Q/L264R, |
| D027E/S058M/D137Q/G163P/L227M/N233Q/L264R, |
| D027Q/F051T/L075G/D130A/V187H/I252Q/L264R, |
| D027Q/F051T/L075Q/D130A/V187T/I252Q/L264R, |
| D027Q/F051T/S058M/L075Q/G091Q/I252Q/L264R, |
| D027Q/L075G/G091Q/D130A/V187H/I252Q/L264R, |
| D027S/F051T/L075G/G091Q/V187T/I252Q/L264R, |
| D027S/F051T/S058M/L075Q/V187N/I252Q/L264R, |
| D027S/F051T/S058M/L075R/D130A/I252Q/L264R, |
| D048Q/S058M/D130A/D137Q/G163P/L227M/L264R, |
| D048Q/S058M/D130A/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075Q/G091Q/D130A/V187H/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/L075Q/D130A/V187N, |
| G023K/K024A/L075Q/D111A/D130A/T189Q/L264R, |
| G023K/L075R/N094R/V154I/G156W/V187N/L264R, |
| G023Q/D027S/F051T/E056K/D130A/I252Q/L264R, |
| G023Q/D027S/L075Q/G091Q/V187T/I252Q/L264R, |
| G023Q/D027S/S058M/L075Q/D130A/I252Q/L264R, |
| G023Q/E056K/L075Q/D111A/G156W/V187N/L264R, |
| G023Q/E056K/L075Q/D130A/V154I/G156W/T189Q, |
| G023Q/F051T/L075Q/G091Q/V187H/I252Q/L264R, |
| G023Q/F051T/S058M/G091Q/D130A/I252Q/L264R, |
| G023Q/K024A/L075Q/V077I/D130A/G156W/V187N, |
| G023Q/L075G/G091Q/D130A/V187T/I252Q/L264R, |
| G023Q/L075Q/D111A/D130A/V154I/G156W/L264R, |
| G023Q/L075Q/D130A/V154I/G156W/T189Q/L264R, |
| G023Q/L075Q/D130A/V154I/V187N/T189Q/L264R, |
| G023Q/S058M/L075G/G091Q/D130A/I252Q/L264R, |
| K024A/L075Q/D111A/D130A/V154I/G156W/L264R, |
| Q004D/N011K/D027N/S058M/I090F/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023Q/K024A/L075Q/V077I/D130A/G156W/V187Q, |
| A018K/G023Q/K024A/L075R/N094R/D130A/V154I/G156W, |
| D027E/D048Q/S058M/D137Q/G163P/L227M/N233Q/L264R, |
| D027E/S058M/D130A/D137Q/G163P/L227M/N233Q/L264R, |
| D048Q/S058M/D130A/D137Q/G163P/L227M/N233Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/S058M/L075Q/V187H/I252Q/L264R, |
| G023K/L075Q/D111A/V154I/G156W/V187N/T189Q/L264R, |
| G023Q/D027Q/F051T/L075Q/G091Q/D130A/I252Q/L264R, |
| G023Q/D027Q/F051T/S058M/L075R/D130A/V187T/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/S058M/G091Q/D130A/V187H/I252Q/L264R, |
| G023Q/E056K/L075Q/N094R/D111A/G156W/T189Q/L264R, |
| G023Q/F051T/L075Q/G091Q/D130A/V187H/I252Q/L264R, |
| G023Q/F051T/L075Q/G091Q/D130A/V187T/I252Q/L264R, |
| G023Q/F051T/L075R/G091Q/D130A/V187T/I252Q/L264R, |
| G023Q/K024A/L075Q/V077I/N094R/D130A/V154I/V187N, |
| G023Q/L075Q/N094R/D111A/D130A/G156W/T189Q/L264R, |
| G023Q/S058M/L075R/G091Q/D130A/V187H/I252Q/L264R, |
| K024A/D111A/D130A/V154I/G156W/V187T/T189Q/L264R, |
| N011K/G023Q/D027S/L075Q/N094R/V154I/G156W/T189Q, |

TALBE 3-16-continued

| TLL variants with Performance Index >1 compared to Reference sequence SEQ ID NO: 2 for p-nitrophenyl palmitate hydrolysis at pH 8 are shown below. |
|---|
| N011K/G023Q/L075Q/D111A/D130A/V154I/V187N/L264R, A018K/G023K/K024A/L075R/V077I/D130A/V154I/G156W/V187N, A018K/G023K/K024A/V077I/D130A/V154I/G156W/V187T/T189Q, A018K/G023Q/K024A/L075R/N094R/D130A/V154I/G156W/V187N, D027Q/F051T/S058M/L075G/G091Q/D130A/V187T/I252Q/L264R, G023K/D027S/F051T/E056K/S058M/L075R/G091Q/V187H/I252Q, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023Q/D027S/L075Q/N094R/D130A/V154I/G156W/V187N/L264R, G023Q/F051T/S058M/L075Q/G091Q/D130A/V187H/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T |

TABLE 3-17

| TLL variants with Performance Index for expression ≥0.5 compared to TLL SEQ ID NO: 1 and Performance Index >1 for p-nitrophenyl palmitate hydrolysis at pH 8 compared to SEQ ID NO: 2 are shown below. |
|---|
| A018K/E045F, D027S/N033D, D111A/L264R, D130A/L264R, D130A/V187T, G023K/L264R, L075R/L264R, S058M/L264R, V187T/L264R, A018K/L075D/T189D, A018K/N033D/T189D, A018K/P029E/T189D, D027S/L075Q/G091Q, D027S/N033D/T189D, D111A/D130A/L264R, D130A/V187N/L264R, F051T/I252Q/L264R, G023K/D130A/L264R, G023K/E056K/V187T, G023K/L075R/L264R, G023K/V187N/L264R, G023K/V187T/L264R, G163P/L227M/L264R, L075G/D130A/V187H, L075Q/V187N/L264R, L075Q/V187T/L264R, L075R/D130A/L264R, L075R/D130A/V187T, L075R/V187T/L264R, Q004D/D027S/P256T, V187N/T189Q/L264R, A018K/E045F/L075D/T189D, A018K/G023K/D111A/T189Q, A018K/L075Q/V077I/N094R, A018K/P029E/N073R/L075D, D027E/D048Q/G163P/L264R, D027E/D130A/N233Q/L264R, D027E/D137Q/G163P/L227M, D027E/G163P/L227M/L264R, D027E/S058M/G163P/L264R, D027S/D130A/I252Q/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/L075D, D048Q/D130A/G163P/L264R, D048Q/G163P/N233Q/L264R, E056K/D130A/V187N/L264R, F051T/D130A/I252Q/L264R, F051T/L075G/I252Q/L264R, F051T/L075Q/I252Q/L264R, G023K/D027Q/F051T/L075Q, G023K/D130A/V187N/L264R, G023K/D130A/V187T/L264R, G023K/E056K/L075R/L264R, G023K/L075R/D130A/L264R, G023K/L075R/V187T/L264R, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, P029E/N073R/L075D/T189D, Q004D/D027N/E056K/P256T, Q004D/N011K/D027S/P256T, S058M/G163P/L227M/L264R, S058M/G163P/N233Q/L264R, S058M/L075Q/G091Q/I252Q, S058M/L075Q/I252Q/L264R, A018K/D027S/P029E/N033D/L075D, A018K/D130A/G156W/V187N/L264R, A018K/G023Q/K024A/L075Q/G156W, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/D130A/G163P/L227M/L264R, D048Q/D137Q/G163P/L227M/L264R, D048Q/D137Q/G163P/N233Q/L264R, D048Q/S058M/D137Q/G163P/N233E, D048Q/S058M/D137Q/N233Q/L264R, D048Q/S058M/G163P/N233Q/L264R, D130A/D137Q/G163P/L227M/L264R, D130A/D137Q/G163P/N233Q/L264R, E056K/L075G/V187N/I252Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/L075R/D130A/V187N/L264R, G023K/N094R/G156W/V187N/T189Q, G023Q/E056K/V187N/I252Q/L264R, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, K024A/L075R/V154I/G156W/V187Q, L075G/D130A/V187T/I252Q/L264R, N011K/G023K/D111A/G156W/L264R, S058M/D130A/D137Q/G163P/L264R, S058M/D130A/G163P/L227M/L264R, |

TABLE 3-17-continued

| TLL variants with Performance Index for expression ≥0.5 compared to TLL SEQ ID NO: 1 and Performance Index >1 for p-nitrophenyl palmitate hydrolysis at pH 8 compared to SEQ ID NO: 2 are shown below. |
|---|
| S058M/G163P/L227M/N233Q/L264R, A018K/D027S/N033D/N073R/L075D/T189D, A018K/G023Q/N094R/D130A/G156W/V187Q, A018K/K024A/D111A/V187N/T189Q/L264R, A018K/K024A/L075Q/N094R/V154I/G156W, A018K/N094R/D111A/D130A/V154I/V187N, D027E/D048Q/D130A/D137H/G163P/L264R, D027E/D048Q/D130A/G163P/L227M/L264R, D027E/D048Q/D137Q/G163P/L227M/L264R, D027E/D048Q/S058M/G163P/L227M/L264R, D027E/D048Q/S058M/G163P/N233Q/L264R, D027E/D130A/D137Q/G163P/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/D130A/V187N/I252Q/L264R, G023K/F051T/L075Q/D130A/I252Q/L264R, G023K/K024A/L075Q/V154I/G156W/V187Q, G023K/K024A/L075R/D130A/V154I/V187N, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/D130A/V187T/I252Q/L264R, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023Q/L075R/V077I/N094R/G156W/V187N, A018K/K024A/D130A/V154I/G156W/V187T/L264R, A018K/K024A/L075Q/D130A/V154I/G156W/V187T, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/L075Q/D130A/V187N, G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, A018K/G023K/K024A/L075Q/N094R/D130A/G156W/V187Q, A018K/G023K/K024A/L075Q/V077I/D130A/V154I/G156W, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023K/D027S/F051T/E056K/L075Q/G091Q/V187H/I252Q, G023K/D027S/F051T/S058M/L075Q/V187H/I252Q/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, |

TABLE 3-17-continued

| TLL variants with Performance Index for expression ≥0.5 compared to TLL SEQ ID NO: 1 and Performance Index >1 for p-nitrophenyl palmitate hydrolysis at pH 8 compared to SEQ ID NO: 2 are shown below. |
|---|
| G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023K/L075R/V077I/D130A/V154I/G156W/V187T/T189Q, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T |

TABLE 3-18

| TLL variants with Performance Index for expression ≥0.5 compared to TLL SEQ ID NO: 1 and Performance Index ≥50% of the maximum PI value for for p-nitrophenyl palmitate hydrolysis at pH 8 compared to SEQ ID NO: 2 are shown below. |
|---|
| D130A/L264R, D130A/V187T, A018K/L075D/T189D, A018K/P029E/T189D, D027S/N033D/T189D, G023K/V187N/L264R, L075G/D130A/V187H, L075Q/V187N/L264R, L075R/D130A/L264R, L075R/D130A/V187T, Q004D/D027S/P256T, A018K/L075Q/V077I/N094R, D027S/D130A/I252Q/L264R, D027S/P029E/E045F/T189D, D027S/P029E/L075D/T189D, D027S/P029E/N033D/L075D, D048Q/D130A/G163P/L264R, F051T/L075Q/I252Q/L264R, G023K/L075R/D130A/L264R, G023K/L075R/V187T/L264R, G023Q/F051T/I252Q/L264R, G023Q/G091Q/I252Q/L264R, G091Q/V187T/I252Q/L264R, L075G/V187H/I252Q/L264R, P029E/N073R/L075D/T189D, Q004D/N011K/D027S/P256T, S058M/G163P/L227M/L264R, S058M/L075Q/I252Q/L264R, A018K/D027S/P029E/N033D/L075D, A018K/G023Q/K024A/L075Q/G156W, A018K/P029E/N033D/N073R/L075D, D027E/D048Q/G163P/N233Q/L264R, D027E/D130A/G163P/L227M/L264R, D027E/G163P/L227M/N233Q/L264R, D027S/F051T/V187N/I252Q/L264R, D027S/L075R/V154I/T189Q/L264R, D048Q/D137Q/G163P/N233Q/L264R, D130A/D137Q/G163P/N233Q/L264R, F051T/D130A/V187T/I252Q/L264R, F051T/L075G/D130A/I252Q/L264R, F051T/L075Q/V187N/I252Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/L075R/D130A/V187N/L264R, G023Q/K024A/L075Q/G156W/V187Q, G023Q/L075Q/G091Q/I252Q/L264R, K024A/L075R/V154I/G156W/V187Q, S058M/G163P/L227M/N233Q/L264R, A018K/D027S/N033D/N073R/L075D/T189D, A018K/K024A/L075Q/N094R/V154I/G156W, D027E/D048Q/D130A/G163P/L227M/L264R, D027E/D048Q/D137Q/G163P/L227M/L264R, D027E/D048Q/S058M/G163P/N233Q/L264R, D027E/D137Q/G163P/L227M/N233Q/L264R, D027E/S058M/D130A/L227M/N233Q/L264R, D027Q/L075Q/D130A/V187T/I252Q/L264R, D027Q/S058M/L075R/D130A/V187T/I252Q, F051T/E056K/D130A/V187N/I252Q/L264R, F051T/L075G/G091Q/D130A/I252Q/L264R, F051T/L075G/G091Q/V187T/I252Q/L264R, G023K/D027S/L075R/D130A/V187T/I252Q, G023K/E056K/L075R/D130A/T189Q/L264R, G023K/F051T/D130A/V187N/I252Q/L264R, G023K/K024A/L075Q/V154I/G156W/V187Q, G023K/K024A/L075R/D130A/V154I/V187N, G023Q/L075Q/G091Q/V187N/I252Q/L264R, A018K/D027S/P029E/N033D/N073R/L075D/T189D, A018K/G023K/K024A/L075Q/N094R/G156W/V187Q, A018K/K024A/L075Q/D130A/V154I/G156W/V187T, D027E/S058M/D130A/G163P/L227M/N233Q/L264R, D027Q/F051T/L075Q/D130A/V187T/I252Q/L264R, D027Q/F051T/S058M/L075Q/G091Q/I252Q/L264R, D027S/F051T/S058M/L075Q/V187N/I252Q/L264R, F051T/L075R/G091Q/D130A/V187T/I252Q/L264R, G023Q/D027S/F051T/E056K/D130A/I252Q/L264R, G023Q/F051T/S058M/G091Q/D130A/I252Q/L264R, A018K/G023K/K024A/L075Q/N094R/D130A/G156W/V187Q, G023Q/D027Q/F051T/L075Q/G091Q/D130A/I252Q/L264R, G023Q/D027S/E056K/S058M/L075G/G091Q/V187T/L264R, G023Q/F051T/L075Q/G091Q/D130A/V187T/I252Q/L264R, G023Q/F051T/L075R/G091Q/D130A/V187T/I252Q/L264R, G023K/K024A/L075Q/N094R/V154I/G156W/V187N/T189Q/L264R, N011K/G023Q/E056K/L075R/D111A/D130A/V154I/G156W/V187N/L264R |

TABLE 3-19

| TLL variants with Performance Index >1 compared to TLL SEQ ID NO: 1 for p-nitrophenyl caprylate (octanoate) hydrolysis at pH 6 are shown below. |
| --- |
| D027E/G163P, K024A/L075Q, P029E/N033D, A018K/D027S/E045F, A018K/L075D/T189D, A018K/L075Q/V187T, A018K/N073R/L075D, A018K/P029E/T189D, A049V/V187T/T189D, D027S/N033D/T189D, G023K/V187N/L264R, G023Q/L075Q/V187T, L075G/D130A/V187H, L075Q/D111A/D130A, L075Q/G156W/T189D, L075Q/G156W/V187N, L075R/D130A/L264R, L075R/D130A/V187T, N073R/L075D/T189D, P029E/N033D/E045F, P029E/N033D/L075D, A018K/D027S/N033D/L075D, A018K/D027S/P029E/T189D, A018K/G023Q/A049V/T189D, A018K/G023Q/L075R/D130A, A018K/G023Q/V077I/V187T, A018K/L075Q/V077I/N094R, A018K/P029E/N033D/T189D, D027E/D137Q/L227M/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075Q/G156W/V187N, G023K/L075R/D130A/L264R, G023Q/E045F/A049V/T189D, G023Q/K024A/L075R/V154I, K024A/L075Q/D130A/V154I, K024A/L075R/G156W/V187N, L075Q/D130A/G156W/V187N, L075Q/V077I/G156W/V187N, L075Q/V077I/V187T/T189D, P029E/E045F/L075D/T189D, P029E/N033D/L075D/T189D, P029E/N073R/L075D/T189D, A018K/D027S/N033D/L075D/T189D, A018K/D027S/P029E/E045F/T189D, A018K/D027S/P029E/N033D/L075D, A018K/D027S/P029E/N073R/L075D, A018K/G023K/K024A/L075R/N094R, A018K/G023Q/E045F/A049V/L075Q, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/K024A/L075R/D130A/V154I, A018K/K024A/N094R/D130A/V187N, A018K/L075Q/D111A/D130A/V187T, A018K/L075Q/N094R/G156W/V187N, A018K/P029E/N033D/N073R/L075D, D027E/D048Q/S058M/G163P/N233Q, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/N094R/G156W/V187N/T189Q, G023Q/A049V/L075Q/G156W/V187T, G023Q/D027S/V154I/V187N/L264R, G023Q/K024A/L075Q/G156W/V187Q, K024A/L075R/V154I/G156W/V187Q, L075R/D130A/V154I/T189Q/L264R, L075R/D130A/V187T/T189Q/L264R, N011K/D027N/E056K/N233Q/P256T, N011K/G023K/E056K/L075Q/T189Q, A018K/D027S/P029E/N033D/E045F/L075D, A018K/D027S/P029E/N073R/L075D/T189D, A018K/G023K/D111A/D130A/V154I/T189Q, A018K/G023K/K024A/N094R/D130A/V154I, A018K/G023K/L075Q/D130A/G156W/V187N, A018K/G023K/L075R/N094R/D130A/V187N, A018K/G023Q/E045F/A049V/L075Q/V187T, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075R/D130A/V187N/T189Q, D027E/D048Q/D130A/D137Q/G163P/L264R, D027E/D048Q/D137Q/G163P/L227M/L264R, D027E/D048Q/S058M/G163P/N233Q/L264R, D027Q/E056K/S058M/I090F/N233Q/P256T, D027Q/F051T/L075Q/D130A/V187H/L264R, D027Q/S058M/L075R/D130A/V187T/I252Q, D027S/P029E/N033D/E045F/N073R/T189D, G023K/K024A/L075Q/N094R/D130A/G156W, G023K/K024A/L075Q/V154I/G156W/V187Q, G023Q/K024A/L075Q/D130A/V154I/G156W, K024A/L075Q/D111A/V154I/V187N/T189Q, K024A/L075Q/V154I/V187T/T189Q/L264R, L075R/D130A/V154I/G156W/V187N/L264R, N011K/E056K/L075Q/D130A/V187N/T189Q, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075R/N094R/D130A/V154I, A018K/G023K/K024A/L075R/V154I/G156W/V187Q, A018K/G023Q/E045F/L075Q/V077I/G156W/V187T, A018K/G023Q/K024A/L075Q/V077I/N094R/V154I, A018K/G023Q/L075R/V077I/N094R/G156W/V187N, A018K/K024A/L075Q/D130A/V154I/G156W/V187T, D027E/D130A/D137Q/G163P/L227M/N233Q/L264R, D048Q/D130A/D137Q/G163P/L227M/N233Q/L264R, E056K/L075Q/D111A/D130A/G156W/V187N/T189Q, G023K/D027Q/F051T/L075G/D130A/V187H/L264R, G023K/L075R/N094R/V154I/G156W/V187N/L264R, G023Q/D027S/L075Q/G091Q/V187T/I252Q/L264R, G023Q/E056K/L075R/D111A/D130A/V187N/T189Q, G023Q/L075Q/D130A/V154I/G156W/T189Q/L264R, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/N094R/D130A/G156W, A018K/G023Q/K024A/L075R/N094R/D130A/V154I/G156W, G023K/D027S/E056K/L075G/D130A/V187T/I252Q/L264R, G023K/L075Q/D111A/V154I/G156W/V187N/T189Q/L264R, G023Q/L075Q/N094R/D111A/D130A/G156W/T189Q/L264R, A018K/G023K/L075Q/N094R/D111A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, N011K/G023K/L075R/D111A/D130A/V154I/V187N/T189Q/L264R, A018K/G023Q/D027S/P029E/S058M/L075Q/V077I/R108K/H135F/V187H, G023K/D027S/F051T/E056K/S058M/L075G/G091Q/D130A/I252Q/L264R |

TABLE 3-20

| TLL variants with Performance Index for expression ≥0.5 and Performance Index >1 for p-nitrophenyl caprylate (octanoate) hydrolysis at pH 6 compared to TLL SEQ ID NO: 1 are shown below. |
| --- |
| D027E/G163P, P029E/N033D, A018K/L075D/T189D, A018K/P029E/T189D, D027S/N033D/T189D, G023K/V187N/L264R, L075G/D130A/V187H, L075R/D130A/L264R, L075R/D130A/V187T, P029E/N033D/E045F, A018K/D027S/P029E/T189D, A018K/L075Q/V077I/N094R, D027E/D137Q/L227M/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075R/D130A/L264R, P029E/N073R/L075D/T189D, A018K/D027S/P029E/N033D/L075D, A018K/G023Q/K024A/L075Q/G156W, A018K/K024A/L075R/D130A/V154I, A018K/K024A/N094R/D130A/V187N, A018K/P029E/N033D/N073R/L075D, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, K024A/L075R/V154I/G156W/V187Q, A018K/D027S/P029E/N033D/E045F/L075D, A018K/G023Q/N094R/D130A/G156W/V187Q, A018K/K024A/L075Q/N094R/V154I/G156W, D027E/D048Q/D130A/D137Q/G163P/L264R, D027E/D048Q/D137Q/G163P/L227M/L264R, D027E/D048Q/S058M/G163P/N233Q/L264R, D027Q/S058M/L075R/D130A/V187T/I252Q, G023K/K024A/L075Q/V154I/G156W/V187Q, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023Q/L075R/V077I/N094R/G156W/V187N, A018K/K024A/L075Q/D130A/V154I/G156W/V187T, D027E/D130A/D137Q/G163P/L227M/N233Q/L264R, D048Q/D130A/D137Q/G163P/L227M/N233Q/L264R, G023Q/E056K/L075R/D111A/D130A/V187N/T189Q, A018K/G023K/K024A/L075Q/N094R/D130A/G156W/V187Q, A018K/G023K/K024A/L075Q/V077I/N094R/D130A/G156W, G023K/K024A/L075Q/N094R/V154I/G156W/V187N/T189Q/L264R, A018K/G023Q/D027S/P029E/S058M/L075Q/V077I/R108K/H135F/V187H |

TABLE 3-21

| TLL variants with Performance Index for expression ≥0.5 and Performance Index ≥50% of the maximum PI value for p-nitrophenyl caprylate (octanoate) hydrolysis at pH 6 compared to TLL SEQ ID NO: 1 are shown below. |
| --- |
| A018K/P029E/T189D, D027S/N033D/T189D, G023K/V187N/L264R, L075R/D130A/V187T, A018K/D027S/P029E/T189D, A018K/L075Q/V077I/N094R, D027S/P029E/E045F/T189D, D027S/P029E/N033D/E045F, D027S/P029E/N033D/L075D, D048Q/D130A/G163P/L264R, D130A/G163P/L227M/L264R, P029E/N073R/L075D/T189D, A018K/G023Q/K024A/L075Q/G156W, A018K/K024A/L075R/D130A/V154I, G023K/E056K/D130A/V187T/L264R, G023K/L075Q/V077I/D130A/G156W, K024A/L075R/V154I/G156W/V187Q, A018K/D027S/P029E/N033D/E045F/L075D, A018K/K024A/L075Q/N094R/V154I/G156W, D027E/D048Q/D130A/D137Q/G163P/L264R, D027E/D048Q/D137Q/G163P/L227M/L264R, G023K/K024A/L075Q/V154I/G156W/V187Q, A018K/D027S/P029E/N033D/N073R/L075D/T189D, A018K/G023K/K024A/L075Q/N094R/G156W/V187Q, D027E/D130A/D137Q/G163P/L227M/N233Q/L264R, D048Q/D130A/D137Q/G163P/L227M/N233Q/L264R, A018K/G023K/K024A/L075Q/V077I/N094R/D130A/G156W |

TABLE 3-22

| TLL variants with Performance Index >1 compared to Reference sequence SEQ ID NO: 2 for p-nitrophenyl caprylate (octanoate) hydrolysis at pH 6 are shown below. |
| --- |
| D027E/G163P, K024A/L075Q, A018K/D027S/E045F, A018K/L075D/T189D, A018K/L075Q/V187T, A018K/N073R/L075D, A018K/P029E/T189D, A049V/V187T/T189D, D027S/N033D/T189D, G023K/V187N/L264R, G023Q/L075Q/V187T, L075G/D130A/V187H, L075Q/D111A/D130A, L075Q/G156W/T189D, L075Q/G156W/V187N, L075R/D130A/L264R, L075R/D130A/V187T, N073R/L075D/T189D, P029E/N033D/L075D, A018K/D027S/N033D/L075D, A018K/D027S/P029E/T189D, A018K/G023Q/A049V/T189D, A018K/G023Q/L075R/D130A, A018K/G023Q/V077I/V187T, A018K/L075Q/V077I/N094R, A018K/P029E/N033D/T189D, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, G023K/L075Q/G156W/V187N, G023K/L075R/D130A/L264R, G023Q/E045F/A049V/T189D, G023Q/K024A/L075R/V154I, K024A/L075Q/D130A/V154I, |

TABLE 3-22-continued

| TLL variants with Performance Index >1 compared to Reference sequence SEQ ID NO: 2 for p-nitrophenyl caprylate (octanoate) hydrolysis at pH 6 are shown below. |
|---|
| K024A/L075R/G156W/V187N, L075Q/D130A/G156W/V187N, L075Q/V077I/G156W/V187N, L075Q/V077I/V187T/T189D, P029E/E045F/L075D/T189D, P029E/N033D/L075D/T189D, P029E/N073R/L075D/T189D, A018K/D027S/N033D/L075D/T189D, A018K/D027S/P029E/E045F/T189D, A018K/D027S/P029E/N033D/L075D, A018K/D027S/P029E/N073R/L075D, A018K/G023K/K024A/L075R/N094R, A018K/G023Q/E045F/A049V/L075Q, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/K024A/L075R/D130A/V154I, A018K/K024A/N094R/D130A/V187N, A018K/L075Q/D111A/D130A/V187T, A018K/L075Q/N094R/G156W/V187N, A018K/P029E/N033D/N073R/L075D, D027E/D048Q/S058M/G163P/N233Q, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/K024A/L075R/D130A/G156W, G023K/L075Q/D111A/D130A/V187T, G023K/L075Q/V077I/D130A/G156W, G023K/N094R/G156W/V187N/T189Q, G023Q/A049V/L075Q/G156W/V187T, G023Q/K024A/L075Q/G156W/V187Q, K024A/L075R/V154I/G156W/V187Q, L075R/D130A/V154I/T189Q/L264R, L075R/D130A/V187T/T189Q/L264R, N011K/D027N/E056K/N233Q/P256T, N011K/G023K/E056K/L075Q/T189Q, A018K/D027S/P029E/N033D/E045F/L075D, A018K/D027S/P029E/N073R/L075D/T189D, A018K/G023K/D111A/D130A/V154I/T189Q, A018K/G023K/K024A/N094R/D130A/V154I, A018K/G023K/L075Q/D130A/G156W/V187N, A018K/G023K/L075R/N094R/D130A/V187N, A018K/G023Q/E045F/A049V/L075Q/V187T, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075R/D130A/V187N/T189Q, D027E/D048Q/D130A/D137Q/G163P/L264R, D027E/D048Q/D137Q/G163P/L227M/L264R, D027E/D048Q/S058M/G163P/N233Q/L264R, D027Q/E056K/S058M/I090F/N233Q/P256T, D027Q/F051T/L075Q/D130A/V187H/L264R, D027Q/S058M/L075R/D130A/V187T/I252Q, D027S/P029E/N033D/E045F/N073R/T189D, G023K/K024A/L075Q/N094R/D130A/G156W, G023K/K024A/L075Q/V154I/G156W/V187Q, G023Q/K024A/L075Q/D130A/V154I/G156W, K024A/L075Q/D111A/V154I/V187N/T189Q, K024A/L075Q/V154I/V187T/T189Q/L264R, L075R/D130A/V154I/G156W/V187N/L264R, N011K/E056K/L075Q/D130A/V187N/T189Q, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075R/N094R/D130A/V154I, A018K/G023K/K024A/L075R/V154I/G156W/V187Q, A018K/G023Q/E045F/L075Q/V077I/G156W/V187T, A018K/G023Q/K024A/L075Q/V077I/N094R/V154I, A018K/G023Q/L075R/V077I/N094R/G156W/V187N, A018K/K024A/L075Q/D130A/V154I/G156W/V187T, D027E/D130A/D137Q/G163P/L227M/N233Q/L264R, D048Q/D130A/D137Q/G163P/L227M/N233Q/L264R, E056K/L075Q/D111A/D130A/G156W/V187N/T189Q, G023K/D027Q/F051T/L075G/D130A/V187H/L264R, G023K/L075R/N094R/V154I/G156W/V187N/L264R, G023Q/D027S/L075Q/G091Q/V187T/I252Q/L264R, G023Q/L075Q/D130A/V154I/G156W/T189Q/L264R, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/N094R/D130A/G156W, A018K/G023Q/K024A/L075R/N094R/D130A/V154I/G156W, G023K/D027S/E056K/L075G/D130A/V187T/I252Q/L264R, G023K/L075Q/D111A/V154I/G156W/V187N/T189Q/L264R, G023Q/L075Q/N094R/D111A/D130A/G156W/T189Q/L264R, A018K/G023K/L075Q/N094R/D111A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, N011K/G023K/L075R/D111A/D130A/V154I/V187N/T189Q/L264R, A018K/G023Q/D027S/P029E/S058M/L075Q/V077I/R108K/H135F/V187H, G023K/D027S/F051T/E056K/S058M/L075G/G091Q/D130A/I252Q/L264R |

TABLE 3-23

| TLL variants with Performance Index for expression ≥0.5 compared to TLL SEQ ID NO: 1 and Performance Index >1 for p-nitrophenyl caprylate (octanoate) hydrolysis at pH 6 compared to SEQ ID NO: 2 are shown below. |
|---|
| D027E/G163P, A018K/L075D/T189D, A018K/P029E/T189D, D027S/N033D/T189D, G023K/V187N/L264R, L075G/D130A/V187H, L075R/D130A/L264R, L075R/D130A/V187T, A018K/D027S/P029E/T189D, A018K/L075Q/V077I/N094R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D027Q/F051T/L075Q, |

TABLE 3-23-continued

| TLL variants with Performance Index for expression ≥0.5 compared to TLL SEQ ID NO: 1 and Performance Index >1 for p-nitrophenyl caprylate (octanoate) hydrolysis at pH 6 compared to SEQ ID NO: 2 are shown below. |
|---|
| G023K/L075R/D130A/L264R, P029E/N073R/L075D/T189D, A018K/D027S/P029E/N033D/L075D, A018K/G023Q/K024A/L075Q/G156W, A018K/K024A/L075R/D130A/V154I, A018K/K024A/N094R/D130A/V187N, A018K/P029E/N033D/N073R/L075D, D027S/L075R/V154I/T189Q/L264R, D130A/D137Q/G163P/N233Q/L264R, G023K/D027S/E056K/V187T/L264R, G023K/E056K/D130A/V187T/L264R, G023K/E056K/L075R/D130A/V187T, G023K/E056K/L075R/V187T/L264R, G023K/L075Q/V077I/D130A/G156W, G023K/N094R/G156W/V187N/T189Q, G023Q/K024A/L075Q/G156W/V187Q, K024A/L075R/V154I/G156W/V187Q, A018K/D027S/P029E/N033D/E045F/L075D, A018K/G023Q/N094R/D130A/G156W/V187Q, A018K/K024A/L075Q/N094R/V154I/G156W, D027E/D048Q/D130A/D137Q/G163P/L264R, D027E/D048Q/D137Q/G163P/L227M/L264R, D027E/D048Q/S058M/G163P/N233Q/L264R, D027Q/S058M/L075R/D130A/V187T/I252Q, G023K/K024A/L075Q/V154I/G156W/V187Q, K024A/L075Q/D111A/V154I/V187N/T189Q, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023Q/L075R/V077I/N094R/G156W/V187N, A018K/K024A/L075Q/D130A/V154I/G156W/V187T, D027E/D130A/D137Q/G163P/L227M/N233Q/L264R, D048Q/D130A/D137Q/G163P/L227M/N233Q/L264R, A018K/G023K/K024A/L075Q/N094R/D130A/G156W/V187Q, A018K/G023K/K024A/L075Q/V077I/N094R/D130A/G156W, G023K/K024A/L075Q/N094R/V154I/G156W/V187N/T189Q/L264R, A018K/G023Q/D027S/P029E/S058M/L075Q/V077I/R108K/H135F/V187H |

TABLE 3-24

| TLL variants with Performance Index for expression ≥0.5 compared to TLL SEQ ID NO: 1 and Performance Index ≥50% of the maximum PI value for p-nitrophenyl caprylate (octanoate) hydrolysis at pH 6 compared to SEQ ID NO: 2 are shown below. |
|---|
| A018K/P029E/T189D, D027S/N033D/T189D, G023K/V187N/L264R, L075R/D130A/V187T, A018K/D027S/P029E/T189D, A018K/L075Q/V077I/N094R, D027S/P029E/E045F/T189D, D027S/P029E/N033D/E045F, D027S/P029E/N033D/L075D, D048Q/D130A/G163P/L264R, D130A/G163P/L227M/L264R, P029E/N073R/L075D/T189D, A018K/G023Q/K024A/L075Q/G156W, A018K/K024A/L075R/D130A/V154I, G023K/E056K/D130A/V187T/L264R, G023K/L075Q/V077I/D130A/G156W, K024A/L075R/V154I/G156W/V187Q, A018K/D027S/P029E/N033D/E045F/L075D, A018K/K024A/L075Q/N094R/V154I/G156W, D027E/D048Q/D130A/D137Q/G163P/L264R, D027E/D048Q/D137Q/G163P/L227M/L264R, G023K/K024A/L075Q/V154I/G156W/V187Q, A018K/D027S/P029E/N033D/N073R/L075D/T189D, A018K/G023K/K024A/L075Q/N094R/G156W/V187Q, D027E/D130A/D137Q/G163P/L227M/N233Q/L264R, D048Q/D130A/D137Q/G163P/L227M/N233Q/L264R, A018K/G023K/K024A/L075Q/V077I/N094R/D130A/G156W |

TABLE 3-25

| TLL variants with increased pNPP/pNPB or pNPO/pNPB specific activity ratio compared to TLL SEQ ID NO: 1 are shown below. |
|---|
| A018K/E045F, D111A/L264R, D130A/V187T, G023K/L264R, L075R/L264R, S058M/L264R, V187T/L264R, A018K/E045F/T189D, A018K/G023K/L075Q, A018K/N033D/T189D, D027N/N233Q/P256T, D027Q/N233Q/P256T, D027Q/S058M/P256T, D111A/D130A/L264R, D130A/V154I/G156W, D130A/V187N/L264R, F051T/I252Q/L264R, G023K/D130A/L264R, G023K/E056K/V187T, G023K/L075R/L264R, G023K/V187T/L264R, G163P/L227M/L264R, L075Q/V187T/L264R, Q004D/D027S/P256T, A018K/D130A/G156W/V187T, A018K/G023K/D111A/T189Q, A018K/G023Q/A049V/V187T, A018K/G023Q/V077I/G156W, D027E/D048Q/G163P/L264R, D027E/D130A/N233Q/L264R, D027E/G163P/L227M/L264R, D027S/D130A/I252Q/L264R, D027S/E045F/N073R/L075D, D027S/N033D/E045F/T189D, D048Q/D130A/G163P/L264R, D111A/D130A/V154I/G156W, D111A/D130A/V187T/L264R, E056K/D130A/V187N/L264R, F051T/D130A/I252Q/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/L075R/V187T/L264R, G023Q/E045F/A049V/V187T, G023Q/E045F/L075Q/G156W, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, N011K/S058M/N233Q/P256T, P029E/E045F/N073R/T189D, Q004D/D027N/E056K/P256T, Q004D/N011K/D027N/P256T, Q004D/N011K/D027S/P256T, S058M/G163P/L227M/L264R, S058M/G163P/N233Q/L264R, S058M/L075Q/I252Q/L264R, A018K/D130A/G156W/V187N/L264R, A018K/E045F/A049V/L075Q/T189D, A018K/G023K/K024A/D130A/V154I, |

TABLE 3-25-continued

| TLL variants with increased pNPP/pNPB or pNPO/pNPB specific activity ratio compared to TLL SEQ ID NO: 1 are shown below. |
|---|
| A018K/G023K/V077I/D130A/V187N, A018K/G023Q/A049V/L075Q/V187T, A018K/G023Q/E045F/V077I/T189D, A018K/G023Q/K024A/L075Q/G156W, A018K/K024A/N094R/G156W/V187T, A018K/L075Q/N094R/D130A/V187N, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027N/E056K/S058M/N233Q/P256T, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075R/V154I/T189Q/L264R, D027S/N033D/E045F/N073R/L075D, D027S/P029E/N033D/E045F/N073R, D048Q/D130A/G163P/L227M/L264R, D048Q/D137Q/G163P/L227M/L264R, D048Q/D137Q/G163P/N233Q/L264R, D048Q/S058M/D137Q/N233Q/L264R, D130A/D137Q/G163P/L227M/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/E056K/D130A/V187N/L264R, G023K/K024A/D111A/D130A/V187T, G023K/K024A/D111A/G156W/T189Q, G023K/L075Q/V077I/D130A/G156W, G023K/L075R/D130A/V187N/L264R, G023K/N094R/G156W/V187N/T189Q, G023Q/E045F/A049V/V077I/T189D, G023Q/E045F/L075Q/V077I/V187T, G023Q/E056K/V187N/I252Q/L264R, G023Q/F051T/L075Q/G091Q/I252Q, G023Q/L075G/G091Q/I252Q/L264R, G023Q/L075Q/D130A/I252Q/L264R, G023Q/L075Q/G091Q/I252Q/L264R, K024A/L075R/V154I/G156W/V187Q, L075G/D130A/V187T/I252Q/L264R, L075Q/D111A/D130A/V187T/T189Q, L075Q/V077I/D130A/G156W/V187N, N011K/D027N/S058M/N233Q/P256T, N011K/D027Q/S058M/N233Q/P256T, S058M/D130A/G163P/L227M/L264R, S058M/G163P/L227M/N233Q/L264R, A018K/G023Q/A049V/G156W/V187T/T189D, A018K/G023Q/E045F/L075Q/G156W/V187T, A018K/G023Q/K024A/V077I/V154I/V187N, A018K/G023Q/K024A/V154I/G156W/V187Q, A018K/K024A/D111A/V187N/T189Q/L264R, A018K/K024A/V077I/N094R/D130A/G156W, D027E/D048Q/D130A/D137H/G163P/L264R, D027E/D048Q/D130A/G163P/L227M/L264R, D027E/D048Q/D137Q/G163P/L227M/L264R, D027E/D130A/D137Q/G163P/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D130A/V154I/G156W/V187T/L264R, G023K/E056K/L075R/D130A/V187T/L264R, G023K/F051T/D130A/V187N/I252Q/L264R, G023K/F051T/L075Q/D130A/I252Q/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D111A/V154I/V187N/T189Q, K024A/L075Q/D130A/G156W/T189Q/L264R, L075Q/G091Q/D130A/V187H/I252Q/L264R, N011K/D027Q/E056K/S058M/N233Q/P256T, N011K/D027S/E056K/S058M/N233Q/P256T, Q004D/D027N/E056K/S058M/N233Q/P256T, Q004D/N011K/D027N/I090F/N233Q/P256T, Q004D/N011K/D027S/I090F/N233Q/P256T, S058M/D130A/D137Q/G163P/L227M/L264R, S058M/D130A/G163P/L227M/N233Q/L264R, A018K/G023Q/E045F/A049V/L075Q/G156W/V187T, A018K/K024A/D130A/V154I/G156W/V187T/L264R, A018K/K024A/N094R/D130A/G156W/V187T/L264R, A018K/L075Q/D130A/G156W/V187N/T189Q/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/G091Q/V187N/I252Q, |

TABLE 3-25-continued

| TLL variants with increased pNPP/pNPB or pNPO/pNPB specific activity ratio compared to TLL SEQ ID NO: 1 are shown below. |
|---|
| G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, Q004D/N011K/D027N/S058M/I090F/N233Q/P256T, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/L075Q/N094R/D111A/D130A/V154I/T189Q, A018K/G023K/K024A/L075Q/N094R/D130A/V154I/G156W/V187N, D027Q/F051T/S058M/L075G/G091Q/D130A/V187T/I252Q/L264R, G023Q/F051T/S058M/L075Q/G091Q/D130A/V187H/I252Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R |

TABLE 3-26

| TLL variants with Performance Index for expression ≥0.5 and increased pNPP/pNPB or pNPO/pNPB specific activity ratio compared to TLL SEQ ID NO: 1 are shown below. |
|---|
| A018K/E045F, D111A/L264R, D130A/V187T, G023K/L264R, L075R/L264R, S058M/L264R, V187T/L264R, A018K/N033D/T189D, D027Q/S058M/P256T, D111A/D130A/L264R, D130A/V154I/G156W, D130A/V187N/L264R, F051T/I252Q/L264R, G023K/D130A/L264R, G023K/E056K/V187T, G023K/L075R/L264R, G023K/V187T/L264R, G163P/L227M/L264R, L075Q/V187T/L264R, Q004D/D027S/P256T, A018K/D130A/G156W/V187T, A018K/G023K/D111A/T189Q, A018K/G023Q/A049V/V187T, A018K/G023Q/V077I/G156W, D027E/D048Q/G163P/L264R, D027E/D130A/N233Q/L264R, D027E/G163P/L227M/L264R, D027S/D130A/I252Q/L264R, D027S/N033D/E045F/T189D, D048Q/D130A/G163P/L264R, D111A/D130A/V154I/G156W, D111A/D130A/V187T/L264R, E056K/D130A/V187N/L264R, F051T/D130A/I252Q/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/L075R/V187T/L264R, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, Q004D/D027N/E056K/P256T, Q004D/N011K/D027S/P256T, S058M/G163P/L227M/L264R, S058M/G163P/N233Q/L264R, S058M/L075Q/I252Q/L264R, A018K/D130A/G156W/V187N/L264R, A018K/G023K/K024A/D130A/V154I, A018K/G023K/V077I/D130A/V187N, A018K/G023Q/K024A/L075Q/G156W, A018K/K024A/N094R/G156W/V187T, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027E/S058M/D130A/G163P/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/D130A/G163P/L227M/L264R, D048Q/D137Q/G163P/L227M/L264R, D048Q/D137Q/G163P/N233Q/L264R, D048Q/S058M/D137Q/N233Q/L264R, D130A/D137Q/G163P/L227M/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/E056K/D130A/V187N/L264R, G023K/K024A/D111A/D130A/V187T, G023K/K024A/D111A/G156W/T189Q, G023K/L075Q/V077I/D130A/G156W, G023K/L075R/D130A/V187N/L264R, G023K/N094R/G156W/V187N/T189Q, G023Q/E056K/V187N/I252Q/L264R, G023Q/F051T/L075Q/G091Q/I252Q, G023Q/L075G/G091Q/I252Q/L264R, G023Q/L075Q/D130A/I252Q/L264R, G023Q/L075Q/G091Q/I252Q/L264R, K024A/L075R/V154I/G156W/V187Q, L075G/D130A/V187T/I252Q/L264R, N011K/D027N/S058M/N233Q/P256T, S058M/D130A/G163P/L227M/L264R, S058M/G163P/L227M/N233Q/L264R, A018K/G023Q/A049V/G156W/V187T/T189D, A018K/G023Q/K024A/V077I/V154I/V187N, A018K/G023Q/K024A/V154I/G156W/V187Q, A018K/K024A/D111A/V187N/T189Q/L264R, D027E/D048Q/D130A/D137H/G163P/L264R, D027E/D048Q/D130A/G163P/L227M/L264R, D027E/D048Q/D137Q/G163P/L227M/L264R, D027E/D130A/D137Q/G163P/N233Q/L264R, D027E/D137Q/G163P/L227M/N233Q/L264R, D027E/S058M/D130A/G163P/L227M/L264R, |

TABLE 3-26-continued

| TLL variants with Performance Index for expression ≥0.5 and increased pNPP/pNPB or pNPO/pNPB specific activity ratio compared to TLL SEQ ID NO: 1 are shown below. |
| --- |
| D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/G163P/L227M/N233Q/L264R, F051T/E056K/D130A/V187N/I252Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D130A/V154I/G156W/V187T/L264R, G023K/E056K/L075R/D130A/V187T/L264R, G023K/F051T/D130A/V187N/I252Q/L264R, G023K/F051T/L075Q/D130A/I252Q/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, Q004D/N011K/D027N/I090F/N233Q/P256T, S058M/D130A/D137Q/G163P/L227M/L264R, S058M/D130A/G163P/L227M/N233Q/L264R, A018K/K024A/D130A/V154I/G156W/V187T/L264R, A018K/K024A/N094R/D130A/G156W/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/G091Q/V187N/I252Q, G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, D027Q/F051T/S058M/L075G/G091Q/D130A/V187T/I252Q/L264R, G023Q/F051T/S058M/L075Q/G091Q/D130A/V187H/I252Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R |

TABLE 3-27

| TLL variants with Performance Index for expression ≥0.5 and pNPP/pNPB or pNPO/pNPB ≥50% of the maximum specific activity ratio compared to TLL SEQ ID NO: 1 are shown below. |
| --- |
| D130A/V187T, D027Q/S058M/P256T, F051T/I252Q/L264R, A018K/G023K/D111A/T189Q, A018K/G023Q/A049V/V187T, D027S/D130A/I252Q/L264R, D027S/N033D/E045F/T189D, F051T/D130A/I252Q/L264R, F051T/L075G/I252Q/L264R, F051T/L075Q/I252Q/L264R, G023K/D130A/V187T/T189Q, G023K/L075R/V187T/L264R, G023Q/F051T/I252Q/L264R, G023Q/G091Q/I252Q/L264R, G023Q/L075Q/V187T/L264R, G091Q/V187T/I252Q/L264R, L075G/V187H/I252Q/L264R, Q004D/N011K/D027S/P256T, S058M/G163P/L227M/L264R, S058M/L075Q/I252Q/L264R, D027E/D048Q/D137Q/L227M/L264R, |

TABLE 3-27-continued

| TLL variants with Performance Index for expression ≥0.5 and pNPP/pNPB or pNPO/pNPB ≥50% of the maximum specific activity ratio compared to TLL SEQ ID NO: 1 are shown below. |
|---|
| D027E/D048Q/G163P/N233Q/L264R, D027E/D130A/D137Q/G163P/L264R, D027E/D130A/G163P/L227M/L264R, D027E/G163P/L227M/N233Q/L264R, D027S/F051T/V187N/I252Q/L264R, D027S/L075G/D130A/I252Q/L264R, D048Q/D137Q/G163P/N233Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023K/K024A/D111A/G156W/T189Q, G023Q/E056K/V187N/I252Q/L264R, G023Q/L075Q/G091Q/I252Q/L264R, N011K/D027N/S058M/N233Q/P256T, A018K/G023Q/K024A/V077I/V154I/V187N, A018K/K024A/D111A/V187N/T189Q/L264R, D027E/D048Q/D130A/G163P/L227M/L264R, D027E/D048Q/D137Q/G163P/L227M/L264R, D027E/S058M/D130A/L227M/N233Q/L264R, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/F051T/D130A/V187N/I252Q/L264R, G023K/F051T/L075Q/D130A/I252Q/L264R, G023Q/F051T/G091Q/V187N/I252Q/L264R, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, A018K/K024A/D130A/V154I/G156W/V187T/L264R, D027E/S058M/D130A/G163P/L227M/N233Q/L264R, D027Q/F051T/L075Q/D130A/V187T/I252Q/L264R, D027Q/F051T/S058M/L075Q/G091Q/I252Q/L264R, D027S/F051T/S058M/L075Q/V187N/I252Q/L264R, D027S/F051T/S058M/L075R/D130A/I252Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/G091Q/V187N/I252Q, G023Q/D027S/F051T/E056K/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, D027Q/F051T/S058M/L075G/G091Q/D130A/V187T/I252Q/L264R, G023Q/F051T/S058M/L075Q/G091Q/D130A/V187H/I252Q/L264R |

TABLE 3-28

| TLL variants with increased pNPP/pNPB or pNPO/pNPB specific activity ratio compared to Reference sequence SEQ ID NO: 2 are shown below. |
|---|
| A018K/E045F, D130A/V187T, G023K/L264R, S058M/L264R, A018K/E045F/T189D, A018K/G023K/L075Q, D027N/N233Q/P256T, D027Q/N233Q/P256T, D130A/V187N/L264R, F051T/I252Q/L264R, G023K/D130A/L264R, G023K/V187T/L264R, Q004D/D027S/P256T, D027E/D130A/N233Q/L264R, D027E/G163P/L227M/L264R, D027S/D130A/I252Q/L264R, D027S/E045F/N073R/L075D, D048Q/D130A/G163P/L264R, E056K/D130A/V187N/L264R, F051T/D130A/I252Q/L264R, F051T/L075G/I252Q/L264R, F051T/L075Q/I252Q/L264R, G023K/D130A/V187N/L264R, G023K/E056K/L075R/L264R, G023K/L075R/V187T/L264R, G023Q/E045F/A049V/V187T, G023Q/E045F/L075Q/G156W, G023Q/F051T/I252Q/L264R, G023Q/G091Q/I252Q/L264R, G023Q/L075Q/V187T/L264R, G091Q/V187T/I252Q/L264R, L075G/D130A/V187T/I252Q, L075G/V187H/I252Q/L264R, N011K/S058M/N233Q/P256T, P029E/E045F/N073R/T189D, Q004D/N011K/D027S/P256T, S058M/G163P/L227M/L264R, S058M/L075Q/I252Q/L264R, A018K/D130A/G156W/V187N/L264R, A018K/G023Q/E045F/V077I/T189D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/N033D/E045F/N073R/L075D, D027S/P029E/N033D/E045F/N073R, D048Q/D137Q/G163P/N233Q/L264R, D048Q/S058M/D137Q/N233Q/L264R, D130A/D137Q/G163P/L227M/L264R, E056K/L075G/V187N/I252Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023K/L075R/D130A/V187N/L264R, G023Q/E045F/A049V/V077I/T189D, G023Q/E045F/L075Q/V077I/V187T, G023Q/E056K/V187N/I252Q/L264R, G023Q/L075G/G091Q/I252Q/L264R, G023Q/L075Q/D130A/I252Q/L264R, G023Q/L075Q/G091Q/I252Q/L264R, L075G/D130A/V187T/I252Q/L264R, S058M/G163P/L227M/N233Q/L264R, A018K/G023Q/K024A/V154I/G156W/V187Q, A018K/K024A/D111A/V187N/T189Q/L264R, A018K/K024A/V077I/N094R/D130A/G156W, D027E/D048Q/D130A/D137H/G163P/L264R, |

TABLE 3-28-continued

| TLL variants with increased pNPP/pNPB or pNPO/pNPB specific activity ratio compared to Reference sequence SEQ ID NO: 2 are shown below. |
|---|
| D027E/D048Q/D130A/G163P/L227M/L264R, D027E/D048Q/D137Q/G163P/L227M/L264R, D027E/D137Q/G163P/L227M/N233Q/L264R, D027E/S058M/D130A/G163P/L227M/L264R, D027E/S058M/D130A/L227M/N233Q/L264R, D027Q/F051T/G091Q/D130A/I252Q/L264R, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/G163P/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/F051T/D130A/V187N/I252Q/L264R, G023K/F051T/L075Q/D130A/I252Q/L264R, G023Q/D027S/F051T/L075Q/V187T/L264R, G023Q/F051T/G091Q/V187N/I252Q/L264R, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D130A/G156W/T189Q/L264R, L075Q/G091Q/D130A/V187H/I252Q/L264R, N011K/D027Q/E056K/S058M/N233Q/P256T, N011K/D027S/E056K/S058M/N233Q/P256T, Q004D/D027N/E056K/S058M/N233Q/P256T, Q004D/N011K/D027S/I090F/N233Q/P256T, A018K/K024A/D130A/V154I/G156W/V187T/L264R, A018K/K024A/N094R/D130A/G156W/V187T/L264R, D027E/D048Q/D130A/D137Q/G163P/N233Q/L264R, D027E/D048Q/S058M/D130A/D137Q/G163P/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/G091Q/V187N/I252Q, G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, Q004D/N011K/D027N/S058M/I090F/N233Q/P256T, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/L075Q/N094R/D130A/V154I/G156W/V187N, D027Q/F051T/S058M/L075G/G091Q/D130A/V187T/I252Q/L264R, G023Q/F051T/S058M/L075Q/G091Q/D130A/V187H/I252Q/L264R |

TABLE 3-29

| TLL variants with Performance Index for expression ≥0.5 compared to TLL SEQ ID NO: 1 and increased pNPP/pNPB or pNPO/pNPB specific activity ratio compared to SEQ ID NO: 2 are shown below. |
|---|
| A018K/E045F, D130A/V187T, G023K/L264R, S058M/L264R, D130A/V187N/L264R, F051T/I252Q/L264R, G023K/D130A/L264R, G023K/V187T/L264R, Q004D/D027S/P256T, D027E/D130A/N233Q/L264R, D027E/G163P/L227M/L264R, D027S/D130A/I252Q/L264R, D048Q/D130A/G163P/L264R, E056K/D130A/V187N/L264R, F051T/D130A/I252Q/L264R, F051T/L075G/I252Q/L264R, F051T/L075Q/I252Q/L264R, G023K/D130A/V187N/L264R, G023K/E056K/L075R/L264R, G023K/L075R/V187T/L264R, G023Q/F051T/I252Q/L264R, G023Q/G091Q/I252Q/L264R, G023Q/L075Q/V187T/L264R, G091Q/V187T/I252Q/L264R, L075G/D130A/V187T/I252Q, L075G/V187H/I252Q/L264R, Q004D/N011K/D027S/P256T, S058M/G163P/L227M/L264R, S058M/L075Q/I252Q/L264R, A018K/D130A/G156W/V187N/L264R, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027S/F051T/V187N/I252Q/L264R, D027S/L075G/D130A/I252Q/L264R, D027S/L075G/G091Q/I252Q/L264R, D048Q/D137Q/G163P/N233Q/L264R, D048Q/S058M/D137Q/N233Q/L264R, D130A/D137Q/G163P/L227M/L264R, E056K/L075G/V187N/I252Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023K/L075R/D130A/V187N/L264R, |

TABLE 3-29-continued

| TLL variants with Performance Index for expression ≥0.5 compared to TLL SEQ ID NO: 1 and increased pNPP/pNPB or pNPO/pNPB specific activity ratio compared to SEQ ID NO: 2 are shown below. |
|---|
| G023Q/E056K/V187N/I252Q/L264R, G023Q/L075G/G091Q/I252Q/L264R, G023Q/L075Q/D130A/I252Q/L264R, G023Q/L075Q/G091Q/I252Q/L264R, L075G/D130A/V187T/I252Q/L264R, S058M/G163P/L227M/N233Q/L264R, A018K/G023Q/K024A/V154I/G156W/V187Q, A018K/K024A/D111A/V187N/T189Q/L264R, D027E/D048Q/D130A/D137H/G163P/L264R, D027E/D048Q/D130A/G163P/L227M/L264R, D027E/D048Q/D137Q/G163P/L227M/L264R, D027E/D137Q/G163P/L227M/N233Q/L264R, D027E/S058M/D130A/G163P/L227M/L264R, D027E/S058M/D130A/L227M/N233Q/L264R, D027Q/F051T/G091Q/D130A/I252Q/L264R, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/G163P/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/F051T/D130A/V187N/I252Q/L264R, G023K/F051T/L075Q/D130A/I252Q/L264R, G023Q/D027S/F051T/L075Q/V187T/L264R, G023Q/F051T/G091Q/V187N/I252Q/L264R, G023Q/L075G/G091Q/D130A/I252Q/L264R, G023Q/L075Q/G091Q/V187N/I252Q/L264R, L075Q/G091Q/D130A/V187H/I252Q/L264R, A018K/K024A/D130A/V154I/G156W/V187T/L264R, A018K/K024A/N094R/D130A/G156W/V187T/L264R, D027E/D048Q/D130A/D137Q/G163P/N233Q/L264R, D027E/D048Q/S058M/D130A/D137Q/G163P/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/G091Q/V187N/I252Q, G023Q/D027S/F051T/E056K/D130A/I252Q/L264R, G023Q/D027S/S058M/L075Q/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, D027Q/F051T/S058M/L075G/G091Q/D130A/V187T/I252Q/L264R, G023Q/F051T/S058M/L075Q/G091Q/D130A/V187H/I252Q/L264R |

TABLE 3-30

| TLL variants with Performance Index for expression ≥0.5 compared to TLL SEQ ID NO: 1 and pNPP/pNPB or pNPO/pNPB ≥50% of the maximum specific activity ratio compared to SEQ ID NO: 2 are shown below. |
|---|
| D130A/V187T, F051T/I252Q/L264R, D027S/D130A/I252Q/L264R, F051T/D130A/I252Q/L264R, F051T/L075G/I252Q/L264R, F051T/L075Q/I252Q/L264R, G023K/L075R/V187T/L264R, G023Q/F051T/I252Q/L264R, G023Q/G091Q/I252Q/L264R, G023Q/L075Q/V187T/L264R, G091Q/V187T/I252Q/L264R, L075G/V187H/I252Q/L264R, Q004D/N011K/D027S/P256T, S058M/G163P/L227M/L264R, S058M/L075Q/I252Q/L264R, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/G163P/L227M/N233Q/L264R, D027S/F051T/V187N/I252Q/L264R, D027S/L075G/D130A/I252Q/L264R, D048Q/D137Q/G163P/N233Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023Q/E056K/V187N/I252Q/L264R, G023Q/L075Q/G091Q/I252Q/L264R, A018K/K024A/D111A/V187N/T189Q/L264R, D027E/D048Q/D130A/G163P/L227M/L264R, D027E/D048Q/D137Q/G163P/L227M/L264R, D027E/S058M/D130A/L227M/N233Q/L264R, D027Q/L075Q/D130A/V187T/I252Q/L264R, D027S/F051T/L075Q/D130A/I252Q/L264R, D027S/L075Q/G091Q/V187H/I252Q/L264R, D048Q/S058M/D130A/L227M/N233Q/L264R, |

TABLE 3-30-continued

| TLL variants with Performance Index for expression ≥0.5 compared to TLL SEQ ID NO: 1 and pNPP/pNPB or pNPO/pNPB ≥50% of the maximum specific activity ratio compared to SEQ ID NO: 2 are shown below. |
|---|
| F051T/E056K/D130A/V187N/I252Q/L264R, F051T/L075G/G091Q/V187H/I252Q/L264R, F051T/L075G/G091Q/V187T/I252Q/L264R, G023K/F051T/D130A/V187N/I252Q/L264R, G023K/F051T/L075Q/D130A/I252Q/L264R, G023Q/F051T/G091Q/V187N/I252Q/L264R, G023Q/L075G/G091Q/D130A/I252Q/L264R, G023Q/L075Q/G091Q/V187N/I252Q/L264R, L075Q/G091Q/D130A/V187H/I252Q/L264R, A018K/K024A/D130A/V154I/G156W/V187T/L264R, D027E/S058M/D130A/G163P/L227M/N233Q/L264R, D027Q/F051T/L075Q/D130A/V187T/I252Q/L264R, D027Q/F051T/S058M/L075Q/G091Q/I252Q/L264R, D027S/F051T/S058M/L075Q/V187N/I252Q/L264R, D027S/F051T/S058M/L075R/D130A/I252Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023Q/D027S/F051T/E056K/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, F051T/E056K/L075G/G091Q/D130A/V187H/I252Q/L264R, G023K/D027S/F051T/S058M/L075Q/V187H/I252Q/L264R, G023Q/D027Q/F051T/L075Q/G091Q/D130A/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, D027Q/F051T/S058M/L075G/G091Q/D130A/V187T/I252Q/L264R, G023Q/F051T/S058M/L075Q/G091Q/D130A/V187H/I252Q/L264R |

TABLE 3-31

| TLL variants with increased pNPB/pNPP specific activity ratio compared to TLL SEQ ID NO: 1 are shown below. |
|---|
| A018K/L075D, A018K/T189D, D027N/E056K, D027N/N233Q, D027S/N033D, D027S/P256T, D130A/L264R, D130A/V187N, E045F/N073R, K024A/L075Q, K024A/V154I, L075Q/D130A, N094R/G156W, P029E/N033D, A018K/A049V/V187T, A018K/E045F/N073R, A018K/E045F/V187T, A018K/G023K/G156W, A018K/K024A/V154I, A018K/L075D/T189D, A049V/V187T/T189D, D027E/S058M/G163P, D027N/S058M/P256T, D027S/L075Q/G091Q, D027S/N033D/T189D, D027S/S058M/P256T, D130A/V187T/L264R, E045F/L075D/T189D, E056K/D130A/L264R, G023K/D130A/V187T, G023Q/A049V/T189D, G023Q/D130A/G156W, G023Q/K024A/G156W, G023Q/L075Q/V187T, K024A/D130A/V154I, L075G/D130A/V187H, L075Q/D111A/D130A, L075Q/G156W/V187N, L075Q/V187N/L264R, L075R/D130A/L264R, L075R/D130A/V187T, L075R/V187T/L264R, N011K/D027S/S058M, N011K/N233Q/P256T, N073R/L075D/T189D, N094R/D130A/V187T, P029E/N033D/E045F, V187N/T189Q/L264R, A018K/D027S/N033D/L075D, A018K/D111A/G156W/T189Q, A018K/E045F/A049V/G156W, A018K/E045F/A049V/V187T, A018K/E045F/L075D/T189D, A018K/E045F/L075Q/T189D, A018K/G023K/D111A/T189Q, A018K/G023Q/A049V/V187T, A018K/G023Q/E045F/T189D, A018K/G023Q/E045F/V187T, A018K/G023Q/L075R/D130A, A018K/G023Q/V077I/V187T, A018K/L075Q/G156W/V187T, A018K/L075Q/N094R/D130A, A018K/L075Q/V077I/N094R, A018K/P029E/N073R/L075D, A018K/V154I/G156W/V187T, D027E/D137Q/G163P/L227M, D027E/S058M/G163P/L264R, D027N/E056K/N233Q/P256T, D027N/E056K/S058M/P256T, D027N/S058M/N233Q/P256T, D027Q/E056K/N233Q/P256T, D027S/E045F/L075D/T189D, D027S/E045F/N073R/T189D, D027S/E056K/D111A/V154I, D027S/E056K/I090F/P256T, D027S/N033D/E045F/N073R, D027S/N033D/E045F/T189D, D027S/N033D/L075D/T189D, D027S/N033D/N073R/T189D, D027S/P029E/E045F/L075D, D027S/P029E/E045F/N073R, D027S/P029E/L075D/T189D, D027S/P029E/N033D/L075D, D048Q/G163P/N233Q/L264R, D111A/D130A/V154I/G156W, E045F/A049V/G156W/V187T, E045F/L075Q/G156W/V187T, E056K/D130A/V187T/L264R, G023K/D027Q/F051T/L075Q, G023K/D130A/G156W/T189Q, G023K/K024A/V154I/V187N, G023K/L075Q/G156W/V187N, G023K/L075R/D130A/L264R, G023Q/A049V/V077I/G156W, G023Q/D027S/D111A/G156W, G023Q/K024A/D130A/G156W, G023Q/K024A/L075R/V154I, G023Q/K024A/V077I/G156W, G023Q/V154I/G156W/V187N, K024A/L075R/G156W/V187N, L075G/G091Q/V187N/L264R, L075Q/D130A/G156W/V187N, L075Q/V077I/G156W/V187N, L075Q/V187N/T189Q/L264R, L075R/D130A/V187T/L264R, N011K/D027N/E056K/S058M, N011K/D027Q/S058M/P256T, N011K/D027S/E056K/P256T, N011K/D027S/N233Q/P256T, N011K/E056K/N233Q/P256T, N033D/E045F/N073R/T189A, P029E/E045F/N073R/L075D, P029E/N033D/L075D/T189D, P029E/N073R/L075D/T189D, Q004D/D027N/S058M/P256T, Q004D/D027S/I090F/P256T, S058M/D137Q/G163P/N233Q, S058M/L075Q/G091Q/I252Q, A018K/A049V/L075Q/V187T/T189D, A018K/D027S/E045F/L075D/T189D, A018K/D027S/N033D/L075D/T189D, A018K/D027S/P029E/N033D/L075D, A018K/E045F/A049V/L075Q/V187T, A018K/G023K/D130A/V154I/G156W, A018K/G023K/K024A/D130A/G156W, A018K/G023K/K024A/L075R/N094R, A018K/G023Q/A049V/L075Q/G156W, A018K/G023Q/A049V/L075Q/V187T, A018K/G023Q/E045F/A049V/V187T, A018K/G023Q/E045F/L075Q/V187T, A018K/G023Q/K024A/D130A/V154I, A018K/G023Q/K024A/D130A/V187Q, A018K/G023Q/L075Q/G156W/V187T, A018K/G023Q/L075Q/V187T/T189D, |

TABLE 3-31-continued

| TLL variants with increased pNPB/pNPP specific activity ratio compared to TLL SEQ ID NO: 1 are shown below. |
|---|
| A018K/G023Q/V077I/D130A/G156W, A018K/G023Q/V077I/V187T/T189D, A018K/K024A/L075Q/D130A/L264R, A018K/K024A/L075Q/V154I/T189D, A018K/K024A/N094R/D130A/V187N, A018K/K024A/N094R/G156W/V187T, A018K/L075Q/D111A/D130A/V187T, A018K/L075Q/N094R/G156W/V187N, A018K/P029E/E045F/N073R/L075D, A018K/P029E/N033D/N073R/L075D, A018K/V077I/G156W/V187T/T189D, D027E/S058M/D137Q/G163P/N233Q, D027E/S058M/G163P/L227M/L264R, D027Q/E056K/I090F/N233Q/P256T, D027Q/E056K/S058M/N233Q/P256T, D027S/P029E/N033D/E045F/N073R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/D137Q/G163P/N233Q/L264R, D130A/G163P/L227M/N233Q/L264R, E045F/A049V/L075Q/V187T/T189D, G023K/E056K/L075R/D130A/V187T, G023K/E056K/L075R/V187T/L264R, G023K/K024A/D111A/D130A/V187T, G023K/K024A/L075R/D130A/G156W, G023K/L075Q/D111A/D130A/V187T, G023K/L075Q/D130A/V154I/T189Q, G023K/N094R/G156W/V187N/T189Q, G023Q/A049V/L075Q/G156W/V187T, G023Q/E045F/A049V/G156W/T189D, G023Q/E045F/A049V/L075Q/V077I, G023Q/K024A/L075Q/G156W/V187Q, G023Q/K024A/L075R/D130A/V154I, G023Q/K024A/L075R/V077I/D130A, G023Q/L075Q/V077I/D130A/G156W, K024A/L075R/D111A/V154I/V187T, K024A/L075R/G156W/V187N/T189Q, L075Q/D130A/V187T/T189Q/L264R, L075Q/N094R/D130A/G156W/V187T, L075R/D130A/V154I/T189Q/L264R, L075R/D130A/V187T/T189Q/L264R, N011K/D027N/S058M/N233Q/P256T, N011K/D027Q/E056K/S058M/N233Q, N011K/D027Q/S058M/N233Q/P256T, N011K/D027S/E056K/N233Q/P256T, N011K/D027S/I090F/N233Q/P256T, N011K/G023K/D111A/G156W/L264R, P029E/N033D/E045F/L075D/T189D, Q004D/D027N/E056K/S058M/P256T, Q004D/D027N/I090F/N233Q/P256T, Q004D/D027Q/E056K/S058M/P256T, Q004D/N011K/D027N/N233Q/P256T, S058M/D130A/D137Q/G163P/L264R, S058M/D137Q/G163P/L227M/L264R, V077I/D130A/V154I/G156W/V187N, A018K/D027S/N033D/E045F/N073R/L075D, A018K/D027S/N033D/N073R/L075D/T189D, A018K/G023K/K024A/N094R/D130A/V154I, A018K/G023K/K024A/V077I/G156W/V187Q, A018K/G023K/L075Q/D130A/G156W/V187N, A018K/G023K/L075Q/V077I/G156W/V187Q, A018K/G023K/L075R/N094R/D130A/V187N, A018K/G023Q/A049V/G156W/V187T/T189D, A018K/G023Q/A049V/L075Q/V077I/G156W, A018K/G023Q/A049V/V077I/V187T/T189D, A018K/G023Q/E045F/A049V/G156W/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075R/D130A/V187N/T189Q, A018K/L075Q/D111A/V154I/G156W/V187N, A018K/L075Q/D111A/V154I/T189Q/L264R, A018K/L075Q/D130A/V187N/T189Q/L264R, A018K/N094R/D111A/D130A/V154I/V187N, A018K/P029E/N033D/E045F/L075D/T189D, D027E/D048Q/S058M/D130A/G163P/L264R, D027E/D048Q/S058M/G163P/L227M/L264R, D027E/D048Q/S058M/G163P/N233Q/L264R, D027Q/E056K/S058M/D130A/I252Q/L264R, D027Q/F051T/L075Q/D130A/V187H/L264R, D027Q/S058M/L075R/D130A/V187T/I252Q, D027S/E056K/S058M/V187T/I252Q/L264R, D027S/P029E/N033D/E045F/N073R/L075D, D027S/P029E/N033D/E045F/N073R/T189D, D027S/P029E/N033D/N073R/L075D/T189D, D048Q/S058M/D130A/D137Q/G163P/L264R, D048Q/S058M/D137Q/G163P/N233Q/L264R, G023K/D027Q/F051T/E056K/S058M/L075Q, G023K/D027S/L075R/D130A/V187T/I252Q, G023K/E056K/L075R/D130A/T189Q/L264R, G023K/E056K/L075R/D130A/V187N/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075Q/V154I/G156W/V187Q, G023K/K024A/L075R/D130A/V154I/V187N, G023K/N094R/D111A/G156W/V187T/L264R, G023Q/D027S/N094R/V154I/G156W/T189Q, G023Q/E056K/L075Q/D130A/V154I/L264R, G023Q/F051T/D130A/V187T/I252Q/L264R, G023Q/K024A/L075Q/D130A/V154I/G156W, G023Q/K024A/V077I/D130A/V154I/G156W, G023Q/L075Q/N094R/D111A/G156W/L264R, K024A/L075Q/D111A/V154I/V187N/T189Q, K024A/L075Q/N094R/D130A/V154I/L264R, K024A/L075Q/V077I/N094R/D130A/V187N, K024A/L075Q/V154I/V187T/T189Q/L264R, L075Q/D111A/D130A/V154I/G156W/T189Q, L075Q/D130A/V154I/G156W/V187N/L264R, L075Q/N094R/D111A/G156W/T189Q/L264R, L075R/D130A/V154I/G156W/V187N/L264R, N011K/D027N/E056K/I090F/N233Q/P256T, N011K/D027S/E056K/I090F/N233Q/P256T, Q004D/N011K/D027N/S058M/N233Q/P256T, Q004D/N011K/D027S/S058M/N233Q/P256T, S058M/D130A/D137Q/G163P/N233Q/L264R, A018K/D027S/P029E/N033D/N073R/L075D/T189D, A018K/D111A/D130A/V154I/G156W/V187T/T189Q, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/L075Q/G156W/V187T/T189D, A018K/G023Q/K024A/L075Q/V077I/N094R/V154I, A018K/G023Q/K024A/L075R/N094R/G156W/V187N, A018K/G023Q/L075R/V077I/N094R/G156W/V187N, A018K/K024A/L075Q/D130A/V154I/G156W/V187T, A018K/L075Q/N094R/D111A/V154I/V187T/L264R, |

TABLE 3-31-continued

| TLL variants with increased pNPB/pNPP specific activity ratio compared to TLL SEQ ID NO: 1 are shown below. |
|---|
| D027E/D048Q/S058M/D130A/G163P/L227M/L264R, D027Q/F051T/L075G/D130A/V187H/I252Q/L264R, D027S/E056K/L075R/D111A/G156W/V187N/L264R, D027S/F051T/L075G/G091Q/V187T/I252Q/L264R, D048Q/S058M/D137Q/G163P/L227M/N233Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/F051T/E056K/L075R/D130A/V187T/I252Q, G023K/K024A/L075Q/D111A/D130A/T189Q/L264R, G023K/K024A/N094R/V154I/G156W/V187N/T189Q, G023K/L075Q/D111A/D130A/V154I/G156W/L264R, G023K/L075Q/N094R/D130A/V154I/V187N/L264R, G023Q/E056K/L075Q/D111A/G156W/V187N/L264R, G023Q/E056K/L075R/D111A/D130A/V187N/T189Q, G023Q/F051T/G091Q/D130A/V187H/I252Q/L264R, G023Q/L075Q/D111A/D130A/V154I/G156W/L264R, G023Q/L075Q/D130A/V154I/V187N/T189Q/L264R, G023Q/L075Q/V077I/N094R/D130A/G156W/V187N, K024A/L075Q/D111A/D130A/V154I/G156W/L264R, K024A/L075R/D130A/V154I/G156W/T189Q/L264R, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/L075R/V077I/N094R/D130A/G156W/V187Q, A018K/G023Q/E045F/L075Q/V077I/G156W/V187T/T189D, A018K/G023Q/K024A/L075R/N094R/D130A/V154I/G156W, A018K/G023Q/K024A/L075R/V077I/N094R/D130A/G156W, G023K/D027S/F051T/E056K/L075Q/G091Q/V187H/I252Q, G023K/D027S/F051T/E056K/L075R/D130A/V187T/L264R, G023K/E056K/L075Q/D130A/V154I/V187N/T189Q/L264R, G023Q/D027Q/F051T/S058M/L075R/D130A/V187T/L264R, G023Q/D027S/E056K/L075R/D111A/V154I/G156W/L264R, G023Q/D027S/F051T/S058M/G091Q/D130A/V187N/I252Q, G023Q/D027S/L075R/N094R/V154I/G156W/V187N/T189Q, G023Q/K024A/L075Q/V077I/N094R/D130A/V154I/V187N, G023Q/L075Q/N094R/D111A/D130A/G156W/T189Q/L264R, G023Q/L075Q/N094R/D130A/V154I/G156W/T189Q/L264R, K024A/D111A/D130A/V154I/G156W/V187T/T189Q/L264R, A018K/G023K/K024A/L075Q/N094R/D111A/D130A/V154I/T189Q, A018K/G023K/K024A/L075R/V077I/D130A/V154I/G156W/V187N, A018K/G023Q/D027S/P029E/L075Q/V077I/R108K/H135F/V187H, G023K/D027S/F051T/E056K/S058M/L075R/G091Q/V187H/I252Q, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/L075R/D111A/D130A/V154I/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/K024A/L075Q/V077I/N094R/D130A/V154I/G156W/V187Q, N011K/G023Q/D027S/E056K/L075R/D130A/V154I/G156W/T189Q/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, N011K/G023Q/D027S/L075Q/N094R/D111A/V154I/G156W/V187N/T189Q/L264R |

TABLE 3-32

| TLL variants with Performance Index for expression ≥0.5 and increased pNPB/pNPP specific activity ratio compared to TLL SEQ ID NO: 1 are shown below. |
|---|
| A018K/L075D, D027S/N033D, D027S/P256T, D130A/L264R, D130A/V187N, E045F/N073R, K024A/V154I, N094R/G156W, P029E/N033D, A018K/A049V/V187T, A018K/E045F/N073R, A018K/E045F/V187T, A018K/K024A/V154I, A018K/L075D/T189D, D027E/S058M/G163P, D027N/S058M/P256T, D027S/L075Q/G091Q, D027S/N033D/T189D, D027S/S058M/P256T, D130A/V187T/L264R, E056K/D130A/L264R, G023K/D130A/V187T, G023Q/A049V/T189D, G023Q/D130A/G156W, G023Q/K024A/G156W, K024A/D130A/V154I, L075G/D130A/V187H, |

TABLE 3-32-continued

| TLL variants with Performance Index for expression ≥0.5 and increased pNPB/pNPP specific activity ratio compared to TLL SEQ ID NO: 1 are shown below. |
| --- |
| L075Q/V187N/L264R, L075R/D130A/L264R, L075R/D130A/V187T, L075R/V187T/L264R, |
| N011K/N233Q/P256T, N094R/D130A/V187T, P029E/N033D/E045F, V187N/T189Q/L264R, |
| A018K/D111A/G156W/T189Q, A018K/E045F/A049V/G156W, A018K/E045F/L075D/T189D, |
| A018K/G023K/D111A/T189Q, A018K/G023Q/A049V/V187T, A018K/L075Q/V077I/N094R, |
| A018K/P029E/N073R/L075D, D027E/D137Q/G163P/L227M, D027E/S058M/G163P/L264R, |
| D027N/S058M/N233Q/P256T, D027Q/E056K/N233Q/P256T, D027S/E045F/L075D/T189D, |
| D027S/E045F/N073R/T189D, D027S/N033D/E045F/N073R, D027S/N033D/E045F/T189D, |
| D027S/N033D/L075D/T189D, D027S/N033D/N073R/T189D, D027S/P029E/E045F/N073R, |
| D027S/P029E/L075D/T189D, D027S/P029E/N033D/L075D, D048Q/G163P/N233Q/L264R, |
| D111A/D130A/V154I/G156W, E045F/A049V/G156W/V187T, E045F/L075Q/G156W/V187T, |
| E056K/D130A/V187T/L264R, G023K/D027Q/F051T/L075Q, G023K/D130A/G156W/T189Q, |
| G023K/K024A/V154I/V187N, G023K/L075R/D130A/L264R, G023Q/A049V/V077I/G156W, |
| G023Q/K024A/D130A/G156W, G023Q/K024A/V077I/G156W, L075G/G091Q/V187N/L264R, |
| L075R/D130A/V187T/L264R, N011K/D027Q/S058M/P256T, N011K/D027S/N233Q/P256T, |
| N033D/E045F/N073R/T189A, P029E/N073R/L075D/T189D, Q004D/D027N/S058M/P256T, |
| S058M/D137Q/G163P/N233Q, S058M/L075Q/G091Q/I252Q, A018K/D027S/E045F/L075D/T189D, |
| A018K/D027S/P029E/N033D/L075D, A018K/G023K/D130A/V154I/G156W, |
| A018K/G023K/K024A/D130A/G156W, A018K/G023Q/K024A/D130A/V187Q, |
| A018K/G023Q/V077I/D130A/G156W, A018K/K024A/N094R/D130A/V187N, |
| A018K/K024A/N094R/G156W/V187T, A018K/P029E/N033D/N073R/L075D, |
| D027E/S058M/D137Q/G163P/N233Q, D027E/S058M/G163P/L227M/L264R, |
| D048Q/S058M/D130A/N233Q/L264R, D048Q/S058M/D137Q/G163P/N233E, |
| D048Q/S058M/G163P/L227M/L264R, D048Q/S058M/G163P/N233Q/L264R, |
| D130A/D137Q/G163P/N233Q/L264R, E045F/A049V/L075Q/V187T/T189D, |
| G023K/E056K/L075R/D130A/V187T, G023K/E056K/L075R/V187T/L264R, |
| G023K/K024A/D111A/D130A/V187T, G023K/N094R/G156W/V187N/T189Q, |
| G023Q/K024A/L075Q/G156W/V187Q, G023Q/L075Q/V077I/D130A/G156W, |
| N011K/D027N/S058M/N233Q/P256T, N011K/D027S/I090F/N233Q/P256T, |
| N011K/G023K/D111A/G156W/L264R, Q004D/N011K/D027N/N233Q/P256T, |
| S058M/D130A/D137Q/G163P/L264R, S058M/D137Q/G163P/L227M/L264R, |
| V077I/D130A/V154I/G156W/V187N, A018K/D027S/N033D/E045F/N073R/L075D, |
| A018K/D027S/N033D/N073R/L075D/T189D, A018K/G023K/K024A/V077I/G156W/V187Q, |
| A018K/G023K/L075Q/V077I/G156W/V187Q, A018K/G023Q/A049V/G156W/V187T/T189D, |
| A018K/G023Q/K024A/L075R/N094R/G156W, A018K/G023Q/N094R/D130A/G156W/V187Q, |
| A018K/K024A/L075Q/N094R/V154I/G156W, A018K/N094R/D111A/D130A/V154I/V187N, |
| D027E/D048Q/S058M/D130A/G163P/L264R, D027E/D048Q/S058M/G163P/L227M/L264R, |
| D027E/D048Q/S058M/G163P/N233Q/L264R, D027Q/E056K/S058M/D130A/I252Q/L264R, |
| D027Q/S058M/L075R/D130A/V187T/I252Q, D027S/E056K/S058M/V187T/I252Q/L264R, |
| D048Q/S058M/D130A/D137Q/G163P/L264R, D048Q/S058M/D137Q/G163P/N233Q/L264R, |
| G023K/D027Q/F051T/E056K/S058M/L075Q, G023K/D027S/L075R/D130A/V187T/I252Q, |
| G023K/E056K/L075R/D130A/T189Q/L264R, G023K/E056K/L075R/D130A/V187N/L264R, |
| G023K/F051T/G091Q/D130A/V187H/L264R, G023K/K024A/L075Q/D111A/D130A/T189Q, |
| G023K/K024A/L075Q/V154I/G156W/V187Q, G023K/K024A/L075R/D130A/V154I/V187N, |
| G023K/N094R/D111A/G156W/V187T/L264R, G023Q/D027S/N094R/V154I/G156W/T189Q, |
| G023Q/E056K/L075Q/D130A/V154I/L264R, G023Q/F051T/D130A/V187T/I252Q/L264R, |
| G023Q/K024A/V077I/D130A/V154I/G156W, K024A/L075Q/D111A/V154I/V187N/T189Q, |
| K024A/L075Q/N094R/D130A/V154I/L264R, K024A/L075Q/V077I/N094R/D130A/V187N, |
| N011K/D027S/E056K/I090F/N233Q/P256T, Q004D/N011K/D027N/S058M/N233Q/P256T, |
| Q004D/N011K/D027S/S058M/N233Q/P256T, S058M/D130A/D137Q/G163P/N233Q/L264R, |
| A018K/D027S/P029E/N033D/N073R/L075D/T189D, |
| A018K/D111A/D130A/V154I/G156W/V187T/T189Q, |
| A018K/G023K/K024A/L075Q/N094R/G156W/V187Q, |
| A018K/G023K/K024A/L075Q/N094R/V154I/V187Q, |
| A018K/G023K/K024A/L075R/N094R/D130A/V154I, |
| A018K/G023K/L075Q/V077I/N094R/V154I/G156W, |
| A018K/G023Q/L075R/V077I/N094R/G156W/V187N, |
| A018K/K024A/L075Q/D130A/V154I/G156W/V187T, |
| D027E/D048Q/S058M/D130A/G163P/L227M/L264R, |
| D048Q/S058M/D137Q/G163P/L227M/N233Q/L264R, |
| G023K/D027S/F051T/S058M/L075Q/D130A/V187N, |
| G023K/K024A/N094R/V154I/G156W/V187N/T189Q, |
| G023Q/E056K/L075R/D111A/D130A/V187N/T189Q, |
| G023Q/F051T/G091Q/D130A/V187H/I252Q/L264R, |
| G023Q/L075Q/V077I/N094R/D130A/G156W/V187N, |
| N011K/D027N/E056K/S058M/I090F/N233Q/P256T, |
| N011K/G023Q/L075Q/V154I/V187N/T189Q/L264R, |
| Q004D/N011K/D027S/E056K/S058M/N233Q/P256T, |
| A018K/G023K/K024A/L075Q/N094R/D130A/G156W/V187Q, |
| A018K/G023K/K024A/L075Q/V077I/D130A/V154I/G156W, |
| A018K/G023Q/K024A/L075R/V077I/N094R/D130A/G156W, |
| G023K/D027S/F051T/E056K/L075Q/G091Q/V187H/I252Q, |
| G023Q/D027Q/F051T/S058M/L075R/D130A/V187T/L264R, |
| G023Q/D027S/E056K/L075R/D111A/V154I/G156W/L264R, |
| G023Q/D027S/F051T/S058M/G091Q/D130A/V187N/I252Q, |
| G023Q/D027S/L075R/N094R/V154I/G156W/V187N/T189Q, |
| A018K/G023Q/D027S/P029E/L075Q/V077I/R108K/H135F/V187H, |
| G023K/K024A/L075Q/N094R/V154I/G156W/V187N/T189Q/L264R, |

TABLE 3-32-continued

| TLL variants with Performance Index for expression ≥0.5 and increased pNPB/pNPP specific activity ratio compared to TLL SEQ ID NO: 1 are shown below. |
|---|
| G023Q/F051T/S058M/L075G/G091Q/D130A/V187T/I252Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 3-33

| TLL variants with Performance Index for expression ≥0.5 and pNPB/pNPP ≥50% of the maximum specific activity ratio compared to TLL SEQ ID NO: are shown below. |
|---|
| A018K/L075D, D027S/P256T, E045F/N073R, K024A/V154I, N094R/G156W, A018K/E045F/N073R, A018K/L075D/T189D, D027S/N033D/T189D, E056K/D130A/L264R, G023Q/A049V/T189D, K024A/D130A/V154I, L075R/D130A/L264R, L075R/D130A/V187T, N094R/D130A/V187T, P029E/N033D/E045F, A018K/E045F/A049V/G156W, A018K/E045F/L075D/T189D, A018K/P029E/N073R/L075D, D027Q/E056K/N233Q/P256T, D027S/E045F/L075D/T189D, D027S/E045F/N073R/T189D, D027S/N033D/E045F/N073R, D027S/N033D/L075D/T189D, D027S/P029E/E045F/N073R, D027S/P029E/N033D/L075D, E045F/A049V/G156W/V187T, E045F/L075Q/G156W/V187T, G023K/D027Q/F051T/L075Q, G023K/L075R/D130A/L264R, G023Q/A049V/V077I/G156W, L075G/G091Q/V187N/L264R, N011K/D027S/N233Q/P256T, N033D/E045F/N073R/T189A, P029E/N073R/L075D/T189D, S058M/D137Q/G163P/N233Q, A018K/D027S/E045F/L075D/T189D, A018K/D027S/P029E/N033D/L075D, A018K/G023Q/V077I/D130A/G156W, A018K/K024A/N094R/D130A/V187N, A018K/P029E/N033D/N073R/L075D, E045F/A049V/L075Q/V187T/T189D, G023K/E056K/L075R/D130A/V187T, G023K/E056K/L075R/V187T/L264R, G023K/K024A/D111A/D130A/V187T, G023K/N094R/G156W/V187N/T189Q, G023Q/L075Q/V077I/D130A/G156W, N011K/D027S/I090F/N233Q/P256T, Q004D/N011K/D027N/N233Q/P256T, V077I/D130A/V154I/G156W/V187N, A018K/D027S/N033D/E045F/N073R/L075D, A018K/D027S/N033D/N073R/L075D/T189D, A018K/G023K/L075Q/V077I/G156W/V187Q, A018K/G023Q/K024A/L075R/N094R/G156W, D027E/D048Q/S058M/D130A/G163P/L264R, D027E/D048Q/S058M/G163P/N233Q/L264R, D027S/E056K/S058M/V187T/I252Q/L264R, G023K/K024A/L075Q/D111A/D130A/T189Q, G023Q/D027S/N094R/V154I/G156W/T189Q, G023Q/E056K/L075Q/D130A/V154I/L264R, G023Q/K024A/V077I/D130A/V154I/G156W, K024A/L075Q/V077I/N094R/D130A/V187N, Q004D/N011K/D027N/S058M/N233Q/P256T, A018K/D027S/P029E/N033D/N073R/L075D/T189D, A018K/G023K/K024A/L075Q/N094R/V154I/V187Q, A018K/G023K/L075Q/V077I/N094R/V154I/G156W, A018K/G023Q/L075R/V077I/N094R/G156W/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/V077I/D130A/V154I/G156W, A018K/G023Q/K024A/L075R/V077I/N094R/D130A/G156W, G023K/D027S/F051T/E056K/L075Q/G091Q/V187H/I252Q, G023Q/D027S/E056K/L075R/D111A/V154I/G156W/L264R, G023Q/D027S/L075R/N094R/V154I/G156W/V187N/T189Q, A018K/G023Q/D027S/P029E/L075Q/V077I/R108K/H135F/V187H, G023K/K024A/L075Q/N094R/V154I/G156W/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/E045F/A049V/S058M/N073S/L075Q/R108K/V187T/T189D |

TABLE 3-34

| TLL variants with increased pNPB/pNPP specific activity ratio compared to Reference sequence SEQ ID NO: 2 are shown below. |
|---|
| A018K/L075D, D027N/E056K, D027S/N033D, D027S/P256T, D130A/V187N, E045F/N073R, K024A/L075Q, K024A/V154I, L075Q/D130A, N094R/G156W, P029E/N033D, A018K/E045F/N073R, A018K/E045F/V187T, A018K/G023K/G156W, A018K/K024A/V154I, A018K/L075D/T189D, A049V/V187T/T189D, D027E/S058M/G163P, D027S/L075Q/G091Q, D027S/N033D/T189D, D027S/S058M/P256T, D130A/V187T/L264R, E045F/L075D/T189D, E056K/D130A/L264R, G023K/D130A/V187T, G023Q/A049V/T189D, G023Q/K024A/G156W, G023Q/L075Q/V187T, K024A/D130A/V154I, L075G/D130A/V187H, L075Q/D111A/D130A, L075Q/G156W/V187N, L075R/D130A/L264R, L075R/D130A/V187T, L075R/V187T/L264R, N011K/D027S/S058M, N073R/L075D/T189D, N094R/D130A/V187T, P029E/N033D/E045F, A018K/D027S/N033D/L075D, |

TABLE 3-34-continued

| TLL variants with increased pNPB/pNPP specific activity ratio compared to Reference sequence SEQ ID NO: 2 are shown below. |
|---|
| A018K/D111A/G156W/T189Q, A018K/E045F/A049V/G156W, A018K/E045F/L075D/T189D, A018K/E045F/L075Q/T189D, A018K/G023K/D111A/T189Q, A018K/G023Q/A049V/V187T, A018K/G023Q/E045F/T189D, A018K/G023Q/E045F/V187T, A018K/G023Q/L075R/D130A, A018K/G023Q/V077I/V187T, A018K/L075Q/G156W/V187T, A018K/L075Q/N094R/D130A, A018K/L075Q/V077I/N094R, A018K/P029E/N073R/L075D, A018K/V154I/G156W/V187T, D027E/D137Q/G163P/L227M, D027N/E056K/N233Q/P256T, D027N/E056K/S058M/P256T, D027N/S058M/N233Q/P256T, D027Q/E056K/N233Q/P256T, D027S/E045F/L075D/T189D, D027S/E045F/N073R/T189D, D027S/E056K/D111A/V154I, D027S/E056K/I090F/P256T, D027S/N033D/E045F/N073R, D027S/N033D/L075D/T189D, D027S/N033D/N073R/T189D, D027S/P029E/E045F/L075D, D027S/P029E/E045F/N073R, D027S/P029E/L075D/T189D, D027S/P029E/N033D/L075D, E045F/A049V/G156W/V187T, E045F/L075Q/G156W/V187T, G023K/D027Q/F051T/L075Q, G023K/D130A/G156W/T189Q, G023K/K024A/V154I/V187N, G023K/L075Q/G156W/V187N, G023K/L075R/D130A/L264R, G023Q/A049V/V077I/G156W, G023Q/D027S/D111A/G156W, G023Q/K024A/L075R/V154I, G023Q/V154I/G156W/V187N, K024A/L075R/G156W/V187N, L075G/G091Q/V187N/L264R, L075Q/D130A/G156W/V187N, L075Q/V077I/G156W/V187N, L075Q/V187N/T189Q/L264R, N011K/D027N/E056K/S058M, N011K/D027Q/S058M/P256T, N011K/D027S/E056K/P256T, N011K/D027S/N233Q/P256T, N011K/E056K/N233Q/P256T, N033D/E045F/N073R/T189A, P029E/E045F/N073R/L075D, P029E/N033D/L075D/T189D, P029E/N073R/L075D/T189D, Q004D/D027N/S058M/P256T, Q004D/D027S/I090F/P256T, S058M/D137Q/G163P/N233Q, A018K/A049V/L075Q/V187T/T189D, A018K/D027S/E045F/L075D/T189D, A018K/D027S/N033D/L075D/T189D, A018K/D027S/P029E/N033D/L075D, A018K/E045F/A049V/L075Q/V187T, A018K/G023K/D130A/V154I/G156W, A018K/G023K/K024A/L075R/N094R, A018K/G023Q/A049V/L075Q/G156W, A018K/G023Q/A049V/L075Q/V187T, A018K/G023Q/E045F/A049V/V187T, A018K/G023Q/E045F/L075Q/V187T, A018K/G023Q/K024A/D130A/V154I, A018K/G023Q/K024A/D130A/V187Q, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/T189D, A018K/K024A/N094R/D130A/V187N, A018K/L075Q/D111A/D130A/V187T, A018K/L075Q/N094R/G156W/V187N, A018K/P029E/E045F/N073R/L075D, A018K/P029E/N033D/N073R/L075D, A018K/V077I/G156W/V187T/T189D, D027E/S058M/D137Q/G163P/N233Q, D027Q/E056K/I090F/N233Q/P256T, D027Q/E056K/S058M/N233Q/P256T, D027S/P029E/N033D/E045F/N073R, D048Q/S058M/D130A/N233Q/L264R, D048Q/S058M/D137Q/G163P/N233E, D048Q/S058M/G163P/L227M/L264R, D048Q/S058M/G163P/N233Q/L264R, D130A/G163P/L227M/N233Q/L264R, E045F/A049V/L075Q/V187T/T189D, G023K/E056K/L075R/D130A/V187T, G023K/E056K/L075R/V187T/L264R, G023K/K024A/D111A/D130A/V187T, G023K/K024A/L075R/D130A/G156W, G023K/L075Q/D111A/D130A/V187T, G023K/L075Q/D130A/V154I/T189Q, G023K/N094R/G156W/V187N/T189Q, G023Q/A049V/L075Q/G156W/V187T, G023Q/E045F/A049V/G156W/T189D, G023Q/E045F/A049V/L075Q/V077I, G023Q/K024A/L075Q/G156W/V187Q, G023Q/K024A/L075R/D130A/V154I, G023Q/K024A/L075R/V077I/D130A, G023Q/L075Q/V077I/D130A/G156W, K024A/L075R/D111A/V154I/V187T, K024A/L075R/G156W/V187N/T189Q, L075Q/D130A/V187T/T189Q/L264R, L075Q/N094R/D130A/G156W/V187T, L075R/D130A/V154I/T189Q/L264R, N011K/D027Q/E056K/S058M/N233Q, N011K/D027Q/S058M/N233Q/P256T, N011K/D027S/E056K/N233Q/P256T, N011K/D027S/I090F/N233Q/P256T, N011K/G023K/D111A/G156W/L264R, P029E/N033D/E045F/L075D/T189D, Q004D/D027N/E056K/S058M/P256T, Q004D/D027N/I090F/N233Q/P256T, Q004D/D027Q/E056K/S058M/P256T, Q004D/N011K/D027N/N233Q/P256T, S058M/D130A/D137Q/G163P/L264R, S058M/D137Q/G163P/L227M/L264R, V077I/D130A/V154I/G156W/V187N, A018K/D027S/N033D/E045F/N073R/L075D, A018K/D027S/N033D/N073R/L075D/T189D, A018K/G023K/K024A/N094R/D130A/V154I, A018K/G023K/K024A/V077I/G156W/V187Q, A018K/G023K/L075Q/D130A/G156W/V187N, A018K/G023K/L075Q/V077I/G156W/V187Q, A018K/G023K/L075R/N094R/D130A/V187N, A018K/G023Q/A049V/L075Q/V077I/G156W, A018K/G023Q/A049V/V077I/V187T/T189D, A018K/G023Q/E045F/A049V/G156W/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/L075Q/G156W/V187T/T189D, A018K/G023Q/L075Q/V077I/N094R/V154I, A018K/G023Q/N094R/D130A/G156W/V187Q, A018K/K024A/L075Q/N094R/V154I/G156W, A018K/K024A/L075Q/N094R/V154I/V187N, A018K/K024A/L075R/D130A/V187N/T189Q, A018K/L075Q/D111A/V154I/G156W/V187N, A018K/L075Q/D111A/V154I/T189Q/L264R, A018K/L075Q/D130A/V187N/T189Q/L264R, A018K/N094R/D111A/D130A/V154I/V187N, A018K/P029E/N033D/E045F/L075D/T189D, D027E/D048Q/S058M/D130A/G163P/L264R, D027E/D048Q/S058M/G163P/L227M/L264R, D027E/D048Q/S058M/G163P/N233Q/L264R, D027Q/E056K/S058M/D130A/I252Q/L264R, D027Q/F051T/L075Q/D130A/V187H/L264R, D027Q/S058M/L075R/D130A/V187T/I252Q, D027S/E056K/S058M/V187T/I252Q/L264R, D027S/P029E/N033D/E045F/N073R/L075D, D027S/P029E/N033D/E045F/N073R/T189D, D027S/P029E/N033D/N073R/L075D/T189D, D048Q/S058M/D130A/D137Q/G163P/L264R, G023K/E056K/L075R/D130A/V187N/L264R, G023K/K024A/L075Q/D111A/D130A/T189Q, G023K/K024A/L075Q/N094R/D130A/G156W, G023K/K024A/L075Q/V154I/G156W/V187Q, G023K/N094R/D111A/G156W/V187T/L264R, G023Q/D027S/N094R/V154I/G156W/T189Q, G023Q/E056K/L075Q/D130A/V154I/L264R, G023Q/K024A/L075Q/D130A/V154I/G156W, G023Q/K024A/V077I/D130A/V154I/G156W, G023Q/L075Q/N094R/D111A/G156W/L264R, K024A/L075Q/D111A/V154I/V187N/T189Q, K024A/L075Q/N094R/D130A/V154I/L264R, |

TABLE 3-34-continued

| TLL variants with increased pNPB/pNPP specific activity ratio compared to Reference sequence SEQ ID NO: 2 are shown below. |
|---|
| K024A/L075Q/V077I/N094R/D130A/V187N, L075Q/D111A/D130A/V154I/G156W/T189Q, L075Q/D130A/V154I/G156W/V187N/L264R, L075Q/N094R/D111A/G156W/T189Q/L264R, L075R/D130A/V154I/G156W/V187N/L264R, N011K/D027N/E056K/I090F/N233Q/P256T, Q004D/N011K/D027N/S058M/N233Q/P256T, Q004D/N011K/D027S/S058M/N233Q/P256T, S058M/D130A/D137Q/G163P/N233Q/L264R, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/L075Q/G156W/V187T/T189D, A018K/G023Q/K024A/L075Q/V077I/N094R/V154I, A018K/G023Q/K024A/L075R/N094R/G156W/V187N, A018K/G023Q/L075R/V077I/N094R/G156W/V187N, A018K/L075Q/N094R/D111A/V154I/V187T/L264R, D027S/E056K/L075R/D111A/G156W/V187N/L264R, D027S/F051T/L075G/G091Q/V187T/I252Q/L264R, D048Q/S058M/D137Q/G163P/L227M/N233Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/F051T/E056K/L075R/D130A/V187T/I252Q, G023K/K024A/L075Q/D111A/D130A/T189Q/L264R, G023K/K024A/N094R/V154I/G156W/V187N/T189Q, G023K/L075Q/D111A/D130A/V154I/G156W/L264R, G023K/L075Q/N094R/D130A/V154I/V187N/L264R, G023Q/E056K/L075R/D111A/D130A/V187N/T189Q, G023Q/F051T/G091Q/D130A/V187H/I252Q/L264R, G023Q/L075Q/D111A/D130A/V154I/G156W/L264R, G023Q/L075Q/D130A/V154I/V187N/T189Q/L264R, G023Q/L075Q/V077I/N094R/D130A/G156W/V187N, K024A/L075Q/D111A/D130A/V154I/G156W/L264R, K024A/L075R/D130A/V154I/G156W/T189Q/L264R, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/L075R/V077I/N094R/D130A/G156W/V187Q, A018K/G023Q/E045F/L075Q/V077I/G156W/V187T/T189D, A018K/G023Q/K024A/L075R/N094R/D130A/V154I/G156W, A018K/G023Q/K024A/L075R/V077I/N094R/D130A/G156W, G023K/D027S/F051T/E056K/L075Q/G091Q/V187H/I252Q, G023K/D027S/F051T/E056K/L075R/D130A/V187T/L264R, G023K/E056K/L075Q/D130A/V154I/V187N/T189Q/L264R, G023Q/D027S/E056K/L075R/D111A/V154I/G156W/L264R, G023Q/D027S/F051T/S058M/G091Q/D130A/V187N/I252Q, G023Q/D027S/L075R/N094R/V154I/G156W/V187N/T189Q, G023Q/K024A/L075Q/V077I/N094R/D130A/V154I/V187N, G023Q/L075Q/N094R/D111A/D130A/G156W/T189Q/L264R, G023Q/L075Q/N094R/D130A/V154I/G156W/T189Q/L264R, K024A/D111A/D130A/V154I/G156W/V187T/T189Q/L264R, A018K/G023K/K024A/L075Q/N094R/D111A/D130A/V154I/T189Q, A018K/G023K/K024A/L075R/V077I/D130A/V154I/G156W/V187N, A018K/G023Q/D027S/P029E/L075Q/V077I/R108K/H135F/V187H, G023K/D027S/F051T/E056K/S058M/L075R/G091Q/V187H/I252Q, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/L075R/D111A/D130A/V154I/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/K024A/L075Q/V077I/N094R/D130A/V154I/G156W/V187Q, N011K/G023Q/D027S/E056K/L075R/D130A/V154I/G156W/T189Q/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, N011K/G023Q/D027S/L075Q/N094R/D111A/V154I/G156W/V187N/T189Q/L264R |

TABLE 3-35

| TLL variants with Performance Index for expression ≥0.5 compared to TLL SEQ ID NO: 1 and increased pNPB/pNPP specific activity ratio compared to Reference sequence SEQ ID NO: 2 are shown below. |
|---|
| A018K/L075D, D027S/N033D, D027S/P256T, D130A/V187N, E045F/N073R, K024A/V154I, N094R/G156W, P029E/N033D, A018K/E045F/N073R, A018K/E045F/V187T, A018K/K024A/V154I, A018K/L075D/T189D, D027E/S058M/G163P, D027S/L075Q/G091Q, D027S/N033D/T189D, D027S/S058M/P256T, D130A/V187T/L264R, E056K/D130A/L264R, G023K/D130A/V187T, G023Q/A049V/T189D, G023Q/K024A/G156W, K024A/D130A/V154I, L075G/D130A/V187H, L075R/D130A/L264R, L075R/D130A/V187T, L075R/V187T/L264R, N094R/D130A/V187T, P029E/N033D/E045F, A018K/D111A/G156W/T189Q, A018K/E045F/A049V/G156W, A018K/E045F/L075D/T189D, A018K/G023K/D111A/T189Q, A018K/G023Q/A049V/V187T, A018K/L075Q/V077I/N094R, A018K/P029E/N073R/L075D, D027E/D137Q/G163P/L227M, D027N/S058M/N233Q/P256T, D027Q/E056K/N233Q/P256T, D027S/E045F/L075D/T189D, D027S/E045F/N073R/T189D, D027S/N033D/E045F/N073R, D027S/N033D/L075D/T189D, D027S/N033D/N073R/T189D, D027S/P029E/E045F/N073R, D027S/P029E/L075D/T189D, D027S/P029E/N033D/L075D, E045F/A049V/G156W/V187T, E045F/L075Q/G156W/V187T, G023K/D027Q/F051T/L075Q, G023K/D130A/G156W/T189Q, G023K/K024A/V154I/V187N, G023K/L075R/D130A/L264R, G023Q/A049V/V077I/G156W, L075G/G091Q/V187N/L264R, N011K/D027Q/S058M/P256T, N011K/D027S/N233Q/P256T, N033D/E045F/N073R/T189A, P029E/N073R/L075D/T189D, Q004D/D027N/S058M/P256T, S058M/D137Q/G163P/N233Q, A018K/D027S/E045F/L075D/T189D, A018K/D027S/P029E/N033D/L075D, A018K/G023K/D130A/V154I/G156W, A018K/G023Q/K024A/D130A/V187Q, A018K/G023Q/V077I/D130A/G156W, A018K/K024A/N094R/D130A/V187N, A018K/P029E/N033D/N073R/L075D, D027E/S058M/D137Q/G163P/N233Q, D048Q/S058M/D130A/N233Q/L264R, D048Q/S058M/D137Q/G163P/N233E, D048Q/S058M/G163P/L227M/L264R, D048Q/S058M/G163P/N233Q/L264R, E045F/A049V/L075Q/V187T/T189D, G023K/E056K/L075R/D130A/V187T, G023K/E056K/L075R/V187T/L264R, G023K/K024A/D111A/D130A/V187T, G023K/N094R/G156W/V187N/T189Q, G023Q/K024A/L075Q/G156W/V187Q, G023Q/L075Q/V077I/D130A/G156W, N011K/D027S/I090F/N233Q/P256T, N011K/G023K/D111A/G156W/L264R, Q004D/N011K/D027N/N233Q/P256T, S058M/D130A/D137Q/G163P/L264R, S058M/D137Q/G163P/L227M/L264R, V077I/D130A/V154I/G156W/V187N, A018K/D027S/N033D/E045F/N073R/L075D, A018K/D027S/N033D/N073R/L075D/T189D, A018K/G023K/K024A/V077I/G156W/V187Q, A018K/G023K/L075Q/V077I/G156W/V187Q, A018K/G023Q/K024A/L075R/N094R/G156W, A018K/G023Q/N094R/D130A/G156W/V187Q, A018K/K024A/L075Q/N094R/V154I/G156W, A018K/N094R/D111A/D130A/V154I/V187N, D027E/D048Q/S058M/D130A/G163P/L264R, D027E/D048Q/S058M/G163P/L227M/L264R, D027E/D048Q/S058M/G163P/N233Q/L264R, D027Q/E056K/S058M/D130A/I252Q/L264R, D027Q/S058M/L075R/D130A/V187T/I252Q, D027S/E056K/S058M/V187T/I252Q/L264R, D048Q/S058M/D130A/D137Q/G163P/L264R, G023K/E056K/L075R/D130A/V187N/L264R, G023K/K024A/L075Q/D111A/D130A/T189Q, G023K/K024A/L075Q/V154I/G156W/V187Q, G023K/N094R/D111A/G156W/V187T/L264R, G023Q/D027S/N094R/V154I/G156W/T189Q, G023Q/E056K/L075Q/D130A/V154I/L264R, G023Q/K024A/V077I/D130A/V154I/G156W, K024A/L075Q/D111A/V154I/V187N/T189Q, K024A/L075Q/N094R/D130A/V154I/L264R, K024A/L075Q/V077I/N094R/D130A/V187N, Q004D/N011K/D027N/S058M/N233Q/P256T, Q004D/N011K/D027S/S058M/N233Q/P256T, S058M/D130A/D137Q/G163P/N233Q/L264R, A018K/D027S/P029E/N033D/N073R/L075D/T189D, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, D048Q/S058M/D137Q/G163P/L227M/N233Q/L264R, G023K/D027S/F051T/S058M/L075Q/D130A/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, G023Q/L075Q/V077I/N094R/D130A/G156W/V187N, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023Q/K024A/L075R/V077I/N094R/D130A/G156W, G023K/D027S/F051T/E056K/L075Q/G091Q/V187H/I252Q, G023Q/D027S/E056K/L075R/D111A/V154I/G156W/L264R, G023Q/D027S/F051T/S058M/G091Q/D130A/V187N/I252Q, G023Q/D027S/L075R/N094R/V154I/G156W/V187N/T189Q, A018K/G023Q/D027S/P029E/L075Q/V077I/R108K/H135F/V187H, G023K/K024A/L075Q/N094R/V154I/G156W/V187N/T189Q/L264R, G023Q/F051T/S058M/L075G/G091Q/D130A/V187T/I252Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D |

TABLE 3-36

| TLL variants with Performance Index for expression ≥0.5 compared to TLL SEQ ID NO: 1 and pNPB/pNPP ≥50% of the maximum specific activity ratio compared to Reference sequence SEQ ID NO: 2 are shown below. |
|---|
| A018K/L075D, D027S/P256T, E045F/N073R, K024A/V154I, N094R/G156W, A018K/E045F/N073R, A018K/L075D/T189D, D027S/N033D/T189D, E056K/D130A/L264R, G023Q/A049V/T189D, K024A/D130A/V154I, L075R/D130A/L264R, L075R/D130A/V187T, N094R/D130A/V187T, P029E/N033D/E045F, A018K/E045F/A049V/G156W, A018K/E045F/L075D/T189D, A018K/P029E/N073R/L075D, D027Q/E056K/N233Q/P256T, D027S/E045F/L075D/T189D, D027S/E045F/N073R/T189D, D027S/N033D/E045F/N073R, D027S/N033D/L075D/T189D, D027S/P029E/E045F/N073R, D027S/P029E/N033D/L075D, E045F/A049V/G156W/V187T, E045F/L075Q/G156W/V187T, G023K/D027Q/F051T/L075Q, G023K/L075R/D130A/L264R, G023Q/A049V/V077I/G156W, L075G/G091Q/V187N/L264R, N011K/D027S/N233Q/P256T, N033D/E045F/N073R/T189A, P029E/N073R/L075D/T189D, S058M/D137Q/G163P/N233Q, A018K/D027S/E045F/L075D/T189D, A018K/D027S/P029E/N033D/L075D, A018K/G023Q/V077I/D130A/G156W, A018K/K024A/N094R/D130A/V187N, A018K/P029E/N033D/N073R/L075D, E045F/A049V/L075Q/V187T/T189D, G023K/E056K/L075R/D130A/V187T, G023K/E056K/L075R/V187T/L264R, G023K/K024A/D111A/D130A/V187T, G023K/N094R/G156W/V187N/T189Q, G023Q/L075Q/V077I/D130A/G156W, N011K/D027S/I090F/N233Q/P256T, Q004D/N011K/D027N/N233Q/P256T, V077I/D130A/V154I/G156W/V187N, A018K/D027S/N033D/E045F/N073R/L075D, A018K/D027S/N033D/N073R/L075D/T189D, A018K/G023K/L075Q/V077I/G156W/V187Q, A018K/G023Q/K024A/L075R/N094R/G156W, D027E/D048Q/S058M/D130A/G163P/L264R, D027E/D048Q/S058M/G163P/N233Q/L264R, D027S/E056K/S058M/V187T/I252Q/L264R, G023K/K024A/L075Q/D111A/D130A/T189Q, G023Q/D027S/N094R/V154I/G156W/T189Q, G023Q/E056K/L075Q/D130A/V154I/L264R, G023Q/K024A/V077I/D130A/V154I/G156W, K024A/L075Q/V077I/N094R/D130A/V187N, Q004D/N011K/D027N/S058M/N233Q/P256T, A018K/D027S/P029E/N033D/N073R/L075D/T189D, A018K/G023K/K024A/L075Q/N094R/V154I/V187Q, A018K/G023K/L075Q/V077I/N094R/V154I/G156W, A018K/G023Q/L075R/V077I/N094R/G156W/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/V077I/D130A/V154I/G156W, A018K/G023Q/K024A/L075R/V077I/N094R/D130A/G156W, G023K/D027S/F051T/E056K/L075Q/G091Q/V187H/I252Q, G023Q/D027S/E056K/L075R/D111A/V154I/G156W/L264R, G023Q/D027S/L075R/N094R/V154I/G156W/V187N/T189Q, A018K/G023Q/D027S/P029E/L075Q/V077I/R108K/H135F/V187H, G023K/K024A/L075Q/N094R/V154I/G156W/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/E045F/A049V/S058M/N073S/L075Q/R108K/V187T/T189D |

Example 4

Thermal Stability of TLL Combinatorial Variants

The thermal stability of TLL variants created as described in Example 2 was assayed as described in Example 1 (Thermostability Assay). The performance index was calculated for the variants compared to TLL, SEQ ID NO:1 or the reference sequence SEQ ID NO: 2.

TABLE 4-1

| TLL variants with Performance Index >1 compared to TLL SEQ ID NO: 1 in the Thermostability assay are shown below. |
|---|
| A018K/D027S, A018K/L075D, A018K/L075Q, A018K/T189D, D027E/G163P, D027N/E056K, D027N/N233Q, D027S/N033D, D027S/P256T, D111A/L264R, D130A/L264R, D130A/T189Q, D130A/V187N, D130A/V187T, E045F/N073R, G023K/D130A, G023K/L264R, G023Q/L075Q, K024A/L075Q, K024A/V154I, L075Q/D130A, L075Q/G156W, L075R/L264R, L227M/L264R, N011K/D027S, N073R/L075D, N094R/G156W, P029E/N033D, S058M/L264R, V187T/L264R, A018K/A049V/L075Q, A018K/A049V/V187T, A018K/D027S/E045F, A018K/D027S/N073R, A018K/D027S/T189D, A018K/E045F/T189D, A018K/E045F/V187T, A018K/G023K/G156W, A018K/G023K/L075Q, A018K/G023Q/L075Q, A018K/K024A/V154I, A018K/L075D/T189D, A018K/L075Q/G156W, A018K/L075Q/V187T, A018K/N033D/L075D, A018K/N033D/T189D, A018K/N073R/L075D, A018K/P029E/T189D, A018K/V154I/G156W, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D111A/D130A/L264R, D130A/T189Q/L264R, |

TABLE 4-1-continued

| TLL variants with Performance Index >1 compared to TLL SEQ ID NO: 1 in the Thermostability assay are shown below. |
|---|
| D130A/V154I/G156W, D130A/V187N/L264R, D130A/V187T/L264R, E045F/L075D/T189D, E045F/N073R/L075D, E056K/D130A/L264R, E056K/D130A/T189Q, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/D111A/L264R, G023Q/D130A/G156W, G023Q/E056K/L075R, G023Q/K024A/G156W, G023Q/L075Q/V187T, G163P/L227M/L264R, K024A/D130A/V154I, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/N094R/V154I, L075Q/V077I/T189D, L075Q/V154I/V187T, L075Q/V187T/L264R, L075Q/V187T/T189D, L075R/D130A/L264R, L075R/D130A/V187T, L075R/V187N/L264R, L075R/V187T/L264R, N011K/D027S/S058M, N011K/N233Q/P256T, N033D/N073R/T189D, N073R/L075D/T189D, N094R/D130A/V187T, P029E/E045F/L075D, P029E/L075D/T189D, P029E/N033D/L075D, P029E/N073R/L075D, Q004D/D027S/P256T, Q004D/N233Q/P256T, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/N073R, A018K/D027S/E045F/T189D, A018K/D027S/N033D/L075D, A018K/D027S/P029E/T189D, A018K/D111A/G156W/T189Q, A018K/D130A/G156W/V187T, A018K/E045F/A049V/G156W, A018K/E045F/A049V/V187T, A018K/E045F/L075D/T189D, A018K/E045F/L075Q/V187T, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/K024A/D130A/G156W, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/L075D, A018K/P029E/N033D/T189D, A018K/P029E/N073R/L075D, A049V/L075Q/V187T/T189D, D027E/D048Q/G163P/L264R, D027E/D130A/N233Q/L264R, D027E/D137Q/G163P/L227M, D027E/D137Q/L227M/L264R, D027E/G163P/L227M/L264R, D027E/L227M/N233Q/L264R, D027E/S058M/G163P/L264R, D027N/E056K/N233Q/P256T, D027N/E056K/S058M/P256T, D027N/S058M/N233Q/P256T, D027Q/E056K/N233Q/P256T, D027S/E056K/D111A/V154I, D027S/N033D/E045F/N073R, D027S/N033D/L075D/T189D, D027S/N033D/N073R/L075D, D027S/N033D/N073R/T189D, D027S/P029E/L075D/T189D, D027S/P029E/N033D/E045F, D027S/P029E/N033D/L075D, D027S/P029E/N033D/T189D, D048Q/D130A/G163P/L264R, D048Q/G163P/N233Q/L264R, D111A/D130A/V154I/G156W, D111A/D130A/V154I/L264R, D130A/G163P/L227M/L264R, D130A/G163P/N233Q/L264R, E045F/A049V/G156W/V187T, E045F/L075Q/G156W/V187T, E056K/D130A/V187N/L264R, E056K/D130A/V187T/L264R, E056K/L075Q/V187N/L264R, F051T/D130A/I252Q/L264R, F051T/L075G/I252Q/L264R, G023K/D027Q/F051T/L075Q, G023K/D027S/L075Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/E056K/D130A/L264R, G023K/E056K/L075R/L264R, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187T/L264R, G023Q/A049V/L075Q/T189D, G023Q/A049V/L075Q/V077I, G023Q/A049V/V077I/G156W, G023Q/D027S/D111A/G156W, G023Q/E045F/A049V/T189D, G023Q/E045F/A049V/V187T, G023Q/E045F/L075Q/G156W, G023Q/K024A/D130A/G156W, G023Q/K024A/L075R/G156W, G023Q/K024A/L075R/V154I, G023Q/K024A/V077I/G156W, G023Q/L075Q/D130A/L264R, G023Q/L075Q/G156W/V187N, G023Q/L075Q/G156W/V187T, G023Q/V154I/G156W/V187N, G091Q/V187T/I252Q/L264R, K024A/D130A/V154I/V187T, K024A/L075Q/D130A/G156W, K024A/L075Q/D130A/V154I, K024A/L075Q/V187T/T189Q, K024A/L075R/G156W/V187N, L075G/D130A/V187T/I252Q, L075G/G091Q/V187N/L264R, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, L075R/D130A/V187T/L264R, N011K/D027N/E056K/S058M, N011K/D027Q/S058M/P256T, N011K/D027S/E056K/P256T, N011K/D027S/N233Q/P256T, N011K/E056K/N233Q/P256T, N011K/G023K/L075Q/D111A, N011K/S058M/N233Q/P256T, P029E/E045F/L075D/T189D, P029E/E045F/N073R/L075D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027N/P256T, Q004D/N011K/D027Q/N233Q, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/A049V/L075Q/V187T/T189D, A018K/D027S/E045F/L075D/T189D, A018K/D027S/N033D/L075D/T189D, A018K/D027S/N033D/N073R/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/D130A/G156W/V187T/L264R, A018K/E045F/A049V/L075Q/G156W, A018K/E045F/A049V/L075Q/T189D, A018K/E045F/A049V/L075Q/V187T, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/D130A/V187Q, A018K/G023Q/K024A/L075Q/G156W, A018K/G023Q/L075Q/G156W/V187T, |

TABLE 4-1-continued

| TLL variants with Performance Index >1 compared to TLL SEQ ID NO: 1 in the Thermostability assay are shown below. |
|---|
| A018K/G023Q/L075Q/V187T/T189D, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/D130A/V187N, A018K/K024A/N094R/G156W/V187T, A018K/L075Q/D111A/D130A/V187T, A018K/L075Q/N094R/D130A/V187N, A018K/L075Q/N094R/G156W/V187N, A018K/L075Q/V077I/N094R/G156W, A018K/L075Q/V187T/T189Q/L264R, A018K/N033D/E045F/L075D/T189D, A018K/P029E/N033D/N073R/L075D, A018K/V077I/G156W/V187T/T189D, D027E/D048Q/D137Q/L227M/L264R, D027E/D048Q/G163P/N233Q/L264R, D027E/D048Q/S058M/G163P/N233Q, D027E/D130A/D137Q/G163P/L264R, D027E/D130A/G163P/L227M/L264R, D027E/D130A/G163P/N233Q/L264R, D027E/D137Q/G163P/L227M/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027N/E056K/S058M/N233Q/P256T, D027Q/E056K/S058M/N233Q/P256T, D027Q/F051T/L075Q/D130A/L264R, D027S/E056K/D111A/V187N/L264R, D027S/E056K/S058M/N233Q/P256T, D027S/L075G/D130A/I252Q/L264R, D027S/L075G/G091Q/I252Q/L264R, D027S/L075Q/D111A/D130A/V187N, D027S/N033D/N073R/L075D/T189D, D027S/P029E/E045F/N073R/T189D, D027S/P029E/N033D/N073R/L075D, D027S/P029E/N073R/L075D/T189D, D048Q/D130A/D137Q/G163P/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/G163P/L227M/N233Q/L264R, D130A/V154I/G156W/V187N/T189Q, E045F/A049V/L075Q/V187T/T189D, E056K/D130A/V187H/I252Q/L264R, E056K/L075G/V187N/I252Q/L264R, E056K/L075Q/G156W/T189Q/L264R, E056K/L075R/D130A/V187T/L264R, E056K/N094R/G156W/V187N/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075R/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/V154I/V187N/L264R, G023Q/E045F/A049V/G156W/T189D, G023Q/E045F/A049V/L075Q/V077I, G023Q/E045F/A049V/V077I/T189D, G023Q/E045F/L075Q/G156W/T189D, G023Q/E045F/L075Q/V077I/V187T, G023Q/F051T/L075Q/G091Q/I252Q, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075G/D130A/V187T/I252Q/L264R, L075Q/D111A/D130A/V187T/T189Q, L075Q/D111A/V187N/T189Q/L264R, L075Q/D130A/V187T/T189Q/L264R, L075Q/N094R/D130A/G156W/V187T, L075Q/V077I/D130A/G156W/V187N, L075Q/V154I/V187N/T189Q/L264R, L075R/D111A/D130A/V187N/T189Q, L075R/D130A/V154I/T189Q/L264R, L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/K074S/L075D/T189D, Q004D/D027N/E056K/S058M/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, S058M/D130A/D137Q/G163P/L264R, S058M/D130A/G163P/L227M/L264R, S058M/D137Q/G163P/L227M/L264R, S058M/D137Q/G163P/L227M/N233Q, S058M/G163P/L227M/N233Q/L264R, V077I/D130A/V154I/G156W/V187N, |

TABLE 4-1-continued

| TLL variants with Performance Index >1 compared to TLL SEQ ID NO: 1 in the Thermostability assay are shown below. |
|---|
| A018K/A049V/L075Q/G156W/V187T/T189D, A018K/D027S/N033D/E045F/L075D/T189D, A018K/D027S/N033D/E045F/N073R/L075D, A018K/D027S/P029E/N033D/L075D/T189D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D111A/L264R, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/G156W, A018K/G023Q/A049V/L075Q/V077I/V187T, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/G156W/V187T/T189D, A018K/G023Q/E045F/L075Q/G156W/V187T, A018K/G023Q/K024A/L075R/N094R/G156W, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/G156W/V187N, A018K/L075Q/D111A/V154I/T189Q/L264R, A018K/L075Q/D130A/V154I/T189Q/L264R, A018K/L075Q/D130A/V187N/T189Q/L264R, A018K/L075R/D130A/V154I/G156W/V187N, A018K/N033D/E045F/N073R/L075D/T189D, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/D130A/G163P/L264R, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/S058M/L075R/D130A/V187T/I252Q, D027S/E056K/S058M/V187T/I252Q/L264R, D027S/F051T/L075Q/D130A/I252Q/L264R, D027S/L075Q/D111A/G156W/V187N/T189Q, D027S/L075Q/G091Q/V187H/I252Q/L264R, D027S/P029E/N033D/N073R/L075D/T189D, D048Q/D130A/G163P/L227M/N233Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/G163P/N233Q/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/L075G/G091Q/D130A/I252Q/L264R, F051T/L075G/G091Q/V187H/I252Q/L264R, F051T/L075G/G091Q/V187T/I252Q/L264R, F051T/L075R/D130A/V187N/I252Q/L264R, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075G/D130A/V187T/I252Q/L264R, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/F051T/L075Q/V187T/L264R, G023Q/D027S/L075G/D130A/V187H/L264R, G023Q/D027S/L075Q/D111A/G156W/L264R, G023Q/D027S/L075Q/D130A/V187T/I252Q, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/N094R/D111A/G156W/L264R, G023Q/L075Q/V077I/N094R/D130A/V187Q, G023Q/L075R/V154I/G156W/V187N/L264R, K024A/D111A/D130A/V187T/T189Q/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/L075R/D111A/V154I/G156W/V187N, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075Q/N094R/D111A/G156W/T189Q/L264R, L075R/D130A/V154I/G156W/V187N/L264R, N011K/D027N/E056K/I090F/N233Q/P256T, N011K/D027N/E056K/S058M/N233Q/P256T, N011K/D027N/S058M/I090F/N233Q/P256T, |

TABLE 4-1-continued

| TLL variants with Performance Index >1 compared to TLL SEQ ID NO: 1 in the Thermostability assay are shown below. |
|---|
| N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/D130A/V154I/G156W/V187T/L264R, A018K/K024A/L075Q/D111A/G156W/V187N/L264R, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/K024A/N094R/D130A/G156W/V187T/L264R, A018K/L075Q/D111A/D130A/V154I/G156W/L264R, A018K/L075Q/D130A/G156W/V187N/T189Q/L264R, A018K/L075Q/N094R/D111A/V154I/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/L075Q/G091Q/D130A/V187T/I252Q, D027Q/L075G/G091Q/D130A/V187H/I252Q/L264R, D027S/F051T/L075G/G091Q/V187T/I252Q/L264R, D027S/F051T/S058M/L075R/D130A/I252Q/L264R, D027S/L075R/V154I/G156W/V187N/T189Q/L264R, D027S/P029E/N033D/E045F/N073R/L075D/T189D, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, E056K/L075Q/D111A/D130A/G156W/V187N/T189Q, F051T/L075G/G091Q/D130A/V187N/I252Q/L264R, F051T/L075R/G091Q/D130A/V187T/I252Q/L264R, G023K/D027Q/F051T/L075G/D130A/V187H/L264R, G023K/D027S/F051T/S058M/G091Q/V187N/I252Q, G023K/D027S/F051T/S058M/L075Q/D130A/V187N, G023K/D027S/L075Q/N094R/V154I/G156W/T189Q, G023K/F051T/L075Q/G091Q/D130A/V187H/I252Q, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/N094R/V154I/G156W/V187N, G023K/K024A/L075Q/V077I/D130A/G156W/V187Q, G023K/K024A/N094R/V154I/G156W/V187N/T189Q, G023K/L075Q/D111A/D130A/V154I/G156W/L264R, G023K/L075Q/D111A/V154I/G156W/T189Q/L264R, |

TABLE 4-1-continued

| TLL variants with Performance Index >1 compared to TLL SEQ ID NO: 1 in the Thermostability assay are shown below. |
|---|
| G023K/L075Q/D130A/G156W/V187N/T189Q/L264R, G023K/L075Q/N094R/D130A/V154I/V187N/L264R, G023K/L075Q/N094R/V154I/G156W/V187T/L264R, G023K/L075R/N094R/V154I/G156W/V187N/L264R, G023Q/D027S/L075Q/V154I/G156W/V187N/L264R, G023Q/D027S/S058M/L075Q/D130A/I252Q/L264R, G023Q/E045F/L075Q/V077I/G156W/V187T/T189D, G023Q/E056K/L075Q/D111A/G156W/V187N/L264R, G023Q/E056K/L075Q/D130A/V154I/G156W/T189Q, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, G023Q/F051T/L075R/G091Q/V187N/I252Q/L264R, G023Q/F051T/S058M/G091Q/D130A/I252Q/L264R, G023Q/K024A/L075Q/V077I/D130A/G156W/V187N, G023Q/K024A/L075Q/V077I/D130A/V154I/G156W, G023Q/L075G/G091Q/D130A/V187T/I252Q/L264R, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, G023Q/S058M/L075G/G091Q/D130A/I252Q/L264R, K024A/L075Q/D111A/D130A/V154I/G156W/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/A018K/K024A/V077I/V154I/G156W/T189Q, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, N011K/G023Q/L075Q/V154I/V187N/T189Q/L264R, Q004D/N011K/D027Q/E056K/S058M/N233Q/P256T, Q004D/N011K/D027S/E056K/S058M/N233Q/P256T, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/L075Q/V077I/D130A/V154I/G156W/V187N, A018K/G023K/L075R/V077I/N094R/D130A/G156W/V187Q, A018K/G023Q/E045F/L075Q/V077I/G156W/V187T/T189D, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, A018K/K024A/L075R/D130A/V154I/G156W/V187T/L264R, A018K/L075Q/N094R/D111A/V154I/G156W/T189Q/L264R, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/E056K/L075G/D130A/V187T/I252Q/L264R, G023K/D027S/F051T/E056K/L075Q/G091Q/V187H/I252Q, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/K024A/L075Q/N094R/V154I/G156W/V187T/L264R, G023K/K024A/L075R/N094R/V154I/G156W/V187T/T189Q, G023K/L075Q/D111A/V154I/G156W/V187N/T189Q/L264R, G023K/L075Q/N094R/D130A/V154I/G156W/V187N/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/L075R/N094R/V154I/G156W/V187N/T189Q, G023Q/D027S/S058M/G091Q/D130A/V187H/I252Q/L264R, G023Q/E056K/L075Q/D111A/V154I/V187N/T189Q/L264R, G023Q/E056K/L075Q/N094R/D111A/G156W/T189Q/L264R, G023Q/F051T/L075Q/G091Q/D130A/V187H/I252Q/L264R, |

TABLE 4-1-continued

| TLL variants with Performance Index >1 compared to TLL SEQ ID NO: 1 in the Thermostability assay are shown below. |
|---|
| G023Q/F051T/L075R/G091Q/D130A/V187T/I252Q/L264R, |
| G023Q/K024A/L075Q/V077I/D130A/V154I/G156W/V187N, |
| G023Q/K024A/L075Q/V077I/N094R/D130A/V154I/V187N, |
| G023Q/L075Q/D111A/D130A/V154I/G156W/V187N/L264R, |
| G023Q/L075Q/N094R/D111A/D130A/G156W/T189Q/L264R, |
| G023Q/L075Q/V077I/N094R/D130A/V154I/G156W/V187Q, |
| G023Q/S058M/L075R/G091Q/D130A/V187H/I252Q/L264R, |
| K024A/D111A/D130A/V154I/G156W/V187T/T189Q/L264R, |
| N011K/G023K/D027S/L075Q/D111A/D130A/V154I/T189Q, |
| N011K/G023K/D027S/L075R/V154I/G156W/V187N/T189Q, |
| N011K/G023K/E056K/L075Q/D130A/V154I/T189Q/L264R, |
| N011K/G023K/L075Q/D111A/G156W/V187N/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/D111A/D130A/V154I/V187N/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075Q/N094R/D130A/V154I/G156W/V187N, |
| A018K/G023K/K024A/L075Q/N094R/D130A/V187T/T189Q/L264K, |
| A018K/G023K/K024A/L075R/V077I/D130A/V154I/G156W/V187N, |
| A018K/G023K/K024A/V077I/D130A/V154I/G156W/V187T/T189Q, |
| A018K/G023K/L075Q/N094R/D111A/V154I/G156W/T189Q/L264R, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |
| A018K/G023Q/K024A/L075R/N094R/D130A/V154I/G156W/V187N, |
| A018K/K024A/L075Q/N094R/V154I/G156W/V187N/T189Q/L264R, |
| D027Q/F051T/S058M/L075G/G091Q/D130A/V187T/I252Q/L264R, |
| D027S/E056K/L075Q/N094R/D111A/D130A/V154I/G156W/L264R, |
| D027S/E056K/L075Q/N094R/D111A/D130A/V187N/T189Q/L264R, |
| G023K/D027S/F051T/E056K/S058M/L075Q/G091Q/V187N/L264R, |
| G023K/D027S/F051T/E056K/S058M/L075R/G091Q/V187H/I252Q, |
| G023K/D027S/L075Q/D111A/D130A/V154I/G156W/T189Q/L264R, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023K/L075Q/D111A/D130A/V154I/G156W/V187T/T189Q/L264R, |
| G023Q/D027S/F051T/E056K/L075G/G091Q/V187N/I252Q/L264R, |
| G023Q/D027S/L075Q/N094R/D111A/D130A/V154I/G156W/L264R, |
| G023Q/D027S/L075Q/N094R/D130A/V154I/G156W/V187N/L264R, |
| G023Q/E056K/L075Q/D111A/D130A/V154I/G156W/T189Q/L264R, |
| G023Q/F051T/S058M/L075G/G091Q/D130A/V187T/I252Q/L264R, |
| N011K/G023K/D027S/E056K/L075R/D111A/G156W/V187N/L264R, |
| N011K/G023K/L075R/D111A/D130A/V154I/V187N/T189Q/L264R, |
| N011K/G023Q/L075Q/D111A/V154I/G156W/V187N/T189Q/L264R, |
| N011K/G023K/L075R/V077I/D130A/V154I/G156W/V187T/T189Q, |
| A018K/G023Q/D027S/E045F/A049V/N073S/L075Q/R108K/V187T/T189D, |
| A018K/G023Q/D027S/E045F/A049V/S058M/L075Q/R108K/V187T/T189D, |
| A018K/G023Q/D027S/E045F/A049V/S058M/N073S/L075Q/V187T/T189D, |
| A018K/G023Q/D027S/P029E/S058M/L075Q/V077I/H135F/G156W/V187T, |
| A018K/G023Q/D027S/P029E/S058M/L075Q/V077I/R108K/H135F/V187H, |
| A018K/G023Q/D027S/S058M/L075Q/V077I/R108K/H135F/G156W/V187H, |
| A018K/G023Q/K024A/L075Q/V077I/N094R/D130A/V154I/G156W/V187Q, |
| G023Q/D027S/F051T/E056K/L075R/G091Q/D130A/V187H/I252Q/L264R, |
| G023Q/D027S/F051T/E056K/S058M/L075R/G091Q/D130A/V187H/I252Q, |
| N011K/A018K/G023K/K024A/L075R/V077I/D130A/V154I/V187T/T189Q, |
| N011K/G023K/L075R/N094R/D111A/V154I/G156W/V187N/T189Q/L264R, |
| N011K/G023Q/D027S/E056K/L075R/D130A/V154I/G156W/T189Q/L264R, |
| N011K/G023Q/E056K/L075R/D111A/D130A/V154I/G156W/V187N/L264R, |
| A018K/G023K/L075R/N094R/D111A/D130A/V154I/G156W/V187N/T189Q/L264R, |
| A018K/G023Q/D027S/E045F/A049V/S058M/N073S/L075Q/R108K/V187T/T189D, |
| A018K/G023Q/D027S/P029E/S058M/L075Q/V077I/R108K/H135F/G156W/V187T, |
| N011K/G023Q/D027S/L075Q/N094R/D111A/V154I/G156W/V187N/T189Q/L264R, |
| A018K/G023Q/D027S/P029E/E045F/A049V/S058M/N073S/L075Q/R108K/V187T/T189D |

TABLE 4-2

| TLL variants with Performance Index for expression ≥0.5 and Performance Index >1 in the Thermostability assay compared to TLL SEQ ID NO: 1 are shown below. |
| --- |
| A018K/L075D, D027E/G163P, D027S/N033D, D027S/P256T, D111A/L264R, D130A/L264R, D130A/V187N, D130A/V187T, E045F/N073R, G023K/L264R, K024A/V154I, L075R/L264R, L227M/L264R, N094R/G156W, P029E/N033D, S058M/L264R, V187T/L264R, A018K/A049V/V187T, A018K/E045F/V187T, A018K/K024A/V154I, A018K/L075D/T189D, A018K/N033D/T189D, A018K/P029E/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D111A/D130A/L264R, D130A/V154I/G156W, D130A/V187N/L264R, D130A/V187T/L264R, E056K/D130A/L264R, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/D130A/G156W, G023Q/K024A/G156W, G163P/L227M/L264R, K024A/D130A/V154I, L075G/D130A/V187H, L075Q/V187T/L264R, L075R/D130A/L264R, L075R/D130A/V187T, L075R/V187N/L264R, L075R/V187T/L264R, N011K/N233Q/P256T, N094R/D130A/V187T, Q004D/D027S/P256T, V187N/T189Q/L264R, A018K/D027S/P029E/T189D, A018K/D111A/G156W/T189Q, A018K/D130A/G156W/V187T, A018K/E045F/A049V/G156W, A018K/E045F/L075D/T189D, A018K/G023K/D111A/T189Q, A018K/G023Q/A049V/V187T, A018K/G023Q/V077I/G156W, A018K/K024A/D130A/G156W, A018K/L075Q/V077I/N094R, A018K/N033D/L075D/T189D, A018K/P029E/N073R/L075D, D027E/D048Q/G163P/L264R, D027E/D130A/N233Q/L264R, D027E/D137Q/G163P/L227M, D027E/D137Q/L227M/L264R, D027E/G163P/L227M/L264R, D027E/L227M/N233Q/L264R, D027E/S058M/G163P/L264R, D027N/S058M/N233Q/P256T, D027Q/E056K/N233Q/P256T, D027S/N033D/E045F/N073R, D027S/N033D/L075D/T189D, D027S/N033D/N073R/T189D, D027S/P029E/L075D/T189D, D027S/P029E/N033D/E045F, D027S/P029E/N033D/L075D, D048Q/D130A/G163P/L264R, D048Q/G163P/N233Q/L264R, D111A/D130A/V154I/G156W, D130A/G163P/L227M/L264R, E045F/A049V/G156W/V187T, E045F/L075Q/G156W/V187T, E056K/D130A/V187N/L264R, E056K/D130A/V187T/L264R, F051T/D130A/I252Q/L264R, F051T/L075G/I252Q/L264R, G023K/D027Q/F051T/L075Q, G023K/D130A/G156W/T189Q, G023K/D130A/V187N/L264R, G023K/D130A/V187T/L264R, G023K/D130A/V187T/T189Q, G023K/E056K/L075R/L264R, G023K/K024A/V154I/V187N, G023K/L075R/D130A/L264R, G023K/L075R/V187T/L264R, G023Q/A049V/V077I/G156W, G023Q/K024A/D130A/G156W, G023Q/K024A/L075R/G156W, G023Q/K024A/V077I/G156W, G023Q/L075Q/D130A/L264R, G091Q/V187T/I252Q/L264R, K024A/D130A/V154I/V187T, L075G/D130A/V187T/I252Q, L075G/G091Q/V187N/L264R, L075R/D130A/V187T/L264R, N011K/D027Q/S058M/P256T, N011K/D027S/N233Q/P256T, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/L252Q/L264R, A018K/D027S/E045F/L075D/T189D, A018K/D027S/P029E/N033D/L075D, A018K/D130A/G156W/V187N/L264R, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/K024A/L075Q/G156W, A018K/K024A/L075R/D130A/V154I, A018K/K024A/N094R/D130A/V187N, A018K/K024A/N094R/G156W/V187T, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/D130A/G163P/N233Q/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027Q/F051T/L075Q/D130A/L264R, D027S/E056K/D111A/V187N/L264R, D027S/L075G/D130A/I252Q/L264R, D027S/L075G/G091Q/I252Q/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/V154I/G156W/V187N/T189Q, E045F/A049V/L075Q/V187T/T189D, E056K/L075G/V187N/I252Q/L264R, E056K/L075R/D130A/V187T/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, K024A/L075R/V154I/G156W/V187Q, L075G/D130A/V187T/I252Q/L264R, N011K/D027N/S058M/N233Q/P256T, N011K/D027S/I090F/N233Q/P256T, N011K/G023K/D111A/G156W/L264R, Q004D/N011K/D027N/N233Q/P256T, S058M/D130A/D137Q/G163P/L264R, S058M/D130A/G163P/L227M/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/D027S/N033D/E045F/N073R/L075D, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, |

TABLE 4-2-continued

| TLL variants with Performance Index for expression ≥0.5 and Performance Index >1 in the Thermostability assay compared to TLL SEQ ID NO: 1 are shown below. |
|---|
| A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/D130A/G163P/L264R, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D048Q/D130A/G163P/L227M/N233Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/V154I/G156W/V187Q, G023K/K024A/L075R/D130A/V154I/V187N, G023K/L075G/D130A/V187T/I252Q/L264R, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/K024A/V077I/D130A/V154I/G156W, G023Q/L075G/G091Q/D130A/I252Q/L264R, K024A/L075Q/D111A/V154I/V187N/T189Q, K024A/L075Q/N094R/D130A/V154I/L264R, K024A/L075Q/V077I/N094R/D130A/V187N, L075Q/G091Q/D130A/V187H/I252Q/L264R, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/D130A/V154I/G156W/V187T/L264R, A018K/K024A/L075Q/D130A/V154I/G156W/V187T, A018K/K024A/L075Q/V077I/N094R/D130A/G156W, A018K/K024A/N094R/D130A/G156W/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, F051T/L075G/G091Q/D130A/V187N/I252Q/L264R, F051T/L075R/G091Q/D130A/V187T/I252Q/L264R, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/D027S/S058M/L075Q/D130A/I252Q/L264R, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, |

TABLE 4-2-continued

| TLL variants with Performance Index for expression ≥0.5 and Performance Index >1 in the Thermostability assay compared to TLL SEQ ID NO: 1 are shown below. |
|---|
| G023Q/F051T/S058M/G091Q/D130A/I252Q/L264R, G023Q/L075G/G091Q/D130A/V187T/I252Q/L264R, G023Q/L075Q/V077I/N094R/D130A/G156W/V187N, G023Q/S058M/L075G/G091Q/D130A/I252Q/L264R, N011K/A018K/K024A/V077I/V154I/G156W/T189Q, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, A018K/G023Q/D027S/P029E/L075Q/V077I/R108K/H135F/V187H, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075G/G091Q/D130A/V187T/I252Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 4-3

| TLL variants with Performance Index for expression ≥0.5 and Performance Index ≥50% of the maximum PI value in the Thermostability assay compared to TLL SEQ ID NO: 1 are shown below. |
|---|
| E045F/N073R, A018K/E045F/V187T, A018K/V154I/G156W, D111A/D130A/L264R, V187N/T189Q/L264R, A018K/D111A/G156W/T189Q, A018K/D130A/G156W/V187T, A018K/E045F/A049V/G156W, A018K/G023Q/V077I/G156W, A018K/D027S/E045F/L075D/T189D, A018K/D130A/G156W/V187N/L264R, A018K/G023K/D130A/V154I/G156W, A018K/G023Q/K024A/L075Q/G156W, D027S/E056K/D111A/V187N/L264R, G023K/K024A/D111A/D130A/V187T, G023K/L075Q/V187H/I252Q/L264R, N011K/G023K/D111A/G156W/L264R, S058M/D137Q/G163P/L227M/N233Q, S058M/G163P/L227M/N233Q/L264R, A018K/G023K/L075Q/V077I/G156W/V187Q, A018K/G023Q/A049V/G156W/V187T/T189D, A018K/G023Q/K024A/V154I/G156W/V187Q, A018K/K024A/L075Q/N094R/V154I/G156W, D048Q/S058M/D130A/D137Q/G163P/L264R, G023K/K024A/L075Q/D111A/D130A/T189Q, G023K/K024A/L075R/D130A/V154I/V187N, G023K/L075G/D130A/V187T/I252Q/L264R, G023K/N094R/D111A/G156W/V187T/L264R, G023Q/E056K/D111A/D130A/V187N/T189Q, G023Q/E056K/L075Q/D130A/V154I/L264R, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/L075Q/V077I/N094R/V154I/G156W, A018K/G023Q/L075R/V077I/N094R/G156W/V187N, A018K/K024A/L075Q/V077I/N094R/D130A/G156W, A018K/K024A/N094R/D130A/G156W/V187T/L264R, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, G023K/D027S/F051T/E056K/L075Q/G091Q/V187H/I252Q, |

TABLE 4-3-continued

| TLL variants with Performance Index for expression ≥0.5 and Performance Index ≥50% of the maximum PI value in the Thermostability assay compared to TLL SEQ ID NO: 1 are shown below. |
|---|
| G023Q/D027S/E056K/L075R/D111A/V154I/G156W/L264R, G023Q/D027S/L075R/N094R/V154I/G156W/V187N/T189Q, A018K/G023Q/D027S/P029E/L075Q/V077I/R108K/H135F/V187H, A018K/G023Q/D027S/P029E/S058M/L075Q/V077I/H135F/G156W/V187T, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 4-4

| TLL variants with Performance Index >1 compared to Reference sequence SEQ ID NO: 2 in the Thermostability assay are shown below. |
|---|
| A018K/D027S, A018K/L075D, A018K/L075Q, A018K/T189D, D027E/G163P, D027S/N033D, D027S/P256T, D111A/L264R, D130A/L264R, D130A/T189Q, D130A/V187N, D130A/V187T, E045F/N073R, F051T/L075R, G023K/D130A, G023K/L264R, G023Q/L075Q, K024A/L075Q, K024A/V154I, L075Q/D130A, L075Q/G156W, L075R/L264R, L227M/L264R, N011K/D027S, N073R/L075D, P029E/N033D, S058M/L264R, V187T/L264R, A018K/A049V/L075Q, A018K/A049V/V187T, A018K/D027S/N073R, A018K/D027S/T189D, A018K/E045F/V187T, A018K/G023K/G156W, A018K/G023K/L075Q, A018K/G023Q/L075Q, A018K/K024A/V154I, A018K/L075D/T189D, A018K/L075Q/G156W, A018K/L075Q/V187T, A018K/N033D/L075D, A018K/N033D/T189D, A018K/N073R/L075D, A018K/P029E/T189D, A018K/V154I/G156W, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D111A/D130A/L264R, D130A/T189Q/L264R, D130A/V154I/G156W, D130A/V187N/L264R, D130A/V187T/L264R, E045F/L075D/T189D, E045F/N073R/L075D, E056K/D130A/L264R, E056K/D130A/T189Q, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/D111A/L264R, G023Q/D130A/G156W, G023Q/E056K/L075R, G023Q/K024A/G156W, G023Q/L075Q/V187T, G163P/L227M/L264R, K024A/D130A/V154I, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/N094R/V154I, L075Q/V077I/T189D, L075Q/V154I/V187T, L075Q/V187T/L264R, L075Q/V187T/T189D, L075R/D130A/L264R, L075R/D130A/V187T, L075R/V187N/L264R, L075R/V187T/L264R, N011K/D027S/S058M, N011K/N233Q/P256T, N073R/L075D/T189D, N094R/D130A/V187T, P029E/E045F/L075D, P029E/L075D/T189D, P029E/N033D/L075D, P029E/N073R/L075D, Q004D/D027S/P256T, Q004D/N233Q/P256T, S058M/L227M/L264R, V077I/D130A/V154I, V187N/T189Q/L264R, A018K/A049V/L075Q/T189D, A018K/A049V/L075Q/V187T, A018K/D027S/E045F/N073R, A018K/D027S/E045F/T189D, A018K/D027S/N033D/L075D, A018K/D027S/P029E/T189D, A018K/D111A/G156W/T189Q, A018K/D130A/G156W/V187T, A018K/E045F/A049V/G156W, A018K/E045F/A049V/V187T, A018K/E045F/L075D/T189D, A018K/E045F/L075Q/V187T, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/K024A/D130A/G156W, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/N033D/L075D/T189D, A018K/N073R/L075D/T189D, A018K/P029E/N033D/T189D, A018K/P029E/N073R/L075D, A049V/L075Q/V187T/T189D, D027E/D048Q/G163P/L264R, D027E/D130A/N233Q/L264R, D027E/D137Q/G163P/L227M, D027E/D137Q/L227M/L264R, D027E/G163P/L227M/L264R, D027E/L227M/N233Q/L264R, D027E/S058M/G163P/L264R, D027N/E056K/N233Q/P256T, D027N/E056K/S058M/P256T, D027N/S058M/N233Q/P256T, D027Q/E056K/N233Q/P256T, D027S/D130A/I252Q/L264R, D027S/E056K/D111A/V154I, D027S/N033D/E045F/N073R, D027S/N033D/L075D/T189D, D027S/N033D/N073R/L075D, D027S/N033D/N073R/T189D, D027S/P029E/L075D/T189D, D027S/P029E/N033D/E045F, D027S/P029E/N033D/L075D, D027S/P029E/N033D/T189D, D048Q/D130A/G163P/L264R, D048Q/G163P/N233Q/L264R, D111A/D130A/V154I/G156W, D111A/D130A/V154I/L264R, D130A/G163P/L227M/L264R, D130A/G163P/N233Q/L264R, E045F/A049V/G156W/V187T, E056K/D130A/V187N/L264R, E056K/D130A/V187T/L264R, E056K/L075Q/V187N/L264R, F051T/D130A/I252Q/L264R, F051T/L075G/I252Q/L264R, G023K/D027Q/F051T/L075Q, G023K/D027S/L075Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/E056K/D130A/L264R, G023K/E056K/L075R/L264R, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187T/L264R, G023Q/A049V/L075Q/T189D, G023Q/A049V/L075Q/V077I, G023Q/A049V/V077I/G156W, G023Q/D027S/D111A/G156W, G023Q/E045F/A049V/T189D, G023Q/E045F/A049V/V187T, G023Q/E045F/L075Q/G156W, G023Q/K024A/L075R/G156W, G023Q/K024A/L075R/V154I, G023Q/K024A/V077I/G156W, G023Q/L075Q/D130A/L264R, G023Q/L075Q/G156W/V187N, G023Q/L075Q/G156W/V187T, G023Q/V154I/G156W/V187N, G091Q/V187T/I252Q/L264R, K024A/D130A/V154I/V187T, K024A/L075Q/D130A/G156W, K024A/L075Q/D130A/V154I, |

TABLE 4-4-continued

| TLL variants with Performance Index >1 compared to Reference sequence SEQ ID NO: 2 in the Thermostability assay are shown below. |
| --- |
| K024A/L075Q/V187T/T189Q, K024A/L075R/G156W/V187N, L075G/D130A/V187T/I252Q, L075G/G091Q/V187N/L264R, L075G/V187H/I252Q/L264R, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, L075R/D130A/V187T/L264R, N011K/D027N/E056K/S058M, N011K/D027Q/S058M/P256T, N011K/D027S/E056K/P256T, N011K/D027S/N233Q/P256T, N011K/E056K/N233Q/P256T, N011K/G023K/L075Q/D111A, P029E/E045F/N073R/L075D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027N/P256T, Q004D/N011K/D027Q/N233Q, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/A049V/L075Q/V187T/T189D, A018K/D027S/E045F/L075D/T189D, A018K/D027S/N033D/L075D/T189D, A018K/D027S/N033D/N073R/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/D130A/G156W/V187T/L264R, A018K/E045F/A049V/L075Q/T189D, A018K/E045F/A049V/L075Q/V187T, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/D130A/V187N, A018K/K024A/N094R/G156W/V187T, A018K/L075Q/D111A/D130A/V187T, A018K/L075Q/N094R/D130A/V187N, A018K/L075Q/N094R/G156W/V187N, A018K/L075Q/V077I/N094R/G156W, A018K/L075Q/V187T/T189Q/L264R, A018K/N033D/E045F/L075D/T189D, A018K/P029E/N033D/N073R/L075D, A018K/V077I/G156W/V187T/T189D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/D130A/G163P/N233Q/L264R, D027E/D137Q/G163P/L227M/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027N/E056K/S058M/N233Q/P256T, D027Q/E056K/S058M/N233Q/P256T, D027Q/F051T/L075Q/D130A/L264R, D027S/E056K/D111A/V187N/L264R, D027S/E056K/S058M/N233Q/P256T, D027S/L075G/D130A/I252Q/L264R, D027S/L075G/G091Q/I252Q/L264R, D027S/L075Q/D111A/D130A/V187N, D027S/N033D/N073R/L075D/T189D, D027S/P029E/N033D/N073R/L075D, D027S/P029E/N073R/L075D/T189D, D048Q/D130A/D137Q/G163P/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/G163P/L227M/N233Q/L264R, D130A/V154I/G156W/V187N/T189Q, E045F/A049V/L075Q/V187T/T189D, E056K/D130A/V187H/I252Q/L264R, E056K/L075G/V187N/I252Q/L264R, E056K/L075Q/G156W/T189Q/L264R, E056K/L075R/D130A/V187T/L264R, E056K/N094R/G156W/V187N/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/L075R/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/V154I/V187N/L264R, G023Q/E045F/A049V/G156W/T189D, G023Q/E045F/L075Q/G156W/T189D, G023Q/F051T/L075Q/G091Q/I252Q, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075G/G091Q/I252Q/L264R, |

TABLE 4-4-continued

| TLL variants with Performance Index >1 compared to Reference sequence SEQ ID NO: 2 in the Thermostability assay are shown below. |
|---|

G023Q/L075Q/D130A/I252Q/L264R, G023Q/L075Q/G091Q/I252Q/L264R,
G023Q/L075Q/V077I/D130A/G156W, G023Q/L075Q/V077I/G156W/V187N,
G091Q/D130A/V187H/I252Q/L264R, K024A/L075Q/D111A/G156W/V187T,
K024A/L075Q/V077I/G156W/V187N, K024A/L075Q/V077I/V154I/V187N,
K024A/L075R/D111A/V154I/V187T, K024A/L075R/G156W/V187N/T189Q,
K024A/L075R/V154I/G156W/V187Q, L075G/D130A/V187T/I252Q/L264R,
L075Q/D111A/D130A/V187T/T189Q, L075Q/D111A/V187N/T189Q/L264R,
L075Q/D130A/V187T/T189Q/L264R, L075Q/N094R/D130A/G156W/V187T,
L075Q/V077I/D130A/G156W/V187N, L075Q/V154I/V187N/T189Q/L264R,
L075R/D111A/D130A/V187N/T189Q, L075R/D130A/V154I/T189Q/L264R,
L075R/D130A/V187T/T189Q/L264R, L075R/G156W/V187T/T189Q/L264R,
L075R/V077I/N094R/V154I/G156W, N011K/D027N/E056K/N233Q/P256T,
N011K/D027N/E056K/S058M/P256T, N011K/D027N/S058M/N233Q/P256T,
N011K/D027Q/S058M/N233Q/P256T, N011K/D027S/E056K/N233Q/P256T,
N011K/G023K/D111A/G156W/L264R, N011K/G023K/E056K/L075Q/T189Q,
N011K/G023Q/L075Q/V187N/T189Q, P029E/N033D/K074S/L075D/T189D,
P029E/N033D/N073R/L075D/T189D, Q004D/D027N/E056K/S058M/P256T,
Q004D/D027Q/E056K/N233Q/P256T, Q004D/D027Q/E056K/S058M/P256T,
Q004D/D027S/E056K/N233Q/P256T, Q004D/D027S/S058M/N233Q/P256T,
Q004D/N011K/D027N/N233Q/P256T, Q004D/N011K/D027Q/E056K/N233Q,
S058M/D130A/D137Q/G163P/L264R, S058M/D130A/G163P/L227M/L264R,
S058M/D137Q/G163P/L227M/L264R, S058M/D137Q/G163P/L227M/N233Q,
S058M/G163P/L227M/N233Q/L264R, V077I/D130A/V154I/G156W/V187N,
A018K/A049V/L075Q/G156W/V187T/T189D, A018K/D027S/N033D/E045F/N073R/L075D,
A018K/D027S/P029E/N033D/L075D/T189D, A018K/D027S/P029E/N073R/L075D/T189D,
A018K/G023K/D111A/D130A/V154I/T189Q, A018K/G023K/K024A/L075R/D111A/L264R,
A018K/G023K/K024A/L075R/D130A/V187N, A018K/G023K/K024A/N094R/D130A/V154I,
A018K/G023K/K024A/V077I/G156W/V187Q, A018K/G023K/L075Q/D130A/G156W/V187N,
A018K/G023K/L075Q/V077I/G156W/V187Q, A018K/G023K/L075R/N094R/D130A/V187N,
A018K/G023K/L075R/V077I/D130A/V154I, A018K/G023Q/A049V/G156W/V187T/T189D,
A018K/G023Q/A049V/L075Q/V077I/G156W, A018K/G023Q/A049V/L075Q/V077I/V187T,
A018K/G023Q/E045F/A049V/G156W/V187T, A018K/G023Q/E045F/A049V/L075Q/T189D,
A018K/G023Q/E045F/A049V/L075Q/V077I, A018K/G023Q/E045F/A049V/L075Q/V187T,
A018K/G023Q/E045F/G156W/V187T/T189D, A018K/G023Q/E045F/L075Q/G156W/V187T,
A018K/G023Q/K024A/L075R/N094R/G156W, A018K/G023Q/K024A/V077I/V154I/V187N,
A018K/G023Q/K024A/V154I/G156W/V187Q, A018K/G023Q/L075Q/G156W/V187T/T189D,
A018K/G023Q/L075Q/V077I/D130A/G156W, A018K/G023Q/L075Q/V077I/D130A/V187N,
A018K/G023Q/L075Q/V077I/G156W/V187N, A018K/G023Q/L075Q/V077I/N094R/V154I,
A018K/G023Q/L075Q/V077I/V187T/T189D, A018K/G023Q/N094R/D130A/G156W/V187Q,
A018K/K024A/L075Q/N094R/V154I/G156W, A018K/K024A/L075Q/N094R/V154I/V187N,
A018K/K024A/L075Q/V077I/D130A/V187N, A018K/K024A/L075R/D130A/V187N/T189Q,
A018K/K024A/V077I/N094R/D130A/G156W, A018K/L075Q/D111A/V154I/G156W/V187N,
A018K/L075Q/D111A/V154I/T189Q/L264R, A018K/L075Q/D130A/V154I/T189Q/L264R,
A018K/L075Q/D130A/V187N/T189Q/L264R, A018K/L075R/D130A/V154I/G156W/V187N,
A018K/N033D/E045F/N073R/L075D/T189D, A018K/N094R/D111A/D130A/V154I/V187N,
D027E/D048Q/D130A/D137H/G163P/L264R, D027E/D048Q/D130A/D137Q/G163P/L264R,
D027E/D048Q/D130A/G163P/L227M/L264R, D027E/D048Q/D137Q/G163P/L227M/L264R,
D027E/D048Q/D137Q/G163P/N233Q/L264R, D027E/D048Q/S058M/D130A/G163P/L264R,
D027E/D048Q/S058M/G163P/L227M/L264R, D027E/D048Q/S058M/G163P/N233Q/L264R,
D027E/D130A/D137Q/G163P/L227M/L264R, D027E/D130A/D137Q/G163P/N233Q/L264R,
D027E/D130A/G163P/L227M/N233Q/L264R, D027E/D137Q/G163P/L227M/N233Q/L264R,
D027E/S058M/D130A/G163P/L227M/L264R, D027E/S058M/D130A/G163P/N233Q/L264R,
D027E/S058M/D130A/L227M/N233Q/L264R, D027E/S058M/D137Q/G163P/L227M/L264R,
D027E/S058M/D137Q/G163P/N233Q/L264R, D027Q/E056K/S058M/D130A/I252Q/L264R,
D027Q/F051T/G091Q/D130A/I252Q/L264R, D027Q/F051T/L075G/D130A/I252Q/L264R,
D027Q/F051T/L075G/G091Q/V187N/I252Q, D027Q/F051T/L075Q/D130A/V187H/L264R,
D027Q/S058M/L075R/D130A/V187T/I252Q, D027S/E056K/S058M/V187T/I252Q/L264R,
D027S/F051T/L075Q/D130A/I252Q/L264R, D027S/L075Q/D111A/G156W/V187N/T189Q,
D027S/L075Q/G091Q/V187H/I252Q/L264R, D027S/P029E/N033D/N073R/L075D/T189D,
D048Q/D130A/G163P/L227M/N233Q/L264R, D048Q/D137Q/G163P/L227M/N233Q/L264R,
D048Q/S058M/D130A/D137Q/G163P/L264R, D048Q/S058M/D130A/G163P/L227M/L264R,
D048Q/S058M/D130A/G163P/N233Q/L264R, D048Q/S058M/D130A/L227M/N233Q/L264R,
D048Q/S058M/D137Q/G163P/L227M/L264R, D048Q/S058M/D137Q/G163P/N233Q/L264R,
D048Q/S058M/G163P/L227M/N233Q/L264R, F051T/L075G/G091Q/D130A/I252Q/L264R,
F051T/L075G/G091Q/V187H/I252Q/L264R, F051T/L075G/G091Q/V187T/I252Q/L264R,
F051T/L075R/D130A/V187N/I252Q/L264R, G023K/D027S/L075R/D130A/V187T/I252Q,
G023K/D027S/L075R/V187N/I252Q/L264R, G023K/D130A/V154I/G156W/V187T/L264R,
G023K/E056K/L075R/D130A/V187N/L264R, G023K/E056K/L075R/D130A/V187T/L264R,
G023K/F051T/G091Q/D130A/V187H/L264R, G023K/F051T/L075Q/D130A/I252Q/L264R,
G023K/K024A/L075Q/D111A/D130A/T189Q, G023K/K024A/L075Q/G156W/V187T/T189Q,
G023K/K024A/L075Q/N094R/D130A/G156W, G023K/K024A/L075Q/V154I/G156W/V187Q,
G023K/K024A/L075R/D130A/V154I/V187N, G023K/L075G/D130A/V187T/I252Q/L264R,
G023K/L075Q/D111A/D130A/V154I/V187N, G023K/L075Q/N094R/V154I/V187T/L264R,
G023K/L075Q/V077I/D130A/G156W/V187Q, G023K/N094R/D111A/G156W/V187T/L264R,
G023Q/A049V/L075Q/G156W/V187T/T189D, G023Q/D027Q/E056K/L075R/I252Q/L264R,
G023Q/D027S/F051T/L075Q/V187T/I252Q, G023Q/D027S/F051T/L075Q/V187T/L264R,
G023Q/D027S/L075G/D130A/V187H/L264R, G023Q/D027S/L075Q/D111A/G156W/L264R,

TABLE 4-4-continued

| TLL variants with Performance Index >1 compared to Reference sequence SEQ ID NO: 2 in the Thermostability assay are shown below. |
|---|
| G023Q/D027S/L075Q/D130A/V187T/I252Q, G023Q/D027S/L075R/D111A/V187N/L264R, G023Q/D027S/N094R/V154I/G156W/T189Q, G023Q/E045F/A049V/L075Q/G156W/V187T, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/N094R/D111A/G156W/L264R, G023Q/L075Q/V077I/N094R/D130A/V187Q, G023Q/L075R/V154I/G156W/V187N/L264R, K024A/D111A/D130A/V187T/T189Q/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/L075R/D111A/V154I/G156W/V187N, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075Q/N094R/D111A/G156W/T189Q/L264R, L075R/D130A/V154I/G156W/V187N/L264R, N011K/D027N/E056K/S058M/N233Q/P256T, N011K/D027N/S058M/I090F/N233Q/P256T, N011K/D027Q/E056K/S058M/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/D130A/V154I/G156W/V187T/L264R, A018K/K024A/L075Q/D111A/G156W/V187N/L264R, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/K024A/N094R/D130A/G156W/V187T/L264R, A018K/L075Q/D111A/D130A/V154I/G156W/L264R, A018K/L075Q/D130A/G156W/V187N/T189Q/L264R, A018K/L075Q/N094R/D111A/V154I/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/L075Q/G091Q/D130A/V187T/I252Q, D027Q/F051T/S058M/L075Q/G091Q/I252Q/L264R, D027Q/L075G/G091Q/D130A/V187H/I252Q/L264R, D027S/F051T/L075G/G091Q/V187T/I252Q/L264R, D027S/F051T/S058M/L075R/D130A/I252Q/L264R, D027S/L075R/V154I/G156W/V187N/T189Q/L264R, D027S/P029E/N033D/E045F/N073R/L075D/T189D, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, |

TABLE 4-4-continued

| TLL variants with Performance Index >1 compared to Reference sequence SEQ ID NO: 2 in the Thermostability assay are shown below. |
|---|
| D048Q/S058M/D137Q/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/G091Q/V187N/I252Q, |
| G023K/D027S/F051T/S058M/L075Q/D130A/V187N, |
| G023K/D027S/L075Q/N094R/V154I/G156W/T189Q, |
| G023K/F051T/L075Q/G091Q/D130A/V187H/I252Q, |
| G023K/K024A/L075Q/D111A/D130A/T189Q/L264R, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/K024A/N094R/V154I/G156W/V187N/T189Q, |
| G023K/L075Q/D111A/D130A/V154I/G156W/L264R, |
| G023K/L075Q/D111A/V154I/G156W/T189Q/L264R, |
| G023K/L075Q/D130A/G156W/V187N/T189Q/L264R, |
| G023K/L075Q/N094R/D130A/V154I/V187N/L264R, |
| G023K/L075Q/N094R/V154I/G156W/V187T/L264R, |
| G023K/L075R/N094R/V154I/G156W/V187N/L264R, |
| G023Q/D027S/L075Q/V154I/G156W/V187N/L264R, |
| G023Q/D027S/S058M/L075Q/D130A/I252Q/L264R, |
| G023Q/E045F/L075Q/V077I/G156W/V187T/T189D, |
| G023Q/E056K/L075Q/D111A/G156W/V187N/L264R, |
| G023Q/E056K/L075Q/D130A/V154I/G156W/T189Q, |
| G023Q/E056K/L075R/D111A/D130A/V187N/T189Q, |
| G023Q/F051T/G091Q/D130A/V187H/I252Q/L264R, |
| G023Q/F051T/L075Q/G091Q/V187H/I252Q/L264R, |
| G023Q/F051T/L075R/G091Q/V187N/I252Q/L264R, |
| G023Q/F051T/S058M/G091Q/D130A/I252Q/L264R, |
| G023Q/K024A/L075Q/V077I/D130A/G156W/V187N, |
| G023Q/K024A/L075Q/V077I/D130A/V154I/G156W, |
| G023Q/L075G/G091Q/D130A/V187T/I252Q/L264R, |
| G023Q/L075Q/D111A/D130A/V154I/G156W/L264R, |
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| G023Q/S058M/L075G/G091Q/D130A/I252Q/L264R, |
| K024A/L075Q/D111A/D130A/V154I/G156W/L264R, |
| K024A/L075Q/D111A/D130A/V187N/T189Q/L264R, |
| K024A/L075R/D130A/V154I/G156W/T189Q/L264R, |
| L075Q/D111A/D130A/G156W/V187N/T189Q/L264R, |
| N011K/A018K/K024A/V077I/V154I/G156W/T189Q, |
| N011K/E056K/L075Q/D111A/D130A/V154I/L264R, |
| N011K/E056K/L075Q/D130A/V154I/V187N/T189Q, |
| N011K/G023K/L075Q/D111A/D130A/V154I/V187N, |
| Q004D/N011K/D027Q/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| A018K/K024A/L075Q/V077I/N094R/D130A/V154I/G156W, |
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| D027E/D048Q/S058M/D137Q/G163P/L227M/N233Q/L264R, |
| D027E/S058M/D130A/D137Q/G163P/L227M/N233Q/L264R, |
| D048Q/S058M/D130A/D137Q/G163P/L227M/N233Q/L264R, |
| F051T/E056K/L075G/G091Q/D130A/V187H/I252Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/E056K/L075Q/D130A/V154I/V187N/T189Q/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |

TABLE 4-4-continued

| TLL variants with Performance Index >1 compared to Reference sequence SEQ ID NO: 2 in the Thermostability assay are shown below. |
|---|
| G023K/L075Q/N094R/D130A/V154I/G156W/V187N/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/L075R/N094R/V154I/G156W/V187N/T189Q, G023Q/D027S/S058M/G091Q/D130A/V187H/I252Q/L264R, G023Q/E056K/L075Q/N094R/D111A/G156W/T189Q/L264R, G023Q/F051T/L075Q/G091Q/D130A/V187H/I252Q/L264R, G023Q/F051T/L075R/G091Q/D130A/V187T/I252Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/V077I/N094R/D130A/V154I/G156W/V187Q, G023Q/S058M/L075R/G091Q/D130A/V187H/I252Q/L264R, K024A/D111A/D130A/V154I/G156W/V187T/T189Q/L264R, N011K/G023K/D027S/L075Q/D111A/D130A/V154I/T189Q, N011K/G023K/D027S/L075R/V154I/G156W/V187N/T189Q, N011K/G023K/E056K/L075Q/D130A/V154I/T189Q/L264R, N011K/G023K/L075Q/D111A/G156W/V187N/T189Q/L264R, N011K/G023Q/D027S/L075Q/N094R/V154I/G156W/T189Q, N011K/G023Q/D027S/N094R/V154I/G156W/T189Q/L264R, N011K/G023Q/L075Q/D111A/D130A/V154I/V187N/L264R, N011K/G023Q/L075Q/N094R/V154I/G156W/T189Q/L264R, A018K/G023K/K024A/L075Q/N094R/D111A/D130A/V154I/T189Q, A018K/G023K/K024A/L075Q/N094R/D130A/V154I/G156W/V187N, A018K/G023K/K024A/L075Q/N094R/D130A/V187T/T189Q/L264K, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, A018K/K024A/L075Q/N094R/V154I/G156W/V187N/T189Q/L264R, D027Q/F051T/S058M/L075G/G091Q/D130A/V187T/I252Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/F051T/E056K/L075G/G091Q/V187N/I252Q/L264R, G023Q/D027S/L075Q/N094R/D111A/D130A/V154I/G156W/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/D027S/E056K/L075R/D111A/G156W/V187N/L264R, N011K/G023K/L075R/D111A/D130A/V154I/V187N/T189Q/L264R, N011K/G023Q/L075Q/D111A/V154I/G156W/V187N/T189Q/L264R, N011K/G023K/L075R/V077I/D130A/V154I/G156W/V187T/T189Q, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/E045F/A049V/S058M/N073S/L075Q/V187T/T189D, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/S058M/L075Q/V077I/R108K/H135F/G156W/V187H, A018K/G023Q/K024A/L075Q/V077I/N094R/D130A/V154I/G156W/V187Q, G023Q/D027S/F051T/E056K/L075R/G091Q/D130A/V187H/I252Q/L264R, G023Q/D027S/F051T/E056K/S058M/L075R/G091Q/D130A/V187H/I252Q, N011K/A018K/G023K/K024A/L075R/V077I/D130A/V154I/V187T/T189Q, N011K/G023K/L075R/N094R/D111A/V154I/G156W/V187N/T189Q/L264R, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, |

TABLE 4-4-continued

| TLL variants with Performance Index >1 compared to Reference sequence SEQ ID NO: 2 in the Thermostability assay are shown below. |
|---|
| N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D |

TABLE 4-5

| TLL variants with Performance Index for expression ≥0.5 compared to TLL SEQ ID NO: 1 and Performance Index >1 in the Thermostability assay compared to Reference sequence SEQ ID NO: 2 are shown below. |
|---|
| A018K/L075D, D027E/G163P, D027S/N033D, D027S/P256T, D111A/L264R, D130A/L264R, D130A/V187N, D130A/V187T, E045F/N073R, F051T/L075R, G023K/L264R, K024A/V154I, L075R/L264R, L227M/L264R, P029E/N033D, S058M/L264R, V187T/L264R, A018K/A049V/V187T, A018K/E045F/V187T, A018K/K024A/V154I, A018K/L075D/T189D, A018K/N033D/T189D, A018K/P029E/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D111A/D130A/L264R, D130A/V154I/G156W, D130A/V187N/L264R, D130A/V187T/L264R, E056K/D130A/L264R, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/D130A/G156W, G023Q/K024A/G156W, G163P/L227M/L264R, K024A/D130A/V154I, L075G/D130A/V187H, L075Q/V187T/L264R, L075R/D130A/L264R, L075R/D130A/V187T, L075R/V187N/L264R, L075R/V187T/L264R, N011K/N233Q/P256T, N094R/D130A/V187T, Q004D/D027S/P256T, V187N/T189Q/L264R, A018K/D027S/P029E/T189D, A018K/D111A/G156W/T189Q, A018K/D130A/G156W/V187T, A018K/E045F/A049V/G156W, A018K/E045F/L075D/T189D, A018K/G023K/D111A/T189Q, A018K/G023Q/A049V/V187T, A018K/G023Q/V077I/G156W, A018K/K024A/D130A/G156W, A018K/L075Q/V077I/N094R, A018K/N033D/L075D/T189D, A018K/P029E/N073R/L075D, D027E/D048Q/G163P/L264R, D027E/D130A/N233Q/L264R, D027E/D137Q/G163P/L227M, D027E/D137Q/L227M/L264R, D027E/G163P/L227M/L264R, D027E/L227M/N233Q/L264R, D027E/S058M/G163P/L264R, D027N/S058M/N233Q/P256T, D027Q/E056K/N233Q/P256T, D027S/D130A/I252Q/L264R, D027S/N033D/E045F/N073R, D027S/N033D/L075D/T189D, D027S/N033D/N073R/T189D, D027S/P029E/L075D/T189D, D027S/P029E/N033D/E045F, D027S/P029E/N033D/L075D, D048Q/D130A/G163P/L264R, D048Q/G163P/N233Q/L264R, D111A/D130A/V154I/G156W, D130A/G163P/L227M/L264R, E045F/A049V/G156W/V187T, E056K/D130A/V187N/L264R, E056K/D130A/V187T/L264R, F051T/D130A/I252Q/L264R, F051T/L075G/I252Q/L264R, G023K/D027Q/F051T/L075Q, G023K/D130A/G156W/T189Q, G023K/D130A/V187N/L264R, G023K/D130A/V187T/L264R, G023K/D130A/V187T/T189Q, G023K/E056K/L075R/L264R, G023K/K024A/V154I/V187N, G023K/L075R/D130A/L264R, G023K/L075R/V187T/L264R, G023Q/A049V/V077I/G156W, G023Q/K024A/L075R/G156W, G023Q/K024A/V077I/G156W, G023Q/L075Q/D130A/L264R, G091Q/V187T/I252Q/L264R, K024A/D130A/V154I/V187T, L075G/D130A/V187T/I252Q, L075G/G091Q/V187N/L264R, L075G/V187H/I252Q/L264R, L075R/D130A/V187T/L264R, N011K/D027Q/S058M/P256T, N011K/D027S/N233Q/P256T, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/D027S/E045F/L075D/T189D, A018K/D027S/P029E/N033D/L075D, A018K/D130A/G156W/V187N/L264R, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/K024A/L075Q/G156W, A018K/K024A/L075R/D130A/V154I, A018K/K024A/N094R/D130A/V187N, A018K/K024A/N094R/G156W/V187T, A018K/P029E/N033D/N073R/L075D, D027E/D048Q/D137Q/L227M/L264R, D027E/D048Q/G163P/N233Q/L264R, D027E/D130A/D137Q/G163P/L264R, D027E/D130A/G163P/L227M/L264R, D027E/D130A/G163P/N233Q/L264R, D027E/D137Q/G163P/N233Q/L264R, D027E/G163P/L227M/N233Q/L264R, D027E/S058M/D130A/G163P/L264R, D027E/S058M/D137Q/G163P/N233Q, D027E/S058M/G163P/L227M/L264R, D027Q/F051T/L075Q/D130A/L264R, D027S/E056K/D111A/V187N/L264R, D027S/L075G/D130A/I252Q/L264R, D027S/L075G/G091Q/I252Q/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/L227M/L264R, D130A/D137Q/G163P/N233Q/L264R, D130A/V154I/G156W/V187N/T189Q, E045F/A049V/L075Q/V187T/T189D, E056K/L075G/V187N/I252Q/L264R, E056K/L075R/D130A/V187T/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/L075R/D130A/V187N/L264R, G023K/L075R/D130A/V187T/L264R, |

TABLE 4-5-continued

| TLL variants with Performance Index for expression ≥0.5 compared to TLL SEQ ID NO: 1 and Performance Index >1 in the Thermostability assay compared to Reference sequence SEQ ID NO: 2 are shown below. |
| --- |
| G023K/N094R/G156W/V187N/T189Q, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, K024A/L075R/V154I/G156W/V187Q, L075G/D130A/V187T/I252Q/L264R, N011K/D027N/S058M/N233Q/P256T, N011K/G023K/D111A/G156W/L264R, Q004D/N011K/D027N/N233Q/P256T, S058M/D130A/D137Q/G163P/L264R, S058M/D130A/G163P/L227M/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/D027S/N033D/E045F/N073R/L075D, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/D130A/G163P/L264R, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D048Q/D130A/G163P/L227M/N233Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/V154I/G156W/V187Q, G023K/K024A/L075R/D130A/V154I/V187N, G023K/L075G/D130A/V187T/I252Q/L264R, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/K024A/V077I/D130A/V154I/G156W, G023Q/L075G/G091Q/D130A/I252Q/L264R, K024A/L075Q/D111A/V154I/V187N/T189Q, K024A/L075Q/N094R/D130A/V154I/L264R, K024A/L075Q/V077I/N094R/D130A/V187N, L075Q/G091Q/D130A/V187H/I252Q/L264R, Q004D/N011K/D027N/I090F/N233Q/P256T, Q004D/N011K/D027N/S058M/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/D130A/V154I/G156W/V187T/L264R, A018K/K024A/L075Q/D130A/V154I/G156W/V187T, A018K/K024A/L075Q/V077I/N094R/D130A/G156W, A018K/K024A/N094R/D130A/G156W/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075R/D130A/I252Q/L264R, D048Q/D130A/D137Q/G163P/L227M/N233Q/L264R, D048Q/S058M/D130A/D137Q/G163P/L227M/L264R, |

TABLE 4-5-continued

| TLL variants with Performance Index for expression ≥0.5 compared to TLL SEQ ID NO: 1 and Performance Index >1 in the Thermostability assay compared to Reference sequence SEQ ID NO: 2 are shown below. |
|---|
| D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, F051T/L075G/G091Q/D130A/V187N/I252Q/L264R, F051T/L075R/G091Q/D130A/V187T/I252Q/L264R, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/D027S/S058M/L075Q/D130A/I252Q/L264R, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/L075Q/V077I/N094R/D130A/G156W/V187N, G023Q/S058M/L075G/G091Q/D130A/I252Q/L264R, N011K/A018K/K024A/V077I/V154I/G156W/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, A018K/G023Q/D027S/P029E/L075Q/V077I/R108K/H135F/V187H, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075G/G091Q/D130A/V187T/I252Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 4-6

| TLL variants with Performance Index for expression ≥0.5 compared to TLL SEQ ID NO: 1 and Performance Index ≥50% of the maximum PI value in the Thermostability assay compared to Reference sequence SEQ ID NO: 2 are shown below. |
|---|
| A018K/L075D, D027E/G163P, E045F/N073R, L227M/L264R, A018K/E045F/V187T, A018K/L075D/T189D, G163P/L227M/L264R, L075R/V187N/L264R, A018K/E045F/A049V/G156W, D027E/D048Q/G163P/L264R, D027E/D130A/N233Q/L264R, D027E/G163P/L227M/L264R, D027E/L227M/N233Q/L264R, D027E/S058M/G163P/L264R, D027S/P029E/N033D/E045F, D048Q/G163P/N233Q/L264R, D130A/G163P/L227M/L264R, F051T/D130A/I252Q/L264R, F051T/L075G/I252Q/L264R, G023K/D130A/V187T/L264R, G023Q/L075Q/D130A/L264R, L075G/G091Q/V187N/L264R, S058M/G163P/L227M/L264R, S058M/G163P/N233Q/L264R, A018K/D027S/E045F/L075D/T189D, D027E/D130A/D137Q/G163P/L264R, D027E/D130A/G163P/L227M/L264R, D027E/D130A/G163P/N233Q/L264R, D027E/D137Q/G163P/N233Q/L264R, D027E/S058M/D130A/G163P/L264R, D027E/S058M/G163P/L227M/L264R, D027S/E056K/D111A/V187N/L264R, D048Q/D130A/G163P/L227M/L264R, D048Q/D137Q/G163P/L227M/L264R, D048Q/S058M/D130A/N233Q/L264R, D048Q/S058M/D137Q/N233Q/L264R, D048Q/S058M/G163P/L227M/L264R, D048Q/S058M/G163P/N233Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, |

TABLE 4-6-continued

| TLL variants with Performance Index for expression ≥0.5 compared to TLL SEQ ID NO: 1 and Performance Index ≥50% of the maximum PI value in the Thermostability assay compared to Reference sequence SEQ ID NO: 2 are shown below. |
|---|
| F051T/S058M/L075Q/G091Q/I252Q, G023K/E056K/L075R/V187N/L264R, G023K/L075Q/V187H/I252Q/L264R, G023Q/F051T/L075Q/G091Q/I252Q, G023Q/L075Q/D130A/I252Q/L264R, L075G/D130A/V187T/I252Q/L264R, S058M/D130A/G163P/L227M/L264R, S058M/D137Q/G163P/L227M/L264R, S058M/D137Q/G163P/L227M/N233Q, D027E/D048Q/D130A/D137H/G163P/L264R, D027E/D048Q/D130A/D137Q/G163P/L264R, D027E/D048Q/D137Q/G163P/N233Q/L264R, D027E/D048Q/S058M/D130A/G163P/L264R, D027E/D048Q/S058M/G163P/L227M/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D137Q/G163P/L227M/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027S/E056K/S058M/V187T/I252Q/L264R, D027S/F051T/L075Q/D130A/I252Q/L264R, D048Q/D130A/G163P/L227M/N233Q/L264R, D048Q/D137Q/G163P/L227M/N233Q/L264R, D048Q/S058M/D137Q/G163P/N233Q/L264R, D048Q/S058M/G163P/L227M/N233Q/L264R, F051T/L075G/G091Q/D130A/I252Q/L264R, G023K/D027S/L075R/V187N/I252Q/L264R, G023K/L075G/D130A/V187T/I252Q/L264R, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, S058M/D130A/D137Q/G163P/L227M/L264R, S058M/D130A/D137Q/G163P/N233Q/L264R, S058M/D130A/G163P/L227M/N233Q/L264R, D027E/D048Q/D130A/D137Q/G163P/N233Q/L264R, D027E/D048Q/D137Q/G163P/L227M/N233Q/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, D027E/S058M/D137Q/G163P/L227M/N233Q/L264R, D027Q/F051T/L075Q/D130A/V187T/I252Q/L264R, D027Q/L075G/G091Q/D130A/V187H/I252Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, G023K/D027S/F051T/S058M/L075Q/D130A/V187N, G023Q/D027S/S058M/L075Q/D130A/I252Q/L264R, G023Q/F051T/G091Q/D130A/V187H/I252Q/L264R, G023Q/F051T/L075Q/G091Q/V187H/I252Q/L264R, N011K/A018K/K024A/V077I/V154I/G156W/T189Q, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023Q/D027Q/F051T/S058M/L075R/D130A/V187T/L264R, G023Q/D027S/E056K/S058M/L075G/G091Q/V187T/L264R, G023Q/D027S/F051T/S058M/G091Q/D130A/V187N/I252Q, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, A018K/G023K/K024A/V077I/D130A/V154I/G156W/V187T/T189Q, D027Q/F051T/S058M/L075G/G091Q/D130A/V187T/I252Q/L264R, N011K/A018K/G023K/K024A/L075R/V077I/D130A/V154I/V187T/T189Q, A018K/G023Q/D027S/E045F/A049V/S058M/N073S/L075Q/R108K/V187T/T189D |

Example 5

Detergent Stability of TLL Combinatorial Variants

The detergent stability of TLL variants created as described in Example 2 was assayed as described in Example 1 (Detergent Stability assay). The performance index was calculated for the variants compared to TLL, SEQ ID NO:1 or the reference sequence SEQ ID NO: 2.

TABLE 5-1

| TLL variants with Performance Index >1 compared to TLL SEQ ID NO: 1 in the Detergent stability assay are shown below. |
|---|
| A018K/D027S, A018K/L075Q, A018K/T189D, D027E/G163P, D027N/E056K, D027N/N233Q, D027S/N033D, D027S/P256T, D111A/L264R, D130A/T189Q, D130A/V187N, G023K/D130A, G023Q/L075Q, K024A/L075Q, K024A/V154I, L075Q/D130A, L075Q/G156W, N011K/D027S, N073R/L075D, N094R/G156W, P029E/N033D, A018K/A049V/L075Q, A018K/A049V/V187T, |

TABLE 5-1-continued

| TLL variants with Performance Index >1 compared to TLL SEQ ID NO: 1 in the Detergent stability assay are shown below. |
| --- |
| A018K/D027S/E045F, A018K/D027S/N073R, A018K/D027S/T189D, A018K/E045F/T189D, A018K/E045F/V187T, A018K/G023K/G156W, A018K/G023K/L075Q, A018K/G023Q/L075Q, A018K/K024A/V154I, A018K/L075Q/G156W, A018K/L075Q/V187T, A018K/N033D/T189D, A018K/N073R/L075D, A018K/V154I/G156W, A049V/L075Q/T189D, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D111A/D130A/L264R, D130A/T189Q/L264R, D130A/V154I/G156W, D130A/V187T/L264R, E045F/L075D/T189D, E045F/N073R/L075D, E056K/D130A/L264R, G023K/D130A/L264R, G023K/D130A/V187T, G023K/V187N/L264R, G023K/V187T/L264R, G023Q/A049V/T189D, G023Q/D111A/L264R, G023Q/D130A/G156W, G023Q/E056K/L075R, G023Q/K024A/G156W, G023Q/L075Q/V187T, I090F/N233Q/P256T, K024A/D130A/V154I, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/V077I/T189D, L075Q/V154I/V187T, L075Q/V187N/L264R, L075Q/V187T/T189D, L075R/D130A/V187T, N011K/D027S/S058M, N011K/N233Q/P256T, N033D/E045F/L075D, N033D/N073R/T189D, N073R/L075D/T189D, N094R/D130A/V187T, P029E/E045F/L075D, P029E/L075D/T189D, P029E/N033D/E045F, P029E/N033D/L075D, P029E/N073R/L075D, Q004D/D027S/P256T, Q004D/S058M/N233Q, V077I/D130A/V154I, V077I/V187A/T189D, V187N/T189Q/L264R, A018K/A049V/L075Q/T189D, A018K/A049V/L075Q/V187T, A018K/D027S/L075D/T189D, A018K/D027S/N033D/L075D, A018K/D027S/P029E/T189D, A018K/D111A/G156W/T189Q, A018K/D130A/G156W/V187T, A018K/E045F/A049V/G156W, A018K/E045F/A049V/V187T, A018K/E045F/L075Q/T189D, A018K/E045F/L075Q/V187T, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/K024A/D130A/G156W, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/N033D/L075D/T189D, A018K/N073R/L075D/T189D, A018K/P029E/N033D/L075D, A018K/P029E/N033D/T189D, A018K/V154I/G156W/V187T, A049V/L075Q/V077I/T189D, A049V/L075Q/V187T/T189D, D027E/D137Q/G163P/L227M, D027N/E056K/N233Q/P256T, D027N/E056K/S058M/P256T, D027N/S058M/N233Q/P256T, D027Q/E056K/N233Q/P256T, D027Q/S058M/I090F/P256T, D027S/D130A/I252Q/L264R, D027S/E056K/D111A/V154I, D027S/E056K/I090F/P256T, D027S/N033D/E045F/T189D, D027S/N033D/L075D/T189D, D027S/N033D/N073R/L075D, D027S/N033D/N073R/T189D, D027S/P029E/E045F/L075D, D027S/P029E/L075D/T189D, D027S/P029E/N033D/L075D, D027S/P029E/N033D/N073R, D027S/P029E/N033D/T189D, D111A/D130A/V154I/G156W, D111A/D130A/V154I/L264R, D111A/D130A/V187T/L264R, E045F/A049V/G156W/V187T, E045F/L075Q/G156W/V187T, E056K/D130A/V187T/L264R, E056K/L075Q/V187N/L264R, G023K/D027Q/F051T/L075Q, G023K/D027S/L075Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187T/L264R, G023Q/A049V/L075Q/T189D, G023Q/A049V/V077I/G156W, G023Q/E045F/A049V/T189D, G023Q/E045F/A049V/V187T, G023Q/E045F/L075Q/G156W, G023Q/E045F/L075Q/V187T, G023Q/F051T/I252Q/L264R, G023Q/G091Q/I252Q/L264R, G023Q/K024A/D130A/G156W, G023Q/K024A/L075R/G156W, G023Q/K024A/L075R/V154I, G023Q/K024A/V077I/G156W, G023Q/L075Q/D130A/L264R, G023Q/L075Q/G156W/V187N, G023Q/L075Q/G156W/V187T, G023Q/L075Q/V187T/L264R, G023Q/V154I/G156W/V187N, K024A/D130A/V154I/V187T, K024A/L075Q/D130A/G156W, K024A/L075Q/D130A/V154I, K024A/L075Q/V187T/T189Q, K024A/L075R/G156W/V187N, L075G/D130A/V187T/I252Q, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, N011K/D027N/E056K/S058M, N011K/D027N/S058M/P256T, N011K/D027Q/S058M/P256T, N011K/D027S/E056K/P256T, N011K/D027S/N233Q/P256T, N011K/D027S/S058M/N233Q, N011K/E056K/N233Q/P256T, N011K/G023K/L075Q/D111A, N011K/S058M/N233Q/P256T, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027Q/N233Q, Q004D/N011K/D027S/P256T, Q004D/N011K/E056K/S058M, S058M/D137Q/G163P/N233Q, S058M/L075Q/G091Q/I252Q, A018K/A049V/L075Q/V187T/T189D, A018K/D027S/N033D/L075D/T189D, A018K/D027S/N033D/N073R/T189D, A018K/D027S/P029E/E045F/T189D, A018K/D027S/P029E/N033D/L075D, A018K/D027S/P029E/N073R/L075D, A018K/E045F/A049V/L075Q/T189D, A018K/E045F/A049V/L075Q/V187T, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, |

TABLE 5-1-continued

| TLL variants with Performance Index >1 compared to TLL SEQ ID NO: 1 in the Detergent stability assay are shown below. |
| --- |
| A018K/G023Q/V077I/V187T/T189D, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/G156W/V187T, A018K/L075Q/D111A/D130A/V187T, A018K/L075Q/G156W/V187T/T189D, A018K/L075Q/N094R/D130A/V187N, A018K/L075Q/N094R/G156W/V187N, A018K/L075Q/V077I/N094R/G156W, A018K/V077I/G156W/V187T/T189D, D027E/D048Q/L227M/N233Q/L264R, D027E/D048Q/S058M/G163P/N233Q, D027E/S058M/D137Q/G163P/N233Q, D027N/E056K/S058M/N233Q/P256T, D027Q/E056K/I090F/N233Q/P256T, D027Q/E056K/S058M/N233Q/P256T, D027S/E056K/D111A/V187N/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/L075Q/D111A/D130A/V187N, D027S/N033D/N073R/L075D/T189D, D027S/P029E/E045F/N073R/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/S058M/D130A/N233Q/L264R, D048Q/S058M/D137Q/G163P/N233E, D048Q/S058M/G163P/N233Q/L264R, D130A/V154I/G156W/V187N/T189Q, E045F/A049V/L075Q/V187T/T189D, E056K/D130A/V187H/I252Q/L264R, E056K/L075Q/G156W/T189Q/L264R, E056K/L075R/D130A/V187T/L264R, E056K/N094R/G156W/V187N/L264R, E056K/S058M/I090F/N233Q/P256T, F051T/L075G/G091Q/D130A/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/V154I/V187N/L264R, G023Q/E045F/A049V/G156W/T189D, G023Q/E045F/A049V/L075Q/V077I, G023Q/E045F/A049V/V077I/T189D, G023Q/E045F/L075Q/G156W/T189D, G023Q/E045F/L075Q/V077I/V187T, G023Q/F051T/L075Q/G091Q/I252Q, G023Q/K024A/L075Q/D130A/G156W, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, G023Q/L075Q/V077I/G156W/V187N, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075Q/D111A/V187N/T189Q/L264R, L075Q/D130A/V187T/T189Q/L264R, L075Q/N094R/D130A/G156W/V187T, L075Q/V077I/D130A/G156W/V187N, L075Q/V154I/V187N/T189Q/L264R, L075R/D130A/V154I/T189Q/L264R, L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/E045F/L075D/T189D, P029E/N033D/K074S/L075D/T189D, P029E/N033D/N073R/L075D/T189D, Q004D/D027N/E056K/S058M/P256T, Q004D/D027N/I090F/N233Q/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, Q004D/N011K/I090F/N233Q/P256T, S058M/G163P/L227M/N233Q/L264R, V077I/D130A/V154I/G156W/V187N, A018K/A049V/L075Q/G156W/V187T/T189D, A018K/D027S/N033D/E045F/L075D/T189D, A018K/D027S/P029E/N033D/L075D/T189D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/G156W, A018K/G023Q/A049V/L075Q/V077I/V187T, A018K/G023Q/E045F/A049V/G156W/V187T, A018K/G023Q/E045F/A049V/L075Q/T189D, A018K/G023Q/E045F/A049V/L075Q/V187T, A018K/G023Q/E045F/G156W/V187T/T189D, A018K/G023Q/E045F/L075Q/G156W/V187T, A018K/G023Q/K024A/L075R/N094R/G156W, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, |

TABLE 5-1-continued

| TLL variants with Performance Index >1 compared to TLL SEQ ID NO: 1 in the Detergent stability assay are shown below. |
|---|
| A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D111A/V154I/G156W/V187N, A018K/L075R/D130A/V154I/G156W/V187N, A018K/N094R/D111A/D130A/V154I/V187N, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/G091Q/D130A/V187N/I252Q/L264R, D027S/L075Q/D111A/G156W/V187N/T189Q, D027S/L075Q/G091Q/V187H/I252Q/L264R, D027S/P029E/N033D/E045F/N073R/T189D, D027S/P029E/N033D/N073R/L075D/T189D, D048Q/S058M/D130A/D137Q/G163P/L264R, D048Q/S058M/D130A/G163P/N233Q/L264R, D048Q/S058M/D137Q/G163P/L227M/L264R, D111A/D130A/V154I/G156W/V187N/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027S/F051T/L075Q/V187T/I252Q, G023Q/D027S/F051T/L075Q/V187T/L264R, G023Q/D027S/L075G/D130A/V187H/L264R, G023Q/D027S/L075Q/D130A/V187T/I252Q, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/G091Q/V187N/I252Q/L264R, G023Q/L075Q/V077I/N094R/D130A/V187Q, G023Q/L075R/V154I/G156W/V187N/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/D027N/E056K/I090F/N233Q/P256T, N011K/D027N/E056K/S058M/N233Q/P256T, N011K/D027Q/E056K/S058M/N233Q/P256T, N011K/D027S/E056K/I090F/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, A018K/D027S/P029E/N033D/N073R/L075D/T189D, A018K/D111A/D130A/V154I/G156W/V187T/T189Q, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/L075Q/D130A/G156W/V187T/T189Q, A018K/K024A/L075Q/D130A/V154I/G156W/V187T, A018K/K024A/L075Q/V077I/N094R/D130A/G156W, D027E/S058M/D130A/D137Q/G163P/N233Q/L264R, D027Q/F051T/L075G/D130A/V187H/I252Q/L264R, |

TABLE 5-1-continued

| TLL variants with Performance Index >1 compared to TLL SEQ ID NO: 1 in the Detergent stability assay are shown below. |
|---|
| D027Q/F051T/L075Q/D130A/V187T/I252Q/L264R, |
| D027Q/F051T/L075Q/G091Q/D130A/V187T/I252Q, |
| D027Q/L075G/G091Q/D130A/V187H/I252Q/L264R, |
| D027S/F051T/L075G/G091Q/V187T/I252Q/L264R, |
| D027S/F051T/S058M/L075R/D130A/I252Q/L264R, |
| D027S/L075R/V154I/G156W/V187N/T189Q/L264R, |
| D048Q/S058M/D130A/D137Q/G163P/L227M/L264R, |
| D048Q/S058M/D130A/D137Q/L227M/N233Q/L264R, |
| D048Q/S058M/D137Q/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/G091Q/V187N/I252Q, |
| G023K/D027S/F051T/S058M/L075Q/D130A/V187N, |
| G023K/D027S/L075Q/N094R/V154I/G156W/T189Q, |
| G023K/F051T/L075Q/G091Q/D130A/V187H/I252Q, |
| G023K/K024A/L075Q/D111A/D130A/T189Q/L264R, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/K024A/N094R/V154I/G156W/V187N/T189Q, |
| G023K/L075Q/D111A/D130A/V154I/G156W/L264R, |
| G023K/L075Q/D111A/V154I/G156W/T189Q/L264R, |
| G023K/L075Q/D130A/G156W/V187N/T189Q/L264R, |
| G023K/L075Q/N094R/V154I/G156W/V187T/L264R, |
| G023K/L075R/N094R/V154I/G156W/V187N/L264R, |
| G023Q/D027S/L075Q/V154I/G156W/V187N/L264R, |
| G023Q/D027S/S058M/L075Q/D130A/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D111A/G156W/V187N/L264R, |
| G023Q/E056K/L075Q/D130A/V154I/G156W/T189Q, |
| G023Q/E056K/L075R/D111A/D130A/V187N/T189Q, |
| G023Q/F051T/G091Q/D130A/V187H/I252Q/L264R, |
| G023Q/F051T/L075Q/G091Q/V187H/I252Q/L264R, |
| G023Q/F051T/L075R/G091Q/V187N/I252Q/L264R, |
| G023Q/K024A/L075Q/V077I/D130A/G156W/V187N, |
| G023Q/K024A/L075Q/V077I/D130A/V154I/G156W, |
| G023Q/L075G/G091Q/D130A/V187T/I252Q/L264R, |
| G023Q/L075Q/D111A/D130A/V154I/G156W/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| G023Q/S058M/L075G/G091Q/D130A/I252Q/L264R, |
| K024A/L075Q/D111A/D130A/V154I/G156W/L264R, |
| K024A/L075Q/D111A/D130A/V187N/T189Q/L264R, |
| K024A/L075R/D130A/V154I/G156W/T189Q/L264R, |
| L075Q/D111A/D130A/G156W/V187N/T189Q/L264R, |
| N011K/D027N/E056K/S058M/I090F/N233Q/P256T, |
| N011K/D027S/D111A/D130A/V154I/V187N/T189Q, |
| N011K/E056K/L075Q/D111A/D130A/V154I/L264R, |
| N011K/E056K/L075Q/D130A/V154I/V187N/T189Q, |
| N011K/G023K/L075Q/D111A/D130A/V154I/V187N, |
| N011K/G023Q/L075Q/V154I/V187N/T189Q/L264R, |
| Q004D/N011K/D027Q/E056K/S058M/N233Q/P256T, |
| Q004D/N011K/D027S/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| A018K/K024A/L075Q/V077I/N094R/D130A/V154I/G156W, |
| D048Q/S058M/D130A/D137Q/G163P/L227M/N233Q/L264R, |
| F051T/E056K/L075G/G091Q/D130A/V187H/I252Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/E056K/L075Q/D130A/V154I/V187N/T189Q/L264R, |

TABLE 5-1-continued

| TLL variants with Performance Index >1 compared to TLL SEQ ID NO: 1 in the Detergent stability assay are shown below. |
|---|
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |
| G023K/L075Q/N094R/D130A/V154I/G156W/V187N/L264R, |
| G023Q/D027Q/F051T/S058M/L075R/D130A/V187T/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/D027S/L075R/N094R/V154I/G156W/V187N/T189Q, |
| G023Q/D027S/S058M/G091Q/D130A/V187H/I252Q/L264R, |
| G023Q/E056K/L075Q/D111A/V154I/V187N/T189Q/L264R, |
| G023Q/E056K/L075Q/N094R/D111A/G156W/T189Q/L264R, |
| G023Q/F051T/L075Q/G091Q/D130A/V187H/I252Q/L264R, |
| G023Q/F051T/L075R/G091Q/D130A/V187T/I252Q/L264R, |
| G023Q/K024A/L075Q/V077I/D130A/V154I/G156W/V187N, |
| G023Q/K024A/L075Q/V077I/N094R/D130A/V154I/V187N, |
| G023Q/L075Q/D111A/D130A/V154I/G156W/V187N/L264R, |
| G023Q/L075Q/N094R/D111A/D130A/G156W/T189Q/L264R, |
| G023Q/L075Q/V077I/N094R/D130A/V154I/G156W/V187Q, |
| G023Q/S058M/L075R/G091Q/D130A/V187H/I252Q/L264R, |
| N011K/G023K/D027S/L075R/V154I/G156W/V187N/T189Q, |
| N011K/G023K/E056K/L075Q/D130A/V154I/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075Q/N094R/D130A/V154I/G156W/V187N, |
| A018K/G023K/K024A/L075R/V077I/D130A/V154I/G156W/V187N, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |
| A018K/G023Q/K024A/L075R/N094R/D130A/V154I/G156W/V187N, |
| D027Q/F051T/S058M/L075G/G091Q/D130A/V187T/I252Q/L264R, |
| D027S/E056K/L075Q/N094R/D111A/D130A/V154I/G156W/L264R, |
| G023K/D027S/F051T/E056K/S058M/L075Q/G091Q/V187N/L264R, |
| G023K/D027S/F051T/E056K/S058M/L075R/G091Q/V187H/I252Q, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023K/L075Q/D111A/D130A/V154I/G156W/V187T/T189Q/L264R, |
| G023Q/D027S/F051T/E056K/L075G/G091Q/V187N/I252Q/L264R, |
| G023Q/D027S/L075Q/N094R/D130A/V154I/G156W/V187N/L264R, |
| G023Q/E056K/L075Q/D111A/D130A/V154I/G156W/T189Q/L264R, |
| G023Q/F051T/S058M/L075G/G091Q/D130A/V187T/I252Q/L264R, |
| N011K/G023K/D027S/E056K/L075R/D111A/G156W/V187N/L264R, |
| N011K/G023K/L075R/D111A/D130A/V154I/V187N/T189Q/L264R, |
| N011K/G023Q/L075Q/D111A/V154I/G156W/V187N/T189Q/L264R, |
| N011K/G023K/L075R/V077I/D130A/V154I/G156W/V187T/T189Q, |
| A018K/G023Q/D027S/E045F/A049V/N073S/L075Q/R108K/V187T/T189D, |
| A018K/G023Q/D027S/E045F/A049V/S058M/L075Q/R108K/V187T/T189D, |
| A018K/G023Q/D027S/E045F/A049V/S058M/N073S/L075Q/V187T/T189D, |
| A018K/G023Q/D027S/P029E/S058M/L075Q/V077I/H135F/G156W/V187T, |
| A018K/G023Q/D027S/P029E/S058M/L075Q/V077I/R108K/H135F/V187H, |
| A018K/G023Q/D027S/S058M/L075Q/V077I/R108K/H135F/G156W/V187H, |
| A018K/G023Q/K024A/L075Q/V077I/N094R/D130A/V154I/G156W/V187Q, |
| G023Q/D027S/F051T/E056K/L075R/G091Q/D130A/V187H/I252Q/L264R, |
| G023Q/D027S/F051T/E056K/S058M/L075R/G091Q/D130A/V187H/I252Q, |
| G023Q/L075R/N094R/D111A/D130A/V154I/G156W/V187N/T189Q/L264R, |
| N011K/A018K/G023K/K024A/L075R/V077I/D130A/V154I/V187T/T189Q, |
| N011K/G023Q/D027S/E056K/L075R/D130A/V154I/G156W/T189Q/L264R, |
| N011K/G023Q/E056K/L075R/D111A/D130A/V154I/G156W/V187N/L264R, |
| A018K/G023Q/D027S/E045F/A049V/S058M/N073S/L075Q/R108K/V187T/T189D, |
| A018K/G023Q/D027S/P029E/S058M/L075Q/V077I/R108K/H135F/G156W/V187T, |
| N011K/G023Q/D027S/L075Q/N094R/D111A/V154I/G156W/V187N/T189Q/L264R, |
| A018K/G023Q/D027S/P029E/E045F/A049V/S058M/N073S/L075Q/R108K/V187T/T189D, |
| A018K/G023Q/D027S/P029E/N033D/E045F/A049V/S058M/N073S/K074S/L075Q/V077I/N101D/R108K/H135F/D137V/G156W/V187T/T189D |

TABLE 5-2

TLL variants with Performance Index for expression ≥0.5 and Performance Index >1 in the Detergent stability assay compared to TLL SEQ ID NO: 1 are shown below.

D027E/G163P, D027S/N033D, D027S/P256T, D111A/L264R, D130A/V187N, K024A/V154I, N094R/G156W, P029E/N033D, A018K/A049V/V187T, A018K/E045F/V187T, A018K/K024A/V154I, A018K/N033D/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D111A/D130A/L264R, D130A/V154I/G156W, D130A/V187T/L264R, E056K/D130A/L264R, G023K/D130A/L264R, G023K/D130A/V187T, G023K/V187N/L264R, G023K/V187T/L264R, G023Q/A049V/T189D, G023Q/D130A/G156W, G023Q/K024A/G156W, I090F/N233Q/P256T, K024A/D130A/V154I, L075G/D130A/V187H, L075Q/V187N/L264R, L075R/D130A/V187T, N011K/N233Q/P256T, N094R/D130A/V187T, P029E/N033D/E045F, Q004D/D027S/P256T, Q004D/S058M/N233Q, V187N/T189Q/L264R, A018K/D027S/P029E/T189D, A018K/D111A/G156W/T189Q, A018K/D130A/G156W/V187T, A018K/E045F/A049V/G156W, A018K/G023K/D111A/T189Q, A018K/G023Q/A049V/V187T, A018K/G023Q/V077I/G156W, A018K/K024A/D130A/G156W, A018K/L075Q/V077I/N094R, A018K/N033D/L075D/T189D, D027E/D137Q/G163P/L227M, D027N/S058M/N233Q/P256T, D027Q/E056K/N233Q/P256T, D027S/D130A/I252Q/L264R, D027S/N033D/E045F/T189D, D027S/N033D/L075D/T189D, D027S/N033D/N073R/T189D, D027S/P029E/L075D/T189D, D027S/P029E/N033D/L075D, D111A/D130A/V154I/G156W, D111A/D130A/V187T/L264R, E045F/A049V/G156W/V187T, E045F/L075Q/G156W/V187T, E056K/D130A/V187T/L264R, G023K/D027Q/F051T/L075Q, G023K/D130A/G156W/T189Q, G023K/D130A/V187N/L264R, G023K/D130A/V187T/L264R, G023K/D130A/V187T/T189Q, G023K/K024A/V154I/V187N, G023K/L075R/D130A/L264R, G023K/L075R/V187T/L264R, G023Q/A049V/V077I/G156W, G023Q/F051T/I252Q/L264R, G023Q/G091Q/I252Q/L264R, G023Q/K024A/D130A/G156W, G023Q/K024A/L075R/G156W, G023Q/K024A/V077I/G156W, G023Q/L075Q/D130A/L264R, G023Q/L075Q/V187T/L264R, K024A/D130A/V154I/V187T, L075G/D130A/V187T/I252Q, N011K/D027Q/S058M/P256T, N011K/D027S/N233Q/P256T, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/D137Q/G163P/N233Q, S058M/L075Q/G091Q/I252Q, A018K/D027S/P029E/N033D/L075D, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/K024A/L075Q/G156W, A018K/K024A/L075R/D130A/V154I, A018K/K024A/N094R/G156W/V187T, D027E/S058M/D137Q/G163P/N233Q, D027S/E056K/D111A/V187N/L264R, D027S/F051T/V187N/I252Q/L264R, D027S/L075G/D130A/I252Q/L264R, D027S/L075G/G091Q/I252Q/L264R, D048Q/S058M/D130A/N233Q/L264R, D048Q/S058M/D137Q/G163P/N233E, D048Q/S058M/G163P/N233Q/L264R, D130A/V154I/G156W/V187N/T189Q, E045F/A049V/L075Q/V187T/T189D, E056K/L075R/D130A/V187T/L264R, F051T/L075G/G091Q/D130A/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, K024A/L075R/V154I/G156W/V187Q, N011K/D027N/S058M/N233Q/P256T, N011K/D027S/I090F/N233Q/P256T, N011K/G023K/D111A/G156W/L264R, Q004D/N011K/D027N/N233Q/P256T, S058M/G163P/L227M/N233Q/L264R, V077I/D130A/V154I/G156W/V187N, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027Q/E056K/S058M/D130A/I252Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D048Q/S058M/D130A/D137Q/G163P/L264R, D048Q/S058M/D137Q/G163P/L227M/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/K024A/V077I/D130A/V154I/G156W, G023Q/L075G/G091Q/D130A/I252Q/L264R, G023Q/L075Q/G091Q/V187N/I252Q/L264R, K024A/L075Q/D111A/V154I/V187N/T189Q,

TABLE 5-2-continued

| TLL variants with Performance Index for expression ≥0.5 and Performance Index >1 in the Detergent stability assay compared to TLL SEQ ID NO: 1 are shown below. |
|---|
| K024A/L075Q/N094R/D130A/V154I/L264R, K024A/L075Q/V077I/N094R/D130A/V187N, L075Q/G091Q/D130A/V187H/I252Q/L264R, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, A018K/D027S/P029E/N033D/N073R/L075D/T189D, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, A018K/K024A/L075Q/V077I/N094R/D130A/G156W, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, D048Q/S058M/D130A/D137Q/G163P/L227M/L264R, D048Q/S058M/D130A/D137Q/L227M/N233Q/L264R, D048Q/S058M/D137Q/G163P/L227M/N233Q/L264R, F051T/L075G/G091Q/D130A/V187N/I252Q/L264R, F051T/L075R/G091Q/D130A/V187T/I252Q/L264R, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/D027S/S058M/L075Q/D130A/I252Q/L264R, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, G023Q/L075G/G091Q/D130A/V187T/I252Q/L264R, G023Q/L075Q/V077I/N094R/D130A/G156W/V187N, G023Q/S058M/L075G/G091Q/D130A/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D048Q/S058M/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, G023Q/S058M/L075R/G091Q/D130A/V187H/I252Q/L264R, A018K/G023Q/D027S/P029E/L075Q/V077I/R108K/H135F/V187H, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075G/G091Q/D130A/V187T/I252Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 5-3

| TLL variants with Performance Index for expression ≥0.5 and Performance Index ≥50% of the maximum PI value in the Detergent stability assay compared to TLL SEQ ID NO: 1 are shown below. |
|---|
| D027S/P256T, K024A/V154I, A018K/A049V/V187T, A018K/K024A/V154I, A018K/V154I/G156W, D027N/S058M/P256T, D027S/S058M/P256T, G023Q/A049V/T189D, L075Q/V187N/L264R, N011K/N233Q/P256T, P029E/N033D/E045F, Q004D/D027S/P256T, A018K/D111A/G156W/T189Q, A018K/D130A/G156W/V187T, A018K/G023K/D111A/T189Q, A018K/G023Q/A049V/V187T, A018K/G023Q/V077I/G156W, D027N/S058M/N233Q/P256T, D027Q/E056K/N233Q/P256T, D027S/N033D/E045F/T189D, D111A/D130A/V154I/G156W, E045F/L075Q/G156W/V187T, G023K/D130A/G156W/T189Q, G023K/D130A/V187T/T189Q, G023K/K024A/V154I/V187N, |

TABLE 5-3-continued

| TLL variants with Performance Index for expression ≥0.5 and Performance Index ≥50% of the maximum PI value in the Detergent stability assay compared to TLL SEQ ID NO: 1 are shown below. |
|---|
| G023Q/A049V/V077I/G156W, G023Q/K024A/L075R/G156W, K024A/D130A/V154I/V187T, N011K/D027Q/S058M/P256T, N011K/D027S/N233Q/P256T, Q004D/D027N/E056K/P256T, Q004D/D027N/S058M/P256T, Q004D/D027Q/N233Q/P256T, Q004D/D027Q/S058M/P256T, Q004D/N011K/D027S/P256T, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/L075Q/G156W, D027S/E056K/D111A/V187N/L264R, D130A/V154I/G156W/V187N/T189Q, G023K/E056K/L075R/D130A/V187T, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/N094R/G156W/V187N/T189Q, G023Q/K024A/L075Q/G156W/V187Q, G023Q/L075Q/V077I/D130A/G156W, K024A/L075R/V154I/G156W/V187Q, N011K/D027N/S058M/N233Q/P256T, N011K/D027S/I090F/N233Q/P256T, N011K/G023K/D111A/G156W/L264R, Q004D/N011K/D027N/N233Q/P256T, S058M/G163P/L227M/N233Q/L264R, V077I/D130A/V154I/G156W/V187N, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, D048Q/S058M/D130A/D137Q/G163P/L264R, G023K/D130A/V154I/G156W/V187T/L264R, G023K/E056K/L075R/D130A/V187T/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/N094R/V154I/G156W/T189Q, G023Q/E056K/D111A/D130A/V187N/T189Q, G023Q/E056K/L075Q/D130A/V154I/L264R, G023Q/K024A/D130A/V154I/G156W/V187Q, G023Q/K024A/V077I/D130A/G156W/V187N, G023Q/K024A/V077I/D130A/V154I/G156W, K024A/L075Q/D111A/V154I/V187N/T189Q, K024A/L075Q/N094R/D130A/V154I/L264R, K024A/L075Q/V077I/N094R/D130A/V187N, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/K024A/L075Q/D130A/V154I/G156W/V187T, G023K/D027S/F051T/S058M/G091Q/V187N/I252Q, G023K/K024A/N094R/V154I/G156W/V187N/T189Q, G023Q/E056K/L075R/D111A/D130A/V187N/T189Q, G023Q/L075Q/V077I/N094R/D130A/G156W/V187N, N011K/D027N/E056K/S058M/I090F/N233Q/P256T, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, G023K/D027S/F051T/E056K/L075Q/G091Q/V187H/I252Q, G023Q/D027S/E056K/L075R/D111A/V154I/G156W/L264R, G023Q/D027S/L075R/N094R/V154I/G156W/V187N/T189Q, A018K/G023Q/D027S/P029E/L075Q/V077I/R108K/H135F/V187H, G023K/K024A/L075Q/N094R/V154I/G156W/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023Q/D027S/P029E/S058M/L075Q/V077I/R108K/H135F/G156W/V187T |

TABLE 5-4

| TLL variants with Performance Index >1 compared to Reference sequence SEQ ID NO: 2 in the Detergent stability assay are shown below. |
|---|
| A018K/D027S, A018K/L075D, A018K/L075Q, D027E/G163P, D027N/E056K, D027N/N233Q, D027S/N033D, D027S/P256T, D111A/L264R, D130A/L264R, G023K/D130A, G023Q/L075Q, K024A/L075Q, K024A/V154I, L075Q/D130A, L075Q/G156W, N073R/L075D, P029E/N033D, A018K/A049V/L075Q, A018K/A049V/V187T, A018K/D027S/N073R, A018K/D027S/T189D, A018K/E045F/T189D, A018K/G023K/G156W, A018K/G023K/L075Q, A018K/G023Q/L075Q, A018K/K024A/V154I, A018K/L075D/T189D, A018K/L075Q/G156W, A018K/L075Q/V187T, A018K/N033D/L075D, A018K/N033D/T189D, A018K/N073R/L075D, A018K/P029E/T189D, A018K/V154I/G156W, A049V/L075Q/T189D, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D130A/V187T/L264R, E045F/L075D/T189D, E045F/N073R/L075D, E056K/D130A/L264R, G023K/D130A/L264R, G023K/D130A/V187T, G023K/V187N/L264R, G023K/V187T/L264R, G023Q/A049V/T189D, G023Q/E056K/L075R, G023Q/L075Q/V187T, I090F/N233Q/P256T, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, |

TABLE 5-4-continued

| TLL variants with Performance Index >1 compared to Reference sequence SEQ ID NO: 2 in the Detergent stability assay are shown below. |
|---|
| L075Q/G156W/V187T, L075Q/V077I/T189D, L075Q/V154I/V187T, L075Q/V187N/L264R, L075Q/V187T/T189D, L075R/D130A/V187T, N011K/D027S/S058M, N011K/N233Q/P256T, N033D/E045F/L075D, N033D/N073R/T189D, N073R/L075D/T189D, N094R/D130A/V187T, P029E/E045F/L075D, P029E/L075D/T189D, P029E/N033D/E045F, P029E/N033D/L075D, P029E/N073R/L075D, Q004D/D027S/P256T, S058M/L227M/L264R, V077I/D130A/V154I, A018K/A049V/L075Q/T189D, A018K/D027S/L075D/T189D, A018K/D027S/N033D/L075D, A018K/D027S/P029E/T189D, A018K/D111A/G156W/T189Q, A018K/D130A/G156W/V187T, A018K/E045F/L075D/T189D, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/L075Q/G156W/T189D, A018K/L075Q/G156W/V187T, A018K/L075Q/N094R/D130A, A018K/N033D/L075D/T189D, A018K/N073R/L075D/T189D, A018K/P029E/N033D/L075D, A018K/P029E/N033D/T189D, A018K/V154I/G156W/V187T, A049V/L075Q/V077I/T189D, A049V/L075Q/V187T/T189D, D027E/D137Q/G163P/L227M, D027N/E056K/N233Q/P256T, D027N/E056K/S058M/P256T, D027N/S058M/N233Q/P256T, D027Q/E056K/N233Q/P256T, D027S/D130A/I252Q/L264R, D027S/E056K/D111A/V154I, D027S/E056K/I090F/P256T, D027S/N033D/E045F/T189D, D027S/N033D/L075D/T189D, D027S/N033D/N073R/L075D, D027S/N033D/N073R/T189D, D027S/P029E/E045F/L075D, D027S/P029E/L075D/T189D, D027S/P029E/N033D/L075D, D027S/P029E/N033D/N073R, D027S/P029E/N033D/T189D, D111A/D130A/V154I/G156W, D111A/D130A/V154I/L264R, E045F/L075Q/G156W/V187T, E056K/D130A/V187N/L264R, E056K/D130A/V187T/L264R, E056K/L075Q/V187N/L264R, F051T/L075Q/I252Q/L264R, G023K/D027Q/F051T/L075Q, G023K/D027S/L075Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187T/L264R, G023Q/A049V/L075Q/T189D, G023Q/A049V/V077I/G156W, G023Q/E045F/A049V/T189D, G023Q/E045F/L075Q/G156W, G023Q/E045F/L075Q/V187T, G023Q/F051T/I252Q/L264R, G023Q/G091Q/I252Q/L264R, G023Q/K024A/L075R/G156W, G023Q/K024A/L075R/V154I, G023Q/K024A/V077I/G156W, G023Q/L075Q/D130A/L264R, G023Q/L075Q/G156W/V187N, G023Q/L075Q/G156W/V187T, G023Q/L075Q/V187T/L264R, G023Q/V154I/G156W/V187N, K024A/D130A/V154I/V187T, K024A/L075Q/D130A/G156W, K024A/L075Q/D130A/V154I, K024A/L075Q/V187T/T189Q, K024A/L075R/G156W/V187N, L075G/D130A/V187T/I252Q, L075G/G091Q/V187N/L264R, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, N011K/D027N/E056K/S058M, N011K/D027Q/S058M/P256T, N011K/D027S/E056K/P256T, N011K/D027S/N233Q/P256T, N011K/D027S/S058M/N233Q, N011K/E056K/N233Q/P256T, N011K/G023K/L075Q/D111A, N011K/S058M/N233Q/P256T, P029E/E045F/L075D/T189D, P029E/E045F/N073R/L075D, P029E/N033D/E045F/L075D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/A049V/L075Q/V187T/T189D, A018K/D027S/N033D/L075D/T189D, A018K/D027S/N033D/N073R/T189D, A018K/D027S/P029E/E045F/T189D, A018K/D027S/P029E/N033D/L075D, A018K/D027S/P029E/N073R/L075D, A018K/E045F/A049V/L075Q/T189D, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V187T, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/G023Q/L075Q/V187T/T189D, A018K/G023Q/V077I/V187T/T189D, A018K/K024A/L075Q/V154I/G156W, A018K/K024A/L075Q/V154I/T189D, A018K/K024A/L075R/D130A/V154I, A018K/L075Q/D111A/D130A/V187T, A018K/L075Q/G156W/V187T/T189D, A018K/L075Q/V077I/N094R/G156W, A018K/V077I/G156W/V187T/T189D, D027E/D048Q/G163P/N233Q/L264R, D027E/D048Q/L227M/N233Q/L264R, D027E/G163P/L227M/N233Q/L264R, D027E/S058M/D137Q/G163P/N233Q, D027N/E056K/S058M/N233Q/P256T, D027Q/E056K/I090F/N233Q/P256T, D027Q/E056K/S058M/N233Q/P256T, D027S/E056K/D111A/V187N/L264R, D027S/E056K/S058M/N233Q/P256T, D027S/F051T/V187N/I252Q/L264R, D027S/L075G/D130A/I252Q/L264R, D027S/L075G/G091Q/I252Q/L264R, D027S/N033D/N073R/L075D/T189D, D027S/P029E/N033D/N073R/L075D, D027S/P029E/N073R/L075D/T189D, D048Q/D137Q/G163P/N233Q/L264R, D048Q/S058M/D130A/N233Q/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/N233Q/L264R, D130A/V154I/G156W/V187N/T189Q, E056K/D130A/V187H/I252Q/L264R, E056K/L075Q/G156W/T189Q/L264R, E056K/L075R/D130A/V187T/L264R, E056K/N094R/G156W/V187N/L264R, E056K/S058M/I090F/N233Q/P256T, F051T/L075G/D130A/I252Q/L264R, F051T/L075G/G091Q/D130A/L264R, F051T/L075Q/G091Q/D130A/L264R, F051T/L075Q/V187N/I252Q/L264R, F051T/S058M/L075Q/G091Q/I252Q, |

TABLE 5-4-continued

| TLL variants with Performance Index >1 compared to Reference sequence SEQ ID NO: 2 in the Detergent stability assay are shown below. |
|---|
| G023K/D027S/E056K/V187T/L264R, G023K/D111A/V154I/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/L075G/I252Q/L264R, G023Q/D027S/V154I/V187N/L264R, G023Q/E045F/A049V/G156W/T189D, G023Q/E045F/L075Q/G156W/T189D, G023Q/E045F/L075Q/V077I/V187T, G023Q/F051T/L075Q/G091Q/I252Q, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075Q/D111A/V187N/T189Q/L264R, L075Q/N094R/D130A/G156W/V187T, L075Q/V077I/D130A/G156W/V187N, L075Q/V154I/V187N/T189Q/L264R, L075R/D130A/V154I/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/K074S/L075D/T189D, P029E/N033D/N073R/L075D/T189D, Q004D/D027N/E056K/S058M/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/I090F/N233Q/P256T, S058M/D130A/D137Q/G163P/L264R, S058M/D130A/G163P/L227M/L264R, S058M/G163P/L227M/N233Q/L264R, V077I/D130A/V154I/G156W/V187N, A018K/A049V/L075Q/G156W/V187T/T189D, A018K/D027S/N033D/E045F/L075D/T189D, A018K/D027S/P029E/N033D/L075D/T189D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/E045F/G156W/V187T/T189D, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/L075Q/D111A/V154I/G156W/V187N, A018K/L075R/D130A/V154I/G156W/V187N, D027E/D048Q/S058M/D130A/G163P/L264R, D027E/S058M/D130A/G163P/N233Q/L264R, D027E/S058M/D130A/L227M/N233Q/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/G091Q/D130A/V187N/I252Q/L264R, D027S/L075Q/D111A/G156W/V187N/T189Q, D027S/L075Q/G091Q/V187H/I252Q/L264R, D027S/P029E/N033D/N073R/L075D/T189D, D048Q/D137Q/G163P/L227M/N233Q/L264R, D048Q/S058M/D130A/D137Q/G163P/L264R, D048Q/S058M/D130A/G163P/N233Q/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, D111A/D130A/V154I/G156W/V187N/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027S/F051T/L075Q/V187T/I252Q, G023Q/D027S/F051T/L075Q/V187T/L264R, G023Q/D027S/L075G/D130A/V187H/L264R, G023Q/D027S/L075Q/D130A/V187T/I252Q, |

TABLE 5-4-continued

| TLL variants with Performance Index >1 compared to Reference sequence SEQ ID NO: 2 in the Detergent stability assay are shown below. |
|---|
| G023Q/D027S/N094R/V154I/G156W/T189Q, G023Q/E045F/A049V/L075Q/G156W/V187T, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/D111A/V154I/T189Q/L264R, G023Q/L075Q/G091Q/V187N/I252Q/L264R, G023Q/L075Q/V077I/N094R/D130A/V187Q, G023Q/L075R/V154I/G156W/V187N/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/D027N/E056K/I090F/N233Q/P256T, N011K/D027N/E056K/S058M/N233Q/P256T, N011K/D027Q/E056K/S058M/N233Q/P256T, N011K/D027S/E056K/I090F/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/L075Q/V077I/N094R/V154I/G156W, A018K/G023Q/E045F/L075Q/G156W/V187T/T189D, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/K024A/L075Q/D130A/G156W/V187T/T189Q, A018K/K024A/L075Q/D130A/V154I/G156W/V187T, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/G163P/L227M/N233Q/L264R, D027E/S058M/D137Q/G163P/L227M/N233Q/L264R, D027Q/F051T/L075G/D130A/V187H/I252Q/L264R, D027Q/F051T/L075Q/D130A/V187T/I252Q/L264R, D027Q/F051T/L075Q/G091Q/D130A/V187T/I252Q, D027Q/L075G/G091Q/D130A/V187H/I252Q/L264R, D027S/F051T/L075G/G091Q/V187T/I252Q/L264R, D027S/F051T/S058M/L075R/D130A/I252Q/L264R, D027S/L075R/V154I/G156W/V187N/T189Q/L264R, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, E056K/L075Q/D111A/D130A/G156W/V187N/T189Q, F051T/L075G/G091Q/D130A/V187N/I252Q/L264R, F051T/L075R/G091Q/D130A/V187T/I252Q/L264R, G023K/D027Q/F051T/L075G/D130A/V187H/L264R, G023K/D027S/F051T/S058M/G091Q/V187N/I252Q, G023K/D027S/F051T/S058M/L075Q/D130A/V187N, G023K/D027S/L075Q/N094R/V154I/G156W/T189Q, G023K/F051T/L075Q/G091Q/D130A/V187H/I252Q, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/N094R/V154I/G156W/V187N, G023K/K024A/L075Q/V077I/D130A/G156W/V187Q, G023K/K024A/N094R/V154I/G156W/V187N/T189Q, G023K/L075Q/D111A/D130A/V154I/G156W/L264R, G023K/L075Q/D111A/V154I/G156W/T189Q/L264R, |

TABLE 5-4-continued

| TLL variants with Performance Index >1 compared to Reference sequence SEQ ID NO: 2 in the Detergent stability assay are shown below. |
|---|
| G023K/L075Q/D130A/G156W/V187N/T189Q/L264R, G023K/L075Q/N094R/V154I/G156W/V187T/L264R, G023K/L075R/N094R/V154I/G156W/V187N/L264R, G023Q/D027S/L075Q/V154I/G156W/V187N/L264R, G023Q/D027S/S058M/L075Q/D130A/I252Q/L264R, G023Q/E045F/L075Q/V077I/G156W/V187T/T189D, G023Q/E056K/L075Q/D111A/G156W/V187N/L264R, G023Q/E056K/L075Q/D130A/V154I/G156W/T189Q, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, G023Q/F051T/L075R/G091Q/V187N/I252Q/L264R, G023Q/K024A/L075Q/V077I/D130A/G156W/V187N, G023Q/K024A/L075Q/V077I/D130A/V154I/G156W, G023Q/L075G/G091Q/D130A/V187T/I252Q/L264R, G023Q/L075Q/D111A/D130A/V154I/G156W/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, G023Q/S058M/L075G/G091Q/D130A/I252Q/L264R, K024A/L075Q/D111A/D130A/V154I/G156W/L264R, K024A/L075R/D130A/V154I/G156W/T189Q/L264R, L075Q/D111A/D130A/G156W/V187N/T189Q/L264R, N011K/A018K/K024A/V077I/V154I/G156W/T189Q, N011K/D027N/E056K/S058M/I090F/N233Q/P256T, N011K/E056K/L075Q/D111A/D130A/V154I/L264R, N011K/E056K/L075Q/D130A/V154I/V187N/T189Q, N011K/G023K/L075Q/D111A/D130A/V154I/V187N, Q004D/N011K/D027Q/E056K/S058M/N233Q/P256T, Q004D/N011K/D027S/E056K/S058M/N233Q/P256T, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/L075Q/V077I/D130A/V154I/G156W/V187N, A018K/G023K/L075R/V077I/N094R/D130A/G156W/V187Q, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/L075Q/V077I/D130A/V154I/G156W/V187N, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/E056K/L075G/D130A/V187T/I252Q/L264R, G023K/D027S/F051T/E056K/L075Q/G091Q/V187H/I252Q, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/K024A/L075Q/N094R/V154I/G156W/V187T/L264R, G023K/K024A/L075R/N094R/V154I/G156W/V187T/T189Q, G023K/L075Q/D111A/V154I/G156W/V187N/T189Q/L264R, G023K/L075Q/N094R/D130A/V154I/G156W/V187N/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/L075R/N094R/V154I/G156W/V187N/T189Q, G023Q/D027S/S058M/G091Q/D130A/V187H/I252Q/L264R, G023Q/E056K/L075Q/N094R/D111A/G156W/T189Q/L264R, G023Q/F051T/L075Q/G091Q/D130A/V187H/I252Q/L264R, G023Q/F051T/L075R/G091Q/D130A/V187T/I252Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/V077I/N094R/D130A/V154I/G156W/V187Q, G023Q/S058M/L075R/G091Q/D130A/V187H/I252Q/L264R, N011K/G023K/D027S/L075R/V154I/G156W/V187N/T189Q, N011K/G023K/E056K/L075Q/D130A/V154I/T189Q/L264R, N011K/G023Q/D027S/L075Q/N094R/V154I/G156W/T189Q, N011K/G023Q/D027S/N094R/V154I/G156W/T189Q/L264R, N011K/G023Q/L075Q/N094R/V154I/G156W/T189Q/L264R, A018K/G023K/K024A/L075Q/N094R/D111A/D130A/V154I/T189Q, |

TABLE 5-4-continued

| TLL variants with Performance Index >1 compared to Reference sequence SEQ ID NO: 2 in the Detergent stability assay are shown below. |
|---|
| A018K/G023K/K024A/L075Q/N094R/D130A/V154I/G156W/V187N, A018K/G023K/K024A/L075R/V077I/D130A/V154I/G156W/V187N, A018K/G023K/K024A/V077I/D130A/V154I/G156W/V187T/T189Q, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, D027Q/F051T/S058M/L075G/G091Q/D130A/V187T/I252Q/L264R, D027S/E056K/L075Q/N094R/D111A/D130A/V154I/G156W/L264R, G023K/D027S/F051T/E056K/S058M/L075Q/G091Q/V187N/L264R, G023K/D027S/F051T/E056K/S058M/L075R/G091Q/V187H/I252Q, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/F051T/E056K/L075G/G091Q/V187N/I252Q/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, G023Q/F051T/S058M/L075Q/G091Q/D130A/V187H/I252Q/L264R, N011K/G023K/D027S/E056K/L075R/D111A/G156W/V187N/L264R, N011K/G023K/L075R/D111A/D130A/V154I/V187N/T189Q/L264R, N011K/G023Q/L075Q/D111A/V154I/G156W/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/S058M/L075Q/V077I/R108K/H135F/G156W/V187H, A018K/G023Q/K024A/L075Q/V077I/N094R/D130A/V154I/G156W/V187Q, G023Q/D027S/F051T/E056K/L075R/G091Q/D130A/V187H/I252Q/L264R, G023Q/D027S/F051T/E056K/S058M/L075R/G091Q/D130A/V187H/I252Q, N011K/A018K/G023K/K024A/L075R/V077I/D130A/V154I/V187T/T189Q, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023Q/D027S/P029E/S058M/L075Q/V077I/R108K/H135F/G156W/V187T, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D |

TABLE 5-5

| TLL variants with Performance Index for expression ≥0.5 compared to TLL SEQ ID NO: 1 and Performance Index >1 in the Detergent stability assay compared to Reference sequence SEQ ID NO: 2 are shown below. |
|---|
| A018K/L075D, D027E/G163P, D027S/N033D, D027S/P256T, D111A/L264R, D130A/L264R, K024A/V154I, P029E/N033D, A018K/A049V/V187T, A018K/K024A/V154I, A018K/L075D/T189D, A018K/N033D/T189D, A018K/P029E/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D130A/V187T/L264R, E056K/D130A/L264R, G023K/D130A/L264R, G023K/D130A/V187T, G023K/V187N/L264R, G023K/V187T/L264R, G023Q/A049V/T189D, I090F/N233Q/P256T, L075G/D130A/V187H, L075Q/V187N/L264R, L075R/D130A/V187T, N011K/N233Q/P256T, N094R/D130A/V187T, P029E/N033D/E045F, Q004D/D027S/P256T, A018K/D027S/P029E/T189D, A018K/D111A/G156W/T189Q, A018K/D130A/G156W/V187T, A018K/E045F/L075D/T189D, A018K/G023K/D111A/T189Q, A018K/G023Q/A049V/V187T, A018K/G023Q/V077I/G156W, A018K/N033D/L075D/T189D, D027E/D137Q/G163P/L227M, D027N/S058M/N233Q/P256T, D027Q/E056K/N233Q/P256T, D027S/D130A/I252Q/L264R, D027S/N033D/E045F/T189D, D027S/N033D/L075D/T189D, D027S/N033D/N073R/T189D, D027S/P029E/L075D/T189D, D027S/P029E/N033D/L075D, D111A/D130A/V154I/G156W, E045F/L075Q/G156W/V187T, E056K/D130A/V187N/L264R, E056K/D130A/V187T/L264R, F051T/L075Q/I252Q/L264R, G023K/D027Q/F051T/L075Q, G023K/D130A/G156W/T189Q, G023K/D130A/V187N/L264R, G023K/D130A/V187T/L264R, G023K/D130A/V187T/T189Q, G023K/K024A/V154I/V187N, G023K/L075R/D130A/L264R, G023K/L075R/V187T/L264R, G023Q/A049V/V077I/G156W, G023Q/F051T/I252Q/L264R, G023Q/G091Q/I252Q/L264R, G023Q/K024A/L075R/G156W, G023Q/K024A/V077I/G156W, G023Q/L075Q/D130A/L264R, G023Q/L075Q/V187T/L264R, K024A/D130A/V154I/V187T, L075G/D130A/V187T/I252Q, L075G/G091Q/V187N/L264R, N011K/D027Q/S058M/P256T, N011K/D027S/N233Q/P256T, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/D137Q/G163P/N233Q, S058M/G163P/L227M/L264R, S058M/G163P/N233Q/L264R, S058M/L075Q/G091Q/I252Q, S058M/L075Q/I252Q/L264R, A018K/D027S/P029E/N033D/L075D, A018K/G023K/D130A/V154I/G156W, A018K/G023K/K024A/D130A/G156W, A018K/G023K/K024A/D130A/V154I, A018K/G023K/V077I/D130A/V187N, |

TABLE 5-5-continued

| TLL variants with Performance Index for expression ≥0.5 compared to TLL SEQ ID NO: 1 and Performance Index >1 in the Detergent stability assay compared to Reference sequence SEQ ID NO: 2 are shown below. |
|---|
| A018K/G023Q/K024A/L075Q/G156W, A018K/K024A/L075R/D130A/V154I, D027E/D048Q/G163P/N233Q/L264R, D027E/G163P/L227M/N233Q/L264R, D027E/S058M/D137Q/G163P/N233Q, D027S/E056K/D111A/V187N/L264R, D027S/F051T/V187N/I252Q/L264R, D027S/L075G/D130A/I252Q/L264R, D027S/L075G/G091Q/I252Q/L264R, D048Q/D137Q/G163P/N233Q/L264R, D048Q/S058M/D130A/N233Q/L264R, D048Q/S058M/D137Q/G163P/N233E, D048Q/S058M/D137Q/N233Q/L264R, D048Q/S058M/G163P/L227M/L264R, D048Q/S058M/G163P/N233Q/L264R, D130A/D137Q/G163P/N233Q/L264R, D130A/V154I/G156W/V187N/T189Q, E056K/L075R/D130A/V187T/L264R, F051T/L075G/D130A/I252Q/L264R, F051T/L075G/G091Q/D130A/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187N/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/L075R/D130A/V187N/L264R, G023K/L075R/D130A/V187T/L264R, G023K/N094R/G156W/V187N/T189Q, G023Q/D027S/L075G/I252Q/L264R, G023Q/F051T/L075Q/G091Q/I252Q, G023Q/K024A/L075Q/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/D130A/G156W, K024A/L075R/V154I/G156W/V187Q, N011K/D027N/S058M/N233Q/P256T, N011K/D027S/I090F/N233Q/P256T, N011K/G023K/D111A/G156W/L264R, Q004D/N011K/D027N/N233Q/P256T, S058M/D130A/D137Q/G163P/L264R, S058M/D130A/G163P/L227M/L264R, S058M/G163P/L227M/N233Q/L264R, V077I/D130A/V154I/G156W/V187N, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, D027E/D048Q/S058M/D130A/G163P/L264R, D027E/S058M/D130A/G163P/N233Q/L264R, D027E/S058M/D130A/L227M/N233Q/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D048Q/D137Q/G163P/L227M/N233Q/L264R, D048Q/S058M/D130A/D137Q/G163P/L264R, D048Q/S058M/D130A/L227M/N233Q/L264R, D048Q/S058M/D137Q/G163P/L227M/L264R, D048Q/S058M/D137Q/G163P/N233Q/L264R, D048Q/S058M/G163P/L227M/N233Q/L264R, F051T/L075G/G091Q/D130A/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/K024A/V077I/D130A/V154I/G156W, G023Q/L075G/G091Q/D130A/I252Q/L264R, G023Q/L075Q/G091Q/V187N/I252Q/L264R, K024A/L075Q/D111A/V154I/V187N/T189Q, K024A/L075Q/N094R/D130A/V154I/L264R, K024A/L075Q/V077I/N094R/D130A/V187N, L075Q/G091Q/D130A/V187H/I252Q/L264R, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/K024A/L075Q/D130A/V154I/G156W/V187T, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, D048Q/D130A/D137Q/G163P/L227M/N233Q/L264R, |

TABLE 5-5-continued

| TLL variants with Performance Index for expression ≥0.5 compared to TLL SEQ ID NO: 1 and Performance Index >1 in the Detergent stability assay compared to Reference sequence SEQ ID NO: 2 are shown below. |
|---|
| D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, D048Q/S058M/D137Q/G163P/L227M/N233Q/L264R, F051T/L075G/G091Q/D130A/V187N/I252Q/L264R, F051T/L075R/G091Q/D130A/V187T/I252Q/L264R, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/D027S/S058M/L075Q/D130A/I252Q/L264R, G023Q/E056K/L075R/D111A/D130A/V187N/T189Q, G023Q/F051T/G091Q/D130A/V187H/I252Q/L264R, G023Q/F051T/L075Q/G091Q/V187H/I252Q/L264R, G023Q/L075G/G091Q/D130A/V187T/I252Q/L264R, G023Q/L075Q/V077I/N094R/D130A/G156W/V187N, G023Q/S058M/L075G/G091Q/D130A/I252Q/L264R, N011K/A018K/K024A/V077I/V154I/G156W/T189Q, N011K/D027N/E056K/S058M/I090F/N233Q/P256T, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, D027E/D048Q/D130A/D137Q/G163P/L227M/N233Q/L264R, D027E/D048Q/S058M/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, A018K/G023Q/D027S/P029E/L075Q/V077I/R108K/H135F/V187H, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075G/G091Q/D130A/V187T/I252Q/L264R, G023Q/F051T/S058M/L075Q/G091Q/D130A/V187H/I252Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023Q/D027S/P029E/S058M/L075Q/V077I/R108K/H135F/G156W/V187T |

TABLE 5-6

| TLL variants with Performance Index for expression ≥0.5 compared to TLL SEQ ID NO: 1 and Performance Index ≥50% of the maximum PI value in the Detergent stability assay compared to Reference sequence SEQ ID NO: 2 are shown below. |
|---|
| D027S/N033D, D027S/L075Q/G091Q, D027S/N033D/T189D, E056K/D130A/L264R, G023K/D130A/L264R, G023K/D130A/V187T, G023K/V187N/L264R, G023K/V187T/L264R, L075G/D130A/V187H, A018K/D027S/P029E/T189D, D027Q/E056K/N233Q/P256T, D027S/N033D/E045F/T189D, D027S/N033D/L075D/T189D, D027S/N033D/N073R/T189D, D027S/P029E/L075D/T189D, D027S/P029E/N033D/L075D, E056K/D130A/V187T/L264R, G023K/D027Q/F051T/L075Q, G023K/D130A/V187N/L264R, G023K/K024A/V154I/V187N, G023K/L075R/D130A/L264R, G023K/L075R/V187T/L264R, L075G/D130A/V187T/I252Q, P029E/N073R/L075D/T189D, Q004D/D027Q/N233Q/P256T, Q004D/N011K/D027S/P256T, A018K/D027S/P029E/N033D/L075D, A018K/G023K/D130A/V154I/G156W, D027S/L075G/D130A/I252Q/L264R, D027S/L075G/G091Q/I252Q/L264R, G023K/D027S/E056K/V187T/L264R, G023K/E056K/D130A/V187N/L264R, G023K/E056K/D130A/V187T/L264R, G023K/E056K/L075R/V187N/L264R, G023K/E056K/L075R/V187T/L264R, G023K/L075Q/V077I/D130A/G156W, G023K/L075Q/V187/I252Q/L264R, G023K/L075R/D130A/V187N/L264R, G023Q/F051T/L075Q/G091Q/I252Q, G023Q/L075G/G091Q/I252Q/L264R, G023Q/L075Q/G091Q/I252Q/L264R, A018K/G023K/L075Q/V077I/G156W/V187Q, D027Q/E056K/S058M/D130A/I252Q/L264R, D027Q/F051T/G091Q/D130A/I252Q/L264R, |

TABLE 5-6-continued

| TLL variants with Performance Index for expression ≥0.5 compared to TLL SEQ ID NO: 1 and Performance Index ≥50% of the maximum PI value in the Detergent stability assay compared to Reference sequence SEQ ID NO: 2 are shown below. |
|---|
| D027Q/F051T/L075G/G091Q/V187N/I252Q, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, F051T/L075G/G091Q/D130A/I252Q/L264R, F051T/L075G/G091Q/V187H/I252Q/L264R, G023K/D027S/L075R/D130A/V187T/I252Q, G023K/D027S/L075R/V187N/I252Q/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/V154I/G156W/V187Q, G023K/K024A/L075R/D130A/V154I/V187N, G023Q/D027S/F051T/L075Q/V187T/L264R, G023Q/D027S/L075G/D130A/V187H/L264R, G023Q/D027S/L075Q/D130A/V187T/I252Q, G023Q/E056K/L075Q/D130A/V154I/L264R, G023Q/F051T/L075G/G091Q/V187N/I252Q, G023Q/F051T/L075Q/D130A/V187H/I252Q, G023Q/L075G/G091Q/D130A/I252Q/L264R, N011K/D027S/E056K/I090F/N233Q/P256T, Q004D/N011K/D027S/S058M/N233Q/P256T, A018K/G023K/L075Q/V077I/N094R/V154I/G156W, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, F051T/L075R/G091Q/D130A/V187T/I252Q/L264R, G023K/D027S/F051T/S058M/L075Q/D130A/V187N, G023Q/D027S/S058M/L075Q/D130A/I252Q/L264R, G023Q/F051T/G091Q/D130A/V187H/I252Q/L264R, G023Q/S058M/L075G/G091Q/D130A/I252Q/L264R, N011K/A018K/K024A/V077I/V154I/G156W/T189Q, A018K/G023K/K024A/L075Q/V077I/D130A/V154I/G156W, A018K/G023K/K024A/L075Q/V077I/N094R/D130A/G156W, F051T/E056K/L075G/G091Q/D130A/V187H/I252Q/L264R, G023K/D027S/F051T/E056K/L075Q/G091Q/V187H/I252Q, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/S058M/L075R/G091Q/D130A/V187H/I252Q/L264R, A018K/G023K/K024A/V077I/D130A/V154I/G156W/V187T/T189Q, A018K/G023Q/D027S/P029E/L075Q/V077I/R108K/H135F/V187H, D027Q/F051T/S058M/L075G/G091Q/D130A/V187T/I252Q/L264R, N011K/G023K/L075R/V077I/D130A/V154I/G156W/V187T/T189Q, N011K/A018K/G023K/K024A/L075R/V077I/D130A/V154I/V187T/T189Q |

Example 6

LAS Stability of TLL Combinatorial Variants

The LAS-stability of TLL variants created as described in Example 2 was assayed as described in Example 1 (LAS-stability assay). The performance index was calculated for the variants compared to TLL, SEQ ID NO:1 or the reference sequence SEQ ID NO: 2.

TABLE 6-1

| TLL variants with Performance Index >1 compared to TLL SEQ ID NO: 1 in the LAS stability assay are shown below. |
|---|
| A018K/L075Q, A018K/T189D, D027E/G163P, D027N/E056K, D027N/N233Q, D027S/N033D, D027S/P256T, D111A/L264R, D130A/T189Q, D130A/V187N, D130A/V187T, G023K/D130A, G023Q/L075Q, K024A/L075Q, K024A/V154I, L075Q/D130A, L075Q/G156W, N011K/D027S, N073R/L075D, N094R/G156W, P029E/N033D, A018K/A049V/L075Q, A018K/A049V/V187T, A018K/D027S/E045F, A018K/D027S/N073R, A018K/D027S/T189D, A018K/E045F/T189D, A018K/E045F/V187T, A018K/G023K/G156W, A018K/G023K/L075Q, A018K/G023Q/L075Q, A018K/K024A/V154I, A018K/L075Q/G156W, A018K/L075Q/V187T, A018K/N033D/T189D, A018K/N073R/L075D, A018K/P029E/T189D, A018K/V154I/G156W, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D111A/D130A/L264R, D130A/V154I/G156W, E045F/L075D/T189D, E056K/D130A/L264R, G023K/D130A/V187T, G023K/V187N/L264R, G023K/V187T/L264R, G023Q/A049V/T189D, G023Q/D130A/G156W, G023Q/E056K/L075R, G023Q/K024A/G156W, G023Q/L075Q/V187T, I090F/N233Q/P256T, K024A/D130A/V154I, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/N094R/V154I, L075Q/V077I/T189D, L075Q/V154I/V187T, L075Q/V187N/L264R, L075Q/V187T/T189D, L075R/D130A/L264R, L075R/D130A/V187T, N011K/D027S/S058M, N011K/N233Q/P256T, N033D/E045F/L075D, N033D/N073R/T189D, N073R/L075D/T189D, N094R/D130A/V187T, P029E/L075D/T189D, P029E/N033D/E045F, P029E/N033D/L075D, |

TABLE 6-1-continued

| TLL variants with Performance Index >1 compared to TLL SEQ ID NO: 1 in the LAS stability assay are shown below. |
|---|
| P029E/N073R/L075D, Q004D/D027S/P256T, Q004D/S058M/N233Q, V077I/D130A/V154I, V077I/V187A/T189D, A018K/A049V/L075Q/T189D, A018K/D027S/N033D/L075D, A018K/D027S/P029E/T189D, A018K/D111A/G156W/T189Q, A018K/D130A/G156W/V187T, A018K/E045F/A049V/G156W, A018K/E045F/A049V/V187T, A018K/E045F/L075Q/T189D, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/G156W, A018K/G023Q/V077I/V187T, A018K/G023Q/V187T/T189D, A018K/K024A/D130A/G156W, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/L075D, A018K/P029E/N033D/T189D, A049V/L075Q/V077I/T189D, A049V/L075Q/V187T/T189D, D027N/E056K/N233Q/P256T, D027N/E056K/S058M/P256T, D027N/S058M/N233Q/P256T, D027Q/E056K/N233Q/P256T, D027S/E056K/D111A/V154I, D027S/E056K/I090F/P256T, D027S/N033D/E045F/T189D, D027S/N033D/L075D/T189D, D027S/N033D/N073R/L075D, D027S/N033D/N073R/T189D, D027S/P029E/E045F/L075D, D027S/P029E/L075D/T189D, D027S/P029E/N033D/L075D, D027S/P029E/N033D/N073R, D027S/P029E/N033D/T189D, D048Q/D137Q/G163P/L227M, D111A/D130A/V154I/G156W, D111A/D130A/V154I/L264R, D111A/D130A/V187T/L264R, E045F/L075Q/G156W/V187T, E056K/D130A/V187T/L264R, E056K/L075Q/V187N/L264R, F051T/D130A/I252Q/L264R, G023K/D027Q/F051T/L075Q, G023K/D027S/L075Q/L264R, G023K/D111A/D130A/L264R, G023K/D130A/G156W/T189Q, G023K/D130A/V187T/L264R, G023K/D130A/V187T/T189Q, G023K/E056K/L075R/L264R, G023K/K024A/V154I/V187N, G023K/L075Q/D130A/V187N, G023K/L075Q/G156W/L264R, G023K/L075Q/G156W/V187N, G023Q/A049V/L075Q/T189D, G023Q/A049V/L075Q/V077I, G023Q/A049V/V077I/G156W, G023Q/D027S/D111A/G156W, G023Q/E045F/A049V/T189D, G023Q/E045F/A049V/V187T, G023Q/E045F/L075Q/G156W, G023Q/E045F/L075Q/V187T, G023Q/K024A/D130A/G156W, G023Q/K024A/L075R/G156W, G023Q/K024A/L075R/V154I, G023Q/K024A/V077I/G156W, G023Q/L075Q/G156W/V187N, G023Q/L075Q/G156W/V187T, G023Q/V154I/G156W/V187N, K024A/D130A/V154I/V187T, K024A/L075Q/D130A/G156W, K024A/L075Q/D130A/V154I, K024A/L075Q/V187T/T189Q, K024A/L075R/G156W/V187N, L075G/D130A/V187T/I252Q, L075Q/D130A/G156W/V187N, L075Q/D130A/V154I/G156W, L075Q/G156W/V187T/L264R, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, N011K/D027N/E056K/S058M, N011K/D027N/S058M/P256T, N011K/D027Q/S058M/P256T, N011K/D027S/E056K/P256T, N011K/D027S/N233Q/P256T, N011K/E056K/N233Q/P256T, N011K/E056K/S058M/P256T, N011K/G023K/L075Q/D111A, N011K/S058M/N233Q/P256T, P029E/E045F/L075D/T189D, P029E/E045F/N073R/L075D, P029E/E045F/N073R/T189D, P029E/N033D/L075D/T189D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027Q/N233Q, Q004D/N011K/D027S/P256T, S058M/L075Q/G091Q/I252Q, A018K/A049V/L075Q/V187T/T189D, A018K/D027S/N033D/L075D/T189D, A018K/D027S/N033D/N073R/T189D, A018K/D027S/P029E/E045F/T189D, A018K/D027S/P029E/N033D/L075D, A018K/D027S/P029E/N073R/L075D, A018K/E045F/A049V/L075Q/G156W, A018K/G023K/D130A/V154I/G156W, A018K/G023K/K024A/D130A/G156W, A018K/G023K/K024A/D130A/V154I, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/V187T/T189D, A018K/K024A/L075Q/V154I/G156W, A018K/K024A/L075Q/V154I/T189D, A018K/K024A/L075R/D130A/V154I, A018K/K024A/N094R/D130A/V187N, A018K/K024A/N094R/G156W/V187T, A018K/L075Q/D111A/D130A/V187T, A018K/L075Q/G156W/V187T/T189D, A018K/L075Q/N094R/D130A/V187N, A018K/L075Q/N094R/G156W/V187N, A018K/L075Q/V077I/N094R/G156W, A018K/V077I/G156W/V187T/T189D, D027E/D048Q/D137Q/L227M/L264R, D027E/D048Q/G163P/N233Q/L264R, D027E/D048Q/S058M/G163P/N233Q, D027E/G163P/L227M/N233Q/L264R, D027E/S058M/D137Q/G163P/N233Q, D027N/E056K/S058M/N233Q/P256T, D027N/S058M/I090F/N233Q/P256T, D027Q/E056K/I090F/N233Q/P256T, D027Q/E056K/S058M/N233Q/P256T, D027S/E056K/D111A/V187N/L264R, D027S/E056K/S058M/N233Q/P256T, D027S/L075R/V154I/T189Q/L264R, D027S/N033D/N073R/L075D/T189D, D027S/P029E/E045F/N073R/T189D, D027S/P029E/N033D/N073R/L075D, D027S/P029E/N073R/L075D/T189D, D048Q/S058M/G163P/N233Q/L264R, D130A/G163P/L227M/N233Q/L264R, D130A/V154I/G156W/V187N/T189Q, E056K/D130A/V187H/I252Q/L264R, E056K/L075Q/G156W/T189Q/L264R, E056K/L075R/D130A/V187T/L264R, E056K/N094R/G156W/V187N/L264R, F051T/S058M/L075Q/G091Q/I252Q, G023K/D027S/E056K/V187T/L264R, G023K/D111A/V154I/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, |

TABLE 6-1-continued

| TLL variants with Performance Index >1 compared to TLL SEQ ID NO: 1 in the LAS stability assay are shown below. |
|---|
| G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187N/L264R, G023K/N094R/G156W/V187N/T189Q, G023Q/A049V/L075Q/G156W/V187T, G023Q/A049V/L075Q/V187T/T189D, G023Q/D027S/D111A/T189Q/L264R, G023Q/D027S/L075G/I252Q/L264R, G023Q/D027S/V154I/V187N/L264R, G023Q/E045F/A049V/G156W/T189D, G023Q/E045F/L075Q/G156W/T189D, G023Q/F051T/L075Q/G091Q/I252Q, G023Q/K024A/L075Q/D130A/G156W, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075Q/V077I/D130A/G156W, G023Q/L075Q/V077I/G156W/V187N, K024A/L075Q/D111A/G156W/V187T, K024A/L075Q/V077I/G156W/V187N, K024A/L075Q/V077I/V154I/V187N, K024A/L075R/D111A/V154I/V187T, K024A/L075R/G156W/V187N/T189Q, K024A/L075R/V154I/G156W/V187Q, L075Q/D111A/D130A/V187T/T189Q, L075Q/D111A/V187N/T189Q/L264R, L075Q/D130A/V187T/T189Q/L264R, L075Q/N094R/D130A/G156W/V187T, L075Q/V077I/D130A/G156W/V187N, L075Q/V154I/V187N/T189Q/L264R, L075R/D111A/D130A/V187N/T189Q, L075R/D130A/V154I/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/N233Q/P256T, N011K/D027S/E056K/N233Q/P256T, N011K/D027S/I090F/N233Q/P256T, N011K/G023K/D111A/G156W/L264R, N011K/G023K/E056K/L075Q/T189Q, N011K/G023Q/L075Q/V187N/T189Q, P029E/N033D/K074S/L075D/T189D, P029E/N033D/N073R/L075D/T189D, Q004D/D027N/E056K/S058M/P256T, Q004D/D027N/I090F/N233Q/P256T, Q004D/D027Q/E056K/N233Q/P256T, Q004D/D027Q/E056K/S058M/P256T, Q004D/D027S/E056K/N233Q/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, S058M/G163P/L227M/N233Q/L264R, V077I/D130A/V154I/G156W/V187N, A018K/A049V/L075Q/G156W/V187T/T189D, A018K/D027S/N033D/E045F/L075D/T189D, A018K/D027S/P029E/N033D/L075D/T189D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/G156W, A018K/G023Q/A049V/L075Q/V077I/V187T, A018K/G023Q/E045F/A049V/G156W/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/L075Q/D111A/V154I/G156W/V187N, A018K/L075R/D130A/V154I/G156W/V187N, A018K/N033D/E045F/N073R/L075D/T189D, A018K/N094R/D111A/D130A/V154I/V187N, D027E/D137Q/G163P/L227M/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D027S/G091Q/D130A/V187N/I252Q/L264R, D027S/L075Q/D111A/G156W/V187N/T189Q, D027S/P029E/N033D/N073R/L075D/T189D, D048Q/D130A/G163P/L227M/N233Q/L264R, D048Q/S058M/D130A/G163P/N233Q/L264R, D048Q/S058M/D137Q/G163P/L227M/L264R, D111A/D130A/V154I/G156W/V187N/L264R, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027S/F051T/L075Q/V187T/I252Q, G023Q/D027S/L075G/D130A/V187H/L264R, G023Q/D027S/L075Q/D111A/G156W/L264R, G023Q/D027S/L075R/D111A/V187N/L264R, G023Q/D027S/N094R/V154I/G156W/T189Q, G023Q/E045F/L075Q/V077I/G156W/V187T, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/G156W/V187N, |

TABLE 6-1-continued

| TLL variants with Performance Index >1 compared to TLL SEQ ID NO: 1 in the LAS stability assay are shown below. |
|---|
| G023Q/K024A/V077I/D130A/V154I/G156W, G023Q/L075Q/D111A/V154I/T189Q/L264R, G023Q/L075Q/G091Q/V187N/I252Q/L264R, G023Q/L075Q/V077I/N094R/D130A/V187Q, G023Q/L075R/V154I/G156W/V187N/L264R, K024A/D111A/D130A/V187T/T189Q/L264R, K024A/L075Q/D111A/V154I/V187N/T189Q, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/G156W/T189Q, L075Q/D111A/D130A/V154I/V187N/T189Q, L075R/D130A/V154I/G156W/V187N/L264R, N011K/D027N/E056K/I090F/N233Q/P256T, N011K/D027N/E056K/S058M/N233Q/P256T, N011K/D027N/S058M/I090F/N233Q/P256T, N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, A018K/D027S/P029E/N033D/N073R/L075D/T189D, A018K/D111A/D130A/V154I/G156W/V187T/T189Q, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/L075Q/D130A/G156W/V187T/T189Q, A018K/K024A/L075Q/D130A/V154I/G156W/V187T, D027Q/F051T/L075Q/G091Q/D130A/V187T/I252Q, D027Q/L075G/G091Q/D130A/V187H/I252Q/L264R, D027S/L075R/V154I/G156W/V187N/T189Q/L264R, E056K/L075Q/D111A/D130A/G156W/V187N/T189Q, G023K/D027Q/F051T/L075G/D130A/V187H/L264R, G023K/D027S/F051T/S058M/G091Q/V187N/I252Q, G023K/D027S/F051T/S058M/L075Q/D130A/V187N, G023K/D027S/L075Q/N094R/V154I/G156W/T189Q, G023K/F051T/E056K/L075R/D130A/V187T/I252Q, G023K/F051T/L075Q/G091Q/D130A/V187H/I252Q, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/N094R/V154I/G156W/V187N, G023K/K024A/L075Q/V077I/D130A/G156W/V187Q, G023K/K024A/N094R/V154I/G156W/V187N/T189Q, G023K/L075Q/D111A/D130A/V154I/G156W/L264R, G023K/L075Q/D111A/V154I/G156W/T189Q/L264R, G023K/L075Q/D130A/G156W/V187N/T189Q/L264R, G023K/L075Q/N094R/V154I/G156W/V187T/L264R, G023K/L075R/N094R/V154I/G156W/V187N/L264R, G023Q/D027S/L075Q/V154I/G156W/V187N/L264R, G023Q/D027S/S058M/L075Q/D130A/I252Q/L264R, G023Q/E045F/A049V/V077I/G156W/V187T/T189D, G023Q/E045F/L075Q/V077I/G156W/V187T/T189D, G023Q/E056K/L075Q/D111A/G156W/V187N/L264R, G023Q/E056K/L075Q/D130A/V154I/G156W/T189Q, G023Q/E056K/L075R/D111A/D130A/V187N/T189Q, G023Q/F051T/G091Q/D130A/V187H/I252Q/L264R, G023Q/K024A/L075Q/V077I/D130A/G156W/V187N, G023Q/K024A/L075Q/V077I/D130A/V154I/G156W, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, K024A/L075Q/D111A/D130A/V154I/G156W/L264R, K024A/L075Q/D111A/D130A/V187N/T189Q/L264R, K024A/L075R/D130A/V154I/G156W/T189Q/L264R, |

TABLE 6-1-continued

| TLL variants with Performance Index >1 compared to TLL SEQ ID NO: 1 in the LAS stability assay are shown below. |
|---|
| L075Q/D111A/D130A/G156W/V187N/T189Q/L264R, |
| N011K/D027N/E056K/S058M/I090F/N233Q/P256T, |
| N011K/E056K/L075Q/D111A/D130A/V154I/L264R, |
| N011K/E056K/L075Q/D130A/V154I/V187N/T189Q, |
| N011K/G023K/L075Q/D111A/D130A/V154I/V187N, |
| N011K/G023Q/L075Q/V154I/V187N/T189Q/L264R, |
| Q004D/D027N/E056K/S058M/I090F/N233Q/P256T, |
| Q004D/N011K/D027N/S058M/I090F/N233Q/P256T, |
| Q004D/N011K/D027Q/E056K/S058M/N233Q/P256T, |
| Q004D/N011K/D027Q/S058M/I090F/N233Q/P256T, |
| Q004D/N011K/D027S/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| F051T/E056K/L075G/G091Q/D130A/V187H/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/E056K/L075Q/D130A/V154I/V187N/T189Q/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |
| G023K/L075Q/N094R/D130A/V154I/G156W/V187N/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/D027S/L075R/N094R/V154I/G156W/V187N/T189Q, |
| G023Q/E056K/L075Q/D111A/V154I/V187N/T189Q/L264R, |
| G023Q/E056K/L075Q/N094R/D111A/G156W/T189Q/L264R, |
| G023Q/F051T/L075Q/G091Q/D130A/V187H/I252Q/L264R, |
| G023Q/K024A/L075Q/V077I/D130A/V154I/G156W/V187N, |
| G023Q/K024A/L075Q/V077I/N094R/D130A/V154I/V187N, |
| G023Q/L075Q/D111A/D130A/V154I/G156W/V187N/L264R, |
| G023Q/L075Q/N094R/D111A/D130A/G156W/T189Q/L264R, |
| G023Q/L075Q/V077I/N094R/D130A/V154I/G156W/V187Q, |
| N011K/G023K/D027S/L075Q/D111A/D130A/V154I/T189Q, |
| N011K/G023K/D027S/L075R/V154I/G156W/V187N/T189Q, |
| N011K/G023K/E056K/L075Q/D130A/V154I/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075R/V077I/D130A/V154I/G156W/V187N, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |
| A018K/G023Q/K024A/L075R/N094R/D130A/V154I/G156W/V187N, |
| D027Q/F051T/S058M/L075G/G091Q/D130A/V187T/I252Q/L264R, |
| D027S/E056K/L075Q/N094R/D111A/D130A/V154I/G156W/L264R, |
| D027S/E056K/L075Q/N094R/D111A/D130A/V187N/T189Q/L264R, |
| G023K/D027S/F051T/E056K/S058M/L075Q/G091Q/V187N/L264R, |
| G023K/D027S/F051T/E056K/S058M/L075R/G091Q/V187H/I252Q, |
| G023K/D027S/L075Q/D111A/D130A/V154I/G156W/T189Q/L264R, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023K/L075Q/D111A/D130A/V154I/G156W/V187T/T189Q/L264R, |
| G023Q/D027S/F051T/E056K/L075G/G091Q/V187N/I252Q/L264R, |
| G023Q/D027S/L075Q/N094R/D111A/D130A/V154I/G156W/L264R, |
| G023Q/D027S/L075Q/N094R/D130A/V154I/G156W/V187N/L264R, |
| G023Q/E056K/L075Q/D111A/D130A/V154I/G156W/T189Q/L264R, |
| G023Q/F051T/S058M/L075G/G091Q/D130A/V187T/I252Q/L264R, |
| N011K/G023K/D027S/E056K/L075R/D111A/G156W/V187N/L264R, |

TABLE 6-1-continued

| TLL variants with Performance Index >1 compared to TLL SEQ ID NO: 1 in the LAS stability assay are shown below. |
|---|
| N011K/G023K/L075R/D111A/D130A/V154I/V187N/T189Q/L264R, N011K/G023Q/L075Q/D111A/V154I/G156W/V187N/T189Q/L264R, N011K/G023K/L075R/V077I/D130A/V154I/G156W/V187T/T189Q, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/E045F/A049V/S058M/N073S/L075Q/V187T/T189D, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/S058M/L075Q/V077I/R108K/H135F/G156W/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023K/K024A/L075R/V077I/D130A/V154I/V187T/T189Q, N011K/G023K/L075R/N094R/D111A/V154I/G156W/V187N/T189Q/L264R, N011K/G023Q/D027S/E056K/L075R/D130A/V154I/G156W/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 6-2

| TLL variants with Performance Index for expression ≥0.5 and Performance Index >1 in the LAS stability assay compared to TLL SEQ ID NO: 1 are shown below. |
|---|
| D027E/G163P, D027S/N033D, D027S/P256T, D111A/L264R, D130A/V187N, D130A/V187T, K024A/V154I, N094R/G156W, P029E/N033D, A018K/A049V/V187T, A018K/E045F/V187T, A018K/K024A/V154I, A018K/N033D/T189D, A018K/P029E/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D111A/D130A/L264R, D130A/V154I/G156W, E056K/D130A/L264R, G023K/D130A/V187T, G023K/V187N/L264R, G023K/V187T/L264R, G023Q/A049V/T189D, G023Q/D130A/G156W, G023Q/K024A/G156W, I090F/N233Q/P256T, K024A/D130A/V154I, L075G/D130A/V187H, L075Q/V187N/L264R, L075R/D130A/L264R, L075R/D130A/V187T, N011K/N233Q/P256T, N094R/D130A/V187T, P029E/N033D/E045F, Q004D/D027S/P256T, Q004D/S058M/N233Q, A018K/D027S/P029E/T189D, A018K/D111A/G156W/T189Q, A018K/D130A/G156W/V187T, A018K/E045F/A049V/G156W, A018K/G023K/D111A/T189Q, A018K/G023Q/A049V/V187T, A018K/G023Q/V077I/G156W, A018K/K024A/D130A/G156W, A018K/L075Q/V077I/N094R, A018K/N033D/L075D/T189D, D027N/S058M/N233Q/P256T, D027Q/E056K/N233Q/P256T, D027S/N033D/E045F/T189D, D027S/N033D/L075D/T189D, D027S/N033D/N073R/T189D, D027S/P029E/L075D/T189D, D027S/P029E/N033D/L075D, D048Q/D137Q/G163P/L227M, D111A/D130A/V154I/G156W, D111A/D130A/V187T/L264R, E045F/L075Q/G156W/V187T, E056K/D130A/V187T/L264R, F051T/D130A/I252Q/L264R, G023K/D027Q/F051T/L075Q, G023K/D130A/G156W/T189Q, G023K/D130A/V187T/L264R, G023K/D130A/V187T/T189Q, G023K/E056K/L075R/L264R, G023K/K024A/V154I/V187N, G023Q/A049V/V077I/G156W, G023Q/K024A/D130A/G156W, G023Q/K024A/L075R/G156W, G023Q/K024A/V077I/G156W, K024A/D130A/V154I/V187T, L075G/D130A/V187T/I252Q, N011K/D027Q/S058M/P256T, N011K/D027S/N233Q/P256T, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/L075Q/G091Q/I252Q, A018K/D027S/P029E/N033D/L075D, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/K024A/L075Q/G156W, A018K/K024A/L075R/D130A/V154I, A018K/K024A/N094R/D130A/V187N, A018K/K024A/N094R/G156W/V187T, D027E/D048Q/D137Q/L227M/L264R, D027E/D048Q/G163P/N233Q/L264R, D027E/G163P/L227M/N233Q/L264R, D027E/S058M/D137Q/G163P/N233Q, D027S/E056K/D111A/V187N/L264R, D027S/L075R/V154I/T189Q/L264R, D048Q/S058M/G163P/N233Q/L264R, D130A/V154I/G156W/V187N/T189Q, E056K/L075R/D130A/V187T/L264R, F051T/S058M/L075Q/G091Q/I252Q, G023K/D027S/E056K/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075Q/V187H/I252Q/L264R, G023K/L075R/D130A/V187N/L264R, G023K/N094R/G156W/V187N/T189Q, G023Q/D027S/L075G/I252Q/L264R, G023Q/F051T/L075Q/G091Q/I252Q, G023Q/K024A/L075Q/G156W/V187Q, G023Q/L075Q/V077I/D130A/G156W, K024A/L075R/V154I/G156W/V187Q, N011K/D027N/S058M/N233Q/P256T, |

TABLE 6-2-continued

| TLL variants with Performance Index for expression ≥0.5 and Performance Index >1 in the LAS stability assay compared to TLL SEQ ID NO: 1 are shown below. |
|---|
| N011K/D027S/I090F/N233Q/P256T, N011K/G023K/D111A/G156W/L264R, Q004D/N011K/D027N/N233Q/P256T, S058M/G163P/L227M/N233Q/L264R, V077I/D130A/V154I/G156W/V187N, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, A018K/K024A/L075Q/V077I/D130A/V187N, A018K/N094R/D111A/D130A/V154I/V187N, D027E/D137Q/G163P/L227M/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D048Q/D130A/G163P/L227M/N233Q/L264R, D048Q/S058M/D137Q/G163P/L227M/L264R, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/L075G/D130A/V187H/L264R, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/K024A/V077I/D130A/V154I/G156W, G023Q/L075Q/G091Q/V187N/I252Q/L264R, K024A/L075Q/D111A/V154I/V187N/T189Q, K024A/L075Q/N094R/D130A/V154I/L264R, K024A/L075Q/V077I/N094R/D130A/V187N, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, A018K/D027S/P029E/N033D/N073R/L075D/T189D, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, D027Q/L075G/G091Q/D130A/V187H/I252Q/L264R, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/D027S/S058M/L075Q/D130A/I252Q/L264R, G023Q/E056K/L075R/D111A/D130A/V187N/T189Q, G023Q/F051T/G091Q/D130A/V187H/I252Q/L264R, G023Q/L075Q/V077I/N094R/D130A/G156W/V187N, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, F051T/E056K/L075G/G091Q/D130A/V187H/I252Q/L264R, G023K/D027S/F051T/E056K/L075Q/G091Q/V187H/I252Q, G023Q/D027S/E056K/L075R/D111A/V154I/G156W/L264R, G023Q/D027S/E056K/S058M/L075G/G091Q/V187T/L264R, G023Q/D027S/F051T/S058M/G091Q/D130A/V187N/I252Q, G023Q/D027S/L075R/N094R/V154I/G156W/V187N/T189Q, G023Q/F051T/L075Q/G091Q/D130A/V187H/I252Q/L264R, A018K/G023Q/D027S/P029E/L075Q/V077I/R108K/H135F/V187H, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075G/G091Q/D130A/V187T/I252Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 6-3

| TLL variants with Performance Index for expression ≥0.5 and Performance Index ≥50% of the maximum PI value in the LAS stability assay compared to TLL SEQ ID NO: 1 are shown below. |
|---|
| D027S/P256T, D130A/V187T, K024A/V154I, A018K/A049V/V187T, A018K/E045F/V187T, A018K/K024A/V154I, A018K/V154I/G156W, D027N/S058M/P256T, D027Q/S058M/P256T, D027S/L075Q/G091Q, D027S/N033D/T189D, D027S/S058M/P256T, D130A/V154I/G156W, G023K/D130A/V187T, G023K/V187T/L264R, G023Q/A049V/T189D, I090F/N233Q/P256T, K024A/D130A/V154I, L075Q/V187N/L264R, L075R/D130A/L264R, N011K/N233Q/P256T, N094R/D130A/V187T, Q004D/D027S/P256T, Q004D/S058M/N233Q, A018K/D027S/P029E/T189D, A018K/D111A/G156W/T189Q, A018K/D130A/G156W/V187T, A018K/G023K/D111A/T189Q, A018K/G023Q/A049V/V187T, A018K/G023Q/V077I/G156W, A018K/K024A/D130A/G156W, D027N/S058M/N233Q/P256T, D027Q/E056K/N233Q/P256T, D027S/N033D/E045F/T189D, D027S/N033D/L075D/T189D, D027S/N033D/N073R/T189D, D027S/P029E/L075D/T189D, D027S/P029E/N033D/L075D, D048Q/D137Q/G163P/L227M, D111A/D130A/V154I/G156W, E045F/L075Q/G156W/V187T, F051T/D130A/I252Q/L264R, G023K/D027Q/F051T/L075Q, G023K/D130A/G156W/T189Q, G023K/D130A/V187T/T189Q, G023K/E056K/L075R/L264R, G023K/K024A/V154I/V187N, G023Q/A049V/V077I/G156W, G023Q/K024A/D130A/G156W, G023Q/K024A/L075R/G156W, G023Q/K024A/V077I/G156W, K024A/D130A/V154I/V187T, N011K/D027Q/S058M/P256T, N011K/D027S/N233Q/P256T, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/L075Q/G091Q/I252Q, A018K/D027S/P029E/N033D/L075D, A018K/G023K/D130A/V154I/G156W, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/K024A/L075Q/G156W, A018K/K024A/L075R/D130A/V154I, A018K/K024A/N094R/G156W/V187T, D027E/D048Q/D137Q/L227M/L264R, D027E/G163P/L227M/N233Q/L264R, D027S/E056K/D111A/V187N/L264R, D027S/L075R/V154I/T189Q/L264R, D130A/V154I/G156W/V187N/T189Q, E056K/L075R/D130A/V187T/L264R, F051T/S058M/L075Q/G091Q/I252Q, G023K/D027S/E056K/V187T/L264R, G023K/E056K/L075R/D130A/V187T, G023K/E056K/L075R/V187N/L264R, G023K/E056K/L075R/V187T/L264R, G023K/K024A/D111A/D130A/V187T, G023K/K024A/D111A/G156W/T189Q, G023K/L075Q/V077I/D130A/G156W, G023K/L075R/D130A/V187N/L264R, G023K/N094R/G156W/V187N/T189Q, G023Q/D027S/L075G/I252Q/L264R, G023Q/F051T/L075Q/G091Q/I252Q, G023Q/K024A/L075Q/G156W/V187Q, G023Q/L075Q/V077I/D130A/G156W, K024A/L075R/V154I/G156W/V187Q, N011K/D027N/S058M/N233Q/P256T, N011K/D027S/I090F/N233Q/P256T, N011K/G023K/D111A/G156W/L264R, Q004D/N011K/D027N/N233Q/P256T, V077I/D130A/V154I/G156W/V187N, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, A018K/G023Q/K024A/V077I/V154I/V187N, A018K/G023Q/K024A/V154I/G156W/V187Q, A018K/G023Q/N094R/D130A/G156W/V187Q, A018K/K024A/L075Q/N094R/V154I/G156W, A018K/N094R/D111A/D130A/V154I/V187N, D027Q/E056K/S058M/D130A/I252Q/L264R, D027Q/F051T/L075G/G091Q/V187N/I252Q, D027S/E056K/S058M/V187T/I252Q/L264R, D048Q/D130A/G163P/L227M/N233Q/L264R, D048Q/S058M/D137Q/G163P/L227M/L264R, G023K/D027Q/F051T/E056K/S058M/L075Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/N094R/V154I/G156W/T189Q, G023Q/E056K/D111A/D130A/V187N/T189Q, G023Q/E056K/L075Q/D130A/V154I/L264R, G023Q/F051T/L075G/G091Q/V187N/I252Q, G023Q/K024A/D130A/V154I/G156W/V187Q, G023Q/K024A/V077I/D130A/G156W/V187N, G023Q/K024A/V077I/D130A/V154I/G156W, K024A/L075Q/D111A/V154I/V187N/T189Q, K024A/L075Q/N094R/D130A/V154I/L264R, K024A/L075Q/V077I/N094R/D130A/V187N, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, A018K/D111A/D130A/V154I/G156W/V187T/T189Q, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, G023K/D027S/F051T/S058M/G091Q/V187N/I252Q, G023K/D027S/F051T/S058M/L075Q/D130A/V187N, G023K/K024A/N094R/V154I/G156W/V187N/T189Q, G023Q/E056K/L075R/D111A/D130A/V187N/T189Q, G023Q/F051T/G091Q/D130A/V187H/I252Q/L264R, G023Q/L075Q/V077I/N094R/D130A/G156W/V187N, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, F051T/E056K/L075G/G091Q/D130A/V187H/I252Q/L264R, G023K/D027S/F051T/E056K/L075Q/G091Q/V187H/I252Q, G023Q/D027S/E056K/L075R/D111A/V154I/G156W/L264R, G023Q/D027S/F051T/S058M/G091Q/D130A/V187N/I252Q, |

TABLE 6-3-continued

| TLL variants with Performance Index for expression ≥0.5 and Performance Index ≥50% of the maximum PI value in the LAS stability assay compared to TLL SEQ ID NO: 1 are shown below. |
|---|
| G023Q/D027S/L075R/N094R/V154I/G156W/V187N/T189Q, A018K/G023Q/D027S/P029E/L075Q/V077I/R108K/H135F/V187H, G023K/K024A/L075Q/N094R/V154I/G156W/V187N/T189Q/L264R, G023Q/F051T/S058M/L075G/G091Q/D130A/V187T/I252Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 6-4

| TLL variants with Performance Index >1 compared to Reference sequence SEQ ID NO: 2 in the LAS stability assay are shown below. |
|---|
| D130A/V187T, N011K/D027S, A018K/D027S/N073R, D027N/N233Q/P256T, D027S/L075Q/G091Q, E045F/L075D/T189D, G023K/V187T/L264R, I090F/N233Q/P256T, N033D/E045F/L075D, N033D/N073R/T189D, Q004D/S058M/N233Q, A018K/L075Q/G156W/T189D, A018K/L075Q/V187T/T189D, A049V/L075Q/V077I/T189D, D027S/E056K/D111A/V154I, D027S/N033D/L075D/T189D, D027S/N033D/N073R/L075D, D027S/P029E/E045F/L075D, D027S/P029E/N033D/N073R, D048Q/D137Q/G163P/L227M, G023K/D027S/L075Q/L264R, G023K/E056K/L075R/L264R, G023Q/A049V/L075Q/V077I, G023Q/D027S/D111A/G156W, K024A/L075Q/D130A/V154I, N011K/D027Q/S058M/P256T, N011K/E056K/N233Q/P256T, N011K/G023K/L075Q/D111A, Q004D/D027N/S058M/P256T, Q004D/D027Q/N233Q/P256T, Q004D/N011K/D027N/P256T, Q004D/N011K/D027S/P256T, D027E/D048Q/D137Q/L227M/L264R, D027E/G163P/L227M/N233Q/L264R, D027N/S058M/I090F/N233Q/P256T, D027S/P029E/N033D/N073R/L075D, E056K/D130A/V187H/I252Q/L264R, E056K/L075R/D130A/V187T/L264R, G023K/D027S/E056K/V187T/L264R, G023K/E056K/L075R/V187N/L264R, G023K/E056K/L075R/V187T/L264R, G023K/K024A/D111A/D130A/V187T, G023Q/D027S/L075G/I252Q/L264R, G023Q/K024A/L075Q/D130A/G156W, L075R/D111A/D130A/V187N/T189Q, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/N233Q/P256T, N011K/D027S/E056K/N233Q/P256T, N011K/G023K/E056K/L075Q/T189Q, Q004D/D027S/E056K/N233Q/P256T, Q004D/N011K/D027Q/S058M/N233Q, A018K/D027S/P029E/N033D/L075D/T189D, A018K/G023K/D111A/D130A/V154I/T189Q, D027Q/E056K/S058M/D130A/I252Q/L264R, D027S/E056K/S058M/V187T/I252Q/L264R, D027S/G091Q/D130A/V187N/I252Q/L264R, D027S/L075Q/D111A/G156W/V187N/T189Q, D048Q/D130A/G163P/L227M/N233Q/L264R, G023K/D027S/L075R/V187N/I252Q/L264R, G023K/K024A/L075Q/D111A/D130A/T189Q, G023K/L075Q/V077I/D130A/G156W/V187Q, G023Q/D027S/F051T/L075Q/V187T/I252Q, G023Q/D027S/L075R/D111A/V187N/L264R, G023Q/E056K/D111A/D130A/V187N/T189Q, G023Q/E056K/L075Q/D130A/V154I/L264R, N011K/D027N/E056K/S058M/N233Q/P256T, N011K/D027Q/E056K/S058M/N233Q/P256T, N011K/D027Q/S058M/I090F/N233Q/P256T, N011K/D027S/E056K/S058M/N233Q/P256T, N011K/G023K/D027S/V154I/G156W/T189Q, N011K/G023Q/L075Q/D130A/V187N/T189Q, P029E/N033D/K074S/L075D/N101D/T189D, Q004D/D027S/E056K/S058M/N233Q/P256T, Q004D/N011K/D027N/I090F/N233Q/P256T, Q004D/N011K/D027S/S058M/N233Q/P256T, D027Q/F051T/L075Q/G091Q/D130A/V187T/I252Q, G023K/D027S/F051T/S058M/G091Q/V187N/I252Q, G023K/D027S/L075Q/N094R/V154I/G156W/T189Q, G023K/F051T/L075Q/G091Q/D130A/V187H/I252Q, G023K/L075Q/D111A/D130A/V154I/G156W/L264R, G023Q/L075Q/D130A/V154I/V187N/T189Q/L264R, N011K/E056K/L075Q/D130A/V154I/V187N/T189Q, N011K/G023K/L075Q/D111A/D130A/V154I/V187N, Q004D/N011K/D027N/S058M/I090F/N233Q/P256T, Q004D/N011K/D027Q/E056K/S058M/N233Q/P256T, F051T/E056K/L075G/G091Q/D130A/V187H/I252Q/L264R, G023K/D027S/F051T/E056K/L075Q/G091Q/V187H/I252Q, G023K/D027S/F051T/E056K/L075R/D130A/V187T/L264R, G023K/F051T/E056K/L075R/G091Q/D130A/V187T/L264R, G023Q/D027S/E056K/S058M/L075R/G091Q/V187N/I252Q, G023Q/D027S/F051T/S058M/G091Q/D130A/V187N/I252Q, N011K/G023K/D027S/L075Q/D111A/D130A/V154I/T189Q, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/S058M/V077I/R108K/H135F/G156W, A018K/G023Q/E045F/A049V/N073S/L075Q/R108K/V187T/T189D, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, |

TABLE 6-4-continued

| TLL variants with Performance Index >1 compared to Reference sequence SEQ ID NO: 2 in the LAS stability assay are shown below. |
|---|
| G023K/E056K/L075Q/D111A/D130A/V154I/G156W/T189Q/L264R, G023Q/D027S/F051T/E056K/L075G/G091Q/V187N/I252Q/L264R, G023Q/F051T/S058M/L075G/G091Q/D130A/V187T/I252Q/L264R, A018K/G023Q/D027S/E045F/A049V/S058M/N073S/L075Q/V187T/T189D, A018K/G023Q/D027S/S058M/L075Q/V077I/R108K/H135F/G156W/V187H, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/L075R/N094R/D111A/D130A/V154I/G156W/V187N/T189Q/L264R, N011K/A018K/G023K/K024A/L075R/V077I/D130A/V154I/V187T/T189Q, N011K/G023Q/D027S/E056K/L075R/D130A/V154I/G156W/T189Q/L264R |

TABLE 6-5

| TLL variants with Performance Index for expression ≥0.5 compared to TLL SEQ ID NO: 1 and Performance Index >1 in the Detergent stability assay compared to Reference sequence SEQ ID NO: 2 are shown below. |
|---|
| D130A/V187T, D027S/L075Q/G091Q, G023K/V187T/L264R, I090F/N233Q/P256T, Q004D/S058M/N233Q, D027S/N033D/L075D/T189D, D048Q/D137Q/G163P/L227M, G023K/E056K/L075R/L264R, N011K/D027Q/S058M/P256T, Q004D/D027N/S058M/P256T, Q004D/D027Q/N233Q/P256T, Q004D/N011K/D027S/P256T, D027E/D048Q/D137Q/L227M/L264R, D027E/G163P/L227M/N233Q/L264R, E056K/L075R/D130A/V187T/L264R, G023K/D027S/E056K/V187T/L264R, G023K/E056K/L075R/V187N/L264R, G023K/E056K/L075R/V187T/L264R, G023K/K024A/D111A/D130A/V187T, G023Q/D027S/L075G/I252Q/L264R, N011K/D027N/S058M/N233Q/P256T, D027Q/E056K/S058M/D130A/I252Q/L264R, D027S/E056K/S058M/V187T/I252Q/L264R, D048Q/D130A/G163P/L227M/N233Q/L264R, G023K/D027S/L075R/V187N/I252Q/L264R, G023K/K024A/L075Q/D111A/D130A/T189Q, G023Q/E056K/D111A/D130A/V187N/T189Q, G023Q/E056K/L075Q/D130A/V154I/L264R, Q004D/N011K/D027N/I090F/N233Q/P256T, Q004D/N011K/D027S/S058M/N233Q/P256T, G023K/D027S/F051T/S058M/G091Q/V187N/I252Q, F051T/E056K/L075G/G091Q/D130A/V187H/I252Q/L264R, G023K/D027S/F051T/E056K/L075Q/G091Q/V187H/I252Q, G023Q/D027S/F051T/S058M/G091Q/D130A/V187N/I252Q, G023Q/F051T/S058M/L075G/G091Q/D130A/V187T/I252Q/L264R, N011K/A018K/G023K/K024A/L075R/V077I/D130A/V154I/V187T/T189Q |

TABLE 6-6

| TLL variants with Performance Index for expression ≥0.5 compared to TLL SEQ ID NO: 1 and Performance Index ≥50% of the maximum PI value in the LAS stability assay compared to Reference sequence SEQ ID NO: 2 are shown below. |
|---|
| D130A/V187T, G023K/V187T/L264R, I090F/N233Q/P256T, Q004D/S058M/N233Q, D048Q/D137Q/G163P/L227M, G023K/E056K/L075R/L264R, Q004D/D027Q/N233Q/P256T, Q004D/N011K/D027S/P256T, D027E/D048Q/D137Q/L227M/L264R, D027E/G163P/L227M/N233Q/L264R, E056K/L075R/D130A/V187T/L264R, G023K/E056K/L075R/V187N/L264R, G023K/K024A/D111A/D130A/V187T, G023Q/D027S/L075G/I252Q/L264R, N011K/D027N/S058M/N233Q/P256T, D027Q/E056K/S058M/D130A/I252Q/L264R, D027S/E056K/S058M/V187T/I252Q/L264R, D048Q/D130A/G163P/L227M/N233Q/L264R, G023Q/E056K/L075Q/D130A/V154I/L264R, Q004D/N011K/D027S/S058M/N233Q/P256T, G023K/D027S/F051T/S058M/G091Q/V187N/I252Q, F051T/E056K/L075G/G091Q/D130A/V187H/I252Q/L264R, G023K/D027S/F051T/E056K/L075Q/G091Q/V187H/I252Q |

Example 7

Fabric Adhesion of TLL Combinatorial Variants

The adherence of the TLL variants created as described in Example 2 to cotton fabric in a detergent solution was assayed as described in Example 1(Adhesion Assay). The performance index for increased or decreased adhesion was calculated for the variants compared to TLL, SEQ ID NO:1 or the reference sequence SEQ ID NO: 2.

TABLE 7-1

| TLL variants with Performance Index >1 in the Fabric Adhesion assay compared to TLL SEQ ID NO: 1 are shown below. |
|---|
| A018K/L075Q, D111A/L264R, D130A/L264R, D130A/V187N, D130A/V187T, G023K/L264R, L075R/L264R, S058M/L264R, V187T/L264R, A018K/A049V/V187T, A018K/G023Q/L075Q, A018K/K024A/V154I, A018K/L075Q/G156W, A018K/N033D/T189D, A018K/P029E/T189D, D111A/D130A/L264R, D130A/V187N/L264R, D130A/V187T/L264R, F051T/I252Q/L264R, G023K/D130A/L264R, G023K/D130A/V187T, G023K/E056K/V187T, G023K/L075R/L264R, G023K/V187N/L264R, G023K/V187T/L264R, G023Q/A049V/T189D, G023Q/L075Q/V187T, G163P/L227M/L264R, K024A/L075Q/V077I, L075Q/G156W/T189D, L075Q/G156W/V187N, L075Q/G156W/V187T, L075Q/V154I/V187T, L075Q/V187N/L264R, L075Q/V187T/T189D, L075R/D130A/L264R, L075R/D130A/V187T, N073R/L075D/T189D, P029E/L075D/T189D, A018K/D027S/P029E/T189D, A018K/G023K/D111A/T189Q, A018K/G023Q/A049V/V187T, A018K/G023Q/L075Q/T189D, A018K/G023Q/L075Q/V187T, A018K/G023Q/L075R/D130A, A018K/K024A/D130A/G156W, D027E/D130A/N233Q/L264R, D027E/G163P/L227M/L264R, D027E/S058M/G163P/L264R, D027S/D130A/I252Q/L264R, D027S/N033D/E045F/T189D, D027S/P029E/L075D/T189D, D048Q/D130A/G163P/L264R, D048Q/G163P/N233Q/L264R, D111A/D130A/V154I/G156W, D111A/D130A/V187T/L264R, E056K/D130A/V187N/L264R, E056K/D130A/V187T/L264R, F051T/L075G/I252Q/L264R, F051T/L075Q/I252Q/L264R, G023K/D130A/V187N/L264R, G023K/D130A/V187T/L264R, G023K/D130A/V187T/T189Q, G023K/E056K/L075R/L264R, G023K/K024A/V154I/V187N, G023K/L075Q/D130A/V187N, G023K/L075R/V187T/L264R, G023Q/A049V/L075Q/T189D, G023Q/F051T/I252Q/L264R, G023Q/G091Q/I252Q/L264R, G023Q/L075Q/D130A/L264R, G023Q/L075Q/G156W/V187N, G023Q/L075Q/V187T/L264R, G091Q/V187T/I252Q/L264R, K024A/D130A/V154I/V187T, K024A/L075R/G156W/V187N, L075G/D130A/V187T/I252Q, L075G/V187H/I252Q/L264R, L075Q/D130A/G156W/V187N, L075Q/V077I/D130A/V187Q, L075Q/V077I/V154I/V187Q, L075R/D111A/V154I/G156W, L075R/D130A/V154I/L264R, P029E/N033D/L075D/T189D, S058M/G163P/L227M/L264R, S058M/G163P/N233Q/L264R, S058M/L075Q/G091Q/I252Q, S058M/L075Q/I252Q/L264R, A018K/D130A/G156W/V187N/L264R, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/L075Q/G156W/V187T, A018K/K024A/L075R/N094R/D130A, A018K/K024A/N094R/D130A/V187N, A018K/K024A/N094R/G156W/V187T, A018K/L075Q/D111A/D130A/V187T, D027E/D048Q/D137Q/L227M/L264R, D027E/D130A/G163P/L227M/L264R, D027E/D130A/G163P/N233Q/L264R, D027E/D137Q/G163P/N233Q/L264R, D027E/G163P/L227M/N233Q/L264R, D027E/S058M/D130A/G163P/L264R, D027E/S058M/G163P/L227M/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D027S/P029E/N073R/L075D/T189D, D048Q/D130A/G163P/L227M/L264R, D048Q/D137Q/G163P/L227M/L264R, D048Q/S058M/D137Q/N233Q/L264R, D130A/D137Q/G163P/L227M/L264R, D130A/D137Q/G163P/N233Q/L264R, D130A/V154I/G156W/V187N/T189Q, E056K/L075G/V187N/I252Q/L264R, E056K/L075Q/G156W/T189Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, F051T/L075R/V187N/I252Q/L264R, G023K/E056K/D130A/V187N/L264R, G023K/E056K/D130A/V187T/L264R, G023K/E056K/L075R/V187T/L264R, G023K/L075Q/D111A/D130A/V187T, G023K/L075Q/D130A/G156W/L264R, G023K/L075Q/V077I/D130A/G156W, G023K/L075R/D130A/V187N/L264R, G023K/L075R/D130A/V187T/L264R, G023Q/E056K/V187N/I252Q/L264R, G023Q/F051T/L075Q/G091Q/I252Q, G023Q/K024A/L075Q/G156W/V187N, G023Q/K024A/L075R/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/V154I/G156W/V187Q, L075G/D130A/V187T/I252Q/L264R, L075Q/D111A/V187N/T189Q/L264R, L075Q/V154I/V187N/T189Q/L264R, L075R/D130A/V154I/T189Q/L264R, L075R/D130A/V187T/T189Q/L264R, N011K/G023K/D111A/G156W/L264R, S058M/D130A/G163P/L227M/L264R, A018K/A049V/L075Q/G156W/V187T/T189D, A018K/G023K/K024A/L075R/D130A/V187N, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023Q/A049V/G156W/V187T/T189D, A018K/G023Q/K024A/V077I/V154I/V187N, A018K/G023Q/K024A/V154I/G156W/V187Q, A018K/G023Q/L075Q/G156W/V187T/T189D, A018K/G023Q/L075Q/V077I/D130A/V187N, A018K/G023Q/L075Q/V077I/G156W/V187N, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/G091Q/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, |

TABLE 7-1-continued

| TLL variants with Performance Index >1 in the Fabric Adhesion assay compared to TLL SEQ ID NO: 1 are shown below. |
|---|
| D027S/F051T/L075Q/D130A/I252Q/L264R, D027S/L075Q/G091Q/V187H/I252Q/L264R, D048Q/D137Q/G163P/L227M/N233Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, D111A/D130A/V154I/G156W/V187N/L264R, F051T/E056K/D130A/V187N/I252Q/L264R, F051T/E056K/L075Q/V187H/I252Q/L264R, F051T/L075G/G091Q/V187H/I252Q/L264R, F051T/L075G/G091Q/V187T/I252Q/L264R, F051T/L075R/D130A/V187N/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187T/L264R, G023K/F051T/D130A/V187N/I252Q/L264R, G023K/F051T/L075Q/D130A/I252Q/L264R, G023K/K024A/L075Q/V154I/G156W/V187Q, G023K/L075Q/D111A/D130A/V154I/V187N, G023K/L075Q/N094R/V154I/V187T/L264R, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D111A/V154I/V187N/T189Q, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/E056K/L075Q/D130A/V187N/T189Q, S058M/D130A/D137Q/G163P/L227M/L264R, S058M/D130A/D137Q/G163P/N233Q/L264R, S058M/D130A/G163P/L227M/N233Q/L264R, A018K/D111A/D130A/V154I/G156W/V187T/T189Q, A018K/G023K/K024A/L075Q/D130A/G156W/V187N, A018K/G023K/K024A/L075Q/N094R/G156W/V187Q, A018K/G023K/K024A/L075Q/V077I/N094R/G156W, A018K/G023K/K024A/N094R/V154I/V187T/L264R, A018K/G023Q/K024A/L075Q/V077I/N094R/V154I, A018K/G023Q/K024A/L075R/D130A/V154I/V187N, A018K/K024A/D130A/V154I/G156W/V187T/L264R, A018K/K024A/L075Q/D111A/G156W/V187N/L264R, A018K/K024A/L075Q/D130A/G156W/V187T/T189Q, A018K/K024A/L075Q/D130A/V154I/G156W/V187T, A018K/K024A/N094R/D130A/G156W/V187T/L264R, A018K/L075Q/D111A/V154I/V187T/T189Q/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075G/D130A/V187H/I252Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/L075G/G091Q/V187T/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027Q/F051T/L075G/D130A/V187H/L264R, G023K/D027S/F051T/S058M/L075Q/D130A/V187N, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/V077I/D130A/G156W/V187Q, G023K/L075R/N094R/V154I/G156W/V187N/L264R, G023Q/D027S/F051T/E056K/D130A/I252Q/L264R, G023Q/D027S/L075Q/G091Q/V187T/I252Q/L264R, G023Q/D027S/S058M/L075Q/D130A/I252Q/L264R, G023Q/E056K/L075Q/D111A/G156W/V187N/L264R, G023Q/E056K/L075R/D111A/D130A/V187N/T189Q, G023Q/F051T/L075Q/G091Q/V187H/I252Q/L264R, G023Q/F051T/L075R/G091Q/V187N/I252Q/L264R, G023Q/F051T/S058M/G091Q/D130A/I252Q/L264R, G023Q/K024A/L075Q/V077I/D130A/G156W/V187N, G023Q/L075G/G091Q/D130A/V187T/I252Q/L264R, G023Q/L075Q/D130A/V154I/G156W/T189Q/L264R, G023Q/L075Q/D130A/V154I/V187N/T189Q/L264R, |

TABLE 7-1-continued

| TLL variants with Performance Index >1 in the Fabric Adhesion assay compared to TLL SEQ ID NO: 1 are shown below. |
|---|
| G023Q/L075Q/V077I/N094R/D130A/G156W/V187N, G023Q/S058M/L075G/G091Q/D130A/I252Q/L264R, K024A/L075Q/D111A/D130A/V154I/G156W/L264R, L075Q/D111A/D130A/G156W/V187N/T189Q/L264R, N011K/A018K/K024A/V077I/V154I/G156W/T189Q, A018K/G023K/K024A/L075Q/D130Y/V154I/V187N/T189Q, A018K/G023K/K024A/L075R/D111A/V154I/V187T/L264R, A018K/G023Q/K024A/L075Q/V077I/D130A/G156W/V187Q, A018K/K024A/L075R/D130A/V154I/G156W/V187T/L264R, D027E/D048Q/D130A/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023K/D027S/E056K/L075G/D130A/V187T/I252Q/L264R, G023K/D027S/F051T/S058M/L075Q/V187H/I252Q/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/L075Q/N094R/D111A/D130A/G156W/T189Q/L264R, G023Q/S058M/L075R/G091Q/D130A/V187H/I252Q/L264R, K024A/D111A/D130A/V154I/G156W/V187T/T189Q/L264R, N011K/G023K/D027S/L075R/V154I/G156W/V187N/T189Q, A018K/G023K/K024A/L075Q/N094R/D130A/V187T/T189Q/L264K, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, D027Q/F051T/S058M/L075G/G091Q/D130A/V187T/I252Q/L264R, G023K/K024A/L075Q/N094R/V154I/G156W/V187N/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D130A/V154I/G156W/V187N/L264R, G023Q/F051T/S058M/L075Q/G091Q/D130A/V187H/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, N011K/A018K/G023K/K024A/L075R/V077I/D130A/V154I/V187T/T189Q, N011K/G023Q/E056K/L075R/D111A/D130A/V154I/G156W/V187N/L264R |

TABLE 7-2

| TLL variants with Performance Index for expression ≥0.5 and Performance Index >1 in the Fabric Adhesion assay compared to TLL SEQ ID NO: 1 are shown below. |
|---|
| D111A/L264R, D130A/L264R, D130A/V187N, D130A/V187T, G023K/L264R, L075R/L264R, S058M/L264R, V187T/L264R, A018K/A049V/V187T, A018K/K024A/V154I, A018K/N033D/T189D, A018K/P029E/T189D, D111A/D130A/L264R, D130A/V187N/L264R, D130A/V187T/L264R, F051T/I252Q/L264R, G023K/D130A/L264R, G023K/D130A/V187T, G023K/E056K/V187T, G023K/L075R/L264R, G023K/V187N/L264R, G023K/V187T/L264R, G023Q/A049V/T189D, G163P/L227M/L264R, L075Q/V187N/L264R, L075R/D130A/L264R, L075R/D130A/V187T, A018K/D027S/P029E/T189D, A018K/G023K/D111A/T189Q, A018K/G023Q/A049V/V187T, A018K/K024A/D130A/G156W, D027E/D130A/N233Q/L264R, D027E/G163P/L227M/L264R, D027E/S058M/G163P/L264R, D027S/D130A/I252Q/L264R, D027S/N033D/E045F/T189D, D027S/P029E/L075D/T189D, D048Q/D130A/G163P/L264R, D048Q/G163P/N233Q/L264R, D111A/D130A/V154I/G156W, D111A/D130A/V187T/L264R, E056K/D130A/V187N/L264R, E056K/D130A/V187T/L264R, F051T/L075G/I252Q/L264R, F051T/L075Q/I252Q/L264R, G023K/D130A/V187N/L264R, G023K/D130A/V187T/L264R, G023K/D130A/V187T/T189Q, G023K/E056K/L075R/L264R, G023K/K024A/V154I/V187N, G023K/L075R/V187T/L264R, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, S058M/G163P/L227M/L264R, S058M/G163P/N233Q/L264R, S058M/L075Q/G091Q/I252Q, S058M/L075Q/I252Q/L264R, A018K/D130A/G156W/V187N/L264R, A018K/G023K/K024A/D130A/G156W, A018K/G023K/K024A/D130A/V154I, A018K/G023K/V077I/D130A/V187N, A018K/G023Q/K024A/D130A/V187Q, A018K/K024A/N094R/D130A/V187N, A018K/K024A/N094R/G156W/V187T, D027E/D048Q/D137Q/L227M/L264R, D027E/D130A/G163P/L227M/L264R, D027E/D130A/G163P/N233Q/L264R, D027E/D137Q/G163P/N233Q/L264R, D027E/G163P/L227M/N233Q/L264R, D027E/S058M/D130A/G163P/L264R, D027E/S058M/G163P/L227M/L264R, |

TABLE 7-2-continued

| TLL variants with Performance Index for expression ≥0.5 and Performance Index >1 in the Fabric Adhesion assay compared to TLL SEQ ID NO: 1 are shown below. |
|---|
| D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/D130A/G163P/L227M/L264R, D048Q/D137Q/G163P/L227M/L264R, D048Q/S058M/D137Q/N233Q/L264R, D130A/D137Q/G163P/L227M/L264R, D130A/D137Q/G163P/N233Q/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/G091Q/D130A/L264R, F051T/L075Q/V187N/I252Q/L264R, G023K/E056K/D130A/V187N/L264R, G023K/E056K/D130A/V187T/L264R, G023K/E056K/L075R/V187T/L264R, G023K/L075Q/V077I/D130A/G156W, G023K/L075R/D130A/V187N/L264R, G023K/L075R/D130A/V187T/L264R, G023Q/E056K/V187N/I252Q/L264R, G023Q/F051T/L075Q/G091Q/I252Q, G023Q/L075G/G091Q/I252Q/L264R, G023Q/L075Q/D130A/I252Q/L264R, G023Q/L075Q/G091Q/I252Q/L264R, K024A/L075R/V154I/G156W/V187Q, L075G/D130A/V187T/I252Q/L264R, N011K/G023K/D111A/G156W/L264R, S058M/D130A/G163P/L227M/L264R, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/V077I/V154I/V187N, A018K/G023Q/K024A/V154I/G156W/V187Q, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/D137Q/G163P/L227M/N233Q/L264R, D048Q/S058M/D130A/G163P/L227M/L264R, D048Q/S058M/D130A/L227M/N233Q/L264R, D048Q/S058M/D137Q/G163P/L227M/L264R, D048Q/S058M/D137Q/G163P/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187T/L264R, G023K/F051T/D130A/V187N/I252Q/L264R, G023K/F051T/L075Q/D130A/I252Q/L264R, G023K/K024A/L075Q/V154I/G156W/V187Q, G023K/N094R/D111A/G156W/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/L227M/L264R, S058M/D130A/D137Q/G163P/N233Q/L264R, S058M/D130A/G163P/L227M/N233Q/L264R, A018K/D111A/D130A/V154I/G156W/V187T/T189Q, A018K/G023K/K024A/L075Q/N094R/G156W/V187Q, A018K/K024A/D130A/V154I/G156W/V187T/L264R, A018K/K024A/L075Q/D130A/V154I/G156W/V187T, A018K/K024A/N094R/D130A/G156W/V187T/L264R, D027E/D048Q/D130A/D137Q/G163P/N233Q/L264R, D027E/D048Q/D137Q/G163P/L227M/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/S058M/D130A/D137Q/G163P/L227M/L264R, D027E/S058M/D130A/G163P/L227M/N233Q/L264R, D027E/S058M/D137Q/G163P/L227M/N233Q/L264R, D027Q/F051T/L075Q/D130A/V187T/I252Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027S/F051T/S058M/L075Q/D130A/V187N, G023Q/D027S/F051T/E056K/D130A/I252Q/L264R, G023Q/D027S/S058M/L075Q/D130A/I252Q/L264R, G023Q/E056K/L075R/D111A/D130A/V187N/T189Q, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, |

TABLE 7-2-continued

| TLL variants with Performance Index for expression ≥0.5 and Performance Index >1 in the Fabric Adhesion assay compared to TLL SEQ ID NO: 1 are shown below. |
|---|
| G023Q/L075Q/V077I/N094R/D130A/G156W/V187N, G023Q/S058M/L075G/G091Q/D130A/I252Q/L264R, N011K/A018K/K024A/V077I/V154I/G156W/T189Q, D027E/D048Q/D130A/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023K/D027S/F051T/S058M/L075Q/V187H/I252Q/L264R, G023Q/D027Q/F051T/L075Q/G091Q/D130A/I252Q/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, A018K/G023K/K024A/V077I/D130A/V154I/G156W/V187T/T189Q, D027Q/F051T/S058M/L075G/G091Q/D130A/V187T/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023K/L075R/V077I/D130A/V154I/G156W/V187T/T189Q, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R |

TABLE 7-3

| TLL variants with Performance Index for expression ≥0.5 and Performance Index ≥50% of the maximum PI value in the Fabric Adhesion assay compared to TLL SEQ ID NO: 1 are shown below. |
|---|
| D111A/L264R, D130A/L264R, D130A/V187N, D130A/V187T, G023K/L264R, L075R/L264R, S058M/L264R, V187T/L264R, A018K/A049V/V187T, A018K/K024A/V154I, D111A/D130A/L264R, D130A/V187N/L264R, D130A/V187T/L264R, F051T/I252Q/L264R, G023K/D130A/L264R, G023K/E056K/V187T, G023K/L075R/L264R, G023K/V187T/L264R, L075Q/V187N/L264R, L075R/D130A/L264R, A018K/G023K/D111A/T189Q, D027E/D130A/N233Q/L264R, D027S/D130A/I252Q/L264R, D048Q/D130A/G163P/L264R, D111A/D130A/V187T/L264R, E056K/D130A/V187N/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/K024A/V154I/V187N, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, S058M/G163P/L227M/L264R, S058M/L075Q/I252Q/L264R, A018K/D130A/G156W/V187N/L264R, A018K/G023K/K024A/D130A/V154I, A018K/G023K/V077I/D130A/V187N, A018K/G023Q/K024A/D130A/V187Q, A018K/K024A/N094R/D130A/V187N, D027E/D048Q/D137Q/L227M/L264R, D027E/D130A/G163P/L227M/L264R, D027E/D130A/G163P/N233Q/L264R, D027E/G163P/L227M/N233Q/L264R, D027E/S058M/D130A/G163P/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/S058M/D137Q/N233Q/L264R, D130A/D137Q/G163P/L227M/L264R, D130A/D137Q/G163P/N233Q/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023K/E056K/D130A/V187T/L264R, G023K/L075R/D130A/V187N/L264R, G023Q/E056K/V187N/I252Q/L264R, G023Q/L075Q/D130A/I252Q/L264R, G023Q/L075Q/G091Q/I252Q/L264R, L075G/D130A/V187T/I252Q/L264R, A018K/G023K/K024A/V077I/G156W/V187Q, A018K/G023Q/A049V/G156W/V187T/T189D, A018K/G023Q/K024A/V077I/V154I/V187N, A018K/G023Q/N094R/D130A/G156W/V187Q, A018K/K024A/D111A/V187N/T189Q/L264R, A018K/K024A/L075Q/V077I/D130A/V187N, A018K/N094R/D111A/D130A/V154I/V187N, D027E/D048Q/D130A/D137H/G163P/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/F051T/D130A/V187N/I252Q/L264R, G023K/F051T/L075Q/D130A/I252Q/L264R, G023K/K024A/L075Q/V154I/G156W/V187Q, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, |

TABLE 7-3-continued

| TLL variants with Performance Index for expression ≥0.5 and Performance Index ≥50% of the maximum PI value in the Fabric Adhesion assay compared to TLL SEQ ID NO: 1 are shown below. |
|---|
| G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/N233Q/L264R, A018K/D111A/D130A/V154I/G156W/V187T/T189Q, A018K/K024A/D130A/V154I/G156W/V187T/L264R, A018K/K024A/N094R/D130A/G156W/V187T/L264R, D027E/D048Q/S058M/D130A/D137Q/G163P/L264R, D027E/D048Q/S058M/D130A/G163P/N233Q/L264R, D027E/S058M/D130A/G163P/L227M/N233Q/L264R, D027E/S058M/D137Q/G163P/L227M/N233Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023Q/D027S/F051T/E056K/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, D027E/S058M/D130A/D137Q/G163P/L227M/N233Q/L264R, G023K/D027S/F051T/S058M/L075Q/V187H/I252Q/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023Q/E056K/L075R/D111A/D130A/V154I/G156W/V187N/L264R |

TABLE 7-4

| TLL variants with Performance Index >1 in the Fabric Adhesion assay compared to Reference sequence SEQ ID NO: 2 are shown below. |
|---|
| D111A/L264R, D130A/L264R, D130A/V187N, D130A/V187T, G023K/L264R, L075R/L264R, S058M/L264R, V187T/L264R, A018K/A049V/V187T, A018K/K024A/V154I, A018K/N033D/T189D, D111A/D130A/L264R, D130A/V187N/L264R, D130A/V187T/L264R, F051T/I252Q/L264R, G023K/D130A/L264R, G023K/E056K/V187T, G023K/L075R/L264R, G023K/V187T/L264R, G023Q/L075Q/V187T, L075Q/G156W/V187N, L075Q/G156W/V187T, L075Q/V187N/L264R, L075R/D130A/L264R, A018K/D027S/P029E/T189D, A018K/G023K/D111A/T189Q, A018K/G023Q/L075Q/T189D, A018K/G023Q/L075Q/V187T, A018K/G023Q/L075R/D130A, D027E/D130A/N233Q/L264R, D027E/G163P/L227M/L264R, D027S/D130A/I252Q/L264R, D048Q/D130A/G163P/L264R, D111A/D130A/V154I/G156W, D111A/D130A/V187T/L264R, E056K/D130A/V187N/L264R, E056K/D130A/V187T/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/K024A/V154I/V187N, G023K/L075Q/D130A/V187N, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, K024A/L075R/G156W/V187N, L075G/D130A/V187T/I252Q, L075G/V187H/I252Q/L264R, L075Q/V077I/D130A/V187Q, P029E/N033D/L075D/T189D, S058M/G163P/L227M/L264R, S058M/L075Q/I252Q/L264R, A018K/D130A/G156W/V187N/L264R, A018K/G023K/K024A/D130A/G156W, A018K/G023K/K024A/D130A/V154I, A018K/G023K/V077I/D130A/V187N, A018K/G023Q/K024A/D130A/V187Q, A018K/G023Q/L075Q/G156W/V187T, A018K/K024A/N094R/D130A/V187N, A018K/L075Q/D111A/D130A/V187T, D027E/D048Q/D137Q/L227M/L264R, D027E/D130A/G163P/L227M/L264R, D027E/D130A/G163P/N233Q/L264R, D027E/G163P/L227M/N233Q/L264R, D027E/S058M/D130A/G163P/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D027S/P029E/N073R/L075D/T189D, D048Q/S058M/D137Q/N233Q/L264R, D130A/D137Q/G163P/L227M/L264R, D130A/D137Q/G163P/N233Q/L264R, D130A/V154I/G156W/V187N/T189Q, E056K/L075G/V187N/I252Q/L264R, E056K/L075Q/G156W/T189Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/V187N/I252Q/L264R, |

TABLE 7-4-continued

| TLL variants with Performance Index >1 in the Fabric Adhesion assay compared to Reference sequence SEQ ID NO: 2 are shown below. |
|---|
| G023K/E056K/D130A/V187N/L264R, G023K/E056K/D130A/V187T/L264R, G023K/L075Q/D130A/G156W/L264R, G023K/L075R/D130A/V187N/L264R, G023Q/E056K/V187N/I252Q/L264R, G023Q/K024A/L075Q/G156W/V187N, G023Q/K024A/L075R/G156W/V187Q, G023Q/L075G/G091Q/I252Q/L264R, G023Q/L075Q/D130A/I252Q/L264R, G023Q/L075Q/G091Q/I252Q/L264R, G023Q/L075Q/V077I/G156W/V187N, G091Q/D130A/V187H/I252Q/L264R, K024A/L075Q/D111A/G156W/V187T, L075G/D130A/V187T/I252Q/L264R, L075Q/D111A/V187N/T189Q/L264R, L075R/D130A/V154I/T189Q/L264R, L075R/D130A/V187T/T189Q/L264R, S058M/D130A/G163P/L227M/L264R, A018K/G023K/K024A/L075R/D130A/V187N, A018K/G023K/K024A/V077I/G156W/V187Q, A018K/G023K/L075Q/D130A/G156W/V187N, A018K/G023K/L075Q/G156W/V187N/L264R, A018K/G023Q/A049V/G156W/V187T/T189D, A018K/G023Q/K024A/V077I/V154I/V187N, A018K/G023Q/L075Q/G156W/V187T/T189D, A018K/G023Q/L075Q/V077I/G156W/V187N, A018K/G023Q/N094R/D130A/G156W/V187Q, A018K/K024A/D111A/V187N/T189Q/L264R, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/N094R/D111A/D130A/V154I/V187N, D027E/D048Q/D130A/D137H/G163P/L264R, D027E/D048Q/D137Q/G163P/L227M/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, F051T/E056K/D130A/V187N/I252Q/L264R, F051T/E056K/L075Q/V187H/I252Q/L264R, F051T/L075G/G091Q/V187H/I252Q/L264R, F051T/L075G/G091Q/V187T/I252Q/L264R, F051T/L075R/D130A/V187N/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/F051T/D130A/V187N/I252Q/L264R, G023K/F051T/L075Q/D130A/I252Q/L264R, G023K/K024A/L075Q/V154I/G156W/V187Q, G023K/L075Q/D111A/D130A/V154I/V187N, G023K/L075Q/N094R/V154I/V187T/L264R, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, G023Q/L075R/V154I/G156W/V187N/L264R, K024A/L075Q/D111A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/E056K/L075Q/D130A/V187N/T189Q, S058M/D130A/D137Q/G163P/L227M/L264R, S058M/D130A/D137Q/G163P/N233Q/L264R, A018K/D111A/D130A/V154I/G156W/V187T/T189Q, A018K/G023K/K024A/L075Q/D130A/G156W/V187N, A018K/G023K/K024A/N094R/V154I/V187T/L264R, A018K/G023Q/K024A/L075R/D130A/V154I/V187N, A018K/K024A/D130A/V154I/G156W/V187T/L264R, A018K/K024A/L075Q/D111A/G156W/V187N/L264R, A018K/K024A/L075Q/D130A/G156W/V187T/T189Q, A018K/K024A/N094R/D130A/G156W/V187T/L264R, A018K/L075Q/D111A/V154I/V187T/T189Q/L264R, D027E/D048Q/S058M/D130A/D137Q/G163P/L264R, D027E/D048Q/S058M/D130A/G163P/N233Q/L264R, D027E/D048Q/S058M/D137Q/G163P/L227M/L264R, D027E/S058M/D130A/G163P/L227M/N233Q/L264R, D027E/S058M/D137Q/G163P/L227M/N233Q/L264R, D027Q/F051T/L075G/D130A/V187H/I252Q/L264R, D027Q/F051T/S058M/L075Q/G091Q/I252Q/L264R, D027Q/L075G/G091Q/D130A/V187H/I252Q/L264R, D027S/F051T/L075G/G091Q/V187T/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027Q/F051T/L075G/D130A/V187H/L264R, G023K/K024A/L075Q/D111A/D130A/T189Q/L264R, G023K/K024A/L075Q/D111A/V154I/G156W/V187N, G023K/K024A/L075Q/D130A/V187T/T189Q/L264R, G023K/K024A/L075Q/V077I/D130A/G156W/V187Q, G023Q/D027S/F051T/E056K/D130A/I252Q/L264R, G023Q/D027S/L075Q/G091Q/V187T/I252Q/L264R, G023Q/E056K/L075Q/D111A/G156W/V187N/L264R, G023Q/F051T/L075Q/G091Q/V187H/I252Q/L264R, G023Q/F051T/L075R/G091Q/V187N/I252Q/L264R, G023Q/F051T/S058M/G091Q/D130A/I252Q/L264R, G023Q/L075G/G091Q/D130A/V187T/I252Q/L264R, |

TABLE 7-4-continued

| TLL variants with Performance Index >1 in the Fabric Adhesion assay compared to Reference sequence SEQ ID NO: 2 are shown below. |
|---|
| G023Q/L075Q/D130A/V154I/G156W/T189Q/L264R, |
| G023Q/S058M/L075G/G091Q/D130A/I252Q/L264R, |
| K024A/L075Q/D111A/D130A/V154I/G156W/L264R, |
| L075Q/D111A/D130A/G156W/V187N/T189Q/L264R, |
| A018K/G023K/K024A/L075Q/D130Y/V154I/V187N/T189Q, |
| A018K/G023K/K024A/L075R/D111A/V154I/V187T/L264R, |
| A018K/G023Q/K024A/L075Q/V077I/D130A/G156W/V187Q, |
| A018K/K024A/L075R/D130A/V154I/G156W/V187T/L264R, |
| D027E/S058M/D130A/D137Q/G163P/L227M/N233Q/L264R, |
| G023K/D027S/E056K/L075G/D130A/V187T/I252Q/L264R, |
| G023K/D027S/F051T/S058M/L075Q/V187H/I252Q/L264R, |
| G023Q/D027S/E056K/L075R/D111A/V154I/G156W/L264R, |
| G023Q/D027S/E056K/S058M/L075G/G091Q/V187T/L264R, |
| G023Q/D027S/S058M/G091Q/D130A/V187H/I252Q/L264R, |
| G023Q/F051T/L075Q/G091Q/D130A/V187H/I252Q/L264R, |
| G023Q/F051T/L075Q/G091Q/D130A/V187T/I252Q/L264R, |
| G023Q/F051T/L075R/G091Q/D130A/V187T/I252Q/L264R, |
| G023Q/L075Q/N094R/D111A/D130A/G156W/T189Q/L264R, |
| G023Q/S058M/L075R/G091Q/D130A/V187H/I252Q/L264R, |
| K024A/D111A/D130A/V154I/G156W/V187T/T189Q/L264R, |
| N011K/G023K/D027S/L075R/V154I/G156W/V187N/T189Q, |
| A018K/G023K/K024A/L075R/V077I/D130A/V154I/G156W/V187N, |
| G023K/K024A/L075Q/N094R/V154I/G156W/V187N/T189Q/L264R, |
| G023Q/D027S/L075Q/N094R/D130A/V154I/G156W/V187N/L264R, |
| G023Q/F051T/S058M/L075Q/G091Q/D130A/V187H/I252Q/L264R, |
| N011K/G023K/L075R/D111A/D130A/V154I/V187N/T189Q/L264R, |
| N011K/G023Q/E056K/L075R/D111A/D130A/V154I/G156W/V187N/L264R |

TABLE 7-5

| TLL variants with Performance Index for expression ≥0.5 compared to TLL SEQ ID NO: 1 and Performance Index >1 in the Fabric Adhesion assay compared to Reference sequence SEQ ID NO: 2 are shown below. |
|---|
| D111A/L264R, D130A/L264R, D130A/V187N, D130A/V187T, G023K/L264R, L075R/L264R, S058M/L264R, V187T/L264R, A018K/A049V/V187T, A018K/K024A/V154I, A018K/N033D/T189D, D111A/D130A/L264R, D130A/V187N/L264R, D130A/V187T/L264R, F051T/I252Q/L264R, G023K/D130A/L264R, G023K/E056K/V187T, G023K/L075R/L264R, G023K/V187T/L264R, L075Q/V187N/L264R, L075R/D130A/L264R, A018K/D027S/P029E/T189D, A018K/G023K/D111A/T189Q, D027E/D130A/N233Q/L264R, D027E/G163P/L227M/L264R, D027S/D130A/I252Q/L264R, D048Q/D130A/G163P/L264R, D111A/D130A/V154I/G156W, D111A/D130A/V187T/L264R, E056K/D130A/V187N/L264R, E056K/D130A/V187T/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/K024A/V154I/V187N, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, L075G/V187H/I252Q/L264R, S058M/G163P/L227M/L264R, S058M/L075Q/I252Q/L264R, A018K/D130A/G156W/V187N/L264R, A018K/G023K/K024A/D130A/G156W, A018K/G023K/K024A/D130A/V154I, A018K/G023K/V077I/D130A/V187N, A018K/G023Q/K024A/D130A/V187Q, A018K/K024A/N094R/D130A/V187N, D027E/D048Q/D137Q/L227M/L264R, D027E/D130A/G163P/L227M/L264R, D027E/D130A/G163P/N233Q/L264R, D027E/G163P/L227M/N233Q/L264R, D027E/S058M/D130A/G163P/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/S058M/D137Q/N233Q/L264R, D130A/D137Q/G163P/L227M/L264R, D130A/D137Q/G163P/N233Q/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/G091Q/D130A/L264R, F051T/L075G/V187N/I252Q/L264R, F051T/L075Q/V187N/I252Q/L264R, G023K/E056K/D130A/V187N/L264R, G023K/E056K/D130A/V187T/L264R, G023K/L075R/D130A/V187N/L264R, G023Q/E056K/V187N/I252Q/L264R, G023Q/L075G/G091Q/I252Q/L264R, G023Q/L075Q/D130A/I252Q/L264R, G023Q/L075Q/G091Q/I252Q/L264R, L075G/D130A/V187T/I252Q/L264R, S058M/D130A/G163P/L227M/L264R, A018K/G023K/K024A/V077I/G156W/V187Q, A018K/G023Q/A049V/G156W/V187T/T189D, A018K/G023Q/K024A/V077I/V154I/V187N, A018K/G023Q/N094R/D130A/G156W/V187Q, A018K/K024A/D111A/V187N/T189Q/L264R, A018K/K024A/L075Q/V077I/D130A/V187N, A018K/N094R/D111A/D130A/V154I/V187N, D027E/D048Q/D130A/D137H/G163P/L264R, D027E/D048Q/D137Q/G163P/L227M/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/L075Q/D130A/V187T/I252Q/L264R, D027Q/S058M/L075R/D130A/V187T/I252Q, D027S/F051T/L075Q/D130A/I252Q/L264R, |

TABLE 7-5-continued

| TLL variants with Performance Index for expression ≥0.5 compared to TLL SEQ ID NO: 1 and Performance Index >1 in the Fabric Adhesion assay compared to Reference sequence SEQ ID NO: 2 are shown below. |
|---|
| D027S/L075Q/G091Q/V187H/I252Q/L264R, D048Q/S058M/D130A/G163P/L227M/L264R, D048Q/S058M/D130A/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/F051T/D130A/V187N/I252Q/L264R, G023K/F051T/L075Q/D130A/I252Q/L264R, G023K/K024A/L075Q/V154I/G156W/V187Q, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/L227M/L264R, S058M/D130A/D137Q/G163P/N233Q/L264R, A018K/D111A/D130A/V154I/G156W/V187T/T189Q, A018K/K024A/D130A/V154I/G156W/V187T/L264R, A018K/K024A/N094R/D130A/G156W/V187T/L264R, D027E/D048Q/S058M/D130A/D137Q/G163P/L264R, D027E/D048Q/S058M/D130A/G163P/N233Q/L264R, D027E/D048Q/S058M/D137Q/G163P/L227M/L264R, D027E/S058M/D130A/G163P/L227M/N233Q/L264R, D027E/S058M/D137Q/G163P/L227M/N233Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023Q/D027S/F051T/E056K/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, D027E/S058M/D130A/D137Q/G163P/L227M/N233Q/L264R, G023K/D027S/F051T/S058M/L075Q/V187H/I252Q/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023Q/E056K/L075R/D111A/D130A/V154I/G156W/V187N/L264R |

TABLE 7-6

| TLL variants with Performance Index for expression ≥0.5 compared to TLL SEQ ID NO: 1 and Performance Index ≥50% of the maximum PI value in the Fabric Adhesion assay compared to Reference sequence SEQ ID NO: 2 are shown below. |
|---|
| D111A/L264R, D130A/L264R, D130A/V187N, D130A/V187T, G023K/L264R, L075R/L264R, S058M/L264R, V187T/L264R, A018K/A049V/V187T, A018K/K024A/V154I, D111A/D130A/L264R, D130A/V187N/L264R, D130A/V187T/L264R, F051T/I252Q/L264R, G023K/D130A/L264R, G023K/E056K/V187T, G023K/L075R/L264R, G023K/V187T/L264R, L075Q/V187N/L264R, L075R/D130A/L264R, A018K/G023K/D111A/T189Q, D027E/D130A/N233Q/L264R, D027S/D130A/I252Q/L264R, D048Q/D130A/G163P/L264R, D111A/D130A/V187T/L264R, E056K/D130A/V187N/L264R, F051T/L075G/I252Q/L264R, F051T/L075Q/I252Q/L264R, G023K/D130A/V187N/L264R, G023K/D130A/V187T/T189Q, G023K/E056K/L075R/L264R, G023K/K024A/V154I/V187N, G023Q/F051T/I252Q/L264R, G023Q/G091Q/I252Q/L264R, G023Q/L075Q/D130A/L264R, G023Q/L075Q/V187T/L264R, G091Q/V187T/I252Q/L264R, K024A/D130A/V154I/V187T, L075G/D130A/V187T/I252Q, S058M/G163P/L227M/L264R, S058M/L075Q/I252Q/L264R, A018K/D130A/G156W/V187N/L264R, A018K/G023K/K024A/D130A/V154I, A018K/G023K/V077I/D130A/V187N, A018K/G023Q/K024A/D130A/V187Q, A018K/K024A/N094R/D130A/V187N, D027E/D048Q/D137Q/L227M/L264R, D027E/D130A/G163P/L227M/L264R, D027E/D130A/G163P/N233Q/L264R, D027E/G163P/L227M/N233Q/L264R, D027E/S058M/D130A/G163P/L264R, D027S/F051T/V187N/I252Q/L264R, D027S/L075G/D130A/I252Q/L264R, D027S/L075G/G091Q/I252Q/L264R, D027S/L075R/V154I/T189Q/L264R, D048Q/S058M/D137Q/N233Q/L264R, |

TABLE 7-6-continued

| TLL variants with Performance Index for expression ≥0.5 compared to TLL SEQ ID NO: 1 and Performance Index ≥50% of the maximum PI value in the Fabric Adhesion assay compared to Reference sequence SEQ ID NO: 2 are shown below. |
|---|
| D130A/D137Q/G163P/L227M/L264R, D130A/D137Q/G163P/N233Q/L264R, D130A/V154I/G156W/V187N/T189Q, E056K/L075G/V187N/I252Q/L264R, F051T/D130A/V187T/I252Q/L264R, F051T/L075G/D130A/I252Q/L264R, F051T/L075G/V187N/I252Q/L264R, F051T/L075Q/V187N/I252Q/L264R, G023K/E056K/D130A/V187N/L264R, G023K/E056K/D130A/V187T/L264R, G023K/L075R/D130A/V187N/L264R, G023Q/E056K/V187N/I252Q/L264R, G023Q/L075Q/D130A/I252Q/L264R, G023Q/L075Q/G091Q/I252Q/L264R, L075G/D130A/V187T/I252Q/L264R, A018K/G023K/K024A/V077I/G156W/V187Q, A018K/G023Q/A049V/G156W/V187T/T189D, A018K/G023Q/K024A/V077I/V154I/V187N, A018K/G023Q/N094R/D130A/G156W/V187Q, A018K/K024A/D111A/V187N/T189Q/L264R, A018K/K024A/L075Q/V077I/D130A/V187N, A018K/N094R/D111A/D130A/V154I/V187N, D027E/D048Q/D130A/D137H/G163P/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/L227M/L264R, D027E/S058M/D137Q/G163P/N233Q/L264R, D027Q/L075Q/D130A/V187T/I252Q/L264R, D027Q/S058M/L075R/D130A/V187T/I252Q, D027S/F051T/L075Q/D130A/I252Q/L264R, D027S/L075Q/G091Q/V187H/I252Q/L264R, D048Q/S058M/D130A/G163P/L227M/L264R, D048Q/S058M/D130A/L227M/N233Q/L264R, F051T/E056K/D130A/V187N/I252Q/L264R, F051T/L075G/G091Q/V187H/I252Q/L264R, F051T/L075G/G091Q/V187T/I252Q/L264R, G023K/D027Q/F051T/E056K/S058M/L075Q, G023K/D027S/L075R/D130A/V187T/I252Q, G023K/D130A/V154I/G156W/V187T/L264R, G023K/E056K/L075R/D130A/T189Q/L264R, G023K/F051T/D130A/V187N/I252Q/L264R, G023K/F051T/L075Q/D130A/I252Q/L264R, G023K/K024A/L075Q/V154I/G156W/V187Q, G023Q/D027S/F051T/L075Q/V187T/L264R, G023Q/D027S/L075G/D130A/V187H/L264R, G023Q/D027S/L075Q/D130A/V187T/I252Q, G023Q/F051T/G091Q/V187N/I252Q/L264R, G023Q/F051T/L075G/G091Q/V187N/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, G023Q/L075Q/G091Q/V187N/I252Q/L264R, K024A/L075Q/D111A/V154I/V187N/T189Q, L075Q/G091Q/D130A/V187H/I252Q/L264R, S058M/D130A/D137Q/G163P/N233Q/L264R, A018K/D111A/D130A/V154I/G156W/V187T/T189Q, A018K/K024A/D130A/V154I/G156W/V187T/L264R, A018K/K024A/N094R/D130A/G156W/V187T/L264R, D027E/D048Q/S058M/D130A/D137Q/G163P/L264R, D027E/D048Q/S058M/D130A/G163P/N233Q/L264R, D027E/S058M/D130A/G163P/L227M/N233Q/L264R, D027E/S058M/D137Q/G163P/L227M/N233Q/L264R, D027Q/F051T/S058M/L075Q/G091Q/I252Q/L264R, D027Q/L075G/G091Q/D130A/V187H/I252Q/L264R, D027S/F051T/S058M/L075Q/V187N/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023Q/D027S/F051T/E056K/D130A/I252Q/L264R, G023Q/F051T/L075Q/G091Q/V187H/I252Q/L264R, G023Q/F051T/S058M/G091Q/D130A/I252Q/L264R, G023Q/L075G/G091Q/D130A/V187T/I252Q/L264R, G023Q/S058M/L075G/G091Q/D130A/I252Q/L264R, D027E/S058M/D130A/D137Q/G163P/L227M/N233Q/L264R, G023K/D027S/F051T/S058M/L075Q/V187H/I252Q/L264R, G023Q/D027S/E056K/L075R/D111A/V154I/G156W/L264R, G023Q/D027S/E056K/S058M/L075G/G091Q/V187T/L264R, G023Q/D027S/S058M/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/S058M/L075R/G091Q/D130A/V187H/I252Q/L264R, G023K/K024A/L075Q/N094R/V154I/G156W/V187N/T189Q/L264R, G023Q/F051T/S058M/L075Q/G091Q/D130A/V187H/I252Q/L264R, N011K/G023Q/E056K/L075R/D111A/D130A/V154I/G156W/V187N/L264R |

TABLE 7-7

| TLL variants with Performance Index <1 in the Fabric Adhesion assay compared to TLL SEQ ID NO: 1 are shown below. |
|---|
| A018K/D027S, A018K/E045F, A018K/L075D, A018K/T189D, D027E/G163P, D027N/E056K, D027N/N233Q, D027S/N033D, D027S/P256T, D130A/T189Q, E045F/N073R, E045F/T189D, F051T/L075R, G023K/D130A, G023Q/L075Q, K024A/L075Q, K024A/V154I, L075Q/D130A, L075Q/G156W, L227M/L264R, N011K/D027S, N033D/E045F, N073R/L075D, N094R/G156W, P029E/N033D, A018K/A049V/L075Q, A018K/D027S/E045F, A018K/D027S/N073R, A018K/D027S/T189D, A018K/E045F/N073R, A018K/E045F/T189D, A018K/E045F/V187T, A018K/G023K/G156W, A018K/G023K/L075Q, A018K/L075D/T189D, A018K/L075Q/V187T, |

TABLE 7-7-continued

TLL variants with Performance Index <1 in the Fabric Adhesion assay compared to TLL SEQ ID NO: 1 are shown below.

A018K/N033D/L075D, A018K/N073R/L075D, A018K/V154I/G156W, A049V/L075Q/T189D, A049V/V187T/T189D, D027E/S058M/G163P, D027N/N233Q/P256T, D027N/S058M/P256T, D027Q/N233Q/P256T, D027Q/S058M/P256T, D027S/L075Q/G091Q, D027S/N033D/T189D, D027S/N073R/L075D, D027S/N233Q/P256T, D027S/S058M/P256T, D130A/T189Q/L264R, D130A/V154I/G156W, E045F/L075D/T189D, E045F/N073R/L075D, E056K/D130A/L264R, E056K/D130A/T189Q, G023Q/D111A/L264R, G023Q/D130A/G156W, G023Q/E045F/V077I, G023Q/E056K/L075R, G023Q/K024A/G156W, G023Q/L075Q/V077I, I090F/N233Q/P256T, K024A/D130A/V154I, K024A/L075Q/G156W, L075G/D130A/V187H, L075Q/D111A/D130A, L075Q/D130A/V187T, L075Q/N094R/V154I, L075Q/V077I/T189D, L075Q/V187T/L264R, L075R/V187N/L264R, L075R/V187T/L264R, N011K/D027S/S058M, N011K/N233Q/P256T, N033D/E045F/L075D, N033D/E045F/N073R, N033D/N073R/T189D, N094R/D130A/V187T, P029E/E045F/L075D, P029E/N033D/E045F, P029E/N033D/L075D, P029E/N073R/L075D, Q004D/D027S/P256T, Q004D/N233Q/P256T, Q004D/S058M/N233Q, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/N073R, A018K/D027S/E045F/T189D, A018K/D027S/L075D/T189D, A018K/D027S/N033D/L075D, A018K/D111A/G156W/T189Q, A018K/D130A/G156W/V187T, A018K/E045F/A049V/G156W, A018K/E045F/A049V/V187T, A018K/E045F/L075D/T189D, A018K/E045F/L075Q/T189D, A018K/E045F/L075Q/V187T, A018K/G023Q/A049V/T189D, A018K/G023Q/E045F/T189D, A018K/G023Q/E045F/V187T, A018K/G023Q/G156W/V187T, A018K/G023Q/L075Q/V077I, A018K/G023Q/V077I/G156W, A018K/G023Q/V077I/V187T, A018K/G023Q/V187T/T189D, A018K/L075Q/G156W/T189D, A018K/L075Q/G156W/V187T, A018K/L075Q/N094R/D111A, A018K/L075Q/N094R/D130A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/L075D, A018K/P029E/N033D/T189D, A018K/P029E/N073R/L075D, A018K/V154I/G156W/V187T, A049V/L075Q/V077I/T189D, A049V/L075Q/V187T/T189D, D027E/D048Q/G163P/L264R, D027E/D137Q/G163P/L227M, D027E/D137Q/L227M/L264R, D027E/L227M/N233Q/L264R, D027N/E056K/N233Q/P256T, D027N/E056K/S058M/P256T, D027N/S058M/N233Q/P256T, D027Q/E056K/N233Q/P256T, D027Q/S058M/I090F/P256T, D027S/E045F/L075D/T189D, D027S/E045F/N073R/L075D, D027S/E045F/N073R/T189D, D027S/E056K/D111A/V154I, D027S/E056K/I090F/P256T, D027S/N033D/E045F/N073R, D027S/N033D/L075D/T189D, D027S/N033D/N073R/L075D, D027S/N033D/N073R/T189D, D027S/P029E/E045F/L075D, D027S/P029E/E045F/N073R, D027S/P029E/E045F/T189D, D027S/P029E/N033D/E045F, D027S/P029E/N033D/L075D, D027S/P029E/N033D/N073R, D027S/P029E/N033D/T189D, D048Q/D137Q/G163P/L227M, D111A/D130A/V154I/L264R, D130A/G163P/L227M/L264R, D130A/G163P/N233Q/L264R, E045F/A049V/G156W/V187T, E045F/L075Q/G156W/V187T, E056K/L075Q/V187N/L264R, F051T/D130A/I252Q/L264R, G023K/D027Q/F051T/L075Q, G023K/D027S/L075Q/L264R, G023K/D111A/D130A/L264R, G023K/D130A/G156W/T189Q, G023K/E056K/D130A/L264R, G023K/E056K/D130A/V187N, G023K/E056K/V187T/L264R, G023K/L075Q/G156W/L264R, G023K/L075Q/G156W/V187N, G023K/L075R/D130A/L264R, G023K/L075R/V187N/L264R, G023Q/A049V/L075Q/V077I, G023Q/A049V/V077I/G156W, G023Q/D027S/D111A/G156W, G023Q/E045F/A049V/T189D, G023Q/E045F/A049V/V187T, G023Q/E045F/L075Q/G156W, G023Q/E045F/L075Q/V187T, G023Q/K024A/D130A/G156W, G023Q/K024A/L075R/G156W, G023Q/K024A/L075R/V154I, G023Q/K024A/V077I/G156W, G023Q/L075Q/G156W/V187T, G023Q/V154I/G156W/V187N, K024A/L075Q/D130A/G156W, K024A/L075Q/D130A/V154I, K024A/L075Q/V187T/T189Q, L075G/G091Q/V187N/L264R, L075Q/D130A/V154I/G156W, L075Q/G156W/V187T/L264R, L075Q/V077I/G156W/V187N, L075Q/V077I/N094R/G156W, L075Q/V077I/V187T/T189D, L075Q/V187N/T189Q/L264R, L075R/D130A/V187T/L264R, N011K/D027N/E056K/S058M, N011K/D027N/S058M/P256T, N011K/D027Q/S058M/P256T, N011K/D027S/E056K/P256T, N011K/D027S/N233Q/P256T, N011K/D027S/S058M/N233Q, N011K/E056K/N233Q/P256T, N011K/E056K/S058M/P256T, N011K/G023K/L075Q/D111A, N011K/S058M/N233Q/P256T, N033D/E045F/N073R/T189A, P029E/E045F/L075D/T189D, P029E/E045F/N073R/L075D, P029E/E045F/N073R/T189D, P029E/N033D/E045F/L075D, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/D027S/I090F/P256T, Q004D/N011K/D027N/P256T, Q004D/N011K/D027Q/N233Q, Q004D/N011K/D027S/P256T, Q004D/N011K/E056K/S058M, S058M/D137Q/G163P/N233Q, A018K/A049V/L075Q/V187T/T189D, A018K/D027S/E045F/L075D/T189D, A018K/D027S/E045F/N073R/D137V, A018K/D027S/N033D/E045F/T189D, A018K/D027S/N033D/L075D/T189D, A018K/D027S/N033D/N073R/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187T/L264R, A018K/E045F/A049V/L075Q/G156W, A018K/E045F/A049V/L075Q/T189D, A018K/E045F/A049V/L075Q/V187T, A018K/E045F/N073R/L075D/T189D, A018K/G023K/D130A/V154I/G156W, A018K/G023K/K024A/L075R/N094R, A018K/G023K/L075Q/D130A/V154I, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/L075Q/G156W, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/L075Q/G156W/V187T/T189D, A018K/L075Q/N094R/D130A/V187N, A018K/L075Q/N094R/G156W/V187N, A018K/L075Q/V077I/N094R/G156W, A018K/L075Q/V187T/T189Q/L264R,

TABLE 7-7-continued

| TLL variants with Performance Index <1 in the Fabric Adhesion assay compared to TLL SEQ ID NO: 1 are shown below. |
|---|
| A018K/N033D/E045F/L075D/T189D, A018K/P029E/E045F/N073R/L075D, A018K/P029E/N033D/N073R/L075D, A018K/V077I/G156W/V187T/T189D, D027E/D048Q/G163P/N233Q/L264R, D027E/D048Q/L227M/N233Q/L264R, D027E/D048Q/S058M/G163P/N233Q, D027E/D130A/D137Q/G163P/L264R, D027E/D137Q/G163P/L227M/L264R, D027E/S058M/D137Q/G163P/N233Q, D027N/E056K/S058M/N233Q/P256T, D027N/S058M/I090F/N233Q/P256T, D027Q/E056K/I090F/N233Q/P256T, D027Q/E056K/S058M/N233Q/P256T, D027Q/F051T/L075Q/D130A/L264R, D027S/E056K/D111A/V187N/L264R, D027S/E056K/S058M/N233Q/P256T, D027S/L075Q/D111A/D130A/V187N, D027S/N033D/E045F/N073R/L075D, D027S/N033D/N073R/L075D/T189D, D027S/P029E/E045F/N073R/L075D, D027S/P029E/E045F/N073R/T189D, D027S/P029E/N033D/E045F/N073R, D027S/P029E/N033D/N073R/L075D, D048Q/D130A/D137Q/G163P/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D048Q/S058M/G163P/L227M/L264R, D048Q/S058M/G163P/N233Q/L264R, D130A/G163P/L227M/N233Q/L264R, E045F/A049V/L075Q/V187T/T189D, E056K/D130A/V187H/I252Q/L264R, E056K/L075R/D130A/V187N/L264R, E056K/L075R/D130A/V187T/L264R, E056K/N094R/G156W/V187N/L264R, E056K/S058M/I090F/N233Q/P256T, F051T/S058M/L075Q/G091Q/I252Q, G023K/D027S/E056K/V187T/L264R, G023K/D111A/V154I/V187T/L264R, G023K/E056K/L075R/D130A/V187T, G023K/E056K/L075R/V187N/L264R, G023K/K024A/D111A/D130A/V187T, G023K/K024A/D111A/G156W/T189Q, G023K/K024A/L075R/D130A/G156W, G023K/L075Q/D130A/V154I/T189Q, G023K/L075Q/V187H/I252Q/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/L075G/I252Q/L264R, G023Q/D027S/V154I/V187N/L264R, G023Q/E045F/A049V/G156W/T189D, G023Q/E045F/A049V/L075Q/V077I, G023Q/E045F/A049V/V077I/T189D, G023Q/E045F/L075Q/G156W/T189D, G023Q/E045F/L075Q/V077I/V187T, G023Q/K024A/L075Q/D130A/G156W, G023Q/K024A/L075Q/G156W/V187Q, G023Q/K024A/L075Q/V077I/V187Q, G023Q/K024A/L075R/D130A/V154I, G023Q/K024A/L075R/V077I/D130A, G023Q/K024A/V077I/D130A/V154I, G023Q/L075Q/V077I/D130A/G156W, K024A/L075R/D111A/V154I/V187T, K024A/L075R/G156W/V187N/T189Q, L075Q/D111A/D130A/V187T/T189Q, L075Q/D130A/V187T/T189Q/L264R, L075Q/N094R/D130A/G156W/V187T, L075Q/V077I/D130A/G156W/V187N, L075R/D111A/D130A/V187N/T189Q, L075R/G156W/V187T/T189Q/L264R, L075R/V077I/N094R/V154I/G156W, N011K/D027N/E056K/N233Q/P256T, N011K/D027N/E056K/S058M/P256T, N011K/D027N/S058M/N233Q/P256T, N011K/D027Q/E056K/S058M/N233Q, N011K/D027Q/I090F/N233Q/P256T, N011K/D027Q/S058M/I090F/P256T, N011K/D027Q/S058M/N233Q/P256T, N011K/D027S/E056K/N233Q/P256T, N011K/D027S/I090F/N233Q/P256T, N011K/G023K/E056K/L075Q/T189Q, N011K/G023Q/L075Q/V187N/T189Q, P029E/N033D/E045F/L075D/T189D, P029E/N033D/K074S/L075D/T189D, P029E/N033D/N073R/L075D/T189D, Q004D/D027N/E056K/S058M/P256T, Q004D/D027N/I090F/N233Q/P256T, Q004D/D027Q/E056K/N233Q/P256T, Q004D/D027Q/E056K/S058M/P256T, Q004D/D027S/E056K/N233Q/P256T, Q004D/D027S/E056K/S058M/P256T, Q004D/D027S/S058M/N233Q/P256T, Q004D/N011K/D027N/N233Q/P256T, Q004D/N011K/D027Q/E056K/N233Q, Q004D/N011K/D027Q/S058M/N233Q, Q004D/N011K/I090F/N233Q/P256T, S058M/D130A/D137Q/G163P/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/D027S/N033D/E045F/L075D/T189D, A018K/D027S/N033D/E045F/N073R/L075D, A018K/D027S/N033D/N073R/L075D/T189D, A018K/D027S/P029E/N033D/E045F/L075D, A018K/D027S/P029E/N033D/L075D/T189D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D111A/L264R, A018K/G023K/K024A/N094R/D130A/V154I, A018K/G023K/L075R/N094R/D130A/V187N, A018K/G023K/L075R/V077I/D130A/V154I, A018K/G023Q/A049V/L075Q/V077I/G156W, A018K/G023Q/A049V/L075Q/V077I/V187T, A018K/G023Q/A049V/V077I/V187T/T189D, A018K/G023Q/E045F/A049V/G156W/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/G156W/V187T/T189D, A018K/G023Q/E045F/L075Q/G156C/V187T, A018K/G023Q/E045F/L075Q/G156W/V187T, A018K/G023Q/K024A/L075R/N094R/G156W, A018K/G023Q/L075Q/V077I/D130A/G156W, A018K/G023Q/L075Q/V077I/N094R/V154I, A018K/G023Q/L075Q/V077I/V187T/T189D, A018K/K024A/L075Q/N094R/V154I/V187N, A018K/K024A/V077I/N094R/D130A/G156W, A018K/L075Q/D111A/V154I/G156W/V187N, A018K/L075Q/D111A/V154I/T189Q/L264R, A018K/N033D/E045F/N073R/L075D/T189D, A018K/P029E/N033D/E045F/L075D/T189D, D027E/D048Q/D137Q/G163P/N233Q/L264R, D027E/D048Q/S058M/D130A/G163P/L264R, D027E/D048Q/S058M/D130A/L227M/N233Q, D027E/D048Q/S058M/G163P/L227M/L264R, D027E/D048Q/S058M/G163P/N233Q/L264R, D027E/D130A/D137Q/G163P/L227M/L264R, D027Q/E056K/S058M/D130A/I252Q/L264R, D027Q/E056K/S058M/I090F/N233Q/P256T, D027Q/F051T/L075G/D130A/I252Q/L264R, D027S/E056K/S058M/V187T/I252Q/L264R, D027S/G091Q/D130A/V187N/I252Q/L264R, D027S/L075Q/D111A/G156W/V187N/T189Q, D027S/P029E/N033D/E045F/N073R/L075D, D027S/P029E/N033D/E045F/N073R/T189D, D027S/P029E/N033D/N073R/L075D/T189D, D048Q/D130A/G163P/L227M/N233Q/L264R, |

TABLE 7-7-continued

| TLL variants with Performance Index <1 in the Fabric Adhesion assay compared to TLL SEQ ID NO: 1 are shown below. |
| --- |
| D048Q/S058M/D130A/D137Q/G163P/L264R, D048Q/S058M/D130A/G163P/N233Q/L264R, D048Q/S058M/G163P/L227M/N233Q/L264R, E045F/A049V/L075Q/V077I/V187T/T189D, F051T/L075G/G091Q/D130A/I252Q/L264R, G023K/E056K/L075R/D130A/V187N/L264R, G023K/F051T/G091Q/D130A/V187H/L264R, G023K/K024A/L075Q/D111A/D130A/T189Q, G023K/K024A/L075Q/G156W/V187T/T189Q, G023K/K024A/L075Q/N094R/D130A/G156W, G023K/K024A/L075R/D130A/V154I/V187N, G023K/L075G/D130A/V187T/I252Q/L264R, G023K/L075Q/V077I/D130A/G156W/V187Q, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/L075Q/D111A/G156W/L264R, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/E056K/D111A/D130A/V187N/T189Q, G023Q/E056K/L075Q/D130A/V154I/L264R, G023Q/F051T/D130A/V187T/I252Q/L264R, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/V154I/G156W, G023Q/L075Q/D111A/V154I/T189Q/L264R, G023Q/L075Q/N094R/D111A/G156W/L264R, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/G156W/T189Q/L264R, K024A/L075R/D111A/V154I/G156W/V187N, L075Q/D111A/D130A/V154I/G156W/T189Q, L075Q/N094R/D111A/G156W/T189Q/L264R, N011K/D027N/E056K/I090F/N233Q/P256T, N011K/D027N/E056K/S058M/N233Q/P256T, N011K/D027N/S058M/I090F/N233Q/P256T, N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/I090F/P256T, N011K/D027S/E056K/S058M/N233Q/P256T, N011K/D027S/S058M/I090F/N233Q/P256T, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, A018K/D027S/P029E/N033D/N073R/L075D/T189D, A018K/E045F/L075Q/V077I/G156W/V187T/T189D, A018K/G023K/K024A/L075Q/N094R/V154I/V187Q, A018K/G023K/K024A/L075R/N094R/D130A/V154I, A018K/G023K/K024A/L075R/V154I/G156W/V187Q, A018K/G023K/L075Q/V077I/N094R/V154I/G156W, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075Q/V077I/D130A/G156W, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/L075Q/V077I/N094R/D130A/G156W, A018K/L075Q/D111A/D130A/V154I/G156W/L264R, A018K/L075Q/D130A/G156W/V187N/T189Q/L264R, A018K/L075Q/N094R/D111A/V154I/V187T/L264R, D027E/D130A/D137Q/G163P/L227M/N233Q/L264R, D027E/S058M/D130A/D137Q/G163P/N233Q/L264R, D027Q/F051T/L075Q/G091Q/D130A/V187T/I252Q, D027S/E056K/L075R/D111A/G156W/V187N/L264R, D027S/L075R/V154I/G156W/V187N/T189Q/L264R, D027S/P029E/N033D/E045F/N073R/L075D/T189D, D048Q/D130A/D137Q/G163P/L227M/N233Q/L264R, D048Q/S058M/D130A/D137Q/L227M/N233Q/L264R, D048Q/S058M/D137Q/G163P/L227M/N233Q/L264R, E056K/L075Q/D111A/D130A/G156W/V187N/T189Q, G023K/D027S/F051T/S058M/G091Q/V187N/I252Q, G023K/D027S/L075Q/N094R/V154I/G156W/T189Q, G023K/F051T/E056K/L075R/D130A/V187T/I252Q, G023K/F051T/L075Q/G091Q/D130A/V187H/I252Q, G023K/K024A/L075Q/N094R/V154I/G156W/V187N, G023K/K024A/N094R/V154I/G156W/V187N/T189Q, G023K/L075Q/D111A/D130A/V154I/G156W/L264R, G023K/L075Q/D111A/V154I/G156W/T189Q/L264R, G023K/L075Q/D130A/G156W/V187N/T189Q/L264R, G023K/L075Q/N094R/D130A/V154I/V187N/L264R, G023K/L075Q/N094R/V154I/G156W/V187T/L264R, G023Q/D027S/L075Q/V154I/G156W/V187N/L264R, G023Q/E045F/A049V/V077I/G156W/V187T/T189D, G023Q/E045F/L075Q/V077I/G156W/V187T/T189D, G023Q/E056K/L075Q/D130A/V154I/G156W/T189Q, G023Q/F051T/E056K/L075R/G091Q/V187H/I252Q, G023Q/F051T/G091Q/D130A/V187H/I252Q/L264R, G023Q/K024A/L075Q/V077I/D130A/V154I/G156W, G023Q/L075Q/D111A/D130A/V154I/G156W/L264R, G023Q/L075Q/V077I/N094R/D130A/G156W/V187Q, |

TABLE 7-7-continued

| TLL variants with Performance Index <1 in the Fabric Adhesion assay compared to TLL SEQ ID NO: 1 are shown below. |
|---|
| K024A/L075Q/D111A/D130A/V187N/T189Q/L264R, K024A/L075R/D130A/V154I/G156W/T189Q/L264R, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, N011K/G023Q/L075Q/V154I/V187N/T189Q/L264R, Q004D/D027N/E056K/S058M/I090F/N233Q/P256T, Q004D/N011K/D027N/S058M/I090F/N233Q/P256T, Q004D/N011K/D027Q/E056K/S058M/N233Q/P256T, Q004D/N011K/D027Q/S058M/I090F/N233Q/P256T, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/L075Q/V077I/D130A/V154I/G156W/V187N, A018K/G023K/L075R/V077I/N094R/D130A/G156W/V187Q, A018K/G023Q/E045F/L075Q/V077I/G156W/V187T/T189D, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, A018K/L075Q/N094R/D111A/V154I/G156W/T189Q/L264R, D027E/D048Q/S058M/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/K024A/L075Q/N094R/V154I/G156W/V187T/L264R, G023K/K024A/L075R/N094R/V154I/G156W/V187T/T189Q, G023K/L075Q/D111A/V154I/G156W/V187N/T189Q/L264R, G023K/L075Q/N094R/D130A/V154I/G156W/V187N/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/L075R/N094R/V154I/G156W/V187N/T189Q, G023Q/E056K/L075Q/D111A/V154I/V187N/T189Q/L264R, G023Q/E056K/L075Q/N094R/D111A/G156W/T189Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D130A/V154I/G156W/T189Q/L264R, G023Q/L075Q/V077I/N094R/D130A/V154I/G156W/V187Q, N011K/G023K/D027S/L075Q/D111A/D130A/V154I/T189Q, N011K/G023K/E056K/L075Q/D130A/V154I/T189Q/L264R, N011K/G023K/L075Q/D111A/G156W/V187N/T189Q/L264R, N011K/G023Q/D027S/L075Q/N094R/V154I/G156W/T189Q, N011K/G023Q/D027S/N094R/V154I/G156W/T189Q/L264R, N011K/G023Q/L075Q/D111A/D130A/V154I/V187N/L264R, N011K/G023Q/L075Q/N094R/V154I/G156W/T189Q/L264R, A018K/G023K/K024A/L075Q/N094R/D111A/D130A/V154I/T189Q, A018K/G023K/K024A/L075Q/N094R/D130A/V154I/G156W/V187N, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, A018K/K024A/L075Q/N094R/V154I/G156W/V187N/T189Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023Q/D027S/F051T/E056K/L075G/G091Q/V187N/I252Q/L264R, G023Q/D027S/L075Q/N094R/D111A/D130A/V154I/G156W/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/D027S/E056K/L075R/D111A/G156W/V187N/L264R, N011K/G023Q/L075Q/D111A/V154I/G156W/V187N/T189Q/L264R, A018K/G023Q/D027S/E045F/A049V/N073S/L075Q/R108K/V187T/T189D, A018K/G023Q/D027S/E045F/A049V/S058M/L075Q/R108K/V187T/T189D, |

TABLE 7-7-continued

| TLL variants with Performance Index <1 in the Fabric Adhesion assay compared to TLL SEQ ID NO: 1 are shown below. |
|---|
| A018K/G023Q/D027S/E045F/A049V/S058M/N073S/L075Q/V187T/T189D, A018K/G023Q/D027S/P029E/S058M/L075Q/V077I/H135F/G156W/V187T, A018K/G023Q/D027S/S058M/L075Q/V077I/R108K/H135F/G156W/V187H, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/G023K/L075R/N094R/D111A/V154I/G156W/V187N/T189Q/L264R, N011K/G023Q/D027S/E056K/L075R/D130A/V154I/G156W/T189Q/L264R, N011K/G023Q/L075Q/N094R/D111A/D130A/V154I/G156W/V187N/L264R, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 7-8

| TLL variants with Performance Index for expression ≥0.5 and Performance Index <1 in the Fabric Adhesion assay compared to TLL SEQ ID NO: 1 are shown below. |
|---|
| A018K/E045F, A018K/L075D, D027E/G163P, D027S/N033D, D027S/P256T, E045F/N073R, F051T/L075R, K024A/V154I, L227M/L264R, N033D/E045F, N094R/G156W, P029E/N033D, A018K/E045F/N073R, A018K/E045F/V187T, A018K/L075D/T189D, A018K/V154I/G156W, D027E/S058M/G163P, D027N/S058M/P256T, D027Q/S058M/P256T, D027S/L075Q/G091Q, D027S/N033D/T189D, D027S/S058M/P256T, D130A/V154I/G156W, E056K/D130A/L264R, G023Q/D130A/G156W, G023Q/K024A/G156W, I090F/N233Q/P256T, K024A/D130A/V154I, L075G/D130A/V187H, L075Q/V187T/L264R, L075R/V187N/L264R, L075R/V187T/L264R, N011K/N233Q/P256T, N094R/D130A/V187T, P029E/N033D/E045F, Q004D/D027S/P256T, Q004D/S058M/N233Q, V187N/T189Q/L264R, A018K/D111A/G156W/T189Q, A018K/D130A/G156W/V187T, A018K/E045F/A049V/G156W, A018K/E045F/L075D/T189D, A018K/G023Q/V077I/G156W, A018K/L075QA/V077I/N094R, A018K/N033D/L075D/T189D, A018K/P029E/N073R/L075D, D027E/D048Q/G163P/L264R, D027E/D137Q/G163P/L227M, D027E/D137Q/L227M/L264R, D027E/L227M/N233Q/L264R, D027N/S058M/N233Q/P256T, D027Q/E056K/N233Q/P256T, D027S/E045F/L075D/T189D, D027S/E045F/N073R/T189D, D027S/N033D/E045F/N073R, D027S/N033D/L075D/T189D, D027S/N033D/N073R/T189D, D027S/P029E/E045F/N073R, D027S/P029E/E045F/T189D, D027S/P029E/N033D/E045F, D027S/P029E/N033D/L075D, D048Q/D137Q/G163P/L227M, D130A/G163P/L227M/L264R, E045F/A049V/G156W/V187T, E045F/L075Q/G156W/V187T, F051T/D130A/I252Q/L264R, G023K/D027Q/F051T/L075Q, G023K/D130A/G156W/T189Q, G023K/E056K/D130A/V187N, G023K/E056K/V187T/L264R, G023K/L075R/D130A/L264R, G023Q/A049V/V077I/G156W, G023Q/K024A/D130A/G156W, G023Q/K024A/L075R/G156W, G023Q/K024A/V077I/G156W, L075G/G091Q/V187N/L264R, L075R/D130A/V187T/L264R, N011K/D027Q/S058M/P256T, N011K/D027S/N233Q/P256T, N033D/E045F/N073R/T189A, P029E/N073R/L075D/T189D, Q004D/D027N/E056K/P256T, Q004D/D027N/S058M/P256T, Q004D/D027Q/N233Q/P256T, Q004D/D027Q/S058M/P256T, Q004D/N011K/D027S/P256T, S058M/D137Q/G163P/N233Q, A018K/D027S/E045F/L075D/T189D, A018K/D027S/P029E/N033D/L075D, A018K/E045F/N073R/L075D/T189D, A018K/G023K/D130A/V154I/G156W, A018K/G023Q/K024A/L075Q/G156W, A018K/G023Q/V077I/D130A/G156W, A018K/K024A/L075R/D130A/V154I, A018K/P029E/N033D/N073R/L075D, D027E/D048Q/G163P/N233Q/L264R, D027E/D130A/D137Q/G163P/L264R, D027E/S058M/D137Q/G163P/N233Q, D027Q/F051T/L075Q/D130A/L264R, D027S/E056K/D111A/V187N/L264R, D048Q/D137Q/G163P/N233Q/L264R, D048Q/S058M/D130A/N233Q/L264R, D048Q/S058M/D137Q/G163P/N233E, D048Q/S058M/G163P/L227M/L264R, D048Q/S058M/G163P/N233Q/L264R, E045F/A049V/L075Q/V187T/T189D, E056K/L075R/D130A/V187N/L264R, E056K/L075R/D130A/V187T/L264R, F051T/S058M/L075Q/G091Q/I252Q, G023K/D027S/E056K/V187T/L264R, G023K/E056K/L075R/D130A/V187T, G023K/E056K/L075R/V187N/L264R, G023K/K024A/D111A/D130A/V187T, G023K/K024A/D111A/G156W/T189Q, G023K/L075Q/V187H/I252Q/L264R, G023K/N094R/G156W/V187N/T189Q, G023Q/D027S/L075G/I252Q/L264R, G023Q/K024A/L075Q/G156W/V187Q, G023Q/L075Q/V077I/D130A/G156W, N011K/D027N/S058M/N233Q/P256T, N011K/D027S/I090F/N233Q/P256T, Q004D/N011K/D027N/N233Q/P256T, S058M/D130A/D137Q/G163P/L264R, S058M/D137Q/G163P/L227M/L264R, S058M/D137Q/G163P/L227M/N233Q, S058M/G163P/L227M/N233Q/L264R, V077I/D130A/V154I/G156W/V187N, A018K/D027S/N033D/E045F/N073R/L075D, A018K/D027S/N033D/N073R/L075D/T189D, A018K/D027S/P029E/N033D/E045F/L075D, A018K/G023Q/K024A/L075R/N094R/G156W, D027E/D048Q/D137Q/G163P/N233Q/L264R, D027E/D048Q/S058M/D130A/G163P/L264R, D027E/D048Q/S058M/D130A/L227M/N233Q, D027E/D048Q/S058M/G163P/L227M/L264R, D027E/D048Q/S058M/G163P/N233Q/L264R, D027E/D130A/D137Q/G163P/L227M/L264R, D027Q/E056K/S058M/D130A/I252Q/L264R, D027S/E056K/S058M/V187T/I252Q/L264R, |

TABLE 7-8-continued

| TLL variants with Performance Index for expression ≥0.5 and Performance Index <1 in the Fabric Adhesion assay compared to TLL SEQ ID NO: 1 are shown below. |
|---|
| D048Q/D130A/G163P/L227M/N233Q/L264R, D048Q/S058M/D130A/D137Q/G163P/L264R, D048Q/S058M/G163P/L227M/N233Q/L264R, F051T/L075G/G091Q/D130A/I252Q/L264R, G023K/E056K/L075R/D130A/V187N/L264R, G023K/F051T/G091Q/D130A/V187H/L264R, G023K/K024A/L075Q/D111A/D130A/T189Q, G023K/K024A/L075R/D130A/V154I/V187N, G023K/L075G/D130A/V187T/I252Q/L264R, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/K024A/V077I/D130A/V154I/G156W, K024A/L075Q/N094R/D130A/V154I/L264R, K024A/L075Q/V077I/N094R/D130A/V187N, N011K/D027S/E056K/I090F/N233Q/P256T, Q004D/N011K/D027N/I090F/N233Q/P256T, Q004D/N011K/D027N/S058M/N233Q/P256T, Q004D/N011K/D027S/S058M/N233Q/P256T, A018K/D027S/P029E/N033D/N073R/L075D/T189D, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/V077I/N094R/D130A/G156W, D027E/D130A/D137Q/G163P/L227M/N233Q/L264R, D048Q/D130A/D137Q/G163P/L227M/N233Q/L264R, D048Q/S058M/D130A/D137Q/L227M/N233Q/L264R, D048Q/S058M/D137Q/G163P/L227M/N233Q/L264R, G023K/D027S/F051T/S058M/G091Q/V187N/I252Q, G023K/K024A/N094R/V154I/G156W/V187N/T189Q, G023Q/F051T/E056K/L075R/G091Q/V187H/I252Q, G023Q/F051T/G091Q/D130A/V187H/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D027E/D048Q/S058M/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027S/F051T/S058M/G091Q/D130A/V187N/I252Q, G023Q/D027S/L075R/N094R/V154I/G156W/V187N/T189Q, A018K/G023Q/D027S/P029E/L075Q/V077I/R108K/H135F/V187H, G023Q/F051T/S058M/L075G/G091Q/D130A/V187T/I252Q/L264R, A018K/G023Q/D027S/P029E/S058M/L075Q/V077I/H135F/G156W/V187T, A018K/G023K/L075R/N094R/D111A/D130A/V154I/G156W/V187N/T189Q/L264R, A018K/G023Q/D027S/E045F/A049V/S058M/N073S/L075Q/R108K/V187T/T189D, A018K/G023Q/D027S/P029E/S058M/L075Q/V077I/R108K/H135F/G156W/V187T |

TABLE 7-9

| TLL variants with Performance Index for expression ≥0.5 and Performance Index ≤50% of the maximum PI value in the Fabric Adhesion assay compared to TLL SEQ ID NO: 1 are shown below. |
|---|
| A018K/E045F, A018K/L075D, D027E/G163P, D027S/P256T, E045F/N073R, F051T/L075R, K024A/V154I, L227M/L264R, N033D/E045F, A018K/E045F/N073R, A018K/E045F/V187T, A018K/V154I/G156W, D027N/S058M/P256T, D027Q/S058M/P256T, D027S/L075Q/G091Q, D027S/S058M/P256T, E056K/D130A/L264R, G023Q/K024A/G156W, I090F/N233Q/P256T, N011K/N233Q/P256T, N094R/D130A/V187T, P029E/N033D/E045F, Q004D/D027S/P256T, Q004D/S058M/N233Q, A018K/D111A/G156W/T189Q, A018K/E045F/A049V/G156W, A018K/E045F/L075D/T189D, A018K/P029E/N073R/L075D, D027E/D137Q/L227M/L264R, D027N/S058M/N233Q/P256T, D027Q/E056K/N233Q/P256T, D027S/E045F/L075D/T189D, D027S/E045F/N073R/T189D, D027S/N033D/E045F/N073R, D027S/N033D/L075D/T189D, D027S/P029E/E045F/N073R, D027S/P029E/E045F/T189D, D027S/P029E/N033D/E045F, D048Q/D137Q/G163P/L227M, E045F/A049V/G156W/V187T, E045F/L075Q/G156W/V187T, G023K/E056K/D130A/V187N, G023K/E056K/V187T/L264R, G023Q/K024A/L075R/G156W, L075G/G091Q/V187N/L264R, N011K/D027Q/S058M/P256T, N011K/D027S/N233Q/P256T, N033D/E045F/N073R/T189A, Q004D/D027N/E056K/P256T, Q004D/D027N/S058M/P256T, Q004D/D027Q/N233Q/P256T, Q004D/D027Q/S058M/P256T, Q004D/N011K/D027S/P256T, A018K/D027S/E045F/L075D/T189D, A018K/E045F/N073R/L075D/T189D, A018K/K024A/L075R/D130A/V154I, D027E/D130A/D137Q/G163P/L264R, D027Q/F051T/L075Q/D130A/L264R, D027S/E056K/D111A/V187N/L264R, D048Q/D137Q/G163P/N233Q/L264R, D048Q/S058M/G163P/L227M/L264R, E045F/A049V/L075Q/V187T/T189D, E056K/L075R/D130A/V187N/L264R, G023K/D027S/E056K/V187T/L264R, G023K/E056K/L075R/V187N/L264R, G023K/K024A/D111A/D130A/V187T, G023K/L075Q/V187H/I252Q/L264R, G023Q/D027S/L075G/I252Q/L264R, G023Q/L075Q/V077I/D130A/G156W, N011K/D027N/S058M/N233Q/P256T, N011K/D027S/I090F/N233Q/P256T, Q004D/N011K/D027N/N233Q/P256T, S058M/D137Q/G163P/L227M/N233Q, |

TABLE 7-9-continued

| TLL variants with Performance Index for expression ≥0.5 and Performance Index ≤50% of the maximum PI value in the Fabric Adhesion assay compared to TLL SEQ ID NO: 1 are shown below. |
|---|
| V077I/D130A/V154I/G156W/V187N, A018K/D027S/N033D/E045F/N073R/L075D, A018K/D027S/N033D/N073R/L075D/T189D, A018K/D027S/P029E/N033D/E045F/L075D, D027E/D048Q/S058M/D130A/G163P/L264R, D027E/D048Q/S058M/D130A/L227M/N233Q, D027Q/E056K/S058M/D130A/I252Q/L264R, D027S/E056K/S058M/V187T/I252Q/L264R, D048Q/D130A/G163P/L227M/N233Q/L264R, D048Q/S058M/G163P/L227M/N233Q/L264R, G023K/E056K/L075R/D130A/V187N/L264R, G023K/K024A/L075Q/D111A/D130A/T189Q, G023K/K024A/L075R/D130A/V154I/V187N, G023K/L075G/D130A/V187T/I252Q/L264R, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/K024A/V077I/D130A/V154I/G156W, N011K/D027S/E056K/I090F/N233Q/P256T, Q004D/N011K/D027N/S058M/N233Q/P256T, Q004D/N011K/D027S/S058M/N233Q/P256T, D048Q/S058M/D130A/D137Q/L227M/N233Q/L264R, G023Q/F051T/E056K/L075R/G091Q/V187H/I252Q, G023Q/F051T/G091Q/D130A/V187H/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/V077I/D130A/V154I/G156W, A018K/G023Q/K024A/L075R/V077I/N094R/D130A/G156W, F051T/E056K/L075G/G091Q/D130A/V187H/I252Q/L264R, G023Q/D027S/L075R/N094R/V154I/G156W/V187N/T189Q, A018K/G023Q/D027S/P029E/L075Q/V077I/R108K/H135F/V187H, G023Q/F051T/S058M/L075G/G091Q/D130A/V187T/I252Q/L264R, A018K/G023Q/D027S/P029E/S058M/L075Q/V077I/H135F/G156W/V187T, A018K/G023Q/D027S/E045F/A049V/S058M/N073S/L075Q/R108K/V187T/T189D |

TABLE 7-10

| TLL variants with Performance Index <1 in the Fabric Adhesion assay compared to Reference sequence SEQ ID NO: 2 are shown below. |
|---|
| A018K/D027S, A018K/E045F, A018K/L075D, A018K/T189D, D027E/G163P, D027N/E056K, D027N/N233Q, D027S/P256T, D130A/T189Q, E045F/N073R, E045F/T189D, F051T/L075R, G023K/D130A, G023Q/L075Q, K024A/V154I, L227M/L264R, N011K/D027S, N033D/E045F, N073R/L075D, A018K/A049V/L075Q, A018K/D027S/E045F, A018K/D027S/N073R, A018K/D027S/T189D, A018K/E045F/N073R, A018K/E045F/T189D, A018K/E045F/V187T, A018K/G023K/G156W, A018K/G023K/L075Q, A018K/N033D/L075D, A018K/N073R/L075D, A018K/V154I/G156W, A049V/L075Q/T189D, A049V/V187T/T189D, D027N/N233Q/P256T, D027N/S058M/P256T, D027Q/N233Q/P256T, D027Q/S058M/P256T, D027S/L075Q/G091Q, D027S/N073R/L075D, D027S/N233Q/P256T, D027S/S058M/P256T, D130A/V154I/G156W, E045F/L075D/T189D, E045F/N073R/L075D, E056K/D130A/L264R, E056K/D130A/T189Q, G023Q/D111A/L264R, G023Q/E045F/V077I, G023Q/E056K/L075R, G023Q/K024A/G156W, G023Q/L075Q/V077I, I090F/N233Q/P256T, K024A/L075Q/G156W, L075Q/D130A/V187T, L075Q/N094R/V154I, L075Q/V077I/T189D, N011K/D027S/S058M, N011K/N233Q/P256T, N033D/E045F/L075D, N033D/E045F/N073R, N033D/N073R/T189D, N094R/D130A/V187T, P029E/E045F/L075D, P029E/N033D/E045F, P029E/N033D/L075D, P029E/N073R/L075D, Q004D/D027S/P256T, Q004D/N233Q/P256T, Q004D/S058M/N233Q, S058M/L227M/L264R, V077I/D130A/V154I, V077I/V187A/T189D, A018K/A049V/L075Q/T189D, A018K/D027S/E045F/N073R, A018K/D027S/E045F/T189D, A018K/D027S/L075D/T189D, A018K/D027S/N033D/L075D, A018K/D111A/G156W/T189Q, A018K/E045F/A049V/G156W, A018K/E045F/A049V/V187T, A018K/E045F/L075D/T189D, A018K/E045F/L075Q/T189D, A018K/E045F/L075Q/V187T, A018K/G023Q/A049V/T189D, A018K/G023Q/E045F/T189D, A018K/G023Q/G156W/V187T, A018K/G023Q/V077I/V187T, A018K/L075Q/G156W/T189D, A018K/L075Q/G156W/V187T, A018K/L075Q/N094R/D111A, A018K/L075Q/N094R/D130A, A018K/L075Q/V187T/T189D, A018K/N073R/L075D/T189D, A018K/P029E/N033D/T189D, A018K/P029E/N073R/L075D, A018K/V154I/G156W/V187T, A049V/L075Q/V077I/T189D, A049V/L075Q/V187T/T189D, D027E/D137Q/L227M/L264R, D027N/E056K/N233Q/P256T, D027N/E056K/S058M/P256T, D027N/S058M/N233Q/P256T, D027Q/E056K/N233Q/P256T, D027Q/S058M/I090F/P256T, D027S/E045F/L075D/T189D, D027S/E045F/N073R/L075D, D027S/E045F/N073R/T189D, D027S/E056K/D111A/V154I, D027S/E056K/I090F/P256T, D027S/N033D/E045F/N073R, D027S/N033D/L075D/T189D, D027S/N033D/N073R/L075D, D027S/P029E/E045F/L075D, D027S/P029E/E045F/N073R, D027S/P029E/E045F/T189D, D027S/P029E/N033D/E045F, D027S/P029E/N033D/N073R, D048Q/D137Q/G163P/L227M, E045F/A049V/G156W/V187T, E045F/L075Q/G156W/V187T, G023K/D027S/L075Q/L264R, G023K/D111A/D130A/L264R, G023K/E056K/D130A/L264R, G023K/E056K/D130A/V187N, G023K/E056K/V187T/L264R, G023K/L075Q/G156W/L264R, G023K/L075R/V187N/L264R, G023Q/A049V/L075Q/V077I, G023Q/D027S/D111A/G156W, G023Q/E045F/A049V/T189D, G023Q/E045F/A049V/V187T, G023Q/E045F/L075Q/G156W, G023Q/E045F/L075Q/V187T, G023Q/K024A/L075R/G156W, G023Q/V154I/G156W/V187N, K024A/L075Q/D130A/G156W, K024A/L075Q/D130A/V154I, L075G/G091Q/V187N/L264R, L075Q/D130A/V154I/G156W, L075Q/G156W/V187T/L264R, L075Q/V077I/G156W/V187N, L075Q/V077I/V187T/T189D, L075Q/V187N/T189Q/L264R, N011K/D027N/E056K/S058M, N011K/D027N/S058M/P256T, N011K/D027Q/S058M/P256T, N011K/D027S/E056K/P256T, N011K/D027S/N233Q/P256T, |

TABLE 7-10-continued

| TLL variants with Performance Index <1 in the Fabric Adhesion assay compared to Reference sequence SEQ ID NO: 2 are shown below. |
|---|
| N011K/D027S/S058M/N233Q, N011K/E056K/N233Q/P256T, N011K/E056K/S058M/P256T, |
| N011K/G023K/L075Q/D111A, N011K/S058M/N233Q/P256T, N033D/E045F/N073R/T189A, |
| P029E/E045F/L075D/T189D, P029E/E045F/N073R/L075D, P029E/E045F/N073R/T189D, |
| P029E/N033D/E045F/L075D, Q004D/D027N/E056K/P256T, Q004D/D027N/S058M/P256T, |
| Q004D/D027Q/N233Q/P256T, Q004D/D027Q/S058M/P256T, Q004D/D027S/I090F/P256T, |
| Q004D/N011K/D027N/P256T, Q004D/N011K/D027Q/N233Q, Q004D/N011K/D027S/P256T, |
| Q004D/N011K/E056K/S058M, A018K/A049V/L075Q/V187T/T189D, |
| A018K/D027S/E045F/L075D/T189D, A018K/D027S/E045F/N073R/D137V, |
| A018K/D027S/N033D/E045F/T189D, A018K/D027S/N033D/N073R/T189D, |
| A018K/D027S/N073R/L075D/T189D, A018K/D027S/P029E/E045F/T189D, |
| A018K/D027S/P029E/N073R/L075D, A018K/D130A/G156W/V187T/L264R, |
| A018K/E045F/A049V/L075Q/G156W, A018K/E045F/A049V/L075Q/T189D, |
| A018K/E045F/A049V/L075Q/V187T, A018K/E045F/N073R/L075D/T189D, |
| A018K/G023K/L075Q/D130A/V154I, A018K/G023Q/A049V/L075Q/G156W, |
| A018K/G023Q/A049V/L075Q/V077I, A018K/G023Q/A049V/L075Q/V187T, |
| A018K/G023Q/A049V/V077I/V187T, A018K/G023Q/E045F/A049V/L075Q, |
| A018K/G023Q/E045F/A049V/V187T, A018K/G023Q/E045F/L075Q/V187T, |
| A018K/G023Q/E045F/V077I/T189D, A018K/G023Q/K024A/D130A/V154I, |
| A018K/G023Q/V077I/V187T/T189D, A018K/K024A/L075Q/V154I/T189D, |
| A018K/K024A/L075R/D130A/V154I, A018K/L075Q/G156W/V187T/T189D, |
| A018K/L075Q/V187T/T189Q/L264R, A018K/N033D/E045F/L075D/T189D, |
| A018K/P029E/E045F/N073R/L075D, A018K/V077I/G156W/V187T/T189D, |
| D027E/D048Q/L227M/N233Q/L264R, D027E/D048Q/S058M/G163P/N233Q, |
| D027E/D130A/D137Q/G163P/L264R, D027E/D137Q/G163P/L227M/L264R, |
| D027N/E056K/S058M/N233Q/P256T, D027N/S058M/I090F/N233Q/P256T, |
| D027Q/E056K/I090F/N233Q/P256T, D027Q/E056K/S058M/N233Q/P256T, |
| D027Q/F051T/L075Q/D130A/L264R, D027S/E056K/D111A/V187N/L264R, |
| D027S/E056K/S058M/N233Q/P256T, D027S/L075Q/D111A/D130A/V187N, |
| D027S/N033D/E045F/N073R/L075D, D027S/P029E/E045F/N073R/L075D, |
| D027S/P029E/E045F/N073R/T189D, D027S/P029E/N033D/E045F/N073R, |
| D027S/P029E/N033D/N073R/L075D, D048Q/D130A/D137Q/G163P/L264R, |
| D048Q/D137Q/G163P/N233Q/L264R, D048Q/S058M/D137Q/G163P/L264R, |
| D048Q/S058M/G163P/L227M/L264R, D130A/G163P/L227M/N233Q/L264R, |
| E045F/A049V/L075Q/V187T/T189D, E056K/D130A/V187H/I252Q/L264R, |
| E056K/L075R/D130A/V187N/L264R, E056K/N094R/G156W/V187N/L264R, |
| E056K/S058M/I090F/N233Q/P256T, F051T/S058M/L075Q/G091Q/I252Q, |
| G023K/D027S/E056K/V187T/L264R, G023K/D111A/V154I/V187T/L264R, |
| G023K/E056K/L075R/V187N/L264R, G023K/K024A/D111A/D130A/V187T, |
| G023K/K024A/L075R/D130A/G156W, G023K/L075Q/D130A/V154I/T189Q, |
| G023K/L075Q/V187H/I252Q/L264R, G023Q/A049V/L075Q/G156W/T189D, |
| G023Q/A049V/L075Q/V187T/T189D, G023Q/D027S/D111A/T189Q/L264R, |
| G023Q/D027S/L075G/I252Q/L264R, G023Q/D027S/V154I/V187N/L264R, |
| G023Q/E045F/A049V/G156W/T189D, G023Q/E045F/A049V/L075Q/V077I, |
| G023Q/E045F/A049V/V077I/T189D, G023Q/E045F/L075Q/G156W/T189D, |
| G023Q/E045F/L075Q/V077I/V187T, G023Q/K024A/L075Q/D130A/G156W, |
| G023Q/K024A/L075R/D130A/V154I, G023Q/K024A/L075R/V077I/D130A, |
| G023Q/L075Q/V077I/D130A/G156W, K024A/L075R/D111A/V154I/V187T, |
| K024A/L075R/G156W/V187N/T189Q, L075Q/D111A/D130A/V187T/T189Q, |
| L075Q/D130A/V187T/T189Q/L264R, L075Q/N094R/D130A/G156W/V187T, |
| L075Q/V077I/D130A/G156W/V187N, L075R/D111A/D130A/V187N/T189Q, |
| L075R/V077I/N094R/V154I/G156W, N011K/D027N/E056K/N233Q/P256T, |
| N011K/D027N/E056K/S058M/P256T, N011K/D027N/S058M/N233Q/P256T, |
| N011K/D027Q/E056K/S058M/N233Q, N011K/D027Q/I090F/N233Q/P256T, |
| N011K/D027Q/S058M/I090F/P256T, N011K/D027Q/S058M/N233Q/P256T, |
| N011K/D027S/E056K/N233Q/P256T, N011K/D027S/I090F/N233Q/P256T, |
| N011K/G023Q/L075Q/V187N/T189Q, P029E/N033D/E045F/L075D/T189D, |
| P029E/N033D/K074S/L075D/T189D, Q004D/D027N/E056K/S058M/P256T, |
| Q004D/D027N/I090F/N233Q/P256T, Q004D/D027Q/E056K/N233Q/P256T, |
| Q004D/D027Q/E056K/S058M/P256T, Q004D/D027S/E056K/N233Q/P256T, |
| Q004D/D027S/E056K/S058M/P256T, Q004D/D027S/S058M/N233Q/P256T, |
| Q004D/N011K/D027N/N233Q/P256T, Q004D/N011K/D027Q/E056K/N233Q, |
| Q004D/N011K/D027Q/S058M/N233Q, Q004D/N011K/I090F/N233Q/P256T, |
| S058M/D137Q/G163P/L227M/N233Q, V077I/D130A/V154I/G156W/V187N, |
| A018K/D027S/N033D/E045F/L075D/T189D, A018K/D027S/N033D/E045F/N073R/L075D, |
| A018K/D027S/N033D/N073R/L075D/T189D, A018K/D027S/P029E/N033D/E045F/L075D, |
| A018K/D027S/P029E/N033D/L075D/T189D, A018K/D027S/P029E/N073R/L075D/T189D, |
| A018K/E045F/A049V/L075Q/V077I/V187T, A018K/G023K/D111A/D130A/V154I/T189Q, |
| A018K/G023K/K024A/L075R/D111A/L264R, A018K/G023K/L075R/N094R/D130A/V187N, |
| A018K/G023K/L075R/V077I/D130A/V154I, A018K/G023Q/A049V/L075Q/V077I/G156W, |
| A018K/G023Q/A049V/V077I/V187T/T189D, A018K/G023Q/E045F/A049V/G156W/V187T, |
| A018K/G023Q/E045F/A049V/L075Q/T189D, A018K/G023Q/E045F/A049V/L075Q/V077I, |
| A018K/G023Q/E045F/A049V/L075Q/V187T, A018K/G023Q/E045F/G156W/V187T/T189D, |
| A018K/G023Q/E045F/L075Q/G156C/V187T, A018K/G023Q/E045F/L075Q/G156W/V187T, |
| A018K/G023Q/K024A/L075R/N094R/G156W, A018K/G023Q/L075Q/V077I/D130A/G156W, |
| A018K/G023Q/L075Q/V077I/N094R/V154I, A018K/K024A/V077I/N094R/D130A/G156W, |
| A018K/L075Q/D111A/V154I/G156W/V187N, A018K/L075Q/D111A/V154I/T189Q/L264R, |
| A018K/N033D/E045F/N073R/L075D/T189D, A018K/P029E/N033D/E045F/L075D/T189D, |

TABLE 7-10-continued

| TLL variants with Performance Index <1 in the Fabric Adhesion assay compared to Reference sequence SEQ ID NO: 2 are shown below. |
| --- |
| D027E/D048Q/S058M/D130A/G163P/L264R, D027E/D048Q/S058M/D130A/L227M/N233Q, D027Q/E056K/S058M/D130A/I252Q/L264R, D027Q/E056K/S058M/I090F/N233Q/P256T, D027S/E056K/S058M/V187T/I252Q/L264R, D027S/G091Q/D130A/V187N/I252Q/L264R, D027S/L075Q/D111A/G156W/V187N/T189Q, D027S/P029E/N033D/E045F/N073R/L075D, D027S/P029E/N033D/E045F/N073R/T189D, D027S/P029E/N033D/N073R/L075D/T189D, D048Q/D130A/G163P/L227M/N233Q/L264R, D048Q/S058M/G163P/L227M/N233Q/L264R, E045F/A049V/L075Q/V077I/V187T/T189D, F051T/L075G/G091Q/D130A/I252Q/L264R, G023K/E056K/L075R/D130A/V187N/L264R, G023K/K024A/L075Q/D111A/D130A/T189Q, G023K/K024A/L075Q/G156W/V187T/T189Q, G023K/K024A/L075R/D130A/V154I/V187N, G023K/L075G/D130A/V187T/I252Q/L264R, G023K/L075Q/V077I/D130A/G156W/V187Q, G023Q/A049V/L075Q/G156W/V187T/T189D, G023Q/D027S/F051T/L075Q/V187T/I252Q, G023Q/D027S/L075Q/D111A/G156W/L264R, G023Q/D027S/L075R/D111A/V187N/L264R, G023Q/D027S/N094R/V154I/G156W/T189Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/E056K/D111A/D130A/V187N/T189Q, G023Q/E056K/L075Q/D130A/V154I/L264R, G023Q/F051T/D130A/V187T/I252Q/L264R, G023Q/K024A/L075Q/D130A/V154I/G156W, G023Q/K024A/V077I/D130A/V154I/G156W, G023Q/L075Q/N094R/D111A/G156W/L264R, G023Q/L075Q/V077I/N094R/D130A/V187Q, K024A/D111A/D130A/V187T/T189Q/L264R, K024A/L075Q/D130A/G156W/T189Q/L264R, K024A/L075R/D111A/V154I/G156W/V187N, L075Q/D111A/D130A/V154I/G156W/T189Q, L075Q/N094R/D111A/G156W/T189Q/L264R, N011K/D027N/E056K/I090F/N233Q/P256T, N011K/D027N/E056K/S058M/N233Q/P256T, N011K/D027N/S058M/I090F/N233Q/P256T, N011K/D027Q/E056K/S058M/N233Q/P256T, N011K/D027Q/S058M/I090F/N233Q/P256T, N011K/D027S/E056K/I090F/N233Q/P256T, N011K/D027S/E056K/S058M/I090F/P256T, N011K/D027S/E056K/S058M/N233Q/P256T, N011K/D027S/S058M/I090F/N233Q/P256T, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/S058M/N233Q/P256T, Q004D/N011K/D027Q/E056K/S058M/N233Q, Q004D/N011K/D027S/I090F/N233Q/P256T, Q004D/N011K/D027S/S058M/N233Q/P256T, A018K/E045F/L075Q/V077I/G156W/V187T/T189D, A018K/G023Q/E045F/A049V/L075Q/G156W/V187T, A018K/G023Q/E045F/L075Q/G156W/V187T/T189D, A018K/G023Q/E045F/L075Q/V077I/G156W/V187T, A018K/G023Q/K024A/L075R/N094R/G156W/V187N, A018K/L075Q/D111A/D130A/V154I/G156W/L264R, A018K/L075Q/D130A/G156W/V187N/T189Q/L264R, A018K/L075Q/N094R/D111A/V154I/V187T/L264R, D027E/S058M/D130A/D137Q/G163P/N233Q/L264R, D027Q/F051T/L075Q/G091Q/D130A/V187T/I252Q, D027S/E056K/L075R/D111A/G156W/V187N/L264R, D027S/L075R/V154I/G156W/V187N/T189Q/L264R, D027S/P029E/N033D/E045F/N073R/L075D/T189D, D048Q/S058M/D130A/D137Q/L227M/N233Q/L264R, E056K/L075Q/D111A/D130A/G156W/V187N/T189Q, G023K/D027S/L075Q/N094R/V154I/G156W/T189Q, G023K/F051T/E056K/L075R/D130A/V187T/I252Q, G023K/F051T/L075Q/G091Q/D130A/V187H/I252Q, G023K/K024A/L075Q/N094R/V154I/G156W/V187N, G023K/L075Q/D111A/D130A/V154I/G156W/L264R, G023K/L075Q/D111A/V154I/G156W/T189Q/L264R, G023K/L075Q/D130A/G156W/V187N/T189Q/L264R, G023K/L075Q/N094R/D130A/V154I/V187N/L264R, G023Q/D027S/L075Q/V154I/G156W/V187N/L264R, G023Q/E045F/A049V/V077I/G156W/V187T/T189D, G023Q/E045F/L075Q/V077I/G156W/V187T/T189D, G023Q/F051T/E056K/L075R/G091Q/V187H/I252Q, G023Q/F051T/G091Q/D130A/V187H/I252Q/L264R, K024A/L075Q/D111A/D130A/V187N/T189Q/L264R, K024A/L075R/D130A/V154I/G156W/T189Q/L264R, N011K/D027N/E056K/S058M/I090F/N233Q/P256T, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, N011K/G023Q/L075Q/V154I/V187N/T189Q/L264R, Q004D/D027N/E056K/S058M/I090F/N233Q/P256T, Q004D/N011K/D027N/S058M/I090F/N233Q/P256T, Q004D/N011K/D027Q/E056K/S058M/N233Q/P256T, Q004D/N011K/D027Q/S058M/I090F/N233Q/P256T, Q004D/N011K/D027S/E056K/S058M/N233Q/P256T, A018K/G023K/K024A/L075Q/V077I/D130A/V154I/G156W, A018K/G023K/L075R/V077I/N094R/D130A/G156W/V187Q, A018K/G023Q/E045F/L075Q/V077I/G156W/V187T/T189D, A018K/G023Q/K024A/L075R/V077I/N094R/D130A/G156W, A018K/G023Q/L075Q/V077I/D130A/V154I/G156W/V187N, A018K/L075Q/N094R/D111A/V154I/G156W/T189Q/L264R, |

TABLE 7-10-continued

| TLL variants with Performance Index <1 in the Fabric Adhesion assay compared to Reference sequence SEQ ID NO: 2 are shown below. |
|---|
| F051T/E056K/L075G/G091Q/D130A/V187H/I252Q/L264R, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/K024A/L075R/N094R/V154I/G156W/V187T/T189Q, G023K/L075Q/D111A/V154I/G156W/V187N/T189Q/L264R, G023Q/D027S/L075Q/D130A/V154I/G156W/T189Q/L264R, G023Q/D027S/L075R/N094R/V154I/G156W/V187N/T189Q, G023Q/E056K/L075Q/D111A/V154I/V187N/T189Q/L264R, G023Q/L075Q/D111A/D130A/V154I/G156W/V187N/L264R, G023Q/L075Q/N094R/D130A/V154I/G156W/T189Q/L264R, N011K/G023K/D027S/L075Q/D111A/D130A/V154I/T189Q, N011K/G023K/E056K/L075Q/D130A/V154I/T189Q/L264R, N011K/G023K/L075Q/D111A/G156W/V187N/T189Q/L264R, N011K/G023Q/D027S/L075Q/N094R/V154I/G156W/T189Q, N011K/G023Q/L075Q/D111A/D130A/V154I/V187N/L264R, A018K/G023K/K024A/L075Q/N094R/D130A/V154I/G156W/V187N, A018K/G023Q/D027S/L075Q/V077I/R108K/H135F/G156W/V187T, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/K024A/L075Q/N094R/V154I/G156W/V187N/T189Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023Q/D027S/L075Q/N094R/D111A/D130A/V154I/G156W/L264R, G023Q/F051T/S058M/L075G/G091Q/D130A/V187T/I252Q/L264R, N011K/G023K/D027S/E056K/L075R/D111A/G156W/V187N/L264R, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/E045F/A049V/S058M/N073S/L075Q/V187T/T189D, A018K/G023Q/D027S/P029E/S058M/L075Q/V077I/H135F/G156W/V187T, A018K/G023Q/D027S/S058M/L075Q/V077I/R108K/H135F/G156W/V187H, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/G023K/L075R/N094R/D111A/V154I/G156W/V187N/T189Q/L264R, N011K/G023Q/D027S/E056K/L075R/D130A/V154I/G156W/T189Q/L264R, N011K/G023Q/L075Q/N094R/D111A/D130A/V154I/G156W/V187N/L264R, A018K/G023Q/D027S/E045F/A049V/S058M/N073S/L075Q/R108K/V187T/T189D, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 7-11

| TLL variants with Performance Index for expression ≥0.5 compared to TLL SEQ ID NO: 1 and Performance Index <1 in the Fabric Adhesion assay compared to Reference sequence SEQ ID NO: 2 are shown below. |
|---|
| A018K/E045F, A018K/L075D, D027E/G163P, D027S/P256T, E045F/N073R, F051T/L075R, K024A/V154I, L227M/L264R, N033D/E045F, A018K/E045F/N073R, A018K/E045F/V187T, A018K/V154I/G156W, D027N/S058M/P256T, D027Q/S058M/P256T, D027S/L075Q/G091Q, D027S/S058M/P256T, D130A/V154I/G156W, E056K/D130A/L264R, G023Q/K024A/G156W, I090F/N233Q/P256T, N011K/N233Q/P256T, N094R/D130A/V187T, P029E/N033D/E045F, Q004D/D027S/P256T, Q004D/S058M/N233Q, A018K/D111A/G156W/T189Q, A018K/E045F/A049V/G156W, A018K/E045F/L075D/T189D, A018K/P029E/N073R/L075D, D027E/D137Q/L227M/L264R, D027N/S058M/N233Q/P256T, D027Q/E056K/N233Q/P256T, D027S/E045F/L075D/T189D, D027S/E045F/N073R/T189D, D027S/N033D/E045F/N073R, D027S/N033D/L075D/T189D, D027S/P029E/E045F/N073R, D027S/P029E/E045F/T189D, D027S/P029E/N033D/E045F, D048Q/D137Q/G163P/L227M, E045F/A049V/G156W/V187T, E045F/L075Q/G156W/V187T, G023K/E056K/D130A/V187N, G023K/E056K/V187T/L264R, G023Q/K024A/L075R/G156W, L075G/G091Q/V187N/L264R, N011K/D027Q/S058M/P256T, N011K/D027S/N233Q/P256T, N033D/E045F/N073R/T189A, Q004D/D027N/E056K/P256T, Q004D/D027N/S058M/P256T, Q004D/D027Q/N233Q/P256T, Q004D/D027Q/S058M/P256T, Q004D/N011K/D027S/P256T, A018K/D027S/E045F/L075D/T189D, A018K/E045F/N073R/L075D/T189D, A018K/K024A/L075R/D130A/V154I, D027E/D130A/D137Q/G163P/L264R, D027Q/F051T/L075Q/D130A/L264R, D027S/E056K/D111A/V187N/L264R, D048Q/D137Q/G163P/N233Q/L264R, |

TABLE 7-11-continued

| TLL variants with Performance Index for expression ≥0.5 compared to TLL SEQ ID NO: 1 and Performance Index <1 in the Fabric Adhesion assay compared to Reference sequence SEQ ID NO: 2 are shown below. |
|---|
| D048Q/S058M/G163P/L227M/L264R, E045F/A049V/L075Q/V187T/T189D, E056K/L075R/D130A/V187N/L264R, F051T/S058M/L075Q/G091Q/I252Q, G023K/D027S/E056K/V187T/L264R, G023K/E056K/L075R/V187N/L264R, G023K/K024A/D111A/D130A/V187T, G023K/L075Q/V187H/I252Q/L264R, G023Q/D027S/L075G/I252Q/L264R, G023Q/L075Q/V077I/D130A/G156W, N011K/D027N/S058M/N233Q/P256T, N011K/D027S/I090F/N233Q/P256T, Q004D/N011K/D027N/N233Q/P256T, S058M/D137Q/G163P/L227M/N233Q, V077I/D130A/V154I/G156W/V187N, A018K/D027S/N033D/E045F/N073R/L075D, A018K/D027S/N033D/N073R/L075D/T189D, A018K/D027S/P029E/N033D/E045F/L075D, A018K/G023Q/K024A/L075R/N094R/G156W, D027E/D048Q/S058M/D130A/G163P/L264R, D027E/D048Q/S058M/D130A/L227M/N233Q, D027Q/E056K/S058M/D130A/I252Q/L264R, D027S/E056K/S0581M/V187T/I252Q/L264R, D048Q/D130A/G163P/L227M/N233Q/L264R, D048Q/S058M/G163P/L227M/N233Q/L264R, F051T/L075G/G091Q/D130A/I252Q/L264R, G023K/E056K/L075R/D130A/V187N/L264R, G023K/K024A/L075Q/D111A/D130A/T189Q, G023K/K024A/L075R/D130A/V154I/V187N, G023K/L075G/D130A/V187T/I252Q/L264R, G023Q/D027S/N094R/V154I/G156W/T189Q, G023Q/E056K/D111A/D130A/V187N/T189Q, G023Q/E056K/L075Q/D130A/V154I/L264R, G023Q/F051T/D130A/V187T/I252Q/L264R, G023Q/K024A/V077I/D130A/V154I/G156W, N011K/D027S/E056K/I090F/N233Q/P256T, Q004D/N011K/D027N/S058M/N233Q/P256T, Q004D/N011K/D027S/S058M/N233Q/P256T, D048Q/S058M/D130A/D137Q/L227M/N233Q/L264R, G023Q/F051T/E056K/L075R/G091Q/V187H/I252Q, G023Q/F051T/G091Q/D130A/V187H/I252Q/L264R, N011K/D027N/E056K/S058M/I090F/N233Q/P256T, N011K/G023Q/L075Q/V154I/V187N/T189Q/L264R, Q004D/N011K/D027S/E056K/S058M/N233Q/P256T, A018K/G023K/K024A/L075Q/V077I/D130A/V154I/G156W, A018K/G023Q/K024A/L075R/V077I/N094R/D130A/G156W, F051T/E056K/L075G/G091Q/D130A/V187H/I252Q/L264R, G023Q/D027S/L075R/N094R/V154I/G156W/V187N/T189Q, A018K/G023Q/D027S/P029E/L075Q/V077I/R108K/H135F/V187H, G023Q/F051T/S058M/L075G/G091Q/D130A/V187T/I252Q/L264R, A018K/G023Q/D027S/P029E/S058M/L075Q/V077I/H135F/G156W/V187T, A018K/G023Q/D027S/E045F/A049V/S058M/N073S/L075Q/R108K/V187T/T189D |

TABLE 7-12

| TLL variants with Performance Index for expression ≥0.5 compared to TLL SEQ ID NO: 1 and Performance Index ≤50% of the maximum PI value in the Fabric Adhesion assay compared to Reference sequence SEQ ID NO: 2 are shown below. |
|---|
| A018K/E045F, A018K/L075D, D027E/G163P, E045F/N073R, F051T/L075R, K024A/V154I, L227M/L264R, N033D/E045F, A018K/E045F/N073R, A018K/V154I/G156W, D027S/L075Q/G091Q, D027S/S058M/P256T, E056K/D130A/L264R, I090F/N233Q/P256T, N011K/N233Q/P256T, Q004D/S058M/N233Q, A018K/D111A/G156W/T189Q, A018K/E045F/L075D/T189D, D027E/D137Q/L227M/L264R, D027Q/E056K/N233Q/P256T, D027S/E045F/L075D/T189D, D027S/E045F/N073R/T189D, D027S/N033D/E045F/N073R, D027S/P029E/E045F/N073R, D027S/P029E/N033D/E045F, D048Q/D137Q/G163P/L227M, G023K/E056K/D130A/V187N, G023K/E056K/V187T/L264R, G023Q/K024A/L075R/G156W, L075G/G091Q/V187N/L264R, N033D/E045F/N073R/T189A, Q004D/D027N/S058M/P256T, Q004D/D027Q/N233Q/P256T, Q004D/D027Q/S058M/P256T, Q004D/N011K/D027S/P256T, A018K/D027S/E045F/L075D/T189D, A018K/E045F/N073R/L075D/T189D, A018K/K024A/L075R/D130A/V154I, D027Q/F051T/L075Q/D130A/L264R, D048Q/D137Q/G163P/N233Q/L264R, E045F/A049V/L075Q/V187T/T189D, E056K/L075R/D130A/V187N/L264R, G023K/E056K/L075R/V187N/L264R, G023K/K024A/D111A/D130A/V187T, G023K/L075Q/V187H/I252Q/L264R, G023Q/D027S/L075G/I252Q/L264R, N011K/D027N/S058M/N233Q/P256T, N011K/D027S/I090F/N233Q/P256T, S058M/D137Q/G163P/L227M/N233Q, A018K/D027S/N033D/E045F/N073R/L075D, A018K/D027S/N033D/N073R/L075D/T189D, A018K/D027S/P029E/N033D/E045F/L075D, D027E/D048Q/S058M/D130A/G163P/L264R, D027E/D048Q/S058M/D130A/L227M/N233Q, D027S/E056K/S058M/V187T/I252Q/L264R, D048Q/D130A/G163P/L227M/N233Q/L264R, D048Q/S058M/G163P/L227M/N233Q/L264R, G023K/K024A/L075Q/D111A/D130A/T189Q, G023K/L075G/D130A/V187T/I252Q/L264R, G023Q/E056K/D111A/D130A/V187N/T189Q, G023Q/K024A/V077I/D130A/V154I/G156W, N011K/D027S/E056K/I090F/N233Q/P256T, Q004D/N011K/D027S/S058M/N233Q/P256T, D048Q/S058M/D130A/D137Q/L227M/N233Q/L264R, G023Q/F051T/E056K/L075R/G091Q/V187H/I252Q, G023Q/F051T/G091Q/D130A/V187H/I252Q/L264R, N011K/D027N/E056K/S058M/I090F/N233Q/P256T, Q004D/N011K/D027S/E056K/S058M/N233Q/P256T, A018K/G023Q/K024A/L075R/V077I/N094R/D130A/G156W, A018K/G023Q/D027S/P029E/L075Q/V077I/R108K/H135F/V187H, G023Q/F051T/S058M/L075G/G091Q/D130A/V187T/I252Q/L264R, |

TABLE 7-12-continued

| TLL variants with Performance Index for expression ≥0.5 compared to TLL SEQ ID NO: 1 and Performance Index ≤50% of the maximum PI value in the Fabric Adhesion assay compared to Reference sequence SEQ ID NO: 2 are shown below. |
|---|
| A018K/G023Q/D027S/P029E/S058M/L075Q/V077I/H135F/G156W/V187T, A018K/G023Q/D027S/E045F/A049V/S058M/N073S/L075Q/R108K/V187T/T189D |

Example 8

Cleaning Performance of TLL Combinatorial Variants

The cleaning performance of TLL variants created as described in Example 2 was assayed as described in Example 1 (CS-61 microswatch Assay) using Tide® half dose+adjuvant or Tide® full dose. The performance index was calculated for the variants compared to TLL, SEQ ID NO:1 or the reference sequence SEQ ID NO: 2.

TABLE 8-1

| TLL variants with Performance Index >1 compared to TLL SEQ ID NO: 1 in the CS-61 microswatch Assay using Tide ® half dose + adjuvant are shown below. |
|---|
| A018K/L075Q, A018K/T189D, D027S/N033D, D130A/L264R, D130A/V187T, G023K/D130A, K024A/L075Q, L075Q/D130A, L075Q/G156W, L075R/L264R, N033D/E045F, P029E/N033D, V187T/L264R, A018K/A049V/L075Q, A018K/D027S/E045F, A018K/D027S/N073R, A018K/D027S/T189D, A018K/E045F/T189D, A018K/E045F/V187T, A018K/G023K/L075Q, A018K/G023Q/L075Q, A018K/L075D/T189D, A018K/L075Q/G156W, A018K/L075Q/V187T, A018K/N033D/L075D, A018K/N073R/L075D, A018K/P029E/T189D, A049V/V187T/T189D, D027E/S058M/G163P, D027S/L075Q/G091Q, D027S/N033D/T189D, D027S/N233Q/P256T, D111A/D130A/L264R, E045F/N073R/L075D, E056K/D130A/T189Q, F051T/I252Q/L264R, G023K/E056K/V187T, G023K/V187N/L264R, G023Q/A049V/T189D, G023Q/D111A/L264R, G023Q/E056K/L075R, G023Q/L075Q/V077I, G023Q/L075Q/V187T, G163P/L227M/L264R, K024A/L075Q/V077I, L075G/D130A/V187H, L075Q/D111A/D130A, L075Q/D130A/V187T, L075Q/G156W/T189D, L075Q/G156W/V187N, L075Q/V077I/T189D, L075Q/V154I/V187T, L075Q/V187N/L264R, L075Q/V187T/L264R, L075Q/V187T/T189D, L075R/D130A/L264R, L075R/D130A/V187T, L075R/V187N/L264R, N033D/E045F/L075D, N033D/E045F/N073R, N033D/N073R/T189D, N073R/L075D/T189D, P029E/E045F/L075D, P029E/L075D/T189D, P029E/N033D/E045F, P029E/N033D/L075D, P029E/N073R/L075D, Q004D/N233Q/P256T, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/T189D, A018K/D027S/N033D/L075D, A018K/D027S/P029E/T189D, A018K/D130A/G156W/V187T, A018K/E045F/L075Q/T189D, A018K/E045F/L075Q/V187T, A018K/G023Q/A049V/T189D, A018K/G023Q/E045F/T189D, A018K/G023Q/E045F/V187T, A018K/G023Q/L075Q/T189D, A018K/G023Q/L075Q/V077I, A018K/G023Q/L075Q/V187T, A018K/G023Q/L075R/D130A, A018K/G023Q/V187T/T189D, A018K/L075Q/G156W/T189D, A018K/L075Q/N094R/D111A, A018K/L075Q/N094R/V187Q, A018K/L075Q/V077I/N094R, A018K/N033D/L075D/T189D, A018K/N073R/L075D/T189D, A018K/P029E/N033D/T189D, A049V/L075Q/V077I/T189D, A049V/L075Q/V187T/T189D, D027E/D130A/N233Q/L264R, D027E/D137Q/G163P/L227M, D027E/D137Q/L227M/L264R, D027E/L227M/N233Q/L264R, D027E/S058M/G163P/L264R, D027S/D130A/I252Q/L264R, D027S/E056K/D111A/V154I, D027S/N033D/E045F/T189D, D027S/N033D/L075D/T189D, D027S/N033D/N073R/T189D, D027S/P029E/E045F/L075D, D027S/P029E/L075D/T189D, D027S/P029E/N033D/E045F, D027S/P029E/N033D/L075D, D027S/P029E/N033D/T189D, D048Q/D130A/G163P/L264R, D048Q/G163P/N233Q/L264R, D111A/D130A/V154I/L264R, D130A/G163P/L227M/L264R, D130A/G163P/N233Q/L264R, E056K/D130A/V187N/L264R, E056K/L075Q/V187N/L264R, F051T/D130A/I252Q/L264R, F051T/L075G/I252Q/L264R, F051T/L075Q/I252Q/L264R, G023K/D027Q/F051T/L075Q, G023K/D130A/G156W/T189Q, G023K/D130A/V187T/L264R, G023K/D130A/V187T/T189Q, G023K/E056K/V187T/L264R, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187N/L264R, G023Q/A049V/L075Q/T189D, G023Q/A049V/L075Q/V077I, G023Q/A049V/V077I/G156W, G023Q/D027S/D111A/G156W, G023Q/E045F/A049V/T189D, G023Q/E045F/L075Q/G156W, G023Q/E045F/L075Q/V187T, G023Q/K024A/L075R/V154I, G023Q/L075Q/D130A/L264R, G023Q/L075Q/G156W/V187N, G023Q/L075Q/G156W/V187T, G023Q/L075Q/V187T/L264R, K024A/D130A/V154I/V187T, K024A/L075Q/D130A/G156W, K024A/L075Q/V187T/T189Q, K024A/L075R/G156W/V187N, L075G/D130A/V187T/I252Q, L075G/V187H/I252Q/L264R, L075Q/D130A/G156W/V187N, L075Q/D130A/V154I/G156W, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D130A/V154I/L264R, L075R/D130A/V187T/L264R, N011K/D027N/S058M/P256T, N011K/D027S/N233Q/P256T, N011K/E056K/S058M/P256T, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027S/I090F/P256T, Q004D/N011K/D027N/P256T, S058M/D137Q/G163P/N233Q, S058M/G163P/L227M/L264R, S058M/G163P/N233Q/L264R, S058M/L075Q/G091Q/I252Q, A018K/D027S/E045F/N073R/D137V, |

TABLE 8-1-continued

| TLL variants with Performance Index >1 compared to TLL SEQ ID NO: 1 in the CS-61 microswatch Assay using Tide ® half dose + adjuvant are shown below. |
|---|
| A018K/D027S/N033D/E045F/T189D, A018K/D027S/N033D/L075D/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/E045F/N073R/L075D/T189D, A018K/G023K/D130A/V154I/G156W, A018K/G023K/K024A/D130A/G156W, A018K/G023K/K024A/L075R/N094R, A018K/G023K/L075Q/D130A/V154I, A018K/G023Q/A049V/L075Q/G156W, A018K/G023Q/A049V/L075Q/V187T, A018K/G023Q/A049V/V077I/V187T, A018K/G023Q/E045F/L075Q/V187T, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/N094R/D130A, A018K/K024A/N094R/D130A/V187N, A018K/L075Q/D111A/D130A/V187T, A018K/L075Q/N094R/D130A/V187N, A018K/L075Q/N094R/G156W/V187N, A018K/L075Q/V077I/N094R/G156W, A018K/N033D/E045F/L075D/T189D, A018K/P029E/E045F/N073R/L075D, A018K/P029E/N033D/N073R/L075D, D027E/D130A/G163P/N233Q/L264R, D027E/D137Q/G163P/L227M/L264R, D027E/D137Q/G163P/N233Q/L264R, D027E/G163P/L227M/N233Q/L264R, D027E/S058M/D130A/G163P/L264R, D027E/S058M/G163P/L227M/L264R, D027S/E056K/D111A/V187N/L264R, D027S/E056K/S058M/N233Q/P256T, D027S/L075G/D130A/I252Q/L264R, D027S/L075G/G091Q/I252Q/L264R, D027S/L075R/V154I/T189Q/L264R, D027S/N033D/E045F/N073R/L075D, D027S/N033D/N073R/L075D/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/L264R, D048Q/S058M/D137Q/G163P/N233E, D130A/D137Q/G163P/L227M/L264R, D130A/D137Q/G163P/N233Q/L264R, E056K/D130A/V187H/I252Q/L264R, E056K/L075G/V187N/I252Q/L264R, E056K/L075Q/G156W/T189Q/L264R, E056K/L075R/D130A/V187T/L264R, F051T/L075G/D130A/I252Q/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/D111A/V154I/V187T/L264R, G023K/E056K/D130A/V187T/L264R, G023K/E056K/L075R/D130A/V187T, G023K/E056K/L075R/V187N/L264R, G023K/E056K/L075RM87T/L264R, G023K/K024A/L075R/D130A/G156W, G023K/L075Q/D111A/D130A/V187T, G023K/L075Q/D130A/G156W/L264R, G023K/L075Q/V077I/D130A/G156W, G023K/L075Q/V187H/I252Q/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/D111A/T189Q/L264R, G023Q/D027S/V154I/V187N/L264R, G023Q/E045F/L075Q/G156W/T189D, G023Q/E045F/L075Q/V077I/V187T, G023Q/E056K/V187N/I252Q/L264R, G023Q/F051T/L075Q/G091Q/I252Q, G023Q/K024A/L075Q/G156W/V187N, G023Q/K024A/L075Q/V077I/V187Q, G023Q/K024A/L075R/D130A/V154I, G023Q/K024A/L075R/G156W/V187Q, G023Q/K024A/V077I/D130A/V154I, G023Q/L075G/G091Q/I252Q/L264R, G023Q/L075Q/D130A/I252Q/L264R, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/V154I/G156W/V187Q, L075G/D130A/V187T/I252Q/L264R, L075Q/D111A/D130A/V187T/T189Q, L075Q/D111A/V187N/T189Q/L264R, L075Q/N094R/D130A/G156W/V187T, L075Q/V154I/V187N/T189Q/L264R, L075R/D111A/D130A/V187N/T189Q, L075R/D130A/V154I/T189Q/L264R, L075R/D130A/V187T/T189Q/L264R, L075R/G156W/V187T/T189Q/L264R, N011K/D027N/E056K/N233Q/P256T, N011K/D027N/E056K/S058M/P256T, N011K/G023K/D111A/G156W/L264R, N011K/G023K/E056K/L075Q/T189Q, N011K/G023Q/L075Q/V187N/T189Q, P029E/N033D/E045F/L075D/T189D, P029E/N033D/K074S/L075D/T189D, P029E/N033D/N073R/L075D/T189D, Q004D/D027Q/E056K/N233Q/P256T, Q004D/N011K/D027Q/E056K/N233Q, Q004D/N011K/I090F/N233Q/P256T, S058M/D130A/D137Q/G163P/L264R, S058M/D130A/G163P/L227M/L264R, S058M/D137Q/G163P/L227M/L264R, S058M/G163P/L227M/N233Q/L264R, A018K/A049V/L075Q/G156W/V187T/T189D, A018K/D027S/N033D/E045F/L075D/T189D, A018K/D027S/P029E/N073R/L075D/T189D, A018K/G023K/D111A/D130A/V154I/T189Q, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/V187T, A018K/G023Q/E045F/A049V/L075Q/T189D, A018K/G023Q/E045F/A049V/L075Q/V077I, A018K/G023Q/E045F/L075Q/G156W/V187T, A018K/G023Q/K024A/V077I/V154I/V187N, A018K/G023Q/L075Q/G156W/V187T/T189D, A018K/G023Q/L075Q/V077I/D130A/V187N, A018K/G023Q/L075Q/V077I/G156W/V187N, A018K/G023Q/L075Q/V077I/V187T/T189D, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/N094R/V154I/V187N, |

TABLE 8-1-continued

| TLL variants with Performance Index >1 compared to TLL SEQ ID NO: 1 in the CS-61 microswatch Assay using Tide ® half dose + adjuvant are shown below. |
|---|
| A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D027S/P029E/N033D/E045F/N073R/L075D, D027S/P029E/N033D/E045F/N073R/T189D, D027S/P029E/N033D/N073R/L075D/T189D, D048Q/D137Q/G163P/L227M/N233Q/L264R, D048Q/S058M/D130A/D137Q/G163P/L264R, D048Q/S058M/D130A/G163P/L227M/L264R, D048Q/S058M/D130A/G163P/N233Q/L264R, D048Q/S058M/D137Q/G163P/L227M/L264R, D048Q/S058M/G163P/L227M/N233Q/L264R, D111A/D130A/V154I/G156W/V187N/L264R, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075M252Q/L264R, G023Q/D027S/F051T/L075Q/V187T/I252Q, G023Q/D027S/L075G/D130A/V187H/L264R, G023Q/D027S/L075Q/D130A/V187T/I252Q, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/F051T/D130A/V187T/I252Q/L264R, G023Q/F051T/G091Q/V187N/I252Q/L264R, G023Q/F051T/L075G/G091Q/V187N/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/V077I/D130A/G156W/V187N, G023Q/L075Q/V077I/N094R/D130A/V187Q, G023Q/L075R/V154I/G156W/V187N/L264R, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, K024A/L075Q/V154I/V187N/T189Q/L264R, K024A/L075Q/V154I/V187T/T189Q/L264R, K024A/L075R/D111A/V154I/G156W/V187N, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075Q/N094R/D111A/G156W/T189Q/L264R, N011K/D027N/S058M/I090F/N233Q/P256T, N011K/D027Q/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027S/E056K/S058M/N233Q/P256T, Q004D/N011K/D027Q/E056K/S058M/N233Q, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/E045F/L075Q/V077I/G156W/V187T/T189D, A018K/G023K/K024A/L075Q/D130A/G156W/V187N, A018K/G023K/K024A/L075Q/N094R/G156W/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/L075Q/D111A/G156W/V187N/L264R, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/L075Q/D111A/D130A/V154I/G156W/L264R, A018K/L075Q/D111A/V154I/V187T/T189Q/L264R, A018K/L075Q/N094R/D111A/V154I/V187T/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D048Q/S058M/D137Q/G163P/L227M/L264R, D027E/D130A/D137Q/G163P/L227M/N233Q/L264R, |

TABLE 8-1-continued

| TLL variants with Performance Index >1 compared to TLL SEQ ID NO: 1 in the CS-61 microswatch Assay using Tide ® half dose + adjuvant are shown below. |
|---|
| D027E/S058M/D130A/D137Q/G163P/L227M/L264R, |
| D027E/S058M/D130A/D137Q/G163P/N233Q/L264R, |
| D027E/S058M/D137Q/G163P/L227M/N233Q/L264R, |
| D027Q/F051T/L075G/D130A/V187H/I252Q/L264R, |
| D027Q/F051T/L075Q/G091Q/D130A/V187T/I252Q, |
| D027Q/F051T/S058M/L075Q/G091Q/I252Q/L264R, |
| D027Q/L075G/G091Q/D130A/V187H/I252Q/L264R, |
| D027S/F051T/L075G/G091Q/V187T/I252Q/L264R, |
| D027S/F051T/S058M/L075R/D130A/I252Q/L264R, |
| D027S/L075R/V154I/G156W/V187N/T189Q/L264R, |
| D048Q/D130A/D137Q/G163P/L227M/N233Q/L264R, |
| D048Q/S058M/D130A/D137Q/G163P/L227M/L264R, |
| D048Q/S058M/D130A/G163P/L227M/N233Q/L264R, |
| D048Q/S058M/D137Q/G163P/L227M/N233Q/L264R, |
| E056K/L075Q/D111A/D130A/G156W/V187N/T189Q, |
| F051T/L075G/G091Q/D130A/V187N/I252Q/L264R, |
| F051T/L075R/G091Q/D130A/V187T/I252Q/L264R, |
| G023K/D027Q/F051T/L075G/D130A/V187H/L264R, |
| G023K/D027S/F051T/S058M/L075Q/D130A/V187N, |
| G023K/D027S/L075Q/N094R/V154I/G156W/T189Q, |
| G023K/F051T/E056K/L075R/D130A/V187T/I252Q, |
| G023K/F051T/L075Q/G091Q/D130A/V187H/I252Q, |
| G023K/K024A/L075Q/D111A/D130A/T189Q/L264R, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/L075Q/N094R/V154I/G156W/V187T/L264R, |
| G023K/L075R/N094R/V154I/G156W/V187N/L264R, |
| G023Q/D027S/L075Q/G091Q/V187T/I252Q/L264R, |
| G023Q/D027S/S058M/L075Q/D130A/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D111A/G156W/V187N/L264R, |
| G023Q/E056K/L075Q/D130A/V154I/G156W/T189Q, |
| G023Q/E056K/L075R/D111A/D130A/V187N/T189Q, |
| G023Q/F051T/G091Q/D130A/V187H/I252Q/L264R, |
| G023Q/F051T/L075Q/G091Q/V187H/I252Q/L264R, |
| G023Q/F051T/L075R/G091Q/V187N/I252Q/L264R, |
| G023Q/K024A/L075Q/V077I/D130A/G156W/V187N, |
| G023Q/K024A/L075Q/V077I/D130A/V154I/G156W, |
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| G023Q/S058M/L075G/G091Q/D130A/I252Q/L264R, |
| K024A/L075Q/D111A/D130A/V187N/T189Q/L264R, |
| K024A/L075R/D130A/V154I/G156W/T189Q/L264R, |
| L075Q/D111A/D130A/G156W/V187N/T189Q/L264R, |
| N011K/A018K/K024A/V077I/V154I/G156W/T189Q, |
| N011K/E056K/L075Q/D130A/V154I/V187N/T189Q, |
| N011K/G023K/L075Q/D111A/D130A/V154I/V187N, |
| Q004D/N011K/D027Q/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/L075Q/V077I/D130A/V154I/G156W/V187N, |
| A018K/K024A/L075Q/V077I/N094R/D130A/V154I/G156W, |
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| D027E/D048Q/S058M/D137Q/G163P/L227M/N233Q/L264R, |
| D027E/S058M/D130A/D137Q/G163P/L227M/N233Q/L264R, |
| D048Q/S058M/D130A/D137Q/G163P/L227M/N233Q/L264R, |
| F051T/E056K/L075G/G091Q/D130A/V187H/I252Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/F051T/E056K/L075R/G091Q/D130A/V187T/L264R, |
| G023K/K024A/L075Q/N094R/V154I/G156W/V187T/L264R, |

TABLE 8-1-continued

| TLL variants with Performance Index >1 compared to TLL SEQ ID NO: 1 in the CS-61 microswatch Assay using Tide ® half dose + adjuvant are shown below. |
|---|
| G023K/K024A/L075R/N094R/V154I/G156W/V187T/T189Q, G023K/L075Q/D111A/V154I/G156W/V187N/T189Q/L264R, G023K/L075Q/N094R/D130A/V154I/G156W/V187N/L264R, G023Q/D027Q/F051T/S058M/L075R/D130A/V187T/L264R, G023Q/D027S/E056K/L075R/D111A/V154I/G156W/L264R, G023Q/D027S/E056K/S058M/L075R/G091Q/V187N/I252Q, G023Q/D027S/F051T/S058M/G091Q/D130A/V187N/I252Q, G023Q/D027S/L075Q/D130A/V154I/G156W/T189Q/L264R, G023Q/D027S/S058M/G091Q/D130A/V187H/I252Q/L264R, G023Q/E056K/L075Q/D111A/V154I/V187N/T189Q/L264R, G023Q/E056K/L075Q/N094R/D111A/G156W/T189Q/L264R, G023Q/F051T/L075Q/G091Q/D130A/V187H/I252Q/L264R, G023Q/F051T/L075Q/G091Q/D130A/V187T/I252Q/L264R, G023Q/K024A/L075Q/V077I/D130A/V154I/G156W/V187N, G023Q/K024A/L075Q/V077I/N094R/D130A/V154I/V187N, G023Q/L075Q/N094R/D111A/D130A/G156W/T189Q/L264R, G023Q/L075Q/V077I/N094R/D130A/V154I/G156W/V187Q, N011K/G023K/E056K/L075Q/D130A/V154I/T189Q/L264R, N011K/G023Q/D027S/L075Q/N094R/V154I/G156W/T189Q, N011K/G023Q/D027S/N094R/V154I/G156W/T189Q/L264R, N011K/G023Q/L075Q/D111A/D130A/V154I/V187N/L264R, N011K/G023Q/L075Q/N094R/V154I/G156W/T189Q/L264R, A018K/G023K/K024A/L075Q/N094R/D111A/D130A/V154I/T189Q, A018K/G023K/K024A/L075R/V077I/D130A/V154I/G156W/V187N, A018K/G023K/K024A/V077I/D130A/V154I/G156W/V187T/T189Q, A018K/G023K/L075Q/N094R/D111A/V154I/G156W/T189Q/L264R, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, A018K/K024A/L075Q/N094R/V154I/G156W/V187N/T189Q/L264R, D027Q/F051T/S058M/L075G/G091Q/D130A/V187T/I252Q/L264R, D027S/E056K/L075Q/N094R/D111A/D130A/V154I/G156W/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023Q/D027S/L075Q/N094R/D130A/V154I/G156W/V187N/L264R, G023Q/E056K/L075Q/D111A/D130A/V154I/G156W/T189Q/L264R, N011K/G023K/L075R/D111A/D130A/V154I/V187N/T189Q/L264R, N011K/G023Q/L075Q/D111A/V154I/G156W/V187N/T189Q/L264R, N011K/G023K/L075R/V077I/D130A/V154I/G156W/V187T/T189Q, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023K/K024A/L075R/V077I/D130A/V154I/V187T/T189Q, N011K/G023K/L075R/N094R/D111A/V154I/G156W/V187N/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T, A018K/G023Q/D027S/P029E/E045F/A049V/S058M/N073S/L075Q/R108K/V187T/T189D, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 8-2

| TLL variants with Performance Index for expression ≥0.5 and Performance Index >1 in the CS-61 microswatch Assay using Tide ® half dose + adjuvant compared to TLL SEQ ID NO: 1 are shown below. |
|---|
| D027S/N033D, D130A/L264R, D130A/V187T, L075R/L264R, N033D/E045F, P029E/N033D, V187T/L264R, A018K/E045F/V187T, A018K/L075D/T189D, A018K/P029E/T189D, |

TABLE 8-2-continued

| TLL variants with Performance Index for expression ≥0.5 and Performance Index >1 in the CS-61 microswatch Assay using Tide ® half dose + adjuvant compared to TLL SEQ ID NO: 1 are shown below. |
|---|
| D027E/S058M/G163P, D027S/L075Q/G091Q, D027S/N033D/T189D, D111A/D130A/L264R, F051T/I252Q/L264R, G023K/E056K/V187T, G023K/V187N/L264R, G023Q/A049V/T189D, G163P/L227M/L264R, L075G/D130A/V187H, L075Q/V187N/L264R, L075Q/V187T/L264R, L075R/D130A/L264R, L075R/D130A/V187T, L075R/V187N/L264R, P029E/N033D/E045F, V187N/T189Q/L264R, A018K/D027S/P029E/T189D, A018K/D130A/G156W/V187T, A018K/L075Q/V077I/N094R, A018K/N033D/L075D/T189D, D027E/D130A/N233Q/L264R, D027E/D137Q/G163P/L227M, D027E/D137Q/L227M/L264R, D027E/L227M/N233Q/L264R, D027E/S058M/G163P/L264R, D027S/D130A/I252Q/L264R, D027S/N033D/E045F/T189D, D027S/N033D/L075D/T189D, D027S/N033D/N073R/T189D, D027S/P029E/L075D/T189D, D027S/P029E/N033D/E045F, D027S/P029E/N033D/L075D, D048Q/D130A/G163P/L264R, D048Q/G163P/N233Q/L264R, D130A/G163P/L227M/L264R, E056K/D130A/V187N/L264R, F051T/D130A/I252Q/L264R, F051T/L075G/I252Q/L264R, F051T/L075Q/I252Q/L264R, G023K/D027Q/F051T/L075Q, G023K/D130A/G156W/T189Q, G023K/D130A/V187T/L264R, G023K/D130A/V187T/T189Q, G023K/E056K/V187T/L264R, G023K/K024A/V154I/V187N, G023K/L075R/D130A/L264R, G023Q/A049V/V077I/G156W, G023Q/L075Q/D130A/L264R, G023Q/L075Q/V187T/L264R, K024A/D130A/V154I/V187T, L075G/D130A/V187T/I252Q, L075G/V187H/I252Q/L264R, L075R/D130A/V187T/L264R, N011K/D027S/N233Q/P256T, P029E/N073R/L075D/T189D, S058M/D137Q/G163P/N233Q, S058M/G163P/L227M/L264R, S058M/G163P/N233Q/L264R, S058M/L075Q/G091Q/I252Q, A018K/D027S/P029E/N033D/L075D, A018K/D130A/G156W/V187N/L264R, A018K/E045F/N073R/L075D/T189D, A018K/G023K/D130A/V154I/G156W, A018K/G023K/K024A/D130A/G156W, A018K/G023Q/K024A/D130A/V187Q, A018K/G023Q/K024A/L075Q/G156W, A018K/G023Q/V077I/D130A/G156W, A018K/K024A/N094R/D130A/V187N, A018K/P029E/N033D/N073R/L075D, D027E/D130A/G163P/N233Q/L264R, D027E/D137Q/G163P/N233Q/L264R, D027E/G163P/L227M/N233Q/L264R, D027E/S058M/D130A/G163P/L264R, D027E/S058M/G163P/L227M/L264R, D027S/E056K/D111A/V187N/L264R, D027S/L075G/D130A/I252Q/L264R, D027S/L075G/G091Q/I252Q/L264R, D027S/L075R/V154I/T189Q/L264R, D048Q/D130A/G163P/L227M/L264R, D048Q/D137Q/G163P/L227M/L264R, D048Q/D137Q/G163P/N233Q/L264R, D048Q/S058M/D130A/N233Q/L264R, D048Q/S058M/D137Q/G163P/N233E, D130A/D137Q/G163P/L227M/L264R, D130A/D137Q/G163P/N233Q/L264R, E056K/L075G/V187N/I252Q/L264R, E056K/L075R/D130A/V187T/L264R, F051T/L075G/D130A/I252Q/L264R, F051T/L075G/V187N/I252Q/L264R, F051T/L075Q/G091Q/D130A/L264R, F051T/L075Q/V187N/I252Q/L264R, F051T/S058M/L075Q/G091Q/I252Q, G023K/D027S/E056K/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075Q/V187H/I252Q/L264R, G023K/L075R/D130A/V187T/L264R, G023K/N094R/G156W/V187N/T189Q, G023Q/E056K/V187N/I252Q/L264R, G023Q/F051T/L075Q/G091Q/I252Q, G023Q/L075G/G091Q/I252Q/L264R, G023Q/L075Q/D130A/I252Q/L264R, G023Q/L075Q/V077I/D130A/G156W, K024A/L075R/V154I/G156W/V187Q, L075G/D130A/V187T/I252Q/L264R, N011K/G023K/D111A/G156W/L264R, S058M/D130A/D137Q/G163P/L264R, S058M/D130A/G163P/L227M/L264R, S058M/D137Q/G163P/L227M/L264R, S058M/G163P/L227M/N233Q/L264R, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/V077I/V154I/V187N, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137Q/G163P/L264R, D027E/D048Q/D130A/G163P/L227M/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/D137Q/G163P/N233Q/L264R, D027E/D130A/G163P/L227M/N233Q/L264R, D027E/D137Q/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027E/S058M/D137Q/G163P/N233Q/L264R, D027Q/E056K/S058M/D130A/I252Q/L264R, D027Q/F051T/G091Q/D130A/I252Q/L264R, D027Q/F051T/L075G/G091Q/V187N/I252Q, D027Q/L075Q/D130A/V187T/I252Q/L264R, D027Q/S058M/L075R/D130A/V187T/I252Q, D027S/E056K/S058M/V187T/I252Q/L264R, D027S/F051T/L075Q/D130A/I252Q/L264R, D027S/L075Q/G091Q/V187H/I252Q/L264R, D048Q/D137Q/G163P/L227M/N233Q/L264R, D048Q/S058M/D130A/D137Q/G163P/L264R, D048Q/S058M/D130A/G163P/L227M/L264R, D048Q/S058M/D137Q/G163P/L227M/L264R, D048Q/S058M/G163P/L227M/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/V154I/G156W/V187Q, G023K/K024A/L075R/D130A/V154I/V187N, G023K/N094R/D111A/G156W/V187T/L264R, G023Q/D027S/L075G/D130A/V187H/L264R, G023Q/D027S/L075Q/D130A/V187T/I252Q, G023Q/F051T/D130A/V187T/I252Q/L264R, G023Q/F051T/G091Q/V187N/I252Q/L264R, G023Q/F051T/L075G/G091Q/V187N/I252Q, G023Q/K024A/D130A/V154I/G156W/V187Q, G023Q/K024A/V077I/D130A/G156W/V187N, K024A/L075Q/N094R/D130A/V154I/L264R, K024A/L075Q/V077I/N094R/D130A/V187N, L075Q/G091Q/D130A/V187H/I252Q/L264R, S058M/D130A/D137Q/G163P/L227M/L264R, S058M/D130A/D137Q/G163P/N233Q/L264R, S058M/D130A/G163P/L227M/N233Q/L264R, |

TABLE 8-2-continued

TLL variants with Performance Index for expression ≥0.5 and Performance Index >1 in the CS-61 microswatch Assay using Tide ® half dose + adjuvant compared to TLL SEQ ID NO: 1 are shown below.

A018K/D027S/P029E/N033D/N073R/L075D/T189D,
A018K/G023K/K024A/L075Q/N094R/G156W/V187Q,
A018K/G023K/K024A/L075R/N094R/D130A/V154I,
A018K/G023K/L075Q/V077I/N094R/V154I/G156W,
A018K/G023Q/L075R/V077I/N094R/G156W/V187N,
A018K/K024A/L075Q/D130A/V154I/G156W/V187T,
A018K/K024A/L075Q/V077I/N094R/D130A/G156W,
D027E/D048Q/S058M/D130A/D137Q/G163P/L264R,
D027E/D048Q/S058M/D130A/G163P/L227M/L264R,
D027E/D048Q/S058M/D130A/G163P/N233Q/L264R,
D027E/D048Q/S058M/D137Q/G163P/L227M/L264R,
D027E/D130A/D137Q/G163P/L227M/N233Q/L264R,
D027E/S058M/D130A/D137Q/G163P/L227M/L264R,
D027E/S058M/D137Q/G163P/L227M/N233Q/L264R,
D027Q/F051T/S058M/L075Q/G091Q/I252Q/L264R,
D027Q/L075G/G091Q/D130A/V187H/I252Q/L264R,
D027S/F051T/S058M/L075R/D130A/I252Q/L264R,
D048Q/D130A/D137Q/G163P/L227M/N233Q/L264R,
D048Q/S058M/D130A/D137Q/G163P/L227M/L264R,
D048Q/S058M/D130A/G163P/L227M/N233Q/L264R,
D048Q/S058M/D137Q/G163P/L227M/N233Q/L264R,
F051T/L075G/G091Q/D130A/V187N/I252Q/L264R,
F051T/L075R/G091Q/D130A/V187T/I252Q/L264R,
G023K/D027S/F051T/S058M/L075Q/D130A/V187N,
G023Q/D027S/S058M/L075Q/D130A/I252Q/L264R,
G023Q/E056K/L075R/D111A/D130A/V187N/T189Q,
G023Q/F051T/G091Q/D130A/V187H/I252Q/L264R,
G023Q/F051T/L075Q/G091Q/V187H/I252Q/L264R,
G023Q/L075Q/V077I/N094R/D130A/G156W/V187N,
G023Q/S058M/L075G/G091Q/D130A/I252Q/L264R,
N011K/A018K/K024A/V077I/V154I/G156W/T189Q,
A018K/G023K/K024A/L075Q/N094R/D130A/G156W/V187Q,
A018K/G023K/K024A/L075Q/V077I/N094R/D130A/G156W,
D027E/D048Q/D130A/D137Q/G163P/L227M/N233Q/L264R,
D027E/D048Q/S058M/D137Q/G163P/L227M/N233Q/L264R,
D027E/S058M/D130A/D137Q/G163P/L227M/N233Q/L264R,
D048Q/S058M/D130A/D137Q/G163P/L227M/N233Q/L264R,
F051T/E056K/L075G/G091Q/D130A/V187H/I252Q/L264R,
G023K/D027S/F051T/E056K/L075Q/G091Q/V187H/I252Q,
G023Q/D027Q/F051T/S058M/L075R/D130A/V187T/L264R,
G023Q/D027S/E056K/L075R/D111A/V154I/G156W/L264R,
G023Q/D027S/F051T/S058M/G091Q/D130A/V187N/I252Q,
G023Q/D027S/S058M/G091Q/D130A/V187H/I252Q/L264R,
G023Q/F051T/L075Q/G091Q/D130A/V187H/I252Q/L264R,
G023Q/F051T/L075Q/G091Q/D130A/V187T/I252Q/L264R,
A018K/G023K/K024A/V077I/D130A/V154I/G156W/V187T/T189Q,
A018K/G023Q/D027S/P029E/L075Q/V077I/R108K/H135F/V187H,
D027Q/F051T/S058M/L075G/G091Q/D130A/V187T/I252Q/L264R,
G023K/K024A/L075Q/N094R/V154I/G156W/V187N/T189Q/L264R,
N011K/G023K/L075R/V077I/D130A/V154I/G156W/V187T/T189Q,
A018K/G023Q/D027S/P029E/S058M/L075Q/V077I/H135F/G156W/V187T,
A018K/G023Q/D027S/P029E/S058M/L075Q/V077I/R108K/H135F/V187H,
N011K/A018K/G023K/K024A/L075R/V077I/D130A/V154I/V187T/T189Q,
N011K/G023Q/E056K/L075R/D111A/D130A/V154I/G156W/V187N/L264R,
A018K/G023K/L075R/N094R/D111A/D130A/V154I/G156W/V187N/T189Q/L264R,
A018K/G023Q/D027S/P029E/S058M/L075Q/V077I/R108K/H135F/G156W/V187T

TABLE 8-3

TLL variants with Performance Index for expression ≥0.5 and Performance Index ≥50% of the maximum PI value in the CS-61 microswatch Assay using Tide ® half dose + adjuvant compared to TLL SEQ ID NO: 1 are shown below.

P029E/N033D, A018K/L075D/T189D, A018K/P029E/T189D, D027S/N033D/T189D, G023K/V187N/L264R, G023Q/A049V/T189D, L075G/D130A/V187H, L075Q/V187N/L264R, L075R/D130A/V187T, L075R/V187N/L264R, P029E/N033D/E045F, A018K/D027S/P029E/T189D, A018K/L075Q/V077I/N094R, A018K/N033D/L075D/T189D, D027E/D137Q/G163P/L227M, D027E/L227M/N233Q/L264R, D027S/N033D/L075D/T189D, D027S/P029E/L075D/T189D, D027S/P029E/N033D/L075D, D048Q/D130A/G163P/L264R, D130A/G163P/L227M/L264R, G023K/D027Q/F051T/L075Q, G023K/D130A/V187T/L264R, G023Q/A049V/V077I/G156W, L075G/D130A/V187T/I252Q, L075R/D130A/V187T/L264R, P029E/N073R/L075D/T189D, S058M/D137Q/G163P/N233Q, A018K/G023K/K024A/D130A/G156W, A018K/G023Q/K024A/D130A/V187Q, A018K/K024A/N094R/D130A/V187N,

TABLE 8-3-continued

| TLL variants with Performance Index for expression ≥0.5 and Performance Index ≥50% of the maximum PI value in the CS-61 microswatch Assay using Tide ® half dose + adjuvant compared to TLL SEQ ID NO: 1 are shown below. |
|---|
| A018K/P029E/N033D/N073R/L075D, D027E/D130A/G163P/N233Q/L264R, D027E/D137Q/G163P/N233Q/L264R, D130A/D137Q/G163P/N233Q/L264R, E056K/L075R/D130A/V187T/L264R, G023K/D027S/E056K/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075R/D130A/V187T/L264R, K024A/L075R/V154I/G156W/V187Q, N011K/G023K/D111A/G156W/L264R, S058M/D130A/G163P/L227M/L264R, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027Q/E056K/S058M/D130A/I252Q/L264R, D027Q/S058M/L075R/D130A/V187T/I252Q, D027S/E056K/S058M/V187T/I252Q/L264R, D048Q/D137Q/G163P/L227M/N233Q/L264R, F051T/L075G/G091Q/D130A/I252Q/L264R, G023K/D027S/L075R/D130A/V187T/I252Q, G023K/D027S/L075R/V187N/I252Q/L264R, G023K/F051T/D130A/V187N/I252Q/L264R, G023K/K024A/L075Q/V154I/G156W/V187Q, G023K/K024A/L075R/D130A/V154I/V187N, G023K/N094R/D111A/G156W/V187T/L264R, G023Q/F051T/D130A/V187T/I252Q/L264R, G023Q/K024A/V077I/D130A/G156W/V187N, K024A/L075Q/V077I/N094R/D130A/V187N, A018K/D027S/P029E/N033D/N073R/L075D/T189D, A018K/G023K/K024A/L075R/N094R/D130A/V154I, A018K/K024A/L075Q/D130A/V154I/G156W/V187T, D027E/D048Q/S058M/D130A/G163P/L227M/L264R, D027E/D130A/D137Q/G163P/L227M/N233Q/L264R, D048Q/D130A/D137Q/G163P/L227M/N233Q/L264R, G023Q/L075Q/V077I/N094R/D130A/G156W/V187N, N011K/A018K/K024A/V077I/V154I/G156W/T189Q, A018K/G023K/K024A/L075Q/N094R/D130A/G156W/V187Q, A018K/G023K/K024A/L075Q/V077I/N094R/D130A/G156W, D027E/D048Q/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027S/E056K/L075R/D111A/V154I/G156W/L264R, G023Q/D027S/F051T/S058M/G091Q/D130A/V187N/I252Q, A018K/G023Q/D027S/P029E/L075Q/V077I/R108K/H135F/V187H, G023K/K024A/L075Q/N094R/V154I/G156W/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, N011K/G023Q/E056K/L075R/D111A/D130A/V154I/G156W/V187N/L264R, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T |

TABLE 8-4

| TLL variants with Performance Index >1 compared to Reference sequence SEQ ID NO: 2 in the CS-61 microswatch Assay using Tide ® half dose + adjuvant are shown below. |
|---|
| A018K/L075Q, A018K/T189D, G023K/D130A, K024A/L075Q, L075Q/D130A, L075Q/G156W, P029E/N033D, A018K/A049V/L075Q, A018K/D027S/N073R, A018K/D027S/T189D, A018K/E045F/T189D, A018K/G023K/L075Q, A018K/G023Q/L075Q, A018K/L075Q/G156W, A018K/L075Q/V187T, A018K/N033D/L075D, A018K/N073R/L075D, A018K/P029E/T189D, A049V/V187T/T189D, D027S/N033D/T189D, D027S/N233Q/P256T, E056K/D130A/T189Q, G023K/V187N/L264R, G023Q/A049V/T189D, G023Q/D111A/L264R, G023Q/E056K/L075R, G023Q/L075Q/V077I, G023Q/L075Q/V187T, K024A/L075Q/V077I, L075G/D130A/V187H, L075Q/D130A/V187T, L075Q/G156W/T189D, L075Q/G156W/V187N, L075Q/V077I/T189D, L075Q/V154I/V187T, L075Q/V187T/T189D, L075R/D130A/V187T, L075R/V187N/L264R, N073R/L075D/T189D, P029E/E045F/L075D, P029E/L075D/T189D, P029E/N033D/E045F, P029E/N073R/L075D, Q004D/N233Q/P256T, S058M/L227M/L264R, V077I/V187A/T189D, A018K/A049V/L075Q/T189D, A018K/A049V/L075Q/V187T, A018K/D027S/N033D/L075D, A018K/D027S/P029E/T189D, A018K/E045F/L075Q/T189D, A018K/G023Q/E045F/T189D, A018K/G023Q/E045F/V187T, A018K/G023Q/L075Q/T189D, A018K/G023Q/L075Q/V077I, A018K/G023Q/L075Q/V187T, A018K/G023Q/V187T/T189D, A018K/L075Q/N094R/D111A, A018K/L075Q/N094R/V187Q, A018K/L075Q/V077I/N094R, A018K/N033D/L075D/T189D, A018K/N073R/L075D/T189D, A049V/L075Q/V077I/T189D, A049V/L075Q/V187T/T189D, D027E/D137Q/G163P/L227M, D027S/N033D/L075D/T189D, D027S/P029E/E045F/L075D, D027S/P029E/L075D/T189D, D027S/P029E/N033D/L075D, D027S/P029E/N033D/T189D, D048Q/D130A/G163P/L264R, D130A/G163P/L227M/L264R, D130A/G163P/N233Q/L264R, E056K/L075Q/V187N/L264R, G023K/D130A/V187T/L264R, G023K/L075Q/D130A/V187N, G023K/L075Q/G156W/L264R, G023K/L075Q/G156W/V187N, G023K/L075R/V187N/L264R, G023Q/A049V/L075Q/T189D, G023Q/A049V/L075Q/V077I, G023Q/D027S/D111A/G156W, G023Q/E045F/A049V/T189D, G023Q/E045F/L075Q/G156W, G023Q/E045F/L075Q/V187T, G023Q/K024A/L075R/V154I, G023Q/L075Q/G156W/V187N, G023Q/L075Q/G156W/V187T, |

TABLE 8-4-continued

| TLL variants with Performance Index >1 compared to Reference sequence SEQ ID NO: 2 in the CS-61 microswatch Assay using Tide ® half dose + adjuvant are shown below. |
| --- |
| K024A/L075Q/V187T/T189Q, K024A/L075R/G156W/V187N, L075G/D130A/V187T/I252Q, L075Q/D130A/G156W/V187N, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D130A/V154I/L264R, N011K/E056K/S058M/P256T, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027S/I090F/P256T, Q004D/N011K/D027N/P256T, A018K/D027S/E045F/N073R/D137V, A018K/D027S/N033D/E045F/T189D, A018K/D027S/N033D/L075D/T189D, A018K/D027S/N073R/L075D/T189D, A018K/D027S/P029E/E045F/T189D, A018K/D027S/P029E/N073R/L075D, A018K/G023K/K024A/D130A/G156W, A018K/G023K/K024A/L075R/N094R, A018K/G023K/L075Q/D130A/V154I, A018K/G023Q/A049V/L075Q/G156W, A018K/G023Q/L075Q/G156W/V187T, A018K/G023Q/L075Q/V187T/T189D, A018K/K024A/L075Q/D130A/L264R, A018K/K024A/L075Q/V154I/G156W, A018K/K024A/L075R/N094R/D130A, A018K/K024A/N094R/D130A/V187N, A018K/L075Q/D111A/D130A/V187T, A018K/L075Q/N094R/G156W/V187N, A018K/L075Q/V077I/N094R/G156W, A018K/N033D/E045F/L075D/T189D, A018K/P029E/E045F/N073R/L075D, D027E/D130A/G163P/N233Q/L264R, D027E/D137Q/G163P/L227M/L264R, D027E/D137Q/G163P/N233Q/L264R, D027S/N033D/N073R/L075D/T189D, D027S/P029E/N033D/N073R/L075D, D027S/P029E/N073R/L075D/T189D, D048Q/D130A/D137Q/G163P/L264R, D130A/D137Q/G163P/N233Q/L264R, E056K/D130A/V187H/I252Q/L264R, E056K/L075Q/G156W/T189Q/L264R, E056K/L075R/D130A/V187T/L264R, G023K/D027S/E056K/V187T/L264R, G023K/D111A/V154I/V187T/L264R, G023K/E056K/L075R/D130A/V187T, G023K/E056K/L075R/V187N/L264R, G023K/E056K/L075R/V187T/L264R, G023K/L075Q/D111A/D130A/V187T, G023K/L075Q/D130A/G156W/L264R, G023K/L075Q/V077I/D130A/G156W, G023K/L075R/D130A/V187T/L264R, G023Q/A049V/L075Q/G156W/T189D, G023Q/A049V/L075Q/G156W/V187T, G023Q/A049V/L075Q/V187T/T189D, G023Q/D027S/V154I/V187N/L264R, G023Q/E045F/L075Q/V077I/V187T, G023Q/K024A/L075Q/G156W/V187N, G023Q/K024A/L075Q/V077I/V187Q, G023Q/K024A/L075R/G156W/V187Q, G023Q/K024A/V077I/D130A/V154I, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/V154I/G156W/V187Q, L075Q/D111A/V187N/T189Q/L264R, L075Q/V154I/V187N/T189Q/L264R, L075R/D111A/D130A/V187N/T189Q, L075R/D130A/V154I/T189Q/L264R, L075R/D130A/V187T/T189Q/L264R, L075R/G156W/V187T/T189Q/L264R, N011K/G023K/D111A/G156W/L264R, N011K/G023K/E056K/L075Q/T189Q, P029E/N033D/E045F/L075D/T189D, P029E/N033D/K074S/L075D/T189D, P029E/N033D/N073R/L075D/T189D, Q004D/D027Q/E056K/N233Q/P256T, Q004D/N011K/D027Q/E056K/N233Q, Q004D/N011K/I090F/N233Q/P256T, A018K/A049V/L075Q/G156W/V187T/T189D, A018K/D027S/N033D/E045F/L075D/T189D, A018K/D027S/P029E/N073R/L075D/T189D, A018K/G023K/D111A/D130A/V154I/T189Q, A018K/G023K/K024A/L075R/D130A/V187N, A018K/G023K/L075Q/D130A/G156W/V187N, A018K/G023K/L075Q/G156W/V187N/L264R, A018K/G023K/L075R/V077I/D130A/V154I, A018K/G023Q/A049V/L075Q/V077I/V187T, A018K/G023Q/E045F/A049V/L075Q/T189D, A018K/G023Q/L075Q/G156W/V187T/T189D, A018K/G023Q/L075Q/V077I/D130A/V187N, A018K/G023Q/L075Q/V077I/G156W/V187N, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/L075R/D130A/V154I/G156W/V187N, D027E/D048Q/D130A/D137Q/G163P/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027Q/E056K/S058M/D130A/I252Q/L264R, D027Q/F051T/L075G/D130A/I252Q/L264R, D027Q/F051T/L075Q/D130A/V187H/L264R, D027Q/S058M/L075R/D130A/V187T/I252Q, D027S/E056K/S058M/V187T/I252Q/L264R, D027S/P029E/N033D/E045F/N073R/T189D, D027S/P029E/N033D/N073R/L075D/T189D, D048Q/D137Q/G163P/L227M/N233Q/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/D130A/V187T/I252Q, G023K/D027S/L075R/V187N/I252Q/L264R, G023K/F051T/D130A/V187N/I252Q/L264R, G023K/K024A/L075Q/V154I/G156W/V187Q, G023K/K024A/L075R/D130A/V154I/V187N, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/E045F/L075Q/V077I/G156W/V187T, G023Q/E045F/L075Q/V077I/V187T/T189D, G023Q/K024A/L075Q/D130A/V154I/V187N, G023Q/L075Q/V077I/N094R/D130A/V187Q, K024A/D111A/D130A/V187T/T189Q/L264R, K024A/L075Q/V077I/N094R/D130A/V187N, K024A/L075Q/V154I/V187N/T189Q/L264R, K024A/N094R/V154I/G156W/T189Q/L264R, L075Q/D111A/D130A/V154I/V187N/T189Q, L075Q/N094R/D111A/G156W/T189Q/L264R, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, P029E/N033D/K074S/L075D/N101D/T189D, Q004D/N011K/D027Q/E056K/S058M/N233Q, A018K/G023K/K024A/L075Q/V077I/N094R/G156W, A018K/G023K/K024A/L075R/N094R/D130A/V154I, A018K/G023K/K024A/L075R/V154I/G156W/V187Q, |

TABLE 8-4-continued

| TLL variants with Performance Index >1 compared to Reference sequence SEQ ID NO: 2 in the CS-61 microswatch Assay using Tide ® half dose + adjuvant are shown below. |
|---|
| A018K/G023K/K024A/N094R/V154I/V187T/L264R, |
| A018K/G023Q/K024A/L075Q/V077I/D130A/G156W, |
| A018K/G023Q/K024A/L075Q/V077I/N094R/V154I, |
| A018K/G023Q/K024A/L075R/D130A/V154I/V187N, |
| A018K/G023Q/K024A/L075R/V077I/D130A/G156W, |
| A018K/K024A/L075Q/D111A/G156W/V187N/L264R, |
| A018K/K024A/L075Q/D130A/G156W/V187T/T189Q, |
| A018K/K024A/L075Q/D130A/V154I/G156W/V187T, |
| A018K/L075Q/D111A/D130A/V154I/G156W/L264R, |
| A018K/L075Q/D111A/V154I/V187T/T189Q/L264R, |
| A018K/L075Q/N094R/D111A/V154I/V187T/L264R, |
| D027E/D130A/D137Q/G163P/L227M/N233Q/L264R, |
| D027E/S058M/D130A/D137Q/G163P/N233Q/L264R, |
| D027Q/F051T/L075G/D130A/V187H/I252Q/L264R, |
| D027Q/F051T/L075Q/G091Q/D130A/V187T/I252Q, |
| D027S/F051T/L075G/G091Q/V187T/I252Q/L264R, |
| D048Q/D130A/D137Q/G163P/L227M/N233Q/L264R, |
| E056K/L075Q/D111A/D130A/G156W/V187N/T189Q, |
| G023K/D027Q/F051T/L075G/D130A/V187H/L264R, |
| G023K/D027S/L075Q/N094R/V154I/G156W/T189Q, |
| G023K/F051T/E056K/L075R/D130A/V187T/I252Q, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/L075Q/N094R/V154I/G156W/V187T/L264R, |
| G023K/L075R/N094R/V154I/G156W/V187N/L264R, |
| G023Q/D027S/L075Q/G091Q/V187T/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D130A/V154I/G156W/T189Q, |
| G023Q/F051T/L075R/G091Q/V187N/I252Q/L264R, |
| G023Q/K024A/L075Q/V077I/D130A/G156W/V187N, |
| G023Q/K024A/L075Q/V077I/D130A/V154I/G156W, |
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| L075Q/D111A/D130A/G156W/V187N/T189Q/L264R, |
| N011K/E056K/L075Q/D130A/V154I/V187N/T189Q, |
| N011K/G023K/L075Q/D111A/D130A/V154I/V187N, |
| Q004D/N011K/D027Q/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/L075Q/V077I/D130A/V154I/G156W/V187N, |
| A018K/K024A/L075Q/V077I/N094R/D130A/V154I/G156W, |
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| F051T/E056K/L075G/G091Q/D130A/V187H/I252Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/N094R/D130A/V154I/G156W/V187N/L264R, |
| G023Q/D027S/E056K/L075R/D111A/V154I/G156W/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/E056K/L075Q/D111A/V154I/V187N/T189Q/L264R, |
| G023Q/K024A/L075Q/V077I/D130A/V154I/G156W/V187N, |
| G023Q/L075Q/V077I/N094R/D130A/V154I/G156W/V187Q, |
| N011K/G023K/E056K/L075Q/D130A/V154I/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075R/V077I/D130A/V154I/G156W/V187N, |

TABLE 8-4-continued

| TLL variants with Performance Index >1 compared to Reference sequence SEQ ID NO: 2 in the CS-61 microswatch Assay using Tide ® half dose + adjuvant are shown below. |
|---|
| A018K/G023K/L075Q/N094R/D111A/V154I/G156W/T189Q/L264R, A018K/G023Q/D027S/P029E/L075Q/V077I/H135F/G156W/V187T, A018K/G023Q/D027S/P029E/L075Q/V077I/R108K/G156W/V187H, A018K/G023Q/D027S/P029E/L075Q/V077I/R108K/H135F/V187H, A018K/G023Q/D027S/P029E/S058M/V077I/R108K/H135F/G156W, A018K/G023Q/E045F/A049V/N073S/L075Q/R108K/V187T/T189D, A018K/G023Q/K024A/L075R/N094R/D130A/V154I/G156W/V187N, A018K/K024A/L075Q/N094R/V154I/G156W/V187N/T189Q/L264R, D027S/E056K/L075Q/N094R/D111A/D130A/V154I/G156W/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023Q/D027S/L075Q/N094R/D130A/V154I/G156W/V187N/L264R, N011K/G023K/L075R/D111A/D130A/V154I/V187N/T189Q/L264R, N011K/G023Q/L075Q/D111A/V154I/G156W/V187N/T189Q/L264R, A018K/G023Q/D027S/E045F/A049V/S058M/L075Q/R108K/V187T/T189D, A018K/G023Q/D027S/P029E/S058M/L075Q/V077I/R108K/H135F/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/G023K/L075R/N094R/D111A/V154I/G156W/V187N/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, A018K/G023K/L075R/N094R/D111A/D130A/V154I/G156W/V187N/T189Q/L264R, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 8-5

| TLL variants with Performance Index for expression ≥0.5 compared to TLL SEQ ID NO: 1 and Performance Index >1 in the CS-61 microswatch Assay using Tide ® half dose + adjuvant compared to Reference sequence SEQ ID NO: 2 are shown below. |
|---|
| P029E/N033D, A018K/P029E/T189D, D027S/N033D/T189D, G023K/V187N/L264R, G023Q/A049V/T189D, L075G/D130A/V187H, L075R/D130A/V187T, L075R/V187N/L264R, P029E/N033D/E045F, A018K/D027S/P029E/T189D, A018K/L075Q/V077I/N094R, A018K/N033D/L075D/T189D, D027E/D137Q/G163P/L227M, D027S/N033D/L075D/T189D, D027S/P029E/L075D/T189D, D027S/P029E/N033D/L075D, D048Q/D130A/G163P/L264R, D130A/G163P/L227M/L264R, G023K/D130A/V187T/L264R, L075G/D130A/V187T/I252Q, P029E/N073R/L075D/T189D, A018K/G023K/K024A/D130A/G156W, A018K/K024A/N094R/D130A/V187N, D027E/D130A/G163P/N233Q/L264R, D027E/D137Q/G163P/N233Q/L264R, D130A/D137Q/G163P/N233Q/L264R, E056K/L075R/D130A/V187T/L264R, G023K/D027S/E056K/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075R/D130A/V187T/L264R, K024A/L075R/V154I/G156W/V187Q, N011K/G023K/D111A/G156W/L264R, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027Q/E056K/S058M/D130A/I252Q/L264R, D027Q/S058M/L075R/D130A/V187T/I252Q, D027S/E056K/S058M/V187T/I252Q/L264R, D048Q/D137Q/G163P/L227M/N233Q/L264R, F051T/L075G/G091Q/D130A/I252Q/L264R, G023K/D027S/L075R/D130A/V187T/I252Q, G023K/D027S/L075R/V187N/I252Q/L264R, G023K/F051T/D130A/V187N/I252Q/L264R, G023K/K024A/L075Q/V154I/G156W/V187Q, G023K/K024A/L075R/D130A/V154I/V187N, G023K/N094R/D111A/G156W/V187T/L264R, K024A/L075Q/V077I/N094R/D130A/V187N, A018K/G023K/K024A/L075R/N094R/D130A/V154I, A018K/K024A/L075Q/D130A/V154I/G156W/V187T, D027E/D130A/D137Q/G163P/L227M/N233Q/L264R, D048Q/D130A/D137Q/G163P/L227M/N233Q/L264R, G023Q/L075Q/V077I/N094R/D130A/G156W/V187N, A018K/G023K/K024A/L075Q/N094R/D130A/G156W/V187Q, A018K/G023K/K024A/L075Q/V077I/N094R/D130A/G156W, D027E/D048Q/D130A/D137Q/G163P/L227M/N233Q/L264R, F051T/E056K/L075G/G091Q/D130A/V187H/I252Q/L264R, G023K/D027S/F051T/E056K/L075Q/G091Q/V187H/I252Q, G023Q/D027S/E056K/L075R/D111A/V154I/G156W/L264R, |

TABLE 8-5-continued

| TLL variants with Performance Index for expression ≥0.5 compared to TLL SEQ ID NO: 1 and Performance Index >1 in the CS-61 microswatch Assay using Tide ® half dose + adjuvant compared to Reference sequence SEQ ID NO: 2 are shown below. |
|---|
| G023Q/D027S/F051T/S058M/G091Q/D130A/V187N/I252Q, A018K/G023Q/D027S/P029E/L075Q/V077I/R108K/H135F/V187H, G023K/K024A/L075Q/N094R/V154I/G156W/V187N/T189Q/L264R, A018K/G023Q/D027S/P029E/S058M/L075Q/V077I/R108K/H135F/V187H, N011K/G023Q/E056K/L075R/D111A/D130A/V154I/G156W/V187N/L264R, A018K/G023K/L075R/N094R/D111A/D130A/V154I/G156W/V187N/T189Q/L264R |

TABLE 8-6

| TLL variants with Performance Index for expression ≥0.5 compared to TLL SEQ ID NO: 1 and Performance Index ≥50% of the maximum PI value in the CS-61 microswatch Assay using Tide ® half dose + adjuvant compared to Reference sequence SEQ ID NO: 2 are shown below. |
|---|
| D027S/N033D/T189D, G023K/V187N/L264R, L075R/D130A/V187T, D048Q/D130A/G163P/L264R, D130A/G163P/L227M/L264R, P029E/N073R/L075D/T189D, A018K/K024A/N094R/D130A/V187N, D027E/D130A/G163P/N233Q/L264R, D027E/D137Q/G163P/N233Q/L264R, D130A/D137Q/G163P/N233Q/L264R, E056K/L075R/D130A/V187T/L264R, G023K/D027S/E056K/V187T/L264R, G023K/E056K/L075R/V187N/L264R, G023K/E056K/L075R/V187T/L264R, G023K/L075R/D130A/V187T/L264R, K024A/L075R/V154I/G156W/V187Q, A018K/K024A/L075Q/N094R/V154I/G156W, D027E/D048Q/D130A/D137Q/G163P/L264R, D027E/D048Q/D137Q/G163P/L227M/L264R, D027E/D048Q/D137Q/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D048Q/D137Q/G163P/L227M/N233Q/L264R, F051T/L075G/G091Q/D130A/I252Q/L264R, G023K/D027S/L075R/V187N/I252Q/L264R, G023K/N094R/D111A/G156W/V187T/L264R, D027E/D048Q/D130A/D137Q/G163P/L227M/N233Q/L264R, A018K/G023K/L075R/N094R/D111A/D130A/V154I/G156W/V187N/T189Q/L264R |

TABLE 8-7

| TLL variants with Performance Index >1 compared to TLL SEQ ID NO: 1 in the CS-61 microswatch Assay using Tide ® full dose are shown below. |
|---|
| A018K/D027S, A018K/L075Q, A018K/T189D, D027N/E056K, D027S/N033D, D130A/L264R, D130A/V187N, E045F/T189D, G023K/D130A, G023K/L264R, K024A/L075Q, K024A/V154I, L075Q/D130A, L075Q/G156W, L227M/L264R, N033D/E045F, P029E/N033D, V187T/L264R, A018K/A049V/L075Q, A018K/D027S/E045F, A018K/D027S/N073R, A018K/D027S/T189D, A018K/E045F/T189D, A018K/G023K/G156W, A018K/G023K/L075Q, A018K/G023Q/L075Q, A018K/K024A/V154I, A018K/L075D/T189D, A018K/L075Q/G156W, A018K/L075Q/V187T, A018K/N033D/L075D, A018K/N073R/L075D, A018K/P029E/T189D, A018K/V154I/G156W, A049V/V187T/T189D, D027E/S058M/G163P, D027Q/N233Q/P256T, D027S/N033D/T189D, D027S/N233Q/P256T, D111A/D130A/L264R, E045F/N073R/L075D, E056K/D130A/T189Q, G023K/D130A/L264R, G023K/D130A/V187T, G023K/E056K/V187T, G023K/V187N/L264R, G023Q/A049V/T189D, G023Q/D111A/L264R, G023Q/E056K/L075R, G023Q/K024A/G156W, G023Q/L075Q/V077I, G023Q/L075Q/V187T, K024A/L075Q/G156W, K024A/L075Q/V077I, L075G/D130A/V187H, L075Q/D111A/D130A, L075Q/D130A/V187T, L075Q/G156W/T189D, L075Q/G156W/V187N, L075Q/G156W/V187T, L075Q/V077I/T189D, L075Q/V154I/V187T, L075Q/V187N/L264R, L075Q/V187T/L264R, L075Q/V187T/T189D, L075R/D130A/L264R, L075R/D130A/V187T, L075R/V187N/L264R, L075R/V187T/L264R, N011K/D027S/S058M, N033D/E045F/N073R, N033D/N073R/T189D, N073R/L075D/T189D, P029E/E045F/L075D, P029E/L075D/T189D, P029E/N033D/E045F, P029E/N033D/L075D, P029E/N073R/L075D, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/N073R, A018K/D027S/E045F/T189D, A018K/D027S/N033D/L075D, A018K/D027S/P029E/T189D, A018K/E045F/L075D/T189D, A018K/E045F/L075Q/T189D, A018K/E045F/L075Q/V187T, A018K/G023K/D111A/T189Q, A018K/G023Q/A049V/T189D, A018K/G023Q/A049V/V187T, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/V187T, A018K/G023Q/V187T/T189D, A018K/L075Q/G156W/T189D, A018K/L075Q/G156W/V187T, A018K/L075Q/N094R/D111A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/T189D, A018K/P029E/N073R/L075D, A049V/L075Q/V077I/T189D, A049V/L075Q/V187T/T189D, D027E/D137Q/G163P/L227M, D027E/D137Q/L227M/L264R, D027E/L227M/N233Q/L264R, D027S/E056K/D111A/V154I, D027S/N033D/E045F/T189D, D027S/N033D/L075D/T189D, D027S/N033D/N073R/T189D, D027S/P029E/E045F/L075D, D027S/P029E/E045F/T189D, D027S/P029E/L075D/T189D, D027S/P029E/N033D/E045F, D027S/P029E/N033D/L075D, D027S/P029E/N033D/T189D, D048Q/D130A/G163P/L264R, D111A/D130A/V154I/L264R, D130A/G163P/L227M/L264R, D130A/G163P/N233Q/L264R, E056K/D130A/V187N/L264R, |

TABLE 8-7-continued

| TLL variants with Performance Index >1 compared to TLL SEQ ID NO: 1 in the CS-61 microswatch Assay using Tide ® full dose are shown below. |
|---|
| E056K/D130A/V187T/L264R, E056K/L075Q/V187N/L264R, G023K/D027Q/F051T/L075Q, G023K/D027S/L075Q/L264R, G023K/D130A/V187T/L264R, G023K/E056K/D130A/L264R, G023K/E056K/V187T/L264R, G023K/K024A/V154I/V187N, G023K/L075Q/D130A/V187N, G023K/L075Q/G156W/L264R, G023K/L075Q/G156W/V187N, G023K/L075R/D130A/L264R, G023K/L075R/V187N/L264R, G023K/L075R/V187T/L264R, G023Q/A049V/L075Q/T189D, G023Q/A049V/L075Q/V077I, G023Q/D027S/D111A/G156W, G023Q/E045F/A049V/T189D, G023Q/E045F/A049V/V187T, G023Q/E045F/L075Q/G156W, G023Q/E045F/L075Q/V187T, G023Q/K024A/L075R/G156W, G023Q/K024A/L075R/V154I, G023Q/L075Q/G156W/V187N, G023Q/L075Q/G156W/V187T, G023Q/L075Q/V187T/L264R, K024A/D130A/V154I/V187T, K024A/L075Q/D130A/G156W, K024A/L075Q/V187T/T189Q, K024A/L075R/G156W/V187N, L075G/D130A/V187T/I252Q, L075Q/D130A/G156W/V187N, L075Q/D130A/V154I/G156W, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, N011K/D027N/S058M/P256T, N011K/D027S/E056K/P256T, N011K/D027S/N233Q/P256T, N011K/G023K/L075Q/D111A, P029E/E045F/L075D/T189D, P029E/E045F/N073R/L075D, P029E/E045F/N073R/T189D, P029E/N033D/E045F/L075D, P029E/N033D/L075D/T189D, P029E/N073R/L075D/T189D, Q004D/D027S/I090F/P256T, Q004D/N011K/D027N/P256T, Q004D/N011K/D027Q/N233Q, S058M/D137Q/G163P/N233Q, S058M/G163P/N233Q/L264R, S058M/L075Q/G091Q/I252Q, A018K/D027S/E045F/N073R/D137V, A018K/D027S/N033D/E045F/T189D, A018K/D027S/N033D/L075D/T189D, A018K/D027S/N073R/L075D/T189D, A018K/D027S/P029E/E045F/T189D, A018K/D027S/P029E/N033D/L075D, A018K/D027S/P029E/N073R/L075D, A018K/D130A/G156W/V187N/L264R, A018K/E045F/A049V/L075Q/V187T, A018K/E045F/N073R/L075D/T189D, A018K/G023K/D130A/V154I/G156W, A018K/G023K/K024A/D130A/G156W, A018K/G023K/K024A/L075R/N094R, A018K/G023K/L075Q/D130A/V154I, A018K/G023K/V077I/D130A/V187N, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/A049V/V187T, A018K/G023Q/E045F/L075Q/V187T, A018K/G023Q/E045F/V077I/T189D, A018K/G023Q/K024A/D130A/V154I, A018K/G023Q/K024A/D130A/V187Q, A018K/G023Q/K024A/L075Q/G156W, A018K/G023Q/L075Q/G156W/V187T, A018K/G023Q/L075Q/V187T/T189D, A018K/G023Q/V077I/D130A/G156W, A018K/G023Q/V077I/V187T/T189D, A018K/K024A/L075Q/D130A/L264R, A018K/K024A/L075Q/V154I/G156W, A018K/K024A/L075Q/V154I/T189D, A018K/K024A/L075R/D130A/V154I, A018K/K024A/L075R/N094R/D130A, A018K/K024A/N094R/D130A/V187N, A018K/L075Q/D111A/D130A/V187T, A018K/L075Q/N094R/D130A/V187N, A018K/L075Q/N094R/G156W/V187N, A018K/L075Q/V077I/N094R/G156W, A018K/N033D/E045F/L075D/T189D, A018K/P029E/E045F/N073R/L075D, A018K/P029E/N033D/N073R/L075D, A018K/V077I/G156W/V187T/T189D, D027E/D048Q/S058M/G163P/N233Q, D027E/D130A/G163P/L227M/L264R, D027E/D130A/G163P/N233Q/L264R, D027E/D137Q/G163P/L227M/L264R, D027E/D137Q/G163P/N233Q/L264R, D027E/S058M/D137Q/G163P/N233Q, D027N/E056K/S058M/N233Q/P256T, D027N/S058M/I090F/N233Q/P256T, D027S/E056K/D111A/V187N/L264R, D027S/E056K/S058M/N233Q/P256T, D027S/L075G/D130A/I252Q/L264R, D027S/L075Q/D111A/D130A/V187N, D027S/L075R/V154I/T189Q/L264R, D027S/N033D/E045F/N073R/L075D, D027S/N033D/N073R/L075D/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/S058M/D130A/N233Q/L264R, D048Q/S058M/D137Q/G163P/L264R, D048Q/S058M/D137Q/G163P/N233E, D130A/D137Q/G163P/N233Q/L264R, E045F/A049V/L075Q/V187T/T189D, E056K/D130A/V187H/I252Q/L264R, E056K/L075Q/G156W/T189Q/L264R, E056K/L075R/D130A/V187T/L264R, F051T/L075G/V187N/I252Q/L264R, F051T/L075Q/G091Q/D130A/L264R, F051T/S058M/L075Q/G091Q/I252Q, G023K/D027S/E056K/V187T/L264R, G023K/D111A/V154I/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/V154I/V187N/L264R, G023Q/E045F/A049V/G156W/T189D, G023Q/E045F/L075Q/G156W/T189D, G023Q/E045F/L075Q/V077I/V187T, G023Q/K024A/L075Q/D130A/G156W, G023Q/K024A/L075Q/G156W/V187N, G023Q/K024A/L075Q/G156W/V187Q, G023Q/K024A/L075Q/V077I/V187Q, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075Q/V077I/D130A/G156W, G023Q/L075Q/V077I/G156W/V187N, G091Q/D130A/V187H/I252Q/L264R, K024A/L075Q/D111A/G156W/V187T, K024A/L075Q/V077I/G156W/V187N, K024A/L075Q/V077I/V154I/V187N, K024A/L075R/V154I/G156W/V187Q, L075Q/D111A/D130A/V187T/T189Q, L075Q/D111A/V187N/T189Q/L264R, L075Q/N094R/D130A/G156W/V187T, L075Q/V077I/D130A/G156W/V187N, L075Q/V154I/V187N/T189Q/L264R, L075R/D111A/D130A/V187N/T189Q, L075R/D130A/V154I/T189Q/L264R, |

TABLE 8-7-continued

| TLL variants with Performance Index >1 compared to TLL SEQ ID NO: 1 in the CS-61 microswatch Assay using Tide ® full dose are shown below. |
|---|
| L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/D027Q/E056K/S058M/N233Q, N011K/G023K/D111A/G156W/L264R, N011K/G023K/E056K/L075Q/T189Q, P029E/N033D/E045F/L075D/T189D, P029E/N033D/K074S/L075D/T189D, P029E/N033D/N073R/L075D/T189D, Q004D/D027S/S058M/N233Q/P256T, Q004D/N011K/D027Q/E056K/N233Q, S058M/D130A/D137Q/G163P/L264R, S058M/G163P/L227M/N233Q/L264R, A018K/A049V/L075Q/G156W/V187T/T189D, A018K/D027S/N033D/E045F/L075D/T189D, A018K/D027S/N033D/N073R/L075D/T189D, A018K/D027S/P029E/N033D/E045F/L075D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D130A/V187N, A018K/G023K/K024A/N094R/D130A/V154I, A018K/G023K/K024A/V077I/G156W/V187Q, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/G156W/V187T/T189D, A018K/G023Q/A049V/L075Q/V077I/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/L075Q/G156W/V187T, A018K/G023Q/K024A/L075R/N094R/G156W, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/N094R/V154I, A018K/G023Q/L075Q/V077I/V187T/T189D, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/N094R/V154I/V187N, A018K/K024A/L075Q/V077I/D130A/V187N, A018K/K024A/L075R/D130A/V187N/T189Q, A018K/K024A/V077I/N094R/D130A/G156W, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137Q/G163P/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027E/S058M/D130A/L227M/N233Q/L264R, D027Q/E056K/S058M/D130A/I252Q/L264R, D027Q/F051T/L075G/D130A/I252Q/L264R, D027Q/F051T/L075G/G091Q/V187N/I252Q, D027Q/F051T/L075Q/D130A/V187H/L264R, D027Q/S058M/L075R/D130A/V187T/I252Q, D027S/E056K/S058M/V187T/I252Q/L264R, D027S/G091Q/D130A/V187N/I252Q/L264R, D027S/P029E/N033D/E045F/N073R/L075D, D027S/P029E/N033D/E045F/N073R/T189D, D027S/P029E/N033D/N073R/L075D/T189D, D048Q/D137Q/G163P/L227M/N233Q/L264R, D048Q/S058M/D130A/G163P/N233Q/L264R, D048Q/S058M/D137Q/G163P/N233Q/L264R, D111A/D130A/V154I/G156W/V187N/L264R, E045F/A049V/L075Q/V077I/V187T/T189D, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/E056K/L075R/D130A/T189Q/L264R, G023K/E056K/L075R/D130A/V187N/L264R, G023K/F051T/D130A/V187N/I252Q/L264R, G023K/K024A/L075Q/D111A/D130A/T189Q, G023K/K024A/L075Q/N094R/D130A/G156W, G023K/K024A/L075Q/V154I/G156W/V187Q, G023K/K024A/L075R/D130A/V154I/V187N, G023K/L075G/D130A/V187T/I252Q/L264R, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/L075Q/D111A/G156W/L264R, G023Q/E045F/A049V/L075Q/G156W/V187T, G023Q/E045F/A049V/L075Q/V077I/V187T, G023Q/E045F/L075Q/V077I/G156W/V187T, G023Q/E045F/L075Q/V077I/V187T/T189D, G023Q/F051T/L075Q/D130A/V187H/I252Q, G023Q/K024A/L075Q/D130A/V154I/G156W, G023Q/K024A/L075Q/D130A/V154I/V187N, G023Q/K024A/L075Q/V154I/G156W/V187N, G023Q/K024A/V077I/D130A/V154I/G156W, G023Q/L075Q/V077I/N094R/D130A/V187Q, G023Q/L075R/V154I/G156W/V187N/L264R, K024A/D111A/D130A/V187T/T189Q/L264R, K024A/L075Q/D130A/G156W/T189Q/L264R, K024A/L075Q/V077I/N094R/D130A/V187N, K024A/L075Q/V154I/G156W/T189Q/L264R, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/G156W/T189Q, L075Q/D111A/D130A/V154I/V187N/T189Q, L075Q/D130A/V154I/G156W/V187N/L264R, L075Q/N094R/D111A/G156W/T189Q/L264R, L075R/D130A/V154I/G156W/V187N/L264R, N011K/D027N/E056K/S058M/N233Q/P256T, N011K/D027N/S058M/I090F/N233Q/P256T, N011K/D027Q/E056K/S058M/N233Q/P256T, N011K/D027S/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027N/E056K/S058M/N233Q/P256T, Q004D/D027S/E056K/S058M/N233Q/P256T, Q004D/N011K/D027N/I090F/N233Q/P256T, Q004D/N011K/D027Q/E056K/S058M/N233Q, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/D130A/G156W/V187N, A018K/G023K/K024A/L075Q/N094R/G156W/V187Q, A018K/G023K/K024A/L075Q/N094R/V154I/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, |

TABLE 8-7-continued

| TLL variants with Performance Index >1 compared to TLL SEQ ID NO: 1 in the CS-61 microswatch Assay using Tide ® full dose are shown below. |
|---|
| A018K/G023K/L075Q/V077I/N094R/V154I/G156W, |
| A018K/G023Q/E045F/A049V/L075Q/G156W/V187T, |
| A018K/G023Q/E045F/L075Q/V077I/G156W/V187T, |
| A018K/G023Q/K024A/L075Q/V077I/D130A/G156W, |
| A018K/G023Q/K024A/L075Q/V077I/N094R/V154I, |
| A018K/G023Q/K024A/L075R/D130A/V154I/V187N, |
| A018K/G023Q/K024A/L075R/N094R/G156W/V187N, |
| A018K/G023Q/K024A/L075R/V077I/D130A/G156W, |
| A018K/G023Q/L075R/V077I/N094R/G156W/V187N, |
| A018K/K024A/L075Q/D111A/G156W/V187N/L264R, |
| A018K/K024A/L075Q/D130A/G156W/V187T/T189Q, |
| A018K/K024A/L075Q/D130A/V154I/G156W/V187T, |
| A018K/K024A/L075Q/V077I/N094R/D130A/G156W, |
| A018K/L075Q/D111A/D130A/V154I/G156W/L264R, |
| A018K/L075Q/D111A/V154I/V187T/T189Q/L264R, |
| A018K/L075Q/N094R/D111A/V154I/V187T/L264R, |
| D027E/D130A/D137Q/G163P/L227M/N233Q/L264R, |
| D027E/S058M/D130A/D137Q/G163P/L227M/L264R, |
| D027E/S058M/D130A/D137Q/G163P/N233Q/L264R, |
| D027Q/F051T/L075G/D130A/V187H/I252Q/L264R, |
| D027Q/F051T/L075Q/G091Q/D130A/V187T/I252Q, |
| D027S/F051T/L075G/G091Q/V187T/I252Q/L264R, |
| D027S/L075R/V154I/G156W/V187N/T189Q/L264R, |
| D027S/P029E/N033D/E045F/N073R/L075D/T189D, |
| D048Q/D130A/D137Q/G163P/L227M/N233Q/L264R, |
| D048Q/S058M/D130A/D137Q/L227M/N233Q/L264R, |
| E056K/L075Q/D111A/D130A/G156W/V187N/T189Q, |
| G023K/D027Q/F051T/L075G/D130A/V187H/L264R, |
| G023K/D027S/F051T/S058M/G091Q/V187N/I252Q, |
| G023K/D027S/L075Q/N094R/V154I/G156W/T189Q, |
| G023K/F051T/E056K/L075R/D130A/V187T/I252Q, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/L075Q/D111A/V154I/G156W/T189Q/L264R, |
| G023K/L075Q/D130A/G156W/V187N/T189Q/L264R, |
| G023K/L075Q/N094R/V154I/G156W/V187T/L264R, |
| G023K/L075R/N094R/V154I/G156W/V187N/L264R, |
| G023Q/D027S/L075Q/G091Q/V187T/I252Q/L264R, |
| G023Q/D027S/S058M/L075Q/D130A/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D111A/G156W/V187N/L264R, |
| G023Q/E056K/L075Q/D130A/V154I/G156W/T189Q, |
| G023Q/F051T/G091Q/D130A/V187H/I252Q/L264R, |
| G023Q/F051T/L075R/G091Q/V187N/I252Q/L264R, |
| G023Q/K024A/L075Q/V077I/D130A/G156W/V187N, |
| G023Q/K024A/L075Q/V077I/D130A/V154I/G156W, |
| G023Q/L075Q/D111A/D130A/V154I/G156W/L264R, |
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187N, |
| G023Q/L075Q/V077I/N094R/D130A/G156W/V187Q, |
| K024A/L075Q/D111A/D130A/V187N/T189Q/L264R, |
| K024A/L075R/D130A/V154I/G156W/T189Q/L264R, |
| L075Q/D111A/D130A/G156W/V187N/T189Q/L264R, |
| N011K/A018K/K024A/V077I/V154I/G156W/T189Q, |
| N011K/D027S/D111A/D130A/V154I/V187N/T189Q, |
| N011K/E056K/L075Q/D130A/V154I/V187N/T189Q, |
| N011K/G023K/L075Q/D111A/D130A/V154I/V187N, |
| Q004D/N011K/D027Q/E056K/S058M/N233Q/P256T, |
| Q004D/N011K/D027S/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| A018K/K024A/L075Q/V077I/N094R/D130A/V154I/G156W, |

TABLE 8-7-continued

| TLL variants with Performance Index >1 compared to TLL SEQ ID NO: 1 in the CS-61 microswatch Assay using Tide ® full dose are shown below. |
|---|
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| D048Q/S058M/D130A/D137Q/G163P/L227M/N233Q/L264R, |
| G023K/D027S/E056K/L075G/D130A/V187T/I252Q/L264R, |
| G023K/D027S/F051T/E056K/L075Q/G091Q/V187H/I252Q, |
| G023K/D027S/F051T/E056K/L075R/D130A/V187T/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |
| G023K/L075Q/N094R/D130A/V154I/G156W/V187N/L264R, |
| G023Q/D027S/E056K/L075R/D111A/V154I/G156W/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/D027S/L075R/N094R/V154I/G156W/V187N/T189Q, |
| G023Q/E056K/L075Q/D111A/V154I/V187N/T189Q/L264R, |
| G023Q/E056K/L075Q/N094R/D111A/G156W/T189Q/L264R, |
| G023Q/K024A/L075Q/V077I/D130A/V154I/G156W/V187N, |
| G023Q/K024A/L075Q/V077I/N094R/D130A/V154I/V187N, |
| G023Q/L075Q/N094R/D111A/D130A/G156W/T189Q/L264R, |
| G023Q/L075Q/N094R/D130A/V154I/G156W/T189Q/L264R, |
| G023Q/L075Q/V077I/N094R/D130A/V154I/G156W/V187Q, |
| K024A/D111A/D130A/V154I/G156W/V187T/T189Q/L264R, |
| N011K/G023K/D027S/L075R/V154I/G156W/V187N/T189Q, |
| N011K/G023K/E056K/L075Q/D130A/V154I/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075R/V077I/D130A/V154I/G156W/V187N, |
| A018K/G023K/K024A/V077I/D130A/V154I/G156W/V187T/T189Q, |
| A018K/G023K/L075Q/N094R/D111A/V154I/G156W/T189Q/L264R, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |
| A018K/G023Q/K024A/L075R/N094R/D130A/V154I/G156W/V187N, |
| A018K/K024A/L075Q/N094R/V154I/G156W/V187N/T189Q/L264R, |
| D027S/E056K/L075Q/N094R/D111A/D130A/V154I/G156W/L264R, |
| D027S/E056K/L075Q/N094R/D111A/D130A/V187N/T189Q/L264R, |
| G023K/D027S/F051T/E056K/S058M/L075Q/G091Q/V187N/L264R, |
| G023K/D027S/F051T/E056K/S058M/L075R/G091Q/V187H/I252Q, |
| G023K/D027S/L075Q/D111A/D130A/V154I/G156W/T189Q/L264R, |
| G023K/E056K/L075Q/D111A/D130A/V154I/G156W/T189Q/L264R, |
| G023K/K024A/L075Q/N094R/V154I/G156W/V187N/T189Q/L264R, |
| G023K/K024A/N094R/D130A/V154I/G156W/V187T/T189Q/L264R, |
| G023Q/D027S/F051T/E056K/L075G/G091Q/V187N/I252Q/L264R, |
| G023Q/D027S/L075Q/N094R/D130A/V154I/G156W/V187N/L264R, |
| N011K/G023K/L075R/D111A/D130A/V154I/V187N/T189Q/L264R, |
| N011K/G023Q/L075Q/D111A/V154I/G156W/V187N/T189Q/L264R, |
| N011K/G023K/L075R/V077I/D130A/V154I/G156W/V187T/T189Q, |
| A018K/G023Q/D027S/E045F/A049V/N073S/L075Q/R108K/V187T/T189D, |
| A018K/G023Q/D027S/E045F/A049V/S058M/L075Q/R108K/V187T/T189D, |
| A018K/G023Q/D027S/P029E/S058M/L075Q/V077I/H135F/G156W/V187T, |
| A018K/G023Q/D027S/P029E/S058M/L075Q/V077I/R108K/H135F/V187H, |
| A018K/G023Q/D027S/S058M/L075Q/V077I/R108K/H135F/G156W/V187H, |
| A018K/G023Q/K024A/L075Q/V077I/N094R/D130A/V154I/G156W/V187Q, |
| G023K/D027S/F051T/E056K/S058M/L075G/G091Q/D130A/I252Q/L264R, |
| G023Q/D027S/F051T/E056K/L075R/G091Q/D130A/V187H/I252Q/L264R, |
| G023Q/D027S/F051T/E056K/S058M/L075R/G091Q/D130A/V187H/I252Q, |
| G023Q/L075R/N094R/D111A/D130A/V154I/G156W/V187N/T189Q/L264R, |
| N011K/A018K/G023K/K024A/L075R/V077I/D130A/V154I/V187T/T189Q, |
| N011K/G023K/L075R/N094R/D111A/V154I/G156W/V187N/T189Q/L264R, |
| N011K/G023Q/L075Q/N094R/D111A/D130A/V154I/G156W/V187N/L264R, |
| A018K/G023K/L075R/N094R/D111A/D130A/V154I/G156W/V187N/T189Q/L264R, |
| A018K/G023Q/D027S/P029E/S058M/L075Q/V077I/R108K/H135F/G156W/V187T, |
| N011K/G023Q/D027S/L075Q/N094R/D111A/V154I/G156W/V187N/T189Q/L264R, |
| A018K/G023Q/D027S/P029E/E045F/A049V/S058M/N073S/L075Q/R108K/V187T/T189D, |
| A018K/G023Q/D027S/P029E/E045F/A049V/S058M/N073S/L075Q/R108K/H135F/V187T/T189D, |
| A018K/G023Q/D027S/P029E/N033D/E045F/A049V/S058M/N073S/K074S/L075Q/V077I/N101D/R108K/H135F/D137V/G156W/V187T/T189D |

TABLE 8-8

| TLL variants with Performance Index for expression ≥0.5 and Performance Index >1 in the CS-61 microswatch Assay using Tide ® full dose compared to TLL SEQ ID NO: 1 are shown below. |
| --- |
| D027S/N033D, D130A/L264R, D130A/V187N, G023K/L264R, K024A/V154I, L227M/L264R, N033D/E045F, P029E/N033D, V187T/L264R, A018K/K024A/V154I, A018K/L075D/T189D, A018K/P029E/T189D, A018K/V154I/G156W, D027E/S058M/G163P, D027S/N033D/T189D, D111A/D130A/L264R, G023K/D130A/L264R, G023K/D130A/V187T, G023K/E056K/V187T, G023K/V187N/L264R, G023Q/A049V/T189D, G023Q/K024A/G156W, L075G/D130A/V187H, L075Q/V187N/L264R, L075Q/V187T/L264R, L075R/D130A/L264R, L075R/D130A/V187T, L075R/V187N/L264R, L075R/V187T/L264R, P029E/N033D/E045F, V187N/T189Q/L264R, A018K/D027S/P029E/T189D, A018K/E045F/L075D/T189D, A018K/G023K/D111A/T189Q, A018K/G023Q/A049V/V187T, A018K/L075Q/V077I/N094R, A018K/N033D/L075D/T189D, A018K/P029E/N073R/L075D, D027E/D137Q/G163P/L227M, D027E/D137Q/L227M/L264R, D027E/L227M/N233Q/L264R, D027S/N033D/E045F/T189D, D027S/N033D/L075D/T189D, D027S/N033D/N073R/T189D, D027S/P029E/E045F/T189D, D027S/P029E/L075D/T189D, D027S/P029E/N033D/E045F, D027S/P029E/N033D/L075D, D048Q/D130A/G163P/L264R, D130A/G163P/L227M/L264R, E056K/D130A/V187N/L264R, E056K/D130A/V187T/L264R, G023K/D027Q/F051T/L075Q, G023K/D130A/V187T/L264R, G023K/E056K/V187T/L264R, G023K/K024A/V154I/V187N, G023K/L075R/D130A/L264R, G023K/L075R/V187T/L264R, G023Q/K024A/L075R/G156W, G023Q/L075Q/V187T/L264R, K024A/D130A/V154I/V187T, L075G/D130A/V187T/I252Q, N011K/D027S/N233Q/P256T, P029E/N073R/L075D/T189D, S058M/D137Q/G163P/N233Q, S058M/G163P/N233Q/L264R, S058M/L075Q/G091Q/I252Q, A018K/D027S/P029E/N033D/L075D, A018K/D130A/G156W/V187N/L264R, A018K/E045F/N073R/L075D/T189D, A018K/G023K/D130A/V154I/G156W, A018K/G023K/K024A/D130A/G156W, A018K/G023K/V077I/D130A/V187N, A018K/G023Q/K024A/D130A/V187Q, A018K/G023Q/K024A/L075Q/G156W, A018K/G023Q/V077I/D130A/G156W, A018K/K024A/L075R/D130A/V154I, A018K/K024A/N094R/D130A/V187N, A018K/P029E/N033D/N073R/L075D, D027E/D130A/G163P/L227M/L264R, D027E/D130A/G163P/N233Q/L264R, D027E/D137Q/G163P/N233Q/L264R, D027E/S058M/D137Q/G163P/N233Q, D027S/E056K/D111A/V187N/L264R, D027S/L075G/D130A/I252Q/L264R, D027S/L075R/V154I/T189Q/L264R, D048Q/S058M/D130A/N233Q/L264R, D048Q/S058M/D137Q/G163P/N233E, D130A/D137Q/G163P/N233Q/L264R, E045F/A049V/L075Q/V187T/T189D, E056K/L075R/D130A/V187T/L264R, F051T/L075G/V187N/I252Q/L264R, F051T/L075Q/G091Q/D130A/L264R, F051T/S058M/L075Q/G091Q/I252Q, G023K/D027S/E056K/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075Q/V187H/I252Q/L264R, G023K/L075R/D130A/V187T/L264R, G023K/N094R/G156W/V187N/T189Q, G023Q/K024A/L075Q/G156W/V187Q, G023Q/L075Q/V077I/D130A/G156W, K024A/L075R/V154I/G156W/V187Q, N011K/G023K/D111A/G156W/L264R, S058M/D130A/D137Q/G163P/L264R, S058M/G163P/L227M/N233Q/L264R, A018K/D027S/N033D/N073R/L075D/T189D, A018K/D027S/P029E/N033D/E045F/L075D, A018K/G023K/K024A/V077I/G156W/V187Q, A018K/G023K/L075Q/V077I/G156W/V187Q, A018K/G023Q/A049V/G156W/V187T/T189D, A018K/G023Q/K024A/L075R/N094R/G156W, A018K/G023Q/N094R/D130A/G156W/V187Q, A018K/K024A/D111A/V187N/T189Q/L264R, A018K/K024A/L075Q/N094R/V154I/G156W, A018K/K024A/L075Q/V077I/D130A/V187N, A018K/N094R/D111A/D130A/V154I/V187N, D027E/D048Q/D130A/D137Q/G163P/L264R, D027E/D048Q/D137Q/G163P/L227M/L264R, D027E/D048Q/D137Q/G163P/N233Q/L264R, D027E/D048Q/S058M/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027E/S058M/D130A/L227M/N233Q/L264R, D027Q/E056K/S058M/D130A/I252Q/L264R, D027Q/F051T/L075G/G091Q/V187N/I252Q, D027Q/S058M/L075R/D130A/V187T/I252Q, D027S/E056K/S058M/V187T/I252Q/L264R, D048Q/D137Q/G163P/L227M/N233Q/L264R, D048Q/S058M/D137Q/G163P/N233Q/L264R, F051T/L075G/G091Q/D130A/I252Q/L264R, G023K/D027Q/F051T/E056K/S058M/L075Q, G023K/D027S/L075R/D130A/V187T/I252Q, G023K/D027S/L075R/V187N/I252Q/L264R, G023K/E056K/L075R/D130A/T189Q/L264R, G023K/E056K/L075R/D130A/V187N/L264R, G023K/F051T/D130A/V187N/I252Q/L264R, G023K/K024A/L075Q/D111A/D130A/T189Q, G023K/K024A/L075Q/V154I/G156W/V187Q, G023K/K024A/L075R/D130A/V154I/V187N, G023K/L075G/D130A/V187T/I252Q/L264R, G023K/N094R/D111A/G156W/V187T/L264R, G023Q/F051T/L075Q/D130A/V187H/I252Q, G023Q/K024A/V077I/D130A/V154I/G156W, K024A/L075Q/V077I/N094R/D130A/V187N, Q004D/N011K/D027N/I090F/N233Q/P256T, Q004D/N011K/D027S/S058M/N233Q/P256T, S058M/D130A/D137Q/G163P/L227M/L264R, S058M/D130A/D137Q/G163P/N233Q/L264R, S058M/D130A/G163P/L227M/N233Q/L264R, A018K/D027S/P029E/N033D/N073R/L075D/T189D, A018K/G023K/K024A/L075Q/N094R/G156W/V187Q, A018K/G023K/K024A/L075Q/N094R/V154I/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, A018K/K024A/L075Q/D130A/V154I/G156W/V187T, A018K/K024A/L075Q/V077I/N094R/D130A/G156W, D027E/D130A/D137Q/G163P/L227M/N233Q/L264R, D027E/S058M/D130A/D137Q/G163P/L227M/L264R, D048Q/D130A/D137Q/G163P/L227M/N233Q/L264R, D048Q/S058M/D130A/D137Q/L227M/N233Q/L264R, G023K/D027S/F051T/S058M/G091Q/V187N/I252Q, G023Q/D027S/S058M/L075Q/D130A/I252Q/L264R, |

TABLE 8-8-continued

| TLL variants with Performance Index for expression ≥0.5 and Performance Index >1 in the CS-61 microswatch Assay using Tide ® full dose compared to TLL SEQ ID NO: 1 are shown below. |
|---|
| G023Q/F051T/G091Q/D130A/V187H/I252Q/L264R, G023Q/L075Q/V077I/N094R/D130A/G156W/V187N, N011K/A018K/K024A/V077I/V154I/G156W/T189Q, Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D027E/D048Q/D130A/D137Q/G163P/L227M/N233Q/L264R, D048Q/S058M/D130A/D137Q/G163P/L227M/N233Q/L264R, G023K/D027S/F051T/E056K/L075Q/G091Q/V187H/I252Q, G023Q/D027S/E056K/L075R/D111A/V154I/G156W/L264R, G023Q/D027S/F051T/S058M/G091Q/D130A/V187N/I252Q, G023Q/D027S/L075R/N094R/V154I/G156W/V187N/T189Q, A018K/G023K/K024A/V077I/D130A/V154I/G156W/V187T/T189Q, A018K/G023Q/D027S/P029E/L075Q/V077I/R108K/H135F/V187H, G023K/K024A/L075Q/N094R/V154I/G156W/V187N/T189Q/L264R, N011K/G023K/L075R/V077I/D130A/V154I/G156W/V187T/T189Q, A018K/G023Q/D027S/P029E/S058M/L075Q/V077I/H135F/G156W/V187T, A018K/G023Q/D027S/P029E/S058M/L075Q/V077I/R108K/H135F/V187H, N011K/A018K/G023K/K024A/L075R/V077I/D130A/V154I/V187T/T189Q, A018K/G023K/L075R/N094R/D111A/D130A/V154I/G156W/V187N/T189Q/L264R, A018K/G023Q/D027S/P029E/S058M/L075Q/V077I/R108K/H135F/G156W/V187T |

TABLE 8-9

| TLL variants with Performance Index for expression ≥0.5 and Performance Index ≥50% of the maximum PI value in the CS-61 microswatch Assay using Tide ® full dose compared to TLL SEQ ID NO: 1 are shown below. |
|---|
| A018K/P029E/T189D, A018K/V154I/G156W, D027S/N033D/T189D, G023K/V187N/L264R, L075R/D130A/V187T, L075R/V187N/L264R, A018K/D027S/P029E/T189D, A018K/L075Q/V077I/N094R, A018K/N033D/L075D/T189D, D027S/P029E/N033D/E045F, D027S/P029E/N033D/L075D, D048Q/D130A/G163P/L264R, G023K/D130A/V187T/L264R, P029E/N073R/L075D/T189D, A018K/D027S/P029E/N033D/L075D, A018K/G023Q/K024A/L075Q/G156W, A018K/K024A/N094R/D130A/V187N, D027E/D130A/G163P/N233Q/L264R, D027E/D137Q/G163P/N233Q/L264R, D130A/D137Q/G163P/N233Q/L264R, E045F/A049V/L075Q/V187T/T189D, E056K/L075R/D130A/V187T/L264R, G023K/D027S/E056K/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075R/D130A/V187T/L264R, K024A/L075R/V154I/G156W/V187Q, A018K/G023K/L075Q/V077I/G156W/V187Q, A018K/K024A/L075Q/V077I/D130A/V187N, D027E/D048Q/D130A/D137Q/G163P/L264R, D027E/D048Q/D137Q/G163P/L227M/L264R, D027E/D048Q/D137Q/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D048Q/D137Q/G163P/L227M/N233Q/L264R, G023K/D027S/L075R/V187N/I252Q/L264R, G023K/K024A/L075Q/V154I/G156W/V187Q, G023K/N094R/D111A/G156W/V187T/L264R, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023Q/L075R/V077I/N094R/G156W/V187N, D048Q/D130A/D137Q/G163P/L227M/N233Q/L264R, D048Q/S058M/D130A/D137Q/L227M/N233Q/L264R, N011K/A018K/K024A/V077I/V154I/G156W/T189Q, Q004D/N011K/D027S/E056K/S058M/N233Q/P256T, A018K/G023K/K024A/L075Q/V077I/N094R/D130A/G156W, D027E/D048Q/D130A/D137Q/G163P/L227M/N233Q/L264R, G023K/D027S/F051T/E056K/L075Q/G091Q/V187H/I252Q, G023Q/D027S/E056K/L075R/D111A/V154I/G156W/L264R, A018K/G023K/K024A/V077I/D130A/V154I/G156W/V187T/T189Q, G023K/K024A/L075Q/N094R/V154I/G156W/V187N/T189Q/L264R, N011K/G023K/L075R/V077I/D130A/V154I/G156W/V187T/T189Q, A018K/G023Q/D027S/P029E/S058M/L075Q/V077I/R108K/H135F/V187H, N011K/A018K/G023K/K024A/L075R/V077I/D130A/V154I/V187T/T189Q, A018K/G023K/L075R/N094R/D111A/D130A/V154I/G156W/V187N/T189Q/L264R |

TABLE 8-10

| TLL variants with Performance Index >1 compared to Reference sequence SEQ ID NO: 2 in the CS-61 microswatch Assay using Tide ® full dose are shown below. |
| --- |
| A018K/L075Q, A018K/T189D, E045F/T189D, G023K/D130A, K024A/L075Q, L075Q/D130A, L075Q/G156W, L227M/L264R, A018K/A049V/L075Q, A018K/D027S/N073R, A018K/D027S/T189D, A018K/E045F/T189D, A018K/G023K/L075Q, A018K/G023Q/L075Q, A018K/L075D/T189D, A018K/L075Q/G156W, A018K/L075Q/V187T, A018K/N033D/L075D, A018K/N073R/L075D, A018K/P029E/T189D, A018K/V154I/G156W, D027S/N033D/T189D, D027S/N233Q/P256T, E056K/D130A/T189Q, G023K/V187N/L264R, G023Q/A049V/T189D, G023Q/D111A/L264R, G023Q/E056K/L075R, G023Q/L075Q/V077I, G023Q/L075Q/V187T, K024A/L075Q/G156W, K024A/L075Q/V077I, L075G/D130A/V187H, L075Q/D130A/V187T, L075Q/G156W/T189D, L075Q/G156W/V187N, L075Q/G156W/V187T, L075Q/V077I/T189D, L075Q/V154I/V187T, L075Q/V187N/L264R, L075Q/V187T/T189D, L075R/D130A/V187T, L075R/V187N/L264R, N073R/L075D/T189D, P029E/E045F/L075D, P029E/L075D/T189D, P029E/N033D/E045F, P029E/N033D/L075D, P029E/N073R/L075D, S058M/L227M/L264R, V077I/D130A/V154I, V077I/V187A/T189D, V187N/T189Q/L264R, A018K/A049V/L075Q/T189D, A018K/A049V/L075Q/V187T, A018K/D027S/E045F/N073R, A018K/D027S/E045F/T189D, A018K/D027S/N033D/L075D, A018K/D027S/P029E/T189D, A018K/E045F/L075Q/V187T, A018K/G023Q/A049V/T189D, A018K/G023Q/E045F/T189D, A018K/G023Q/E045F/V187T, A018K/G023Q/G156W/V187T, A018K/G023Q/L075Q/T189D, A018K/G023Q/L075Q/V077I, A018K/G023Q/L075Q/V187T, A018K/G023Q/L075R/D130A, A018K/G023Q/V077I/V187T, A018K/G023Q/V187T/T189D, A018K/L075Q/G156W/T189D, A018K/L075Q/N094R/D111A, A018K/L075Q/N094R/V187Q, A018K/L075Q/V077I/N094R, A018K/L075Q/V187T/T189D, A018K/N033D/L075D/T189D, A018K/N073R/L075D/T189D, A018K/P029E/N033D/T189D, A049V/L075Q/V187T/T189D, D027S/E056K/D111A/V154I, D027S/N033D/L075D/T189D, D027S/P029E/E045F/L075D, D027S/P029E/L075D/T189D, D027S/P029E/N033D/E045F, D027S/P029E/N033D/L075D, D027S/P029E/N033D/T189D, D048Q/D130A/G163P/L264R, D111A/D130A/V154I/L264R, D130A/G163P/L227M/L264R, D130A/G163P/N233Q/L264R, E056K/L075Q/V187N/L264R, G023K/D027S/L075Q/L264R, G023K/D130A/V187T/L264R, G023K/L075Q/D130A/V187N, G023K/L075Q/G156W/L264R, G023K/L075Q/G156W/V187N, G023K/L075R/V187N/L264R, G023Q/A049V/L075Q/T189D, G023Q/A049V/L075Q/V077I, G023Q/D027S/D111A/G156W, G023Q/E045F/A049V/T189D, G023Q/E045F/L075Q/G156W, G023Q/E045F/L075Q/V187T, G023Q/K024A/L075R/V154I, G023Q/L075Q/G156W/V187N, G023Q/L075Q/G156W/V187T, K024A/L075Q/D130A/G156W, K024A/L075Q/V187T/T189Q, K024A/L075R/G156W/V187N, L075Q/D130A/G156W/V187N, L075Q/D130A/V154I/G156W, L075Q/V077I/D130A/V187Q, L075Q/V077I/G156W/V187N, L075Q/V077I/N094R/G156W, L075Q/V077I/V154I/V187Q, L075Q/V077I/V187T/T189D, L075R/D111A/V154I/G156W, L075R/D130A/V154I/L264R, N011K/D027N/S058M/P256T, N011K/D027S/E056K/P256T, N011K/G023K/L075Q/D111A, P029E/E045F/L075D/T189D, P029E/E045F/N073R/L075D, P029E/E045F/N073R/T189D, P029E/N033D/L075D/T189D, P029E/N073R/L075D/T189D, Q004D/D027S/I090F/P256T, Q004D/N011K/D027N/P256T, Q004D/N011K/D027Q/N233Q, A018K/D027S/E045F/N073R/D137V, A018K/D027S/N033D/E045F/T189D, A018K/D027S/N033D/L075D/T189D, A018K/D027S/N073R/L075D/T189D, A018K/D027S/P029E/E045F/T189D, A018K/D027S/P029E/N033D/L075D, A018K/E045F/A049V/L075Q/V187T, A018K/G023K/K024A/L075R/N094R, A018K/G023K/L075Q/D130A/V154I, A018K/G023Q/A049V/L075Q/G156W, A018K/G023Q/A049V/L075Q/V077I, A018K/G023Q/A049V/L075Q/V187T, A018K/G023Q/A049V/V077I/V187T, A018K/G023Q/E045F/A049V/L075Q, A018K/G023Q/E045F/L075Q/V187T, A018K/G023Q/K024A/D130A/V154I, A018K/G023Q/K024A/L075Q/G156W, A018K/G023Q/L075Q/G156W/V187T, A018K/G023Q/L075Q/V187T/T189D, A018K/G023Q/V077I/V187T/T189D, A018K/K024A/L075Q/D130A/L264R, A018K/K024A/L075Q/V154I/G156W, A018K/K024A/L075R/D130A/V154I, A018K/K024A/L075R/N094R/D130A, A018K/K024A/N094R/D130A/V187N, A018K/L075Q/D111A/D130A/V187T, A018K/L075Q/N094R/G156W/V187N, A018K/L075Q/V077I/N094R/G156W, A018K/N033D/E045F/L075D/T189D, A018K/P029E/E045F/N073R/L075D, A018K/P029E/N033D/N073R/L075D, D027E/D048Q/S058M/G163P/N233Q, D027E/D130A/G163P/L227M/L264R, D027E/D130A/G163P/N233Q/L264R, D027E/D137Q/G163P/L227M/L264R, D027E/D137Q/G163P/N233Q/L264R, D027S/L075Q/D111A/D130A/V187N, D027S/L075R/V154I/T189Q/L264R, D027S/N033D/E045F/N073R/L075D, D027S/N033D/N073R/L075D/T189D, D027S/P029E/N033D/E045F/N073R, D027S/P029E/N033D/N073R/L075D, D027S/P029E/N073R/L075D/T189D, D048Q/D130A/D137Q/G163P/L264R, D048Q/S058M/D137Q/G163P/L264R, D130A/D137Q/G163P/N233Q/L264R, E045F/A049V/L075Q/V187T/T189D, E056K/D130A/V187H/I252Q/L264R, E056K/L075Q/G156W/T189Q/L264R, E056K/L075R/D130A/V187T/L264R, G023K/D027S/E056K/V187T/L264R, G023K/D111A/V154I/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075Q/V187H/I252Q/L264R, G023K/L075R/D130A/V187T/L264R, G023K/N094R/G156W/V187N/T189Q, G023Q/A049V/L075Q/G156W/T189D, G023Q/A049V/L075Q/G156W/V187T, G023Q/A049V/L075Q/V187T/T189D, G023Q/D027S/V154I/V187N/L264R, G023Q/E045F/L075Q/G156W/T189D, G023Q/E045F/L075Q/V077I/V187T, G023Q/K024A/L075Q/D130A/G156W, G023Q/K024A/L075Q/G156W/V187N, G023Q/K024A/L075Q/V077I/V187Q, G023Q/K024A/L075R/G156W/V187Q, G023Q/K024A/L075R/V077I/D130A, G023Q/K024A/V077I/D130A/V154I, G023Q/L075Q/V077I/G156W/V187N, G091Q/D130A/V187H/I252Q/L264R, |

TABLE 8-10-continued

| TLL variants with Performance Index >1 compared to Reference sequence SEQ ID NO: 2 in the CS-61 microswatch Assay using Tide ® full dose are shown below. |
|---|
| K024A/L075Q/D111A/G156W/V187T, K024A/L075Q/V077I/G156W/V187N, K024A/L075Q/V077I/V154I/V187N, K024A/L075R/V154I/G156W/V187Q, L075Q/D111A/V187N/T189Q/L264R, L075Q/N094R/D130A/G156W/V187T, L075Q/V077I/D130A/G156W/V187N, L075Q/V154I/V187N/T189Q/L264R, L075R/D130A/V154I/T189Q/L264R, L075R/D130A/V187T/T189Q/L264R, L075R/G156W/V187T/T189Q/L264R, L075R/V077I/N094R/V154I/G156W, N011K/D027N/E056K/N233Q/P256T, N011K/D027N/E056K/S058M/P256T, N011K/G023K/D111A/G156W/L264R, N011K/G023K/E056K/L075Q/T189Q, P029E/N033D/E045F/L075D/T189D, P029E/N033D/K074S/L075D/T189D, P029E/N033D/N073R/L075D/T189D, Q004D/D027S/S058M/N233Q/P256T, Q004D/N011K/D027Q/E056K/N233Q, S058M/G163P/L227M/N233Q/L264R, A018K/A049V/L075Q/G156W/V187T/T189D, A018K/D027S/N033D/E045F/L075D/T189D, A018K/D027S/P029E/N073R/L075D/T189D, A018K/E045F/A049V/L075Q/V077I/V187T, A018K/G023K/D111A/D130A/V154I/T189Q, A018K/G023K/K024A/L075R/D130A/V187N, A018K/G023K/K024A/N094R/D130A/V154I, A018K/G023K/L075Q/D130A/G156W/V187N, A018K/G023K/L075Q/G156W/V187N/L264R, A018K/G023K/L075Q/V077I/G156W/V187Q, A018K/G023K/L075R/N094R/D130A/V187N, A018K/G023K/L075R/V077I/D130A/V154I, A018K/G023Q/A049V/L075Q/V077I/V187T, A018K/G023Q/E045F/A049V/L075Q/T189D, A018K/G023Q/E045F/A049V/L075Q/V077I, A018K/G023Q/E045F/A049V/L075Q/V187T, A018K/G023Q/E045F/L075Q/G156W/V187T, A018K/G023Q/K024A/L075R/N094R/G156W, A018K/G023Q/L075Q/G156W/V187T/T189D, A018K/G023Q/L075Q/V077I/D130A/G156W, A018K/G023Q/L075Q/V077I/D130A/V187N, A018K/G023Q/L075Q/V077I/G156W/V187N, A018K/G023Q/L075Q/V077I/V187T/T189D, A018K/K024A/L075Q/N094R/V154I/G156W, A018K/K024A/L075Q/V077I/D130A/V187N, A018K/K024A/L075R/D130A/V187N/T189Q, A018K/K024A/V077I/N094R/D130A/G156W, A018K/L075Q/D130A/V154I/T189Q/L264R, A018K/L075Q/D130A/V187N/T189Q/L264R, A018K/L075R/D130A/V154I/G156W/V187N, D027E/D048Q/D130A/D137Q/G163P/L264R, D027E/D048Q/D137Q/G163P/L227M/L264R, D027E/D048Q/D137Q/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027Q/E056K/S058M/D130A/I252Q/L264R, D027Q/F051T/L075G/D130A/I252Q/L264R, D027Q/F051T/L075Q/D130A/V187H/L264R, D027S/P029E/N033D/N073R/L075D/T189D, D048Q/D137Q/G163P/L227M/N233Q/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/V187N/I252Q/L264R, G023K/E056K/L075R/D130A/T189Q/L264R, G023K/E056K/L075R/D130A/V187N/L264R, G023K/K024A/L075Q/N094R/D130A/G156W, G023K/K024A/L075Q/V154I/G156W/V187Q, G023K/L075G/D130A/V187T/I252Q/L264R, G023K/L075Q/D111A/D130A/V154I/V187N, G023K/L075Q/N094R/V154I/V187T/L264R, G023K/L075Q/V077I/D130A/G156W/V187Q, G023K/N094R/D111A/G156W/V187T/L264R, G023Q/A049V/L075Q/G156W/V187T/T189D, G023Q/D027Q/E056K/L075R/I252Q/L264R, G023Q/D027S/F051T/L075Q/V187T/I252Q, G023Q/D027S/L075Q/D111A/G156W/L264R, G023Q/E045F/A049V/L075Q/G156W/V187T, G023Q/E045F/A049V/L075Q/V077I/V187T, G023Q/E045F/L075Q/V077I/V187T/T189D, G023Q/K024A/L075Q/D130A/V154I/G156W, G023Q/K024A/L075Q/D130A/V154I/V187N, G023Q/K024A/L075Q/V154I/G156W/V187N, G023Q/L075Q/V077I/N094R/D130A/V187Q, G023Q/L075R/V154I/G156W/V187N/L264R, K024A/D111A/D130A/V187T/T189Q/L264R, K024A/L075Q/V154I/G156W/T189Q/L264R, K024A/L075Q/V154I/V187N/T189Q/L264R, K024A/L075Q/V154I/V187T/T189Q/L264R, K024A/N094R/V154I/G156W/T189Q/L264R, L075Q/D111A/D130A/V154I/G156W/T189Q, L075Q/D111A/D130A/V154I/V187N/T189Q, L075Q/N094R/D111A/G156W/T189Q/L264R, N011K/D027N/S058M/I090F/N233Q/P256T, N011K/D027Q/E056K/S058M/N233Q/P256T, N011K/D027S/S058M/I090F/N233Q/P256T, N011K/E056K/L075Q/D130A/V187N/T189Q, N011K/G023K/D027S/V154I/G156W/T189Q, N011K/G023Q/L075Q/D130A/V187N/T189Q, N011K/G023Q/L075Q/N094R/D130A/L264R, P029E/N033D/K074S/L075D/N101D/T189D, Q004D/D027S/E056K/S058M/N233Q/P256T, Q004D/N011K/D027Q/E056K/S058M/N233Q, A018K/D027S/P029E/N033D/N073R/L075D/T189D, A018K/G023K/K024A/L075Q/N094R/G156W/V187Q, A018K/G023K/K024A/L075Q/V077I/N094R/G156W, A018K/G023K/K024A/L075R/N094R/D130A/V154I, A018K/G023K/K024A/L075R/V154I/G156W/V187Q, A018K/G023K/K024A/N094R/V154I/V187T/L264R, A018K/G023K/L075Q/V077I/N094R/V154I/G156W, A018K/G023Q/E045F/A049V/L075Q/G156W/V187T, A018K/G023Q/E045F/L075Q/V077I/G156W/V187T, A018K/G023Q/K024A/L075Q/V077I/D130A/G156W, A018K/G023Q/K024A/L075Q/V077I/N094R/V154I, A018K/G023Q/K024A/L075R/D130A/V154I/V187N, A018K/G023Q/K024A/L075R/N094R/G156W/V187N, A018K/G023Q/K024A/L075R/V077I/D130A/G156W, A018K/G023Q/L075R/V077I/N094R/G156W/V187N, A018K/K024A/L075Q/D111A/G156W/V187N/L264R, A018K/K024A/L075Q/D130A/G156W/V187T/T189Q, A018K/L075Q/D111A/V154I/V187T/T189Q/L264R, A018K/L075Q/N094R/D111A/V154I/V187T/L264R, D027E/S058M/D130A/D137Q/G163P/N233Q/L264R, D027Q/F051T/L075G/D130A/V187H/I252Q/L264R, D027Q/F051T/L075Q/G091Q/D130A/V187T/I252Q, D027S/F051T/L075G/G091Q/V187T/I252Q/L264R, D027S/P029E/N033D/E045F/N073R/L075D/T189D, |

TABLE 8-10-continued

| TLL variants with Performance Index >1 compared to Reference sequence SEQ ID NO: 2 in the CS-61 microswatch Assay using Tide ® full dose are shown below. |
|---|
| D048Q/D130A/D137Q/G163P/L227M/N233Q/L264R, |
| D048Q/S058M/D130A/D137Q/L227M/N233Q/L264R, |
| E056K/L075Q/D111A/D130A/G156W/V187N/T189Q, |
| G023K/D027Q/F051T/L075G/D130A/V187H/L264R, |
| G023K/D027S/L075Q/N094R/V154I/G156W/T189Q, |
| G023K/F051T/E056K/L075R/D130A/V187T/I252Q, |
| G023K/K024A/L075Q/D111A/V154I/G156W/V187N, |
| G023K/K024A/L075Q/D130A/V187T/T189Q/L264R, |
| G023K/K024A/L075Q/N094R/V154I/G156W/V187N, |
| G023K/K024A/L075Q/V077I/D130A/G156W/V187Q, |
| G023K/L075Q/D111A/V154I/G156W/T189Q/L264R, |
| G023K/L075Q/D130A/G156W/V187N/T189Q/L264R, |
| G023K/L075Q/N094R/V154I/G156W/V187T/L264R, |
| G023K/L075R/N094R/V154I/G156W/V187N/L264R, |
| G023Q/D027S/L075Q/G091Q/V187T/I252Q/L264R, |
| G023Q/E045F/A049V/V077I/G156W/V187T/T189D, |
| G023Q/E045F/L075Q/V077I/G156W/V187T/T189D, |
| G023Q/E056K/L075Q/D130A/V154I/G156W/T189Q, |
| G023Q/F051T/L075R/G091Q/V187N/I252Q/L264R, |
| G023Q/K024A/L075Q/V077I/D130A/G156W/V187N, |
| G023Q/K024A/L075Q/V077I/D130A/V154I/G156W, |
| G023Q/L075Q/D130A/V154I/G156W/T189Q/L264R, |
| G023Q/L075Q/D130A/V154I/V187N/T189Q/L264R, |
| G023Q/L075Q/V077I/N094R/D130A/G156W/V187Q, |
| K024A/L075Q/D111A/D130A/V187N/T189Q/L264R, |
| L075Q/D111A/D130A/G156W/V187N/T189Q/L264R, |
| N011K/D027S/D111A/D130A/V154I/V187N/T189Q, |
| N011K/E056K/L075Q/D130A/V154I/V187N/T189Q, |
| N011K/G023K/L075Q/D111A/D130A/V154I/V187N, |
| Q004D/N011K/D027Q/E056K/S058M/N233Q/P256T, |
| Q004D/N011K/D027S/E056K/S058M/N233Q/P256T, |
| A018K/G023K/K024A/L075Q/D130Y/V154I/V187N/T189Q, |
| A018K/G023K/K024A/L075Q/N094R/D130A/G156W/V187Q, |
| A018K/G023K/K024A/L075Q/V077I/D130A/V154I/G156W, |
| A018K/G023K/K024A/L075Q/V077I/N094R/D130A/G156W, |
| A018K/G023K/K024A/L075R/D111A/V154I/V187T/L264R, |
| A018K/G023K/L075Q/V077I/D130A/V154I/G156W/V187N, |
| A018K/G023K/L075R/V077I/N094R/D130A/G156W/V187Q, |
| A018K/G023Q/E045F/L075Q/V077I/G156W/V187T/T189D, |
| A018K/G023Q/K024A/L075Q/V077I/D130A/G156W/V187Q, |
| A018K/G023Q/K024A/L075R/D130A/V154I/G156W/V187N, |
| A018K/G023Q/K024A/L075R/N094R/D130A/V154I/G156W, |
| A018K/G023Q/K024A/L075R/V077I/N094R/D130A/G156W, |
| A018K/G023Q/L075Q/V077I/D130A/V154I/G156W/V187N, |
| A018K/K024A/L075Q/V077I/N094R/D130A/V154I/G156W, |
| A018K/K024A/L075R/D130A/V154I/G156W/V187T/L264R, |
| A018K/L075Q/N094R/D111A/V154I/G156W/T189Q/L264R, |
| D027E/D048Q/D130A/D137Q/G163P/L227M/N233Q/L264R, |
| G023K/D027S/F051T/E056K/L075Q/G091Q/V187H/I252Q, |
| G023K/D027S/F051T/E056K/L075R/D130A/V187T/L264R, |
| G023K/F051T/E056K/L075R/G091Q/D130A/V187T/L264R, |
| G023K/K024A/L075Q/N094R/V154I/G156W/V187T/L264R, |
| G023K/K024A/L075R/N094R/V154I/G156W/V187T/T189Q, |
| G023K/L075Q/D111A/V154I/G156W/V187N/T189Q/L264R, |
| G023K/L075Q/N094R/D130A/V154I/G156W/V187N/L264R, |
| G023Q/D027S/E056K/L075R/D111A/V154I/G156W/L264R, |
| G023Q/D027S/E056K/S058M/L075R/G091Q/V187N/I252Q, |
| G023Q/D027S/F051T/S058M/G091Q/D130A/V187N/I252Q, |
| G023Q/D027S/L075Q/D130A/V154I/G156W/T189Q/L264R, |
| G023Q/E056K/L075Q/D111A/V154I/V187N/T189Q/L264R, |
| G023Q/E056K/L075Q/N094R/D111A/G156W/T189Q/L264R, |
| G023Q/L075Q/N094R/D130A/V154I/G156W/T189Q/L264R, |
| G023Q/L075Q/V077I/N094R/D130A/V154I/G156W/V187Q, |
| N011K/G023K/D027S/L075R/V154I/G156W/V187N/T189Q, |
| N011K/G023K/E056K/L075Q/D130A/V154I/T189Q/L264R, |
| N011K/G023Q/D027S/L075Q/N094R/V154I/G156W/T189Q, |
| N011K/G023Q/D027S/N094R/V154I/G156W/T189Q/L264R, |
| N011K/G023Q/L075Q/N094R/V154I/G156W/T189Q/L264R, |
| A018K/G023K/K024A/L075Q/N094R/D111A/D130A/V154I/T189Q, |
| A018K/G023K/K024A/L075R/V077I/D130A/V154I/G156W/V187N, |
| A018K/G023K/L075Q/N094R/D111A/V154I/G156W/T189Q/L264R, |
| A018K/G023Q/D027S/L075Q/V077I/R108K/H135F/G156W/V187T, |
| A018K/G023Q/D027S/P029E/L075Q/V077I/H135F/G156W/V187T, |
| A018K/G023Q/D027S/P029E/L075Q/V077I/R108K/G156W/V187H, |
| A018K/G023Q/D027S/P029E/L075Q/V077I/R108K/H135F/V187H, |
| A018K/G023Q/D027S/P029E/S058M/V077I/R108K/H135F/G156W, |
| A018K/G023Q/E045F/A049V/N073S/L075Q/R108K/V187T/T189D, |

TABLE 8-10-continued

| TLL variants with Performance Index >1 compared to Reference sequence SEQ ID NO: 2 in the CS-61 microswatch Assay using Tide ® full dose are shown below. |
|---|
| A018K/G023Q/K024A/L075R/N094R/D130A/V154I/G156W/V187N, A018K/K024A/L075Q/N094R/V154I/G156W/V187N/T189Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/F051T/E056K/S058M/L075Q/G091Q/V187N/L264R, G023K/D027S/F051T/E056K/S058M/L075R/G091Q/V187H/I252Q, G023K/D027S/L075Q/D111A/D130A/V154I/G156W/T189Q/L264R, G023K/E056K/L075Q/D111A/D130A/V154I/G156W/T189Q/L264R, G023K/K024A/L075Q/N094R/V154I/G156W/V187N/T189Q/L264R, G023K/K024A/N094R/D130A/V154I/G156W/V187T/T189Q/L264R, G023Q/D027S/F051T/E056K/L075G/G091Q/V187N/I252Q/L264R, G023Q/D027S/L075Q/N094R/D130A/V154I/G156W/V187N/L264R, N011K/G023K/L075R/D111A/D130A/V154I/V187N/T189Q/L264R, N011K/G023Q/L075Q/D111A/V154I/G156W/V187N/T189Q/L264R, A018K/G023Q/D027S/E045F/A049V/N073S/L075Q/R108K/V187T/T189D, A018K/G023Q/D027S/E045F/A049V/S058M/L075Q/R108K/V187T/T189D, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023Q/D027S/S058M/L075Q/V077I/R108K/H135F/G156W/V187H, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/G023K/L075R/N094R/D111A/V154I/G156W/V187N/T189Q/L264R, N011K/G023Q/L075Q/N094R/D111A/D130A/V154I/G156W/V187N/L264R, A018K/G023K/L075R/N094R/D111A/D130A/V154I/G156W/V187N/T189Q/L264R, N011K/G023Q/D027S/L075Q/N094R/D111A/V154I/G156W/V187N/T189Q/L264R, A018K/G023Q/D027S/P029E/E045F/A049V/S058M/N073S/L075Q/R108K/V187T/T189D, A018K/G023Q/D027S/P029E/E045F/A049V/S058M/N073S/L075Q/R108K/H135F/V187T/T189D, A018K/G023Q/D027S/P029E/N033D/E045F/A049V/S058M/N073S/K074S/L075Q/V077I/N101D/R108K/H135F/D137V/G156W/V187T/T189D |

TABLE 8-11

| TLL variants with Performance Index for expression ≥0.5 compared to TLL SEQ ID NO: 1 and Performance Index >1 in the CS-61 microswatch Assay using Tide ® full dose compared to Reference sequence SEQ ID NO: 2 are shown below. |
|---|
| L227M/L264R, A018K/L075D/T189D, A018K/P029E/T189D, A018K/V154I/G156W, D027S/N033D/T189D, G023K/V187N/L264R, G023Q/A049V/T189D, L075G/D130A/V187H, L075Q/V187N/L264R, L075R/D130A/V187T, L075R/V187N/L264R, P029E/N033D/E045F, V187N/T189Q/L264R, A018K/D027S/P029E/T189D, A018K/L075Q/V077I/N094R, A018K/N033D/L075D/T189D, D027S/N033D/L075D/T189D, D027S/P029E/L075D/T189D, D027S/P029E/N033D/E045F, D027S/P029E/N033D/L075D, D048Q/D130A/G163P/L264R, D130A/G163P/L227M/L264R, G023K/D130A/V187T/L264R, P029E/N073R/L075D/T189D, A018K/D027S/P029E/N033D/L075D, A018K/G023Q/K024A/L075Q/G156W, A018K/K024A/L075R/D130A/V154I, A018K/K024A/N094R/D130A/V187N, A018K/P029E/N033D/N073R/L075D, D027E/D130A/G163P/L227M/L264R, D027E/D130A/G163P/N233Q/L264R, D027E/D137Q/G163P/N233Q/L264R, D027S/L075R/V154I/T189Q/L264R, D130A/D137Q/G163P/N233Q/L264R, E045F/A049V/L075Q/V187T/T189D, E056K/L075R/D130A/V187T/L264R, G023K/D027S/E056K/V187T/L264R, G023K/E056K/D130A/V187T/L264R, G023K/E056K/L075R/D130A/V187T, G023K/E056K/L075R/V187N/L264R, G023K/E056K/L075R/V187T/L264R, G023K/L075Q/V077I/D130A/G156W, G023K/L075Q/V187H/I252Q/L264R, G023K/L075R/D130A/V187T/L264R, G023K/N094R/G156W/V187N/T189Q, K024A/L075R/V154I/G156W/V187Q, N011K/G023K/D111A/G156W/L264R, S058M/G163P/L227M/N233Q/L264R, A018K/G023K/L075Q/V077I/G156W/V187Q, A018K/G023Q/K024A/L075R/N094R/G156W, A018K/K024A/L075Q/N094R/V154I/G156W, A018K/K024A/L075Q/V077I/D130A/V187N, D027E/D048Q/D130A/D137Q/G163P/L264R, D027E/D048Q/D137Q/G163P/L227M/L264R, D027E/D048Q/D137Q/G163P/N233Q/L264R, D027E/D130A/D137Q/G163P/L227M/L264R, D027E/D130A/G163P/L227M/N233Q/L264R, D027E/D137Q/G163P/L227M/N233Q/L264R, D027Q/E056K/S058M/D130A/I252Q/L264R, D048Q/D137Q/G163P/L227M/N233Q/L264R, F051T/L075G/G091Q/D130A/I252Q/L264R, G023K/D027S/L075R/V187N/I252Q/L264R, G023K/E056K/L075R/D130A/T189Q/L264R, G023K/E056K/L075R/D130A/V187N/L264R, G023K/K024A/L075Q/V154I/G156W/V187Q, G023K/L075G/D130A/V187T/I252Q/L264R, G023K/N094R/D111A/G156W/V187T/L264R, A018K/D027S/P029E/N033D/N073R/L075D/T189D, A018K/G023K/K024A/L075Q/N094R/G156W/V187Q, A018K/G023K/K024A/L075R/N094R/D130A/V154I, A018K/G023K/L075Q/V077I/N094R/V154I/G156W, A018K/G023Q/L075R/V077I/N094R/G156W/V187N, D048Q/D130A/D137Q/G163P/L227M/N233Q/L264R, D048Q/S058M/D130A/D137Q/L227M/N233Q/L264R, |

TABLE 8-11-continued

| TLL variants with Performance Index for expression ≥0.5 compared to TLL SEQ ID NO: 1 and Performance Index >1 in the CS-61 microswatch Assay using Tide ® full dose compared to Reference sequence SEQ ID NO: 2 are shown below. |
|---|
| Q004D/N011K/D027S/E056K/S058M/N233Q/P256T, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023Q/K024A/L075R/V077I/N094R/D130A/G156W, D027E/D048Q/D130A/D137Q/G163P/L227M/N233Q/L264R, G023K/D027S/F051T/E056K/L075Q/G091Q/V187H/I252Q, G023Q/D027S/E056K/L075R/D111A/V154I/G156W/L264R, G023Q/D027S/F051T/S058M/G091Q/D130A/V187N/I252Q, A018K/G023Q/D027S/P029E/L075Q/V077I/R108K/H135F/V187H, G023K/K024A/L075Q/N094R/V154I/G156W/V187N/T189Q/L264R, A018K/G023Q/D027S/P029E/S058M/L075Q/V077I/H135F/G156W/V187T, A018K/G023Q/D027S/P029E/S058M/L075Q/V077I/R108K/H135F/V187H, A018K/G023K/L075R/N094R/D111A/D130A/V154I/G156W/V187N/T189Q/L264R |

TABLE 8-12

| TLL variants with Performance Index for expression ≥0.5 compared to TLL SEQ ID NO: 1 and Performance Index ≥50% of the maximum PI value in the CS-61 microswatch Assay using Tide ® full dose compared to Reference sequence SEQ ID NO: 2 are shown below. |
|---|
| A018K/P029E/T189D, D027S/N033D/T189D, L075R/D130A/V187T, L075R/V187N/L264R, A018K/D027S/P029E/T189D, A018K/L075Q/V077I/N094R, A018K/N033D/L075D/T189D, D027S/P029E/N033D/L075D, D048Q/D130A/G163P/L264R, P029E/N073R/L075D/T189D, A018K/D027S/P029E/N033D/L075D, D027E/D130A/G163P/N233Q/L264R, D027E/D137Q/G163P/N233Q/L264R, D130A/D137Q/G163P/N233Q/L264R, E056K/L075R/D130A/V187T/L264R, G023K/E056K/D130A/V187T/L264R, G023K/E056K/L075R/V187N/L264R, G023K/E056K/L075R/V187T/L264R, G023K/L075Q/V077I/D130A/G156W, G023K/L075R/D130A/V187T/L264R, K024A/L075R/V154I/G156W/V187Q, A018K/K024A/L075Q/V077I/D130A/V187N, D027E/D048Q/D130A/D137Q/G163P/L264R, D027E/D048Q/D137Q/G163P/L227M/L264R, D027E/D048Q/D137Q/G163P/N233Q/L264R, D027E/D130A/D137Q/G163P/L227M/L264R, D027E/D130A/G163P/L227M/N233Q/L264R, D048Q/D137Q/G163P/L227M/N233Q/L264R, G023K/D027S/L075R/V187N/I252Q/L264R, G023K/K024A/L075Q/V154I/G156W/V187Q, A018K/D027S/P029E/N033D/N073R/L075D/T189D, A018K/G023K/K024A/L075R/N094R/D130A/V154I, D048Q/S058M/D130A/D137Q/L227M/N233Q/L264R, Q004D/N011K/D027S/E056K/S058M/N233Q/P256T, A018K/G023K/K024A/L075Q/V077I/N094R/D130A/G156W, D027E/D048Q/D130A/D137Q/G163P/L227M/N233Q/L264R, G023K/D027S/F051T/E056K/L075Q/G091Q/V187H/I252Q |

We claim:

1. A lipolytic enzyme variant or an active fragment thereof comprising an amino acid substitution at a position 130, wherein the lipolytic enzyme variant has at least 85% sequence identity to SEQ ID NO: 1 and the amino acid positions of the variant are numbered by correspondence with the amino acid sequence of Thermomyces lanuginosa lipase set forth in SEQ ID NO: 1, and wherein the amino acid substitution is D130A.

2. The lipolytic enzyme variant or active fragment thereof of claim 1, wherein the lipolytic enzyme variant further comprises amino acid substitutions selected from the group consisting of 4, 11, 18, 23, 24, 27, 29, 33, 45, 48, 49, 51, 56, 58, 73, 75, 77, 90, 91, 94, 111, 137, 154, 156, 163, 187, 189, 227, 233, 252, 256, and 264.

3. The lipolytic enzyme variant or active fragment thereof of claim 2, wherein the variant or active fragment thereof further comprises amino acid modifications:

G023/D027/F051/E056/S058/L075/G091/V187/I252/L264; G023/E056/L075/V187/L264; D027/D048/058/D137/G163/L227/N233/L264; A018/G023/K024/L075N077/N094/V154/G156/V187; A018/G023/K024/L075/N094/D111/V154/G156/V187/T189/

L264; or N011/G023/D027/E056/L075/N094/D111/V154/G156/V187/T189/L264.

4. The lipolytic enzyme variant or active fragment thereof of claim 1, wherein the variant or active fragment has lipolytic activity.

5. The lipolytic enzyme variant or active fragment thereof of claim 1, wherein the variant or active fragment has a performance index (pI) relative to the parent lipolytic enzyme for hydrolysis of p-nitrophenyl butyrate, p-nitrophenyl caprylate, or p-nitrophenyl palmitate that is greater than 1.0.

6. The lipolytic enzyme variant or active fragment thereof of claim 5, wherein the performance index is measured using the p-nitrophenyl butyrate, p-nitrophenyl caprylate, or p-nitrophenyl palmitate assay of Example 1, and, optionally, at a pH of 8.

7. The lipolytic enzyme variant or active fragment thereof of any of claims 1-2, wherein the variant or active fragment thereof comprises:

(i) the amino acid modifications selected from: D130A/L264R, D130A/V187N, L075Q/D130A, E056K/D130A/T189Q, L075G/D130A/V187H, L075Q/D111A/D130A, L075R/D130A/L264R, L075R/D130A/V187T, V077I/D130A/V154I, A018K/G023Q/L075R/D130A, A018K/L075Q/N094R/D130A, G023K/L075R/D130A/L264R, G023Q/L075Q/D130A/L264R, K024A/L075Q/D130A/V154I, L075Q/D130A/G156W/V187N, A018K/G023Q/K024A/D130A/V154I, A018K/G023Q/V0771/D130A/G156W, A018K/K024A/L075Q/D130A/L264R, A018K/K024A/L075R/D130A/V1541, A018K/K024A/N094R/D130A/V187N, A018K/L075Q/D111A/D130A/V187T, A018K/L075Q/N094R/D130A/V187N, D027E/S058M/D130A/G163P/L264R, D027S/L075Q/D111A/D130A/V187N, D048Q/D130A/G163P/L227M/L264R, D048Q/S058M/D130A/N233Q/L264R, D130A/D137Q/G163P/N233Q/L264R, G023K/E056K/L075R/D130A/V187T, G023K/K024A/L075R/D130A/G156W, G023K/L075Q/D111A/D130A/V187T, G023K/L075Q/V0771/D130A/G156W, G023K/L075R/D130A/V187N/L264R, G023Q/K024A/L075R/D130A/V1541, G023Q/L075Q/V0771/D130A/G156W, L075Q/D130A/V187T/T189Q/L264R, L075Q/N094R/D130A/G156W/V187T, L075R/D111A/D130A/V187N/T189Q, L075R/D130A/V154I/T189Q/L264R, L075R/D130A/V187T/T189Q/L264R, S058M/D130A/D137Q/G163P/L264R, S058M/D130A/G163P/L227M/L264R, S058M/G163P/L227M/N233Q/L264R, A018K/G023K/K024A/N094R/D130A/V154I, A018K/G023K/L075Q/D130A/G156W/V187N, A018K/G023K/L075R/N094R/D130A/V187N, A018K/G023Q/N094R/D130A/G156W/V187Q, A018K/K024A/L075Q/V077I/D130A/V187N, A018K/K024A/L075R/D130A/V187N/T189Q, A018K/K024A/V077I/N094R/D130A/G156W, A018K/L075Q/D130A/V187N/T189Q/L264R, A018K/N094R/D111A/D130A/V154I/V187N, D027E/D048Q/S058M/D130A/G163P/L264R, D027Q/E056K/S058M/D130A/I252Q/L264R, D027Q/F051T/L075Q/D130A/V187H/L264R, D027Q/S058M/L075R/D130A/V187T/I252Q, F051T/L075G/G091Q/D130A/I252Q/L264R, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075R/D130A/V154I/V187N, G023Q/E056K/D111A/D130A/V187N/T189Q, G023Q/E056K/L075Q/D130A/V154I/L264R, G023Q/F051T/D130A/V187T/I252Q/L264R, G023Q/K024A/L075Q/D130A/V154I/G156W, K024A/L075Q/N094R/D130A/V154I/L264R, K024A/L075Q/V077I/N094R/D130A/V187N, L075Q/D111A/D130A/V154I/G156W/T189Q, L075Q/D130A/V154I/G156W/V187N/L264R, L075R/D130A/V154I/G156W/V187N/L264R, S058M/D130A/D137Q/G163P/L227M/L264R, S058M/D130A/D137Q/G163P/N233Q/L264R, S058M/D130A/G163P/L227M/N233Q/L264R, A018K/G023K/K024A/L075Q/D130A/G156W/V187N, A018K/G023K/K024A/L075R/N094R/D130A/V154I, A018K/K024A/L075Q/D130A/V154I/G156W/V187T, A018K/K024A/L075Q/V077I/N094R/D130A/G156W, A018K/L075Q/D111A/D130A/V154I/G156W/L264R, D027E/D048Q/S058M/D130A/G163P/L227M/L264R, D027E/D048Q/S058M/D130A/G163P/N233Q/L264R, D027E/S058M/D130A/D137Q/G163P/N233Q/L264R, D027Q/F051T/L075G/D130A/V187H/I252Q/L264R, D048Q/S058M/D130A/D137Q/G163P/L227M/L264R, D048Q/S058M/D130A/G163P/L227M/N233Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/K024A/L075Q/D111A/D130A/T189Q/L264R, G023Q/E056K/L075R/D111A/D130A/V187N/T189Q, G023Q/F051T/G091Q/D130A/V187H/I252Q/L264R, G023Q/L075Q/D111A/D130A/V154I/G156W/L264R, G023Q/L075Q/D130A/V154I/V187N/T189Q/L264R, G023Q/L075Q/V077I/N094R/D130A/G156W/V187N, K024A/L075Q/D111A/D130A/V154I/G156W/L264R, K024A/L075R/D130A/V154I/G156W/T189Q/L264R, N011K/D027S/D111A/D130A/V154I/V187N/T189Q, N011K/E056K/L075Q/D111A/D130A/V154I/L264R, A018K/G023K/K024A/L075Q/N094R/D130A/G156W/V187Q, A018K/G023K/K024A/L075Q/V077I/D130A/V154I/G156W, A018K/G023K/K024A/L075Q/V077I/N094R/D130A/G156W, A018K/G023K/L075R/V077I/N094R/D130A/G156W/V187Q, A018K/G023Q/K024A/L075R/N094R/D130A/V154I/G156W, A018K/G023Q/K024A/L075R/V077I/N094R/D130A/G156W, G023K/E056K/L075Q/D130A/V154I/N187N/T189Q/L264R, G023Q/D027Q/F051T/S058M/L075R/D130A/V187T/L264R, G023Q/D027S/F051T/S058M/G091Q/D130A/V187N/I252Q, G023Q/K024A/L075Q/V077I/N094R/D130A/V154I/V187N, G023Q/L075Q/N094R/D111A/D130A/G156W/T189Q/L264R, G023Q/L075Q/N094R/D130A/V154I/G156W/T189Q/L264R, K024A/D111A/D130A/V154I/G156W/V187T/T189Q/L264R, N011K/G023K/D027S/L075Q/D111A/D130A/V154I/T189Q, A018K/G023K/K024A/L075Q/N094R/D111A/D130A/V154I/T189Q, A018K/G023K/K024A/L075R/V077I/D130A/V154I/G156W/V187N, A018K/G023K/K024A/V077I/D130A/V154I/G156W/V187T/T189Q, G023K/K024A/N094R/D130A/V154I/G156W/V187T/T189Q/L264R, G023K/L075Q/D111A/

D130A/V154I/G156W/V187T/T189Q/L264R, G023Q/D027S/L075Q/N094R/D111A/D130A/V154I/G156W/L264R, G023Q/E056K/L075Q/D111A/D130A/V154I/G156W/T189Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R, optionally wherein the variant or active fragment has a performance index (pI) relative to a reference lipolytic enzyme having the sequence of SEQ ID NO:1 for hydrolysis of p-nitrophenyl butyrate that is greater than 1.0;

(ii) the amino acid modifications selected from: D130A/L264R, L075G/D130A/V187H, L075Q/D111A/D130A, L075Q/D130A/V187T, L075R/D130A/L264R, L075R/D130A/V187T, A018K/G023Q/L075R/D130A, D048Q/D130A/G163P/L264R, D130A/G163P/L227M/L264R, G023K/L075R/D130A/L264R, K024A/L075Q/D130A/G156W, L075Q/D130A/G156W/V187N, L075Q/V077I/D130A/V187Q, L075R/D130A/V154I/L264R, A018K/G023Q/K024A/D130A/V154I, A018K/K024A/L075Q/D130A/L264R, A018K/K024A/N094R/D130A/V187N, A018K/L075Q/D111A/D130A/V187T, A018K/L075Q/N094R/D130A/V187N, D027E/D130A/G163P/N233Q/L264R, D130A/D137Q/G163P/N233Q/L264R, G023K/E056K/D130A/V187T/L264R, G023K/E056K/L075R/D130A/V187T, G023K/K024A/L075R/D130A/G156W, G023K/L075Q/D111A/D130A/V187T, G023K/L075Q/V077I/D130A/G156W, G023Q/K024A/V077I/D130A/V154I, G023Q/L075Q/V077I/D130A/G156W, GL075R/D130A/V154I/T189Q/L264R, L075R/D130A/V187T/T189Q/L264R, A018K/G023K/D111A/D130A/V154I/T189Q A018K/G023K/K024A/L075R/D130A/V187N, A018K/G023K/K024A/N094R/D130A/V154I, A018K/G023K/L075Q/D130A/G156W/V187N, A018K/G023K/L075R/N094R/D130A/V187N, A018K/G023K/L075R/V077I/D130A/V154I, A018K/G023Q/N094R/D130A/G156W/V187Q, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/N094R/D111A/D130A/V154I/V187N, D027E/D048Q/D130A/D137Q/G163P/L264R, D027E/D130A/D137Q/G163P/L227M/L264R, D027E/D130A/G163P/L227M/N233Q/L264R, D027Q/F051T/L075Q/D130A/V187H/L264R, D027Q/S058M/L075R/D130A/V187T/I252Q, D048Q/S058M/D130A/G163P/N233Q/L264R, G023K/D027S/L075R/D130A/V187T/I252Q, G023K/E056K/L075R/D130A/T189Q/L264R, G023K/K024A/L075Q/N094R/D130A/G156W, G023K/K024A/L075R/D130A/V154I/V187N, G023K/L075Q/D111A/D130A/V154I/V187N, G023Q/K024A/L075Q/D130A/V154I/G156W, K024A/L075Q/D130A/G156W/T189Q/L264R, K024A/L075Q/V077I/N094R/D130A/V187N, L075R/D130A/V154I/G156W/V187N/L264R, N011K/E056K/L075Q/D130A/V187N/T189Q, A018K/G023K/K024A/L075Q/D130A/G156W/V187N, A018K/G023K/K024A/L075R/N094R/D130A/V154I, A018K/G023Q/K024A/L075R/D130A/V154I/V187N, A018K/G023Q/K024A/L075R/V077I/D130A/G156W, A018K/K024A/L075Q/D130A/G156W/V187T/T189Q, A018K/K024A/L075Q/V077I/N094R/D130A/G156W, D027E/D130A/D137Q/G163P/L227M/N233Q/L264R, D027Q/F051T/L075G/D130A/V187H/I252Q/L264R, D048Q/D130A/D137Q/G163P/L227M/N233Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/K024A/L075Q/D111A/D130A/T189Q/L264R, G023Q/E056K/L075Q/D130A/V154I/G156W/T189Q, G023Q/E056K/L075R/D111A/D130A/V187N/T189Q, G023Q/L075Q/D111A/D130A/V154I/G156W/L264R, G023Q/L075Q/D130A/V154I/G156W/T189Q/L264R, optionally wherein the variant or active fragment has a performance index (pI) relative to a reference lipolytic enzyme having the sequence of SEQ ID NO:1 for hydrolysis of p-nitrophenyl caprylate that is greater than 1.0; and/or (iii) the amino acid modifications selected from: D130A/L264R, D130A/V187T, D111A/D130A/L264R, D130A/V187N/L264R, G023K/D130A/L264R, L075G/D130A/V187H, L075Q/D111A/D130A, L075R/D130A/L264R, L075R/D130A/V187T, A018K/G023Q/L075R/D130A, D027E/D130A/N233Q/L264R, D027S/D130A/I252Q/L264R, D048Q/D130A/G163P/L264R, E056K/D130A/V187N/L264R, F051T/D130A/I252Q/L264R, G023K/D130A/V187N/L264R, G023K/D130A/V187T/L264R, G023K/L075Q/D130A/V187N, G023K/L075R/D130A/L264R, G023Q/L075Q/D130A/L264R, K024A/D130A/V154I/V187T, K024A/L075Q/D130A/G156W, L075G/D130A/V187T/I252Q, L075Q/D130A/G156W/V187N, L075Q/V077I/D130A/V187Q, A018K/D130A/G156W/V187N/L264R, A018K/K024A/L075Q/D130A/L264R, A018K/K024A/L075R/N094R/D130A, A018K/L075Q/D111A/D130A/V187T, A018K/L075Q/N094R/D130A/V187N, D027E/D130A/D137Q/G163P/L264R, D027E/D130A/G163P/L227M/L264R, D027E/S058M/D130A/G163P/L264R, D027S/L075G/D130A/I252Q/L264R, D048Q/D130A/G163P/L227M/L264R, D130A/D137Q/G163P/L227M/L264R, D130A/D137Q/G163P/N233Q/L264R, F051T/D130A/V187T/I252Q/L264R, F051T/L075G/D130A/I252Q/L264R, F051T/L075Q/G091Q/D130A/L264R, G023K/E056K/D130A/V187N/L264R, G023K/E056K/D130A/V187T/L264R, G023K/E056K/L075R/D130A/V187T, G023K/L075Q/D111A/D130A/V187T, G023K/L075Q/V077I/D130A/G156W, G023K/L075R/D130A/V187N/L264R, G023Q/L075Q/D130A/I252Q/L264R, L075G/D130A/V187T/I252Q/L264R, L075R/D130A/V187T/T189Q/L264R, S058M/D130A/D137Q/G163P/L264R, S058M/D130A/G163P/L227M/L264R, A018K/G023K/L075Q/D130A/G156W/V187N, A018K/G023Q/N094R/D130A/G156W/V187Q, A018K/K024A/L075R/D130A/V187N/T189Q, A018K/K024A/V077I/N094R/D130A/G156W, A018K/L075Q/D130A/V187N/T189Q/L264R, D027E/D048Q/D130A/D137H/G163P/L264R, D027E/D048Q/D130A/G163P/L227M/L264R, D027E/D130A/D137Q/

G163P/N233Q/L264R, D027E/S058M/D130A/G163P/L227M/L264R, D027E/S058M/D130A/G163P/N233Q/L264R, D027E/S058M/D130A/L227M/N233Q/L264R, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D048Q/S058M/D130A/G163P/L227M/L264R, D048Q/S058M/D130A/L227M/N233Q/L264R, F051T/E056K/D130A/V187N/I252Q/L264R, F051T/L075G/G091Q/D130A/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/L075Q/D130A/I252Q/L264R, G023K/K024A/L075Q/N094R/D130A/G156W, G023K/K024A/L075R/D130A/V154I/V187N, G023K/L075Q/D111A/D130A/V154I/V187N, G023Q/D027S/L075G/D130A/V187H/L264R, G023Q/D027S/L075Q/D130A/V187T/I252Q, G023Q/F051T/D130A/V187T/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/K024A/V077I/D130A/G156W/V187N, G023Q/L075G/G091Q/D130A/I252Q/L264R, L075Q/D130A/V154I/G156W/V187N/L264R, L075Q/G091Q/D130A/V187H/I252Q/L264R, L075R/D130A/V154I/G156W/V187N/L264R, N011K/E056K/L075Q/D130A/V187N/T189Q, S058M/D130A/D137Q/G163P/L227M/L264R, S058M/D130A/D137Q/G163P/N233Q/L264R, S058M/D130A/G163P/L227M/N233Q/L264R, A018K/G023K/K024A/L075Q/D130A/G156W/V187N, A018K/G023K/K024A/L075R/N094R/D130A/V154I, A018K/K024A/D130A/V154I/G156W/V187T/L264R, A018K/K024A/L075Q/D130A/V154I/G156W/V187T, D027E/D048Q/D130A/D137Q/G163P/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/S058M/D130A/D137Q/G163P/L227M/L264R, D027E/S058M/D130A/G163P/L227M/N233Q/L264R, D027Q/F051T/L075G/D130A/V187H/I252Q/L264R, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, E056K/L075Q/D111A/D130A/G156W/V187N/T189Q, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027Q/F051T/L075G/D130A/V187H/L264R, G023K/D027S/F051T/S058M/L075Q/D130A/V187N, G023K/K024A/L075Q/D111A/D130A/T189Q/L264R, G023Q/D027S/F051T/E056K/D130A/I252Q/L264R, G023Q/D027S/L075Q/G091Q/V187T/I252Q/L264R, G023Q/D027S/S058M/L075Q/D130A/I252Q/L264R, G023Q/E056K/L075Q/D130A/V154I/G156W/T189Q, G023Q/F051T/S058M/G091Q/D130A/I252Q/L264R, G023Q/K024A/L075Q/V077I/D130A/G156W/V187N, G023Q/L075G/G091Q/D130A/V187T/I252Q/L264R, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/S058M/L075G/G091Q/D130A/I252Q/L264R, K024A/L075Q/D111A/D130A/V154I/G156W/L264R, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/D130A/V154I/G156W, A018K/G023Q/K024A/L075Q/V077I/D130A/G156W/V187Q, A018K/G023Q/K024A/L075R/N094R/D130A/V154I/G156W, D027E/S058M/D130A/D137Q/G163P/L227M/N233Q/L264R, D048Q/S058M/D130A/D137Q/G163P/L227M/N233Q/L264R, G023K/D027S/E056K/L075G/D130A/V187T/I252Q/L264R, G023Q/D027Q/F051T/L075Q/G091Q/D130A/I252Q/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/K024A/L075Q/V077I/N094R/D130A/V154I/V187N, G023Q/L075Q/N094R/D111A/D130A/G156W/T189Q/L264R, G023Q/S058M/L075R/G091Q/D130A/V187H/I252Q/L264R, K024A/D111A/D130A/V154I/G156W/V187T/T189Q/L264R, N011K/G023Q/L075Q/D111A/D130A/V154I/V187N/L264R, A018K/G023K/K024A/L075R/V077I/D130A/V154I/G156W/V187N, A018K/G023K/K024A/V077I/D130A/V154I/G156W/V187T/T189Q, A018K/G023Q/K024A/L075R/N094R/D130A/V154I/G156W/V187N, D027Q/F051T/S058M/L075G/G091Q/D130A/V187T/I252Q/L264R, G023K/E056K/L075Q/D111A/D130A/V154I/G156W/T189Q/L264R, G023K/K024A/N094R/D130A/V154I/G156W/V187T/T189Q/L264R, G023Q/D027S/L075Q/N094R/D130A/V154I/G156W/V187N/L264R, G023Q/F051T/S058M/L075Q/G091Q/D130A/V187H/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, N011K/G023Q/E056K/L075R/D111A/D130A/V154I/G156W/V187N/L264R, A018K/G023K/L075R/N094R/D111A/D130A/V154I/G156W/V187N/T189Q/L264R, optionally wherein the variant or active fragment has a performance index (pI) relative to a reference lipolytic enzyme having the sequence of SEQ ID NO:1 for hydrolysis of D-nitrophenyl palmitate that is greater than 1.0.

8. The lipolytic enzyme variant or active fragment thereof of claim 7, wherein the performance index for (i) hydrolysis of p-nitrophenyl butyrate is measured using a p-nitrophenyl butyrate assay, (ii) hydrolysis of p-nitrophenyl caprylate is measured using a p-nitrophenyl caprylate assay, and/or (iii) hydrolysis of p-nitrophenyl palmitate is measured using a p-nitrophenyl palmitate assay.

9. The lipolytic enzyme variant or active fragment thereof of claim 8, wherein the performance index is measured at a pH of 8.

10. The lipolytic enzyme variant or active fragment thereof of claim 1, wherein either:

(a) the variant comprises amino acid modifications selected from: D130A/L264R, D130A/T189Q, D130A/V187N, D130A/V187T, G023K/D130A, L075Q/D130A, D111A/D130A/L264R, D130A/T189Q/L264R, D130A/V154I/G156W, D130A/V187N/L264R, D130A/V187T/L264R, E056K/D130A/L264R, E056K/D130A/T189Q, G023K/D130A/L264R, G023K/D130A/V187T, G023Q/D130A/G156W, K024A/D130A/V154I, L075G/D130A/V187H, L075Q/D111A/D130A, L075Q/D130A/V187T, L075R/D130A/L264R, L075R/D130A/V187T, N094R/D130A/V187T, V077I/D130A/V154I, A018K/D130A/G156W/V187T, A018K/G023Q/L075R/D130A, A018K/K024A/D130A/G156W, A018K/L075Q/N094R/D130A, D027E/D130A/N233Q/L264R, D048Q/D130A/G163P/L264R, D111A/D130A/V154I/G156W, D111A/D130A/V154I/L264R, D130A/G163P/L227M/L264R, D130A/G163P/N233Q/L264R, E056K/D130A/V187N/L264R, E056K/D130A/V187T/L264R, F051T/D130A/I252Q/L264R, G023K/D111A/D130A/L264R, G023K/D130A/G156W/T189Q, G023K/D130A/V187N/L264R, G023K/D130A/V187T/L264R, G023K/D130A/V187T/T189Q, G023K/E056K/D130A/L264R, G023K/L075Q/D130A/V187N, G023K/L075R/D130A/L264R, G023Q/K024A/D130A/G156W, G023Q/L075Q/D130A/L264R, K024A/D130A/V154I/N187T, K024A/L075Q/D130A/G156W, K024A/L075Q/D130A/V154I, L075G/D130A/V187T/I252Q, L075Q/D130A/G156W/V187N, L075Q/D130A/V154I/G156W, L075Q/V077I/D130A/V187Q, L075R/D130A/V154I/L264R, L075R/D130A/V187T/L264R, A018K/D130A/G156W/V187N/L264R, A018K/D130A/G156W/V187T/L264R, A018K/G023K/D130A/V154I/G156W, A018K/G023K/K024A/D130A/G156W, A018K/G023K/K024A/D130A/V154I, A018K/G023K/L075Q/D130A/V154I, A018K/G023K/V077I/D130A/V187N, A018K/G023Q/K024A/D130A/V154I, A018K/G023Q/K024A/D130A/V187Q, A018K/K024A/L075Q/D130A/L264R, A018K/K024A/L075R/D130A/V154I, A018K/K024A/L075R/N094R/D130A, A018K/K024A/N094R/D130A/V187N, A018K/L075Q/D111A/D130A/V187T, A018K/L075Q/N094R/D130A/V187N, D027E/D130A/D137Q/G163P/L264R, D027E/D130A/G163P/L227M/L264R, D027E/D130A/G163P/N233Q/L264R, D027E/S058M/D130A/G163P/L264R, D027Q/F051T/L075Q/D130A/L264R, D027S/L075G/D130A/I252Q/L264R, D027S/L075Q/D111A/D130A/V187N, D048Q/D130A/D137Q/G163P/L264R, D048Q/D130A/G163P/L227M/L264R, D048Q/S058M/D130A/N233Q/L264R, D130A/D137Q/G163P/L227M/L264R, D130A/D137Q/G163P/N233Q/L264R, D130A/G163P/L227M/N233Q/L264R, D130A/V154I/G156W/V187N/T189Q, E056K/D130A/V187H/I252Q/L264R, E056K/L075R/D130A/V187T/L264R, E056K/N094R/G156W/V187N/L264R, F051T/D130A/V187T/I252Q/L264R, F051T/L075G/D130A/I252Q/L264R, F051T/L075G/G091Q/D130A/L264R, F051T/L075Q/G091Q/D130A/L264R, G023K/E056K/D130A/V187N/L264R, G023K/E056K/D130A/V187T/L264R, G023K/E056K/L075R/D130A/V187T, G023K/K024A/D111A/D130A/V187T, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075R/D130A/V187N/L264R, G023K/L075R/D130A/V187T/L264R, G023Q/K024A/L075R/D130A/V154I, G023Q/K024A/L075R/V077I/D130A, G023Q/K024A/V077I/D130A/V154I, G023Q/L075Q/D130A/I252Q/L264R, G023Q/L075Q/V077I/D130A/G156W, G091Q/D130A/V187H/I252Q/L264R, L075G/D130A/V187T/I252Q/L264R, L075Q/D111A/D130A/V187T/T189Q, L075Q/D130A/V187T/T189Q/L264R, L075Q/N094R/D130A/G156W/V187T, L075Q/V077I/D130A/G156W/V187N, L075R/D111A/D130A/V187N/T189Q, L075R/D130A/V154I/T189Q/L264R, L075R/D130A/V187T/T189Q/L264R, S058M/D130A/D137Q/G163P/L264R, S058M/D130A/G163P/L227M/L264R, V077I/D130A/V154I/G156W/V187N, A018K/G023K/D111A/D130A/V154I/T189Q, A018K/G023K/K024A/L075R/D130A/V187N, A018K/G023K/K024A/N094R/D130A/V154I, A018K/G023K/L075Q/D130A/G156W/V187N, A018K/G023K/L075R/N094R/D130A/V187N, A018K/G023K/L075R/V077I/D130A/V154I, A018K/G023Q/L075Q/V077I/D130A/G156W, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/K024A/V077I/N094R/D130A/G156W, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D048Q/S058M/D130A/G163P/L264R, D027E/D130A/D137Q/G163P/L227M/L264R, D027E/D130A/D137Q/G163P/N233Q/L264R, D027E/D130A/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075Q/D130A/V187H/L264R, D027Q/S058M/L075R/D130A/V187T/I252Q, D027S/F051T/L075Q/D130A/I252Q/L264R, D048Q/D130A/G163P/L227M/N233Q/L264R, D048Q/S058M/D130A/D137Q/G163P/L264R, D048Q/S058M/D130A/G163P/L227M/L264R, D048Q/S058M/D130A/G163P/N233Q/L264R, D048Q/S058M/D130A/L227M/N233Q/L264R, F051T/L075G/G091Q/D130A/I252Q/L264R, F051T/L075R/D130A/V187N/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/F051T/L075Q/D130A/I252Q/L264R, G023K/K024A/L075Q/D111A/D130A/T189Q, G023K/K024A/L075Q/N094R/D130A/G156W, G023K/K024A/L075R/D130A/V154I/V187N, G023K/L075G/D130A/V187T/I252Q/L264R, G023K/L075Q/D111A/D130A/V154I/V187N, G023K/L075Q/V077I/D130A/G156W/V187Q, G023Q/D027S/L075G/D130A/V187H/L264R, G023Q/D027S/L075Q/D130A/

V187T/I252Q, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/V077I/D130A/G156W/V187N, G023Q/K024A/V077I/D130A/V154I/G156W, G023Q/L075G/G091Q/D130A/I252Q/L264R, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/E056K/L075Q/D130A/V187N/T189Q, N011K/G023Q/L075Q/D130A/V187N/T189Q, N011K/G023Q/L075Q/N094R/D130A/L264R, S058M/D130A/D137Q/G163P/L227M/L264R, S058M/D130A/D137Q/G163P/N233Q/L264R, S058M/D130A/G163P/L227M/N233Q/L264R, A018K/D111A/D130A/V154I/G156W/V187T/T189Q, A018K/G023K/K024A/L075Q/D130A/G156W/V187N, A018K/G023K/K024A/L075R/N094R/D130A/V154I, A018K/G023Q/K024A/L075Q/V077I/D130A/G156W, A018K/G023Q/K024A/L075R/D130A/V154I/V187N, A018K/G023Q/K024A/L075R/V077I/D130A/G156W, A018K/K024A/D130A/V154I/G156W/V187T/L264R, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/K024A/N094R/D130A/G156W/V187T/L264R, A018K/L075Q/D111A/D130A/V154I/G156W/L264R, A018K/L075Q/D130A/G156W/V187N/T189Q/L264R, D027E/D048Q/D130A/D137Q/G163P/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027E/S058M/D130A/G163P/L227M/N233Q/L264R, D027Q/F051T/L075Q/D130A/V187T/I252Q/L264R, D027Q/F051T/L075Q/G091Q/D130A/V187T/I252Q, D027Q/L075G/G091Q/D130A/V187H/I252Q/L264R, D027S/F051T/S058M/L075R/D130A/I252Q/L264R, D048Q/D130A/D137Q/G163P/L227M/N233Q/L264R, D048Q/S058M/D130A/D137Q/G163P/L227M/L264R, D048Q/S058M/D130A/D137Q/L227M/N233Q/L264R, D048Q/S058M/D130A/G163P/L227M/N233Q/L264R, E056K/L075Q/D111A/D130A/G156W/V187N/T189Q, F051T/L075G/G091Q/D130A/V187N/I252Q/L264R, F051T/L075R/G091Q/D130A/V187T/I252Q/L264R, G023K/D027Q/F051T/L075G/D130A/V187H/L264R, G023K/D027S/F051T/S058M/L075Q/D130A/V187N, G023K/F051T/L075Q/G091Q/D130A/V187H/I252Q, G023K/K024A/L075Q/D111A/D130A/T189Q/L264R, G023K/K024A/L075Q/D130A/V187T/T189Q/L264R, G023K/K024A/L075Q/V077I/D130A/G156W/V187Q, G023K/L075Q/D111A/D130A/V154I/G156W/L264R, G023K/L075Q/D130A/G156W/V187N/T189Q/L264R, G023K/L075Q/N094R/D130A/V154I/V187N/L264R, G023Q/D027S/S058M/L075Q/D130A/I252Q/L264R, G023Q/E056K/L075Q/D130A/V154I/G156W/T189Q, G023Q/E056K/L075R/D111A/D130A/V187N/T189Q, G023Q/F051T/G091Q/D130A/V187H/I252Q/L264R, G023Q/F051T/S058M/G091Q/D130A/I252Q/L264R, G023Q/K024A/L075Q/V077I/D130A/G156W/V187N, G023Q/K024A/L075Q/V077I/D130A/V154I/G156W, G023Q/L075G/G091Q/D130A/V187T/I252Q/L264R, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, G023Q/S058M/L075G/G091Q/D130A/I252Q/L264R, K024A/L075Q/D111A/D130A/V154I/G156W/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, A018K/G023K/K024A/L075Q/D130Y/V154I/V187N/T189Q, A018K/G023K/K024A/L075Q/N094R/D130A/G156W/V187Q, A018K/G023K/K024A/L075Q/V077I/D130A/V154I/G156W, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/E045F/L075Q/V077I/G156W/V187T/T189D, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, A018K/K024A/L075R/D130A/V154I/G156W/V187T/L264R, D027E/D048Q/D130A/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/E056K/L075G/D130A/V187T/I252Q/L264R, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/L075Q/N094R/D130A/V154I/G156W/V187N/L264R, G023Q/D027Q/F051T/L075Q/G091Q/D130A/I252Q/L264R, G023Q/D027Q/F051T/S058M/L075R/D130A/V187T/L264R, G023Q/D027S/F051T/S058M/G091Q/D130A/V187N/I252Q, G023Q/D027S/L075Q/D130A/V154I/G156W/T189Q/L264R, G023Q/D027S/S058M/G091Q/D130A/V187H/I252Q/L264R, G023Q/F051T/L075Q/G091Q/D130A/V187H/I252Q/L264R, G023Q/F051T/L075R/G091Q/D130A/V187T/I252Q/L264R, G023Q/

K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/V077I/N094R/D130A/V154I/G156W/V187Q, G023Q/S058M/L075R/G091Q/D130A/V187H/I252Q/L264R, K024A/D111A/D130A/V154I/G156W/V187T/T189Q/L264R, N011K/G023K/D027S/L075Q/D111A/D130A/V154I/T189Q, N011K/G023K/E056K/L075Q/D130A/V154I/T189Q/L264R, N011K/G023Q/L075Q/D111A/D130A/V154I/V187N/L264R, A018K/G023G/K024A/L075Q/N094R/D111A/D130A/V154I/T189Q, A018K/G023G/K024A/L075Q/N094R/D130A/V154I/G156W/V187N, A018K/G023G/K024A/L075Q/N094R/D130A/V187T/T189Q/L264K, A018K/G023G/K024A/L075R/V077I/D130A/V154I/G156W/V187N, A018K/G023G/K024A/V077I/D130A/V154I/G156W/V187T/T189Q, A018K/G023Q/K024A/L075R/N094R/D130A/V154I/G156W/V187N, D027Q/F051T/S058M/L075G/G091Q/D130A/V187T/I252Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/L075Q/D111A/D130A/V154I/G156W/T189Q/L264R, G023K/E056K/L075Q/D111A/D130A/V154I/G156W/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023Q/D027S/F051T/E056K/L075R/G091Q/D130A/V187H/I252Q/L264R, G023Q/D027S/F051T/E056K/S058M/L075R/G091Q/D130A/V187H/I252Q, N011K/A018K/G023G/K024A/L075R/V077I/D130A/V154I/V187T/T189Q, N011K/G023Q/D027S/E056K/L075R/D130A/V154I/G156W/T189Q/L264R, N011K/G023Q/E056K/L075R/D111A/D130A/V154I/G156W/V187N/L264R, A018K/G023G/L075R/N094R/D111A/D130A/V154I/G156W/V187N/T189Q/L264R, optionally wherein the variant or active fragment has a performance index (pI) relative to a reference lipolytic enzyme having the sequence of SEQ ID NO: 1 for thermostability that is greater than 1.0; or, (b) the variant comprises amino acid modifications selected from: D130A/T189Q, D130A/V187N, D130A/V187T, G023K/D130A, L075Q/D130A, D111A/D130A/L264R, D130A/V154I/G156W, E056K/D130A/L264R, G023K/D130A/V187T, G023Q/D130A/G156W, K024A/D130A/V154I, L075G/D130A/V187H, L075Q/D111A/D130A, L075Q/D130A/V187T, L075R/D130A/L264R, L075R/D130A/V187T, N094R/D130A/V187T, V077I/D130A/V154I, A018K/D130A/G156W/V187T, A018K/G023Q/L075R/D130A, A018K/K024A/D130A/G156W, A018K/L075Q/N094R/D130A, D111A/D130A/V154I/G156W, D111A/D130A/V154I/L264R, D111A/D130A/V187T/L264R, E056K/D130A/V187T/L264R, F051T/D130A/I252Q/L264R, G023K/D111A/D130A/L264R, G023K/D130A/G156W/T189Q, G023K/D130A/V187T/L264R, G023K/D130A/V187T/T189Q, G023K/L075Q/D130A/V187N, G023Q/K024A/D130A/G156W, K024A/D130A/V154I/V187T, K024A/L075Q/D130A/G156W, K024A/L075Q/D130A/V154I, L075G/D130A/V187T/I252Q, L075Q/D130A/G156W/V187N, L075Q/D130A/V154I/G156W, L075Q/V077I/D130A/V187Q, L075R/D130A/V154I/L264R, A018K/G023G/D130A/V154I/G156W, A018K/G023G/K024A/D130A/G156W, A018K/G023G/K024A/D130A/V154I, A018K/G023G/L075Q/D130A/V154I, A018K/G023G/V077I/D130A/V187N, A018K/G023Q/K024A/D130A/V154I, A018K/G023Q/K024A/D130A/V187Q, A018K/K024A/L075R/D130A/V154I, A018K/K024A/N094R/D130A/V187N, A018K/L075Q/D111A/D130A/V187T, A018K/L075Q/N094R/D130A/V187N, D130A/G163P/L227M/N233Q/L264R, D130A/V154I/G156W/V187N/T189Q, E056K/D130A/V187H/I252Q/L264R, E056K/L075R/D130A/V187T/L264R, G023K/E056K/D130A/V187T/L264R, G023K/E056K/L075R/D130A/V187T, G023K/K024A/D111A/D130A/V187T, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075R/D130A/V187N/L264R, G023Q/K024A/L075Q/D130A/G156W, G023Q/K024A/L075R/D130A/V154I, G023Q/K024A/L075R/V077I/D130A, G023Q/K024A/V077I/D130A/V154I, G023Q/L075Q/V077I/D130A/G156W, L075Q/D111A/D130A/V187T/T189Q, L075Q/D130A/V187T/T189Q/L264R, L075Q/N094R/D130A/G156W/V187T, L075Q/V077I/D130A/G156W/V187N, L075R/D111A/D130A/V187N/T189Q, L075R/D130A/V154I/T189Q/L264R, V077I/D130A/V154I/G156W/V187N, A018K/G023G/D111A/D130A/V154I/T189Q, A018K/G023G/K024A/L075R/D130A/V187N, A018K/G023G/K024A/N094R/D130A/V154I, A018K/G023G/L075Q/D130A/G156W/V187N, A018K/G023G/L075R/N094R/D130A/V187N, A018K/G023G/L075R/V077I/D130A/V154I, A018K/G023Q/L075Q/V077I/D130A/G156W, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/L075R/D130A/V154I/G156W/V187N, A018K/N094R/D111A/D130A/V154I/V187N, D027Q/E056K/S058M/D130A/I252Q/L264R, D027Q/F051T/G091Q/D130A/I252Q/L264R, D027Q/F051T/L075G/D130A/I252Q/L264R, D027Q/S058M/L075R/D130A/V187T/I252Q, D027S/G091Q/D130A/V187N/I252Q/L264R, D048Q/D130A/G163P/L227M/N233Q/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075R/D130A/V154I/V187N, G023K/L075Q/D111A/D130A/V154I/V187N, G023K/L075Q/V077I/D130A/G156W/V187Q, G023Q/D027S/L075G/D130A/V187H/L264R, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/V077I/D130A/G156W/V187N, G023Q/K024A/V077I/D130A/V154I/G156W, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, L075Q/D111A/D130A/V154I/G156W/T189Q, L075Q/D111A/D130A/V154I/V187N/T189Q, L075R/D130A/V154I/G156W/V187N/L264R, N011K/E056K/L075Q/D130A/V187N/T189Q, N011K/G023Q/L075Q/D130A/V187N/T189Q, A018K/D111A/D130A/V154I/G156W/V187T/T189Q, A018K/G023G/K024A/L075Q/D130A/G156W/V187N, A018K/G023G/K024A/L075R/N094R/D130A/V154I, A018K/G023Q/K024A/L075Q/V077I/D130A/G156W, A018K/G023Q/K024A/L075R/D130A/V154I/V187N, A018K/G023Q/K024A/L075R/V077I/D130A/G156W, A018K/K024A/L075Q/D130A/G156W/V187T/T189Q, A018K/K024A/L075Q/D130A/V154I/G156W/V187T, D027Q/F051T/L075Q/G091Q/D130A/V187T/I252Q, D027Q/L075G/G091Q/D130A/V187H/I252Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/F051T/E056K/L075R/D130A/V187T/I252Q, G023K/F051T/L075Q/G091Q/D130A/V187H/I252Q, G023K/K024A/L075Q/D111A/D130A/T189Q/L264R, G023K/K024A/L075Q/D130A/V187T/T189Q/L264R, G023K/K024A/L075Q/V077I/D130A/G156W/V187Q, G023K/L075Q/D111A/D130A/V154I/G156W/L264R, G023K/L075Q/D130A/G156W/V187N/T189Q/L264R, G023Q/D027S/S058M/L075Q/D130A/I252Q/L264R, G023Q/E056K/L075Q/D130A/V154I/G156W/T189Q, G023Q/E056K/L075R/D111A/D130A/V187N/T189Q, G023Q/F051T/G091Q/D130A/V187H/I252Q/L264R, G023Q/K024A/L075Q/V077I/D130A/G156W/V187N, G023Q/K024A/L075Q/V077I/D130A/V154I/G156W, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, K024A/L075Q/D111A/D130A/V154I/G156W/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/E056K/L075Q/D111A/D130A/V154I/L264R, N011K/E056K/L075Q/D130A/V154I/V187N/T189Q, N011K/G023K/L075Q/D111A/D130A/V154I/V187N, A018K/G023G/K024A/L075Q/D130Y/V154I/V187N/T189Q, A018K/G023G/K024A/L075Q/N094R/D130A/G156W/V187Q, A018K/G023G/K024A/L075Q/V077I/D130A/V154I/G156W, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/E045F/L075Q/V077I/G156W/V187T/T189D, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, F051T/E056K/L075G/G091Q/D130A/V187H/I252Q/L264R, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/L075Q/N094R/D130A/V154I/G156W/V187N/L264R, G023Q/D027S/F051T/S058M/G091Q/D130A/V187N/I252Q, G023Q/D027S/L075Q/D130A/V154I/G156W/T189Q/L264R, G023Q/F051T/L075Q/G091Q/D130A/V187H/I252Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/V077I/N094R/D130A/V154I/G156W/V187Q, N011K/G023K/D027S/L075Q/D111A/D130A/V154I/T189Q, N011K/G023K/E056K/L075Q/D130A/V154I/T189Q/L264R, A018K/G023G/K024A/L075Q/N094R/D111A/D130A/V154I/T189Q, A018K/G023G/K024A/L075R/V077I/D130A/V154I/G156W/V187N, A018K/G023Q/K024A/L075R/N094R/D130A/V154I/G156W/V187N, D027Q/F051T/S058M/L075G/G091Q/D130A/V187T/I252Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/L075Q/D111A/D130A/V154I/G156W/T189Q/L264R, G023K/E056K/L075Q/D111A/D130A/V154I/G156W/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023G/K024A/L075R/V077I/D130A/V154I/V187T/T189Q, N011K/G023Q/D027S/E056K/L075R/D130A/V154I/G156W/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, optionally wherein the variant or active fragment has a performance index (pI) for detergent stability which is greater than 1.0; or, (c) the variant comprises amino acid modifications selected from: D130A/T189Q, D130A/V187N, D130A/V187T, G023K/D130A, L075Q/D130A, D111A/D130A/L264R, D130A/V154I/G156W, E056K/D130A/L264R, G023K/D130A/V187T, G023Q/D130A/G156W, K024A/D130A/V154I, L075G/D130A/V187H, L075Q/D111A/D130A, L075Q/D130A/V187T, L075R/D130A/L264R, L075R/D130A/V187T, N094R/D130A/V187T, V077I/D130A/V154I, A018K/D130A/G156W/V187T, A018K/G023Q/L075R/D130A, A018K/K024A/D130A/G156W, A018K/L075Q/N094R/D130A, D111A/D130A/V154I/G156W, D111A/D130A/V154I/L264R, D111A/D130A/V187T/L264R, E056K/D130A/V187T/L264R, F051T/D130A/I252Q/L264R, G023K/D111A/D130A/L264R, G023K/D130A/G156W/T189Q, G023K/D130A/V187T/L264R, G023K/D130A/V187T/T189Q, G023K/L075Q/D130A/V187N, G023Q/K024A/D130A/G156W, K024A/D130A/V154I/V187T, K024A/L075Q/D130A/G156W, K024A/L075Q/D130A/V154I, L075G/D130A/V187T/I252Q, L075Q/D130A/G156W/V187N, L075Q/D130A/V154I/G156W, L075Q/V077I/D130A/V187Q, L075R/D130A/V154I/L264R, A018K/G023G/D130A/V154I/G156W, A018K/G023G/K024A/D130A/G156W, A018K/G023G/K024A/D130A/V154I, A018K/G023G/L075Q/D130A/V154I, A018K/G023G/V077I/D130A/V187N, A018K/G023Q/K024A/D130A/V154I, A018K/G023Q/K024A/D130A/V187Q, A018K/K024A/L075R/D130A/V154I, A018K/K024A/N094R/D130A/V187N, A018K/L075Q/D111A/D130A/V187T, A018K/L075Q/N094R/D130A/V187N, D130A/G163P/L227M/N233Q/L264R, D130A/V154I/G156W/V187N/T189Q, E056K/D130A/V187H/I252Q/L264R, E056K/L075R/D130A/V187T/L264R, G023K/E056K/D130A/V187T/L264R, G023K/E056K/L075R/D130A/V187T, G023K/K024A/D111A/D130A/V187T, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075R/D130A/V187N/L264R, G023Q/K024A/L075Q/D130A/G156W, G023Q/K024A/L075R/D130A/V154I, G023Q/K024A/L075R/V077I/D130A, G023Q/K024A/V077I/D130A/V154I, G023Q/L075Q/V077I/D130A/G156W, L075Q/D111A/D130A/V187T/T189Q, L075Q/D130A/V187T/T189Q/L264R, L075Q/N094R/D130A/G156W/V187T, L075Q/V077I/D130A/G156W/V187N, L075R/D111A/D130A/V187N/T189Q, L075R/D130A/V154I/T189Q/L264R, V077I/D130A/V154I/G156W/V187N, A018K/G023G/D111A/D130A/V154I/T189Q, A018K/G023G/K024A/L075R/D130A/V187N, A018K/G023G/K024A/N094R/D130A/V154I, A018K/G023G/L075Q/D130A/G156W/V187N, A018K/G023G/L075R/N094R/D130A/V187N, A018K/G023G/L075R/V077I/D130A/V154I, A018K/G023Q/L075Q/V077I/D130A/G156W, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/L075R/D130A/V154I/G156W/V187N, A018K/N094R/D111A/D130A/V154I/V187N, D027Q/E056K/S058M/D130A/I252Q/L264R, D027Q/F051T/G091Q/D130A/I252Q/L264R, D027Q/F051T/L075G/D130A/I252Q/L264R, D027Q/S058M/L075R/D130A/V187T/I252Q, D027S/G091Q/D130A/V187N/I252Q/L264R, D048Q/D130A/G163P/L227M/N233Q/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/E056K/L075R/D130A/V187T/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075R/D130A/V154I/V187N, G023K/L075Q/D111A/D130A/V154I/V187N, G023K/L075Q/V077I/D130A/G156W/V187Q, G023Q/D027S/L075G/D130A/V187H/L264R, G023Q/E056K/D111A/D130A/V187N/T189Q, G023Q/E056K/L075Q/D130A/V154I/L264R, G023Q/F051T/D130A/V187T/I252Q/L264R, G023Q/F051T/L075Q/D130A/V187H/I252Q, G023Q/K024A/D130A/V154I/G156W/V187Q, G023Q/K024A/L075Q/D130A/V154I/G156W, G023Q/K024A/L075Q/D130A/V154I/V187N, G023Q/K024A/V077I/D130A/G156W/V187N, G023Q/K024A/V077I/D130A/V154I/G156W, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, L075Q/D111A/D130A/V154I/G156W/T189Q, L075Q/D111A/D130A/V154I/V187N/T189Q, L075R/D130A/V154I/G156W/V187N/L264R, N011K/E056K/L075Q/D130A/V187N/T189Q, N011K/G023Q/L075Q/D130A/V187N/T189Q, A018K/D111A/D130A/V154I/G156W/V187T/T189Q, A018K/G023G/K024A/L075Q/D130A/G156W/V187N, A018K/G023G/K024A/L075R/N094R/D130A/V154I, A018K/G023Q/K024A/L075Q/V077I/D130A/G156W, A018K/G023Q/K024A/L075R/D130A/V154I/V187N, A018K/G023Q/K024A/L075R/V077I/D130A/G156W, A018K/K024A/L075Q/D130A/G156W/V187T/T189Q, A018K/K024A/L075Q/D130A/V154I/G156W/V187T, D027Q/F051T/L075Q/G091Q/D130A/V187T/I252Q, D027Q/L075G/G091Q/D130A/V187H/I252Q/L264R, E056K/L075Q/D111A/D130A/G156W/V187N/T189Q, G023K/D027Q/F051T/L075G/D130A/V187H/L264R, G023K/D027S/F051T/S058M/L075Q/D130A/V187N, G023K/F051T/E056K/L075R/D130A/V187T/I252Q, G023K/F051T/L075Q/G091Q/D130A/V187H/I252Q, G023K/K024A/L075Q/D111A/D130A/T189Q/L264R, G023K/K024A/L075Q/D130A/V187T/T189Q/L264R, G023K/K024A/L075Q/V077I/D130A/G156W/V187Q, G023K/L075Q/D111A/D130A/V154I/G156W/L264R, G023K/L075Q/D130A/G156W/V187N/T189Q/L264R, G023Q/D027S/S058M/L075Q/D130A/I252Q/L264R, G023Q/E056K/L075Q/

D130A/V154I/G156W/T189Q, G023Q/E056K/L075R/D111A/D130A/V187N/T189Q, G023Q/F051T/G091Q/D130A/V187H/I252Q/L264R, G023Q/K024A/L075Q/V077I/D130A/G156W/V187N, G023Q/K024A/L075Q/V077I/D130A/V154I/G156W, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, K024A/L075Q/D111A/D130A/V154I/G156W/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/E056K/L075Q/D111A/D130A/V154I/L264R, N011K/E056K/L075Q/D130A/V154I/V187N/T189Q, N011K/G023K/L075Q/D111A/D130A/V154I/V187N, A018K/G023G/K024A/L075Q/D130Y/V154I/V187N/T189Q, A018K/G023G/K024A/L075Q/N094R/D130A/G156W/V187Q, A018K/G023G/K024A/L075Q/V077I/D130A/V154I/G156W, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/E045F/L075Q/V077I/G156W/V187T/T189D, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, F051T/E056K/L075G/G091Q/D130A/V187H/I252Q/L264R, G023K/D027S/F051T/E056K/L075R/D130A/V187T/L264R, G023K/E056K/L075Q/D130A/V154I/N187N/T189Q/L264R, G023K/F051T/E056K/L075R/G091Q/D130A/V187T/L264R, G023K/L075Q/N094R/D130A/V154I/G156W/V187N/L264R, G023Q/D027S/F051T/S058M/G091Q/D130A/V187N/I252Q, G023Q/D027S/L075Q/D130A/V154I/G156W/T189Q/L264R, G023Q/F051T/L075Q/G091Q/D130A/V187H/I252Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D111A/D130A/G156W/T189Q/L264R, G023Q/L075Q/V077I/N094R/D130A/V154I/G156W/V187Q, N011K/G023K/D027S/L075Q/D111A/D130A/V154I/T189Q, N011K/G023K/E056K/L075Q/D130A/V154I/T189Q/L264R, A018K/G023G/K024A/L075Q/N094R/D111A/D130A/V154I/T189Q, A018K/G023G/K024A/L075R/V077I/D130A/V154I/G156W/V187N, A018K/G023Q/K024A/L075R/N094R/D130A/V154I/G156W/V187N, D027Q/F051T/S058M/L075G/G091Q/D130A/V187T/I252Q/L264R, D027S/E056K/L075Q/N094R/D111A/D130A/V154I/G156W/L264R, D027S/E056K/L075Q/N094R/D111A/D130A/V187N/T189Q/L264R, G023K/D027S/L075Q/D111A/D130A/V154I/G156W/T189Q/L264R, G023K/E056K/L075Q/D111A/D130A/V154I/G156W/T189Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D111A/D130A/V154I/G156W/L264R, G023Q/D027S/L075Q/N094R/D130A/V154I/G156W/V187N/L264R, G023Q/E056K/L075Q/D111A/D130A/V154I/G156W/T189Q/L264R, G023Q/F051T/S058M/L075G/G091Q/D130A/V187T/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023G/K024A/L075R/V077I/D130A/V154I/V187T/T189Q, N011K/G023Q/D027S/E056K/L075R/D130A/V154I/G156W/T189Q/L264R, N011K/G023Q/E056K/L075R/D111A/D130A/V154I/G156W/V187N/L264R, N011K/G023Q/L075Q/N094R/D111A/D130A/V154I/G156W/V187N/L264R, optionally wherein the variant or active fragment has a performance index (pI) for LAS stability which is greater than 1.0; or, (d) the variant comprises amino acid modifications selected from: D130A/L264R, D130A/V187N, D130A/V187T, D111A/D130A/L264R, D130A/V187N/L264R, D130A/V187T/L264R, G023K/D130A/L264R, G023K/D130A/V187T, L075R/D130A/L264R, L075R/D130A/V187T, A018K/G023Q/L075R/D130A, A018K/K024A/D130A/G156W, D027E/D130A/N233Q/L264R, D027S/D130A/I252Q/L264R, D048Q/D130A/G163P/L264R, D048Q/G163P/N233Q/L264R, D111A/D130A/V154I/G156W, D111A/D130A/V187T/L264R, E056K/D130A/V187N/L264R, E056K/D130A/V187T/L264R, G023K/D130A/V187N/L264R, G023K/D130A/V187T/L264R, G023K/D130A/V187T/T189Q, G023K/L075Q/D130A/V187N, G023Q/L075Q/D130A/L264R, K024A/D130A/V154I/V187T, L075G/D130A/V187T/I252Q, L075Q/D130A/G156W/V187N, L075Q/V077I/D130A/V187Q, L075R/D130A/V154I/L264R, A018K/D130A/G156W/V187N/L264R, A018K/G023G/K024A/D130A/G156W, A018K/G023G/K024A/D130A/V154I, A018K/G023G/V077I/D130A/V187N, A018K/G023Q/K024A/D130A/V187Q, A018K/K024A/L075R/N094R/D130A, A018K/K024A/N094R/D130A/V187N, A018K/L075Q/D111A/D130A/V187T, D027E/D130A/G163P/L227M/L264R, D027E/D130A/G163P/N233Q/L264R, D027E/S058M/D130A/G163P/L264R, D027S/L075G/D130A/I252Q/L264R, D048Q/D130A/G163P/L227M/L264R, D130A/D137Q/G163P/L227M/L264R, D130A/D137Q/G163P/N233Q/L264R, D130A/V154I/G156W/V187N/T189Q, F051T/D130A/V187T/I252Q/L264R, F051T/L075G/D130A/I252Q/L264R, F051T/L075G/G091Q/D130A/L264R, F051T/L075Q/G091Q/D130A/L264R, G023K/E056K/D130A/V187N/L264R, G023K/E056K/D130A/V187T/L264R, G023K/L075Q/D111A/D130A/V187T, G023K/L075Q/D130A/G156W/L264R, G023K/L075Q/V077I/D130A/G156W, G023K/L075R/D130A/V187N/L264R, G023K/L075R/D130A/V187T/L264R, G023Q/L075Q/D130A/I252Q/L264R, G091Q/D130A/V187H/I252Q/

L264R, L075G/D130A/V187T/I252Q/L264R, L075R/D130A/V154I/T189Q/L264R, L075R/D130A/V187T/T189Q/L264R, S058M/D130A/G163P/L227M/L264R, A018K/G023G/K024A/L075R/D130A/V187N, A018K/G023G/L075Q/D130A/G156W/V187N, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137H/G163P/L264R, D027E/D048Q/D130A/D137Q/G163P/L264R, D027E/D048Q/D130A/G163P/L227M/L264R, D027E/D130A/D137Q/G163P/N233Q/L264R, D027E/D130A/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027Q/F051T/G091Q/D130A/I252Q/L264R, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D048Q/S058M/D130A/G163P/L227M/L264R, D048Q/S058M/D130A/L227M/N233Q/L264R, D111A/D130A/V154I/G156W/V187N/L264R, F051T/E056K/D130A/V187N/I252Q/L264R, F051T/L075R/D130A/V187N/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187T/L264R, G023K/F051T/D130A/V187N/I252Q/L264R, G023K/F051T/L075Q/D130A/I252Q/L264R, G023K/L075Q/D111A/D130A/V154I/V187N, G023Q/D027S/L075G/D130A/V187H/L264R, G023Q/D027S/L075Q/D130A/V187T/I252Q, G023Q/F051T/L075Q/D130A/V187H/I252Q, G023Q/K024A/D130A/V154I/G156W/V187Q, G023Q/K024A/V077I/D130A/G156W/V187N, G023Q/L075G/G091Q/D130A/I252Q/L264R, L075Q/D111A/D130A/V154I/V187N/T189Q, L075Q/D130A/V154I/G156W/V187N/L264R, L075Q/G091Q/D130A/V187H/I252Q/L264R, L075R/D130A/V154I/G156W/V187N/L264R, N011K/E056K/L075Q/D130A/V187N/T189Q, S058M/D130A/D137Q/G163P/L227M/L264R, S058M/D130A/D137Q/G163P/N233Q/L264R, S058M/D130A/G163P/L227M/N233Q/L264R, A018K/D111A/D130A/V154I/G156W/V187T/T189Q, A018K/G023G/K024A/L075Q/D130A/G156W/V187N, A018K/G023Q/K024A/L075R/D130A/V154I/V187N, A018K/K024A/D130A/V154I/G156W/V187T/L264R, A018K/K024A/L075Q/D130A/G156W/V187T/T189Q, A018K/K024A/L075Q/D130A/V154I/G156W/V187T, A018K/K024A/N094R/D130A/G156W/V187T/L264R, D027E/D048Q/D130A/D137Q/G163P/N233Q/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/S058M/D130A/D137Q/G163P/L227M/L264R, D027E/S058M/D130A/G163P/L227M/N233Q/L264R, D027Q/F051T/L075G/D130A/V187H/I252Q/L264R, D027Q/F051T/L075Q/D130A/V187T/I252Q/L264R, D027Q/L075G/G091Q/D130A/V187H/I252Q/L264R, D027S/F051T/S058M/L075R/D130A/I252Q/L264R, D048Q/S058M/D130A/D137Q/G163P/L227M/L264R, D048Q/S058M/D130A/G163P/L227M/N233Q/L264R, F051T/L075G/G091Q/D130A/V187N/I252Q/L264R, F051T/L075Q/G091Q/D130A/V187H/I252Q/L264R, F051T/L075R/G091Q/D130A/V187T/I252Q/L264R, G023K/D027Q/F051T/L075G/D130A/V187H/L264R, G023K/D027S/F051T/S058M/L075Q/D130A/V187N, G023K/K024A/L075Q/D111A/D130A/T189Q/L264R, G023K/K024A/L075Q/D130A/V187T/T189Q/L264R, G023K/K024A/L075Q/V077I/D130A/G156W/V187Q, G023Q/D027S/F051T/E056K/D130A/I252Q/L264R, G023Q/D027S/S058M/L075Q/D130A/I252Q/L264R, G023Q/E056K/L075R/D111A/D130A/V187N/T189Q, G023Q/F051T/S058M/G091Q/D130A/I252Q/L264R, G023Q/K024A/L075Q/V077I/D130A/G156W/V187N, G023Q/L075G/G091Q/D130A/V187T/I252Q/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/S058M/L075G/G091Q/D130A/I252Q/L264R, K024A/L075Q/D111A/D130A/V154I/G156W/L264R, L075Q/D111A/D130A/G156W/V187N/T189Q/L264R, A018K/G023G/K024A/L075Q/D130Y/V154I/V187N/T189Q, A018K/G023Q/K024A/L075Q/V077I/D130A/G156W/V187Q, A018K/K024A/L075R/D130A/V154I/G156W/V187T/L264R, D027E/D048Q/D130A/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, G023K/D027S/E056K/L075G/D130A/V187T/I252Q/L264R, G023Q/D027Q/F051T/L075Q/G091Q/D130A/I252Q/L264R, G023Q/D027Q/F051T/S058M/L075R/D130A/V187T/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/F051T/L075R/G091Q/D130A/V187T/I252Q/L264R, G023Q/L075Q/N094R/D111A/D130A/G156W/T189Q/L264R, G023Q/S058M/L075R/G091Q/D130A/V187H/I252Q/L264R, K024A/D111A/D130A/V154I/G156W/V187T/T189Q/L264R, A018K/G023G/K024A/L075Q/N094R/D130A/V187T/T189Q/L264K, A018K/G023G/K024A/L075R/V077I/D130A/V154I/G156W/V187N, A018K/G023G/K024A/V077I/D130A/V154I/G156W/V187T/T189Q, D027Q/F051T/S058M/L075G/G091Q/D130A/V187T/I252Q/L264R, G023K/K024A/N094R/D130A/V154I/G156W/V187T/T189Q/L264R, G023K/L075Q/D111A/D130A/V154I/G156W/V187T/T189Q/L264R, G023Q/D027S/L075Q/N094R/D130A/V154I/G156W/V187N/L264R, G023Q/F051T/S058M/L075Q/G091Q/D130A/V187H/I252Q/L264R, N011K/G023K/L075R/D111A/D130A/V154I/V187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, N011K/A018K/G023G/K024A/L075R/V077I/D130A/V154I/V187T/T189Q, N011K/G023Q/E056K/L075R/D111A/D130A/V154I/G156W/V187N/L264R, optionally wherein the variant or active fragment has a performance index (pI) for fabric adhesion which is greater than 1.0, or, (e) the variant comprises amino acid modifications selected from: D130A/T189Q, G023K/D130A, L075Q/D130A, D130A/T189Q/L264R, D130A/V154I/G156W, E056K/D130A/L264R, E056K/D130A/T189Q, G023Q/D130A/G156W, K024A/D130A/V154I, L075G/D130A/V187H, L075Q/D111A/D130A, L075Q/D130A/V187T, N094R/D130A/V187T, V077I/D130A/V154I, A018K/D130A/G156W/V187T, A018K/L075Q/N094R/D130A, D111A/D130A/V154I/L264R, D130A/G163P/L227M/L264R, D130A/G163P/N233Q/L264R, F051T/D130A/I252Q/L264R, G023K/D111A/D130A/L264R, G023K/D130A/G156W/T189Q, G023K/E056K/D130A/L264R, G023K/E056K/D130A/V187N, G023K/L075R/D130A/L264R, G023Q/K024A/D130A/G156W, K024A/L075Q/D130A/G156W, K024A/L075Q/D130A/V154I, L075Q/D130A/V154I/G156W, L075R/D130A/V187T/L264R, A018K/D130A/G156W/V187T/L264R, A018K/G023G/D130A/V154I/G156W, A018K/G023G/L075Q/D130A/V154I, A018K/G023Q/K024A/D130A/V154I, A018K/G023Q/V077I/D130A/G156W, A018K/K024A/L075Q/D130A/L264R, A018K/K024A/L075R/D130A/V154I, A018K/L075Q/N094R/D130A/V187N, D027E/D130A/D137Q/G163P/L264R, D027Q/F051T/L075Q/D130A/L264R, D027S/L075Q/D111A/D130A/V187N, D048Q/D130A/D137Q/G163P/L264R, D048Q/S058M/D130A/N233Q/L264R, D130A/G163P/L227M/N233Q/L264R, E056K/D130A/V187H/I252Q/L264R, E056K/L075R/D130A/V187N/L264R, E056K/L075R/D130A/V187T/L264R, G023K/E056K/L075R/D130A/V187T, G023K/K024A/D111A/D130A/V187T, G023K/K024A/L075R/D130A/G156W, G023K/L075Q/D130A/V154I/T189Q, G023Q/K024A/L075Q/D130A/G156W, G023Q/K024A/L075R/D130A/V154I, G023Q/K024A/L075R/V077I/D130A, G023Q/K024A/V077I/D130A/V154I, G023Q/L075Q/V077I/D130A/G156W, L075Q/D111A/D130A/V187T/T189Q, L075Q/D130A/V187T/T189Q/L264R, L075Q/N094R/D130A/G156W/V187T, L075Q/V077I/D130A/G156W/V187N, L075R/D111A/D130A/V187N/T189Q, S058M/D130A/D137Q/G163P/L264R, V077I/D130A/V154I/G156W/V187N, A018K/G023G/D111A/D130A/V154I/T189Q, A018K/G023G/K024A/N094R/D130A/V154I, A018K/G023G/L075R/N094R/D130A/V187N, A018K/G023G/L075R/V077I/D130A/V154I, A018K/G023Q/L075Q/V077I/D130A/G156W, A018K/K024A/V077I/N094R/D130A/G156W, D027E/D048Q/S058M/D130A/G163P/L264R, D027E/D048Q/S058M/D130A/L227M/N233Q, D027E/D130A/D137Q/G163P/L227M/L264R, D027Q/E056K/S058M/D130A/I252Q/L264R, D027Q/F051T/L075G/D130A/I252Q/L264R, D027S/G091Q/D130A/V187N/I252Q/L264R, D048Q/D130A/G163P/L227M/N233Q/L264R, D048Q/S058M/D130A/D137Q/G163P/L264R, D048Q/S058M/D130A/G163P/N233Q/L264R, F051T/L075G/G091Q/D130A/I252Q/L264R, G023K/E056K/L075R/D130A/V187N/L264R, G023K/F051T/G091Q/D130A/V187H/L264R, G023K/K024A/L075Q/D111A/D130A/T189Q, G023K/K024A/L075Q/N094R/D130A/G156W, G023K/K024A/L075R/D130A/V154I/V187N, G023K/L075G/D130A/V187T/I252Q/L264R, G023K/L075Q/V077I/D130A/G156W/V187Q, G023Q/E056K/D111A/D130A/V187N/T189Q, G023Q/E056K/L075Q/D130A/V154I/L264R, G023Q/F051T/D130A/V187T/I252Q/L264R, G023Q/K024A/L075Q/D130A/V154I/G156W, G023Q/K024A/L075Q/D130A/V154I/V187N, G023Q/K024A/V077I/D130A/V154I/G156W, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, L075Q/D111A/D130A/V154I/G156W/T189Q, N011K/G023Q/L075Q/D130A/V187N/T189Q, N011K/G023Q/L075Q/N094R/D130A/L264R, A018K/G023G/K024A/L075R/N094R/D130A/V154I, A018K/G023Q/K024A/L075Q/V077I/D130A/G156W, A018K/G023Q/K024A/L075R/V077I/D130A/G156W, A018K/K024A/L075Q/V077I/N094R/D130A/G156W, A018K/L075Q/D111A/D130A/V154I/G156W/L264R, A018K/L075Q/D130A/G156W/V187N/T189Q/L264R, D027E/D130A/D137Q/G163P/L227M/N233Q/L264R, D027E/S058M/D130A/D137Q/G163P/N233Q/L264R, D027Q/F051T/L075Q/G091Q/D130A/V187T/I252Q, D048Q/D130A/D137Q/G163P/L227M/N233Q/L264R, D048Q/S058M/D130A/D137Q/L227M/N233Q/L264R, E056K/L075Q/D111A/D130A/G156W/V187N/T189Q, G023K/F051T/E056K/L075R/D130A/V187T/I252Q, G023K/F051T/L075Q/G091Q/D130A/V187H/I252Q, G023K/L075Q/D111A/D130A/V154I/G156W/L264R, G023K/L075Q/D130A/G156W/V187N/T189Q/L264R, G023K/L075Q/N094R/D130A/V154I/V187N/L264R, G023Q/E056K/L075Q/D130A/V154I/G156W/T189Q, G023Q/F051T/G091Q/D130A/V187H/I252Q/L264R, G023Q/K024A/L075Q/V077I/D130A/V154I/G156W, G023Q/L075Q/D111A/D130A/V154I/G156W/L264R, G023Q/L075Q/V077I/N094R/D130A/G156W/V187Q, K024A/L075Q/D111A/D130A/V187N/T189Q/L264R, K024A/L075R/D130A/V154I/G156W/T189Q/L264R, N011K/D027S/D111A/D130A/V154I/V187N/T189Q, N011K/E056K/L075Q/D111A/D130A/V154I/L264R, N011K/E056K/L075Q/D130A/V154I/V187N/T189Q, N011K/G023K/L075Q/D111A/D130A/V154I/V187N, A018K/G023G/K024A/L075Q/N094R/D130A/G156W/V187Q, A018K/G023G/K024A/L075Q/V077I/D130A/V154I/G156W, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, F051T/E056K/L075G/G091Q/D130A/V187H/I252Q/L264R, G023K/D027S/F051T/E056K/L075R/D130A/V187T/L264R, G023K/E056K/L075Q/D130A/V154I/V187N/T189Q/L264R, G023K/F051T/E056K/L075R/G091Q/D130A/V187T/L264R, G023K/L075Q/N094R/D130A/V154I/G156W/V187N/L264R, G023Q/D027S/F051T/S058M/G091Q/D130A/

V187N/I252Q, G023Q/D027S/L075Q/D130A/V154I/G156W/T189Q/L264R, G023Q/K024A/L075Q/V077I/D130A/V154I/G156W/V187N, G023Q/K024A/L075Q/V077I/N094R/D130A/V154I/V187N, G023Q/L075Q/D111A/D130A/V154I/G156W/V187N/L264R, G023Q/L075Q/N094R/D130A/V154I/G156W/T189Q/L264R, G023Q/L075Q/V077I/N094R/D130A/V154I/G156W/V187Q, N011K/G023K/D027S/L075Q/D111A/D130A/V154I/T189Q, N011K/G023K/E056K/L075Q/D130A/V154I/T189Q/L264R, N011K/G023Q/L075Q/D111A/D130A/V154I/N187N/L264R, A018K/G023G/K024A/L075Q/N094R/D111A/D130A/V154I/T189Q, A018K/G023G/K024A/L075Q/N094R/D130A/V154I/G156W/V187N, A018K/G023Q/K024A/L075R/N094R/D130A/V154I/G156W/V187N, D027S/E056K/L075Q/N094R/D111A/D130A/V154I/G156W/L264R, D027S/E056K/L075Q/N094R/D111A/D130A/V187N/T189Q/L264R, G023K/D027S/L075Q/D111A/D130A/V154I/G156W/T189Q/L264R, G023K/E056K/L075Q/D111A/D130A/V154I/G156W/T189Q/L264R, G023Q/D027S/L075Q/N094R/D111A/D130A/V154I/G156W/L264R, G023Q/E056K/L075Q/D111A/D130A/V154I/G156W/T189Q/L264R, G023Q/F051T/S058M/L075G/G091Q/D130A/V187T/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/G023Q/D027S/E056K/L075R/D130A/V154I/G156W/T189Q/L264R, N011K/G023Q/L075Q/N094R/D111A/D130A/V154I/G156W/V187N/L264R, A018K/G023G/L075R/N094R/D111A/D130A/V154I/G156W/V187N/T189Q/L264R, optionally wherein the variant or active fragment has a performance index (pI) for fabric adhesion which is less than 1.0, or, (f) the variant comprises amino acid modifications selected from: D130A/L264R, D130A/V187T, G023K/D130A, L075Q/D130A, D111A/D130A/L264R, E056K/D130A/T189Q L075G/D130A/V187H L075Q/D111A/D130A, L075Q/D130A/V187T, L075R/D130A/L264R, L075R/D130A/V187T, V077I/D130A/V154I, A018K/D130A/G156W/V187T, A018K/G023Q/L075R/D130A, D027E/D130A/N233Q/L264R, D027S/D130A/I252Q/L264R, D048Q/D130A/G163P/L264R, D111A/D130A/V154I/L264R, D130A/G163P/L227M/L264R, D130A/G163P/N233Q/L264R, E056K/D130A/V187N/L264R, F051T/D130A/I252Q/L264R, G023K/D130A/G156W/T189Q, G023K/D130A/V187T/L264R, G023K/D130A/V187T/T189Q, G023K/L075Q/D130A/V187N, G023K/L075R/D130A/L264R, G023Q/L075Q/D130A/L264R, K024A/D130A/V154I/V187T, K024A/L075Q/D130A/G156W, L075G/D130A/V187T/I252Q, L075Q/D130A/G156W/V187N, L075Q/D130A/V154I/G156W, L075Q/V077I/D130A/V187Q, L075R/D130A/V154I/L264R, L075R/D130A/V187T/L264R, A018K/D130A/G156W/V187N/L264R, A018K/G023G/D130A/V154I/G156W, A018K/G023G/K024A/D130A/G156W, A018K/G023G/L075Q/D130A/V154I, A018K/G023Q/K024A/D130A/V187Q, A018K/G023Q/V077I/D130A/G156W, A018K/K024A/L075Q/D130A/L264R, A018K/K024A/L075R/N094R/D130A, A018K/K024A/N094R/D130A/V187N, A018K/L075Q/D111A/D130A/V187T, A018K/L075Q/N094R/D130A/V187N, D027E/D130A/G163P/N233Q/L264R, D027E/S058M/D130A/G163P/L264R, D027S/L075G/D130A/I252Q/L264R, D048Q/D130A/D137Q/G163P/L264R, D048Q/D130A/G163P/L227M/L264R, D048Q/S058M/D130A/N233Q/L264R, D130A/D137Q/G163P/L227M/L264R, D130A/D137Q/G163P/N233Q/L264R, E056K/D130A/V187H/I252Q/L264R, E056K/L075R/D130A/V187T/L264R, F051T/L075G/D130A/I252Q/L264R, F051T/L075Q/G091Q/D130A/L264R, G023K/E056K/D130A/V187T/L264R, G023K/E056K/L075R/D130A/V187T, G023K/K024A/L075R/D130A/G156W, G023K/L075Q/D111A/D130A/V187T, G023K/L075Q/D130A/G156W/L264R, G023K/L075Q/V077I/D130A/G156W, G023K/L075R/D130A/V187T/L264R, G023Q/K024A/L075R/D130A/V154I, G023Q/K024A/V077I/D130A/V154I, G023Q/L075Q/D130A/I252Q/L264R, G023Q/L075Q/V077I/D130A/G156W, G091Q/D130A/V187H/I252Q/L264R, L075G/D130A/V187T/I252Q/L264R, L075Q/D111A/D130A/V187T/T189Q, L075Q/N094R/D130A/G156W/V187T, L075R/D111A/D130A/V187N/T189Q, L075R/D130A/V154I/T189Q/L264R, L075R/D130A/V187T/T189Q/L264R, S058M/D130A/D137Q/G163P/L264R, S058M/D130A/G163P/L227M/L264R, A018K/G023G/D111A/D130A/V154I/T189Q, A018K/G023G/K024A/L075R/D130A/V187N, A018K/G023G/K024A/N094R/D130A/V154I, A018K/G023G/L075Q/D130A/G156W/V187N, A018K/G023G/L075R/N094R/D130A/V187N, A018K/G023G/L075R/V077I/D130A/V154I, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137Q/G163P/L264R, D027E/D048Q/D130A/G163P/L227M/L264R, D027E/D130A/D137Q/G163P/L227M/L264R, D027E/D130A/D137Q/G163P/N233Q/L264R, D027E/D130A/G163P/L227M/N233Q/L264R, D027E/S058M/D130A/G163P/L227M/L264R, D027E/S058M/D130A/G163P/N233Q/L264R, D027E/S058M/D130A/L227M/N233Q/L264R, D027Q/E056K/S058M/D130A/I252Q/L264R, D027Q/F051T/G091Q/D130A/I252Q/L264R, D027Q/F051T/L075G/D130A/I252Q/L264R, D027Q/F051T/L075Q/D130A/V187H/L264R, D027Q/L075Q/D130A/V187T/I252Q/L264R, D027Q/S058M/L075R/D130A/V187T/I252Q, D027S/F051T/L075Q/D130A/I252Q/L264R, D048Q/S058M/D130A/D137Q/G163P/L264R, D048Q/S058M/D130A/G163P/L227M/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/D130A/V187T/I252Q, G023K/D130A/V154I/G156W/V187T/L264R, G023K/E056K/L075R/D130A/T189Q/L264R, G023K/E056K/L075R/D130A/V187N/L264R, G023K/F051T/D130A/V187N/I252Q/L264R, G023K/F051T/G091Q/D130A/V187H/L264R, G023K/K024A/L075Q/D111A/D130A/T189Q, G023K/

K024A/L075Q/N094R/D130A/G156W, G023K/K024A/L075R/D130A/V154I/V187N, G023K/L075Q/D111A/D130A/V154I/V187N, G023K/L075Q/V077I/D130A/G156W/V187Q, G023Q/D027S/L075G/D130A/V187H/L264R, G023Q/D027S/L075Q/D130A/V187T/I252Q, G023Q/F051T/D130A/V187T/I252Q/L264R, G023Q/K024A/D130A/V154I/G156W/V187Q, G023Q/K024A/L075Q/D130A/V154I/G156W, G023Q/K024A/L075Q/D130A/V154I/V187N, G023Q/K024A/V077I/D130A/G156W/V187N, G023Q/L075Q/V077I/N094R/D130A/V187Q, K024A/D111A/D130A/V187T/T189Q/L264R, K024A/L075Q/D130A/G156W/T189Q/L264R, K024A/L075Q/N094R/D130A/V154I/L264R, K024A/L075Q/V077I/N094R/D130A/V187N, L075Q/D111A/D130A/V154I/G156W/T189Q, L075Q/D111A/D130A/V154I/V187N/T189Q, L075Q/D130A/V154I/G156W/V187N/L264R, L075Q/G091Q/D130A/V187H/I252Q/L264R, N011K/E056K/L075Q/D130A/V187N/T189Q, N011K/G023Q/L075Q/D130A/V187N/T189Q, N011K/G023Q/L075Q/N094R/D130A/L264R, S058M/D130A/D137Q/G163P/L227M/L264R, S058M/D130A/D137Q/G163P/N233Q/L264R, S058M/D130A/G163P/L227M/N233Q/L264R, A018K/G023G/K024A/L075Q/D130A/G156W/V187N, A018K/G023G/K024A/L075R/N094R/D130A/V154I, A018K/G023Q/K024A/L075Q/V077I/D130A/G156W, A018K/G023Q/K024A/L075R/D130A/V154I/N187N, A018K/G023Q/K024A/L075R/V077I/D130A/G156W, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/L075Q/D111A/D130A/V154I/G156W/L264R, D027E/D048Q/S058M/D130A/D137Q/G163P/L264R, D027E/D048Q/S058M/D130A/G163P/L227M/L264R, D027E/D048Q/S058M/D130A/G163P/N233Q/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027Q/F051T/L075G/D130A/V187H/I252Q/L264R, D027Q/F051T/L075Q/G091Q/D130A/V187T/I252Q, D027Q/L075G/G091Q/D130A/V187H/I252Q/L264R, D027S/F051T/S058M/L075R/D130A/I252Q/L264R, D048Q/D130A/D137Q/G163P/L227M/N233Q/L264R, D048Q/S058M/D130A/D137Q/G163P/L227M/L264R, D048Q/S058M/D130A/G163P/L227M/N233Q/L264R, E056K/L075Q/D111A/D130A/G156W/V187N/T189Q, F051T/L075G/G091Q/D130A/V187N/I252Q/L264R, F051T/L075R/G091Q/D130A/V187T/I252Q/L264R, G023K/D027Q/F051T/L075G/D130A/V187H/L264R, G023K/D027S/F051T/S058M/L075Q/D130A/V187N, G023K/F051T/E056K/L075R/D130A/V187T/I252Q, G023K/F051T/L075Q/G091Q/D130A/V187H/I252Q, G023K/K024A/L075Q/D111A/D130A/T189Q/L264R, G023K/K024A/L075Q/D130A/V187T/T189Q/L264R, G023K/K024A/L075Q/V077I/D130A/G156W/V187Q, G023Q/D027S/S058M/L075Q/D130A/I252Q/L264R, G023Q/E056K/L075Q/D130I/V154I/G156W/T189Q, G023Q/E056K/L075R/D111A/D130A/V187N/T189Q, G023Q/F051T/G091Q/D130A/V187H/I252Q/L264R, G023Q/K024A/L075Q/V077I/D130A/G156W/V187N, G023Q/K024A/L075Q/V077I/D130A/V154I/G156W, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, G023Q/S058M/L075G/G091Q/D130A/I252Q/L264R, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/E056K/L075Q/D130A/V154I/V187N/T189Q, N011K/G023K/L075Q/D111A/D130A/V154I/V187N, A018K/G023G/K024A/L075Q/D130Y/V154I/V187N/T189Q, A018K/G023G/K024A/L075Q/N094R/D130A/G156W/V187Q, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/L075Q/V077I/D130A/V154I/G156W/V187N, A018K/K024A/L075Q/V077I/N094R/D130A/V154I/G156W, A018K/K024A/L075R/D130A/V154I/G156W/V187T/L264R, D027E/D048Q/D130A/D137Q/G163P/L227M/N233Q/L264R, D027E/S058M/D130A/D137Q/G163P/L227M/N233Q/L264R, D048Q/S058M/D130A/D137Q/G163P/L227M/N233Q/L264R, F051T/E056K/L075G/G091Q/D130A/V187H/I252Q/L264R, G023K/D027S/E056K/L075G/D130A/V187T/I252Q/L264R, G023K/D027S/F051T/E056K/L075R/D130A/V187T/L264R, G023K/F051T/E056K/L075R/G091Q/D130A/V187T/L264R, G023K/L075Q/N094R/D130A/V154I/G156W/V187N/L264R, G023Q/D027Q/F051T/S058M/L075R/D130A/V187T/L264R, G023Q/D027S/F051T/S058M/G091Q/D130A/V187N/I252Q, G023Q/D027S/L075Q/D130A/V154I/G156W/T189Q/L264R, G023Q/D027S/S058M/G091Q/D130A/V187H/I252Q/L264R, G023Q/F051T/L075Q/G091Q/D130A/V187H/I252Q/L264R, G023Q/F051T/L075Q/G091Q/D130A/V187T/I252Q/L264R, G023Q/K024A/L075Q/V077I/D130A/V154I/G156W/V187N, G023Q/K024A/L075Q/V077I/N094R/D130A/V154I/V187N, G023Q/L075Q/N094R/D111A/D130A/G156W/T189Q/L264R, G023Q/L075Q/V077I/N094R/D130A/V154I/G156W/V187Q, N011K/G023K/E056K/L075Q/D130A/V154I/T189Q/L264R, N011K/G023Q/L075Q/D111A/D130A/V154I/V187N/L264R, A018K/G023G/K024A/L075Q/N094R/D111A/D130A/V154I/T189Q, A018K/G023G/K024A/L075R/V077I/D130A/V154I/G156W/V187N, A018K/G023G/K024A/V077I/D130A/V154I/G156W/V187T/T189Q, A018K/G023Q/K024A/L075R/N094R/D130A/V154I/G156W/V187N, D027Q/F051T/S058M/L075G/G091Q/D130A/V187T/I252Q/L264R, D027S/E056K/L075Q/N094R/D111A/D130A/V154I/G156W/L264R, G023K/D027S/L075Q/D111A/D130A/V154I/G156W/T189Q/L264R, G023K/E056K/L075Q/D111A/D130A/V154I/G156W/T189Q/L264R, G023K/K024A/N094R/D130A/V154I/G156W/V187T/T189Q/L264R, G023Q/D027S/L075Q/N094R/D130A/V154I/G156W/V187N/L264R, G023Q/E056K/L075Q/D111A/D130A/V154I/G156W/T189Q/L264R, N011K/G023K/L075R/

D111A/D130A/V154I/N187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023G/K024A/L075R/V077I/D130A/V154I/V187T/T189Q, N011K/G023Q/E056K/L075R/D111A/D130A/V154I/G156W/V187N/L264R, N011K/G023Q/L075Q/N094R/D111A/D130A/V154I/G156W/V187N/L264R, A018K/G023G/L075R/N094R/D111A/D130A/V154I/G156W/V187N/T189Q/L264R, optionally wherein the variant or active fragment has a performance index (pI) for cleaning performance which is greater than 1.0; or, (g) the variant comprises amino acid modifications selected from: D130A/L264R, D130A/V187N, G023K/D130A, L075Q/D130A, D111A/D130A/L264R, E056K/D130A/T189Q, G023K/D130A/L264R, G023K/D130A/V187T, L075G/D130A/V187H, L075Q/D111A/D130A, L075Q/D130A/V187T, L075R/D130A/L264R, L075R/D130A/V187T, V077I/D130A/V154I, A018K/G023Q/L075R/D130A, D048Q/D130A/G163P/L264R, D111A/D130A/V154I/L264R, D130A/G163P/L227M/L264R, D130A/G163P/N233Q/L264R, E056K/D130A/V187N/L264R, E056K/D130A/V187T/L264R, G023K/D130A/V187T/L264R, G023K/E056K/D130A/L264R, G023K/L075Q/D130A/V187N, G023K/L075R/D130A/L264R, K024A/D130A/V154I/V187T, K024A/L075Q/D130A/G156W, L075G/D130A/V187T/I252Q, L075Q/D130A/G156W/V187N, L075Q/D130A/V154I/G156W, L075Q/V077I/D130A/V187Q, L075R/D130A/V154I/L264R, A018K/D130A/G156W/V187N/L264R, A018K/G023G/D130A/V154I/G156W, A018K/G023G/K024A/D130A/G156W, A018K/G023G/L075Q/D130A/V154I, A018K/G023G/V077I/D130A/V187N, A018K/G023Q/K024A/D130A/V154I, A018K/G023Q/K024A/D130A/V187Q, A018K/G023Q/V077I/D130A/G156W, A018K/K024A/L075Q/D130A/L264R, A018K/K024A/L075R/D130A/V154I, A018K/K024A/L075R/N094R/D130A, A018K/K024A/N094R/D130A/V187N, A018K/L075Q/D111A/D130A/V187T, A018K/L075Q/N094R/D130A/V187N, D027E/D130A/G163P/L227M/L264R, D027E/D130A/G163P/N233Q/L264R, D027S/L075G/D130A/I252Q/L264R, D027S/L075Q/D111A/D130A/V187N, D048Q/D130A/D137Q/G163P/L264R, D048Q/S058M/D130A/N233Q/L264R, D130A/D137Q/G163P/N233Q/L264R, E056K/D130A/V187H/I252Q/L264R, E056K/L075R/D130A/V187T/L264R, F051T/L075Q/G091Q/D130A/L264R, G023K/E056K/D130A/V187T/L264R, G023K/E056K/L075R/D130A/V187T, G023K/K024A/L075R/D130A/G156W, G023K/L075Q/D111A/D130A/V187T, G023K/L075Q/D130A/G156W/L264R, G023K/L075Q/D130A/V154I/T189Q, G023K/L075Q/V077I/D130A/G156W, G023K/L075R/D130A/V187T/L264R, G023Q/K024A/L075Q/D130A/G156W, G023Q/K024A/L075R/D130A/V154I, G023Q/K024A/L075R/G156W/V187Q, G023Q/K024A/L075R/V077I/D130A, G023Q/K024A/V077I/D130A/V154I, G023Q/L075Q/V077I/D130A/G156W, G091Q/D130A/V187H/I252Q/L264R, L075Q/D111A/D130A/V187T/T189Q, L075Q/D111A/V187N/T189Q/L264R, L075Q/N094R/D130A/G156W/V187T, L075Q/V077I/D130A/G156W/V187N, L075R/D111A/D130A/V187N/T189Q, L075R/D130A/V154I/T189Q/L264R, L075R/D130A/V187T/T189Q/L264R, S058M/D130A/D137Q/G163P/L264R, A018K/G023G/D111A/D130A/V154I/T189Q, A018K/G023G/K024A/L075R/D130A/V187N, A018K/G023G/K024A/N094R/D130A/V154I, A018K/G023G/L075Q/D130A/G156W/V187N, A018K/G023G/L075R/N094R/D130A/V187N, A018K/G023G/L075R/V077I/D130A/V154I, A018K/G023Q/L075Q/V077I/D130A/G156W, A018K/G023Q/L075Q/V077I/D130A/V187N, A018K/G023Q/N094R/D130A/G156W/V187Q, A018K/K024A/L075Q/V077I/D130A/V187N, A018K/K024A/L075R/D130A/V187N/T189Q, A018K/K024A/V077I/N094R/D130A/G156W, A018K/L075Q/D130A/V154I/T189Q/L264R, A018K/L075Q/D130A/V187N/T189Q/L264R, A018K/L075R/D130A/V154I/G156W/V187N, A018K/N094R/D111A/D130A/V154I/V187N, D027E/D048Q/D130A/D137Q/G163P/L264R, D027E/D130A/D137Q/G163P/L227M/L264R, D027E/D130A/G163P/L227M/N233Q/L264R, D027E/S058M/D130A/L227M/N233Q/L264R, D027Q/E056K/S058M/D130A/I252Q/L264R, D027Q/F051T/L075G/D130A/I252Q/L264R, D027Q/F051T/L075Q/D130A/V187H/L264R, D027Q/S058M/L075R/D130A/V187T/I252Q, D027S/G091Q/D130A/V187N/I252Q/L264R, D048Q/S058M/D130A/G163P/N233Q/L264R, D111A/D130A/V154I/G156W/V187N/L264R, F051T/L075G/G091Q/D130A/I252Q/L264R, G023K/D027S/L075R/D130A/V187T/I252Q, G023K/E056K/L075R/D130A/T189Q/L264R, G023K/E056K/L075R/D130A/V187N/L264R, G023K/F051T/D130A/V187N/I252Q/L264R, G023K/K024A/L075Q/D111A/D130A/T189Q, G023K/K024A/L075Q/N094R/D130A/G156W, G023K/K024A/L075R/D130A/V154I/N187N, G023K/L075G/D130A/V187T/I252Q/L264R, G023K/L075Q/D111A/D130A/V154I/V187N, G023K/L075Q/V077I/D130A/G156W/V187Q, G023Q/F051T/L075Q/D130A/V187H/I252Q, G023Q/K024A/L075Q/D130A/V154I/G156W, G023Q/K024A/L075Q/D130A/V154I/V187N, G023Q/K024A/V077I/D130A/V154I/G156W, G023Q/L075Q/V077I/N094R/D130A/V187Q, K024A/D111A/D130A/V187T/T189Q/L264R, K024A/L075Q/D130A/G156W/T189Q/L264R, K024A/L075Q/V077I/N094R/D130A/V187N, L075Q/D111A/D130A/V154I/G156W/T189Q, L075Q/D111A/D130A/V154I/V187N/T189Q, L075Q/D130A/V154I/G156W/V187N/L264R, L075R/D130A/V154I/G156W/V187N/L264R, N011K/E056K/L075Q/D130A/V187N/T189Q, N011K/G023Q/L075Q/D130A/V187N/T189Q, N011K/G023Q/L075Q/N094R/D130A/L264R, S058M/D130A/D137Q/G163P/L227M/L264R, S058M/D130A/D137Q/G163P/N233Q/L264R, S058M/D130A/G163P/L227M/N233Q/L264R, A018K/G023G/K024A/L075Q/D130A/G156W/V187N, A018K/G023G/K024A/L075R/N094R/D130A/V154I, A018K/G023Q/K024A/L075Q/V077I/D130A/G156W, A018K/G023Q/K024A/L075R/D130A/V154I/N187N, A018K/G023Q/K024A/L075R/V077I/D130A/G156W, A018K/K024A/L075Q/D130A/G156W/V187T/T189Q, A018K/K024A/L075Q/D130A/V154I/G156W/V187T, A018K/K024A/L075Q/V077I/N094R/D130A/G156W, A018K/L075Q/D111A/D130A/V154I/G156W/L264R, D027E/D130A/D137Q/G163P/L227M/N233Q/L264R, D027E/S058M/D130A/D137Q/G163P/L227M/L264R, D027E/S058M/D130A/D137Q/G163P/N233Q/L264R, D027Q/F051T/L075G/D130A/V187H/I252Q/L264R, D027Q/F051T/L075Q/G091Q/D130A/V187T/I252Q, D048Q/D130A/D137Q/G163P/L227M/N233Q/L264R, D048Q/S058M/D130A/D137Q/L227M/N233Q/L264R, E056K/L075Q/D111A/D130A/G156W/V187N/T189Q, G023K/D027Q/F051T/L075G/D130A/V187H/L264R, G023K/F051T/E056K/L075R/D130A/V187T/I252Q, G023K/K024A/L075Q/D130A/V187T/T189Q/L264R, G023K/K024A/L075Q/V077I/D130A/G156W/V187Q, G023K/L075Q/D130A/G156W/V187N/T189Q/L264R, G023Q/D027S/S058M/L075Q/D130A/I252Q/L264R, G023Q/E056K/L075Q/D130A/V154I/G156W/T189Q, G023Q/F051T/G091Q/D130A/V187H/I252Q/L264R, G023Q/K024A/L075Q/V077I/D130A/G156W/V187N, G023Q/K024A/L075Q/V077I/D130A/V154I/G156W, G023Q/L075Q/D111A/D130A/V154I/G156W/L264R, G023Q/L075Q/D130A/V154I/G156W/T189Q/L264R, G023Q/L075Q/D130A/V154I/V187N/T189Q/L264R, G023Q/L075Q/V077I/N094R/D130A/G156W/V187N, G023Q/L075Q/V077I/N094R/D130A/G156W/V187Q, K024A/L075Q/D111A/D130A/V187N/T189Q/L264R, K024A/L075R/D130A/V154I/G156W/T189Q/L264R, L075Q/D111A/D130A/G156W/V187N/T189Q/L264R, N011K/D027S/D111A/D130A/V154I/V187N/T189Q, N011K/E056K/L075Q/D130A/V154I/V187N/T189Q, N011K/G023K/L075Q/D111A/D130A/V154I/V187N, A018K/G023G/K024A/L075Q/D130Y/V154I/V187N/T189Q, A018K/G023G/K024A/L075Q/N094R/D130A/G156W/V187Q, A018K/G023G/K024A/L075Q/V077I/D130A/V154I/G156W, A018K/G023G/K024A/L075Q/V077I/N094R/D130A/G156W, A018K/G023G/L075Q/V077I/D130A/V154I/G156W/V187N, A018K/G023G/L075R/V077I/N094R/D130A/G156W/V187Q, A018K/G023Q/K024A/L075Q/V077I/D130A/G156W/V187Q, A018K/G023Q/K024A/L075R/D130A/V154I/G156W/V187N, A018K/G023Q/K024A/L075R/N094R/D130A/V154I/G156W, A018K/G023Q/K024A/L075R/V077I/N094R/D130A/G156W, A018K/G023Q/L075Q/V077I/D130A/V154I/G156W/V187N, A018K/K024A/L075Q/V077I/N094R/D130A/V154I/G156W, A018K/K024A/L075R/D130A/V154I/G156W/V187T/L264R, D027E/D048Q/D130A/D137Q/G163P/L227M/N233Q/L264R, D048Q/S058M/D130A/D137Q/G163P/L227M/N233Q/L264R, G023K/D027S/E056K/L075G/D130A/V187T/I252Q/L264R, G023K/D027S/F051T/E056K/L075R/D130A/V187T/L264R, G023K/F051T/E056K/L075R/G091Q/D130A/V187T/L264R, G023K/L075Q/N094R/D130A/V154I/G156W/V187N/L264R, G023Q/D027S/F051T/S058M/G091Q/D130A/V187N/I252Q, G023Q/D027S/L075Q/D130A/V154I/G156W/T189Q/L264R, G023Q/K024A/L075Q/V077I/D130A/V154I/G156W/V187N, G023Q/K024A/L075Q/V077I/N094R/D130A/V154I/V187N, G023Q/L075Q/N094R/D111A/D130A/G156W/T189Q/L264R, G023Q/L075Q/N094R/D130A/V154I/G156W/T189Q/L264R, G023Q/L075Q/V077I/N094R/D130A/V154I/G156W/V187Q, K024A/D111A/D130A/V154I/G156W/V187T/T189Q/L264R, N011K/G023K/E056K/L075Q/D130A/V154I/T189Q/L264R, A018K/G023G/K024A/L075Q/N094R/D111A/D130A/V154I/T189Q, A018K/G023G/K024A/L075R/V077I/D130A/V154I/G156W/V187N, A018K/G023G/K024A/V077I/D130A/V154I/G156W/V187T/T189Q, A018K/G023Q/K024A/L075R/N094R/D130A/V154I/G156W/V187N, D027S/E056K/L075Q/N094R/D111A/D130A/V154I/G156W/L264R, D027S/E056K/L075Q/N094R/D111A/D130A/V187N/T189Q/L264R, G023K/D027S/L075Q/D111A/D130A/V154I/G156W/T189Q/L264R, G023K/E056K/L075Q/D111A/D130A/V154I/G156W/T189Q/L264R, G023K/K024A/N094R/D130A/V154I/G156W/V187T/T189Q/L264R, G023Q/D027S/L075Q/N094R/D130A/V154I/G156W/V187N/L264R, N011K/G023K/L075R/D111A/D130A/V154I/N187N/T189Q/L264R, N011K/G023K/L075R/V077I/D130A/V154I/G156W/V187T/T189Q, A018K/G023Q/K024A/L075Q/V077I/N094R/D130A/V154I/G156W/V187Q, G023K/D027S/F051T/E056K/S058M/L075G/G091Q/D130A/I252Q/L264R, G023Q/D027S/F051T/E056K/L075R/G091Q/D130A/V187H/I252Q/L264R, G023Q/D027S/F051T/E056K/S058M/L075R/G091Q/D130A/V187H/I252Q, G023Q/L075R/N094R/D111A/D130A/V154I/G156W/V187N/T189Q/L264R, N011K/A018K/G023G/K024A/L075R/V077I/D130A/V154I/N187T/T189Q, N011K/G023Q/L075Q/N094R/D111A/D130A/V154I/G156W/V187N/L264R, A018K/G023G/L075R/N094R/D111A/D130A/V154I/G156W/V187N/T189Q/L264R, optionally wherein the variant or active fragment has a performance index (pI) for cleaning performance which is greater than 1.0.

11. A composition comprising the lipolytic enzyme variant of claim 1.

12. The composition of claim 11, wherein said composition is a granular, powder, solid, bar, liquid, tablet, gel, unit dose, or paste composition.

13. The composition of claim 11, wherein said composition is a laundry detergent composition, a dish detergent composition, or a hard surface cleaning composition.

14. The composition of claim 11, further comprising at least one bleaching agent and/or at least one additional enzyme selected from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, β-glucanase, arabinosidase, hyaluronidase, chondroitinase, laccase, and amylase.

15. A method of cleaning, comprising contacting a surface or an item with the composition of claim 11.

16. The method of claim 15, wherein said item is dishware or fabric.

* * * * *